(12) United States Patent
Yoshimoto et al.

(10) Patent No.: US 9,565,856 B2
(45) Date of Patent: Feb. 14, 2017

(54) TETRAZOLINONE COMPOUNDS AND ITS USE AS PESTICIDES

(71) Applicant: SUMITOMO CHEMICAL COMPANY, LIMITED, Tokyo (JP)

(72) Inventors: Yuya Yoshimoto, Takarazuka (JP); Sadayuki Arimori, Takarazuka (JP); Yuichi Matsuzaki, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/386,111

(22) PCT Filed: Apr. 26, 2013

(86) PCT No.: PCT/JP2013/062875
§ 371 (c)(1),
(2) Date: Sep. 18, 2014

(87) PCT Pub. No.: WO2013/162072
PCT Pub. Date: Oct. 31, 2013

(65) Prior Publication Data
US 2015/0051171 A1    Feb. 19, 2015

(30) Foreign Application Priority Data

Apr. 27, 2012 (JP) ................................. 2012-102452
Sep. 27, 2012 (JP) ................................. 2012-213693

(51) Int. Cl.
| C07F 7/10 | (2006.01) |
| C07D 403/12 | (2006.01) |
| A01N 55/00 | (2006.01) |
| A01N 43/713 | (2006.01) |

(52) U.S. Cl.
CPC ............ *A01N 43/713* (2013.01); *A01N 55/00* (2013.01); *C07D 403/12* (2013.01); *C07F 7/10* (2013.01)

(58) Field of Classification Search
None
See application file for complete search history.

(56) References Cited

U.S. PATENT DOCUMENTS

| 6,583,090 B1 | 6/2003 | Gewehr et al. |
| 7,056,941 B1 | 6/2006 | Muller et al. |
| 2009/0069179 A1 | 3/2009 | Lohmann et al. |
| 2014/0323305 A1 | 10/2014 | Rheinheimer et al. |

FOREIGN PATENT DOCUMENTS

| CA | 2296729 A1 | 2/1999 |
| IL | 133997 | 2/2003 |
| JP | 2001-510840 A | 8/2001 |
| WO | WO 96/36229 A1 | 11/1996 |
| WO | WO 99/05139 A1 | 2/1999 |
| WO | WO 2013/092224 A1 | 6/2013 |

OTHER PUBLICATIONS

An Office Action (including an English translation thereof) issued in the corresponding Chinese Patent Application No. 201380021504.5 on Jul. 3, 2015.
The International Preliminary Report on Patentability and Written Opinion of the International Searching Authority, dated Oct. 28, 2014, issued in the corresponding International Application No. PCT/JP2013/062875.
The International Search Report, dated Jul. 30, 2013, issued in the corresponding International Application No. PCT/JP2013/062875.
Office Action (including an English translation thereof) issued in the corresponding Chinese Patent Application No. 201380021504.5 on Mar. 18, 2016.
Office Action (including an English translation thereof) issued in the corresponding Israeli Patent Application No. 235265 on Mar. 23, 2016.
Colombian Office Action dated Dec. 1, 2015, for Colombian Application No. 14-230420-2 with the English translation.
An Office Action (including an English translation thereof) issued in the corresponding Chilean Patent Application No. 2014-002879 on Oct. 22, 2015.
Office Action (including an English translation thereof) issued in the corresponding Colombian Patent Application No. 14-230420 on Jun. 28, 2016.

(Continued)

*Primary Examiner* — Alicia L Otton
(74) *Attorney, Agent, or Firm* — Birch, Stewart, Kolasch & Birch, LLP

(57) ABSTRACT

The present invention provides a compound having an excellent efficacy for controlling pests. A tetrazolinone compound of a formula (1): [wherein R1 represents an C6-C16 aryl group, an C1-C12 alkyl group, or a C3-C12 cycloalkyl group, etc., which each optionally be substituted; R2, R3, R4 and R5 represent independently of each other a hydrogen atom, a halogen atom or an C1-C3 alkyl group, etc.; R6 represents an C1-C6 alkyl group, a C3-C6 cycloalkyl group, a halogen atom, a C1-C6 haloalkyl group, an C2-C6 alkenyl group, an C1-C6 alkoxy group, or a C1-C6 haloalkoxy group, etc.; R7, R8 and R9 represent independently of each other a hydrogen atom, a halogen atom, or an C1-C4 alkyl group, etc.; X represents an oxygen atom or a sulfur atom; and R10 represents an C1-C6 alkyl group, etc.] shows an excellent controlling efficacy on pests.

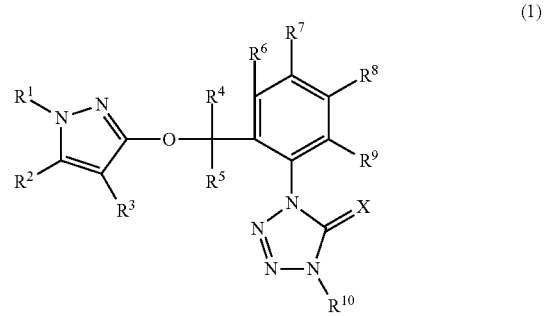

(1)

21 Claims, No Drawings

(56) References Cited

OTHER PUBLICATIONS

Office Action and Search Report (including an English translation thereof) issued in the corresponding Taiwanese Patent Application No. 102114984 on Sep. 12, 2016.
The 3rd Office Action (including an English translation thereof) issued in the corresponding Chinese Patent Application No. 201380021504.5 on Oct. 9, 2016.
The Patent Examination Report No. 1 issued in the corresponding Australian Patent Application No. 2013253325 on Oct. 10, 2016.
Reason for Refusal (including an English translation thereof) issued in the corresponding Japanese Patent Application No. 2013-092076 on Oct. 25, 2016.

TETRAZOLINONE COMPOUNDS AND ITS USE AS PESTICIDES

This application claims priority to and the benefit of Japanese Patent Application Nos. 2012-102452 filed Apr. 27, 2012 and 2012-213693 filed Sep. 27, 2012, the entire contents of which are incorporated herein by reference.

TECHNICAL FIELD

The present invention relates to tetrazolinone compounds and its use.

BACKGROUND ART

Heretofore, various drugs for controlling pests have been widely developed and provides in practice use, but in some cases, these drugs may not exert enough efficacy.

Also, as compounds having tetrazolinone ring, compounds represented by the following formula (A):

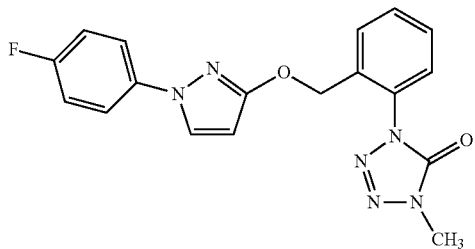

have been known (see Patent Document 1).

CITATION LIST

Patent Document

Patent Document 1: WO 1999/05139 pamphlet

SUMMARY OF THE INVENTION

An object of the present invention is to provide a compound having an excellent efficacy for controlling pests.

The present inventors have intensively studied to find that compounds having an excellent efficacy for controlling pests and as a result, found that a tetrazolinone compound of the following formula (I) has an excellent efficacy for controlling pests, which thus have completed the present invention.

Specifically, the present invention includes the following [1] to [36].

[1] A tetrazolinone compound of a formula (1):

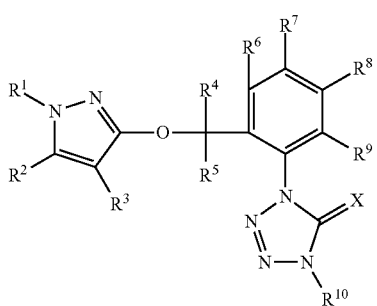

[wherein
$R^1$ represents an C6-C16 aryl group optionally having one or more atoms or groups selected from Group P, an C1-C12 alkyl group optionally having one or more atoms or groups selected from Group P, a C3-C12 cycloalkyl group optionally having one or more atoms or groups selected from Group P, an C2-C12 alkenyl group optionally having one or more atoms or groups selected from Group P, a C3-C12 cycloalkenyl group optionally having one or more atom or groups selected from Group P, an C2-C12 alkynyl group optionally having one or more atoms or groups selected from Group P, an C2-C12 acyl group optionally having one or more atoms or groups selected from Group P or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituents consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbony group, a hydroxycarbonyl group, or a halogen atom;

$R^4$ and $R^5$ represent independently of each other a hydrogen atom, a halogen atom or an C1-C3 alkyl group;

$R^6$ represents
an C1-C6 alkyl group, a C3-C6 cycloalkyl group, a halogen atom, a C1-C6 haloalkyl group, an C2-C6 alkenyl group, an C1-C6 alkoxy group, an C1-C6 alkylthio group, an C2-C6 alkynyl group, a nitro group, a cyano group, an aminocarbonyl group optionally having. C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group, or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, an C2-C6 haloalkenyl group, an C2-C6 alkoxyalkyl group, a C3-C6 cycloalkyl group or a C3-C6 halocycloalkyl group; and X represents an oxygen atom or a sulfur atom;

Group P: a group consisting of a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, an C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonyl group, a C6-C16 haloarylsulfonyl group, an C1-C6 alkylsulfinyl group, a C1-C6 haloalkylsulfinyl group, an C6-C16 arylsulfinyl group, a C6-C16 haloarylsulfinyl group, an aminosulfonyl group optionally having C1-C6 alkyl group or C6-C12 aryl group, and an aminocarbonyl group optionally having C1-C6 alkyl group].

[2] The tetrazolinone compound according to [1] wherein
$R^2$, $R^3$, $R^4$ and $R^5$ represent a hydrogen atom;
$R^{10}$ represents a methyl group; and
X represents an oxygen atom.

[3] The tetrazolinone compound according to [1] wherein
$R^1$ represents an C6-C16 aryl group optionally having one or more atoms and groups selected from Group P (with the proviso that when the C6-C16 aryl group has two or more atoms or groups selected from Group P, the substituents consisting of the atoms and the groups may be same or different to each other);
$R^2$, $R^3$, $R^4$ and $R^5$ represent a hydrogen atom;
$R^{10}$ represents a methyl group; and
X represents an oxygen atom.

[4] The tetrazolinone compound according to [1] wherein
$R^1$ represents an C1-C12 alkyl group optionally having one or more atoms or groups selected from Group P, a C3-C12 cycloalkyl group optionally having one or more atoms or groups selected from Group P, an C2-C12 alkenyl group optionally having one or more atoms or groups selected from Group P, a C3-C12 cycloalkenyl group optionally having one or more atoms or groups selected from Group P, an C2-C12 alkynyl group optionally having one or more atoms or groups selected from Group P, an C2-C12 acyl group optionally having one or more atoms or groups selected from Group P (with the proviso that when the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituents consisting of the atoms and the groups may be same or different to each other);
$R^2$, $R^3$, $R^4$ and $R^5$ represent a hydrogen atom;
$R^{10}$ represents a methyl group; and
X represents an oxygen atom.

[5] The tetrazolinone compound according to [1] wherein
$R^1$ represents a group represented by a formula (2):

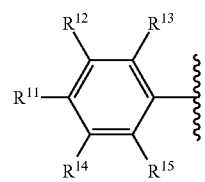

(2)

[wherein
$R^{11}$ represents a halogen atom, a hydrogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, an C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, C2-C6 haloacyl group, C2-C6 acyloxy group, C2-C6 acylthio group, a hydroxycarbonyl group, formyl group, C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonyl group, a C6-C16 haloarylsulfonyl group, an C1-C6 alkylsulfinyl group, a C1-C6 haloalkylsulfinyl group, an C6-C16 arylsulfinyl group, a C6-C16 haloarylsulfinyl group, an aminosulfonyl group optionally having C1-C6 alkyl group or C6-C12 aryl group, or an aminocarbonyl group optionally having C1-C6 alkyl group; and
$R^{12}$, $R^{13}$, $R^{14}$ and $R^{15}$ represent independently of each other a hydrogen atom or a halogen atom];
$R^2$, $R^3$, $R^4$ and $R^5$ represent a hydrogen atom;
$R^7$, $R^8$ and $R^9$ represent independently of each other a hydrogen atom or fluorine atom;
$R^{10}$ represents a methyl group; and
X represents an oxygen atom.

[6] The tetrazolinone compound according to [5] wherein
$R^6$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;
$R^7$, $R^8$ and $R^9$ represent independently of each other a hydrogen atom;
$R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group.

[7] The tetrazolinone compound according to [6] wherein
$R^6$ represents an C1-C3 alkyl group, a C3-C4 cycloalkyl group, a halogen atom, a C1-C3 haloalkyl group, an C2-C3 alkenyl group, an C1-C3 alkoxy group, an C2-C3 alkynyl group or a C1-C3 haloalkoxy group;

$R^{11}$ represents a halogen atom, a hydrogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group.

[8] The tetrazolinone compound according to [6] wherein $R^6$ represents a methyl group, a cyclopropyl group, a chlorine atom, a bromine atom, an ethyl group or a methoxy group;

$R^{11}$ represents a halogen atom, a methyl group, an ethyl group or a methoxy group;

$R^{12}$, $R^{13}$, $R^{14}$ and $R^{15}$ represent independently of each other a hydrogen atom or a fluorine atom.

[9] The tetrazolinone compound according to [1] wherein $R^1$ represents a group represented by a formula (2):

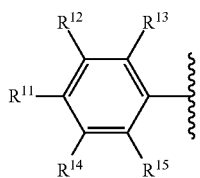

(2)

[wherein $R^{11}$ represents a halogen atom, a hydrogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group;

$R^{12}$, $R^{13}$, $R^{14}$ and $R^{15}$ represent independently of each other a hydrogen atom or a halogen atom];

$R^2$, $R^3$, $R^4$, $R^5$, $R^7$, $R^8$ and $R^9$ represent independently of each other a hydrogen atom;

$R^6$ represents an C1-C3 alkyl group, a halogen atom, a C1-C3 haloalkyl group, an C1-C3 alkoxy group or a C1-C3 haloalkoxy group;

$R^{10}$ represents a methyl group; and

X represents an oxygen atom.

[10] The tetrazolinone compound according to [9] wherein $R^{11}$ represents a halogen atom, a methyl group, an ethyl group or a methoxy group;

$R^{12}$, $R^{13}$, $R^{14}$ and $R^{15}$ represent independently of each other a hydrogen atom or a fluorine atom;

$R^6$ represents a methyl group, a chlorine atom, a bromine atom, an ethyl group or a methoxy group.

[11] The tetrazolinone compound according to [1] wherein $R^6$ represents an C3-C6 cycloalkyl group, an C2-C6 alkenyl group, a C2-C6 haloalkenyl group, an C2-C6 alkynyl group, a C2-C6 haloalkynyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, a C3-C6 alkynyloxy group, a C3-C6 haloalkenyloxy group, a C3-C6 haloalkynyloxy group, a C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group, an C2-C5 alkylthioalkyl group or an aminocarbonyl group optionally having C1-C6 alkyl group.

[12] The tetrazolinone compound according to [1] wherein $R^1$ represents a group represented by a formula (3):

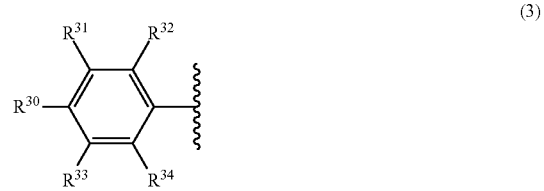

(3)

[wherein $R^{31}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{30}$, $R^{32}$, $R^{33}$ and $R^{34}$ represent independently of each other a hydrogen atom or a halogen atom];

$R^2$, $R^3$, $R^4$ and $R^5$ represent independently of each other a hydrogen atom;

$R^6$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;

$R^7$, $R^8$ and $R^9$ represent independently of each other a hydrogen atom;

$R^{10}$ represents a methyl group; and

X represents an oxygen atom.

[13] The tetrazolinone compound according to [12] wherein $R^6$ represents an C1-C3 alkyl group, a C3-C4 cycloalkyl group, a halogen atom, a C1-C3 haloalkyl group, an C2-C3 alkenyl group, an C1-C3 alkoxy group, an C2-C3 alkynyl group or a C1-C3 haloalkoxy group; $R^{31}$ represents an C1-C3 alkoxy group, a halogen atom, a hydrogen atom, an C1-C3 alkyl group, a C1-C3 haloalkyl group, a C1-C3 haloalkoxy group, an C1-C3 alkylthio group, a C1-C3 haloalkylthio group, a nitro group or a cyano group.

[14] The tetrazolinone compound according to [12] wherein $R^6$ represents a methyl group, a cyclopropyl group, a chlorine atom, a bromine atom, an ethyl group or a methoxy group;

$R^{31}$ represents a methoxy group, a halogen atom, a methyl group or an ethyl group;

$R^{30}$, $R^{32}$, $R^{33}$ and $R^{34}$ represent independently of each other a hydrogen atom or a fluorine atom.

[15] The tetrazolinone compound according to [1] wherein $R^1$ represents a group represented by a formula (4):

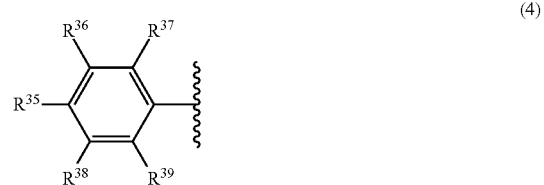

(4)

[wherein $R^{35}$, $R^{36}$, $R^{37}$, $R^{38}$ and $R^{39}$ represent independently of each other a hydrogen atom, an C1-C6 alkoxy group, a halogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a C3-C4 cycloalkyl group, a C3-C4 cycloalkyloxy group, a nitro group or a cyano group];

$R^2$, $R^3$, $R^4$ and $R^5$ represent independently of each other a hydrogen atom;

$R^6$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;

$R^7$, $R^8$ and $R^9$ represent independently of each other a hydrogen atom;

$R^{10}$ represents a methyl group; and

X represents an oxygen atom.

[16] The tetrazolinone compound according to [15] wherein $R^6$ represents an C1-C3 alkyl group, a C3-C4 cycloalkyl group, a halogen atom, a C1-C3 haloalkyl group, an C2-C3 alkenyl group, an C1-C3 alkoxy group, an C2-C3 alkynyl group or a C1-C3 haloalkoxy group; and $R^{35}$, $R^{36}$, $R^{37}$, $R^{38}$ and $R^{39}$ represent independently of each other a hydrogen atom, an C1-C3 alkoxy group, a halogen atom, an C1-C3 alkyl group, a C1-C3 haloalkyl group, a C1-C3 haloalkoxy group, an C1-C3 alkylthio group, a C1-C3 haloalkylthio group, a nitro group or a cyano group.

[17] The tetrazolinone compound according to [15] wherein $R^6$ represents a methyl group, a cyclopropyl group, a chlorine atom, a bromine atom, an ethyl group or a methoxy group;

$R^{35}$, $R^{36}$, $R^{37}$, $R^{38}$ and $R^{39}$ represent independently of each other a hydrogen atom, a methoxy group, an ethoxy group, a halogen atom, a methyl group or an ethyl group.

[18] An agent for controlling pests comprising the tetrazolinone compound according to any one of [1] to [17].

[19] A method for controlling pests comprising applying an effective amount of the tetrazolinone compound according to any one of [1] to [17] to plant or soil.

[20] Use of the tetrazolinone compound according to any one of [1] to [17] for controlling pests.

[21] A tetrazolinone compound represented by a formula (5):

(5)

[wherein $R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{22}$, $R^{23}$, $R^{24}$ and $R^{25}$ represent independently of each other a hydrogen atom or a halogen atom; and $R^{26}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group.

[22] The tetrazolinone compound according to [21] wherein $R^{21}$ represents a halogen atom, a methyl group, an ethyl group or a methoxy group;

$R^{26}$ represents a methyl group, a cyclopropyl group, a chlorine atom, a bromine atom, an ethyl group or a methoxy group; and $R^{22}$, $R^{23}$, $R^{24}$ and $R^{25}$ represent independently of each other a hydrogen atom or fluorine atom.

[23] A tetrazolinone compound represented by a formula (6):

(6)

[wherein $R^{42}$ represents an C1-C6 alkoxy group, a halogen atom, a hydrogen atom, an C1-C6 alkyl group, C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{41}$, $R^{43}$, $R^{44}$ and $R^{45}$ represent independently of each other a hydrogen atom or a halogen atom;

$R^{46}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, C1-C2 haloalkylthio group or an C1-C4 alkylamino group].

[24] The tetrazolinone compound according to [23] wherein $R^{42}$ represents a methoxy group, a halogen atom, a methyl group or an ethyl group;

$R^{46}$ represents a methyl group, a cyclopropyl group, a chlorine atom, a bromine atom, an ethyl group or a methoxy group; and $R^{41}$, $R^{43}$, $R^{44}$ and $R^{45}$ represent independently of each other a hydrogen atom or a fluorine atom.

[25] A tetrazolinone compound represented by a formula (7):

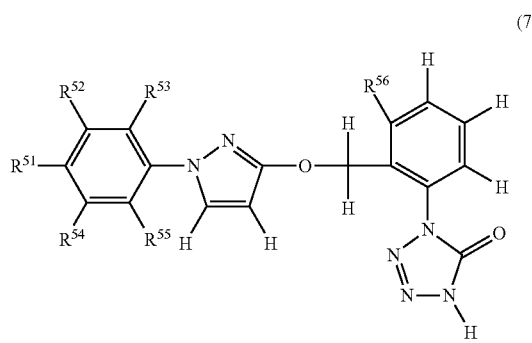

(7)

[wherein
$R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{51}$, $R^{52}$, $R^{54}$ and $R^{55}$ represent independently of each other a hydrogen atom or a halogen atom;
$R^{56}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group].

[26] The tetrazolinone compound according to [25] wherein
$R^{53}$ represents a methoxy group, an ethoxy group, a halogen atom, a methyl group or an ethyl group;
$R^{56}$ represents a methyl group, a cyclopropyl group, a chlorine atom, a bromine atom, an ethyl group or a methoxy group.

[27] A tetrazolinone compound represented by a formula (8):

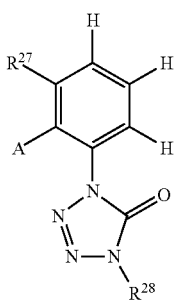

(8)

[wherein
$R^{27}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;
$R^{28}$ represents a methyl group or a hydrogen atom;
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having a heterocyclyl group (with the proviso that the heterocyclyl group includes one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group].

[28] The tetrazolinone compound according to [27] wherein
$R^{27}$ represents a methyl group, a cyclopropyl group, a chlorine atom, a bromine atom, an ethyl group or a methoxy group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

[29] The tetrazolinone compound according to [27] wherein
$R^{27}$ represents a methyl group, an ethyl group, a halogen atom, a trifluoromethyl group or a methoxy group; and
A represents a methyl group, a chloromethyl group or bromomethyl group.

[30] The tetrazolinone compound according to [27] wherein
$R^{27}$ represents an C2-C3 alkyl group, a C3-C4 cycloalkyl group, an C2-C3 alkenyl group, an C2-C3 alkoxy group, an C1-C2 alkylthio group, an C2-C3 alkynyl group, a C1-C3 haloalkoxy group, a C1-C2 haloalkylthio group or an C1-C4 alkylamino group.

[31] A pyrazole compound represented by a formula (9):

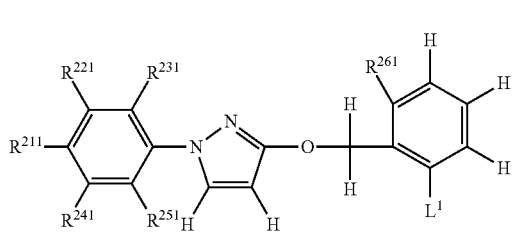

(9)

[wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{221}$, $R^{231}$, $R^{241}$ and $R^{251}$ represent independently of each other a hydrogen atom or a halogen atom;
$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH].

[32] The pyrazole compound according to [31] wherein
$R^{211}$ represents a halogen atom, a methyl group, an ethyl group or methoxy group;
$R^{261}$ represents a methyl group, a cyclopropyl group, a chlorine atom, a bromine atom, an ethyl group or a methoxy group; and
$R^{221}$, $R^{231}$, $R^{241}$ and $R^{251}$ represent independently of each other a hydrogen atom or fluorine atom.

[33] A pyrazole compound represented by a formula (10):

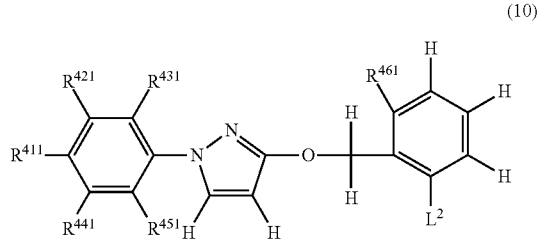

(10)

[wherein
R$^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

R$^{411}$, R$^{431}$, R$^{441}$ and R$^{451}$ represent independently of each other a hydrogen atom or a halogen atom;

R$^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and L$^2$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH].

[34] The pyrazole compound according to [33] wherein
R$^{421}$ represents a methoxy group, a halogen atom, a methyl group or an ethyl group;

R$^{461}$ represents a methyl group, a cyclopropyl group, a chlorine atom, a bromine atom, an ethyl group or a methoxy group; and R$^{411}$, R$^{431}$, R$^{441}$ and R$^{451}$ represent independently of each other a hydrogen atom or a fluorine atom.

[35] A pyrazole compound represented by a formula (11):

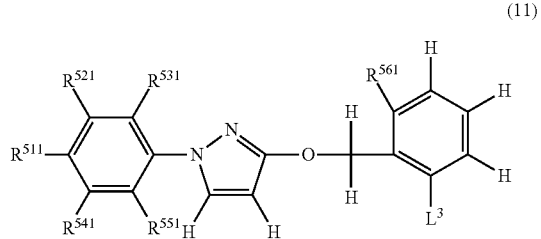

(11)

[wherein
R$^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

R$^{511}$, R$^{521}$, R$^{541}$ and R$^{551}$ represent independently of each other a hydrogen atom or a halogen atom;

R$^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and L$^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH].

[36] The pyrazole compound according to [35] wherein
R$^{531}$ represents a methoxy group, an ethoxy group, a halogen atom, a methyl group or an ethyl group; and R$^{561}$ represents a methyl group, a cyclopropyl group, a chlorine atom, a bromine atom, an ethyl group a methoxy group.

The present invention can control pests.

DESCRIPTION OF EMBODIMENTS

The compound of the present invention (hereinafter, sometimes referred to as "the present compound") is a tetrazolinone compound of a formula (1):

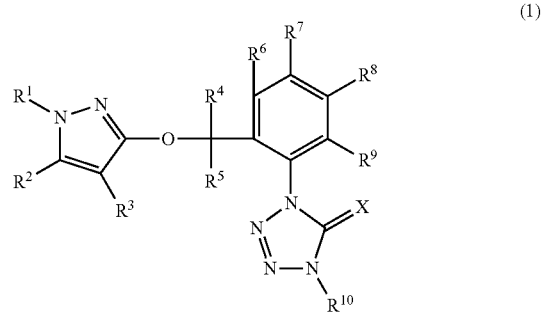

(1)

[wherein
R$^1$ represents an C6-C16 aryl group optionally having one or more atoms or groups selected from Group P, an C1-C12 alkyl group optionally having one or more atoms or groups selected from Group P, a C3-C12 cycloalkyl group optionally having one or more atoms or groups selected from Group P, an C2-C12 alkenyl group optionally having one or more atoms or groups selected from Group P, a C3-C12 cycloalkenyl group optionally having one or more atom or groups selected from Group P, an C2-C12 alkynyl group optionally having one or more atoms or groups selected from Group P, an C2-C12 acyl group optionally having one or more atoms or groups selected from Group P or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituents consisting of the atoms and the groups may be same or different to each other);

R$^2$ and R$^3$ represent independently of each other a hydrogen atom, an C1-C3 alkyl group, a C1-C3 haloalkyl group, an C2-C12 alkoxycarbony group, a hydroxycarbonyl group, or a halogen atom;

R$^4$ and R$^5$ represent independently of each other a hydrogen atom, a halogen atom or an C1-C3 alkyl group;

R$^6$ represents
an C1-C6 alkyl group, a C3-C6 cycloalkyl group, a halogen atom, a C1-C6 haloalkyl group, an C2-C6 alkenyl group, an C1-C6 alkoxy group, an C1-C6 alkylthio group, an C2-C6 alkynyl group, a nitro group, a cyano group, an aminocarbonyl group optionally having C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group, or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, an C2-C6 haloalkenyl group, an C2-C6 alkoxyalkyl group, a C3-C6 cycloalkyl group or a C3-C6 halocycloalkyl group; and X represents an oxygen atom or a sulfur atom;

Group P: a group consisting of a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, an C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonyl group, a C6-C16 haloarylsulfonyl group, an C1-C6 alkylsulfinyl group, a C1-C6 haloalkylsulfinyl group, an C6-C16 arylsulfinyl group, a C6-C16 haloarylsulfinyl group, an aminosulfonyl group optionally having C1-C6 alkyl group or C6-C12 aryl group, and an aminocarbonyl group optionally having C1-C6 alkyl group].

Also, the present invention provides a tetrazolinone compound represented by a formula (II):

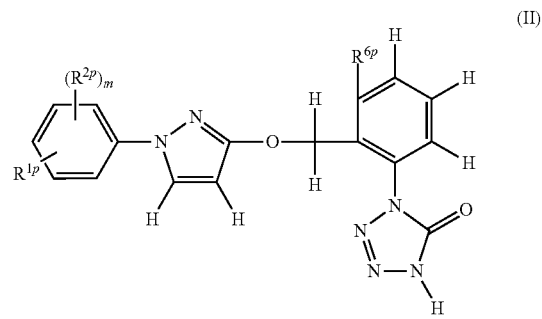

(II)

[wherein
$R^{1p}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{2p}$ represents a halogen atom;

m represents 0, 1, 2, 3 or 4; and $R^{6p}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group], which is used in a preparation of the present compound and has an excellent efficacy for controlling pests.

Specifically, the following compounds are included.

A tetrazolinone compound represented by a formula (5):

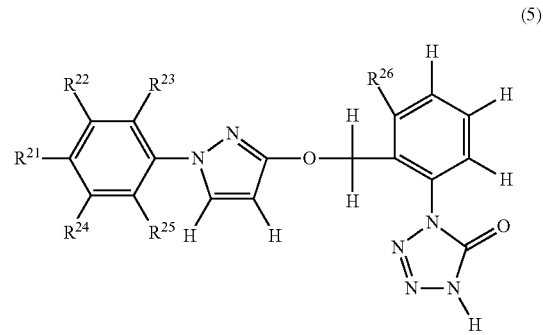

(5)

[wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{22}$, $R^{23}$, $R^{24}$ and $R^{25}$ represent independently of each other a hydrogen atom or a halogen atom; and $R^{26}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group] (hereinafter, referred to as "the present tetrazolinone compound X");

A tetrazolinone compound represented by a formula (6):

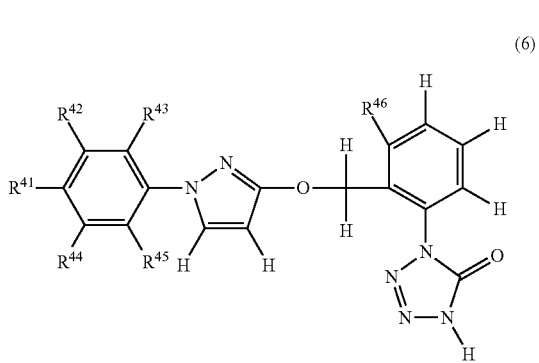

(6)

[wherein
R$^{42}$ represents an C1-C6 alkoxy group, a halogen atom, a hydrogen atom, an C1-C6 alkyl group, C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
R$^{41}$, R$^{43}$, R$^{44}$ and R$^{45}$ represent independently of each other a hydrogen atom or a halogen atom;
R$^{46}$ represents an C1-C3 alkyl group, a C3-C4 cycloalkyl group, a halogen, atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, C1-C2 haloalkylthio group or an C1-C4 alkylamino group] (hereinafter, referred to as "the present tetrazolinone compound X2"); and A tetrazolinone compound represented by a formula (7):

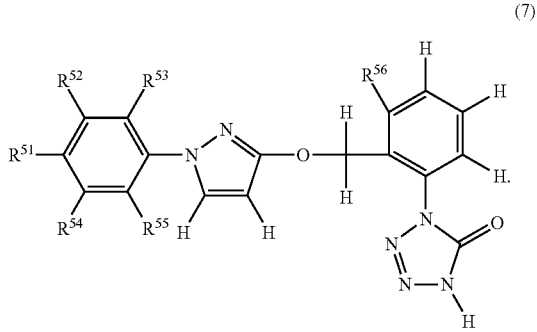

(7)

[wherein
R$^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
R$^{51}$, R$^{52}$, R$^{54}$ and R$^{55}$ represent independently of each other a hydrogen atom or a halogen atom;
R$^{56}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group] (hereinafter, referred to as "the present tetrazolinone compound X3").

The present invention provides a tetrazolinone compound represented by a formula (8):

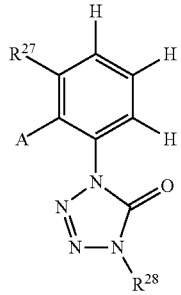

(8)

[wherein
R$^{27}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;
R$^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having a heterocyclyl group (with the proviso that the heterocyclyl group includes one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group] (hereinafter, referred to as "the present tetrazolinone compound Y"),
which is used in a preparation of the present compound and has an excellent efficacy for controlling pests.

The present invention provides a pyrazole compound represented by a formula (III):

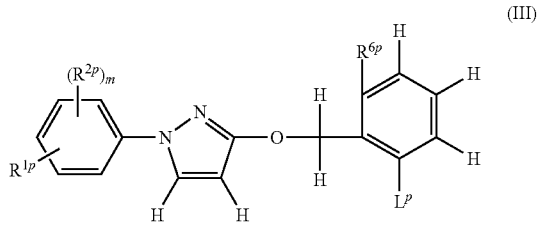

(III)

[wherein
R$^{1p}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;
R$^{2p}$ represents a halogen atom;
m represents 0, 1, 2, 3 or 4;
R$^{6p}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^p$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH],
which is used in a preparation of the present compound and has an excellent efficacy for controlling pests.

Specifically, the following compounds are included.

A pyrazole compound represented by a formula (9):

(9)

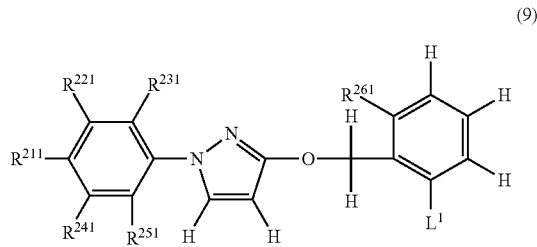

[wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{221}$, $R^{231}$, $R^{241}$ and $R^{251}$ represent independently of each other a hydrogen atom or a halogen atom;
$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^1$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH] (hereinafter, referred to as "the present pyrazole compound Z");

A pyrazole compound represented by a formula (10):

(10)

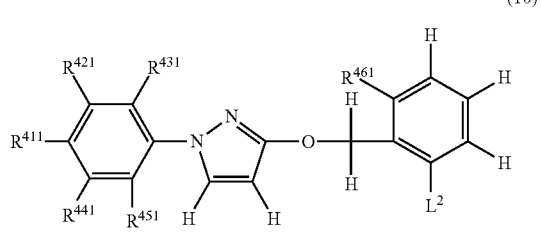

[wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH] (hereinafter, referred to as "the present pyrazole compound Z2"); and A pyrazole compound represented by a formula (11):

(11)

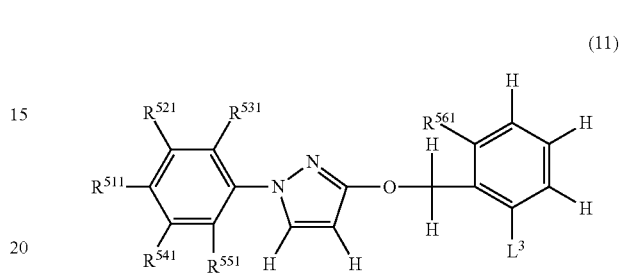

[wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{521}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH] (hereinafter, referred to as "the present pyrazole compound Z3").

Hereinafter, the present invention is explained in detail.
The substituent to be used herein is specifically described below.

The term "halogen atom" includes, for example, a fluorine atom, a chlorine atom, a bromine atom and an iodine atom.

The term "C1-C6 alkyl group" represents a straight or branched alkyl group, and includes, for example, a methyl group, an ethyl group, a propyl group, an isopropyl group, a butyl group, an isobutyl group, a sec-butyl group, a tert-butyl group, a pentyl group, and a hexyl group.

The term "C1-C6 haloalkyl group" represents a group wherein at least one hydrogen atom of the straight or branched C1-C6 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 4-fluorobutyl group, and a 2,2-difluorohexyl group. The halogen atom that can be substituted for a hydrogen atom includes a fluorine atom, a chlorine atom, a bromine atom and an iodine atom.

The term "C2-C6 alkenyl group" represents a straight or branched alkenyl group, and includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, an 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

A term "C2-C6 haloalkenyl group" represents a group wherein at least one hydrogen atom of the straight or branched C2-C6 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoromethyl-3-methyl-2-butenyl group, a 3,5,5-trifluoro-2,4-pentadienyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group, and a 5-bromo-4,5,5-trifluoro-4-trifluoromethyl-2-pentenyl group. The halogen atom that can be substituted for a hydrogen atom includes a fluorine atom, a chlorine atom, a bromine atom and an iodine atom.

The term "C2-C6 alkynyl group" represents a straight or branched alkynyl group, and includes, for example, an ethynyl group, a propargyl group, a 1-butyne-3-yl group, a 3-methyl-1-butyne-3-yl group, a 2-butynyl group, a 3-butynyl group, a 2-pentynyl group, a 3-pentynyl group, a 4-pentynyl group, a 1-hexynyl group, and a 5-hexynyl group.

The term "C2-C6 haloalkynyl group" represents a group wherein at least one hydrogen atom of the straight or branched C2-C6 alkynyl group is substituted with a halogen atom, and includes, for example, a fluoroethynyl group, a 3-chloro-2-propynyl group, a 3-bromo-2-propynyl group, an 3-iodo-2-propynyl group, an 3-chloro-1-propynyl group, a 5-chloro-4-pentynyl group, a 3,3,3-trifluoro-1-propynyl group, a 3,3,3-trifluoro-2-propynyl group, a 3-fluoro-2-propynyl group, a perfluoro-2-butynyl group, a perfluoro-2-pentynyl group, a perfluoro-3-pentynyl group, and a perfluoro-1-hexynyl group. The halogen atom that can be substituted for a hydrogen atom includes a fluorine atom, a chlorine atom, a bromine atom and an iodine atom.

The term "C3-C6 cycloalkyl group" includes, for example, a cyclopropyl group, a cyclobutyl group, a cyclopentyl group, and a cyclohexyl group.

The term "C3-C6 halocycloalkyl group" represents a group wherein at least one hydrogen atom of the C3-C6 cycloalkyl group is substituted with a halogen atom, and includes, for example a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclohexyl group, a 4,4-difluorocyclohexyl group, and a 4-chlorocyclohexyl group. The halogen atom that can be substituted for a hydrogen atom includes a fluorine atom, a chlorine atom, a bromine atom and an iodine atom.

The term "C1-C6 alkoxy group" represents a straight or branched alkoxy group, and includes, for example, a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, and a 4-methylpentyloxy group.

The term "C1-C6 haloalkoxy group" represents a group wherein at least one hydrogen atom of the straight or branched C1-C6 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group, and a periodohexyloxy group. The halogen atom that can be substituted for a hydrogen atom includes a fluorine atom, a chlorine atom, a bromine atom and an iodine atom.

The term "C1-C6 alkylthio group" represents a straight or branched alkylthio group, and includes, for example, a methylthio group, an ethylthio group, a propylthio group, an isopropylthio group, a n-butylthio group, a sec-butylthio group, a tert-butylthio group, a pentylthio group, an isopentylthio group, a neopentylthio group, a n-hexylthio group, an isohexylthio group, and a sec-hexylthio group.

The term "C1-C6 haloalkylthio group" represents a group wherein at least one hydrogen atom of the straight or branched C1-C6 alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 2,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group, and a periodohexylthio group. The halogen atom that can be substituted for a hydrogen atom includes a fluorine atom, a chlorine atom, a bromine atom and an iodine atom.

The term "C3-C6 cycloalkyloxy group" includes, for example, a cyclopropyloxy group, a cyclobutyloxy group, a cyclopentyloxy group, and a cyclohexyloxy group.

The term "C3-C6 halocycloalkyloxy group" represents a group wherein at least one hydrogen atom of the C3-C6 cycloalkyloxy group is substituted with a halogen atom, and includes, for example, a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2-difluoro-1-methylcyclopropyloxy group, a 2,2-dichloro-1-methylcyclopropyloxy group, a 2,2-dibromo-1-methylcyclopropyloxy group, a 1-(trifluoromethyl)cyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group. The halogen atom that can be substituted for a hydrogen atom includes a fluorine atom, a chlorine atom, a bromine atom and an iodine atom.

The term "C3-C6 cycloalkylthio group" includes, for example, a cyclopropylthio group, a cyclobutylthio group, a cyclopentylthio group, and a cyclohexylthio group.

The term "C2-C6 alkenyloxy group" represents a straight or branched alkenyloxy group, and includes, for example, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-2-butenyloxy group, a 2-methyl-3-butenyloxy group, a 3-methyl-3-butenyloxy group, a 1-vinyl-2-propenyloxy group, and a 5-hexenyloxy group.

The term "C3-C6 alkynyloxy group" represents a straight or branched alkynyloxy group, and includes, for example, a propargyloxy group, a 1-butyne-3-yloxy group, a 3-methyl-1-butyne-3-yloxy group, a 2-butynyloxy group, a 3-butynyloxy group, a 2-pentynyloxy group, a 3-pentynyloxy group, a 4-pentynyloxy group, and a 5-hexynyloxy group.

The term "C3-C6 haloalkenyloxy group" represents a group wherein at least one hydrogen atom of the straight or branched an C3-C6 alkenyloxy group is substituted with a halogen atom, and includes, for example, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoromethyl-3-methyl-2-butenyloxy group, a 3,5,5-trifluoro-2,4-pentadienyloxy group, a 4,4,5,5,6,6,6-heptafluoro-2-hexenyloxy group, a 4,5,5,5-tetrafluoro-4-trifluoromethyl-2-pentenyloxy group, and a 5-bromo-4,5,5-trifluoro-4-trifluoromethyl-2-pentenyloxy group. The halogen atom that can be substituted for a hydrogen atom includes a fluorine atom, a chlorine atom, a bromine atom and an iodine atom.

The term "C3-C6 haloalkynyloxy group" represents a group wherein at least one hydrogen atom of the straight or branched C3-C6 alkynyloxy group is substituted with a halogen atom, and includes, for example, a 3-chloro-2-propynyloxy group, a 3-bromo-2-propynyloxy group, an 3-iodo-2-propynyloxy group, a 5-chloro-4-pentynyloxy group, an 3-fluoro-2-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group. The halogen atom that can be substituted for a hydrogen atom includes a fluorine atom, a chlorine atom, a bromine atom and an iodine atom.

The term "C3-C6 alkenylthio group" represents a straight or branched alkenylthio group, and includes, for example, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, and a 5-hexenylthio group.

The term "C3-C6 alkynythio group" represents a straight or branched alkynylthio group, and includes, for example, a propargylthio group, a 1-butyne-3-ylthio group, a 3-methyl-1-butyne-3-ylthio group, a 2-butynylthio group, a 3-butynylthio group, a 2-pentynylthio group, a 3-pentynylthio group, a 4-pentynylthio group, and a 5-hexynylthio group.

The term "C3-C6 haloalkenythio group" represents a group wherein at least one hydrogen atom of the straight or branched C3-C6 alkynythio group is substituted with a halogen atom, and includes, for example, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, a 4,4-difluoro-3-methyl-3-butenylthio group, a 5,5-difluoro-4-pentenylthio group, a 4,5,5-trifluoro-4-pentenylthio group, a 4,4,4-trifluoromethyl-3-methyl-2-butenylthio group, a 3,5,5-trifluoro-2,4-pentadienylthio group, a 4,4,5,5,6,6,6-heptafluoro-2-hexenylthio group, a 4,5,5,5-tetrafluoro-4-trifluoromethyl-2-pentenylthio group, and a 5-bromo-4,5,5-trifluoro-4-trifluoromethyl-2-pentenylthio group. The halogen atom that can be substituted for a hydrogen atom includes a fluorine atom, a chlorine atom, a bromine atom and an iodine atom.

The term of "C3-C6 haloalkynythio group" represents a group wherein at least one hydrogen atom of the straight or branched an C3-C6 alkynythio group is substituted with a halogen atom, and includes, for example, a 3-chloro-2-propynylthio group, a 3-bromo-2-propynylthio group, an 3-iodo-2-propynylthio group, a 5-chloro-4-pentynylthio group, an 3-fluoro-2-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group. The halogen atom that can be substituted for a hydrogen atom includes a fluorine atom, a chlorine atom, a bromine atom and an iodine atom.

The term "C2-C6 acyl group" represents a straight or branched aliphatic acyl group, wherein the total number of carbon atoms including a carbon atom of a carbonyl group is two to six, and includes, for example, an acetyl group, a propionyl group, a butanoyl group, a pentanoyl group, and a hexanoyl group.

The term "C2-C6 haloacyl group" represents a group wherein at least one hydrogen atom of the C2-C6 straight or branched aliphatic acyl group is substituted with a halogen atom and includes, for example, a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a heptabromobutanoyl group, a heptaiodobutanoyl group, a 4,4,4-trifluorobutanoyl group, a 4,4,4-trichlorobutanoyl group, a 4,4,4-tribromobutanoyl group, a 4,4,4-triiodobutanoyl group, a nonafluoropentanoyl group, a nonachloropentanoyl group, a nonabromopentanoyl group, a nonaiodopentanoyl group, and a perfluorohexanoyl group. The halogen atom that can be substituted for a hydrogen atom includes a fluorine atom, a chlorine atom, a bromine atom and an iodine atom.

The term "C2-C6 acyloxy group" represents a straight or branched aliphatic acyloxy group, wherein the total number of carbon atoms including a carbon atom of a carbonyl group is two to six, and includes, for example, an acetoxy group, a propionyloxy group, a butanoyloxy group, a pentanoyloxy group, and a hexanoyloxy group.

The term "C2-C6 acylthio group" represents a straight or branched aliphatic acylthio group, wherein the total number of carbon atoms including a carbon atom of a carbonyl group is two to six, and includes, for example, an acetylthio group, a propionylthio group, a butanoylthio group, a pentanoylthio group, and a hexanoylthio group.

The term "C2-C6 alkoxycarbonyl group" may be either straight or branched, wherein the total number of carbon atoms of the alkoxy moiety and the carbonyl group is two to six, and includes, for example, a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutyloxycarbonyl group.

The term "aminocarbonyl group optionally having C1-C6 alkyl group" represents a group wherein one or two hydrogen atom on nitrogen atom of the aminocarbonyl group is substituted with the straight or branched C1-C6 alkyl group and the C1-C6 alkyl group may be same or different from each other, and includes, for example, an aminocarbonyl group, a methylaminocarbonyl group, an ethylaminocarbonyl group, a propylaminocarbonyl group, an isopropylaminocarbonyl group, a butylaminocarbonyl group, a dimethylaminocarbonyl group, a diethylaminocarbonyl group, a dipropylaminocarbonyl group, a di-isopropylaminocarbonyl group, a pentylaminocarbonyl group and a hexylaminocarbonyl group.

The term "C6-C16 aryl group" includes, for example, a phenyl group, a 1-naphthyl group, a 2-naphthyl group, an 1-acenaphthyl group, a 1-phenanthryl group, an 9-anthryl group, and a 1-pyrenyl group.

The term "C6-C16 haloaryl group" represents a group wherein at least one hydrogen atom of the C6-C16 aryl group is substituted with a halogen atom, and includes, for example, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, an 2-iodophenyl group, an 3-iodophenyl group, an 4-iodophenyl group, a 2,4-difluorophenyl group, a 2,5-difluorophenyl group, a 2,6-difluorophenyl group, a 3,5-difluorophenyl group, a 2,4-dichlorophenyl group, a 2,5-dichlorophenyl group, a 2,6-dichlorophenyl group, a 3,5-dichlorophenyl group, a 2,4,6-trifluorophenyl group, a 2,3,4-trifluorophenyl group, a 2,4,5-trifluorophenyl group, a 3,4,5-trifluorophenyl group, a 2,4,6-trichlorophenyl group, a 2,3,4-trichlorophenyl group, a 2,4,5-trichlorophenyl group, a 3,4,5-trichlorophenyl group, a pentafluorophenyl group, a pentachlorophenyl group, a 2-bromo-3-fluorophenyl group, a 2-bromo-4-fluorophenyl group, a 2-bromo-5-fluorophenyl group, a 2-bromo-6-fluorophenyl group, a 3-bromo-2-fluorophenyl group, a 3-bromo-4-fluorophenyl group, a 3-bromo-5-fluorophenyl group, a 3-bromo-6-fluorophenyl group, a 4-bromo-2-fluorophenyl group, a 4-bromo-3-fluorophenyl group, a 4-bromo-5-fluorophenyl group, a 4-bromo-6-fluorophenyl group, a 5-bromo-2-fluorophenyl group, a 5-bromo-3-fluorophenyl group, a 5-bromo-4-fluorophenyl group, a 5-bromo-6-fluorophenyl group, a 6-bromo-2-fluorophenyl group, a 6-bromo-3-fluorophenyl group, a 6-bromo-4-fluorophenyl group, a 6-bromo-5-fluorophenyl group, a 2-chloro-3-fluorophenyl group, a 2-chloro-4-fluorophenyl group, a 2-chloro-5-fluorophenyl group, a 2-chloro-6-fluorophenyl group, a 3-chloro-2-fluorophenyl group, a 3-chloro-4-fluorophenyl group, a 3-chloro-5-fluorophenyl group, a 3-chloro-6-fluorophenyl group, a 4-chloro-2-fluorophenyl group, a 4-chloro-3-fluorophenyl group, a 4-chloro-5-fluorophenyl group, a 4-chloro-6-fluorophenyl group, a 5-chloro-2-fluorophenyl group, a 5-chloro-3-fluorophenyl group, a 5-chloro-4-fluorophenyl group, a 5-chloro-6-fluorophenyl group, a 6-chloro-2-fluorophenyl group, a 6-chloro-3-fluorophenyl group, a 6-chloro-4-fluorophenyl group, a 6-chloro-5-fluorophenyl group, a 2-fluoro-1-naphthyl group, a 3-fluoro-1-naphthyl group, a 4-fluoro-1-naphthyl group, a 5-fluoro-1-naphthyl group, a 6-fluoro-1-naphthyl group, a 7-fluoro-1-naphthyl group, a 2-chloro-1-naphthyl group, a 3-chloro-1-naphthyl group, a 4-chloro-1-naphthyl group, a 5-chloro-1-naphthyl group, a 6-chloro-1-naphthyl group, a 7-chloro-1-naphthyl group, a 2-bromo-1-naphthyl group, a 3-bromo-1-naphthyl group, a 4-bromo-1-naphthyl group, a 5-bromo-1-naphthyl group, a 6-bromo-1-naphthyl group, a 7-bromo-1-naphthyl group, a heptachloro-1-naphthyl group, a heptafluoro-1-naphthyl group, a 1-fluoro-2-naphthyl group, a 3-fluoro-2-naphthyl group, a 4-fluoro-2-naphthyl group, a 5-fluoro-2-naphthyl group, a 6-fluoro-2-naphthyl group, a 7-fluoro-2-naphthyl group, a 1-chloro-2-naphthyl group, a 3-chloro-2-naphthyl group, a 4-chloro-2-naphthyl group, a 5-chloro-2-naphthyl group, a 6-chloro-2-naphthyl group, a 7-chloro-2-naphthyl group, a 1-bromo-2-naphthyl group, a 3-bromo-2-naphthyl group, a 4-bromo-2-naphthyl group, a 5-bromo-2-naphthyl group, a 6-bromo-2-naphthyl group, a 7-bromo-2-naphthyl group, a heptachloro-2-naphthyl group, a heptafluoro-2-naphthyl group, a 3-fluoro-1-acenaphthyl group, a 9-fluoro-1-phenanthryl group, a 10-fluoro-9-anthryl group, and a 6-fluoro-1-pyrenyl group. The halogen atom that can be substituted for a hydrogen atom includes a fluorine atom, a chlorine atom, a bromine atom and an iodine atom.

The term "C6-C16 aryloxy group" includes, for example, a phenyloxy group, a 1-naphthyloxy group, a 2-naphthyloxy group, an 1-acenaphthyloxy group, a 1-phenanthryloxy group, an 9-anthryloxy group, and a 1-pyrenyloxy group.

The term "C6-C16 haloaryloxy group" represents a group wherein at least one hydrogen atom of the C6-C16 aryloxy group is substituted with a halogen atom, and includes, for example, a 2-fluorophenyloxy group, a 3-fluorophenyloxy group, a 4-fluorophenyloxy group, a 2-chlorophenyloxy, group, a 3-chlorophenyloxy group, a 4-chlorophenyloxy group, a 2-bromophenyloxy group, a 3-bromophenyloxy group, a 4-bromophenyloxy group, an 2-iodophenyloxy group, an 3-iodophenyloxy group, an 4-iodophenyloxy group, a 2,4-difluorophenyloxy group, a 2,5-difluorophenyloxy group, a 2,6-difluorophenyloxy group, a 3,5-difluorophenyloxy group, a 2,4-dichlorophenyloxy group, a 2,5-dichlorophenyloxy group, a 2,6-dichlorophenyloxy group, a 3,5-trifluorophenyloxy group, a 2,4,6-trifluorophenyloxy group, a 2,3,4-trifluorophenyloxy group, a 2,4,5-trifluorophenyloxy group, a 3,4,5-trifluorophenyloxy group, a 2,4,6-trifluorophenyloxy group, a 2,3,4-trifluorophenyloxy group, a 2,4,5-trifluorophenyloxy group, a 3,4,5-trifluorophenyloxy group, a pentafluorophenyloxy group, a pentachlorophenyloxy group, a 2-bromo-3-fluorophenyloxy group, a 2-bromo-4-fluorophenyloxy group, a 2-bromo-5-fluorophenyloxy group, a 2-bromo-6-fluorophenyloxy group, a 3-bromo-2-fluorophenyloxy group, a 3-bromo-4-fluorophenyloxy group, a 3-bromo-5-fluorophenyloxy group, a 3-bromo-6-fluorophenyloxy group, a 4-bromo-2-fluorophenyloxy group, a 4-bromo-3-fluorophenyloxy group, a 4-bromo-5-fluorophenyloxy group, a 4-bromo-6-fluorophenyloxy group, a 5-bromo-2-fluorophenyloxy group, a 5-bromo-3-fluorophenyloxy group, a 5-bromo-4-fluorophenyloxy group, a 5-bromo-6-fluorophenyloxy group, a 6-bromo-2-fluorophenyloxy group, a 6-bromo-3-fluorophenyloxy group, a 6-bromo-4-fluorophenyloxy group, a 6-bromo-5-fluorophenyloxy group, a 2-chloro-3-fluorophenyloxy group, a 2-chloro-4-fluorophenyloxy group, a 2-chloro-5-fluorophenyloxy group, a 2-chloro-6-fluorophenyloxy group, a 3-chloro-2-fluorophenyloxy group, a 3-chloro-4-fluorophenyloxy group, a 3-chloro-5-fluorophenyloxy group, a 3-chloro-6-fluorophenyloxy group, a 4-chloro-2-fluorophenyloxy group, a 4-chloro-3-fluorophenyloxy group, a 4-chloro-5-fluorophenyloxy group, a 4-chloro-6-fluorophenyloxy group, a 5-chloro-2-fluorophenyloxy group, a 5-chloro-3-fluorophenyloxy group, a 5-chloro-4-fluorophenyloxy group, a 5-chloro-6-fluorophenyloxy group, a 6-chloro-2-fluorophenyloxy group, a 6-chloro-3-fluorophenyloxy group, a 6-chloro-4-fluorophenyloxy group, a 6-chloro-5-fluorophenyloxy group, a 2-fluoro-1-naphthyloxy group, a 3-fluoro-1-naphthyloxy group, a 4-fluoro-1-naphthyloxy group, a 5-fluoro-1-naphthyloxy group, a 6-fluoro-1-naphthyloxy group, a 7-fluoro-1-naphthyloxy group, a 2-chloro-1-naphthyloxy group, a 3-chloro-1-naphthyloxy group, a 4-chloro-1-naphthyloxy group, a 5-chloro-1-naphthyloxy group, a 6-chloro-1-naphthyloxy group, a 7-chloro-1-naphthyloxy group, a 2-bromo-1-naphthyloxy group, a 3-bromo-1-naphthyloxy group, a 4-bromo-1-naphthyloxy group, a 5-bromo-1-naphthyloxy group, a 6-bromo-1-naphthyloxy group, a 7-bromo-1-naphthyloxy group, a heptachloro-1-naphthyloxy group, a heptafluoro-1-naphthyloxy group, a 1-fluoro-2-naphthyloxy group, a 3-fluoro-2-naphthyloxy group, a 4-fluoro-2-naphthyloxy group, a 5-fluoro-2-naphthyloxy group, a 6-fluoro-2-naphthyloxy group, a 7-fluoro-2-naphthyloxy group, a 1-chloro-2-naphthyloxy group, a 3-chloro-2-naphthyloxy group, a 4-chloro-2-naphthyloxy group, a 5-chloro-2-naphthyloxy group, a 6-chloro-2-naphthyloxy group, a 7-chloro-2-naphthyloxy group, a 1-bromo-2-naphthyloxy group, a 3-bromo-2-naphthyloxy group, a 4-bromo-2-naphthyloxy group, a 5-bromo-2-naphthyloxy group, a 6-bromo-2-naphthyloxy group, a 7-bromo-2-naphthyloxy group, a heptachloro-2-naphthyloxy group, a heptafluoro-2-naphthyloxy group, a 3-fluoro-1-acenaphthyloxy group, a 9-fluoro-1-phenanthryloxy group, a 10-fluoro-9-anthryloxy group, and a 6-fluoro-1-pyrenyloxy group. The halogen atom that can be substituted for a hydrogen atom includes a fluorine atom, a chlorine atom, a bromine atom and an iodine atom.

The term "C6-C16 arylthio group" includes, for example, a phenylthio group, a 1-naphthylthio group, a 2-naphthylthio group, an 1-acenaphthylthio group, a 1-phenanthrylthio group, an 9-anthrylthio group, and a 1-pyrenylthio group.

The term "C6-C16 haloarylthio group" represents a group wherein at least one hydrogen atom of the C6-C16 arylthio group is substituted with a halogen atom, and includes, for example, a 2-fluorophenylthio group, a 3-fluorophenylthio group, a 4-fluorophenylthio group, a 2-chlorophenylthio group, a 3-chlorophenylthio group, a 4-chlorophenylthio group, a 2-bromophenylthio group, a 3-bromophenylthio group, a 4-bromophenylthio group, an 2-iodophenylthio group, an 3-iodophenylthio group, an 4-iodophenylthio group, a 2,4-difluorophenylthio group, a 2,5-difluorophenylthio group, a 2,6-difluorophenylthio group, a 3,5-difluorophenylthio group, a 2,4-dichlorophenylthio group, a 2,5-dichlorophenylthio group, a 2,6-dichlorophenylthio group, a 3,5-dichlorophenylthio group, a 2,4,6-trifluorophenylthio group, a 2,3,4-trifluorophenylthio group, a 2,4,5-trifluorophenylthio group, a 3,4,5-trifluorophenylthio group, a 2,4,6-trichlorophenylthio group, a 2,3,4-trichlorophenylthio group, a 2,4,5-trichlorophenylthio group, a 3,4,5-trichlorophenylthio group, a pentafluorophenylthio group, a pentachlorophenylthio group, a 2-bromo-3-fluorophenylthio group, a 2-bromo-4-fluorophenylthio group, a 2-bromo-5- fluorophenylthio group, a 2-bromo-6-fluorophenylthio group, a 3-bromo-2-fluorophenylthio group, a 3-bromo-4-fluorophenylthio group, a 3-bromo-5-fluorophenylthio group, a 3-bromo-6-fluorophenylthio group, a 4-bromo-2-fluorophenylthio group, a 4-bromo-3-fluorophenylthio group, a 4-bromo-5-fluorophenylthio group, a 4-bromo-6-fluorophenylthio group, a 5-bromo-2-fluorophenylthio group, a 5-bromo-3-fluorophenylthio group, a 5-bromo-4-fluorophenylthio group, a 5-bromo-6-fluorophenylthio group, a 6-bromo-2-fluorophenylthio group, a 6-bromo-3-fluorophenylthio group, a 6-bromo-4-fluorophenylthio group, a 6-bromo-5-fluorophenylthio group, a 2-chloro-3-fluorophenylthio group, a 2-chloro-4-fluorophenylthio group, a 2-chloro-5-fluorophenylthio group, a 2-chloro-6-fluorophenylthio group, a 3-chloro-2-fluorophenylthio group, a 3-chloro-4-fluorophenylthio group, a 3-chloro-5-fluorophenylthio group, a 3-chloro-6-fluorophenylthio group, a 4-chloro-2-fluorophenylthio group, a 4-chloro-3-fluorophenylthio group, a 4-chloro-5-fluorophenylthio group, a 4-chloro-6-fluorophenylthio group, a 5-chloro-2-fluorophenylthio group, a 5-chloro-3-fluorophenylthio group, a 5-chloro-4-fluorophenylthio group, a 5-chloro-6-fluorophenylthio group, a 6-chloro-2-fluorophenylthio group, a 6-chloro-3-fluorophenylthio group, a 6-chloro-4-fluorophenylthio group, a 6-chloro-5-fluorophenylthio group, a 2-fluoro-1-naphthylthio group, a 3-fluoro-1-naphthylthio group, a 4-fluoro-1-naphthylthio group, a 5-fluoro-1-naphthylthio group, a 6-fluoro-1-naphthylthio group, a 7-fluoro-1-naphthylthio group, a 2-chloro-1-naphthylthio group, a 3-chloro-1-naphthylthio group, a 4-chloro-1-naphthylthio group, a 5-chloro-1-naphthylthio group, a 6-chloro-1-naphthylthio group, a 7-chloro-1-naphthylthio group, a 2-bromo-1-naphthylthio group, a 3-bromo-1-naphthylthio group, a 4-bromo-1-naphthylthio group, a 5-bromo-1-naphthylthio group, a 6-bromo-1-naphthylthio group, a 7-bromo-1-naphthylthio group, a heptachloro-1-naphthylthio group, a heptafluoro-1-naphthylthio group, a 1-fluoro-2-naphthylthio group, a 3-fluoro-2-naphthylthio group, a 4-fluoro-2-naphthylthio group, a 5-fluoro-2-naphthylthio group, a 6-fluoro-2-naphthylthio group, a 7-fluoro-2-naphthylthio group, a 1-chloro-2-naphthylthio group, a 3-chloro-2-naphthylthio group, a 4-chloro-2-naphthylthio group, a 5-chloro-2-naphthylthio group, a 6-chloro-2-naphthylthio group, a 7-chloro-2-naphthylthio group, a 1-bromo-2-naphthylthio group, a 3-bromo-2-naphthylthio group, a 4-bromo-2-naphthylthio group, a 5-bromo-2-naphthylthio group, a 6-bromo-2-naphthylthio group, a 7-bromo-2-naphthylthio group, a heptachloro-2-naphthylthio group, a heptafluoro-2-naphthylthio group, a 3-fluoro-1-acenaphthylthio group, a 9-fluoro-1-phenanthrylthio group, a 10-fluoro-9-anthrylthio group, and a 6-fluoro-1-pyrenylthio group. The halogen atom that can be substituted for a hydrogen atom includes a fluorine atom, a chlorine atom, a bromine atom and an iodine atom.

The term "C7-C18 aralkyl group" includes, for example, a benzyl group, a phenethyl group, a 3-phenylpropyl group, a 4-phenylbutyl group, a 5-phenylpentyl group, a 6-phenylhexyl group, a 7-phenylheptyl group, a 8-phenyloctyl group, a 9-phenylnonyl group, a 10-phenyldecyl group, a 11-phenylundecyl group, a 12-phenyldodecyl group, a 1-naphthylmethyl group, a 2-(1-naphthyl)ethyl group, a 3-(1-naphthyl)propyl group, a 4-(1-naphthyl)butyl group, a 5-(1-naphthyl)pentyl group, a 6-(1-naphthyl)hexyl group, a 7-(1-naphthyl)heptyl group, a 8-(1-naphthyl)octyl group, a 2-naphthylmethyl group, a 2-(2-naphthyl)ethyl group, a 3-(2-naphthyl)propyl group, a 4-(2-naphthyl)butyl group, a 5-(2-naphthyl)pentyl group, a 6-(2-naphthyl)hexyl group, a 7-(2-naphthyl)heptyl group, a 8-(2-naphthyl)octyl group, an 1-anthrylmethyl group, an 2-(1-anthryl)ethyl group, an 3-(1-anthryl)propyl group, an 4-(1-anthryl)butyl group, an 2-anthrylmethyl group, an 2-(2-anthryl)ethyl group, an 3-(2-anthryl)propyl group, an 4-(2-anthryl)butyl group, an 9-anthrylmethyl group, an 2-(9-anthryl)ethyl group, an 3-(9-anthryl)propyl group, and an 4-(9-anthryl)butyl group.

The term "C7-C18 haloaralkyl group" represents a group wherein at least one hydrogen atom of the C7-C18 aralkyl group is substituted with a halogen atom, and includes, for example, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, an 2-iodobenzyl group, an 3-iodobenzyl group, an 4-iodobenzyl group, a 2,4-difluorobenzyl group, a 2,5-difluorobenzyl group, a 2,6-difluorobenzyl group, a 3,5-difluorobenzyl group, a 2,4-dichlorobenzyl group, a 2,5-dichlorobenzyl group, a 2,6-dichlorobenzyl group, a 3,5-dichlorobenzyl group, a 2,4,6-trifluorobenzyl group, a 2,3,4-trifluorobenzyl group, a 2,4,5-trifluorobenzyl group, a 3,4,5-trifluorobenzyl group, a 2,4,6-trichlorobenzyl group, a 2,3,4-trichlorobenzyl group, a 2,4,5-trichlorobenzyl group, a 3,4,5-trichlorobenzyl group, a pentafluorobenzyl group, a pentachlorobenzyl group, a 2-bromo-3-fluorobenzyl group, a 2-bromo-4-fluorobenzyl group, a 2-bromo-5-fluorobenzyl group, a 2-bromo-6-fluorobenzyl group, a 3-bromo-2-fluorobenzyl group, a 3-bromo-4-fluorobenzyl group, a 3-bromo-5-fluorobenzyl group, a 3-bromo-6-fluorobenzyl group, a 4-bromo-2-fluorobenzyl group, a 4-bromo-3-fluorobenzyl group, a 4-bromo-5-fluorobenzyl group, a 4-bromo-6-fluorobenzyl group, a 5-bromo-2-fluorobenzyl group, a 5-bromo-3-fluorobenzyl group, a 5-bromo-4-fluorobenzyl group, a 5-bromo-6-fluorobenzyl group, a 6-bromo-2-fluorobenzyl group, a 6-bromo-3-fluorobenzyl group, a 6-bromo-4-fluorobenzyl group, a 6-bromo-5-fluorobenzyl group, a 2-chloro-3-fluorobenzyl group, a 2-chloro-4-fluorobenzyl group, a 2-chloro-5-fluorobenzyl group, a 2-chloro-6-fluorobenzyl group, a 3-chloro-2-fluorobenzyl group, a 3-chloro-4-fluorobenzyl group, a 3-chloro-5-fluorobenzyl group, a 3-chloro-6-fluorobenzyl group, a 4-chloro-2-fluorobenzyl group, a 4-chloro-3-fluorobenzyl group, a 4-chloro-5-fluorobenzyl group, a 4-chloro-6-fluorobenzyl group, a 5-chloro-2-fluorobenzyl group, a 5-chloro-3-fluorobenzyl group, a 5-chloro-4-fluorobenzyl group, a 5-chloro-6-fluorobenzyl group, a 6-chloro-2-fluorobenzyl group, a 6-chloro-3-fluorobenzyl group, a 6-chloro-4-fluorobenzyl group, a 6-chloro-5-fluorobenzyl group, a 2-(4-fluorophenyl)ethyl group, a 2-(4-chlorophenyl)ethyl group, a 2-(4-bromophenyl)ethyl group, an 2-(4-iodophenyl)ethyl group, a 2-(3-fluorophenyl)ethyl group, a 2-(3-chlorophenyl)ethyl group, a 2-(3-bromophenyl)ethyl group, an 2-(3-iodophenyl)ethyl group, a 2-(2-fluorophenyl)ethyl group, a 2-(2-chlorophenyl)ethyl group, a 2-(2-bromophenyl)ethyl group, an 2-(2-iodophenyl)ethyl group, a 3-(4-fluorophenyl)propyl group, a 3-(4-chlorophenyl)propyl group, a 3-(4-bromophenyl)propyl group, an 3-(4-iodophenyl)propyl group, a 3-(3-fluorophenyl)propyl group, a 3-(3-chlorophenyl)propyl group, a 3-(3-bromophenyl)propyl group, an 3-(3-iodophenyl)propyl group, a 3-(2-fluorophenyl)propyl group, a 3-(2-chlorophenyl)propyl group, a 3-(2-bromophenyl)propyl group, an 3-(2-iodophenyl)propyl group, a 4-(4-fluorophenyl)butyl group, a 4-(4-chlorophenyl)butyl group, a 4-(4-bromophenyl)butyl group, an 4-(4-iodophenyl)butyl group, a 5-(4-fluorophenyl)pentyl group, a 5-(4-chlorophenyl)pentyl group, a 5-(4-bromophenyl)pentyl group, an 5-(4-iodophenyl)pentyl group, a 6-(4-fluorophenyl)hexyl group, a 6-(4-chlorophenyl)hexyl group, a 6-(4- bromophenyl)hexyl group, an 6-(4-iodophenyl)hexyl group, a 7-(4-fluorophenyl)heptyl group, a 7-(4-chlorophenyl)heptyl group, a 7-(4-bromophenyl)heptyl group, an 7-(4-iodophenyl)heptyl group, a 8-(4-fluorophenyl)octyl group, a 8-(4-chlorophenyl)octyl group, a 8-(4-bromophenyl)octyl group, an 8-(4-iodophenyl)octyl group, a 9-(4-fluorophenyl) nonyl group, a 9-(4-chlorophenyl)nonyl group, a 9-(4-bromophenyl)nonyl group, an 9-(4-iodophenyl)nonyl group, a 10-(4-fluorophenyl)decyl group, a 10-(4-chlorophenyl)decyl group, a 10-(4-bromophenyl)decyl group, an 10-(4-iodophenyl)decyl group, a 11-(4-fluorophenyl)undecyl group, a 11-(4-chlorophenyl)undecyl group, a 11-(4-bromophenyl)undecyl group, an 11-(4-iodophenyl)undecyl group, a 12-(4-fluorophenyl)dodecyl group, a 12-(4-chlorophenyl)dodecyl group, a 12-(4-bromophenyl)dodecyl group, an 12-(4-iodophenyl)dodecyl group, a 2-fluoro-1-naphthylmethyl group, a 3-fluoro-1-naphthylmethyl group, a 4-fluoro-1-naphthylmethyl group, a 5-fluoro-1-naphthylmethyl group, a 6-fluoro-1-naphthylmethyl group, a 7-fluoro-1-naphthylmethyl group, a 2-chloro-1-naphthylmethyl group, a 3-chloro-1-naphthylmethyl group, a 4-chloro-1-naphthylmethyl group, a 5-chloro-1-naphthylmethyl group, a 6-chloro-1-naphthylmethyl group, a 7-chloro-1-naphthylmethyl group, a 2-bromo-1-naphthylmethyl group, a 3-bromo-1-naphthylmethyl group, a 4-bromo-1-naphthylmethyl group, a 5-bromo-1-naphthylmethyl group, a 6-bromo-1-naphthylmethyl group, a 7-bromo-1-naphthylmethyl group, a heptachloro-1-naphthylmethyl group, a heptafluoro-1-naphthylmethyl group, a 1-fluoro-2-naphthylmethyl group, a 3-fluoro-2-naphthylmethyl group, a 4-fluoro-2-naphthylmethyl group, a 5-fluoro-2-naphthylmethyl group, a 6-fluoro-2-naphthylmethyl group, a 7-fluoro-2-naphthylmethyl group, a 1-chloro-2-naphthylmethyl group, a 3-chloro-2-naphthylmethyl group, a 4-chloro-2-naphthylmethyl group, a 5-chloro-2-naphthylmethyl group, a 6-chloro-2-naphthylmethyl group, a 7-chloro-2-naphthylmethyl group, a 1-bromo-2-naphthylmethyl group, a 3-bromo-2-naphthylmethyl group, a 4-bromo-2-naphthylmethyl group, a 5-bromo-2-naphthylmethyl group, a 6-bromo-2-naphthylmethyl group, a 7-bromo-2-naphthylmethyl group, a heptachloro-2-naphthylmethyl group, a heptafluoro-2-naphthylmethyl group, a 2-(5-fluoro-1-naphthyl)ethyl group, a 2-(5-chloro-1-naphthyl)ethyl group, a 2-(5-bromo-1-naphthyl)ethyl group, a 2-(6-fluoro-2-naphthyl)ethyl group, a 2-(6-chloro-2-naphthyl)ethyl group, a 2-(6-bromo-2-naphthyl)ethyl group, a 3-(5-fluoro-1-naphthyl)propyl group, a 3-(5-chloro-1-naphthyl)propyl group, a 3-(5-bromo-1-naphthyl)propyl group, a 3-(6-fluoro-2-naphthyl)propyl group, a 3-(6-chloro-2-naphthyl)propyl group, a 3-(6-bromo-2-naphthyl)propyl group, a 4-(5-fluoro-1-naphthyl)butyl group, a 4-(5-chloro-1-naphthyl)butyl group, a 4-(5-bromo-1-naphthyl)butyl group, a 4-(6-fluoro-2-naphthyl)butyl group, a 4-(6-chloro-2-naphthyl)butyl group, a 4-(6-bromo-2-naphthyl)butyl group, a 5-(5-fluoro-1-naphthyl)pentyl group, a 5-(5-chloro-1-naphthyl)pentyl group, a 5-(5-bromo-1-naphthyl)pentyl group, a 5-(6-fluoro-2-naphthyl)pentyl group, a 5-(6-chloro-2-naphthyl)pentyl group, a 5-(6-bromo-2-naphthyl)pentyl group, a 6-(5-fluoro-1-naphthyl)hexyl group, a 6-(5-chloro-1-naphthyl)hexyl group, a 6-(5-bromo-1-naphthyl)hexyl group, a 6-(6-fluoro-2-naphthyl)hexyl group, a 6-(6-chloro-2-naphthyl)hexyl group, a 6-(6-bromo-2-naphthyl)hexyl group, a 6-(5-fluoro-1-naphthyl)heptyl group, a 6-(5-chloro-1-naphthyl)heptyl group, a 6-(5-bromo-1-naphthyl)heptyl group, a 6-(6-fluoro-2-naphthyl)heptyl group, a 6-(6-chloro-2-naphthyl)heptyl group, a 6-(6-bromo-2-naphthyl)heptyl group, a 6-(5-fluoro-1-naphthyl)octyl group, a 6-(5-chloro-1-naphthyl)octyl group, a 6-(5-bromo-1-naphthyl)octyl group, a 6-(6-fluoro-2-naphthyl)octyl group, a 6-(6-chloro-2-naphthyl)octyl group, a 6-(6-bromo-2-naphthyl)octyl group, a 3-fluoro-1-acenaphthylmethyl group, a 9-fluoro-1-phenanthrylmethyl group, a 10-fluoro-9-anthrylmethyl group, a 6-fluoro-1-pyrenylmethyl group, and a 1,1-difluoro(1-phenyl)methyl group. The halogen atom that can be substituted for a hydrogen atom includes a fluorine atom, a chlorine atom, a bromine atom and an iodine atom.

The term "C7-C18 arylalkoxy group" includes, for example, a benzyloxy group, a phenethyloxy group, a 3-phenylpropyloxy group, a 4-phenylbutyloxy group, a 5-phenylpentyloxy group, a 6-phenylhexyloxy group, a 7-phenylheptyloxy group, a 8-phenyloctyloxy group, a 9-phenylnonyloxy group, a 10-phenyldecyloxy group, a 11-phenylundecyloxyoxy group, a 12-phenyldodecyloxy group, a naphthylmethyloxy group, a naphthylethyloxy group, a naphthylpropyloxy group, a naphthylbutyloxy group, a naphthylpentyloxy group, a naphthylhexyloxy group, a naphthylheptyloxy group, a naphthyloctyloxy group, an anthrylmethyloxy group, an anthrylethyloxy group, an anthrylpropyloxy group, and an anthrylbutyloxy group.

The term "C7-C18 haloarylalkoxy group" represents a group wherein at least one hydrogen atom on the aryl moiety of the C7-C18 arylalkoxy group is substituted with a halogen atom, and includes, for example, a 2-fluorobenzyloxy group, a 3-fluorobenzyloxy group, a 4-fluorobenzyloxy group, a 2-chlorobenzyloxy group, a 3-chlorobenzyloxy group, a 4-chlorobenzyloxy group, a 2-bromobenzyloxy group, a 3-bromobenzyloxy group, a 4-bromobenzyloxy group, an 2-iodobenzyloxy group, an 3-iodobenzyloxy group, an 4-iodobenzyloxy group, a 2,4-difluorobenzyloxy group, a 2,5-difluorobenzyloxy group, a 2,6-difluorobenzyloxy group, a 3,5-difluorobenzyloxy group, a 2,4-dichlorobenzyloxy group, a 2,5-dichlorobenzyloxy group, a 2,6-dichlorobenzyloxy group, a 3,5-dichlorobenzyloxy group, a 2,4,6-trifluorobenzyloxy group, a 2,3,4-trifluorobenzyloxy group, a 2,4,5-trifluorobenzyloxy group, a 3,4,5-trifluorobenzyloxy group, a 2,4,6-trichlorobenzyloxy group, a 2,3,4-trichlorobenzyloxy group, a 2,4,5-trichlorobenzyloxy group, a 3,4,5-trichlorobenzyloxy group, a pentafluorobenzyloxy group, a pentachlorobenzyloxy group, a 2-bromo-3-fluorobenzyloxy group, a 2-bromo-4-fluorobenzyloxy group, a 2-bromo-5-fluorobenzyloxy group, a 2-bromo-6-fluorobenzyloxy group, a 3-bromo-2-fluorobenzyloxy group, a 3-bromo-4-fluorobenzyloxy group, a 3-bromo-5-fluorobenzyloxy group, a 3-bromo-6-fluorobenzyloxy group, a 4-bromo-2-fluorobenzyloxy group, a 4-bromo-3-fluorobenzyloxy group, a 4-bromo-5-fluorobenzyloxy group, a 4-bromo-6-fluorobenzyloxy group, a 5-bromo-2-fluorobenzyloxy group, a 5-bromo-3-fluorobenzyloxy group, 5-bromo-4-fluorobenzyloxy group, a 5-bromo-6-fluorobenzyloxy group, a 6-bromo-2-fluorobenzyloxy group, a 6-bromo-3-fluorobenzyloxy group, a 6-bromo-4-fluorobenzyloxy group, a 6-bromo-5-fluorobenzyloxy group, a 2-chloro-3-fluorobenzyloxy group, a 2-chloro-4-fluorobenzyloxy group, a 2-chloro-5-fluorobenzyloxy group, a 2-chloro-6-fluorobenzyloxy group, a 3-chloro-2-fluorobenzyloxy group, a 3-chloro-4-fluorobenzyloxy group, a 3-chloro-5-fluorobenzyloxy group, a 3-chloro-6-fluorobenzyloxy group, a 4-chloro-2-fluorobenzyloxy group, a 4-chloro-3-fluorobenzyloxy group, a 4-chloro-5-fluorobenzyloxy group, a 4-chloro-6-fluorobenzyloxy group, a 5-chloro-2-fluorobenzyloxy group, a 5-chloro-3-fluorobenzyloxy group, a 5-chloro-4-fluorobenzyloxy group, a 5-chloro-6-fluorobenzyloxy group, a 6-chloro-2- fluorobenzyloxy group, a 6-chloro-3-fluorobenzyloxy group, a 6-chloro-4-fluorobenzyloxy group, a 6-chloro-5-fluorobenzyloxy group, a 2-(4-fluorophenyl)ethyloxy group, a 2-(4-chlorophenyl)ethyloxy group, a 2-(4-bromophenyl) ethyloxy group, a 2-(4-iodophenyl)ethyloxy group, a 2-(3-fluorophenyl)ethyloxy group, a 2-(3-chlorophenyl)ethyloxy group, a 2-(3-bromophenyl)ethyloxy group, an 2-(3-iodophenyl)ethyloxy group, a 2-(2-fluorophenyl)ethyloxy group, a 2-(2-chlorophenyl)ethyloxy group, a 2-(2-bromophenyl) ethyloxy group, an 2-(2-iodophenyl)ethyloxy group, a 3-(4-fluorophenyl)propyloxy group, a 3-(4-chlorophenyl)propyloxy group, a 3-(4-bromophenyl)propyloxy group, an 3-(4-iodophenyl)propyloxy group, a 3-(3-fluorophenyl) propyloxy group, a 3-(3-chlorophenyl)propyloxy group, a 3-(3-bromophenyl)propyloxy group, an 3-(3-iodophenyl) propyloxy group, a 3-(2-fluorophenyl)propyloxy group, a 3-(2-chlorophenyl)propyloxy group, a 3-(2-bromophenyl) propyloxy group, an 3-(2-iodophenyl)propyloxy group, a 4-(4-fluorophenyl)butyloxy group, a 4-(4-chlorophenyl)butyloxy group, a 4-(4-bromophenyl)butyloxy group, an 4-(4-iodophenyl)butyloxy group, 5-(4-fluorophenyl)pentyloxy group, a 5-(4-chlorophenyl)pentyloxy group, a 5-(4-bromophenyl)pentyloxy group, an 5-(4-iodophenyl)pentyloxy group, a 6-(4-fluorophenyl)hexyloxy group, a 6-(4-chlorophenyl)hexyloxy group, a 6-(4-bromophenyl)hexyloxy group, an 6-(4-iodophenyl)hexyloxy group, a 7-(4-fluorophenyl)heptyloxy group, a 7-(4-chlorophenyl)heptyloxy group, a 7-(4-bromophenyl)heptyloxy group, an 7-(4-iodophenyl)heptyloxy group, a 8-(4-fluorophenyl)octyloxy group, a 8-(4-chlorophenyl)octyloxy group, a 8-(4-bromophenyl)octyloxy group, an 8-(4-iodophenyl)octyloxy group, a 9-(4-fluorophenyl)nonyloxy group, a 9-(4-chlorophenyl)nonyloxy group, a 9-(4-bromophenyl)nonyloxy group, an 9-(4-iodophenyl)nonyloxy group, a 10-(4-fluorophenyl)decyloxy group, a 10-(4-chlorophenyl)decyloxy group, a 10-(4-bromophenyl)decyloxy group, an 10-(4-iodophenyl)decyloxy group, a 11-(4-fluorophenyl)undecyloxy group, a 11-(4-chlorophenyl)undecyloxy group, a 11-(4-bromophenyl)undecyloxy group, an 11-(4-iodophenyl)undecyloxy group, a 12-(4-fluorophenyl)dodecyloxy group, a 12-(4-chlorophenyl)dodecyloxy group, a 12-(4-bromophenyl)dodecyloxy group, an 12-(4-iodophenyl)dodecyloxy group, a 2-fluoro-1-naphthylmethyloxy group, a 3-fluoro-1-naphthylmethyloxy group, a 4-fluoro-1-naphthylmethyloxy group, a 5-fluoro-1-naphthylmethyloxy group, a 6-fluoro-1-naphthylmethyloxy group, a 7-fluoro-1-naphthylmethyloxy group, a 2-chloro-1-naphthylmethyloxy group, a 3-chloro-1-naphthylmethyloxy group, a 4-chloro-1-naphthylmethyloxy group, a 5-chloro-1-naphthylmethyloxy group, a 6-chloro-1-naphthylmethyloxy group, a 7-chloro-1-naphthylmethyloxy group, a 2-bromo-1-naphthylmethyloxy group, a 3-bromo-1-naphthylmethyloxy group, a 4-bromo-1-naphthylmethyloxy group, a 5-bromo-1-naphthylmethyloxy group, a 6-bromo-1-naphthylmethyloxy group, a 7-bromo-1-naphthylmethyloxy group, a heptachloro-1-naphthylmethyloxy group, a heptafluoro-1-naphthylmethyloxy group, a 1-fluoro-2-naphthylmethyloxy group, a 3-fluoro-2-naphthylmethyloxy group, a 4-fluoro-2-naphthylmethyloxy group, a 5-fluoro-2-naphthylmethyloxy group, a 6-fluoro-2-naphthylmethyloxy group, a 7-fluoro-2-naphthylmethyloxy group, a 1-chloro-2-naphthylmethyloxy group, a 3-chloro-2-naphthylmethyloxy group, a 4-chloro-2-naphthylmethyloxy group, a 5-chloro-2-naphthylmethyloxy group, a 6-chloro-2-naphthylmethyloxy group, a 7-chloro-2-naphthylmethyloxy group, a 1-bromo-2-naphthylmethyloxy group, a 3-bromo-2-naphthylmethyloxy group, a 4-bromo-2-naphthylmethyloxy group, a 5-bromo-2-naphthylmethyloxy group, a 6-bromo-2-naphthylmethyloxy group, a 7-bromo-2-naphthylmethyloxy group, a heptachloro-2-naphthylmethyloxy group, a heptafluoro-2-naphthylmethyloxy group, a 2-(5-fluoro-1-naphthyl)ethyloxy group, a 2-(5-chloro-1-naphthyl)ethyloxy group, a 2-(5-bromo-1-naphthyl)ethyloxy group, a 2-(6-fluoro-2-naphthyl)ethyloxy group, a 2-(6-chloro-2-naphthyl)ethyloxy group, a 2-(6-bromo-2-naphthyl)ethyloxy group, a 3-(5-fluoro-1-naphthyl)propyloxy group, a 3-(5-chloro-1-naphthyl)propyloxy group, a 3-(5-bromo-1-naphthyl)propyloxy group, a 3-(6-fluoro-2-naphthyl)propyloxy group, a 3-(6-chloro-2-naphthyl)propyloxy group, a 3-(6-bromo-2-naphthyl)propyloxy group, a 4-(5-fluoro-1-naphthyl)butyloxy group, a 4-(5-chloro-1-naphthyl)butyloxy group, a 4-(5-bromo-1-naphthyl)butyloxy group, a 4-(6-fluoro-2-naphthyl)butyloxy group, a 4-(6-chloro-2-naphthyl)butyloxy group, a 4-(6-bromo-2-naphthyl)butyloxy group, a 5-(5-fluoro-1-naphthyl)pentyloxy group, a 5-(5-chloro-1-naphthyl)pentyloxy group, a 5-(5-bromo-1-naphthyl)pentyloxy group, a 5-(6-fluoro-2-naphthyl)pentyloxy group, a 5-(6-chloro-2-naphthyl)pentyloxy group, a 5-(6-bromo-2-naphthyl)pentyloxy group, a 6-(5-fluoro-1-naphthyl)hexyloxy group, a 6-(5-chloro-1-naphthyl)hexyloxy group, a 6-(5-bromo-1-naphthyl)hexyloxy group, a 6-(6-fluoro-2-naphthyl)hexyloxy group, a 6-(6-chloro-2-naphthyl)hexyloxy group, a 6-(6-bromo-2-naphthyl)hexyloxy group, a 6-(5-fluoro-1-naphthyl)heptyloxy group, a 6-(5-chloro-1-naphthyl)heptyloxy group, a 6-(5-bromo-1-naphthyl)heptyloxy group, a 6-(6-fluoro-2-naphthyl)heptyloxy group, a 6-(6-chloro-2-naphthyl)heptyloxy group, a 6-(6-bromo-2-naphthyl)heptyloxy group, a 6-(5-fluoro-1-naphthyl)octyloxy group, a 6-(5-chloro-1-naphthyl)octyloxy group, a 6-(5-bromo-1-naphthyl)octyloxy group, a 6-(6-fluoro-2-naphthyl)octyloxy group, a 6-(6-chloro-2-naphthyl)octyloxy group, a 6-(6-bromo-2-naphthyl)octyloxy group, a 3-fluoro-1-acenaphthylmethyloxy group, a 9-fluoro-1-phenanthrylmethyloxy group, a 10-fluoro-9-anthrylmethyloxy group, a 6-fluoro-1-pyrenylmethyloxy group, and a 1,1-difluoro-1-phenylmethyloxy group.

The term "C3-C12 trialkylsilyl group" includes, for example, a trimethylsilyl group, a tert-butyldimethylsilyl group, a triethylsilyl group, an isopropyldimethylsilyl group, a triisopropylsilyl group, a tri(tert-butyl)silyl group, and a tri(n-butyl)silyl group.

The term "C5-C14 trialkylsilylethynyl group" represents an ethynyl group connecting to an alkylsilyl group, wherein the total number of carbon atoms including carbon atoms of the ethynyl group and three hydrogen atoms on the silyl group are substituted with the straight or branched C1-C4 alkyl group and the C1-C4 alkyl group may be same or different from each other, and includes, for example, a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tri(n-butyl)silylethynyl group.

The term "aminosulfonyl group optionally having C1-C6 alkyl group or C6-C12 aryl group" represents a aminosulfonyl group wherein one or two hydrogen atom on the nitrogen atom may be optionally substituted with a straight or branched C1-C6 alkyl group or an C6-C12 aryl group, wherein the substituents on the nitrogen atom may be same or different from each other, and includes, for example, an aminosulfonyl group, a N-methylaminosulfonyl group, an N-ethylaminosulfonyl group, a N-propylaminosulfonyl group, an N-isopropylaminosulfonyl group, a N-butylaminosulfonyl group, a N-pentylaminosulfonyl group, a N-hexylaminosulfonyl group, a N,N-dimethylaminosulfonyl group, a N,N-diethylaminosulfonyl group, a N,N-dipropylaminosulfonyl group, a N,N-diisopropylaminosulfonyl group, an N-ethyl-N-methylaminosulfonyl group, a N-propyl-N-methylaminosulfonyl group, a N-butyl-N-methylaminosulfonyl group, a N-pentyl-N-methylaminosulfonyl group, a N-phenylaminosulfonyl group, a N,N-diphenylaminosulfonyl group, a N-methyl-N-phenylaminosulfonyl group, an N-ethyl-N-phenylaminosulfonyl group, a N-propyl-N-phenylaminosulfonyl group, a N-butyl-N-phenylaminosulfonyl group, a N-pentyl-N-phenylaminosulfonyl group, a N-hexyl-N-phenylaminosulfonyl group, a N-(1-naphthyl)aminosulfonyl group, a N-(1-naphthyl)-N-methylaminosulfonyl group, a N-(2-naphthyl)aminosulfonyl group, and a N-(2-naphthyl)-N-methylaminosulfonyl group.

The term "C1-C6 alkylsulfonyl group" represents a straight or branched alkylsulfonyl group, and includes, for example, a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, an isoamylsulfonyl group, a neopentylsulfonyl group, a 2-pentylsulfonyl group, a 3-pentylsulfonyl group, a 2-methylbutylsulfonyl group, a hexylsulfonyl group, an isohexylsulfonyl group, a 3-methylpentylsulfonyl group, and a 4-methylpentylsulfonyl group.

The term "C1-C6 haloalkylsulfonyl group" represents a group wherein at least one hydrogen atom of the straight or branched an C1-C6 alkylsulfonyl group is substituted with a halogen atom, and includes, for example, a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group, and a periodohexylsulfonyl group. The halogen atom that can be substituted for a hydrogen atom includes a fluorine atom, a chlorine atom, a bromine atom and an iodine atom.

The term "C6-C16 arylsulfonyl group" includes, for example, a phenylsulfonyl group, a 1-naphthylsulfonyl group, a 2-naphthylsulfonyl group, an 1-acenaphthylsulfonyl group, a 1-phenanthrylsulfonyl group, an 9-anthrylsulfonyl group, and a 1-pyrenylsulfonyl group.

The term "C6-C16 haloarylsulfonyl group" represents a group wherein at least one hydrogen atom of the C6-C16 arylsulfonyl group is substituted with a halogen atom, and includes, for example, a 2-fluorophenylsulfonyl group, a 3-fluorophenylsulfonyl group, a 4-fluorophenyl group sulfonyl group, a 2-chlorophenylsulfonyl group, a 3-chlorophenylsulfonyl group, a 4-chlorophenylsulfonyl group, a 2-bromophenylsulfonyl group, a 3-bromophenylsulfonyl group, a 4-bromophenylsulfonyl group, an 2-iodophenylsulfonyl group, an 3-iodophenylsulfonyl group, an 4-iodophenylsulfonyl group, a 2,4-difluorophenylsulfonyl group, a 2,5-difluorophenylsulfonyl group, a 2,6-difluorophenylsulfonyl group, a 3,5-difluorophenylsulfonyl group, a 2,4-dichlorophenylsulfonyl group, a 2,5-dichlorophenylsulfonyl group, a 2,6-dichlorophenylsulfonyl group, a 3,5-dichlorophenylsulfonyl group, a 2,4,6-trifluorophenylsulfonyl group, a 2,3,4-trifluorophenylsulfonyl group, a 2,4,5-trifluorophenylsulfonyl group, a 3,4,5-trifluorophenylsulfonyl group, a 2,4,6-trichlorophenylsulfonyl group, a 2,3,4-trichlorophenylsulfonyl group, a 2,4,5-trichlorophenylsulfonyl group, a 3,4,5-trichlorophenylsulfonyl group, a pentafluorophenylsulfonyl group, a pentachlorophenylsulfonyl group, a 2-bromo-3-fluorophenylsulfonyl group, a 2-bromo-4-fluorophenylsulfonyl group, a 2-bromo-5-fluorophenylsulfonyl group, a 2-bromo-6-fluorophenylsulfonyl group, a 3-bromo-2-fluorophenylsulfonyl group, a 3-bromo-4-fluorophenylsulfonyl group, a 3-bromo-5-fluorophenylsulfonyl group, a 3-bromo-6-fluorophenylsulfonyl group, a 4-bromo-2-fluorophenylsulfonyl group, a 4-bromo-3-fluorophenylsulfonyl group, a 4-bromo-5-fluorophenylsulfonyl group, a 4-bromo-6-fluorophenylsulfonyl group, a 5-bromo-2-fluorophenylsulfonyl group, a 5-bromo-3-fluorophenylsulfonyl group, a 5-bromo-4-fluorophenylsulfonyl group, a 5-bromo-6-fluorophenylsulfonyl group, a 6-bromo-2-fluorophenylsulfonyl group, a 6-bromo-3-fluorophenylsulfonyl group, a 6-bromo-4-fluorophenylsulfonyl group, a 6-bromo-5-fluorophenylsulfonyl group, a 2-chloro-3-fluorophenylsulfonyl group, a 2-chloro-4-fluorophenylsulfonyl group, a 2-chloro-5-fluorophenylsulfonyl group, a 2-chloro-6-fluorophenylsulfonyl group, a 3-chloro-2-fluorophenylsulfonyl group, a 3-chloro-4-fluorophenylsulfonyl group, a 3-chloro-5-fluorophenylsulfonyl group, a 3-chloro-6-fluorophenylsulfonyl group, a 4-chloro-2-fluorophenylsulfonyl group, a 4-chloro-3-fluorophenylsulfonyl group, a 4-chloro-5-fluorophenylsulfonyl group, a 4-chloro-6-fluorophenylsulfonyl group, a 5-chloro-2-fluorophenylsulfonyl group, a 5-chloro-3-fluorophenylsulfonyl group, a 5-chloro-4-fluorophenylsulfonyl group, a 5-chloro-6-fluorophenylsulfonyl group, a 6-chloro-2-fluorophenylsulfonyl group, a 6-chloro-3-fluorophenylsulfonyl group, a 6-chloro-4-fluorophenylsulfonyl group, a 6-chloro-5-fluorophenylsulfonyl group, a 2-fluoro-1-naphthylsulfonyl group, a 3-fluoro-1-naphthylsulfonyl group, a 4-fluoro-1-naphthylsulfonyl group, a 5-fluoro-1-naphthylsulfonyl group, a 6-fluoro-1-naphthylsulfonyl group, a 7-fluoro-1-naphthylsulfonyl group, a 2-chloro-1-naphthylsulfonyl group, a 3-chloro-1-naphthylsulfonyl group, a 4-chloro-1-naphthylsulfonyl group, a 5-chloro-1-naphthylsulfonyl group, a 6-chloro-1-naphthylsulfonyl group, a 7-chloro-1-naphthylsulfonyl group, a 2-bromo-1-naphthylsulfonyl group, a 3-bromo-1-naphthylsulfonyl group, a 4-bromo-1-naphthylsulfonyl group, a 5-bromo-1-naphthylsulfonyl group, a 6-bromo-1-naphthylsulfonyl group, a 7-bromo-1-naphthylsulfonyl group, a heptachloro-1-naphthylsulfonyl group, a heptafluoro-1-naphthylsulfonyl group, a 1-fluoro-2-naphthylsulfonyl group, a 3-fluoro-2-naphthylsulfonyl group, a 4-fluoro-2-naphthylsulfonyl group, a 5-fluoro-2-naphthylsulfonyl group, a 6-fluoro-2-naphthylsulfonyl group, a 7-fluoro-2-naphthylsulfonyl group, a 1-chloro-2-naphthylsulfonyl group, a 3-chloro-2-naphthylsulfonyl group, a 4-chloro-2-naphthylsulfonyl group, a 5-chloro-2-naphthylsulfonyl group, a 6-chloro-2-naphthylsulfonyl group, a 7-chloro-2-naphthylsulfonyl group, a 1-bromo-2-naphthylsulfonyl group, a 3-bromo-2-naphthylsulfonyl group, a 4-bromo-2-naphthylsulfonyl group, a 5-bromo-2-naphthylsulfonyl group, a 6-bromo-2-naphthylsulfonyl group, a 7-bromo-2-naphthylsulfonyl group, a heptachloro-2-naphthylsulfonyl group, a heptafluoro-2-naphthylsulfonyl group, a 3-fluoro-1-acenaphthylsulfonyl group, a 9-fluoro-1-phenanthrylsulfonyl group, a 10-fluoro-9-anthrylsulfonyl group, and a 6-fluoro-1-pyrenylsulfonyl group. The halogen atom that can be substituted for a halogen atom includes a fluorine atom, a chlorine atom, a bromine atom and an iodine atom.

The term "C1-C6 alkylsulfinyl group" represents a straight or branched alkylsulfinyl group, and includes, for example, a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, a neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group, and a 4-methylpentylsulfinyl group.

The term "C1-C6 haloalkylsulfinyl group" represents a group wherein at least one hydrogen atom of the straight or branched an C1-C6 alkylsulfinyl group is substituted with a halogen atom, and includes, for example, a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a perfluoropentylsulfinyl group, a perchloropentylsulfinyl group, a perbromopentylsulfinyl group, a perfluorohexylsulfinyl group, a perchlorohexylsulfinyl group, a perbromohexylsulfinyl group, and a periodohexylsulfinyl group. The halogen atom that can be substituted for a hydrogen atom includes a fluorine atom, a chlorine atom, a bromine atom and an iodine atom.

The term "C6-C16 arylsulfinyl group" includes, for example, a phenylsulfinyl group, a 1-naphthylsulfinyl group, a 2-naphthylsulfinyl group, an 1-acenaphthylsulfinyl group, a 1-phenanthrylsulfinyl group, an 9-anthrylsulfinyl group, and a 1-pyrenylsulfinyl group.

The term "C6-C16 haloarylsulfinyl group" represents a group wherein at least one hydrogen atom of the C6-C16 arylsulfinyl group is substituted with a halogen atom, and includes, for example, a 2-fluorophenylsulfinyl group, a 3-fluorophenylsulfinyl group, a 4-fluorophenyl group sulfinyl group, a 2-chlorophenylsulfinyl group, a 3-chlorophenylsulfinyl group, a 4-chlorophenylsulfinyl group, a 2-bromophenylsulfinyl group, a 3-bromophenylsulfinyl group, a 4-bromophenylsulfinyl group, an 2-iodophenylsulfinyl group, an 3-iodophenylsulfinyl group, an 4-iodophenylsulfinyl group, a 2,4-difluorophenylsulfinyl group, a 2,5-difluorophenylsulfinyl group, a 2,6-difluorophenylsulfinyl group, a 3,5-difluorophenylsulfinyl group, a 2,4-dichlorophenylsulfinyl group, a 2,5-dichlorophenylsulfinyl group, a 2,6-dichlorophenylsulfinyl group, a 3,5-dichlorophenylsulfinyl group, a 2,4,6-trifluorophenylsulfinyl group, a 2,3,4-trifluorophenylsulfinyl group, a 2,4,5-trifluorophenylsulfinyl group, a 3,4,5-trifluorophenylsulfinyl group, a 2,4,6-trichlorophenylsulfinyl group, a 2,3,4-trichlorophenylsulfinyl group, a 2,4,5-trichlorophenylsulfinyl group, a 3,4,5-trichlorophenylsulfinyl group, a pentafluorophenylsulfinyl group, a pentachlorophenylsulfinyl group, a 2-bromo-3-fluorophenylsulfinyl group, a 2-bromo-4-fluorophenylsulfinyl group, a 2-bromo-5-fluorophenylsulfinyl group, a 2-bromo-6-fluorophenylsulfinyl group, a 3-bromo-2-fluorophenylsulfinyl group, a 3-bromo-4-fluorophenylsulfinyl group, a 3-bromo-5-fluorophenylsulfinyl group, a 3-bromo-6-fluorophenylsulfinyl group, a 4-bromo-2-fluorophenylsulfinyl group, a 4-bromo-3-fluorophenylsulfinyl group, a 4-bromo-5-fluorophenylsulfinyl group, a 4-bromo-6-fluorophenylsulfinyl group, a 5-bromo-2-fluorophenylsulfinyl group, a 5-bromo-3-fluorophenylsulfinyl group, a 5-bromo-4-fluorophenylsulfinyl group, a 5-bromo-6-fluorophenylsulfinyl group, a 6-bromo-2-fluorophenylsulfinyl group, a 6-bromo-3-fluorophenylsulfinyl group, a 6-bromo-4-fluorophenylsulfinyl group, a 6-bromo-5-fluorophenylsulfinyl group, a 2-chloro-3-fluorophenylsulfinyl group, a 2-chloro-4-fluorophenylsulfinyl group, a 2-chloro-5-fluorophenylsulfinyl group, a 2-chloro-6-fluorophenylsulfinyl group, a 3-chloro-2-fluorophenylsulfinyl group, a 3-chloro-4-fluorophenylsulfinyl group, a 3-chloro-5-fluorophenylsulfinyl group, a 3-chloro-6-fluorophenylsulfinyl group, a 4-chloro-2-fluorophenylsulfinyl group, a 4-chloro-3-fluorophenylsulfinyl group, a 4-chloro-5-fluorophenylsulfinyl group, a 4-chloro-6-fluorophenylsulfinyl group, a 5-chloro-2-fluorophenylsulfinyl group, a 5-chloro-3-fluorophenylsulfinyl group, a 5-chloro-6-fluorophenylsulfinyl group, a 6-chloro-2-fluorophenylsulfinyl group, a 6-chloro-3-fluorophenylsulfinyl group, a 6-chloro-4-fluorophenylsulfinyl group, a 6-chloro-5-fluorophenylsulfinyl group, a 2-fluoro-1-naphthylsulfinyl group, a 3-fluoro-1-naphthylsulfinyl group, a 4-fluoro-1-naphthylsulfinyl group, a 5-fluoro-1-naphthylsulfinyl group, a 6-fluoro-1-naphthylsulfinyl group, a 7-fluoro-1-naphthylsulfinyl group, a 2-chloro-1-naphthylsulfinyl group, a 3-chloro-1-naphthylsulfinyl group, a 4-chloro-1-naphthylsulfinyl group, a 5-chloro-1-naphthylsulfinyl group, a 6-chloro-1-naphthylsulfinyl group, a 7-chloro-1-naphthylsulfinyl group, a 2-bromo-1-naphthylsulfinyl group, a 3-bromo-1-naphthylsulfinyl group, a 4-bromo-1-naphthylsulfinyl group, a 5-bromo-1-naphthylsulfinyl group, a 6-bromo-1-naphthylsulfinyl group, a 7-bromo-1-naphthylsulfinyl group, a heptachloro-1-naphthylsulfinyl group, a heptafluoro-1-naphthylsulfinyl group, a 1-fluoro-2-naphthylsulfinyl group, a 3-fluoro-2-naphthylsulfinyl group, a 4-fluoro-2-naphthylsulfinyl group, a 5-fluoro-2-naphthylsulfinyl group, a 6-fluoro-2-naphthylsulfinyl group, a 7-fluoro-2-naphthylsulfinyl group, a 1-chloro-2-naphthylsulfinyl group, a 3-chloro-2-naphthylsulfinyl group, a 4-chloro-2-naphthylsulfinyl group, a 5-chloro-2-naphthylsulfinyl group, a 6-chloro-2-naphthylsulfinyl group, a 7-chloro-2-naphthylsulfinyl group, a 1-bromo-2-naphthylsulfinyl group, a 3-bromo-2-naphthylsulfinyl group, a 4-bromo-2-naphthylsulfinyl group, a 5-bromo-2-naphthylsulfinyl group, a 6-bromo-2-naphthylsulfinyl group, a 7-bromo-2-naphthylsulfinyl group, a heptachloro-2-naphthylsulfinyl group, a heptafluoro-2-naphthylsulfinyl group, a 3-fluoro-1-acenaphthylsulfinyl group, a 9-fluoro-1-phenanthrylsulfinyl group, a 10-fluoro-9-anthrylsulfinyl group, and a 6-fluoro-1-pyrenylsulfinyl group. The halogen atom that can be substituted includes a fluorine atom, a chlorine atom, a bromine atom and an iodine atom.

The term "C1-C12 alkyl group" represents a straight or branched alkyl group, and includes, for example, a methyl group, an ethyl group, a n-propyl group, a n-butyl group, a n-pentyl group, a n-hexyl group, a n-heptyl group, an n-octyl group, a n-nonyl group, a n-decyl group, an n-undecyl group, and a n-dodecyl group.

The term "C3-C12 cycloalkyl group" includes, for example, a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The term "C2-C12 alkenyl group" includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, a 1-heptenyl group, an 1-octenyl group, a 1-nonenyl group, a 1-decenyl group, an 1-undecenyl group, and a 1-dodecenyl group.

The term "C3-C12 cycloalkenyl group" includes, for example, a 1-cyclopropenyl group, a 1-cyclobutenyl group, a 1-cyclopentenyl group, a 1-cyclohexenyl group, a 2-cyclohexenyl group, a 3-cyclohexenyl group, a 1-cycloheptenyl group, a 1-cyclooctenyl group, a 1-cyclononenyl group, a 1-cyclodecenyl group, a 1-cycloundecenyl group, a 1-cyclododecenyl group, a 1-cyclopentadienyl group, a 1,3-cyclohexadienyl group, a 1,4-cyclohexadienyl group, and a 1,5-cyclooctadienyl group.

The term "C2-C12 alkynyl group" includes, for example, an ethynyl group, a 1-propynyl group, a 1-butynyl group, a 1-pentynyl group, a 2-pentynyl group, a 3-pentynyl group, a 1-hexynyl group, a 1-heptynyl group, an 1-octynyl group, a 1-nonynyl group, a 1-decynyl group, an 1-undecynyl group, and a 1-dodecynyl group.

The term "C2-C12 acyl group" represents includes, for example, an acetyl group, a propionyl group, a butanoyl group, a pentanoyl group, a hexanoyl group, a heptanoyl group, an octanoyl group, a nonanoyl group, a decanoyl group, an undecanoyl group, and a decanoyl group.

The term "C1-C3 alkyl group" includes, for example, a methyl group, an ethyl group, a propyl group, and a isopropyl group.

The term "C1-C3 haloalkyl group" includes, for example, a chloromethyl group, a dichloromethyl group, a fluoromethyl group, a difluoromethyl group, a chlorofluoromethyl group, a dichlorofluoromethyl group, a trifluoromethyl group, a trichloromethyl group, a tribromomethyl group, a fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, 2-chloro-2-fluoroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group, and 1-(fluoromethyl)-2-fluoroethyl group.

The term "C2-C12 alkoxycarbonyl group" may be either straight or branched, and includes, for example, a methoxycarbonyl group, an ethoxycarbonyl group, propyloxycarbonyl group, an isopropyloxycarbonyl group, a butyloxycarbonyl group, an isobutyloxycarbonyl group, a sec-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group, a 2-methylbutyloxycarbonyl group, a hexyloxycarbonyl group, an isohexyloxycarbonyl group, a 3-methylpentyloxycarbonyl group, a 4-methylpentyloxycarbonyl group, a heptyloxycarbonyl group, a 2-heptyloxycarbonyl group, an octyloxycarbonyl group, a decyloxycarbonyl group, and an undecyloxyoxycarbonyl group.

The term "C1-C4 alkyl group" may be either straight or branched, and includes, for example, a methyl group, an ethyl group, a propyl group, an isopropyl group, a butyl group, an isobutyl group, a sec-butyl group, and a tert-butyl group.

The term "C1-C4 haloalkyl group" represents a group wherein at least one hydrogen atom of the straight or branched C1-C4 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, 3-(fluoromethyl)-2-fluoroethyl group, and a 4-fluorobutyl group.

The term "C3-C5 cycloalkyl group" encompasses a cycloalkyl group having an alkyl group, and includes, for example, a cyclopropyl group, cyclobutyl group, a cyclopentyl group, a 2-methylcyclopropyl group, a 2,2-dimethylcyclopropyl group, and a 2,3-dimethylcyclopropyl group.

The term "C3-C5 halocycloalkyl group" represents a group wherein at least one hydrogen atom of the C3-C5 cycloalkyl group is substituted with a halogen atom, and includes, for example, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group, and a 3-chlorocyclopentyl group.

The term "C1-C4 alkoxy group" may be either straight or branched, and includes, for example, a methoxy group, an ethoxy group, a propyloxy group, an isopropyloxy group, a butyloxy group, an isobutyloxy group, a sec-butyloxy group, and a tert-butyloxy group.

The term "C1-C4 haloalkoxy group" represents a group wherein at least one hydrogen atom of the straight or branched C1-C4 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 2,3,3-trifluoropropoxy group, a nonafluorobutoxy group, a nonachlorobutoxy group, a nonabromobutoxy group, and a nonaiodobutoxy group.

The term "C2-C6 alkoxyalkyl group" may be either a straight or a branched group wherein the total number of carbon atoms of the alkoxy moiety and the alkyl moiety is two to six carbon atoms, and includes, for example, a methoxymethyl group, an ethoxymethyl group, a propyloxymethyl group, an isopropyloxymethyl group, a butyloxymethyl group, an isobutyloxymethyl group, a sec-butyloxymethyl group, a pentyloxymethyl group, a 1-methoxyethyl group, a 2-methoxyethyl group, an 2-ethoxyethyl group, a 2-propyloxyethyl group, an 2-isopropyloxyethyl group, a 2-butyloxyethyl group, a 3-methoxypropyl group, an 3-ethoxypropyl group, a 3-propyloxypropyl group, a 3-methoxybutyl group, an 3-ethoxybutyl group, a 4-methoxybutyl group, an 4-ethoxybutyl group, and a 5-methoxypentyl group.

The term "C1-C6 alkylamino group" includes, for example, a N-methylamino group, an N-ethylamino group, a N-propylamino group, an N-isopropylamino group, a N-butylamino group, a N,N-dimethylamino group, a N,N-diethylamino group, a N,N-dipropylamino group, an N-ethyl-N-methylamino group and a N-propyl-N-methylamino group.

The term "C3-C9 trialkylsilyl group" includes, for example, a trimethylsilyl group, a tert-butyldimethylsilyl group, a triethylsilyl group, an isopropyldimethylsilyl group, and a triisopropylsilyl group.

The term "C1-C4 alkylsulfonyl group" may be either straight or branched, and includes, for example, a methylsulfonyl group, an ethylsulfonyl group, a propylsulfonyl group, an isopropylsulfonyl group, a butylsulfonyl group, an isobutylsulfonyl group, and a sec-butylsulfonyl group.

The term "C1-C4 haloalkylsulfonyl group" represents a group wherein at least one hydrogen atom of the straight or branched C1-C4 alkylsulfonyl group is substituted with a halogen atom, and includes, for example, a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a nonafluorobutylsulfonyl group, a nonachlorobutylsulfonyl group, a nonabromobutylsulfonyl group, and a nonaiodobutylsulfonyl group.

The term "C1-C4 alkylsulfinyl group" may be either straight or branched, and includes, for example, a methylsulfinyl group, an ethylsulfinyl group, a propylsulfinyl group, an isopropylsulfinyl group, a butylsulfinyl group, an isobutylsulfinyl group, and a sec-butylsulfinyl group.

The term "C1-C4 haloalkylsulfinyl group" represents a group wherein at least one hydrogen atom of the straight or branched C1-C4 alkylsulfinyl group is substituted with a halogen atom, and includes, for example, a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a nonafluorobutylsulfinyl group, a nonachlorobutylsulfinyl group, a nonabromobutylsulfinyl group, and a nonaiodobutylsulfinyl group.

The term "C2-C5 alkoxyalkyl group" may be either a straight or a branched group wherein the total number of carbon atoms of the alkoxy moiety and the alkyl moiety is two to five carbon atoms, and includes, for example, a methoxymethyl group, an ethoxymethyl group, a propyloxymethyl group, an isopropyloxymethyl group, a butyloxymethyl group, an isobutyloxymethyl group, a sec-butyloxymethyl group, a 1-methoxyethyl group, a 2-methoxyethyl group, an 2-ethoxyethyl group, a 2-propyloxyethyl group, an 2-isopropyloxyethyl group, a 3-methoxypropyl group, an 3-ethoxypropyl group, a 3-methoxybutyl group, and an 4-methoxybutyl group.

The term "C2-C5 alkylthioalkyl group" may be either straight or branched, and includes, for example, a methylthiomethyl group, an ethylthiomethyl group, a propylthiomethyl group, an isopropylthiomethyl group, a butylthiomethyl group, an isobutylthiomethyl group, a sec-butylthiomethyl group, a 1-methylthioethyl group, a 2-methylthioethyl group, a 2-propylthioethyl group, an 2-isopropylthioethyl group, a 3-methylthiopropyl group, an 3-ethylthiopropyl group, a 3-methylthiobutyl group, and a 4-methylthiobutyl group.

The term "C2-C3 alkenyl group" includes, for example, a vinyl group, a 1-propenyl group, and a 2-propenyl group.

The term "C2-C3 alkynyl group" includes, for example, an ethynyl group, a 1-propynyl group, and a 2-propynyl group.

The term "C3-C4 cycloalkyl group" includes, for example, a cyclopropyl group and a cyclobutyl group.

The term "C1-C3 alkoxy group" includes, for example, a methoxy group, an ethoxy group, a propyloxy group, and an isopropyloxy group.

The term "C1-C3 haloalkoxy group" represents a group wherein at least one hydrogen atom of the straight or branched C1-C3 alkoxy group is substituted with a halogen atom, and includes, for example, a trifluoromethoxy group, a trichloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, and a 3,3,3-trifluoropropoxy group.

The term "C1-C4 alkylamino group" includes, for example, a N-methylamino group, an N-ethylamino group, a N-propylamino group, an N-isopropylamino group, a N,N-dimethylamino group, a N,N-diethylamino group, and an N-ethyl-N-methylamino group.

The term "C1-C2 alkylthio group" includes, for example, a methylthio group and an ethylthio group.

The term "C1-C2 haloalkylthio group" represents a group wherein at least one hydrogen atom of the straight or branched C1-C2 alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, and a 2,2-difluoroethylthio group.

The term "halomethyl group" includes, for example, a chloromethyl group, a bromomethyl group and an iodomethyl group.

The term "(C1-C3 alkoxy)methyl group includes, for example, a methoxymethyl group, an ethoxymethyl group, a n-propyloxymethyl group, and an isopropyloxymethyl group.

The term "(C1-C3 alkylthio)methyl group includes, for example, a methylthiomethyl group, an ethylthiomethyl group, a n-propylthiomethyl group and an isopropylthiomethyl group.

The term "(C1-C6 acyloxy)methyl group includes, for example, a formyloxymethyl group, an acetoxymethyl group, a propionyloxymethyl group, a butanoyloxymethyl group, a pentanoyloxymethyl group, and a hexanoyloxymethyl group.

The term "(C1-C6 alkylsulfonyloxy)methyl group includes, for example, a methylsulfonyloxymethyl group, an ethylsulfonyloxymethyl group, a propylsulfonyloxymethyl group, an isopropylsulfonyloxymethyl group, a butylsulfonyloxymethyl group, an isobutylsulfonyloxymethyl group, a sec-butylsulfonyloxymethyl group, a pentylsulfonyloxymethyl group, an isopentylsulfonyl group, an isoamylsulfonyloxymethyl group, neopentylsulfonyloxymethyl group, a 2-pentylsulfonyloxymethyl group, a 3-pentylsulfonyloxymethyl group, a 2-methylbutylsulfonyloxymethyl group, a hexylsulfonyloxymethyl group, an isohexylsulfonyloxymethyl group, a 3-methylpentylsulfonyloxymethyl group, and a 4-methylpentylsulfonyloxymethyl group.

The term "(C1-C6 haloalkylsulfonyloxy)methyl group includes, for example, a trifluoromethylsulfonyloxymethyl group, a trichloromethylsulfonyloxymethyl group, a tribromomethylsulfonyloxymethyl group, a triiodomethylsulfonyloxymethyl group, a pentafluoroethylsulfonyloxymethyl group, a pentachloroethylsulfonyloxymethyl group, a pentabromoethylsulfonyloxymethyl group, a pentaiodoethylsulfonyloxymethyl group, a 2,2,2-trichloroethylsulfonyloxymethyl group, a 2,2,2-trifluoroethylsulfonyloxymethyl group, a 2,2,2-tribromoethylsulfonyloxymethyl group, a 2,2,2-triiodoethylsulfonyloxymethyl group, heptafluoropropylsulfonyloxymethyl group, a heptachloropropylsulfonyloxymethyl group, a heptabromopropylsulfonyloxymethyl group, a heptaiodopropylsulfonyloxymethyl group, a 3,3,3-trifluoropropylsulfonyloxymethyl group, a 3,3,3-trichloropropylsulfonyloxymethyl group, a 3,3,3-tribromopropylsulfonyloxymethyl group, a 3,3,3-triiodopropylsulfonyloxymethyl group, a nonafluorobutylsulfonyloxymethyl group, a nonachlorobutylsulfonyloxymethyl group, nonabromobutylsulfonyloxymethyl group, a nonaiodobutylsulfonyloxymethyl group, a perfluoropentylsulfonyloxymethyl group, a perchloropentylsulfonyloxymethyl group, a perbromopentylsulfonyloxymethyl group, a perfluorohexylsulfonyloxymethyl group, a perchlorohexylsulfonyloxymethyl group, a perbromohexylsulfonyloxymethyl group, and an periodohexylsulfonyloxymethyl group.

The term "(C6-C16 arylsulfonyloxy)methyl group includes, for example, a phenylsulfonyloxymethyl group, a 4-methylbenzenesulfonyloxymethyl group, a 1-naphthylsulfonyloxymethyl group, a 2-naphthylsulfonyloxymethyl group, an 1-acenaphthylsulfonyloxymethyl group, a 1-phenanthrylsulfonyloxymethyl group, an 9-anthrylsulfonyloxymethyl group, and a 1-pyrenylsulfonyloxymethyl group.

The term "(C6-C16 haloarylsulfonyloxy)methyl group includes, for example, a 2-fluorophenylsulfonyloxymethyl group, a 3-fluorophenylsulfonyloxymethyl group, a 4-fluorophenylsulfonyloxymethyl group, a 2-chlorophenylsulfonyloxymethyl group, a 3-chlorophenylsulfonyloxymethyl group, a 4-chlorophenylsulfonyloxymethyl group, a 2-bromophenylsulfonyloxymethyl group, a 3-bromophenylsulfonyloxymethyl group, a 4-bromophenylsulfonyloxymethyl group, an 2-iodophenylsulfonyloxymethyl group, an 3-iodophenylsulfonyloxymethyl group, an 4-iodophenylsulfonyloxymethyl group, a 2,4-difluorophenylsulfonyloxymethyl group, a 2,5-difluorophenylsulfonyloxymethyl group, a 2,6-difluorophenylsulfonyloxymethyl group, a 3,5-difluorophenylsulfonyloxymethyl group, a 2,4-dichlorophenylsulfonyloxymethyl group, a 2,5-dichlorophenylsulfonyloxymethyl group, a 2,6-dichlorophenylsulfonyloxymethyl group, a 3,5-dichlorophenylsulfonyloxymethyl group, a 2,4,6-trifluorophenylsulfonyloxymethyl group, a 2,3,4-trifluorophenylsulfonyloxymethyl group, a 2,4,5-trifluorophenylsulfonyloxymethyl group, a 3,4,5-trifluorophenylsulfonyloxymethyl group, a 2,4,6-trichlorophenylsulfonyloxymethyl group, a 2,3,4-trichlorophenylsulfonyloxymethyl group, a 2,4,5-trichlorophenylsulfonyloxymethyl group, a 3,4,5-trichlorophenylsulfonyloxymethyl group, a pentafluorophenylsulfonyloxymethyl group, a pentachlorophenylsulfonyloxymethyl group, a 2-bromo-3-fluorophenylsulfonyloxymethyl group, a 2-bromo-4-fluorophenylsulfonyloxymethyl group, a 2-bromo-5-fluorophenylsulfonyloxymethyl group, a 2-bromo-6-fluorophenylsulfonyloxymethyl group, a 3-bromo-2-fluorophenylsulfonyloxymethyl group, a 3-bromo-4-fluorophenylsulfonyloxymethyl group, a 3-bromo-5-fluorophenylsulfonyloxymethyl group, a 3-bromo-6-fluorophenylsulfonyloxymethyl group, a 4-bromo-2-fluorophenylsulfonyloxymethyl group, a 4-bromo-3-fluorophenylsulfonyloxymethyl group, a 4-bromo-5-fluorophenylsulfonyloxymethyl group, a 4-bromo-6-fluorophenylsulfonyloxymethyl group, a 5-bromo-2-fluorophenylsulfonyloxymethyl group, a 5-bromo-3-fluorophenylsulfonyloxymethyl group, a 5-bromo-4-fluorophenylsulfonyloxymethyl group, a 5-bromo-6-fluorophenylsulfonyloxymethyl group, a 6-bromo-2-fluorophenylsulfonyloxymethyl group, a 6-bromo-3-fluorophenylsulfonyloxymethyl group, a 6-bromo-4-fluorophenylsulfonyloxymethyl group, a 6-bromo-5-fluorophenylsulfonyloxymethyl group, a 2-chloro-3-fluorophenylsulfonyloxymethyl group, a 2-chloro-4-fluorophenylsulfonyloxymethyl group, a 2-chloro-5-fluorophenylsulfonyloxymethyl group, a 2-chloro-6-fluorophenylsulfonyloxymethyl group, a 3-chloro-2-fluorophenylsulfonyloxymethyl group, a 3-chloro-4-fluorophenylsulfonyloxymethyl group, a 3-chloro-5-fluorophenylsulfonyloxymethyl group, a 3-chloro-6-fluorophenylsulfonyloxymethyl group, a 4-chloro-2- fluorophenylsulfonyloxymethyl group, a 4-chloro-3-fluorophenylsulfonyloxymethyl group, a 4-chloro-5-fluorophenylsulfonyloxymethyl group, a 4-chloro-6-fluorophenylsulfonyloxymethyl group, a 5-chloro-2-fluorophenylsulfonyloxymethyl group, a 5-chloro-3-fluorophenylsulfonyloxymethyl group, a 5-chloro-4-fluorophenylsulfonyloxymethyl group, a 5-chloro-6-fluorophenylsulfonyloxymethyl group, a 6-chloro-2-fluorophenylsulfonyloxymethyl group, a 6-chloro-3-fluorophenylsulfonyloxymethyl group, a 6-chloro-4-fluorophenylsulfonyloxymethyl group, a 6-chloro-5-fluorophenylsulfonyloxymethyl group, a 2-fluoro-1-naphthylsulfonyloxymethyl group, a 3-fluoro-1-naphthylsulfonyloxymethyl group, a 4-fluoro-1-naphthylsulfonyloxymethyl group, a 5-fluoro-1-naphthylsulfonyloxymethyl group, a 6-fluoro-1-naphthylsulfonyloxymethyl group, a 7-fluoro-1-naphthylsulfonyloxymethyl group, a 2-chloro-1-naphthylsulfonyloxymethyl group, a 3-chloro-1-naphthylsulfonyloxymethyl group, a 4-chloro-1-naphthylsulfonyloxymethyl group, a 5-chloro-1-naphthylsulfonyloxymethyl group, a 6-chloro-1-naphthylsulfonyloxymethyl group, a 7-chloro-1-naphthylsulfonyloxymethyl group, a 2-bromo-1-naphthylsulfonyloxymethyl group, a 3-bromo-1-naphthylsulfonyloxymethyl group, a 4-bromo-1-naphthylsulfonyloxymethyl group, a 5-bromo-1-naphthylsulfonyl oxymethyl group, a 6-bromo-1-naphthylsulfonyloxymethyl group, a 7-bromo-1-naphthylsulfonyloxymethyl group, a heptachloro-1-naphthylsulfonyloxymethyl group, a heptafluoro-1-naphthylsulfonyloxymethyl group, a 1-fluoro-2-naphthylsulfonyloxymethyl group, a 3-fluoro-2-naphthylsulfonyloxymethyl group, a 4-fluoro-2-naphthylsulfonyloxymethyl group, a 5-fluoro-2-naphthylsulfonyloxymethyl group, a 6-fluoro-2-naphthylsulfonyloxymethyl group, a 7-fluoro-2-naphthylsulfonyloxymethyl group, a 1-chloro-2-naphthylsulfonyloxymethyl group, a 3-chloro-2-naphthylsulfonyloxymethyl group, a 4-chloro-2-naphthylsulfonyloxymethyl group, a 5-chloro-2-naphthylsulfonyloxymethyl group, a 6-chloro-2-naphthylsulfonyloxymethyl group, a 7-chloro-2-naphthylsulfonyloxymethyl group, a 1-bromo-2-naphthylsulfonyloxymethyl group, a 3-bromo-2-naphthylsulfonyloxymethyl group, a 4-bromo-2-naphthylsulfonyloxymethyl group, a 5-bromo-2-naphthylsulfonyloxymethyl group, a 6-bromo-2-naphthylsulfonyloxymethyl group, a 7-bromo-2-naphthylsulfonyloxymethyl group, a heptachloro-2-naphthylsulfonyloxymethyl group, a heptafluoro-2-naphthylsulfonyloxymethyl group, a 3-fluoro-1-acenaphthylsulfonyloxymethyl group, a 9-fluoro-1-phenanthrylsulfonyloxymethyl group, a 10-fluoro-9-anthrylsulfonyloxymethyl group, and a 6-fluoro-1-pyrenylsulfonyloxymethyl group.

The term "(C1-C6 alkylamino)methyl group" includes, for example, a N-methylaminomethyl group, an N-ethylaminomethyl group, a N-propylaminomethyl group, an N-isopropylaminomethyl group, a N-butylaminomethyl group, a N,N-dimethylaminomethyl group, a N,N-diethylaminomethyl group, a N,N-dipropylaminomethyl group, a N,N-diisopropylaminomethyl group, an N-ethyl-N-methylaminomethyl group, a N-propyl-N-methylaminomethyl group, a N-butyl-N-methylaminomethyl group, a N-pentyl-N-methylaminomethyl group, a N-propyl-N-ethylaminomethyl group, and a N-butyl-N-ethylaminomethyl group.

The term "a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other) includes, for example, a pyrrolidinylmethyl group, a piperidinylmethyl group, a piperazinylmethyl group, a morpholinylmethyl group, a thiomorpholinylmethyl group, and an azepanylmethyl group.

The term "C1-C5 alkyl group" represents a straight or branched alkyl group, and includes, for example, a methyl group, an ethyl group, a propyl group, an isopropyl group, a butyl group, an isobutyl group, a sec-butyl group, a tert-butyl group, and a pentyl group.

The term "C1-C3 alkylthio group" includes, for example, a methylthio group, an ethylthio group, a n-propylthio group, and an isopropylthio group.

The term "C1-C3 haloalkylthio group" represents a group wherein at least one hydrogen atom of the straight or branched C1-C3 alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, and a 2,3,3-trifluoropropylthio group.

The term "C2-C3 alkyl group" includes, for example, an ethyl group, a propyl group, and an isopropyl group.

The term "C2-C3 alkoxy group" includes, for example, an ethoxy group, a propyloxy group, and an isopropyloxy group.

Examples of an embodiment of the present compound include the compounds of the formula (1) wherein the substituents represent the following ones.

a compound wherein $R^1$ represents a haloaryl group;
a compound wherein $R^1$ represents an aryl group having an C1-C3 alkyl group;
a compound wherein $R^1$ represents an aryl group having an C1-C3 alkoxy group;
a compound wherein $R^1$ represents an aryl group having an C1-C3 haloalkoxy group;
a compound wherein $R^1$ represents a 4-chlorophenyl group;
a compound wherein $R^1$ represents a 4-fluorophenyl group;
a compound wherein $R^1$ represents a 4-bromophenyl group;
a compound wherein $R^1$ represents a 4-methoxyphenyl group;
a compound wherein $R^1$ represents a 4-methylphenyl group;
a compound wherein $R^1$ represents a 4-trifluoromethoxyphenyl group;
a compound wherein $R^2$ represents a hydrogen atom;
a compound wherein $R^3$ represents a hydrogen atom;
a compound wherein $R^4$ represents a hydrogen atom;

a compound wherein $R^5$ represents a hydrogen atom;
a compound wherein $R^6$ represents an C1-C3 alkyl group;
a compound wherein $R^6$ represents a C3-C4 cycloalkyl group;
a compound wherein $R^6$ represents a halogen atom;
a compound wherein $R^6$ represents a C1-C3 haloalkyl group;
a compound wherein represents an C2-C3 alkenyl group;
a compound wherein $R^6$ represents an C1-C3 alkoxy group;
a compound wherein $R^6$ represents a methyl group;
a compound wherein $R^6$ represents an ethyl group;
a compound wherein $R^6$ represents n-propyl group;
a compound wherein $R^6$ represents a cyclopropyl group;
a compound wherein $R^6$ represents a trifluoromethyl group;
a compound wherein $R^6$ represents a difluoromethyl group;
a compound wherein $R^6$ represents a 2-propenyl group;
a compound wherein $R^6$ represents a chlorine atom;
a compound wherein $R^6$ represents a bromine atom;
a compound wherein $R^6$ represents an iodine atom;
a compound wherein $R^6$ represents a fluorine atom;
a compound wherein $R^6$ represents a vinyl group;
a compound wherein $R^6$ represents a methoxy group;
a compound wherein $R^7$ represents a hydrogen atom;
a compound wherein $R^8$ represents a hydrogen atom;
a compound wherein $R^9$ represents a hydrogen atom;
a compound wherein $R^{10}$ represents a methyl group;
a compound wherein X represents an oxygen atom;
a compound wherein X represents a sulfur atom;
a compound wherein $R^1$ represents a haloaryl group and $R^6$ represents a C1-C3 alkyl group;
a compound wherein $R^1$ represents a haloaryl group and $R^6$ represents a C3-C4 cycloalkyl group;
a compound wherein $R^1$ represents a haloaryl group and $R^6$ represents a halogen atom;
a compound wherein $R^1$ represents a haloaryl group and $R^6$ represents a C1-C3 haloalkyl group;
a compound wherein $R^1$ represents a haloaryl group and $R^6$ represents an C2-C3 alkenyl group;
a compound wherein $R^1$ represents a haloaryl group and $R^6$ represents an C1-C3 alkoxy group;
a compound wherein $R^1$ represents a haloaryl group and $R^6$ represents a methyl group;
a compound wherein $R^1$ represents a haloaryl group and $R^6$ represents an ethyl group;
a compound wherein $R^1$ represents a haloaryl group and $R^6$ represents a n-propyl group;
a compound wherein $R^1$ represents a haloaryl group and $R^6$ represents a cyclopropyl group;
a compound wherein $R^1$ represents a haloaryl group and $R^6$ represents a trifluoromethyl group;
a compound wherein $R^1$ represents a haloaryl group and $R^6$ represents a difluoromethyl group;
a compound wherein $R^1$ represents a haloaryl group and $R^6$ represents a 2-propenyl group;
a compound wherein $R^1$ represents a haloaryl group and $R^6$ represents a chlorine atom;
a compound wherein $R^1$ represents a haloaryl group and $R^6$ represents a bromine atom;
a compound wherein $R^1$ represents a haloaryl group and $R^6$ represents an iodine atom;
a compound wherein $R^1$ represents a haloaryl group and $R^6$ represents a fluorine atom;
a compound wherein $R^1$ represents a haloaryl group and $R^6$ represents a vinyl group;
a compound wherein $R^1$ represents a haloaryl group and $R^6$ represents a methoxy group;
a compound wherein $R^1$ represents an aryl group having an C1-C3 alkyl group and $R^6$ represents an C1-C3 alkyl group;
a compound wherein $R^1$ represents an aryl group having an C1-C3 alkyl group and $R^6$ represents a C3-C4 cycloalkyl group;
a compound wherein $R^1$ represents an aryl group having an C1-C3 alkyl group and $R^6$ represents a halogen atom;
a compound wherein $R^1$ represents an aryl group having an C1-C3 alkyl group and $R^6$ represents a C1-C3 haloalkyl group;
a compound wherein $R^1$ represents an aryl group having an C1-C3 alkyl group and $R^6$ represents an C2-C3 alkenyl group;
a compound wherein $R^1$ represents an aryl group having an C1-C3 alkyl group and $R^6$ represents an C1-C3 alkoxy group;
a compound wherein $R^1$ represents an aryl group having an C1-C3 alkyl group and $R^6$ represents a methyl group;
a compound wherein $R^1$ represents an aryl group having an C1-C3 alkyl group and $R^6$ represents an ethyl group;
a compound wherein $R^1$ represents an aryl group having an C1-C3 alkyl group and $R^6$ represents a n-propyl group;
a compound wherein $R^1$ represents an aryl group having an C1-C3 alkyl group and $R^6$ represents a cyclopropyl group;
a compound wherein $R^1$ represents an aryl group having an C1-C3 alkyl group and $R^6$ represents a trifluoromethyl group;
a compound wherein $R^1$ represents an aryl group having an C1-C3 alkyl group and $R^6$ represents a difluoromethyl group;
a compound wherein $R^1$ represents an aryl group having an C1-C3 alkyl group and $R^6$ represents a 2-propenyl group;
a compound wherein $R^1$ represents an aryl group having an C1-C3 alkyl group and $R^6$ represents a chlorine atom;
a compound wherein $R^1$ represents an aryl group having an C1-C3 alkyl group and $R^6$ represents a bromine atom;
a compound wherein $R^1$ represents an aryl group having an C1-C3 alkyl group and $R^6$ represents an iodine atom;
a compound wherein $R^1$ represents an aryl group having an C1-C3 alkyl group and $R^6$ represents a fluorine atom;
a compound wherein $R^1$ represents an aryl group having an C1-C3 alkyl group and $R^6$ represents a vinyl group;
a compound wherein $R^1$ represents an aryl group having an C1-C3 alkyl group and $R^6$ represents a methoxy group; a compound wherein $R^1$ represents an aryl group having an C1-C3 alkoxy group and $R^6$ represents a C1-C3 alkyl group;
a compound wherein $R^1$ represents an aryl group having an C1-C3 alkoxy group and $R^6$ represents a C3-C4 cycloalkyl group;
a compound wherein $R^1$ represents an aryl group having an C1-C3 alkoxy group and $R^6$ represents a halogen atom;
a compound wherein $R^1$ represents an aryl group having an C1-C3 alkoxy group and $R^6$ represents a C1-C3 haloalkyl group;
a compound wherein $R^1$ represents an aryl group having an C1-C3 alkoxy group and $R^6$ represents an C2-C3 alkenyl group;
a compound wherein $R^1$ represents an aryl group having an C1-C3 alkoxy group and $R^6$ represents an C1-C3 alkoxy group;
a compound wherein $R^1$ represents an aryl group having an C1-C3 alkoxy group and $R^6$ represents a methyl group;

a compound wherein $R^1$ represents an aryl group having an C1-C3 alkoxy group and $R^6$ represents an ethyl group;

a compound wherein $R^1$ represents an aryl group having an C1-C3 alkoxy group and $R^6$ represents a n-propyl group;

a compound wherein $R^1$ represents an aryl group having an C1-C3 alkoxy group and $R^6$ represents a cyclopropyl group;

a compound wherein $R^1$ represents an aryl group having an C1-C3 alkoxy group and $R^6$ represents a trifluoromethyl group;

a compound wherein $R^1$ represents an aryl group having an C1-C3 alkoxy group and $R^6$ represents a difluoromethyl group;

a compound wherein $R^1$ represents an aryl group having an C1-C3 alkoxy group and $R^6$ represents a 2-propenyl group;

a compound wherein $R^1$ represents an aryl group having an C1-C3 alkoxy group and $R^6$ represents a chlorine atom;

a compound wherein $R^1$ represents an aryl group having an C1-C3 alkoxy group and $R^6$ represents a bromine atom;

a compound wherein $R^1$ represents an aryl group having an C1-C3 alkoxy group and $R^6$ represents an iodine atom;

a compound wherein $R^1$ represents an aryl group having an C1-C3 alkoxy group and $R^6$ represents a fluorine atom;

a compound wherein $R^1$ represents an aryl group having an C1-C3 alkoxy group and $R^6$ represents a vinyl group;

a compound wherein $R^1$ represents an aryl group having an C1-C3 alkoxy group and $R^6$ represents a methoxy group;

a compound wherein $R^1$ represents an aryl group having an C1-C3 haloalkoxy group and $R^6$ represents an C1-C3 alkyl group;

a compound wherein $R^1$ represents an aryl group having an C1-C3 haloalkoxy group and $R^6$ represents a C3-C4 cycloalkyl group;

a compound wherein $R^1$ represents an aryl group having an C1-C3 haloalkoxy group and $R^6$ represents a halogen atom;

a compound wherein $R^1$ represents an aryl group having an C1-C3 haloalkoxy group and $R^6$ represents a C1-C3 haloalkyl group;

a compound wherein $R^1$ represents an aryl group having an C1-C3 haloalkoxy group and $R^6$ represents an C2-C3 alkenyl group;

a compound wherein $R^1$ represents an aryl group having an C1-C3 haloalkoxy group and $R^6$ represents an C1-C3 alkoxy group;

a compound wherein $R^1$ represents an aryl group having an C1-C3 haloalkoxy group and $R^6$ represents a methyl group;

a compound wherein $R^1$ represents an aryl group having an C1-C3 haloalkoxy group and $R^6$ represents an ethyl group;

a compound wherein $R^1$ represents an aryl group having an C1-C3 haloalkoxy group and $R^6$ represents a n-propyl group;

a compound wherein $R^1$ represents an aryl group having an C1-C3 haloalkoxy group and $R^6$ represents a cyclopropyl group;

a compound wherein $R^1$ represents an aryl group having an C1-C3 haloalkoxy group and $R^6$ represents a trifluoromethyl group;

a compound wherein $R^1$ represents an aryl group having an C1-C3 haloalkoxy group and $R^6$ represents a difluoromethyl group;

a compound wherein $R^1$ represents an aryl group having an C1-C3 haloalkoxy group and $R^6$ represents a 2-propenyl group;

a compound wherein $R^1$ represents an aryl group having an C1-C3 haloalkoxy group and $R^6$ represents a chlorine atom;

a compound wherein $R^1$ represents an aryl group having an C1-C3 haloalkoxy group and $R^6$ represents a bromine atom;

a compound wherein $R^1$ represents an aryl group having an C1-C3 haloalkoxy group and $R^6$ represents an iodine atom;

a compound wherein $R^1$ represents an aryl group having an C1-C3 haloalkoxy group and $R^6$ represents a fluorine atom;

a compound wherein $R^1$ represents an aryl group having an C1-C3 haloalkoxy group and $R^6$ represents a vinyl group;

a compound wherein $R^1$ represents an aryl group having an C1-C3 haloalkoxy group and $R^6$ represents a methoxy group;

a compound wherein $R^1$ represents a 4-chlorophenyl group and $R^6$ represents a methyl group;

a compound wherein $R^1$ represents a 4-chlorophenyl group and $R^6$ represents an ethyl group;

a compound wherein $R^1$ represents a 4-chlorophenyl group and $R^6$ represents a n-propyl group;

a compound wherein $R^1$ represents a 4-chlorophenyl group and $R^6$ represents a cyclopropyl group;

a compound wherein $R^1$ represents a 4-chlorophenyl group and $R^6$ represents a trifluoromethyl group;

a compound wherein $R^1$ represents a 4-chlorophenyl group and $R^6$ represents a difluoromethyl group;

a compound wherein $R^1$ represents a 4-chlorophenyl group and $R^6$ represents a 2-propenyl group;

a compound wherein $R^1$ represents a 4-chlorophenyl group and $R^6$ represents a chlorine atom;

a compound wherein $R^1$ represents a 4-chlorophenyl group and $R^6$ represents a bromine atom;

a compound wherein $R^1$ represents a 4-chlorophenyl group and $R^6$ represents an iodine atom;

a compound wherein $R^1$ represents a 4-chlorophenyl group and $R^6$ represents a fluorine atom;

a compound wherein $R^1$ represents a 4-chlorophenyl group and $R^6$ represents a vinyl group;

a compound wherein $R^1$ represents a 4-chlorophenyl group and $R^6$ represents a methoxy group;

a compound wherein $R^1$ represents a 4-fluorophenyl group and $R^6$ represents a methyl group;

a compound wherein $R^1$ represents a 4-fluorophenyl group and $R^6$ represents an ethyl group;

a compound wherein $R^1$ represents a 4-fluorophenyl group and $R^6$ represents a n-propyl group;

a compound wherein $R^1$ represents a 4-fluorophenyl group and $R^6$ represents a cyclopropyl group;

a compound wherein $R^1$ represents a 4-fluorophenyl group and $R^6$ represents a trifluoromethyl group;

a compound wherein $R^1$ represents a 4-fluorophenyl group and $R^6$ represents a difluoromethyl group;

a compound wherein $R^1$ represents a 4-fluorophenyl group and $R^6$ represents a 2-propenyl group;

a compound wherein $R^1$ represents a 4-fluorophenyl group and $R^6$ represents a chlorine atom;

a compound wherein $R^1$ represents a 4-fluorophenyl group and $R^6$ represents a bromine atom;

a compound wherein $R^1$ represents a 4-fluorophenyl group and $R^6$ represents an iodine atom;

a compound wherein $R^1$ represents a 4-fluorophenyl group and $R^6$ represents a fluorine atom;

a compound wherein $R^1$ represents a 4-fluorophenyl group and $R^6$ represents a vinyl group;

a compound wherein $R^1$ represents a 4-fluorophenyl group and $R^6$ represents a methoxy group;
a compound wherein $R^1$ represents a 4-bromophenyl group and $R^6$ represents a methyl group;
a compound wherein $R^1$ represents a 4-bromophenyl group and $R^6$ represents a n-propyl group;
a compound wherein $R^1$ represents a 4-bromophenyl group and $R^6$ represents a cyclopropyl group;
a compound wherein $R^1$ represents a 4-bromophenyl group and $R^6$ represents a trifluoromethyl group;
a compound wherein $R^1$ represents a 4-bromophenyl group and $R^6$ represents a difluoromethyl group;
a compound wherein $R^1$ represents a 4-bromophenyl group and $R^6$ represents a 2-propenyl group;
a compound wherein $R^1$ represents a 4-bromophenyl group and $R^6$ represents a chlorine atom;
a compound wherein $R^1$ represents a 4-bromophenyl group and $R^6$ represents a bromine atom;
a compound wherein $R^1$ represents a 4-bromophenyl group and $R^6$ represents an iodine atom;
a compound wherein $R^1$ represents a 4-bromophenyl group and $R^6$ represents a fluorine atom;
a compound wherein $R^1$ represents a 4-bromophenyl group and $R^6$ represents a vinyl group;
a compound wherein $R^1$ represents a 4-bromophenyl group and $R^6$ represents a methoxy group;
a compound wherein $R^1$ represents a 4-methoxyphenyl group and $R^6$ represents a methyl group;
a compound wherein $R^1$ represents a 4-methoxyphenyl group and $R^6$ represents an ethyl group;
a compound wherein $R^1$ represents a 4-methoxyphenyl group and $R^6$ represents a n-propyl group;
a compound wherein $R^1$ represents a 4-methoxyphenyl group and $R^6$ represents a cyclopropyl group;
a compound wherein $R^1$ represents a 4-methoxyphenyl group and $R^6$ represents a trifluoromethyl group;
a compound wherein $R^1$ represents a 4-methoxyphenyl group and $R^6$ represents a difluoromethyl group;
a compound wherein $R^1$ represents a 4-methoxyphenyl group and $R^6$ represents a 2-propenyl group;
a compound wherein $R^1$ represents a 4-methoxyphenyl group and $R^6$ represents a chlorine atom;
a compound wherein $R^1$ represents a 4-methoxyphenyl group and $R^6$ represents a bromine atom;
a compound wherein $R^1$ represents a 4-methoxyphenyl group and $R^6$ represents an iodine atom;
a compound wherein $R^1$ represents a 4-methoxyphenyl group and $R^6$ represents a fluorine atom;
a compound wherein $R^1$ represents a 4-methoxyphenyl group and $R^6$ represents a vinyl group;
a compound wherein $R^1$ represents a 4-methoxyphenyl group and $R^6$ represents a methoxy group;
a compound wherein $R^1$ represents a 4-methylphenyl group and $R^6$ represents a methyl group;
a compound wherein $R^1$ represents a 4-methylphenyl group and $R^6$ represents an ethyl group;
a compound wherein $R^1$ represents a 4-methylphenyl group and $R^6$ represents a n-propyl group;
a compound wherein $R^1$ represents a 4-methylphenyl group and $R^6$ represents a cyclopropyl group;
a compound wherein $R^1$ represents a 4-methylphenyl group and $R^6$ represents a trifluoromethyl group;
a compound wherein $R^1$ represents a 4-methylphenyl group and $R^6$ represents a difluoromethyl group;
a compound wherein $R^1$ represents a 4-methylphenyl group and $R^6$ represents a 2-propenyl group;
a compound wherein $R^1$ represents a 4-methylphenyl group and $R^6$ represents a chlorine atom;
a compound wherein $R^1$ represents a 4-methylphenyl group and $R^6$ represents a bromine atom;
a compound wherein $R^1$ represents a 4-methylphenyl group and $R^6$ represents an iodine atom;
a compound wherein $R^1$ represents a 4-methylphenyl group and $R^6$ represents a fluorine atom;
a compound wherein $R^1$ represents a 4-methylphenyl group and $R^6$ represents a vinyl group;
a compound wherein $R^1$ represents a 4-methylphenyl group and $R^6$ represents a methoxy group;
a compound wherein $R^1$ represents a 4-trifluoromethoxyphenyl group and $R^6$ represents an ethyl group;
a compound wherein $R^1$ represents a 4-trifluoromethoxyphenyl group and $R^6$ represents a n-propyl group;
a compound wherein $R^1$ represents a 4-trifluoromethoxyphenyl group and $R^6$ represents a cyclopropyl group;
a compound wherein $R^1$ represents a 4-trifluoromethoxyphenyl group and $R^6$ represents a trifluoromethyl group;
a compound wherein $R^1$ represents a 4 trifluoromethoxyphenyl group and $R^6$ represents a difluoromethyl group;
a compound wherein $R^1$ represents a 4-trifluoromethoxyphenyl group and $R^6$ represents a 2-propenyl group;
a compound wherein $R^1$ represents a 4-trifluoromethoxyphenyl group and $R^6$ represents a chlorine atom;
a compound wherein $R^1$ represents a 4-trifluoromethoxyphenyl group and $R^6$ represents a bromine atom;
a compound wherein $R^1$ represents a 4-trifluoromethoxyphenyl group and $R^6$ represents an iodine atom;
a compound wherein $R^1$ represents a 4-trifluoromethoxyphenyl group and $R^6$ represents a fluorine atom;
a compound wherein $R^1$ represents a 4-trifluoromethoxyphenyl group and $R^6$ represents a vinyl group;
a compound wherein $R^1$ represents a 4-trifluoromethoxyphenyl group and $R^6$ represents a methoxy group;
a compound wherein $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;
a compound wherein $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;
a compound wherein $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;
a compound wherein $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;
a compound wherein $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;
a compound wherein $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^2$ represents a hydrogen atom, represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents a sulfur atom;

a compound wherein $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents a sulfur atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents an aryl group having an C1-C3 haloalkoxy group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents a 4 trifluoromethoxyphenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents an aryl group having an C1-C3 haloalkoxy group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^{10}$ represents a methyl group, and X represents a sulfur atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a halogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a halogen atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a halogen atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents an aryl group having an C1-C3 haloalkoxy group, $R^2$ represents a hydrogen atom, $R^3$ represents a hydrogen atom, $R^4$ represents a hydrogen atom, R⁵ represents a hydrogen atom, R⁶ represents an C1-C3 alkyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a C3-C4 cycloalkyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, represents a halogen atom, R¹⁰ represents a methyl group, and X represents an oxygen atom;

a compound wherein R¹ represents an aryl group having an C1-C3 haloalkoxy group, R² represents a hydrogen atom, R² represents a hydrogen atom, R⁴ represents a hydrogen atom, R⁵ represents a hydrogen atom, R⁶ represents a C1-C3 haloalkyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents an C2-C3 alkenyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents an C1-C3 alkoxy group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a methyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents an ethyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a n-propyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a cyclopropyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a trifluoromethyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a difluoromethyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a 2-propenyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a chlorine atom, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a bromine atom, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents an iodine atom, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a fluorine atom, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a vinyl group, R¹⁰ represents a methyl group, and X represents an oxygen atom;

a compound wherein R¹ represents an aryl group having an C1-C3 haloalkoxy group, R² represents a hydrogen atom, R³ represents a hydrogen atom, R⁴ represents a hydrogen atom, R⁵ represents a hydrogen atom, R⁶ represents a methoxy group, R¹⁰ represents a methyl group, and X represents an oxygen atom;

a compound wherein R¹ represents a 4-chlorophenyl group, R² represents a hydrogen atom, R³ represents a hydrogen atom, R⁴ represents a hydrogen atom, R⁵ represents a hydrogen atom, R⁶ represents a methyl group, R¹⁰ represents a methyl group, and X represents an oxygen atom;

a compound wherein R¹ represents a 4-chlorophenyl group, R² represents a hydrogen atom, R³ represents a hydrogen atom, R⁴ represents a hydrogen atom, R⁵ represents a hydrogen atom, R⁶ represents an ethyl group, R¹⁰ represents a methyl group, and X represents an oxygen atom;

a compound wherein R¹ represents a 4-chlorophenyl group, R² represents a hydrogen atom, R³ represents a hydrogen atom, R⁴ represents a hydrogen atom, R⁵ represents a hydrogen atom, R⁶ represents a n-propyl group, R¹⁰ represents a methyl group, and X represents an oxygen atom;

a compound wherein R¹ represents a 4-chlorophenyl group, R² represents a hydrogen atom, R³ represents a hydrogen atom, R⁴ represents a hydrogen atom, R⁵ represents a hydrogen atom, $R^6$ represents a cyclopropyl group, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a 4-bromophenyl group, represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^{10}$ represents a methyl group, and X represents an oxygen atom;

a compound wherein $R^1$ represents a 4 trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having an C1-C3 alkyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having an C1-C3 alkoxy group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having an C1-C3 haloalkoxy group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-trifluoromethoxyphenyl group, $R^2$ represents a hydrogen atom, $R^3$ represents a hydrogen atom, $R^4$ represents a hydrogen atom, $R^5$ represents a hydrogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a halogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a haloaryl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a halogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a halogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 alkoxy group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents an C1-C3 alkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a C3-C4 cycloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a halogen atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a C1-C3 haloalkyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents an C2-C3 alkenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents an C1-C3 alkoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a cyclopropyl group, represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents an aryl group having a C1-C3 haloalkoxy group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^2$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-chlorophenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-fluorophenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^1$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-bromophenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methoxyphenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a methyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, represents a, hydrogen atom, $R^3$ represents a hydrogen atom, $R^4$ represents a hydrogen atom, $R^5$ represents a hydrogen atom, $R^6$ represents an ethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a n-propyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a cyclopropyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a trifluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a difluoromethyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a 2-propenyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a chlorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a bromine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents an iodine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a fluorine atom, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a vinyl group, $R^7$ represents a hydrogen atom, $R^8$ represents a hydrogen atom, $R^9$ represents a hydrogen atom, $R^{10}$ represents a methyl group, and X represents an oxygen atom;

a compound wherein $R^1$ represents a 4-methylphenyl group, $R^2$ represents a hydrogen atom, $R^3$ represents a hydrogen atom, $R^4$ represents a hydrogen atom, $R^5$ represents a hydrogen atom, $R^6$ represents a methoxy group, $R^7$ represents a hydrogen atom, R⁸ represents a hydrogen atom, R⁹ represents a hydrogen atom, R¹⁰ represents a methyl group, and X represents an oxygen atom; a compound wherein R¹ represents a 4-trifluoromethoxyphenyl group, R² represents a hydrogen atom, R³ represents a hydrogen atom, R⁴ represents a hydrogen atom, R⁶ represents a hydrogen atom, R⁶ represents a methyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents an ethyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a n-propyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a cyclopropyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a trifluoromethyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a difluoromethyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a 2-propenyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a chlorine atom, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a bromine atom, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents an iodine atom, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a fluorine atom, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a trifluoromethoxyphenyl group, R² represents a hydrogen atom, R³ represents a hydrogen atom, R⁴ represents a hydrogen atom, R⁵ represents a hydrogen atom, R⁶ represents a vinyl group, R⁷ represents a hydrogen atom, R⁸ represents a hydrogen atom, R⁹ represents a hydrogen atom, R¹⁰ represents a methyl group, and X represents an oxygen atom;

a compound wherein R¹ represents a 4-trifluoromethoxyphenyl group, R² represents a hydrogen atom, R³ represents a hydrogen atom, R⁴ represents a hydrogen atom, R⁵ represents a hydrogen atom, R⁶ represents a methoxy group, R⁷ represents a hydrogen atom, R⁸ represents a hydrogen atom, R⁹ represents a hydrogen atom, R¹⁰ represents a methyl group, and X represents an oxygen atom.

a tetrazolinone compound wherein

R¹ represents an C1-C4 alkyl group or a hydrogen atom (with the proviso that when the C1-C4 alkyl group has two or more atoms or groups selected from a group P, the substituents consisting of the atoms or the groups may be same or different to each other);

R² and R³ represent independently of each other a hydrogen atom, an C1-C3 alkyl group, a C1-C3 haloalkyl group, an C2-C12 alkoxycarbonyl group, a hydroxycarbonyl group or a halogen atom;

R⁴ and R⁵ represent independently of each other a hydrogen atom, a halogen atom or an C1-C3 alkyl group;

R⁶ represents an aminocarbonyl group optionally having C1-C6 alkyl group, a halogen atom, an C1-C6 alkyl group, a C1-C6 haloalkyl group, an C2-C6 alkenyl group, C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, C1-C4 haloalkylsulfonyl group, C1-C4 alkylsulfinyl group, a C1-C4 haloalkylsulfinyl group, an C2-C5 alkoxyalkyl group or an C2-C5 alkylthioalkyl group;

R⁷, R⁸ and R⁹ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents an oxygen atom or a sulfur atom.

a tetrazolinone compound wherein $R^1$ represents an C1-C4 alkyl group or a hydrogen atom (with the proviso that when the C1-C4 alkyl group has two or more atoms or groups selected from a group P, the substituents consisting of the atoms or the groups may be same or different to each other);

$R^2$, $R^3$, $R^4$ and $R^5$ represent a hydrogen atom;

$R^6$ represents an aminocarbonyl group optionally having C1-C6 alkyl group, a halogen atom, an C1-C6 alkyl group, a C1-C6 haloalkyl group, an C2-C6 alkenyl group, C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, C1-C4 haloalkylsulfonyl group, C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C1-C4 alkyl group (with the proviso that when the C1-C4 alkyl group has two or more atoms or groups selected from a group P, the substituents consisting of the atoms or the groups may be same or different to each other);

$R^2$, $R^3$, $R^4$ and $R^5$ represent a hydrogen atom;

$R^6$ represents an aminocarbonyl group optionally having C1-C6 alkyl group, a halogen atom, an C1-C6 alkyl group, a C1-C6 haloalkyl group, an C2-C6 alkenyl group, C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, C1-C4 haloalkylsulfonyl group, C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C1-C4 alkyl group (with the proviso that when the C1-C4 alkyl group has two or more atoms or groups selected from a group P, the substituents consisting of the atoms or the groups may be same or different to each other);

$R^2$, $R^3$, $R^4$ and $R^5$ represent a hydrogen atom;

$R^6$ represents a halogen atom, a methyl group, a trifluoromethyl group or a methoxy group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C1-C4 alkyl group (with the proviso that when the C1-C4 alkyl group has two or more atoms or groups selected from a group P, the substituents consisting of the atoms or the groups may be same or different to each other);

$R^2$, $R^3$, $R^4$ and $R^5$ represent a hydrogen atom;

$R^6$ represents an aminocarbonyl group optionally having C1-C6 alkyl group, an C2-C6 alkyl group, an C1-C6 haloalkyl group excluding trifluoromethyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C2-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents an aminocarbonyl group optionally having C1-C6 alkyl group, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents a halogen atom, a methyl group, a trifluoromethyl group or a methoxy group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents a halogen atom, a methyl group, a trifluoromethyl group or a methoxy group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents a chlorine atom, a bromine atom, a methyl group or a methoxy group;

$R^8$ and $R^9$ represent independently of each other a hydrogen atom or a fluorine atom;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents an aminocarbonyl group optionally having C1-C6 alkyl group, an C2-C6 alkyl group, an C1-C6 haloalkyl group excluding trifluoromethyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C2-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents an C2-C3 alkyl group, a C1-C3 haloalkyl group excluding trifluoromethyl group, an C2-C3 alkenyl group, an C2-C3 alkynyl group, a C3-C4 cycloalkyl group, a C2-C3 alkoxy group or C1-C3 haloalkoxy group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents a hydrogen atom;

$R^2$, $R^3$, $R^4$ and $R^5$ represent a hydrogen atom;

$R^6$ represents an ethyl group or a cyclopropyl group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents an C6-C16 aryl group optionally having one or more atoms and groups selected from Group P, an C5-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, or an C2-C12 acyl group optionally having one or more atoms and groups selected from Group P (with the proviso that when the C6-C16 aryl group, the C5-C12 alkyl group, the C3-C12 cycloalkyl group, the C2-C12 alkenyl group, the C3-C12 cycloalkenyl group, the C2-C12 alkynyl group or the C2-C12 acyl group has two or more atoms and groups selected from Group P, the substituents consisting of the atoms and the groups may be same of different from each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group;

$R^6$ represents an aminocarbonyl group optionally having C1-C6 alkyl group, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, C3-C6 haloalkenylthio group, C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl, group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents an oxygen atom or a sulfur atom.

a tetrazolinone compound wherein $R^1$ represents an C6-C16 aryl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, or an C2-C12 acyl group optionally having one or more atoms and groups selected from Group P (with the proviso that when the C6-C16 aryl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group;

$R^6$ represents an aminocarbonyl group optionally having C1-C6 alkyl group, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents an oxygen atom or a sulfur atom.

a tetrazolinone compound wherein $R^1$ represents an C6-C16 aryl group optionally having one or more atoms and groups selected from Group P, an C5-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, or C2-C12 acyl group optionally having one or more atoms and groups selected from Group P (with the proviso that when the C6-C16 aryl group, the C5-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents an aminocarbonyl group optionally having C1-C6 alkyl group, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a nitro group, a cyano group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group;

X represents an oxygen atom or a sulfur atom.

a tetrazolinone compound wherein $R^1$ represents a phenyl group optionally having one or more atoms and groups selected from Group P (with the proviso that when the phenyl group has two or more atoms or groups selected from Group P, the substituent consisting of the atoms and the groups may be same or different to each other); $R^2$ and $R^3$ represent independently of each other a hydrogen atom, an C1-C3 alkyl group or a halogen atom;

$R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, an C1-C4 alkoxy group or a C1-C4 haloalkoxy group;

$R^{10}$ represents an C1-C4 alkyl group; and

X represents an oxygen atom.

a tetrazolinone compound wherein $R^1$ represents an C10-C16 aryl group optionally having one or more atoms and groups selected from Group P, an C7-C12 alkyl group optionally having one or more atoms and groups selected from Group P, a C7-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P or a hydrogen atom (with the proviso that when the C10-C16 aryl group, the C7-C12 alkyl group, the C7-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^8$ represent independently of each other a hydrogen atom, a halogen atom or an C1-C3 alkyl group;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents an oxygen atom or a sulfur atom.

a tetrazolinone compound wherein $R^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group (with the proviso that any one or more of $R^4$ and $R^5$ represent a halogen atom or an C1-C3 alkyl group);

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents an oxygen atom or a sulfur atom.

a tetrazolinone compound wherein $R^1$ represents an C6-C16 aryl optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group (with the proviso that any one or more of $R^7$, $R^8$ and $R^9$ represent a C3-C5 cycloalkyl group or a C3-C5 halocycloalkyl group);

$R^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group;

X represents an oxygen atom or a sulfur atom.

a tetrazolinone compound wherein $R^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represent independently of each other an C5-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents an oxygen atom or a sulfur atom.

a tetrazolinone compound wherein $R^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$ and $R^3$ represent independently of each other a hydrogen atom, an C1-C3 alkyl group, a C1-C3 haloalkyl group, an C2-C12 alkoxycarbonyl group, a hydroxycarbonyl group or a halogen atom;

$R^4$ and $R^5$ represent independently of each other a hydrogen atom, a halogen atom or an C1-C3 alkyl group;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represent independently of each other an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group; and X represents a sulfur atom.

a tetrazolinone compound wherein $R^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents a phenyl group optionally having one or more atoms and groups selected from Group P (with the proviso that when the phenyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C10-C16 aryl group optionally having one or more atoms and groups selected from Group P, an C7-C12 alkyl group optionally having one or more atoms and groups selected from Group P, a C7-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group (with the proviso that any one or more of $R^7$, $R^8$ and $R^9$ represent a C3-C5 cycloalkyl group or a C3-C5 halocycloalkyl group);

$R^{10}$ represents a methyl group; and

X represents an oxygen atom.

a tetrazolinone compound wherein $R^1$ represents an C6-C16 aryl group optionally having one or more atoms and groups selected from Group P (with the proviso that when the C6-C16 aryl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents a phenyl group optionally having one or more atoms and groups selected from Group P (with the proviso that when the phenyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C10-C16 aryl group optionally having one or more atoms and groups selected from Group (with the proviso that when the C10-C16 aryl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C6-C16 aryl group optionally having one or more atoms and groups selected from Group P (with the proviso that when the C6-C16 aryl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group (with the proviso that any one or more of $R^7$, $R^8$ and $R^9$ represent a C3-C5 cycloalkyl group or a C3-C5 halocycloalkyl group);

$R^{10}$ represents a methyl group; and

X represents an oxygen atom.

a tetrazolinone compound wherein $R^1$ represents an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, an C2-C12 acyl group optionally having one or more atoms and groups selected from Group P, or a hydrogen atom (with the proviso that when the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

represents a methyl group; and

X represents an oxygen atom.

a tetrazolinone compound wherein $R^1$ represents a group represented by a formula (2):

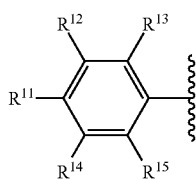

(2)

[wherein $R^{11}$ represents an aminosulfonyl group optionally having C1-C6 alkyl group or C6-C12 aryl group, an aminocarbonyl group optionally having C1-C6 alkyl group, a hydrogen atom, a halogen atom, an C1-C6 alkyl group, a C1-C6 haloalkyl group, an C2-C6 alkenyl group, a C2-C6 haloalkenyl group, an C2-C6 alkynyl group, C2-C6 haloalkynyl group, C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonylnyl group, a C6-C16 haloarylsulfonyl group, an C1-C6 alkylsulfinyl group, a C1-C6 haloalkylsulfinyl group, an C6-C16 arylsulfinyl group, or a C6-C16 haloarylsulfinyl group;

$R^{12}$, $R^{13}$, $R^{14}$ and $R^{15}$ represent independently of each other a hydrogen atom or a halogen atom];

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents a group represented by a formula (2):

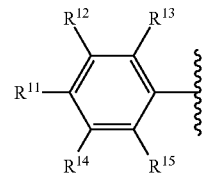

(2)

[wherein $R^{11}$ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{12}$, $R^{13}$, $R^{14}$ and $R^{15}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents a halogen atom, an C1-C3 alkyl group, a C1-C3 haloalkyl group, an C1-C3 alkoxy group or a C1-C3 haloalkoxy group;

$R^{10}$ represents a methyl group; and

X represents an oxygen atom.

a tetrazolinone compound wherein $R^1$ represents a group represented by a formula (2):

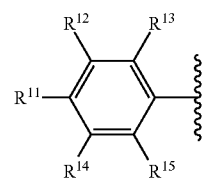

(2)

[wherein $R^{11}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkyl thio group, a nitro group or a cyano group;

$R^{12}$, $R^{13}$, $R^{14}$ and $R^{15}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents a halogen atom, an C1-C3 alkyl group, a C1-C3 haloalkyl group, an C1-C3 alkoxy group or a C1-C3 haloalkoxy group;

$R^{10}$ represents a methyl group; and

X represents an oxygen atom.

a tetrazolinone compound wherein $R^1$ represents a group represented by a formula (2):

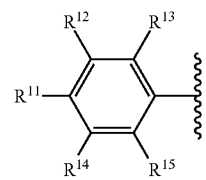

(2)

[wherein

R$^{11}$ represents a halogen atom, a methyl group, an ethyl group a methoxy group;

R$^{12}$, R$^{13}$, R$^{14}$ and R$^{15}$ represent independently of each other a hydrogen atom or fluorine atom];

R$^2$, R$^3$, R$^4$, R$^5$, R$^7$, R$^8$ and R$^9$ represent a hydrogen atom;

R$^6$ represents a chlorine atom, a bromine atom, a methyl group, an ethyl group or a methoxy group;

R$^{10}$ represents a methyl group; and

X represents an oxygen atom.

a tetrazolinone compound wherein

R$^1$ represents an C6-C16 aryl group optionally having one or more atoms and groups selected from Group P, an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

R$^2$ and R$^3$ represent independently of each other a hydrogen atom, an C1-C3 alkyl group, a C1-C3 haloalkyl group, an C2-C12 alkoxycarbonyl group, a hydroxycarbonyl group or a halogen atom;

R$^4$ and R$^5$ represent independently of each other a hydrogen atom, a halogen atom or an C1-C3 alkyl group;

R$^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

R$^7$, R$^8$ and R$^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

R$^{10}$ represents an C1-C6 alkyl group, a C1-C6 haloalkyl group, an C2-C6 alkenyl group, a C2-C6 haloalkenyl group, an C2-C6 alkoxyalkyl group, a C3-C6 cycloalkyl group or a C3-C6 halocycloalkyl group;

X represents an oxygen atom or a sulfur atom.

a tetrazolinone compound wherein

R$^1$ represents an C6-C16 aryl group optionally having one or more atoms and groups selected from Group P, C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P, C2-C12 acyl group optionally having one or more atoms and groups selected from Group P, or a hydrogen atom (with the proviso that when the C6-C16 aryl group, the C1-C12 alkyl group, the C3-C12 cycloalkyl group, the C2-C12 alkenyl group, the C3-C12 cycloalkenyl group, the C2-C12 alkynyl group or the C2-C12 acyl group has two or more atoms or groups selected from Group P, the substituent consisting of the atoms and the groups may be same or different to each other);

R$^2$, R$^3$, R$^4$ and R$^5$ represent a hydrogen atom;

R$^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

R$^7$, R$^8$ and R$^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

R$^{10}$ represents a methyl group; and

X represents an oxygen atom.

a tetrazolinone compound wherein

R$^1$ represents an C6-C16 aryl group optionally having one or more atoms and groups selected from Group P (with the proviso that when the C6-C16 aryl group has two or more atoms or groups selected from Group P, the substituent consisting of the atoms and the groups may be same or different to each other);

R$^2$, R$^3$, R$^4$ and R$^5$ represent a hydrogen atom;

R$^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C1-C12 alkyl group optionally having one or more atoms and groups selected from Group P, a C3-C12 cycloalkyl group optionally having one or more atoms and groups selected from Group P, an C2-C12 alkenyl group optionally having one or more atoms and groups selected from Group P, a C3-C12 cycloalkenyl group optionally having one or more atoms and groups selected from Group P, an C2-C12 alkynyl group optionally having one or more atoms and groups selected from Group P or an C2-C12 acyl group optionally having one or more atoms and groups selected from Group P (with the proviso that when the C1-C12 alkyl group, the C3-C12 cycloalkyl group, the C2-C12 alkenyl group, the C3-C12 cycloalkenyl group, the C2-C12 alkynyl group, or the C2-C12 acyl group has two or more atoms or groups selected from Group P, the substituent consisting of the atoms and the groups may be same or different to each other);

$R^2$, $R^3$, $R^4$ and $R^5$ represent a hydrogen atom;

$R^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom, a halogen atom, an C1-C4 alkyl group, a C1-C4 haloalkyl group, a C3-C5 cycloalkyl group, a C3-C5 halocycloalkyl group, an C1-C4 alkoxy group or a C1-C4 haloalkoxy group;

$R^{10}$ represents a methyl group; and

X represents an oxygen atom.

a tetrazolinone compound wherein $R^1$ represents an C6-C16 aryl group optionally having one or more atoms or groups selected from Group P1, an C1-C12 alkyl group, a C3-C12 cycloalkyl group, an C2-C12 acyl group or a hydrogen atom (with the proviso that when the C6-C16 aryl group has two or more atoms or groups selected from Group P1, the substituent consisting of the atoms and the groups may be same or different to each other);

$R^2$ and $R^3$ represent a hydrogen atom;

$R^4$ and $R^5$ represent a hydrogen atom;

$R^6$ represents an C1-C6 alkyl group, a C3-C6 cycloalkyl group, a halogen atom, a C1-C6 haloalkyl group, an C2-C6 alkenyl group, an C1-C6 alkoxy group, an C1-C6 alkylthio group, an C2-C6 alkynyl group, a nitro group, a cyano group, or a C5-C14 trialkylsilylethynyl group;

$R^7$, $R^8$ and $R^9$ represent independently of each other a hydrogen atom, a halogen atom or an C1-C4 alkyl group;

$R^{10}$ represents an C1-C6 alkyl group or an C2-C6 alkoxyalkyl group; and

X represents an oxygen atom or a sulfur atom;

Group P1: a halogen atom, an C1-C6 alkyl group, an C1-C6 alkoxy group, a C1-C6 haloalkoxy group, an C1-C6 alkylthio group, a C2-C6 haloacyl group, a nitro group and a cyano group.

a tetrazolinone compound wherein $R^1$ represents an C6-C16 aryl group optionally having one or more atoms or groups selected from Group P1, an C1-C12 alkyl group, a C3-C12 cycloalkyl group, an C2-C12 acyl group or a hydrogen atom (with the proviso that when the C6-C16 aryl group has two or more atoms or groups selected from Group P1, the substituent consisting of the atoms and the groups may be same or different to each other);

$R^2$ and $R^3$ represent a hydrogen atom;

$R^4$ and $R^5$ represent a hydrogen atom;

$R^6$ represents a C3-C6 cycloalkyl group, a C1-C6 haloalkyl group, an C2-C6 alkenyl group, an C1-C6 alkylthio group, an C2-C6 alkynyl group or a C5-C14 trialkylsilylethynyl group;

$R^7$, $R^8$ and $R^9$ represent independently of each other a hydrogen atom, a halogen atom or an C1-C4 alkyl group;

$R^{10}$ represents an C1-C6 alkyl group or an C2-C6 alkoxyalkyl group; and

X represents an oxygen atom.

a tetrazolinone compound wherein $R^1$ represents an C6-C16 aryl group optionally having one or more atoms or groups selected from Group P1, a C1-C12 alkyl group, a C3-C12 cycloalkyl group, an C2-C12 acyl group, or a hydrogen atom (with the proviso that when the C6-C16 aryl group has two or more atoms or groups selected from Group P1, the substituent consisting of the atoms and the groups may be same or different to each other);

$R^2$ and $R^3$ represent a hydrogen atom;

$R^4$ and $R^5$ represent a hydrogen atom;

$R^6$ represents an C1-C6 alkyl group, a halogen atom, an C1-C4 alkoxy group, a nitro group or a cyano group;

$R^7$, $R^8$ and $R^9$ represent independently of each other a hydrogen atom, a halogen atom or an C1-C4 alkyl group;

$R^{10}$ represents an C1-C6 alkyl group or an C2-C6 alkoxyalkyl group; and

X represents an oxygen atom.

a tetrazolinone compound wherein $R^1$ represents a group represented by a formula (2):

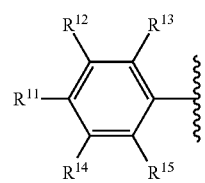

(2)

[wherein $R^{11}$ represents an aminosulfonyl group optionally having C1-C6 alkyl group or C6-C12 aryl group, an aminocarbonyl group optionally having an C1-C6 alkyl group, a hydrogen atom, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonylnyl group, a C6-C16 haloarylsulfonyl group, an C1-C6 alkylsulfinyl group, a C1-C6 haloalkylsulfinyl group, an C6-C16 arylsulfinyl group, or a C6-C16 haloarylsulfinyl group; and $R^{12}$, $R^{13}$, $R^{14}$ and $R^{15}$ represent independently of each other a hydrogen atom or a halogen atom];

$R^2$, $R^3$, $R^4$ and $R^5$ represent a hydrogen atom;

$R^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom or a fluorine atom $R^{10}$ represents a methyl group; and X represents an oxygen atom.

a tetrazolinone compound wherein $R^1$ represents a group represented by a formula (2):

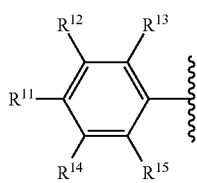

(2)

[wherein $R^{11}$ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent independently of each other a hydrogen atom or halogen atom];

$R^2$, $R^3$, $R^4$, $R^5$, $R^7$, $R^8$ and $R^9$ represent a hydrogen atom;

$R^6$ represents an C2-C3 alkenyl group, an C2-C3 alkynyl group, a C3-C4 cycloalkyl group, an C1-C2 alkylthio group, a C1-C2 haloalkylthio group or an C1-C4 alkylamino group;

$R^{10}$ represents a methyl group; and

X represents an oxygen atom.

a tetrazolinone compound wherein $R^1$ represents a group represented by a formula (2):

(2)

[wherein $R^{11}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, an C1-C3 haloalkylthio group, a nitro group or a cyano group; and $R^{12}$, $R^{13}$, $R^{14}$ and $R^{15}$ represent independently of each other a hydrogen atom or halogen atom];

$R^2$, $R^3$, $R^4$, $R^5$, $R^7$, $R^8$ and $R^9$ represent a hydrogen atom;

$R^6$ represents an C2-C3 alkenyl group, an C2-C3 alkynyl group or a C3-C4 cycloalkyl group;

$R^{10}$ represents a methyl group; and

X represents an oxygen atom.

a tetrazolinone compound wherein $R^1$ represents a group represented by a formula (2):

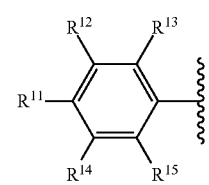

(2)

[wherein $R^{11}$ represents a halogen atom, a methyl group, an ethyl group or a methoxy group; and $R^{12}$, $R^{13}$, $R^{14}$ and $R^{15}$ represent independently of each other a hydrogen atom or a fluorine atom];

$R^2$, $R^3$, $R^4$, $R^5$, $R^7$, $R^8$ and $R^9$ represent a hydrogen atom;

$R^6$ represents a cyclopropyl group;

$R^{10}$ represents a methyl group; and

X represents an oxygen atom.

a tetrazolinone compound wherein
R¹ represents a group represented by a formula (2):

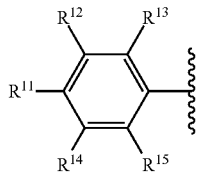

(2)

[wherein
R¹¹ represents a halogen atom, an C1-C6 alkyl group, a C1-C6 haloalkyl group, an C1-C6 alkoxy group, a C1-C6 haloalkoxy group, an C1-C6 alkylthio group, a cyano group, a nitro group or a hydrogen atom; and
R¹², R¹³, R¹⁴ and R¹⁵ represent independently of each other a halogen atom or a hydrogen atom];
R², R³, R⁴, R⁵ and R⁸ represent a hydrogen atom;
R⁶ represents an C1-C6 alkyl group, a halogen atom, a C1-C6 haloalkyl group, an C2-C6 alkenyl group, an C2-C6 alkynyl group, a C3-C6 cycloalkyl group, an C1-C6 alkoxy group, an C1-C6 alkylthio group, a cyano group or a nitro group;
R⁷ represents a halogen atom or a hydrogen atom;
R⁹ represents a halogen atom, an C1-C4 alkyl group or a hydrogen atom;
R¹⁰ represents an C1-C6 alkyl group or an C2-C6 alkoxyalkyl group; and
X represents an oxygen atom or a sulfur atom.
a tetrazolinone compound wherein
R¹ represents a group represented by a formula (2):

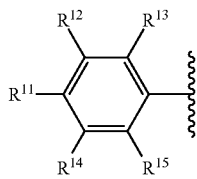

(2)

[wherein
R¹¹ represents a fluorine atom, a chlorine atom, a bromine atom, a methyl group, a methoxy group, an ethoxy group, a methylthio group, a trifluoromethoxy group, a cyano group, a nitro group, a trifluoromethylcarbonyl group or a hydrogen atom; and
R¹², R¹³, R¹⁴ and R¹⁵ represent independently of each other fluorine atom or a hydrogen atom];
R², R³, R⁴, R⁵ and R⁸ represent a hydrogen atom;
R⁶ represents a methyl group, an ethyl group, a propyl group, an isopropyl group, a butyl group, a fluorine atom, a chlorine atom, a bromine atom, an iodine atom, a vinyl group, a propenyl group, an ethynyl group, a 2-trimethylsilylethynyl group, a cyclopropyl group, a difluoromethyl group, a trifluoromethyl group, a methoxy group, an ethoxy group, a methylthio group, a cyano group or a nitro group;
R⁷ represents a fluorine atom or a hydrogen atom;
R⁹ represents a fluorine atom, a methyl group or a hydrogen atom;
R¹⁰ represents a methyl group, an ethyl group or a methoxymethyl group; and
X represents an oxygen atom or a sulfur atom.

a tetrazolinone compound wherein
R¹ represents a group represented by a formula (2):

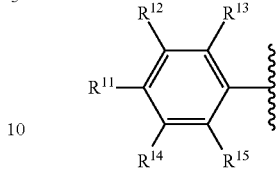

(2)

[wherein
R¹¹ represents a halogen atom, an C1-C6 alkyl group, a C1-C6 haloalkyl group, an C1-C6 alkoxy group, a C1-C6 haloalkoxy group, an C1-C6 alkylthio group, a cyano group, a nitro group or a hydrogen atom; and
R¹², R¹³, R¹⁴ and R¹⁵ represent independently of each other a halogen atom or a hydrogen atom];
R², R³, R⁴, R⁵ and R⁸ represent a hydrogen atom;
R⁶ represents an C1-C6 alkyl group;
R⁷ represents a halogen atom or a hydrogen atom;
R⁹ represents a halogen atom, an C1-C4 alkyl group or a hydrogen atom;
R¹⁰ represents an C1-C6 alkyl group or an C2-C6 alkoxyalkyl group; and
X represents an oxygen atom or a sulfur atom.
a tetrazolinone compound wherein
R¹ represents a group represented by a formula (2):

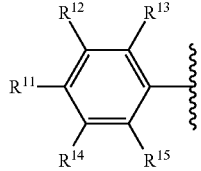

(2)

[wherein
R¹¹ represents a fluorine atom, a chlorine atom, a bromine atom, a methyl group, a methoxy group, an ethoxy group, a methylthio group, a trifluoromethoxy group, a cyano group, a nitro group, a trifluoromethylcarbonyl group or a hydrogen atom; and
R¹², R¹³, R¹⁴ and R¹⁵ represent independently of each other a fluorine atom or a hydrogen atom];
R², R³, R⁴, R⁵ and R⁸ represent a hydrogen atom;
R⁶ represents a methyl group or an ethyl group;
R⁷ represents a fluorine atom or a hydrogen atom;
R⁹ represents a fluorine atom, a methyl group or a hydrogen atom;
R¹⁰ represents a methyl group, an ethyl group or a methoxymethyl group; and
X represents an oxygen atom or a sulfur atom.
a tetrazolinone compound wherein
R¹ represents a group represented by a formula (2):

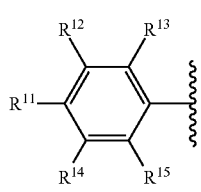

(2)

[wherein
R$^{11}$ represents a halogen atom, an C1-C6 alkyl group, a C1-C6 haloalkyl group, an C1-C6 alkoxy group, a C1-C6 haloalkoxy group, an C1-C6 alkylthio group, a cyano group, a nitro group or a hydrogen atom; and
R$^{12}$, R$^{13}$, R$^{14}$ and R$^{15}$ represent independently of each other a halogen atom or a hydrogen atom];
R$^2$, R$^3$, R$^4$, R$^5$ and R$^8$ represent a hydrogen atom;
R$^6$ represents a methyl group;
R$^7$ represents a halogen atom or a hydrogen atom;
R$^9$ represents a halogen atom, an C1-C4 alkyl group or a hydrogen atom;
R$^{10}$ represents an C1-C6 alkyl group or an C2-C6 alkoxyalkyl group; and
X represents an oxygen atom or a sulfur atom.
a tetrazolinone compound wherein
R$^1$ represents a group represented by a formula (2):

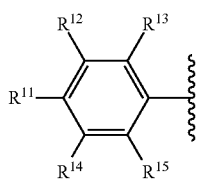
(2)

[wherein
R$^{11}$ represents a fluorine atom, a chlorine atom, a bromine atom, a methyl group, a methoxy group, an ethoxy group, a methylthio group, a trifluoromethoxy group, a cyano group, a nitro group or a hydrogen atom; and
R$^{12}$, R$^{13}$, R$^{14}$ and R$^{15}$ represent independently of each other a fluorine atom or a hydrogen atom];
R$^2$, R$^3$, R$^4$, R$^5$ and R$^8$ represent a hydrogen atom;
R$^6$ represents a methyl group;
R$^7$ represents a fluorine atom or a hydrogen atom;
R$^9$ represents a fluorine atom, a methyl group or a hydrogen atom;
R$^{10}$ represents a methyl group, an ethyl group or a methoxymethyl group; and
X represents an oxygen atom or a sulfur atom.
a tetrazolinone compound wherein
R$^1$ represents a group represented by a formula (2):

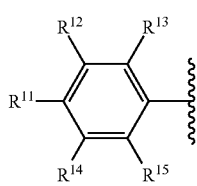
(2)

[wherein
R$^{11}$ represents a halogen atom, an C1-C6 alkyl group, or an C1-C6 alkoxy group; and
R$^{12}$, R$^{13}$, R$^{14}$ and R$^{15}$ represent a hydrogen atom];
R$^2$, R$^3$, R$^4$, R$^5$, R$^7$, R$^8$ and R$^9$ represent a hydrogen atom;
R$^6$ represents a C3-C6 cycloalkyl group;
R$^{10}$ represents an C1-C6 alkyl group; and
X represents an oxygen atom.

a tetrazolinone compound wherein
R$^1$ represents a group represented by a formula (2):

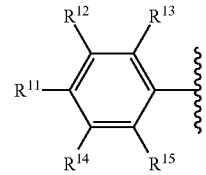
(2)

[wherein
R$^{11}$ represents a fluorine atom, a chlorine atom, a bromine atom, a methyl group or a methoxy group; and
R$^{12}$, R$^{13}$, R$^{14}$ and R$^{15}$ represent a hydrogen atom];
R$^2$, R$^3$, R$^4$, R$^5$, R$^7$, R$^8$ and R$^9$ represent a hydrogen atom;
R$^6$ represents a cyclopropyl group;
R$^{10}$ represents a methyl group; and
X represents an oxygen atom.
a tetrazolinone compound wherein
R$^1$ represents a group represented by a formula (2):

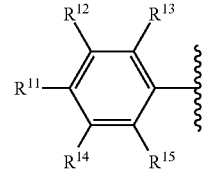
(2)

[wherein
R$^{11}$ represents a halogen atom, an C1-C6 alkyl group, or an C1-C6 alkoxy group; and
R$^{12}$, R$^{13}$, R$^{14}$ and R$^{15}$ represent a hydrogen atom];
R$^2$, R$^3$, R$^4$, R$^5$, R$^7$, R$^8$ and R$^9$ represent a hydrogen atom;
R$^6$ represents a halogen atom;
R$^{10}$ represents an C1-C6 alkyl group; and
X represents an oxygen atom.
a tetrazolinone compound wherein
R$^1$ represents a group represented by a formula (2):

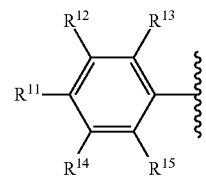
(2)

[wherein
R$^{11}$ represents a fluorine atom, a chlorine atom, a bromine atom, a methyl group or a methoxy group; and
R$^{12}$, R$^{13}$, R$^{14}$ and R$^{15}$ represent a hydrogen atom];
R$^2$, R$^3$, R$^4$, R$^5$, R$^7$, R$^8$ and R$^9$ represent a hydrogen atom;
R$^6$ represents a fluorine atom, a chlorine atom, a bromine atom or an iodine atom;
R$^{10}$ represents a methyl group; and
X represents an oxygen atom.

a tetrazolinone compound wherein
$R^1$ represents a group represented by a formula (2):

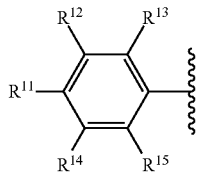

(2)

[wherein
$R^{11}$ represents a halogen atom, an C1-C6 alkyl group, an C1-C6 alkoxy group or a hydrogen atom; and
$R^{12}$, $R^{13}$, $R^{14}$ and $R^{15}$ represent a hydrogen atom];
$R^2$, $R^3$, $R^4$, $R^5$, $R^7$, $R^8$ and $R^9$ represent a hydrogen atom;
$R^6$ represents an C1-C6 alkoxy group;
$R^{10}$ represents an C1-C6 alkyl group; and
X represents an oxygen atom.
a tetrazolinone compound wherein
$R^1$ represents a group represented by a formula (2):

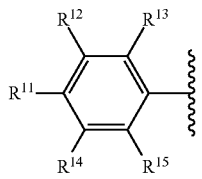

(2)

[wherein
$R^{11}$ represents a fluorine atom, a chlorine atom, a bromine atom, a methyl group, a methoxy group or a hydrogen atom; and
$R^{12}$, $R^{13}$, $R^{14}$ and $R^{15}$ represent a hydrogen atom];
$R^2$, $R^3$, $R^4$, $R^5$, $R^7$, $R^8$ and $R^9$ represent a hydrogen atom;
$R^6$ represents a methoxy group or an ethoxy group;
$R^{10}$ represents a methyl group; and
X represents an oxygen atom.
a tetrazolinone compound wherein
$R^1$ represents a group represented by a formula (2):

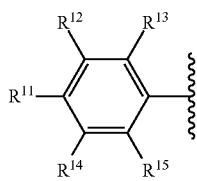

(2)

[wherein
$R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and
$R^{12}$, $R^{13}$, $R^{14}$ and $R^{15}$ represent a hydrogen atom or a halogen atom];
$R^2$, $R^3$, $R^4$, $R^5$, $R^7$, $R^8$ and $R^9$ represent a hydrogen atom;
$R^6$ represents an C1-C3 alkyl group;
$R^{10}$ represents a methyl group; and
X represents an oxygen atom.

a tetrazolinone compound wherein
$R^1$ represents a group represented by a formula (2):

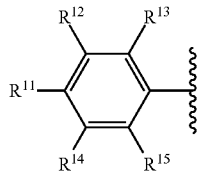

(2)

[wherein
$R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and
$R^{12}$, $R^{13}$, $R^{14}$ and $R^{15}$ represent a hydrogen atom or a halogen atom];
$R^2$, $R^3$, $R^4$, $R^5$, $R^7$, $R^8$ and $R^9$ represent a hydrogen atom;
$R^6$ represents a C3-C4 cycloalkyl group;
$R^{10}$ represents a methyl group; and
X represents an oxygen atom.
a tetrazolinone compound wherein
$R^1$ represents a group represented by a formula (2):

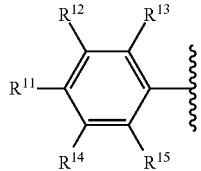

(2)

[wherein
$R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and
$R^{12}$, $R^{13}$, $R^{14}$ and $R^{15}$ represent a hydrogen atom or a halogen atom];
$R^2$, $R^3$, $R^4$, $R^5$, $R^7$, $R^8$ and $R^9$ represent a hydrogen atom;
$R^6$ represents a halogen atom;
$R^{10}$ represents a methyl group; and
X represents an oxygen atom.
a tetrazolinone compound wherein
$R^1$ represents a group represented by a formula (2):

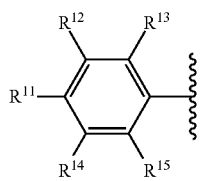

(2)

[wherein
$R^{10}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents a C1-C3 haloalkyl group;

$R^{10}$ represents a methyl group; and

X represents an oxygen atom.

a tetrazolinone compound wherein $R^1$ represents a group represented by a formula (2):

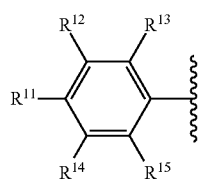

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents an C2-C3 alkenyl group;

$R^{10}$ represents a methyl group; and

X represents an oxygen atom.

a tetrazolinone compound wherein $R^1$ represents a group represented by a formula (2):

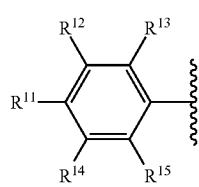

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents an C1-C3 alkoxy group;

$R^{10}$ represents a methyl group; and

X represents an oxygen atom.

a tetrazolinone compound wherein $R^1$ represents a group represented by a formula (2):

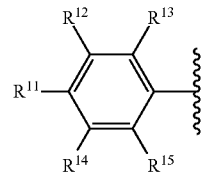

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents an C1-C2 alkylthio group;

$R^{10}$ represents a methyl group; and

X represents an oxygen atom.

a tetrazolinone compound wherein $R^1$ represents a group represented by a formula (2):

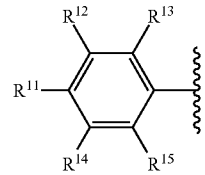

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents an C2-C3 alkynyl group;

$R^{10}$ represents a methyl group; and

X represents an oxygen atom.

a tetrazolinone compound wherein $R^1$ represents a group represented by a formula (2):

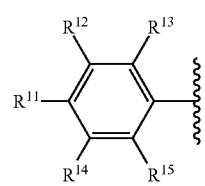

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents a C1-C3 haloalkoxy group;

$R^{10}$ represents a methyl group; and

X represents an oxygen atom.

a tetrazolinone compound wherein $R^1$ represents a group represented by a formula (2):

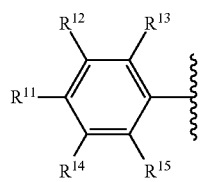

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents a C1-C2 haloalkylthio group;

$R^{10}$ represents a methyl group; and

X represents an oxygen atom.

a tetrazolinone compound wherein $R^1$ represents a group represented by a formula (2):

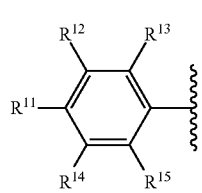

(2)

[wherein $R^{11}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{12}$, $R^{13}$, $R^{14}$ and $R^{15}$ represent a hydrogen atom or a halogen atom];

$R^2$, $R^3$, $R^4$, $R^5$, $R^7$, $R^8$ and $R^9$ represent a hydrogen atom;

$R^6$ represents an C1-C4 alkylamino group;

$R^{10}$ represents a methyl group; and

X represents an oxygen atom.

a tetrazolinone compound wherein $R^1$ represents a group represented by a formula (2):

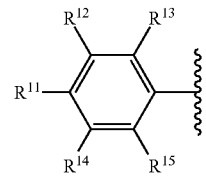

(2)

[wherein $R^{11}$ represents a halogen atom, a methyl group, an ethyl group or a methoxy group; and $R^{12}$, $R^{13}$, $R^{14}$ and $R^{15}$ represent a hydrogen atom or a fluorine atom];

$R^2$, $R^3$, $R^4$, $R^5$, $R^7$, $R^8$ and $R^9$ represent a hydrogen atom;

$R^6$ represents a methyl group;

represents a methyl group; and

X represents an oxygen atom.

a tetrazolinone compound wherein $R^1$ represents a group represented by a formula (2):

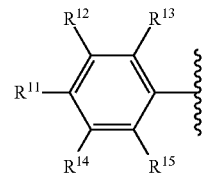

(2)

[wherein $R^{11}$ represents a halogen atom, a methyl group, an ethyl group or a methoxy group; and $R^{12}$, $R^{13}$, $R^{14}$ and $R^{15}$ represent a hydrogen atom or a fluorine atom];

$R^2$, $R^3$, $R^4$, $R^5$, $R^7$, $R^8$ and $R^9$ represent a hydrogen atom;

$R^6$ represents a chlorine atom;

$R^{10}$ represents a methyl group; and

X represents an oxygen atom.

a tetrazolinone compound wherein $R^1$ represents a group represented by a formula (2):

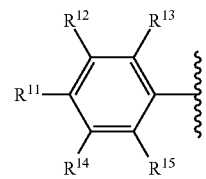

(2)

[wherein $R^{11}$ represents a halogen atom, a methyl group, an ethyl group or a methoxy group; and $R^{12}$, $R^{13}$, $R^{14}$ and $R^{15}$ represent a hydrogen atom or a fluorine atom];

$R^2$, $R^3$, $R^4$, $R^5$, $R^7$, $R^8$ and $R^9$ represent a hydrogen atom;

$R^6$ represents a bromine atom;

$R^{10}$ represents a methyl group; and

X represents an oxygen atom.

a tetrazolinone compound wherein
R¹ represents a group represented by a formula (2):

$$\text{(2)}$$

R¹¹—[benzene ring with R¹², R¹³, R¹⁴, R¹⁵ substituents and wavy bond]

[wherein
R¹¹ represents a halogen atom, a methyl group, an ethyl group or a methoxy group; and
R¹², R¹³, R¹⁴ and R¹⁵ represent a hydrogen atom or a fluorine atom];
R², R³, R⁴, R⁵, R⁷, R⁸ and R⁹ represent a hydrogen atom;
R⁶ represents an ethyl group;
R¹⁰ represents a methyl group; and
X represents an oxygen atom.

a tetrazolinone compound wherein
R¹ represents a group represented by a formula (2):

$$\text{(2)}$$

R¹¹—[benzene ring with R¹², R¹³, R¹⁴, R¹⁵ substituents and wavy bond]

[wherein
R¹¹ represents a halogen atom, a methyl group, an ethyl group or a methoxy group;
R¹², R¹³, R¹⁴ and R¹⁵ represent a hydrogen atom or a fluorine atom];
R², R³, R⁴, R⁵, R⁷, R⁸ and R⁹ represent a hydrogen atom;
R⁶ represents a methoxy group;
R¹⁰ represents a methyl group; and
X represents an oxygen atom.

a tetrazolinone compound wherein
R¹ represents a group represented by a formula (30):

$$\text{(30)}$$

R³⁰⁰—[benzene ring with R³¹⁰, R³²⁰, R³³⁰, R³⁴⁰ substituents and wavy bond]

[wherein
R³¹⁰ represents an aminosulfonyl group optionally having C1-C6 alkyl group or C6-C12 aryl group, an aminocarbonyl group optionally having C1-C6 alkyl group, a hydrogen atom, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonylnyl group, a C6-C16 haloarylsulfonyl group, an C1-C6 alkylsulfinyl group, a C1-C6 haloalkylsulfinyl group, an C6-C16 arylsulfinyl group, or a C6-C16 haloarylsulfinyl group; and
R³⁰⁰, R³²⁰, R³³⁰ and R³⁴⁰ represent independently of each other a hydrogen atom or a halogen atom];
R², R³, R⁴ and R⁵ represent a hydrogen atom;
R⁶ represents a halogen atom, an C1-C6 alkyl group, C1-C6 haloalkyl group, an C1-C6 alkoxy group, a C1-C6 haloalkoxy group, a nitro group or a cyano group;
R⁷, R⁸ and R⁹ represent independently of each other a hydrogen atom or a fluorine atom;
R¹⁰ represents a methyl group; and
X represents an oxygen atom.

a tetrazolinone compound wherein
R¹ represents a group represented by a formula (3):

$$\text{(3)}$$

R³⁰—[benzene ring with R³¹, R³², R³³, R³⁴ substituents and wavy bond]

[wherein
R³¹ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and
R³⁰, R³², R³³ and R³⁴ represent independently of each other a hydrogen atom or a halogen atom];
R², R³, R⁴, R⁵, R⁷, R⁸ and R⁹ represent a hydrogen atom;
R⁶ represents a halogen atom, an C1-C3 alkyl group, a C1-C3 haloalkyl group, an C1-C3 alkoxy group or a C1-C3 haloalkoxy group;
R¹⁰ represents a methyl group; and
X represents an oxygen atom.

a tetrazolinone compound wherein
R¹ represents a group represented by a formula (3):

$$\text{(3)}$$

R³⁰—[benzene ring with R³¹, R³², R³³, R³⁴ substituents and wavy bond]

[wherein $R^{31}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkyl thio group, a nitro group or a cyano group; and $R^{30}$, $R^{32}$, $R^{33}$ and $R^{34}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents a halogen atom, an C1-C3 alkyl group, a C1-C3 haloalkyl group, an C1-C3 alkoxy group or a C1-C3 haloalkoxy group;

$R^{10}$ represents a methyl group; and

X represents an oxygen atom.

a tetrazolinone compound wherein $R^1$ represents a group represented by a formula (3):

(3)

[wherein $R^{31}$ represents a halogen atom, a methyl group, an ethyl group or a methoxy group;

$R^{30}$, $R^{32}$, $R^{33}$ and $R^{34}$ represent independently of each other a hydrogen atom or a fluorine atom];

$R^2$, $R^3$, $R^4$, $R^5$, $R^7$, $R^8$ and $R^9$ represent a hydrogen atom;

$R^6$ represents a chlorine atom, a bromine atom, a methyl group, an ethyl group or a methoxy group;

$R^{10}$ represents a methyl group; and

X represents an oxygen atom.

a tetrazolinone compound wherein $R^1$ represents a group represented by a formula (30):

(30)

[wherein $R^{310}$ represents an aminosulfonyl group optionally having C1-C6 alkyl group or C6-C12 aryl group, an aminocarbonyl group optionally having C1-C6 alkyl group, a hydrogen atom, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, an C3-C6 alkenylthio group, an C3-C6 alkynylthio group, a C3-C6 haloalkenylthio group, a C3-C6 haloalkynylthio group, a C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonylnyl group, a C6-C16 haloarylsulfonyl group, an C1-C6 alkylsulfinyl group, a C1-C6 haloalkylsulfinyl group, an C6-C16 arylsulfinyl group or a C6-C16 haloarylsulfinyl group; and $R^{300}$, $R^{320}$, $R^{330}$ and $R^{340}$ represent independently of each other a hydrogen atom or a halogen atom];

$R^2$, $R^3$, $R^4$ and $R^5$ represent a hydrogen atom;

$R^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents a group represented by a formula (3):

(3)

[wherein $R^{31}$ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{30}$, $R^{32}$, $R^{33}$ and $R^{34}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents an C2-C3 alkenyl group, an C2-C3 alkynyl group, a C3-C4 cycloalkyl group, an C1-C2 alkylthio group, a C1-C2 haloalkylthio group or an C1-C4 alkylamino group;

$R^{10}$ represents a methyl group; and

X represents an oxygen atom.

a tetrazolinone compound wherein $R^1$ represents a group represented by a formula (3):

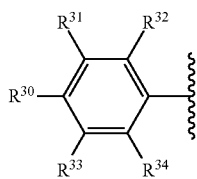

(3)

[wherein $R^{31}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkyl thio group, a nitro group or a cyano group; and $R^{30}$, $R^{32}$, $R^{33}$ and $R^{34}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents an C2-C3 alkenyl group, an C2-C3 alkynyl group or a C3-C4 cycloalkyl group;

$R^{10}$ represents a methyl group; and

X represents an oxygen atom.

a tetrazolinone compound wherein $R^1$ represents a group represented by a formula (3):

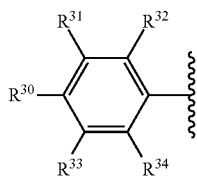

(3)

[wherein $R^{31}$ represents a halogen atom, a methyl group, an ethyl group or a methoxy group; and $R^{30}$, $R^{32}$, $R^{33}$ and $R^{34}$ represent independently of each other a hydrogen atom or a fluorine atom];

$R^2$, $R^3$, $R^4$, $R^5$, $R^7$, $R^8$ and $R^9$ represent a hydrogen atom;

$R^6$ represents a cyclopropyl group;

$R^{10}$ represents a methyl group; and

X represents an oxygen atom.

a tetrazolinone compound wherein $R^1$ represents a group represented by a formula (3):

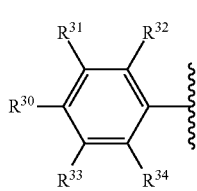

(3)

[wherein $R^{31}$ represents a halogen atom, an C1-C6 alkyl group, an C1-C6 alkoxy group, an C1-C6 alkylthio group or a hydrogen atom; and $R^{30}$, $R^{32}$, $R^{33}$ and $R^{34}$ represent independently of each other a halogen atom or a hydrogen atom];

$R^2$, $R^3$, $R^4$, $R^5$, $R^7$, $R^8$ and $R^9$ represent a hydrogen atom;

$R^6$ represents an C1-C6 alkyl group;

$R^{10}$ represents an C1-C6 alkyl group; and

X represents an oxygen atom.

a tetrazolinone compound wherein $R^1$ represents a group represented by a formula (3):

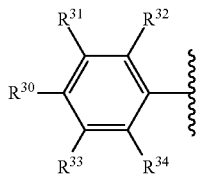

(3)

[wherein $R^{31}$ represents a fluorine atom, a chlorine atom, a bromine atom, a methyl group, a methoxy group, a methylthio group or a hydrogen atom; and $R^{30}$, $R^{32}$, $R^{33}$ and $R^{34}$ represent independently of each other a fluorine atom or a hydrogen atom];

$R^2$, $R^3$, $R^4$, $R^5$, $R^7$, $R^8$ and $R^9$ represent a hydrogen atom;

$R^6$ represents a methyl group;

$R^{10}$ represents a methyl group; and

X represents an oxygen atom.

a tetrazolinone compound wherein $R^1$ represents a group represented by a formula (3):

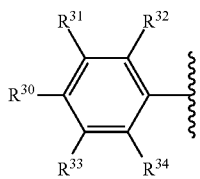

(3)

[wherein $R^{31}$ represents a halogen atom, an C1-C6 alkyl group, an C1-C6 alkoxy group, an C1-C6 alkylthio group or a hydrogen atom; and $R^{30}$, $R^{32}$, $R^{33}$ and $R^{34}$ represent independently of each other a halogen atom or a hydrogen atom];

$R^2$, $R^3$, $R^4$, $R^5$, $R^7$, $R^8$ and $R^9$ represent a hydrogen atom;

$R^6$ represents a methyl group;

$R^{10}$ represents an C1-C6 alkyl group; and

X represents an oxygen atom.

a tetrazolinone compound wherein $R^1$ represents a group represented by a formula (40):

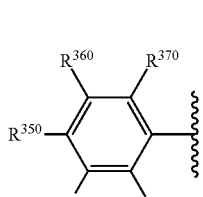

(40)

[wherein $R^{370}$ represents an aminosulfonyl group optionally having C1-C6 alkyl group or C6-C12 aryl group, an aminocarbonyl group optionally having C1-C6 alkyl group, a hydrogen atom, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonylnyl group, a C6-C16 haloarylsulfonyl group, an C1-C6 alkylsulfinyl group, a C1-C6 haloalkylsulfinyl group, an C6-C16 arylsulfinyl group or a C6-C16 haloarylsulfinyl group; and $R^{350}$, $R^{360}$, $R^{380}$ and $R^{390}$ represent independently of each other a hydrogen atom or halogen atom];

$R^2$, $R^3$, $R^4$ and $R^5$ represent a hydrogen atom;

$R^6$ represents a halogen atom, an C1-C6 alkyl group, a C1-C6 haloalkyl group, an C1-C6 alkoxy group, a C1-C6 haloalkoxy group, a nitro group or a cyano group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents a group represented by a formula (4):

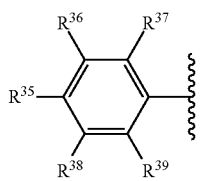

(4)

[wherein $R^{37}$ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{35}$, $R^{36}$, $R^{38}$ and $R^{39}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents a halogen atom, an C1-C3 alkyl group, a C1-C3 haloalkyl group, an C1-C3 alkoxy group or a C1-C3 haloalkoxy group;

$R^{10}$ represents a methyl group; and

X represents an oxygen atom.

a tetrazolinone compound wherein $R^1$ represents a group represented by a formula (4):

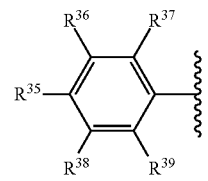

(4)

[wherein $R^{37}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and $R^{35}$, $R^{36}$, $R^{38}$ and $R^{39}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents a halogen atom, an C1-C3 alkyl group, a C1-C3 haloalkyl group, an C1-C3 alkoxy group or a C1-C3 haloalkoxy group;

$R^{10}$ represents a methyl group; and

X represents an oxygen atom.

a tetrazolinone compound wherein $R^1$ represents a group represented by a formula (4):

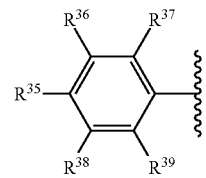

(4)

[wherein $R^{37}$ represents a halogen atom, a methyl group, an ethyl group or a methoxy group; and $R^{35}$, $R^{36}$, $R^{38}$ and $R^{39}$ represent independently of each other a hydrogen atom or a fluorine atom];

$R^2$, $R^3$, $R^4$, $R^5$, $R^7$, $R^8$ and $R^9$ represent a hydrogen atom;

$R^6$ represents a chlorine atom, a bromine atom, a methyl group, an ethyl group or a methoxy group;

$R^{10}$ represents a methyl group; and

X represents an oxygen atom.

a tetrazolinone compound wherein $R^1$ represents a group represented by a formula (40):

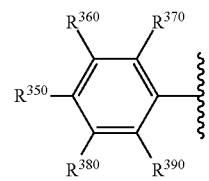

(40)

[wherein $R^{370}$ represents an aminosulfonyl group optionally having C1-C6 alkyl group or C6-C12 aryl group, an aminocarbonyl group optionally having C1-C6 alkyl group, a hydrogen atom, a halogen atom, an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkoxy group, a C1-C6 haloalkoxy group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, a hydroxycarbonyl group, a formyl group, an C2-C6 alkoxycarbonyl group, a nitro group, a cyano group, a hydroxyl group, an C6-C16 aryl group, a C6-C16 haloaryl group, an C6-C16 aryloxy group, a C6-C16 haloaryloxy group, an C6-C16 arylthio group, a C6-C16 haloarylthio group, an C7-C18 aralkyl group, a C7-C18 haloaralkyl group, an C7-C18 arylalkoxy group, a C7-C18 haloarylalkoxy group, a thiol group, a pentafluorosulfuranyl group, a C3-C12 trialkylsilyl group, a C5-C14 trialkylsilylethynyl group, an C1-C6 alkylsulfonyl group, a C1-C6 haloalkylsulfonyl group, an C6-C16 arylsulfonylnyl group, a C6-C16 haloarylsulfonyl group, an C1-C6 alkylsulfinyl group, a C1-C6 haloalkylsulfinyl group, an C6-C16 arylsulfinyl group or C6-C16 haloarylsulfinyl group; and $R^{350}$, $R^{360}$, $R^{380}$ and $R^{390}$ represent independently of each other a hydrogen atom or a halogen atom];

$R^2$, $R^3$, $R^4$ and $R^5$ represent a hydrogen atom;

$R^6$ represents an aminocarbonyl group optionally having C1-C6 alkyl group, an C2-C6 alkenyl group, a C2-C6 haloalkenyl group, an C2-C6 alkynyl group, a C2-C6 haloalkynyl group, a C3-C6 cycloalkyl group, a C3-C6 halocycloalkyl group, an C1-C6 alkylthio group, a C1-C6 haloalkylthio group, a C3-C6 cycloalkyloxy group, a C3-C6 halocycloalkyloxy group, a C3-C6 cycloalkylthio group, an C3-C6 alkenyloxy group, an C3-C6 alkynyloxy group, a C3-C6 haloalkenyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C2-C6 acyl group, a C2-C6 haloacyl group, an C2-C6 acyloxy group, an C2-C6 acylthio group, an C2-C6 alkoxycarbonyl group, a hydroxyl group, a thiol group, an amino group, an C1-C6 alkylamino group, a pentafluorosulfuranyl group, a C3-C9 trialkylsilyl group, a C5-C14 trialkylsilylethynyl group, an C1-C4 alkylsulfonyl group, a C1-C4 haloalkylsulfonyl group, an C1-C4 alkylsulfinyl group, a C1-C4 haloalkylsulfinyl group, an C2-C5 alkoxyalkyl group or an C2-C5 alkylthioalkyl group;

$R^7$, $R^8$ and $R^9$ represent independently of each other a hydrogen atom or a fluorine atom;

$R^{10}$ represents a methyl group; and

X represents an oxygen atom.

a tetrazolinone compound wherein $R^1$ represents a group represented by a formula (4):

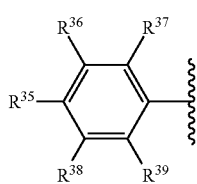

(4)

[wherein $R^{37}$ represents a hydrogen atom, a halogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group; and $R^{35}$, $R^{36}$, $R^{38}$ and $R^{39}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents an C2-C3 alkenyl group, an C2-C3 alkynyl group, a C3-C4 cycloalkyl group, an C1-C2 alkylthio group, a C1-C2 haloalkylthio group or an C1-C4 alkylamino group;

$R^{10}$ represents a methyl group; and

X represents an oxygen atom.

a tetrazolinone compound wherein $R^1$ represents a group represented by a formula (4):

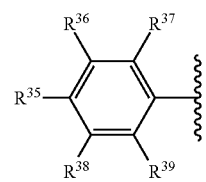

(4)

[wherein $R^{37}$ represents a hydrogen atom, a halogen atom, an C1-C3 alkyl group, a C1-C3 haloalkyl group, an C1-C3 alkoxy group, a C1-C3 haloalkoxy group, an C1-C3 alkylthio group, a C1-C3 haloalkylthio group, a nitro group or a cyano group; and $R^{35}$, $R^{36}$, $R^{38}$ and $R^{39}$ represent independently of each other a hydrogen atom or a halogen atom];

$R^2$, $R^3$, $R^4$, $R^5$, $R^7$, $R^8$ and $R^9$ represent a hydrogen atom;

$R^6$ represents an C2-C3 alkenyl group, an C2-C3 alkynyl group or a C3-C4 cycloalkyl group;

$R^{10}$ represents a methyl group; and

X represents an oxygen atom.

a tetrazolinone compound wherein $R^1$ represents a group represented by a formula (4):

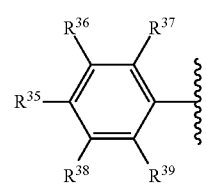

(4)

[wherein $R^{37}$ represents a halogen atom, a methyl group, an ethyl group or a methoxy group; and $R^{35}$, $R^{36}$, $R^{38}$ and $R^{39}$ represent independently of each other a hydrogen atom or a fluorine atom];

$R^2$, $R^3$, $R^4$, $R^5$, $R^7$, $R^8$ and $R^9$ represent a hydrogen atom;

$R^6$ represents an cyclopropyl group;

$R^{10}$ represents a methyl group; and

X represents an oxygen atom.

a tetrazolinone compound wherein
R¹ represents a group represented by a formula (4):

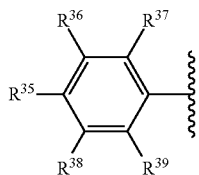
(4)

[wherein
R³⁷ represents a halogen atom, an C1-C6 alkyl group, an C1-C6 alkoxy group, an C1-C6 alkylthio group or a hydrogen atom; and
R³⁵, R³⁶, R³⁸ and R³⁹ represent independently of each other a halogen atom or a hydrogen atom];
R², R³, R⁴, R⁵, R⁷, R⁸ and R⁹ represent a hydrogen atom;
R⁶ represents an C1-C6 alkyl group, a halogen atom, a C3-C6 cycloalkyl group or an C1-C6 alkoxy group;
R¹⁰ represents an C1-C6 alkyl group; and
X represents an oxygen atom.

a tetrazolinone compound wherein
R¹ represents a group represented by a formula (4):

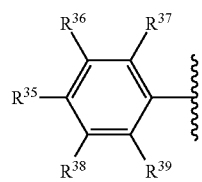
(4)

[wherein
R³⁷ represents a fluorine atom, a chlorine atom, a bromine atom, a methyl group, a methoxy group, a methylthio group or a hydrogen atom; and
R³⁵, R³⁶, R³⁸ and R³⁹ represent a hydrogen atom];
R², R³, R⁴, R⁵, R⁷, R⁸ and R⁹ represent a hydrogen atom;
R⁶ represents a methyl group, an ethyl group, a chlorine atom, a cyclopropyl group or a methoxy group;
R¹⁰ represents a methyl group; and
X represents an oxygen atom.

a tetrazolinone compound wherein
R¹ represents a group represented by a formula (4):

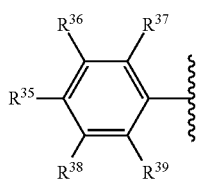
(4)

[wherein
R³⁷ represents a halogen atom, an C1-C6 alkyl group, an C1-C6 alkoxy group, an C1-C6 alkylthio group or a hydrogen atom; and
R³⁵, R³⁶, R³⁸ and R³⁹ represent independently of each other a halogen atom or a hydrogen atom];
R², R³, R⁴, R⁵, R⁷, R⁸ and R⁹ represent a hydrogen atom;
R⁶ represents an C1-C6 alkyl group;
R¹⁰ represents an C1-C6 alkyl group; and
X represents an oxygen atom.

a tetrazolinone compound wherein
R¹ represents a group represented by a formula (4):

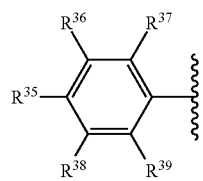
(4)

[wherein
R³⁷ represents a fluorine atom, a chlorine atom, a bromine atom, a methyl group, a methoxy group, a methylthio group or a hydrogen atom; and
R³⁵, R³⁶, R³⁸ and R³⁹ represent independently of each other a fluorine atom or a hydrogen atom];
R², R³, R⁴, R⁵, R⁷, R⁸ and R⁹ represent a hydrogen atom;
R⁶ represents a methyl group or an ethyl group;
R¹⁰ represents a methyl group; and
X represents an oxygen atom.

a tetrazolinone compound wherein
R¹ represents a group represented by a formula (4):

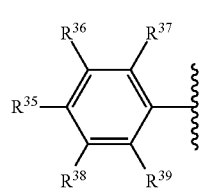
(4)

[wherein
R³⁷ represents a halogen atom, an C1-C6 alkyl group, an C1-C6 alkoxy group, an C1-C6 alkylthio group or a hydrogen atom;
R³⁵, R³⁶, R³⁸ and R³⁹ represent independently of each other a halogen atom or a hydrogen atom];
R², R³, R⁴, R⁵, R⁷, R⁸ and R⁹ represent a hydrogen atom;
R⁶ represents a methyl group;
R¹⁰ represents an C1-C6 alkyl group; and
X represents an oxygen atom.

a tetrazolinone compound wherein
R¹ represents a group represented by a formula (4):

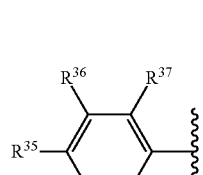
(4)

[wherein
R³⁷ represents a fluorine atom, a chlorine atom, a bromine atom, a methyl group, a methoxy group, a methylthio group or a hydrogen atom;
R³⁵, R³⁶, R³⁸ and R³⁹ represent independently of each other a fluorine atom or a hydrogen atom];
R², R³, R⁴, R⁵, R⁷, R⁸ and R⁹ represent a hydrogen atom;
R⁶ represents a methyl group;

$R^{10}$ represents a methyl group; and
X represents an oxygen atom.
a tetrazolinone compound wherein
$R^1$ represents a group represented by a formula (4):

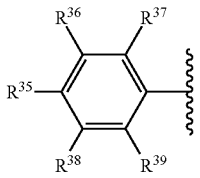

(4)

[wherein
$R^{37}$ represents an C1-C6 alkoxy group; and
$R^{35}$, $R^{36}$, $R^{38}$ and $R^{39}$ represent a hydrogen atom];
$R^2$, $R^3$, $R^4$, $R^5$, $R^7$, $R^8$ and $R^9$ represent a hydrogen atom;
$R^6$ represents an C3-C6 cycloalkyl group;
$R^{10}$ represents an C1-C6 alkyl group; and
X represents an oxygen atom.
a tetrazolinone compound wherein
$R^1$ represents a group represented by a formula (4):

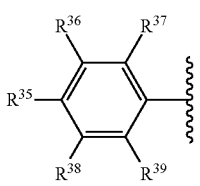

(4)

[wherein
$R^{37}$ represents a methoxy group; and
$R^{35}$, $R^{36}$, $R^{38}$ and $R^{39}$ represent a hydrogen atom];
$R^2$, $R^3$, $R^4$, $R^5$, $R^7$, $R^8$ and $R^9$ represent a hydrogen atom;
$R^6$ represents a cyclopropyl group;
$R^{10}$ represents a methyl group; and
X represents an oxygen atom.
a tetrazolinone compound wherein
$R^1$ represents a group represented by a formula (4):

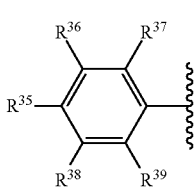

(4)

[wherein
$R^{37}$ represents an C1-C6 alkoxy group; and
$R^{35}$, $R^{36}$, $R^{38}$ and $R^{39}$ represent a hydrogen atom];
$R^2$, $R^3$, $R^4$, $R^5$, $R^7$, $R^8$ and $R^9$ represent a hydrogen atom;
$R^6$ represents a halogen atom;
$R^{10}$ represents an C1-C6 alkyl group; and
X represents an oxygen atom.

a tetrazolinone compound wherein
$R^1$ represents a group represented by a formula (4):

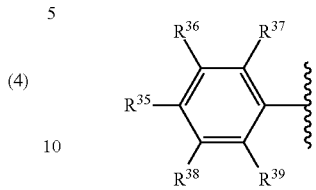

(4)

[wherein
$R^{37}$ represents a methoxy group; and
$R^{35}$, $R^{36}$, $R^{38}$ and $R^{39}$ represent a hydrogen atom];
$R^2$, $R^3$, $R^4$, $R^5$, $R^7$, $R^8$ and $R^9$ represent a hydrogen atom;
$R^6$ represents a chlorine atom;
$R^{10}$ represents a methyl group; and
X represents an oxygen atom.
a tetrazolinone compound wherein
$R^1$ represents a group represented by a formula (4):

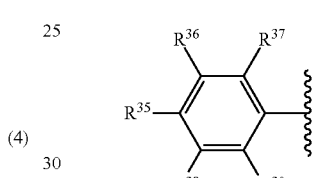

(4)

[wherein
$R^{37}$ represents an C1-C6 alkoxy group or a hydrogen atom; and
$R^{35}$, $R^{36}$, $R^{38}$ and $R^{39}$ represent a hydrogen atom];
$R^2$, $R^3$, $R^4$, $R^5$, $R^7$, $R^8$ and $R^9$ represent a hydrogen atom;
$R^6$ represents an C1-C6 alkoxy group;
$R^{10}$ represents an C1-C6 alkyl group; and
X represents an oxygen atom.
a tetrazolinone compound wherein
$R^1$ represents a group represented by a formula (4):

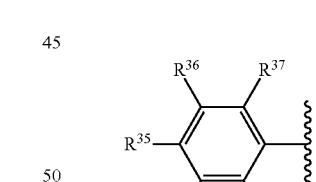

(4)

[wherein
$R^{37}$ represents a methoxy group; and
$R^{35}$, $R^{36}$, $R^{38}$ and $R^{39}$ represent a hydrogen atom];
$R^2$, $R^3$, $R^4$, $R^5$, $R^7$, $R^8$ and $R^9$ represent a hydrogen atom;
$R^6$ represents a methoxy group;
$R^{10}$ represents a methyl group; and
X represents an oxygen atom.

Also, examples of an embodiment of the present tetrazolinone compound Y include compounds wherein the substituents in the formula (8) represent the following ones.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group.

a tetrazolinone compound wherein $R^{27}$ represents a chlorine atom, a bromine atom, a methyl group, an ethyl group, a cyclopropyl group or methoxy group.

a tetrazolinone compound wherein $R^{27}$ represents a halogen atom, a methyl group, a trifluoromethyl group or methoxy group.

a tetrazolinone compound wherein $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group.

a tetrazolinone compound wherein $R^{27}$ represents a halogen atom.

a tetrazolinone compound wherein $R^{27}$ represents an C1-C3 alkyl group.

a tetrazolinone compound wherein $R^{27}$ represents a C1-C3 haloalkyl group.

a tetrazolinone compound wherein $R^{27}$ represents an C2-C3 alkenyl group.

a tetrazolinone compound wherein $R^{27}$ represents an C2-C3 alkynyl group.

a tetrazolinone compound wherein $R^{27}$ represents a C3-C4 cycloalkyl group.

a tetrazolinone compound wherein $R^{27}$ represents an C1-C3 alkoxy group.

a tetrazolinone compound wherein $R^{27}$ represents a C1-C3 haloalkoxy group.

a tetrazolinone compound wherein $R^{27}$ represents an C1-C2 alkylthio group.

a tetrazolinone compound wherein $R^{27}$ represents an C1-C4 alkylamino group.

a tetrazolinone compound wherein $R^{27}$ represents chlorine atom, a bromine atom, a methyl group or a methoxy group.

a tetrazolinone compound wherein $R^{27}$ represents an ethyl group or cyclopropyl group.

a tetrazolinone compound wherein $R^{27}$ represents a chlorine atom.

a tetrazolinone compound wherein $R^{27}$ represents a bromine atom.

a tetrazolinone compound wherein $R^{27}$ represents a methyl group.

a tetrazolinone compound wherein $R^{27}$ represents an ethyl group.

a tetrazolinone compound wherein $R^{27}$ represents a cyclopropyl group.

a tetrazolinone compound wherein $R^{27}$ represents a methoxy group.

a tetrazolinone compound wherein $R^{28}$ represents a methyl group or a hydrogen atom.

a tetrazolinone compound wherein $R^{28}$ represents a methyl group.

a tetrazolinone compound wherein $R^{28}$ represents a hydrogen atom.

a tetrazolinone compound wherein A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein A represents a methyl group, a halomethyl group, a hydroxymethyl group, an (C1-C3 alkoxy)methyl group, an (C1-C6 alkylsulfonyloxy) methyl group, an (C6-C16 arylsulfonyloxy)methyl group, a formyl group or an C2-C6 alkoxycarbonyl group.

a tetrazolinone compound wherein A represents a methyl group, a chloromethyl group or a bromomethyl group.

a tetrazolinone compound wherein A represents a hydroxymethyl group, a (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein A represents a methyl group.

a tetrazolinone compound wherein A represents a halomethyl group.

a tetrazolinone compound wherein A represents a chloromethyl group.

a tetrazolinone compound wherein A represents a bromomethyl group.

a tetrazolinone compound wherein A represents a hydroxymethyl group.

a tetrazolinone compound wherein A represents an (C1-C3 alkoxy)methyl group.

a tetrazolinone compound wherein A represents an (C1-C3 alkylthio)methyl group.

a tetrazolinone compound wherein A represents an (C1-C6 acyloxy)methyl group.

a tetrazolinone compound wherein A represents an (C1-C6 alkylsulfonyloxy)methyl group.

a tetrazolinone compound wherein A represents a (C1-C6 haloalkylsulfonyloxy)methyl group.

a tetrazolinone compound wherein A represents an (C6-C16 arylsulfonyloxy)methyl group.

a tetrazolinone compound wherein A represents a (C6-C16 haloarylsulfonyloxy)methyl group.

a tetrazolinone compound wherein A represents an (C1-C6 alkylamino)methyl group.

a tetrazolinone compound wherein A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein A represents an C2-C6 alkoxycarbonyl group.

a tetrazolinone compound wherein $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group; and $R^{28}$ represents a methyl group or a hydrogen atom.

a tetrazolinone compound wherein $R^{27}$ represents a halogen atom, a methyl group, a trifluoromethyl group or a methoxy group; and $R^{28}$ represents a methyl group or a hydrogen atom.

a tetrazolinone compound wherein $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group; and $R^{28}$ represents a methyl group or a hydrogen atom.

a tetrazolinone compound wherein $R^{27}$ represents a halogen atom; and $R^{28}$ represents methyl group or a hydrogen atom.

a tetrazolinone compound wherein $R^{27}$ represents an C1-C3 alkyl group; and $R^{28}$ represents a methyl group or a hydrogen atom.

a tetrazolinone compound wherein $R^{27}$ represents a C1-C3 haloalkyl group; and $R^{28}$ represents a methyl group or a hydrogen atom.

a tetrazolinone compound wherein $R^{27}$ represents an C2-C3 alkenyl group; and $R^{28}$ represents a methyl group or a hydrogen atom.

a tetrazolinone compound wherein $R^{27}$ represents an C2-C3 alkynyl group; and $R^{10}$ represents a methyl group or a hydrogen atom.

a tetrazolinone compound wherein $R^{27}$ represents a C3-C4 cycloalkyl group; and $R^{28}$ represents a methyl group or a hydrogen atom.

a tetrazolinone compound wherein $R^{27}$ represents an C1-C3 alkoxy group; and $R^{28}$ represents a methyl group or a hydrogen atom.

a tetrazolinone compound wherein $R^{27}$ represents a C1-C3 haloalkoxy group; and $R^{28}$ represents a methyl group or a hydrogen atom.

a tetrazolinone compound wherein $R^{27}$ represents an C1-C2 alkylthio group; and $R^{28}$ represents a methyl group or a hydrogen atom.

a tetrazolinone compound wherein $R^{27}$ represents an C1-C4 alkylamino group; and $R^{28}$ represents a methyl group or a hydrogen atom.

a tetrazolinone compound wherein $R^{27}$ represents a chlorine atom, a bromine atom, a methyl group or s methoxy group; and $R^{28}$ represents a methyl group or a hydrogen atom.

a tetrazolinone compound wherein $R^{27}$ represents an ethyl group or a cyclopropyl group; and $R^{10}$ represents a methyl group or a hydrogen atom.

a tetrazolinone compound wherein $R^{27}$ represents a chlorine atom; and $R^{28}$ represents a methyl group or a hydrogen atom.

a tetrazolinone compound wherein $R^{27}$ represents a bromine atom; and $R^{28}$ represents a methyl group or a hydrogen atom.

a tetrazolinone compound wherein $R^{27}$ represents an ethyl group; and $R^{28}$ represents a methyl group or a hydrogen atom.

a tetrazolinone compound wherein $R^{27}$ represents a cyclopropyl group; and $R^{10}$ represents a methyl group or a hydrogen atom.

a tetrazolinone compound wherein $R^{27}$ represents a methoxy group; and $R^{10}$ represents a methyl group or a hydrogen atom.

a tetrazolinone compound wherein $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C2 haloalkoxy group, an C1-C2 alkylthio group, a C1-C2 haloalkylthio group or an C1-C4 alkylamino group; and $R^{28}$ represents a methyl group.

a tetrazolinone compound wherein $R^{27}$ represents a halogen atom, a methyl group, a trifluoromethyl group or a methoxy group; and $R^{28}$ represents a methyl group.

a tetrazolinone compound wherein $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group; and $R^{28}$ represents a methyl group.

a tetrazolinone compound wherein $R^{27}$ represents halogen atom; and $R^{28}$ represents a methyl group.

a tetrazolinone compound wherein $R^{27}$ represents a C1-C3 alkyl group; and $R^{28}$ represents a methyl group.

a tetrazolinone compound wherein $R^{27}$ represents a C1-C3 haloalkyl group; and $R^{28}$ represents a methyl group.

a tetrazolinone compound wherein $R^{27}$ represents a C1-C3 alkenyl group; and $R^{28}$ represents a methyl group.

a tetrazolinone compound wherein $R^{27}$ represents a C1-C3 alkynyl group; and $R^{28}$ represents a methyl group.

a tetrazolinone compound wherein $R^{27}$ represents a C3-C4 cycloalkyl group; and $R^{28}$ represents a methyl group.

a tetrazolinone compound wherein $R^{27}$ represents a C1-C3 alkoxy group; and $R^{28}$ represents a methyl group.

a tetrazolinone compound wherein $R^{27}$ represents a C1-C3 haloalkoxy group; and $R^{28}$ represents a methyl group.

a tetrazolinone compound wherein $R^{27}$ represents an C1-C2 alkylthio group; and $R^{28}$ represents a methyl group.

a tetrazolinone compound wherein $R^{27}$ represents an C1-C4 alkylamino group; and $R^{28}$ represents a methyl group.

a tetrazolinone compound wherein $R^{27}$ represents a chlorine atom, a bromine atom, a methyl group or a methoxy group; and $R^{28}$ represents a methyl group.

a tetrazolinone compound wherein $R^{27}$ represents an ethyl group or a cyclopropyl group; and $R^{28}$ represents a methyl group.

a tetrazolinone compound wherein $R^{27}$ represents a chlorine atom; and $R^{28}$ represents a methyl group.

a tetrazolinone compound wherein $R^{27}$ represents a bromine atom; and $R^{28}$ represents a methyl group.

a tetrazolinone compound wherein $R^{27}$ represents a methyl group; and $R^{28}$ represents a methyl group.

a tetrazolinone compound wherein $R^{27}$ represents an ethyl group; and $R^{28}$ represents a methyl group.

a tetrazolinone compound wherein $R^{27}$ represents a cyclopropyl group; and $R^{28}$ represents a methyl group.

a tetrazolinone compound wherein $R^{27}$ represents a methoxy group; and $R^{28}$ represents a methyl group.

a tetrazolinone compound wherein $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group; and $R^{28}$ represents a hydrogen atom.

a tetrazolinone compound wherein $R^{27}$ represents a halogen atom, a methyl group, a trifluoromethyl group or a methoxy group; and $R^{28}$ represents a hydrogen atom.

a tetrazolinone compound wherein $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group; and $R^{28}$ represents a hydrogen atom.

a tetrazolinone compound wherein $R^{27}$ represents a halogen atom; and $R^{28}$ represents a hydrogen atom.

a tetrazolinone compound wherein $R^{27}$ represents an C1-C3 alkyl group; and $R^{28}$ represents a hydrogen atom.

a tetrazolinone compound wherein $R^{27}$ represents a C1-C3 haloalkyl group; and $R^{28}$ represents a hydrogen atom.

a tetrazolinone compound wherein $R^{27}$ represents an C2-C3 alkenyl group; and $R^{28}$ represents a hydrogen atom.

a tetrazolinone compound wherein $R^{27}$ represents an C2-C3 alkynyl group; and $R^{28}$ represents a hydrogen atom.

a tetrazolinone compound wherein $R^{27}$ represents a C3-C4 cycloalkyl group; and $R^{28}$ represents a hydrogen atom.

a tetrazolinone compound wherein $R^{27}$ represents an C1-C3 alkoxy group; and $R^{28}$ represents a hydrogen atom.

a tetrazolinone compound wherein $R^{27}$ represents a C1-C3 haloalkoxy group; and $R^{28}$ represents a hydrogen atom.

a tetrazolinone compound wherein $R^{27}$ represents an C1-C2 alkylthio group; and $R^{28}$ represents a hydrogen atom.

a tetrazolinone compound wherein $R^{27}$ represents an C1-C4 alkylamino group; and $R^{28}$ represents a hydrogen atom.

a tetrazolinone compound wherein $R^{27}$ represents chlorine atom, a bromine atom, a methyl group or a methoxy group; and $R^{28}$ represents a hydrogen atom.

a tetrazolinone compound wherein $R^{27}$ represents an ethyl group or a cyclopropyl group; and $R^{28}$ represents a hydrogen atom.

a tetrazolinone compound wherein $R^{27}$ represents a chlorine atom; and $R^{28}$ represents a hydrogen atom.

a tetrazolinone compound wherein $R^{27}$ represents a bromine atom; and $R^{28}$ represents a hydrogen atom.

a tetrazolinone compound wherein $R^{27}$ represents a methyl group; and $R^{28}$ represents a hydrogen atom.

a tetrazolinone compound wherein $R^{27}$ represents an ethyl group; and $R^{28}$ represents a hydrogen atom.

a tetrazolinone compound wherein $R^{27}$ represents a cyclopropyl group; and $R^{28}$ represents a hydrogen atom.

a tetrazolinone compound wherein $R^{27}$ represents methoxy group; and $R^{28}$ represents a hydrogen atom.

a tetrazolinone compound wherein A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group; and $R^{28}$ represents a methyl group or a hydrogen atom.

a tetrazolinone compound wherein A represents a methyl group, a chloromethyl group or a bromomethyl group; and $R^{28}$ represents a methyl group or a hydrogen atom.

a tetrazolinone compound wherein A represents a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group; and $R^{28}$ represents a methyl group or a hydrogen atom.

a tetrazolinone compound wherein A represents a methyl group; and $R^{28}$ represents a methyl group or a hydrogen atom.

a tetrazolinone compound wherein A represents a halomethyl group; and $R^{28}$ represents a methyl group or a hydrogen atom.

a tetrazolinone compound wherein A represents a hydroxymethyl group; and $R^{28}$ represents a methyl group or a hydrogen atom.

a tetrazolinone compound wherein A represents an (C1-C3 alkoxy)methyl group; and $R^{28}$ represents a methyl group or a hydrogen atom.

a tetrazolinone compound wherein A represents an (C1-C3 alkylthio)methyl group; and $R^{28}$ represents a methyl group or a hydrogen atom.

a tetrazolinone compound wherein A represents an (C1-C6 acyloxy)methyl group; and $R^{28}$ represents a methyl group or a hydrogen atom.

a tetrazolinone compound wherein A represents an (C1-C6 alkylsulfonyloxy)methyl group; and $R^{28}$ represents a methyl group or a hydrogen atom.

a tetrazolinone compound wherein A represents a (C1-C6 haloalkylsulfonyloxy)methyl group; and $R^{28}$ represents a methyl group or a hydrogen atom.

a tetrazolinone compound wherein A represents an (C6-C16 arylsulfonyloxy)methyl group; and $R^{28}$ represents a methyl group or a hydrogen atom.

a tetrazolinone compound wherein A represents (C6-C16 haloarylsulfonyloxy)methyl group; and $R^{28}$ represents a methyl group or a hydrogen atom.

a tetrazolinone compound wherein A represents an (C1-C6 alkylamino)methyl group; and $R^{28}$ represents a methyl group or a hydrogen atom.

a tetrazolinone compound wherein A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other); and $R^{28}$ represents a methyl group or a hydrogen atom.

a tetrazolinone compound wherein A represents a formyl group.

a tetrazolinone compound wherein A represents C2-C6 alkoxycarbonyl group; and $R^{28}$ represents a methyl group or a hydrogen atom.

a tetrazolinone compound wherein A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group; and $R^{28}$ represents methyl group.

a tetrazolinone compound wherein A represents a methyl group, a chloromethyl group or a bromomethyl group; and $R^{28}$ represents a methyl group.

a tetrazolinone compound wherein A represents a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group; and $R^{28}$ represents a methyl group.

a tetrazolinone compound wherein A represents a methyl group; and $R^{28}$ represents a methyl group.

a tetrazolinone compound wherein A represents a halomethyl group; and $R^{28}$ represents a methyl group.

a tetrazolinone compound wherein A represents a chloromethyl group; and $R^{28}$ represents a methyl group.

a tetrazolinone compound wherein A represents a bromomethyl group; and $R^{28}$ represents a methyl group.

a tetrazolinone compound wherein A represents a hydroxymethyl group; and $R^{28}$ represents a methyl group.

a tetrazolinone compound wherein A represents an (C1-C3 alkoxy)methyl group; and $R^{28}$ represents a methyl group.

a tetrazolinone compound wherein A represents an (C1-C3 alkylthio)methyl group; and $R^{28}$ represents a methyl group.

a tetrazolinone compound wherein A represents an (C1-C6 acyloxy)methyl group; and $R^{28}$ represents a methyl group.

a tetrazolinone compound wherein A represents an (C1-C6 alkylsulfonyloxy)methyl group; and $R^{28}$ represents a methyl group.

a tetrazolinone compound wherein A represents a (C1-C6 haloalkylsulfonyloxy)methyl group; and $R^{28}$ represents a methyl group.

a tetrazolinone compound wherein A represents an (C6-C16 arylsulfonyloxy)methyl group; and $R^{28}$ represents a methyl group.

a tetrazolinone compound wherein A represents a (C6-C16 haloarylsulfonyloxy)methyl group; and $R^{28}$ represents a methyl group.

a tetrazolinone compound wherein A represents an (C1-C6 alkylamino)methyl group; and $R^{28}$ represents a methyl group.

a tetrazolinone compound wherein A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other); and $R^{28}$ represents a methyl group.

a tetrazolinone compound wherein A represents a formyl group.

a tetrazolinone compound wherein A represents an C2-C6 alkoxycarbonyl group; and $R^{28}$ represents a methyl group.

a tetrazolinone compound wherein A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group; and $R^{28}$ represents a hydrogen atom.

a tetrazolinone compound wherein A represents a methyl group, a chloromethyl group or a bromomethyl group; and $R^{28}$ represents a hydrogen atom.

a tetrazolinone compound wherein A represents hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group; and $R^{28}$ represents a hydrogen atom.

a tetrazolinone compound wherein A represents a methyl group; and $R^{28}$ represents a hydrogen atom.

a tetrazolinone compound wherein A represents a halomethyl group; and $R^{28}$ represents a hydrogen atom.

a tetrazolinone compound wherein A represents a chloromethyl group; and $R^{28}$ represents a hydrogen atom.

a tetrazolinone compound wherein A represents a bromomethyl group; and $R^{28}$ represents a hydrogen atom.

a tetrazolinone compound wherein A represents a hydroxymethyl group; and $R^{28}$ represents a hydrogen atom.

a tetrazolinone compound wherein A represents an (C1-C3 alkoxy)methyl group; and $R^{28}$ represents a hydrogen atom.

a tetrazolinone compound wherein A represents an (C1-C3 alkylthio)methyl group; and $R^{28}$ represents a hydrogen atom.

a tetrazolinone compound wherein A represents an (C1-C6 acyloxy)methyl group; and $R^{28}$ represents a hydrogen atom.

a tetrazolinone compound wherein A represents an (C1-C6 alkylsulfonyloxy)methyl group; and $R^{28}$ represents a hydrogen atom.

a tetrazolinone compound wherein A represents a (C1-C6 haloalkylsulfonyloxy)methyl group; and $R^{28}$ represents a hydrogen atom.

a tetrazolinone compound wherein A represents an (C6-C16 arylsulfonyloxy)methyl group; and $R^{28}$ represents a hydrogen atom.

a tetrazolinone compound wherein A represents a (C6-C16 haloarylsulfonyloxy)methyl group; and $R^{28}$ represents a hydrogen atom.

a tetrazolinone compound wherein A represents a (C6-C16 haloarylsulfonyloxy)methyl group; and $R^{28}$ represents a hydrogen atom.

a tetrazolinone compound wherein A represents an (C1-C6 alkylamino)methyl group; and $R^{28}$ represents a hydrogen atom.

a tetrazolinone compound wherein A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other); and $R^{28}$ represents a hydrogen atom.

a tetrazolinone compound wherein $R^{28}$ represents a hydrogen atom.

a tetrazolinone compound wherein $R^{28}$ represents a formyl group.

a tetrazolinone compound wherein A represents an C2-C6 alkoxycarbonyl group; and $R^{28}$ represents a hydrogen atom.

a tetrazolinone compound wherein $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;

$R^{28}$ represents a methyl group or a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a halogen atom, a methyl group, a trifluoromethyl group or a methoxy group;

$R^{28}$ represents a methyl group or a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a halogen atom;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an C1-C3 alkyl group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a C3-C4 cycloalkyl group;
$R^{28}$ represents a methyl group or a hydrogen atom; and A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an C1-C3 alkoxy group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a chlorine atom;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a bromine atom;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a methyl group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an ethyl group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a cyclopropyl group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a methoxy group;
$R^{28}$ represents a methyl group or a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an C1-C3 alkyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a C3-C4 cycloalkyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a C3-C4 cycloalkyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an ethyl group or a cyclopropyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a chlorine atom;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a bromine atom;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a methyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents an ethyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a cyclopropyl group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a methoxy group;
$R^{28}$ represents a methyl group; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a halogen atom, a methyl group, a trifluoromethyl group or a methoxy group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a halogen atom;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents an C1-C3 alkyl group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a C3-C4 cycloalkyl group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents an C1-C3 alkoxy group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, (C1-C6 haloalkylsulfonyloxy)methyl group, an (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a chlorine atom, a bromine atom, a methyl group or a methoxy group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents an ethyl group or a cyclopropyl group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a chlorine atom;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a bromine atom;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a methyl group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents an ethyl group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a cyclopropyl group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a methoxy group;

$R^{28}$ represents a hydrogen atom; and

A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy)methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other), a formyl group or an C2-C6 alkoxycarbonyl group.

a tetrazolinone compound wherein $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;

$R^{28}$ represents a methyl group or a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkyl group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a C3-C4 cycloalkyl group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkoxy group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group or a cyclopropyl group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a bromine atom;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methyl group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a cyclopropyl group;
$R^{28}$ represents a methyl group or a hydrogen atom; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methoxy group;
$R^{28}$ represents a methyl group or a hydrogen atom; and
A represents a methyl group, a halomethyl group, hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkyl group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a C3-C4 cycloalkyl group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkoxy group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group or a cyclopropyl group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a bromine atom;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methyl group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a cyclopropyl group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methoxy group;
$R^{28}$ represents a methyl group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a halogen atom, a methyl group, a trifluoromethyl group or a methoxy group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a halogen atom;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents an C1-C3 alkyl group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a C3-C4 cycloalkyl group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents an C1-C3 alkoxy group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a chlorine atom, a bromine atom, a methyl group or a methoxy group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents an ethyl group or a cyclopropyl group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a chlorine atom;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a bromine atom;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a methyl group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents an ethyl group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a cyclopropyl group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a methoxy group;

$R^{28}$ represents a hydrogen atom; and

A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group, a chloromethyl group or a bromomethyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents a methyl group, a chloromethyl group or a bromomethyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group, a chloromethyl group or a bromomethyl group.

a tetrazolinone compound wherein
$R^{27}$ represents a halogen atom;
$R^{28}$ represents a methyl group or a hydrogen atom; and
A represents a methyl group, a chloromethyl group or a bromomethyl group.

a tetrazolinone compound wherein
$R^{27}$ represents an C1-C3 alkyl group;
$R^{28}$ represents a methyl group or a hydrogen atom; and
A represents a methyl group, a chloromethyl group or a bromomethyl group.

a tetrazolinone compound wherein
$R^{27}$ represents a C3-C4 cycloalkyl group;
$R^{28}$ represents a methyl group or a hydrogen atom; and
A represents a methyl group, a chloromethyl group or a bromomethyl group.

a tetrazolinone compound wherein
$R^{27}$ represents an C1-C3 alkoxy group;
$R^{28}$ represents a methyl group or a hydrogen atom; and
A represents a methyl group, a chloromethyl group or a bromomethyl group.

a tetrazolinone compound wherein
$R^{27}$ represents a chlorine atom, a bromine atom, a methyl group or a methoxy group;
$R^{28}$ represents a methyl group or a hydrogen atom; and
A represents a methyl group, a chloromethyl group or a bromomethyl group.

a tetrazolinone compound wherein
$R^{27}$ represents an ethyl group or a cyclopropyl group;
$R^{28}$ represents a methyl group or a hydrogen atom; and
A represents a methyl group, a chloromethyl group or a bromomethyl group.

a tetrazolinone compound wherein
$R^{27}$ represents a chlorine atom;
A represents a methyl group, a chloromethyl group or a bromomethyl group.

a tetrazolinone compound wherein
$R^{27}$ represents a bromine atom;
$R^{28}$ represents a methyl group or a hydrogen atom; and
A represents a methyl group, a chloromethyl group or a bromomethyl group.

a tetrazolinone compound wherein
$R^{27}$ represents a methyl group;
$R^{28}$ represents a methyl group or a hydrogen atom; and
A represents a methyl group, a chloromethyl group or a bromomethyl group.

a tetrazolinone compound wherein
$R^{27}$ represents an ethyl group;
$R^{28}$ represents a methyl group or a hydrogen atom; and
A represents a methyl group, a chloromethyl group or a bromomethyl group.

a tetrazolinone compound wherein
$R^{27}$ represents a cyclopropyl group;
$R^{28}$ represents a methyl group or a hydrogen atom; and
A represents a methyl group, a chloromethyl group or a bromomethyl group.

a tetrazolinone compound wherein
$R^{27}$ represents a methoxy group;
$R^{28}$ represents a methyl group or a hydrogen atom; and
A represents a methyl group, a chloromethyl group or a bromomethyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group, a chloromethyl group or a bromomethyl group.

a tetrazolinone compound wherein
$R^{27}$ represents a halogen atom, a methyl group, a trifluoromethyl group or a methoxy group;
$R^{28}$ represents a methyl group; and
A represents a methyl group, a chloromethyl group or a bromomethyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group, a chloromethyl group or a bromomethyl group.

a tetrazolinone compound wherein
$R^{27}$ represents a halogen atom;
$R^{28}$ represents a methyl group; and
A represents a methyl group, a chloromethyl group or a bromomethyl group.

a tetrazolinone compound wherein
$R^{27}$ represents an C1-C3 alkyl group;
$R^{28}$ represents a methyl group; and
A represents a methyl group, a chloromethyl group or a bromomethyl group.

a tetrazolinone compound wherein
$R^{27}$ represents a C3-C4 cycloalkyl group;
$R^{28}$ represents a methyl group; and
A represents a methyl group, a chloromethyl group or a bromomethyl group.

a tetrazolinone compound wherein
$R^{27}$ represents an C1-C3 alkoxy group;
$R^{28}$ represents a methyl group; and
A represents a methyl group, a chloromethyl group or a bromomethyl group.

a tetrazolinone compound wherein
$R^{27}$ represents a chlorine atom, a bromine atom, a methyl group or a methoxy group;
$R^{28}$ represents a methyl group; and
A represents a methyl group, a chloromethyl group or a bromomethyl group.

a tetrazolinone compound wherein
$R^{27}$ represents an ethyl group or a cyclopropyl group;
$R^{28}$ represents a hydrogen atom; and
A represents a methyl group, a chloromethyl group or a bromomethyl group.

a tetrazolinone compound wherein
$R^{27}$ represents a chlorine atom;
$R^{28}$ represents a methyl group; and
A represents a methyl group, a chloromethyl group or a bromomethyl group.

a tetrazolinone compound wherein
$R^{27}$ represents a bromine atom;
$R^{28}$ represents a methyl group; and
A represents a methyl group, a chloromethyl group or a bromomethyl group.

a tetrazolinone compound wherein
$R^{27}$ represents a methyl group;
$R^{28}$ represents a methyl group; and
A represents a methyl group, a chloromethyl group or a bromomethyl group.

a tetrazolinone compound wherein
$R^{27}$ represents an ethyl group;
$R^{28}$ represents a methyl group; and
A represents a methyl group, a chloromethyl group or a bromomethyl group.

a tetrazolinone compound wherein
$R^{27}$ represents a cyclopropyl group;
$R^{28}$ represents a methyl group; and
A represents a methyl group, a chloromethyl group or a bromomethyl group.

a tetrazolinone compound wherein
$R^{27}$ represents a methoxy group;
$R^{28}$ represents a methyl group; and
A represents a methyl group, a chloromethyl group or a bromomethyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a methyl group, a chloromethyl group or a bromomethyl group.

a tetrazolinone compound wherein
$R^{27}$ represents a halogen atom, a methyl group, a trifluoromethyl group or a methoxy group;
$R^{28}$ represents a hydrogen atom; and
A represents a methyl group, a chloromethyl group or a bromomethyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a methyl group, a chloromethyl group or a bromomethyl group.

a tetrazolinone compound wherein
$R^{27}$ represents a halogen atom;
$R^{28}$ represents a hydrogen atom; and
A represents a methyl group, a chloromethyl group or a bromomethyl group.

a tetrazolinone compound wherein
$R^{27}$ represents an C1-C3 alkyl group;
$R^{28}$ represents a hydrogen atom; and
A represents a methyl group, a chloromethyl group or a bromomethyl group.

a tetrazolinone compound wherein
$R^{27}$ represents a C3-C4 cycloalkyl group;
$R^{28}$ represents a hydrogen atom; and
A represents a methyl group, a chloromethyl group or a bromomethyl group.

a tetrazolinone compound wherein
$R^{27}$ represents an C1-C3 alkoxy group;
$R^{28}$ represents a hydrogen atom; and
A represents a methyl group, a chloromethyl group or a bromomethyl group.

a tetrazolinone compound wherein
$R^{27}$ represents a chlorine atom, a bromine atom, a methyl group or a methoxy group;
$R^{28}$ represents a hydrogen atom; and
A represents a methyl group, a chloromethyl group or a bromomethyl group.

a tetrazolinone compound wherein
$R^{27}$ represents an ethyl group or a cyclopropyl group;
$R^{28}$ represents a hydrogen atom; and
A represents a methyl group, a chloromethyl group or a bromomethyl group.

a tetrazolinone compound wherein
$R^{27}$ represents a chlorine atom;
$R^{28}$ represents a hydrogen atom; and
A represents a methyl group, a chloromethyl group or a bromomethyl group.

a tetrazolinone compound wherein
$R^{27}$ represents a bromine atom;
$R^{28}$ represents a hydrogen atom; and
A represents a methyl group, a chloromethyl group or a bromomethyl group.

a tetrazolinone compound wherein
$R^{27}$ represents a methyl group;
$R^{28}$ represents a hydrogen atom; and
A represents a methyl group, a chloromethyl group or a bromomethyl group.

a tetrazolinone compound wherein
$R^{27}$ represents an ethyl group;
$R^{28}$ represents a hydrogen atom; and
A represents a methyl group, a chloromethyl group or a bromomethyl group.

a tetrazolinone compound wherein
$R^{27}$ represents a cyclopropyl group;
$R^{28}$ represents a hydrogen atom; and
A represents a methyl group, a chloromethyl group or a bromomethyl group.

a tetrazolinone compound wherein
$R^{27}$ represents a methoxy group;
$R^{28}$ represents a hydrogen atom; and
A represents a methyl group, a chloromethyl group or a bromomethyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, C2-C3 alkoxy group a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkyl group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a C3-C4 cycloalkyl group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkoxy group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group or a cyclopropyl group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a bromine atom;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methyl group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a cyclopropyl group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methoxy group;
$R^{28}$ represents a methyl group or a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group.
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom;
$R^{28}$ represents a methyl group; and A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkyl group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a C3-C4 cycloalkyl group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkoxy group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group or a cyclopropyl group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a bromine atom;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methyl group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a cyclopropyl group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methoxy group;
$R^{28}$ represents a methyl group; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, a methyl group, a trifluoromethyl group or a methoxy group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkyl group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a C3-C4 cycloalkyl group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an C1-C3 alkoxy group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom, a bromine atom, a methyl group or a methoxy group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group or a cyclopropyl group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a chlorine atom;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a bromine atom;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methyl group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents an ethyl group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a cyclopropyl group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a methoxy group;
$R^{28}$ represents a hydrogen atom; and
A represents a hydroxymethyl group, an (C1-C3 alkoxy) methyl group, an (C1-C6 alkylsulfonyloxy)methyl group, an (C6-C16 arylsulfonyloxy)methyl group, a formyl group or an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents a methyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents a methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group.

a tetrazolinone compound wherein
$R^{27}$ represents a halogen atom;
$R^{28}$ represents a methyl group or a hydrogen atom; and
A represents a methyl group.

a tetrazolinone compound wherein
$R^{27}$ represents an C1-C3 alkyl group;
$R^{28}$ represents a methyl group or a hydrogen atom; and
A represents a methyl group.

a tetrazolinone compound wherein
$R^{27}$ represents a C3-C4 cycloalkyl group;
$R^{28}$ represents a methyl group or a hydrogen atom; and
A represents a methyl group.

a tetrazolinone compound wherein
$R^{27}$ represents an C1-C3 alkoxy group;
$R^{28}$ represents a methyl group or a hydrogen atom; and
A represents a methyl group.

a tetrazolinone compound wherein
$R^{27}$ represents a chlorine atom, a bromine atom, a methyl group or a methoxy group;
$R^{28}$ represents a methyl group or a hydrogen atom; and
A represents a methyl group.

a tetrazolinone compound wherein
$R^{27}$ represents an ethyl group or a cyclopropyl group;
$R^{28}$ represents a methyl group or a hydrogen atom; and
A represents a methyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group.

a tetrazolinone compound wherein
$R^{27}$ represents a halogen atom, a methyl group, a trifluoromethyl group or a methoxy group;
$R^{28}$ represents a methyl group; and
A represents a methyl group.

a tetrazolinone compound wherein
R$^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R$^{28}$ represents a methyl group; and
A represents a methyl group.
a tetrazolinone compound wherein
R$^{27}$ represents a halogen atom;
R$^{28}$ represents a methyl group; and
A represents a methyl group.
a tetrazolinone compound wherein
R$^{27}$ represents an C1-C3 alkyl group;
R$^{28}$ represents a methyl group; and
A represents a methyl group.
a tetrazolinone compound wherein
R$^{27}$ represents a C3-C4 cycloalkyl group;
R$^{28}$ represents a methyl group; and
A represents a methyl group.
a tetrazolinone compound wherein
R$^{27}$ represents a C1-C3 alkoxy group;
R$^{28}$ represents a methyl group; and
A represents a methyl group.
a tetrazolinone compound wherein
R$^{27}$ represents a chlorine atom, a bromine atom, a methyl group or a methoxy group;
R$^{28}$ represents a methyl group; and
A represents a methyl group.
a tetrazolinone compound wherein
R$^{27}$ represents an ethyl group or a cyclopropyl group;
R$^{10}$ represents a methyl group; and
A represents a methyl group.
a tetrazolinone compound wherein
R$^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R$^{28}$ represents a hydrogen atom; and
A represents a methyl group.
a tetrazolinone compound wherein
R$^{27}$ represents a halogen atom, a methyl group, a trifluoromethyl group or a methoxy group;
R$^{28}$ represents a hydrogen atom; and
A represents a methyl group.
a tetrazolinone compound wherein
R$^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R$^{28}$ represents a hydrogen atom; and
A represents a methyl group.
a tetrazolinone compound wherein
R$^{27}$ represents a halogen atom;
R$^{28}$ represents a hydrogen atom; and
A represents a methyl group.
a tetrazolinone compound wherein
R$^{27}$ represents an C1-C3 alkyl group;
R$^{28}$ represents a hydrogen atom; and
A represents a methyl group.
a tetrazolinone compound wherein
R$^{27}$ represents a C3-C4 cycloalkyl group;
R$^{28}$ represents a hydrogen atom; and
A represents a methyl group.
a tetrazolinone compound wherein
R$^{27}$ represents an C1-C3 alkoxy group;
R$^{28}$ represents a hydrogen atom; and
A represents a methyl group.
a tetrazolinone compound wherein
R$^{27}$ represents a chlorine atom, a bromine atom, a methyl group or a methoxy group;
R$^{28}$ represents a hydrogen atom; and
A represents a methyl group.
a tetrazolinone compound wherein
R$^{27}$ represents an ethyl group or a cyclopropyl group;
R$^{28}$ represents a hydrogen atom; and
A represents a methyl group.
a tetrazolinone compound wherein
R$^{27}$ represents a halogen atom, an C1-C3 alkyl group, C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R$^{28}$ represents a methyl group or a hydrogen atom; and
A represents a chloromethyl group.
a tetrazolinone compound wherein
R$^{27}$ represents a halogen atom, a methyl group, a trifluoromethyl group or a methoxy group;
R$^{28}$ represents a methyl group or a hydrogen atom; and
A represents a chloromethyl group.
a tetrazolinone compound wherein
R$^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R$^{28}$ represents a methyl group or a hydrogen atom; and
A represents a chloromethyl group.
a tetrazolinone compound wherein
R$^{27}$ represents a halogen atom;
R$^{28}$ represents a methyl group or a hydrogen atom; and
A represents a chloromethyl group.
a tetrazolinone compound wherein
R$^{27}$ represents an C1-C3 alkyl group;
R$^{28}$ represents a methyl group or a hydrogen atom; and
A represents a chloromethyl group.
a tetrazolinone compound wherein
R$^{27}$ represents a C3-C4 cycloalkyl group;
R$^{28}$ represents a methyl group or a hydrogen atom; and
A represents a chloromethyl group.
a tetrazolinone compound wherein
R$^{27}$ represents an C1-C3 alkoxy group;
R$^{28}$ represents a methyl group or a hydrogen atom; and
A represents a chloromethyl group.
a tetrazolinone compound wherein
R$^{27}$ represents a chlorine atom, a bromine atom, a methyl group or a methoxy group;
R$^{28}$ represents a methyl group or a hydrogen atom; and
A represents a chloromethyl group.
a tetrazolinone compound wherein
R$^{27}$ represents an ethyl group or a cyclopropyl group;
R$^{28}$ represents a methyl group or a hydrogen atom; and
A represents a chloromethyl group.
R$^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a chloromethyl group.
a tetrazolinone compound wherein
$R^{27}$ represents a halogen atom, a methyl group, a trifluoromethyl group or a methoxy group;
$R^{28}$ represents a methyl group; and
A represents a chloromethyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a chloromethyl group.
a tetrazolinone compound wherein
$R^{27}$ represents a halogen atom;
$R^{28}$ represents a methyl group; and
A represents a chloromethyl group.
a tetrazolinone compound wherein
$R^{27}$ represents an C1-C3 alkyl group;
$R^{28}$ represents a methyl group; and
A represents a chloromethyl group.
a tetrazolinone compound wherein
$R^{27}$ represents a C3-C4 cycloalkyl group;
$R^{28}$ represents a methyl group; and
A represents a chloromethyl group.
a tetrazolinone compound wherein
$R^{27}$ represents an C1-C3 alkoxy group;
$R^{28}$ represents a methyl group; and
A represents a chloromethyl group.
a tetrazolinone compound wherein
$R^{27}$ represents a chlorine atom, a bromine atom, a methyl group or a methoxy group;
$R^{28}$ represents a methyl group; and
A represents a chloromethyl group.
a tetrazolinone compound wherein
$R^{27}$ represents an ethyl group or a cyclopropyl group;
$R^{28}$ represents a methyl group; and
A represents a chloromethyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a chloromethyl group.
a tetrazolinone compound wherein
$R^{27}$ represents a halogen atom, a methyl group, a trifluoromethyl group or a methoxy group;
$R^{28}$ represents a hydrogen atom; and
A represents a chloromethyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a chloromethyl group.

a tetrazolinone compound wherein
$R^{27}$ represents a halogen atom;
$R^{28}$ represents a hydrogen atom; and
A represents a chloromethyl group.
a tetrazolinone compound wherein
$R^{27}$ represents an C1-C3 alkyl group;
$R^{28}$ represents a hydrogen atom; and
A represents a chloromethyl group.
a tetrazolinone compound wherein
$R^{27}$ represents a C3-C4 cycloalkyl group;
$R^{28}$ represents a hydrogen atom; and
A represents a chloromethyl group.
a tetrazolinone compound wherein
$R^{27}$ represents an C1-C3 alkoxy group;
$R^{28}$ represents a hydrogen atom; and
A represents a chloromethyl group.
a tetrazolinone compound wherein
$R^{27}$ represents a chlorine atom, a bromine atom, a methyl group or a methoxy group;
$R^{28}$ represents a hydrogen atom; and
A represents a chloromethyl group.
a tetrazolinone compound wherein
$R^{27}$ represents an ethyl group or a cyclopropyl group;
$R^{10}$ represents a hydrogen atom; and
A represents a chloromethyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a bromomethyl group.
a tetrazolinone compound wherein
$R^{27}$ represents a halogen atom, a methyl group, a trifluoromethyl group or a methoxy group;
$R^{28}$ represents a methyl group or a hydrogen atom; and
A represents a bromomethyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a bromomethyl group.
a tetrazolinone compound wherein
$R^{27}$ represents a halogen atom;
$R^{28}$ represents a methyl group or a hydrogen atom; and
A represents a bromomethyl group.
a tetrazolinone compound wherein
$R^{27}$ represents an C1-C3 alkyl group;
$R^{28}$ represents a methyl group or a hydrogen atom; and
A represents a bromomethyl group.
a tetrazolinone compound wherein
$R^{27}$ represents a C3-C4 cycloalkyl group;
$R^{28}$ represents a methyl group or a hydrogen atom; and
A represents a bromomethyl group.
a tetrazolinone compound wherein
$R^{27}$ represents an C1-C3 alkoxy group;
$R^{28}$ represents a methyl group or a hydrogen atom; and
A represents a bromomethyl group.
a tetrazolinone compound wherein
$R^{27}$ represents a chlorine atom, a bromine atom, a methyl group or a methoxy group;

$R^{28}$ represents a methyl group or a hydrogen atom; and
A represents a bromomethyl group.
a tetrazolinone compound wherein
$R^{27}$ represents an ethyl group or a cyclopropyl group;
$R^{28}$ represents a methyl group or a hydrogen atom; and
A represents a bromomethyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a bromomethyl group.
a tetrazolinone compound wherein
$R^{27}$ represents a halogen atom, a methyl group, a trifluoromethyl group or a methoxy group;
$R^{28}$ represents a methyl group; and
A represents a bromomethyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a bromomethyl group.
a tetrazolinone compound wherein
$R^{27}$ represents a halogen atom;
$R^{28}$ represents a methyl group; and
A represents a bromomethyl group.
a tetrazolinone compound wherein
$R^{27}$ represents an C1-C3 alkyl group;
$R^{28}$ represents a methyl group; and
A represents a bromomethyl group.
a tetrazolinone compound wherein
$R^{27}$ represents a C3-C4 cycloalkyl group;
$R^{28}$ represents a methyl group; and
A represents a bromomethyl group.
a tetrazolinone compound wherein
$R^{27}$ represents an C1-C3 alkoxy group;
$R^{28}$ represents a methyl group; and
A represents a bromomethyl group.
a tetrazolinone compound wherein
$R^{27}$ represents a chlorine atom, a bromine atom, a methyl group or a methoxy group;
$R^{28}$ represents a methyl group; and
A represents a bromomethyl group.
a tetrazolinone compound wherein
$R^{27}$ represents an ethyl group or a cyclopropyl group;
$R^{28}$ represents a methyl group; and
A represents a bromomethyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a bromomethyl group.
a tetrazolinone compound wherein
$R^{27}$ represents a halogen atom, a methyl group, a trifluoromethyl group or a methoxy group;
$R^{28}$ represents a hydrogen atom; and
A represents a bromomethyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a bromomethyl group.
a tetrazolinone compound wherein
$R^{27}$ represents a halogen atom;
$R^{28}$ represents a hydrogen atom; and
A represents a bromomethyl group.
a tetrazolinone compound wherein
$R^{27}$ represents an C1-C3 alkyl group;
$R^{28}$ represents a hydrogen atom; and
A represents a bromomethyl group.
a tetrazolinone compound wherein
$R^{27}$ represents a C3-C4 cycloalkyl group;
$R^{28}$ represents a hydrogen atom; and
A represents a bromomethyl group.
a tetrazolinone compound wherein
$R^{27}$ represents an C1-C3 alkoxy group;
$R^{28}$ represents a hydrogen atom; and
A represents a bromomethyl group.
a tetrazolinone compound wherein
$R^{27}$ represents a chlorine atom, a bromine atom, a methyl group or a methoxy group;
$R^{28}$ represents a hydrogen atom; and
A represents a bromomethyl group.
a tetrazolinone compound wherein
$R^{27}$ represents an ethyl group or a cyclopropyl group;
$R^{28}$ represents a hydrogen atom; and
A represents a bromomethyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a hydroxymethyl group.
a tetrazolinone compound wherein
$R^{27}$ represents a halogen atom, a methyl group, a trifluoromethyl group or a methoxy group;
$R^{28}$ represents a methyl group or a hydrogen atom; and
A represents a hydroxymethyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a hydroxymethyl group.
a tetrazolinone compound wherein
$R^{27}$ represents a halogen atom;
$R^{28}$ represents a methyl group or a hydrogen atom; and
A represents a hydroxymethyl group.
a tetrazolinone compound wherein
$R^{27}$ represents an C1-C3 alkyl group;
$R^{28}$ represents a methyl group or a hydrogen atom; and
A represents a hydroxymethyl group.

a tetrazolinone compound wherein
  $R^{27}$ represents a C3-C4 cycloalkyl group;
  $R^{28}$ represents a methyl group or a hydrogen atom; and
  A represents a hydroxymethyl group.
a tetrazolinone compound wherein
  $R^{27}$ represents an C1-C3 alkoxy group;
  $R^{28}$ represents a methyl group or a hydrogen atom; and
  A represents a hydroxymethyl group.
a tetrazolinone compound wherein
  $R^{27}$ represents a chlorine atom, a bromine atom, a methyl group or a methoxy group;
  $R^{28}$ represents a methyl group or a hydrogen atom; and
  A represents a hydroxymethyl group.
a tetrazolinone compound wherein
  $R^{27}$ represents an ethyl group or a cyclopropyl group;
  $R^{28}$ represents a methyl group or a hydrogen atom; and
  A represents a hydroxymethyl group.
a tetrazolinone compound wherein
  $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
  $R^{28}$ represents a methyl group; and
  A represents a hydroxymethyl group.
a tetrazolinone compound wherein
  $R^{27}$ represents a halogen atom, a methyl group, a trifluoromethyl group or a methoxy group;
  $R^{28}$ represents a methyl group; and
  A represents a hydroxymethyl group.
a tetrazolinone compound wherein
  $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
  $R^{28}$ represents a methyl group; and
  A represents a hydroxymethyl group.
a tetrazolinone compound wherein
  $R^{27}$ represents a halogen atom;
  $R^{28}$ represents a methyl group; and
  A represents a hydroxymethyl group.
a tetrazolinone compound wherein
  $R^{27}$ represents an C1-C3 alkyl group;
  $R^{28}$ represents a methyl group; and
  A represents a hydroxymethyl group.
a tetrazolinone compound wherein
  $R^{27}$ represents a C3-C4 cycloalkyl group;
  $R^{28}$ represents a methyl group; and
  A represents a hydroxymethyl group.
a tetrazolinone compound wherein
  $R^{27}$ represents an C1-C3 alkoxy group;
  $R^{28}$ represents a methyl group; and
  A represents a hydroxymethyl group.
a tetrazolinone compound wherein
  $R^{27}$ represents a chlorine atom, a bromine atom, a methyl group or a methoxy group;
  $R^{28}$ represents a methyl group; and
  A represents a hydroxymethyl group.
a tetrazolinone compound wherein
  $R^{27}$ represents an ethyl group or a cyclopropyl group;
  $R^{28}$ represents a methyl group; and
  A represents a hydroxymethyl group.

a tetrazolinone compound wherein
  $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
  $R^{28}$ represents a hydrogen atom; and
  A represents a hydroxymethyl group.
a tetrazolinone compound wherein
  $R^{27}$ represents a halogen atom, a methyl group, a trifluoromethyl group or a methoxy group;
  $R^{28}$ represents a hydrogen atom; and
  A represents a hydroxymethyl group.
a tetrazolinone compound wherein
  $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
  $R^{28}$ represents a hydrogen atom; and
  A represents a hydroxymethyl group.
a tetrazolinone compound wherein
  $R^{27}$ represents a halogen atom;
  $R^{28}$ represents a hydrogen atom; and
  A represents a hydroxymethyl group.
a tetrazolinone compound wherein
  $R^{27}$ represents an C1-C3 alkyl group;
  $R^{28}$ represents a hydrogen atom; and
  A represents a hydroxymethyl group.
a tetrazolinone compound wherein
  $R^{27}$ represents a C3-C4 cycloalkyl group;
  $R^{28}$ represents a hydrogen atom; and
  A represents a hydroxymethyl group.
a tetrazolinone compound wherein
  $R^{27}$ represents an C1-C3 alkoxy group;
  $R^{28}$ represents a hydrogen atom; and
  A represents a hydroxymethyl group.
a tetrazolinone compound wherein
  $R^{27}$ represents a chlorine atom, a bromine atom, a methyl group or a methoxy group;
  $R^{28}$ represents a hydrogen atom; and
  A represents a hydroxymethyl group.
a tetrazolinone compound wherein
  $R^{27}$ represents an ethyl group or a cyclopropyl group;
  $R^{28}$ represents a hydrogen atom; and
  A represents a hydroxymethyl group.
a tetrazolinone compound wherein
  $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
  $R^{28}$ represents a methyl group or a hydrogen atom; and
  A represents an (C1-C3 alkoxy)methyl group.
a tetrazolinone compound wherein
  $R^{27}$ represents a halogen atom, a methyl group, a trifluoromethyl group or a methoxy group;
  $R^{28}$ represents a methyl group or a hydrogen atom; and
  A represents an (C1-C3 alkoxy)methyl group.
a tetrazolinone compound wherein
  $R^{27}$ represents an C2-C3 alkyl group, a C1-C3 haloalkyl group excluding trifluoromethyl group, an C2-C3 alkenyl group, C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;

$R^{28}$ represents a methyl group or a hydrogen atom; and
A represents an (C1-C3 alkoxy)methyl group.
a tetrazolinone compound wherein
  $R^{27}$ represents a halogen atom;
  $R^{28}$ represents a methyl group or a hydrogen atom; and
  A represents an (C1-C3 alkoxy)methyl group.
a tetrazolinone compound wherein
  $R^{27}$ represents an C1-C3 alkyl group;
  $R^{28}$ represents a methyl group or a hydrogen atom; and
  A represents an (C1-C3 alkoxy)methyl group.
a tetrazolinone compound wherein
  $R^{27}$ represents a C3-C4 cycloalkyl group;
  $R^{28}$ represents a methyl group or a hydrogen atom; and
  A represents an (C1-C3 alkoxy)methyl group.
a tetrazolinone compound wherein
  $R^{27}$ represents an C1-C3 alkoxy group;
  $R^{28}$ represents a methyl group or a hydrogen atom; and
  A represents an (C1-C3 alkoxy)methyl group.
a tetrazolinone compound wherein
  $R^{27}$ represents a chlorine atom, a bromine atom, a methyl group or a methoxy group;
  $R^{28}$ represents a methyl group or a hydrogen atom; and
  A represents an (C1-C3 alkoxy)methyl group.
a tetrazolinone compound wherein
  $R^{27}$ represents an ethyl group or a cyclopropyl group;
  $R^{28}$ represents a methyl group or a hydrogen atom; and
  A represents an (C1-C3 alkoxy)methyl group.
a tetrazolinone compound wherein
  $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
  $R^{28}$ represents a methyl group; and
  A represents an (C1-C3 alkoxy)methyl group.
a tetrazolinone compound wherein
  $R^{27}$ represents a halogen atom, a methyl group, a trifluoromethyl group or a methoxy group;
  $R^{28}$ represents a methyl group; and
  A represents an (C1-C3 alkoxy)methyl group.
a tetrazolinone compound wherein
  $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
  $R^{28}$ represents a methyl group; and
  A represents an (C1-C3 alkoxy)methyl group.
a tetrazolinone compound wherein
  $R^{27}$ represents a halogen atom;
  $R^{28}$ represents a methyl group; and
  A represents an (C1-C3 alkoxy)methyl group.
a tetrazolinone compound wherein
  $R^{27}$ represents an C1-C3 alkyl group;
  $R^{28}$ represents a methyl group; and
  A represents an (C1-C3 alkoxy)methyl group.
a tetrazolinone compound wherein
  $R^{27}$ represents a C3-C4 cycloalkyl group;
  $R^{28}$ represents a methyl group; and
  A represents an (C1-C3 alkoxy)methyl group.
a tetrazolinone compound wherein
  $R^{27}$ represents an C1-C3 alkoxy group;
  $R^{28}$ represents a methyl group; and
  A represents an (C1-C3 alkoxy)methyl group.
a tetrazolinone compound wherein
  $R^{27}$ represents a chlorine atom, a bromine atom, a methyl group or a methoxy group;
  $R^{28}$ represents a methyl group; and
  A represents an (C1-C3 alkoxy)methyl group.
a tetrazolinone compound wherein
  $R^{27}$ represents an ethyl group or a cyclopropyl group;
  $R^{28}$ represents a methyl group; and
  A represents an (C1-C3 alkoxy)methyl group.
a tetrazolinone compound wherein
  $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
  $R^{28}$ represents a hydrogen atom; and
  A represents an (C1-C3 alkoxy)methyl group.
a tetrazolinone compound wherein
  $R^{27}$ represents a halogen atom, a methyl group, a trifluoromethyl group or a methoxy group;
  $R^{28}$ represents a hydrogen atom; and
  A represents an (C1-C3 alkoxy)methyl group.
a tetrazolinone compound wherein
  $R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
  $R^{28}$ represents a hydrogen atom; and
  A represents an (C1-C3 alkoxy)methyl group.
a tetrazolinone compound wherein
  $R^{27}$ represents a halogen atom;
  $R^{28}$ represents a hydrogen atom; and
  A represents an (C1-C3 alkoxy)methyl group.
a tetrazolinone compound wherein
  $R^{27}$ represents an C1-C3 alkyl group;
  $R^{28}$ represents a hydrogen atom; and
  A represents an (C1-C3 alkoxy)methyl group.
a tetrazolinone compound wherein
  $R^{27}$ represents a C3-C4 cycloalkyl group;
  $R^{28}$ represents a hydrogen atom; and
  A represents an (C1-C3 alkoxy)methyl group.
a tetrazolinone compound wherein
  $R^{27}$ represents an C1-C3 alkoxy group;
  $R^{28}$ represents a hydrogen atom; and
  A represents an (C1-C3 alkoxy)methyl group.
a tetrazolinone compound wherein
  $R^{27}$ represents a chlorine atom, a bromine atom, a methyl group or a methoxy group;
  $R^{28}$ represents a hydrogen atom; and
  A represents an (C1-C3 alkoxy)methyl group.
a tetrazolinone compound wherein
  $R^{27}$ represents an ethyl group or a cyclopropyl group;
  $R^{28}$ represents a hydrogen atom; and
  A represents an (C1-C3 alkoxy)methyl group.
a tetrazolinone compound wherein
  $R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
  $R^{28}$ represents a methyl group or a hydrogen atom; and
  A represents an (C1-C6 acyloxy)methyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents an (C1-C6 acyloxy)methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents an (C1-C6 acyloxy)methyl group.

a tetrazolinone compound wherein
$R^{27}$ represents a halogen atom;
$R^{28}$ represents a methyl group or a hydrogen atom; and
A represents an (C1-C6 acyloxy)methyl group.

a tetrazolinone compound wherein
$R^{27}$ represents an C1-C3 alkyl group;
$R^{28}$ represents a methyl group or a hydrogen atom; and
A represents an (C1-C6 acyloxy)methyl group.

a tetrazolinone compound wherein
$R^{27}$ represents a C3-C4 cycloalkyl group;
$R^{28}$ represents a methyl group or a hydrogen atom; and
A represents an (C1-C6 acyloxy)methyl group.

a tetrazolinone compound wherein
$R^{27}$ represents an C1-C3 alkoxy group;
$R^{28}$ represents a methyl group or a hydrogen atom; and
A represents an (C1-C6 acyloxy)methyl group.

a tetrazolinone compound wherein
$R^{27}$ represents a chlorine atom, a bromine atom, a methyl group or a methoxy group;
$R^{28}$ represents a methyl group or a hydrogen atom; and
A represents an (C1-C6 acyloxy)methyl group.

a tetrazolinone compound wherein
$R^{27}$ represents an ethyl group or a cyclopropyl group;
$R^{28}$ represents a methyl group or a hydrogen atom; and
A represents an (C1-C6 acyloxy)methyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an (C1-C6 acyloxy)methyl group.

a tetrazolinone compound wherein
$R^{27}$ represents a halogen atom, a methyl group, a trifluoromethyl group or a methoxy group;
$R^{28}$ represents a methyl group; and
A represents an (C1-C6 acyloxy)methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an (C1-C6 acyloxy)methyl group.

a tetrazolinone compound wherein
$R^{27}$ represents a halogen atom;
$R^{28}$ represents a methyl group; and
A represents an (C1-C6 acyloxy)methyl group.

a tetrazolinone compound wherein
$R^{27}$ represents an C1-C3 alkyl group;
$R^{28}$ represents a methyl group; and
A represents an (C1-C6 acyloxy)methyl group.

a tetrazolinone compound wherein
$R^{27}$ represents a C3-C4 cycloalkyl group;
$R^{28}$ represents a methyl group; and
A represents an (C1-C6 acyloxy)methyl group.

a tetrazolinone compound wherein
$R^{27}$ represents an C1-C3 alkoxy group;
$R^{28}$ represents a methyl group; and
A represents an (C1-C6 acyloxy)methyl group.

a tetrazolinone compound wherein
$R^{27}$ represents a chlorine atom, a bromine atom, a methyl group or a methoxy group;
$R^{28}$ represents a methyl group; and
A represents an (C1-C6 acyloxy)methyl group.

a tetrazolinone compound wherein
$R^{27}$ represents an ethyl group or a cyclopropyl group;
$R^{28}$ represents a methyl group; and
A represents an (C1-C6 acyloxy)methyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C1-C6 acyloxy)methyl group.

a tetrazolinone compound wherein
$R^{27}$ represents a halogen atom, a methyl group, a trifluoromethyl group or a methoxy group;
$R^{28}$ represents a hydrogen atom; and
A represents an (C1-C6 acyloxy)methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C1-C6 acyloxy)methyl group.

a tetrazolinone compound wherein
$R^{27}$ represents a halogen atom;
$R^{28}$ represents a hydrogen atom; and
A represents an (C1-C6 acyloxy)methyl group.

a tetrazolinone compound wherein
$R^{27}$ represents an C1-C3 alkyl group;
$R^{28}$ represents a hydrogen atom; and
A represents an (C1-C6 acyloxy)methyl group.

a tetrazolinone compound wherein
$R^{27}$ represents a C3-C4 cycloalkyl group;
$R^{28}$ represents a hydrogen atom; and
A represents an (C1-C6 acyloxy)methyl group.

a tetrazolinone compound wherein
$R^{27}$ represents an C1-C3 alkoxy group;
$R^{28}$ represents a hydrogen atom; and
A represents an (C1-C6 acyloxy)methyl group.

a tetrazolinone compound wherein
$R^{27}$ represents a chlorine atom, a bromine atom, a methyl group or methoxy group;
$R^{28}$ represents a hydrogen atom; and
A represents an (C1-C6 acyloxy)methyl group.

a tetrazolinone compound wherein
$R^{27}$ represents an ethyl group or a cyclopropyl group;
$R^{28}$ represents a hydrogen atom; and
A represents an (C1-C6 acyloxy)methyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents an (C1-C6 alkylsulfonyloxy)methyl group.
a tetrazolinone compound wherein
$R^{27}$ represents a halogen atom, a methyl group, a trifluoromethyl group or a methoxy group;
$R^{28}$ represents a methyl group or a hydrogen atom; and
A represents an (C1-C6 alkylsulfonyloxy)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents an (C1-C6 alkylsulfonyloxy)methyl group.
a tetrazolinone compound wherein
$R^{27}$ represents a halogen atom;
$R^{28}$ represents a methyl group or a hydrogen atom; and
A represents an (C1-C6 alkylsulfonyloxy)methyl group.
a tetrazolinone compound wherein
$R^{27}$ represents an C1-C3 alkyl group;
$R^{28}$ represents a methyl group or a hydrogen atom; and
A represents an (C1-C6 alkylsulfonyloxy)methyl group.
a tetrazolinone compound wherein
$R^{27}$ represents a C3-C4 cycloalkyl group;
$R^{28}$ represents a methyl group or a hydrogen atom; and
A represents an (C1-C6 alkylsulfonyloxy)methyl group.
a tetrazolinone compound wherein
$R^{27}$ represents an C1-C3 alkoxy group;
$R^{28}$ represents a methyl group or a hydrogen atom; and
A represents an (C1-C6 alkylsulfonyloxy)methyl group.
a tetrazolinone compound wherein
$R^{27}$ represents a chlorine atom, a bromine atom, a methyl group or a methoxy group;
$R^{28}$ represents a methyl group or a hydrogen atom; and
A represents an (C1-C6 alkylsulfonyloxy)methyl group.
a tetrazolinone compound wherein
$R^{27}$ represents an ethyl group or a cyclopropyl group;
$R^{28}$ represents a methyl group or a hydrogen atom; and
A represents an (C1-C6 alkylsulfonyloxy)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an (C1-C6 alkylsulfonyloxy)methyl group.
a tetrazolinone compound wherein
$R^{27}$ represents a halogen atom, a methyl group, a trifluoromethyl group or a methoxy group;
$R^{28}$ represents a methyl group; and
A represents an (C1-C6 alkylsulfonyloxy)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an (C1-C6 alkylsulfonyloxy)methyl group.
a tetrazolinone compound wherein
$R^{27}$ represents a halogen atom;
$R^{28}$ represents a methyl group; and
A represents an (C1-C6 alkylsulfonyloxy)methyl group.
a tetrazolinone compound wherein
$R^{27}$ represents an C1-C3 alkyl group;
$R^{28}$ represents a methyl group; and
A represents an (C1-C6 alkylsulfonyloxy)methyl group.
a tetrazolinone compound wherein
$R^{27}$ represents a C3-C4 cycloalkyl group;
$R^{28}$ represents a methyl group; and
A represents an (C1-C6 alkylsulfonyloxy)methyl group.
a tetrazolinone compound wherein
$R^{27}$ represents an C1-C3 alkoxy group;
$R^{28}$ represents a methyl group; and
A represents an (C1-C6 alkylsulfonyloxy)methyl group.
a tetrazolinone compound wherein
$R^{27}$ represents a chlorine atom, a bromine atom, a methyl group or a methoxy group;
$R^{28}$ represents a methyl group; and
A represents an (C1-C6 alkylsulfonyloxy)methyl group.
a tetrazolinone compound wherein
$R^{27}$ represents an ethyl group or a cyclopropyl group;
$R^{28}$ represents a methyl group; and
A represents an (C1-C6 alkylsulfonyloxy)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C1-C6 alkylsulfonyloxy)methyl group.
a tetrazolinone compound wherein
$R^{27}$ represents a halogen atom, a methyl group, a trifluoromethyl group or a methoxy group;
$R^{28}$ represents a hydrogen atom; and
A represents an (C1-C6 alkylsulfonyloxy)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C1-C6 alkylsulfonyloxy)methyl group.
a tetrazolinone compound wherein
$R^{27}$ represents a halogen atom;
$R^{28}$ represents a hydrogen atom; and
A represents an (C1-C6 alkylsulfonyloxy)methyl group.
a tetrazolinone compound wherein
$R^{27}$ represents an C1-C3 alkyl group;
$R^{28}$ represents a hydrogen atom; and
A represents an (C1-C6 alkylsulfonyloxy)methyl group.
a tetrazolinone compound wherein
$R^{27}$ represents a C3-C4 cycloalkyl group;
$R^{28}$ represents a hydrogen atom; and
A represents an (C1-C6 alkylsulfonyloxy)methyl group.

a tetrazolinone compound wherein
R$^{27}$ represents an C1-C3 alkoxy group;
R$^{28}$ represents a hydrogen atom; and
A represents an (C1-C6 alkylsulfonyloxy)methyl group.

a tetrazolinone compound wherein
R$^{27}$ represents a chlorine atom, a bromine atom, a methyl group or a methoxy group;
R$^{28}$ represents a hydrogen atom; and
A represents an (C1-C6 alkylsulfonyloxy)methyl group.

a tetrazolinone compound wherein
R$^{27}$ represents an ethyl group or a cyclopropyl group;
R$^{28}$ represents a hydrogen atom; and
A represents an (C1-C6 alkylsulfonyloxy)methyl group.

a tetrazolinone compound wherein
R$^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R$^{28}$ represents a hydrogen atom; and
A represents an (C1-C6 alkylsulfonyloxy)methyl group.

a tetrazolinone compound wherein
R$^{27}$ represents a halogen atom, a methyl group, a trifluoromethyl group or a methoxy group;
R$^{28}$ represents a methyl group or a hydrogen atom; and
A represents a (C1-C6 haloalkylsulfonyloxy)methyl group.

a tetrazolinone compound wherein
R$^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R$^{28}$ represents a methyl group or a hydrogen atom; and
A represents a (C1-C6 haloalkylsulfonyloxy)methyl group.

a tetrazolinone compound wherein
R$^{27}$ represents a halogen atom;
R$^{28}$ represents a methyl group or a hydrogen atom; and
A represents a (C1-C6 haloalkylsulfonyloxy)methyl group.

a tetrazolinone compound wherein
R$^{27}$ represents an C1-C3 alkyl group;
R$^{28}$ represents a methyl group or a hydrogen atom; and
A represents a (C1-C6 haloalkylsulfonyloxy)methyl group.

a tetrazolinone compound wherein
R$^{27}$ represents a C3-C4 cycloalkyl group;
R$^{28}$ represents a methyl group or a hydrogen atom; and
A represents a (C1-C6 haloalkylsulfonyloxy)methyl group.

a tetrazolinone compound wherein
R$^{27}$ represents an C1-C3 alkoxy group;
R$^{28}$ represents a methyl group or a hydrogen atom; and
A represents a (C1-C6 haloalkylsulfonyloxy)methyl group.

a tetrazolinone compound wherein
R$^{27}$ represents a chlorine atom, a bromine atom, a methyl group or a methoxy group;
R$^{28}$ represents a methyl group or a hydrogen atom; and
A represents a (C1-C6 haloalkylsulfonyloxy)methyl group.

a tetrazolinone compound wherein
R$^{27}$ represents an ethyl group or a cyclopropyl group;
R$^{28}$ represents a methyl group or a hydrogen atom; and
A represents a (C1-C6 haloalkylsulfonyloxy)methyl group.

a tetrazolinone compound wherein
R$^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R$^{28}$ represents a methyl group; and
A represents a (C1-C6 haloalkylsulfonyloxy)methyl group.

a tetrazolinone compound wherein
R$^{27}$ represents a halogen atom, a methyl group, a trifluoromethyl group or a methoxy group;
R$^{28}$ represents a methyl group; and
A represents a (C1-C6 haloalkylsulfonyloxy)methyl group.

a tetrazolinone compound wherein
R$^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R$^{28}$ represents a methyl group; and
A represents a (C1-C6 haloalkylsulfonyloxy)methyl group.

a tetrazolinone compound wherein
R$^{27}$ represents a halogen atom;
R$^{28}$ represents a methyl group; and
A represents a (C1-C6 haloalkylsulfonyloxy)methyl group.

a tetrazolinone compound wherein
R$^{27}$ represents an C1-C3 alkyl group;
R$^{28}$ represents a methyl group; and
A represents a (C1-C6 haloalkylsulfonyloxy)methyl group.

a tetrazolinone compound wherein
R$^{27}$ represents a C3-C4 cycloalkyl group;
R$^{28}$ represents a methyl group; and
A represents a (C1-C6 haloalkylsulfonyloxy)methyl group.

a tetrazolinone compound wherein
R$^{27}$ represents an C1-C3 alkoxy group;
R$^{28}$ represents a methyl group; and
A represents a (C1-C6 haloalkylsulfonyloxy)methyl group.

a tetrazolinone compound wherein
R$^{27}$ represents a chlorine atom, a bromine atom, a methyl group or a methoxy group;
R$^{28}$ represents a methyl group; and
A represents a (C1-C6 haloalkylsulfonyloxy)methyl group.

a tetrazolinone compound wherein
R$^{27}$ represents an ethyl group or a cyclopropyl group;
R$^{28}$ represents a methyl group; and
A represents a (C1-C6 haloalkylsulfonyloxy)methyl group.

a tetrazolinone compound wherein
R$^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R$^{28}$ represents a hydrogen atom; and
A represents a (C1-C6 haloalkylsulfonyloxy)methyl group.

a tetrazolinone compound wherein
R²⁷ represents a halogen atom, a methyl group, a trifluoromethyl group or a methoxy group;
R²⁸ represents a hydrogen atom; and
A represents a (C1-C6 haloalkylsulfonyloxy)methyl group.

a tetrazolinone compound wherein
R²⁷ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R²⁸ represents a hydrogen atom; and
A represents a (C1-C6 haloalkylsulfonyloxy)methyl group.

a tetrazolinone compound wherein
R²⁷ represents a halogen atom;
R²⁸ represents a hydrogen atom; and
A represents a (C1-C6 haloalkylsulfonyloxy)methyl group.

a tetrazolinone compound wherein
R²⁷ represents an C1-C3 alkyl group;
R²⁸ represents a hydrogen atom; and
A represents a (C1-C6 haloalkylsulfonyloxy)methyl group.

a tetrazolinone compound wherein
R²⁷ represents a C3-C4 cycloalkyl group;
R²⁸ represents a hydrogen atom; and
A represents a (C1-C6 haloalkylsulfonyloxy)methyl group.

a tetrazolinone compound wherein
R²⁷ represents an C1-C3 alkoxy group;
R²⁸ represents a hydrogen atom; and
A represents a (C1-C6 haloalkylsulfonyloxy)methyl group.

a tetrazolinone compound wherein
R²⁷ represents a chlorine atom, a bromine atom, a methyl group or a methoxy group;
R²⁸ represents a hydrogen atom; and
A represents a (C1-C6 haloalkylsulfonyloxy)methyl group.

a tetrazolinone compound wherein
R²⁷ represents an ethyl group or a cyclopropyl group;
R²⁸ represents a hydrogen atom; and
A represents a (C1-C6 haloalkylsulfonyloxy)methyl group.

a tetrazolinone compound wherein
R²⁷ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R²⁸ represents a methyl group or a hydrogen atom; and
A represents an (C6-C16 arylsulfonyloxy)methyl group.

a tetrazolinone compound wherein
R²⁷ represents a halogen atom, a methyl group, a trifluoromethyl group or a methoxy group;
R²⁸ represents a methyl group or a hydrogen atom; and
A represents an (C6-C16 arylsulfonyloxy)methyl group.

a tetrazolinone compound wherein
R²⁷ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R²⁸ represents a methyl group or a hydrogen atom; and
A represents an (C6-C16 arylsulfonyloxy)methyl group.

a tetrazolinone compound wherein
R²⁷ represents a halogen atom;
R²⁸ represents a methyl group or a hydrogen atom; and
A represents an (C6-C16 arylsulfonyloxy)methyl group.

a tetrazolinone compound wherein
R²⁷ represents an C1-C3 alkyl group;
R²⁸ represents a methyl group or a hydrogen atom; and
A represents an (C6-C16 arylsulfonyloxy)methyl group.

a tetrazolinone compound wherein
R²⁷ represents a C3-C4 cycloalkyl group;
R²⁸ represents a methyl group or a hydrogen atom; and
A represents an (C6-C16 arylsulfonyloxy)methyl group.

a tetrazolinone compound wherein
R²⁷ represents an C1-C3 alkoxy group;
R²⁸ represents a methyl group or a hydrogen atom; and
A represents an (C6-C16 arylsulfonyloxy)methyl group.

a tetrazolinone compound wherein
R²⁷ represents a chlorine atom, a bromine atom, a methyl group or a methoxy group;
R²⁸ represents a methyl group or a hydrogen atom; and
A represents an (C6-C16 arylsulfonyloxy)methyl group.

a tetrazolinone compound wherein
R²⁷ represents an ethyl group or a cyclopropyl group;
R²⁸ represents a methyl group or a hydrogen atom; and
A represents an (C6-C16 arylsulfonyloxy)methyl group.

a tetrazolinone compound wherein
R²⁷ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R²⁸ represents a methyl group; and
A represents an (C6-C16 arylsulfonyloxy)methyl group.

a tetrazolinone compound wherein
R²⁷ represents a halogen atom, a methyl group, a trifluoromethyl group or a methoxy group;
R²⁸ represents a methyl group; and
A represents an (C6-C16 arylsulfonyloxy)methyl group.

a tetrazolinone compound wherein
R²⁷ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R²⁸ represents a methyl group; and
A represents an (C6-C16 arylsulfonyloxy)methyl group.

a tetrazolinone compound wherein
R²⁷ represents a halogen atom;
R²⁸ represents a methyl group; and
A represents an (C6-C16 arylsulfonyloxy)methyl group.

a tetrazolinone compound wherein
R²⁷ represents an C1-C3 alkyl group;
R²⁸ represents a methyl group; and
A represents an (C6-C16 arylsulfonyloxy)methyl group.

a tetrazolinone compound wherein
R²⁷ represents a C3-C4 cycloalkyl group;
R²⁸ represents a methyl group; and
A represents an (C6-C16 arylsulfonyloxy)methyl group.

a tetrazolinone compound wherein
$R^{27}$ represents an C1-C3 alkoxy group;
$R^{28}$ represents a methyl group; and
A represents an (C6-C16 arylsulfonyloxy)methyl group.
a tetrazolinone compound wherein
$R^{27}$ represents a chlorine atom, a bromine atom, a methyl group or a methoxy group;
$R^{28}$ represents a methyl group; and
A represents an (C6-C16 arylsulfonyloxy)methyl group.
a tetrazolinone compound wherein
$R^{27}$ represents an ethyl group or a cyclopropyl group;
$R^{28}$ represents a methyl group; and
A represents an (C6-C16 arylsulfonyloxy)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C6-C16 arylsulfonyloxy)methyl group.
a tetrazolinone compound wherein
$R^{27}$ represents a halogen atom, a methyl group, a trifluoromethyl group or a methoxy group;
$R^{28}$ represents a hydrogen atom; and
A represents an (C6-C16 arylsulfonyloxy)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C6-C16 arylsulfonyloxy)methyl group.
a tetrazolinone compound wherein
$R^{27}$ represents a halogen atom;
$R^{28}$ represents a hydrogen atom; and
A represents an (C6-C16 arylsulfonyloxy)methyl group.
a tetrazolinone compound wherein
$R^{27}$ represents an C1-C3 alkyl group;
$R^{28}$ represents a hydrogen atom; and
A represents an (C6-C16 arylsulfonyloxy)methyl group.
a tetrazolinone compound wherein
$R^{27}$ represents a C3-C4 cycloalkyl group;
$R^{28}$ represents a hydrogen atom; and
A represents an (C6-C16 arylsulfonyloxy)methyl group.
a tetrazolinone compound wherein
$R^{27}$ represents an C1-C3 alkoxy group;
$R^{28}$ represents a hydrogen atom; and
A represents an (C6-C16 arylsulfonyloxy)methyl group.
a tetrazolinone compound wherein
$R^{27}$ represents a chlorine atom, a bromine atom, a methyl group or a methoxy group;
$R^{28}$ represents a hydrogen atom; and
A represents an (C6-C16 arylsulfonyloxy)methyl group.
a tetrazolinone compound wherein
$R^{27}$ represents an ethyl group or a cyclopropyl group;
$R^{28}$ represents a hydrogen atom; and
A represents an (C6-C16 arylsulfonyloxy)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a (C6-C16 haloarylsulfonyloxy)methyl group.
a tetrazolinone compound wherein
$R^{27}$ represents a halogen atom, a methyl group, a trifluoromethyl group or a methoxy group;
$R^{28}$ represents a methyl group or a hydrogen atom; and
A represents a (C6-C16 haloarylsulfonyloxy)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a (C6-C16 haloarylsulfonyloxy)methyl group.
a tetrazolinone compound wherein
$R^{27}$ represents a halogen atom;
$R^{28}$ represents a methyl group or a hydrogen atom; and
A represents a (C6-C16 haloarylsulfonyloxy)methyl group.
a tetrazolinone compound wherein
$R^{27}$ represents an C1-C3 alkyl group;
$R^{28}$ represents a methyl group or a hydrogen atom; and
A represents a (C6-C16 haloarylsulfonyloxy)methyl group.
a tetrazolinone compound wherein
$R^{27}$ represents a C3-C4 cycloalkyl group;
$R^{28}$ represents a methyl group or a hydrogen atom; and
A represents a (C6-C16 haloarylsulfonyloxy)methyl group.
a tetrazolinone compound wherein
$R^{27}$ represents an C1-C3 alkoxy group;
$R^{28}$ represents a methyl group or a hydrogen atom; and
A represents a (C6-C16 haloarylsulfonyloxy)methyl group.
a tetrazolinone compound wherein
$R^{27}$ represents a chlorine atom, a bromine atom, a methyl group or a methoxy group;
$R^{28}$ represents a methyl group or a hydrogen atom; and
A represents a (C6-C16 haloarylsulfonyloxy)methyl group.
a tetrazolinone compound wherein
$R^{27}$ represents an ethyl group or a cyclopropyl group;
$R^{28}$ represents a methyl group or a hydrogen atom; and
A represents a (C6-C16 haloarylsulfonyloxy)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a (C6-C16 haloarylsulfonyloxy)methyl group.
a tetrazolinone compound wherein
$R^{27}$ represents a halogen atom, a methyl group, a trifluoromethyl group or a methoxy group;
$R^{28}$ represents a methyl group; and
A represents a (C6-C16 haloarylsulfonyloxy)methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a (C6-C16 haloarylsulfonyloxy)methyl group.

a tetrazolinone compound wherein
$R^{27}$ represents a halogen atom;
$R^{28}$ represents a methyl group; and
A represents a (C6-C16 haloarylsulfonyloxy)methyl group.

a tetrazolinone compound wherein
$R^{27}$ represents an C1-C3 alkyl group;
$R^{28}$ represents a methyl group; and
A represents a (C6-C16 haloarylsulfonyloxy)methyl group.

a tetrazolinone compound wherein
$R^{27}$ represents a C3-C4 cycloalkyl group;
$R^{28}$ represents a methyl group; and
A represents a (C6-C16 haloarylsulfonyloxy)methyl group.

a tetrazolinone compound wherein
$R^{27}$ represents an C1-C3 alkoxy group;
$R^{10}$ represents a methyl group; and
A represents a (C6-C16 haloarylsulfonyloxy)methyl group.

a tetrazolinone compound wherein
$R^{27}$ represents a chlorine atom, a bromine atom, a methyl group or a methoxy group;
$R^{28}$ represents a methyl group; and
A represents a (C6-C16 haloarylsulfonyloxy)methyl group.

a tetrazolinone compound wherein
$R^{27}$ represents an ethyl group or a cyclopropyl group;
$R^{28}$ represents a methyl group; and
A represents a (C6-C16 haloarylsulfonyloxy)methyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a (C6-C16 haloarylsulfonyloxy)methyl group.

a tetrazolinone compound wherein
$R^{27}$ represents a halogen atom, a methyl group, a trifluoromethyl group or a methoxy group;
$R^{28}$ represents a hydrogen atom; and
A represents a (C6-C16 haloarylsulfonyloxy)methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a (C6-C16 haloarylsulfonyloxy)methyl group.

a tetrazolinone compound wherein
$R^{27}$ represents a halogen atom;
$R^{28}$ represents a hydrogen atom; and
A represents a (C6-C16 haloarylsulfonyloxy)methyl group.

a tetrazolinone compound wherein
$R^{27}$ represents an C1-C3 alkyl group;
$R^{28}$ represents a hydrogen atom; and
A represents a (C6-C16 haloarylsulfonyloxy)methyl group.

a tetrazolinone compound wherein
$R^{27}$ represents a C3-C4 cycloalkyl group;
$R^{28}$ represents a hydrogen atom; and
A represents a (C6-C16 haloarylsulfonyloxy)methyl group.

a tetrazolinone compound wherein
$R^{27}$ represents an C1-C3 alkoxy group;
$R^{28}$ represents a hydrogen atom; and
A represents a (C6-C16 haloarylsulfonyloxy)methyl group.

a tetrazolinone compound wherein.
$R^{27}$ represents a chlorine atom, a bromine atom, a methyl group or a methoxy group;
$R^{28}$ represents a hydrogen atom; and
A represents a (C6-C16 haloarylsulfonyloxy)methyl group.

a tetrazolinone compound wherein
$R^{27}$ represents an ethyl group or a cyclopropyl group;
$R^{28}$ represents a hydrogen atom; and
A represents a (C6-C16 haloarylsulfonyloxy)methyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, C1-C2 haloalkylthio group or an C1-C4 alkylamino group;
$R^{28}$ represents a methyl group or a hydrogen atom; and
A represents an (C1-C6 alkylamino)methyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents an (C1-C6 alkylamino)methyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents an (C1-C6 alkylamino)methyl group.

a tetrazolinone compound wherein
$R^{27}$ represents a halogen atom;
$R^{28}$ represents a methyl group or a hydrogen atom; and
A represents an (C1-C6 alkylamino)methyl group.

a tetrazolinone compound wherein
$R^{27}$ represents an C1-C3 alkyl group;
$R^{28}$ represents a methyl group or a hydrogen atom; and
A represents an (C1-C6 alkylamino)methyl group.

a tetrazolinone compound wherein
$R^{27}$ represents a C3-C4 cycloalkyl group;
$R^{28}$ represents a methyl group or a hydrogen atom; and
A represents an (C1-C6 alkylamino)methyl group.

a tetrazolinone compound wherein
$R^{27}$ represents an C1-C3 alkoxy group;
$R^{28}$ represents a methyl group or a hydrogen atom; and
A represents an (C1-C6 alkylamino)methyl group.
a tetrazolinone compound wherein
$R^{27}$ represents a chlorine atom, a bromine atom, a methyl group or a methoxy group;
$R^{28}$ represents a methyl group or a hydrogen atom; and
A represents an (C1-C6 alkylamino)methyl group.
a tetrazolinone compound wherein
$R^{27}$ represents an ethyl group or a cyclopropyl group;
$R^{28}$ represents a methyl group or a hydrogen atom; and
A represents an (C1-C6 alkylamino)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an (C1-C6 alkylamino)methyl group.
a tetrazolinone compound wherein
$R^{27}$ represents a halogen atom, a methyl group, a trifluoromethyl group or a methoxy group;
$R^{28}$ represents a methyl group; and
A represents an (C1-C6 alkylamino)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an (C1-C6 alkylamino)methyl group.
a tetrazolinone compound wherein
$R^{27}$ represents a halogen atom;
$R^{28}$ represents a methyl group; and
A represents an (C1-C6 alkylamino)methyl group.
a tetrazolinone compound wherein
$R^{27}$ represents an C1-C3 alkyl group;
$R^{28}$ represents a methyl group; and
A represents an (C1-C6 alkylamino)methyl group.
a tetrazolinone compound wherein
$R^{27}$ represents a C3-C4 cycloalkyl group;
$R^{28}$ represents a methyl group; and
A represents an (C1-C6 alkylamino)methyl group.
a tetrazolinone compound wherein
$R^{27}$ represents an C1-C3 alkoxy group;
$R^{28}$ represents a methyl group; and
A represents an (C1-C6 alkylamino)methyl group.
a tetrazolinone compound wherein
$R^{27}$ represents a chlorine atom, a bromine atom, a methyl group or a methoxy group;
$R^{28}$ represents a methyl group; and
A represents an (C1-C6 alkylamino)methyl group.
a tetrazolinone compound wherein
$R^{27}$ represents an ethyl group or a cyclopropyl group;
$R^{28}$ represents a methyl group; and
A represents an (C1-C6 alkylamino)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C1-C6 alkylamino)methyl group.
a tetrazolinone compound wherein
$R^{27}$ represents a halogen atom, a methyl group, a trifluoromethyl group or a methoxy group;
$R^{28}$ represents a hydrogen atom; and
A represents an (C1-C6 alkylamino)methyl group.
a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents an (C1-C6 alkylamino)methyl group.
a tetrazolinone compound wherein
$R^{27}$ represents a halogen atom;
$R^{28}$ represents a hydrogen atom; and
A represents an (C1-C6 alkylamino)methyl group.
a tetrazolinone compound wherein
$R^{27}$ represents an C1-C3 alkyl group;
$R^{28}$ represents a hydrogen atom; and
A represents an (C1-C6 alkylamino)methyl group.
a tetrazolinone compound wherein
$R^{27}$ represents a C3-C4 cycloalkyl group;
$R^{28}$ represents a hydrogen atom; and
A represents an (C1-C6 alkylamino)methyl group.
a tetrazolinone compound wherein
$R^{27}$ represents an C1-C3 alkoxy group;
$R^{28}$ represents a hydrogen atom; and
A represents an (C1-C6 alkylamino)methyl group.
a tetrazolinone compound wherein
$R^{27}$ represents a chlorine atom, a bromine atom, a methyl group or methoxy group;
$R^{28}$ represents a hydrogen atom; and
A represents an (C1-C6 alkylamino)methyl group.
a tetrazolinone compound wherein
$R^{27}$ represents an ethyl group or a cyclopropyl group;
$R^{28}$ represents a hydrogen atom; and
A represents an (C1-C6 alkylamino)methyl group.
a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents an oxygen atom, a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).
a tetrazolinone compound wherein
$R^{27}$ represents a halogen atom, a methyl group, a trifluoromethyl group or a methoxy group;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C1-C3 alkyl group;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a C3-C4 cycloalkyl group;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C1-C3 alkoxy group;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a chlorine atom, a bromine atom, a methyl group or a methoxy group;
$R^{28}$ represents a methyl group or a hydrogen atom; and A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an ethyl group or a cyclopropyl group;
$R^{28}$ represents a methyl group or a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom, a methyl group, a trifluoromethyl group or a methoxy group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom;
$R^{28}$ represents a methyl group; and A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C1-C3 alkyl group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a C3-C4 cycloalkyl group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C1-C3 alkoxy group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a chlorine atom, a bromine atom, a methyl group or a methoxy group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an ethyl group or a cyclopropyl group;
$R^{28}$ represents a methyl group; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom, a methyl group, a trifluoromethyl group or a methoxy group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C1-C3 alkyl group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a C3-C4 cycloalkyl group;
$R^{28}$ represents a hydrogen atom; and A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an C1-C3 alkoxy group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a chlorine atom, a bromine atom, a methyl group or a methoxy group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents an ethyl group or a cyclopropyl group;
$R^{28}$ represents a hydrogen atom; and
A represents a methyl group having heterocyclyl group (with the proviso that the heterocyclyl group is a five-membered, six-membered or seven-membered ring containing one or more nitrogen atoms as ring-constituent atom and may further include one or more oxygen atoms or sulfur atoms, and the nitrogen atom being the ring-constituent atom for the heterocyclyl group and a methyl group connects to each other).

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents a formyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents a formyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and a tetrazolinone compound wherein
$R^{27}$ represents a halogen atom;
$R^{28}$ represents a methyl group or a hydrogen atom; and
A represents a formyl group.

a tetrazolinone compound wherein
$R^{27}$ represents an C1-C3 alkyl group;
$R^{28}$ represents a methyl group or a hydrogen atom; and
A represents a formyl group.

a tetrazolinone compound wherein
$R^{27}$ represents a C3-C4 cycloalkyl group;
$R^{28}$ represents a methyl group or a hydrogen atom; and
A represents a formyl group.

a tetrazolinone compound wherein
$R^{27}$ represents an C1-C3 alkoxy group;
$R^{28}$ represents a methyl group or a hydrogen atom; and
A represents a formyl group.

a tetrazolinone compound wherein
$R^{27}$ represents a chlorine atom, a bromine atom, a methyl group or a methoxy group;
$R^{28}$ represents a methyl group or a hydrogen atom; and
A represents a formyl group.

a tetrazolinone compound wherein
$R^{27}$ represents an ethyl group or a cyclopropyl group;
$R^{28}$ represents a methyl group or a hydrogen atom; and
A represents a formyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a formyl group.

a tetrazolinone compound wherein
$R^{27}$ represents a halogen atom, a methyl group, a trifluoromethyl group or a methoxy group;
$R^{28}$ represents a methyl group; and
A represents a formyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents a formyl group.

a tetrazolinone compound wherein
$R^{27}$ represents a halogen atom;
$R^{28}$ represents a methyl group; and
A represents a formyl group.

a tetrazolinone compound wherein
$R^{27}$ represents an C1-C3 alkyl group;
$R^{28}$ represents a methyl group; and
A represents a formyl group.

a tetrazolinone compound wherein
$R^{27}$ represents a C3-C4 cycloalkyl group;
$R^{28}$ represents a methyl group; and
A represents a formyl group.

a tetrazolinone compound wherein
$R^{27}$ represents an C1-C3 alkoxy group;
$R^{28}$ represents a methyl group; and
A represents a formyl group.

a tetrazolinone compound wherein
$R^{27}$ represents a chlorine atom, a bromine atom, a methyl group or a methoxy group;
$R^{28}$ represents a methyl group; and
A represents a formyl group.

a tetrazolinone compound wherein
$R^{27}$ represents an ethyl group or a cyclopropyl group;
$R^{28}$ represents a methyl group; and
A represents a formyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a formyl group.

a tetrazolinone compound wherein
$R^{27}$ represents a halogen atom, a methyl group, a trifluoromethyl group or a methoxy group;
$R^{28}$ represents a hydrogen atom; and
A represents a formyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a hydrogen atom; and
A represents a formyl group.

a tetrazolinone compound wherein
$R^{27}$ represents a halogen atom;
$R^{28}$ represents a hydrogen atom; and
A represents a formyl group.

a tetrazolinone compound wherein
$R^{27}$ represents an C1-C3 alkyl group;
$R^{28}$ represents a hydrogen atom; and
A represents a formyl group.

a tetrazolinone compound wherein
$R^{10}$ represents a C3-C4 cycloalkyl group;
$R^{28}$ represents a hydrogen atom; and
A represents a formyl group.

a tetrazolinone compound wherein
$R^{27}$ represents an C1-C3 alkoxy group;
$R^{28}$ represents a hydrogen atom; and
A represents a formyl group.

a tetrazolinone compound wherein
$R^{27}$ represents a chlorine atom, a bromine atom, a methyl group or a methoxy group;
$R^{28}$ represents a hydrogen atom; and
A represents a formyl group.

a tetrazolinone compound wherein
$R^{27}$ represents an ethyl group or a cyclopropyl group;
$R^{28}$ represents a hydrogen atom; and
A represents a formyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group or a hydrogen atom; and
A represents an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group or a hydrogen atom; and
A represents an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{10}$ represents a methyl group or a hydrogen atom; and
A represents an C2-C6 alkoxycarbonyl group.

a tetrazolinone compound wherein
$R^{27}$ represents a halogen atom;
$R^{28}$ represents a methyl group or a hydrogen atom; and
A represents an C2-C6 alkoxycarbonyl group.

a tetrazolinone compound wherein
$R^{27}$ represents an C1-C3 alkyl group;
$R^{28}$ represents a methyl group or a hydrogen atom; and
A represents an C2-C6 alkoxycarbonyl group.

a tetrazolinone compound wherein
$R^{27}$ represents a C3-C4 cycloalkyl group;
$R^{28}$ represents a methyl group or a hydrogen atom; and
A represents an C2-C6 alkoxycarbonyl group.

a tetrazolinone compound wherein
$R^{27}$ represents an C1-C3 alkoxy group;
$R^{28}$ represents a methyl group or a hydrogen atom; and
A represents an C2-C6 alkoxycarbonyl group.

a tetrazolinone compound wherein
$R^{27}$ represents a chlorine atom, a bromine atom, a methyl group or a methoxy group;
$R^{28}$ represents a methyl group or a hydrogen atom; and
A represents an C2-C6 alkoxycarbonyl group.

a tetrazolinone compound wherein
$R^{27}$ represents an ethyl group or a cyclopropyl group;
$R^{28}$ represents a methyl group or a hydrogen atom; and
A represents an C2-C6 alkoxycarbonyl group.

a tetrazolinone compound wherein
$R^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an C2-C6 alkoxycarbonyl group.

a tetrazolinone compound wherein
$R^{27}$ represents a halogen atom, a methyl group, a trifluoromethyl group or a methoxy group;
$R^{28}$ represents a methyl group; and
A represents an C2-C6 alkoxycarbonyl group.

a tetrazolinone compound wherein
$R^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
$R^{28}$ represents a methyl group; and
A represents an C2-C6 alkoxycarbonyl group.

a tetrazolinone compound wherein
$R^{27}$ represents a halogen atom;
$R^{28}$ represents a methyl group; and
A represents an C2-C6 alkoxycarbonyl group.

a tetrazolinone compound wherein
$R^{27}$ represents an C1-C3 alkyl group;
$R^{28}$ represents a methyl group; and
A represents an C2-C6 alkoxycarbonyl group.

a tetrazolinone compound wherein
$R^{27}$ represents a C3-C4 cycloalkyl group;
$R^{28}$ represents a methyl group; and A represents an C2-C6 alkoxycarbonyl group.
a tetrazolinone compound wherein
R$^{27}$ represents an C1-C3 alkoxy group;
R$^{28}$ represents a methyl group; and
A represents an C2-C6 alkoxycarbonyl group.
a tetrazolinone compound wherein
R$^{27}$ represents a chlorine atom, a bromine atom, a methyl group or a methoxy group;
R$^{28}$ represents a methyl group; and
A represents an C2-C6 alkoxycarbonyl group.
a tetrazolinone compound wherein
R$^{27}$ represents an ethyl group or a cyclopropyl group;
R$^{28}$ represents a methyl group; and
A represents an C2-C6 alkoxycarbonyl group.
a tetrazolinone compound wherein
R$^{27}$ represents a halogen atom, an C1-C3 alkyl group, a C1-C3 haloalkyl group, an C2-C3 alkenyl group, an C2-C3 alkynyl group, a C3-C4 cycloalkyl group, an C1-C3 alkoxy group, a C1-C3 haloalkoxy group, an C1-C2 alkylthio group, a C1-C2 haloalkylthio group or an C1-C4 alkylamino group;
R$^{28}$ represents a hydrogen atom; and
A represents an C2-C6 alkoxycarbonyl group.
a tetrazolinone compound wherein
R$^{27}$ represents a halogen atom, a methyl group, a trifluoromethyl group or a methoxy group;
R$^{28}$ represents a hydrogen atom; and
A represents an C2-C6 alkoxycarbonyl group.
a tetrazolinone compound wherein
R$^{27}$ represents an C2-C3 alkyl group, a C1-C3 haloalkyl group excluding trifluoromethyl group, an C2-C3 alkenyl group, an C2-C3 alkynyl group, a C3-C4 cycloalkyl group, an C2-C3 alkoxy group, a C1-C3 haloalkoxy group, an C1-C2 alkylthio group, a C1-C2 haloalkylthio group or an C1-C4 alkylamino group;
R$^{28}$ represents a hydrogen atom; and
A represents an C2-C6 alkoxycarbonyl group.
a tetrazolinone compound wherein
R$^{27}$ represents a halogen atom;
R$^{28}$ represents a hydrogen atom; and
A represents an C2-C6 alkoxycarbonyl group.
a tetrazolinone compound wherein
R$^{27}$ represents an C1-C3 alkyl group;
R$^{28}$ represents a hydrogen atom; and
A represents an C2-C6 alkoxycarbonyl group.
a tetrazolinone compound wherein
R$^{27}$ represents a C3-C4 cycloalkyl group;
R$^{28}$ represents a hydrogen atom; and
A represents an C2-C6 alkoxycarbonyl group.
a tetrazolinone compound wherein
R$^{27}$ represents an C1-C3 alkoxy group;
R$^{28}$ represents a hydrogen atom; and
A represents an C2-C6 alkoxycarbonyl group.
a tetrazolinone compound wherein
R$^{27}$ represents a chlorine atom, a bromine atom, a methyl group or a methoxy group;
R$^{28}$ represents a hydrogen atom; and
A represents an C2-C6 alkoxycarbonyl group.
a tetrazolinone compound wherein
R$^{27}$ represents an ethyl group or a cyclopropyl group;
R$^{28}$ represents a hydrogen atom; and
A represents an C2-C6 alkoxycarbonyl group.
a tetrazolinone compound wherein
A represents a methyl group, a halomethyl group, a hydroxymethyl group or an (C1-C3 alkoxy)methyl group;
R$^{27}$ represents an C1-C3 alkyl group, a halogen atom, an C1-C3 alkoxy group, a C3-C4 cycloalkyl group, an C2-C3 alkenyl group, a C1-C3 haloalkyl group, a C1-C3 haloalkoxy group or an C1-C2 alkylthio group;
R$^{28}$ represents a methyl group or a hydrogen atom.
a tetrazolinone compound wherein
A represents a methyl group, a bromomethyl group, a hydroxymethyl group or a methoxymethyl group;
R$^{27}$ represents a methyl group, an ethyl group, a fluorine atom, a chlorine atom, a bromine atom, an iodine atom, a cyclopropyl group, a vinyl group, a difluoromethyl group, a trifluoromethyl group, a methoxy group, an ethoxy group, a difluoromethoxy group or a methylthio group;
R$^{28}$ represents a methyl group or a hydrogen atom.

Also, examples of an embodiment of the present tetrazolinone compound include the compounds of the formula (5) wherein the substituents represent the following ones.
a tetrazolinone compound wherein
R$^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;
R$^{22}$, R$^{23}$, R$^{24}$ and R$^{25}$ represent independently of each other a hydrogen atom or a halogen atom; and
R$^{26}$ represents an C1-C3 alkyl group.
a tetrazolinone compound wherein
R$^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
R$^{22}$, R$^{23}$, R$^{24}$ and R$^{25}$ represent independently of each other a hydrogen atom or a halogen atom; and
R$^{26}$ represents a C3-C4 cycloalkyl group.
a tetrazolinone compound wherein
R$^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
R$^{22}$, R$^{23}$, R$^{24}$ and R$^{25}$ represent independently of each other a hydrogen atom or a halogen atom; and
R$^{26}$ represents a halogen atom.
a tetrazolinone compound wherein
R$^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
R$^{22}$, R$^{23}$, R$^{24}$ and R$^{25}$ represent independently of each other a hydrogen atom or a halogen atom; and
R$^{26}$ represents a C1-C3 haloalkyl group.
a tetrazolinone compound wherein
R$^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
R$^{22}$, R$^{23}$, R$^{24}$ and R$^{25}$ represent independently of each other a hydrogen atom or a halogen atom; and
R$^{26}$ represents an C2-C3 alkenyl group.

a tetrazolinone compound wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents an C1-C3 alkoxy group.

a tetrazolinone compound wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents an C1-C2 alkylthio group.

a tetrazolinone compound wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents an C2-C3 alkynyl group.

a tetrazolinone compound wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents a C1-C3 haloalkoxy group.

a tetrazolinone compound wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents a C1-C2 haloalkylthio group.

a tetrazolinone compound wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, an C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents an C1-C4 alkylamino group.

a tetrazolinone compound wherein
$R^{21}$ represents a halogen atom, a methyl group, an ethyl group or a methoxy group;
$R^{26}$ represents a methyl group; and
$R^{22}$, $R^{23}$, $R^{24}$ and $R^{25}$ represent independently of each other a hydrogen atom or a fluorine atom.

a tetrazolinone compound wherein
$R^{21}$ represents a halogen atom, a methyl group, an ethyl group or a methoxy group;
$R^{26}$ represents a cyclopropyl group; and
$R^{22}$, $R^{23}$, $R^{24}$ and $R^{25}$ represent independently of each other a hydrogen atom or a fluorine atom.

a tetrazolinone compound wherein
$R^{21}$ represents a halogen atom, a methyl group, an ethyl group or a methoxy group;
$R^{26}$ represents a chlorine atom; and
$R^{22}$, $R^{23}$, $R^{24}$ and $R^{25}$ represent independently of each other a hydrogen atom or a fluorine atom.

a tetrazolinone compound wherein
$R^{21}$ represents a halogen atom, a methyl group, an ethyl group or a methoxy group;
$R^{26}$ represents a bromine atom; and
$R^{22}$, $R^{23}$, $R^{24}$ and $R^{25}$ represent independently of each other a hydrogen atom or a fluorine atom.

a tetrazolinone compound wherein
$R^{21}$ represents a halogen atom, a methyl group, an ethyl group or a methoxy group;
$R^{26}$ represents an ethyl group; and
$R^{22}$, $R^{23}$, $R^{24}$ and $R^{25}$ represent independently of each other a hydrogen atom or a fluorine atom.

a tetrazolinone compound wherein
$R^{21}$ represents a halogen atom, a methyl group, an ethyl group or a methoxy group;
$R^{26}$ represents a methoxy group; and
$R^{22}$, $R^{23}$, $R^{24}$ and $R^{25}$ represent independently of each other a hydrogen atom or a fluorine atom.

a tetrazolinone compound wherein
$R^{21}$ represents a halogen atom;
$R^{22}$, $R^{23}$, $R^{24}$ and $R^{25}$ represent a hydrogen atom;
$R^{26}$ represents an C1-C3 alkyl group.

a tetrazolinone compound wherein
$R^{21}$ represents a chlorine atom;
$R^{22}$, $R^{23}$, $R^{24}$ and $R^{25}$ represent a hydrogen atom;
$R^{26}$ represents a methyl group.

Also, examples of an embodiment of the present tetrazolinone compound include the compounds of the formula (6) wherein the substituents represent the following ones.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents an C1-C3 alkyl group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents a C3-C4 cycloalkyl group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents a halogen atom.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents a C1-C3 haloalkyl group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents an C2-C3 alkenyl group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents an C1-C3 alkoxy group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{241}$, $R^{43}$, $R^{44}$ and $R^{45}$ represent independently of each other a hydrogen atom or a halogen atom; and
$R^{46}$ represents an C1-C2 alkylthio group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents an C2-C3 alkynyl group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents a C1-C3 haloalkoxy group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents a C1-C2 haloalkylthio group.

a tetrazolinone compound wherein
$R^{42}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom; and
$R^{46}$ represents an C1-C4 alkylamino group.

a tetrazolinone compound wherein
$R^{42}$ represents a methoxy group, a halogen atom, a methyl group or an ethyl group;
$R^{46}$ represents a methyl group; and
$R^{41}$, $R^{43}$, $R^{44}$ and $R^{45}$ represent independently of each other a hydrogen atom or a fluorine atom.

a tetrazolinone compound wherein
$R^{42}$ represents a methoxy group, a halogen atom, a methyl group or an ethyl group;
$R^{46}$ represents a cyclopropyl group; and
$R^{41}$, $R^{43}$, $R^{44}$ and $R^{45}$ represent independently of each other a hydrogen atom or a fluorine atom.

a tetrazolinone compound wherein
$R^{42}$ represents a methoxy group, a halogen atom, a methyl group or an ethyl group;
$R^{46}$ represents a chlorine atom; and
$R^{41}$, $R^{43}$, $R^{44}$ and $R^{45}$ represent independently of each other a hydrogen atom or a fluorine atom.

a tetrazolinone compound wherein
$R^{42}$ represents a methoxy group, a halogen atom, a methyl group or an ethyl group;
$R^{46}$ represents a bromine atom; and
$R^{41}$, $R^{43}$, $R^{44}$ and $R^{45}$ represent independently of each other a hydrogen atom or a fluorine atom.

a tetrazolinone compound wherein
$R^{42}$ represents a methoxy group, a halogen atom, a methyl group or an ethyl group;
$R^{46}$ represents an ethyl group; and
$R^{41}$, $R^{43}$, $R^{44}$ and $R^{45}$ represent independently of each other a hydrogen atom or a fluorine atom.

a tetrazolinone compound wherein
$R^{42}$ represents a methoxy group, a halogen atom, a methyl group or an ethyl group;
$R^{46}$ represents a methoxy group; and
$R^{41}$, $R^{43}$, $R^{44}$ and $R^{45}$ represent independently of each other a hydrogen atom or a fluorine atom.

Also, examples of an embodiment of the present tetrazolinone compound include the compounds of the formula (7) wherein the substituents represent the following ones.

a tetrazolinone compound wherein
$R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{51}$, $R^{53}$, $R^{54}$ and $R^{55}$ represent independently of each other a hydrogen atom or a halogen atom; and
$R^{56}$ represents an C1-C3 alkyl group.

a tetrazolinone compound wherein
$R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{51}$, $R^{53}$, $R^{54}$ and $R^{55}$ represent independently of each other a hydrogen atom or a halogen atom; and
$R^{56}$ represents a C3-C4 cycloalkyl group.

a tetrazolinone compound wherein
$R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents a halogen atom.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents a C1-C3 haloalkyl group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents an C2-C3 alkenyl group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents an C1-C3 alkoxy group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents an C1-C2 alkylthio group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents an C2-C3 alkynyl group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents a C1-C3 haloalkoxy group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents a C1-C2 haloalkylthio group.

a tetrazolinone compound wherein $R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{51}$, $R^{53}$, $R^{54}$ and $R^{55}$ represent independently of each other a hydrogen atom or a halogen atom; and $R^{56}$ represents an C1-C4 alkylamino group.

a tetrazolinone compound wherein $R^{53}$ represents a methoxy group, a halogen atom, a methyl group or an ethyl group;

$R^{56}$ represents a methyl group; and $R^{51}$, $R^{53}$, $R^{54}$ and $R^{55}$ represent independently of each other a hydrogen atom or a fluorine atom.

a tetrazolinone compound wherein $R^{53}$ represents a methoxy group, a halogen atom, a methyl group or an ethyl group;

$R^{56}$ represents a cyclopropyl group; and $R^{51}$, $R^{53}$, $R^{54}$ and $R^{55}$ represent independently of each other a hydrogen atom or a fluorine atom.

a tetrazolinone compound wherein $R^{53}$ represents a methoxy group, a halogen atom, a methyl group or an ethyl group;

$R^{56}$ represents a chlorine atom; and $R^{51}$, $R^{53}$, $R^{54}$ and $R^{55}$ represent independently of each other a hydrogen atom or a fluorine atom.

a tetrazolinone compound wherein $R^{53}$ represents a methoxy group, a halogen atom, a methyl group or an ethyl group;

$R^{56}$ represents a bromine atom; and $R^{51}$, $R^{53}$, $R^{54}$ and $R^{55}$ represent independently of each other a hydrogen atom or a fluorine atom.

a tetrazolinone compound wherein $R^{53}$ represents a methoxy group, a halogen atom, a methyl group or an ethyl group;

$R^{56}$ represents an ethyl group; and $R^{51}$, $R^{53}$, $R^{54}$ and $R^{55}$ represent independently of each other a hydrogen atom or a fluorine atom.

a tetrazolinone compound wherein $R^{53}$ represents a methoxy group, a halogen atom, a methyl group or an ethyl group;

$R^{56}$ represents a methoxy group; and $R^{51}$, $R^{53}$, $R^{54}$ and $R^{55}$ represent independently of each other a hydrogen atom or a fluorine atom.

Also, examples of an embodiment of the present pyrazole compound include the compounds of the formula (9) wherein the substituents represent the following ones.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents a C3-C4 cycloalkyl group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents a halogen atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents a C1-C3 haloalkyl group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C2-C3 alkenyl group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkoxy group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C2 alkylthio group; and $L^1$ represents a nitro group, an amino group, an isocyanato group, a carboxyl group, an C2-C6 alkoxycarbonyl group, a halogen atom, a halogenated acyl group, NSO, $CON_2$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C2-C3 alkynyl group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents a C1-C3 haloalkoxy group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents a C1-C2 haloalkylthio group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C4 alkylamino group; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a nitro group.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents an amino group.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents an isocyanato group.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a carboxyl group.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents an C2-C6 alkoxycarbonyl group.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a halogen atom.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a halogenated acyl group.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents NSO.

a pyrazole compound wherein $R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a $CON_3$ group.

a pyrazole compound wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a $CONH_2$ group.

a pyrazole compound wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a CONHCl group.

a pyrazole compound wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a CONHBr group.

a pyrazole compound wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{221}$, $R^{231}$, $R^{241}$ and $R^{251}$ represent independently of each other a hydrogen atom or a halogen atom;

$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^1$ represents a CONHOH group.

a pyrazole compound wherein
$R^{211}$ represents a halogen atom, a methyl group, an ethyl group or a methoxy group;

$R^{261}$ represents a methyl group;

$R^{221}$, $R^{231}$, $R^{241}$ and $R^{251}$ represent independently of each other a hydrogen atom or a fluorine atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{211}$ represents a halogen atom, a methyl group, an ethyl group or a methoxy group;

$R^{261}$ represents a cyclopropyl group;

$R^{221}$, $R^{231}$, $R^{241}$ and $R^{251}$ represent independently of each other a hydrogen atom or a fluorine atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{211}$ represents a halogen atom, a methyl group, an ethyl group or a methoxy group;

$R^{261}$ represents a chlorine atom;

$R^{221}$, $R^{231}$, $R^{241}$ and $R^{251}$ represent independently of each other a hydrogen atom or a fluorine atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{211}$ represents a halogen atom, a methyl group, an ethyl group or a methoxy group;

$R^{261}$ represents a bromine atom;

$R^{221}$, $R^{231}$, $R^{241}$ and $R^{251}$ represent independently of each other a hydrogen atom or a fluorine atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{211}$ represents a halogen atom, a methyl group, an ethyl group or a methoxy group;

$R^{261}$ represents an ethyl group;

$R^{221}$, $R^{231}$, $R^{241}$ and $R^{261}$ represent independently of each other a hydrogen atom or a fluorine atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{211}$ represents a halogen atom, a methyl group, an ethyl group or a methoxy group;

$R^{261}$ represents a methoxy group;

$R^{221}$, $R^{231}$, $R^{241}$ and $R^{261}$ represent independently of each other a hydrogen atom or a fluorine atom; and $L^1$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents a nitro group.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents an amino group.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents an isocyanato group.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents a carboxyl group.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents an C2-C6 alkoxycarbonyl group.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents a halogen atom.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents a halogenated acyl group.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents NSO.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents $CON_3$.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents $CONH_2$.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents CONHCl.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents CONHBr.

a pyrazole compound wherein
$R^{211}$ represents a halogen atom, a methyl group, an ethyl group or a methoxy group;
$R^{261}$ represents a methyl group, a cyclopropyl group, a chlorine atom, a bromine atom, an ethyl group or a methoxy group;
$R^{221}$, $R^{231}$, $R^{241}$ and $R^{251}$ represent independently of each other a hydrogen atom or a fluorine atom; and
$L^1$ represents CONHOH.

a pyrazole compound wherein
$R^{211}$ represents a halogen atom;
$R^{221}$, $R^{231}$, $R^{241}$ and $R^{251}$ represent a hydrogen atom;
$R^{261}$ represents an C1-C3 alkyl group; and
$L^1$ represents a nitro group, an amino group or an isocyanato group.

a pyrazole compound wherein
$R^{211}$ represents a chlorine atom;
$R^{221}$, $R^{231}$, $R^{241}$ and $R^{251}$ represent a hydrogen atom;
$R^{261}$ represents a methyl group; and
$L^1$ represents a nitro group, an amino group or an isocyanato group.

Also, examples of an embodiment of the present pyrazole compound include the compounds of the formula (10) wherein the substituents represent the following ones.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C3-C4 cycloalkyl group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents a halogen atom; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents a C1-C3 haloalkyl group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C2-C3 alkenyl group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkoxy group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{411}$, $R^{441}$ and $R^{451}$ represent independently of each other a hydrogen atom or a halogen atom;
$R^{461}$ represents an C1-C2 alkylthio group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C2-C3 alkynyl group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein,
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents a C1-C3 haloalkoxy group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents a C1-C2 haloalkylthio group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C4 alkylamino group; and
$L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents a nitro group.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents an amino group.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents an isocyanato group.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents a carboxyl group.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents an C2-C6 alkoxycarbonyl group.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents a halogen atom.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents a halogenated acyl group.

a pyrazole compound wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents NSO.

a pyrazole compound wherein $R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{411}$, $R^{431}$, $R^{441}$ and $R^{451}$ represent independently of each other a hydrogen atom or a halogen atom;

$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^2$ represents $CON_3$.

a pyrazole compound wherein $R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{411}$, $R^{431}$, $R^{441}$ and $R^{451}$ represent independently of each other a hydrogen atom or a halogen atom;

$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^2$ represents $CONH_2$.

a pyrazole compound wherein $R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{411}$, $R^{431}$, $R^{441}$ and $R^{451}$ represent independently of each other a hydrogen atom or a halogen atom;

$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^2$ represents CONHCl.

a pyrazole compound wherein $R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{411}$, $R^{431}$, $R^{441}$ and $R^{451}$ represent independently of each other a hydrogen atom or a halogen atom;

$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^2$ represents CONHBr.

a pyrazole compound wherein $R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{411}$, $R^{431}$, $R^{441}$ and $R^{451}$ represent independently of each other a hydrogen atom or a halogen atom;

$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^2$ represents CONHOH.

a pyrazole compound wherein $R^{421}$ represents a methoxy group, a halogen atom, a methyl group or an ethyl group;

$R^{461}$ represents a methyl group;

$R^{411}$, $R^{431}$, $R^{441}$ and $R^{451}$ represent independently of each other a hydrogen atom or a fluorine atom; and $L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{421}$ represents a methoxy group, a halogen atom, a methyl group or an ethyl group;

$R^{461}$ represents a cyclopropyl group;

$R^{411}$, $R^{431}$, $R^{441}$ and $R^{451}$ represent independently of each other a hydrogen atom or a fluorine atom; and $L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{421}$ represents a methoxy group, a halogen atom, a methyl group or an ethyl group;

$R^{461}$ represents a chlorine atom;

$R^{411}$, $R^{431}$, $R^{441}$ and $R^{451}$ represent independently of each other a hydrogen atom or a fluorine atom; and $L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{421}$ represents a methoxy group, a halogen atom, a methyl group or an ethyl group;

$R^{461}$ represents a bromine atom;

$R^{411}$, $R^{431}$, $R^{441}$ and $R^{451}$ represent independently of each other a hydrogen atom or a fluorine atom; and $L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{421}$ represents a methoxy group, a halogen atom, a methyl group or an ethyl group;

$R^{461}$ represents an ethyl group;

$R^{411}$, $R^{431}$, $R^{441}$ and $R^{451}$ represent independently of each other a hydrogen atom or a fluorine atom; and $L^2$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{421}$ represents a methoxy group, a halogen atom, a methyl group or an ethyl group;

$R^{461}$ represents a methoxy group;

$R^{411}$, $R^{431}$, $R^{441}$ and $R^{451}$ represent independently of each other a hydrogen atom or a fluorine atom; and $L^2$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents a nitro group.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents an amino group.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents an isocyanato group.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents a carboxyl group.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents an C2-C6 alkoxycarbonyl group.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents a halogen atom.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents a halogenated acyl group.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents NSO.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents CON$_3$.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents CONH$_2$.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents CONHCl.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents CONHBr.

a pyrazole compound wherein $R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group;

$R^{411}$, $R^{431}$, $R^{441}$ and $R^{451}$ represent independently of each other a hydrogen atom or a fluorine atom; and $L^2$ represents CONHOH.

Also, examples of an embodiment of the present pyrazole compound include the compounds of the formula (11) wherein the substituents represent the following ones.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C3 alkyl group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents a C3-C4 cycloalkyl group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents a halogen atom; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents a C1-C3 haloalkyl group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C2-C3 alkenyl group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C3 alkoxy group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C2 alkylthio group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C2-C3 alkynyl group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$, and $R^{551}$ represent independently of each other a hydrogen atom or a halogen atom;

$R^{561}$ represents a C1-C3 haloalkoxy group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents a C1-C2 haloalkylthio group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C4 alkylamino group; and $L^3$ represents a nitro group, an amino group, an isocyanato group, a carboxyl group, an C2-C6 alkoxycarbonyl group, a halogen atom, a halogenated acyl group, NSO, CON$_3$, CONH$_2$, CONHCl, CONHBr or CONHOH.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents a nitro group.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents an amino group.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents an isocyanato group.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents a carboxyl group.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents an C2-C6 alkoxycarbonyl group.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents a halogen atom.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents a halogenated acyl group.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents NSO.

a pyrazole compound wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{531}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents $CON_3$.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^3$ represents $CONH_2$.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^3$ represents CONHCl.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^3$ represents CONHBr.

a pyrazole compound wherein $R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;

$R^{511}$, $R^{531}$, $R^{541}$ and $R^{551}$ represent independently of each other a hydrogen atom or a halogen atom;

$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and $L^3$ represents CONHOH.

a pyrazole compound wherein $R^{531}$ represents a methoxy group, a halogen atom, a methyl group or an ethyl group;

$R^{561}$ represents a methyl group;

$R^{511}$, $R^{521}$, $R^{541}$ and $R^{551}$ represent independently of each other a hydrogen atom or a fluorine atom; and $L^3$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{531}$ represents a methoxy group, a halogen atom, a methyl group or an ethyl group;

$R^{561}$ represents a cyclopropyl group;

$R^{511}$, $R^{521}$, $R^{541}$ and $R^{551}$ represent independently of each other a hydrogen atom or a fluorine atom; and $L^3$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{531}$ represents a methoxy group, a halogen atom, methyl group or an ethyl group;

$R^{561}$ represents a chlorine atom;

$R^{511}$, $R^{521}$, $R^{541}$ and $R^{551}$ represent independently of each other a hydrogen atom or a fluorine atom; and $L^3$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{531}$ represents a methoxy group, a halogen atom, a methyl group or an ethyl group;

$R^{561}$ represents a bromine atom;

$R^{511}$, $R^{521}$, $R^{541}$ and $R^{551}$ represent independently of each other a hydrogen atom or a fluorine atom; and $L^3$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{531}$ represents a methoxy group, a halogen atom, a methyl group or an ethyl group;

$R^{561}$ represents an ethyl group;

$R^{511}$, $R^{521}$, $R^{541}$ and $R^{551}$ represent independently of each other a hydrogen atom or a fluorine atom; and $L^3$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{531}$ represents a methoxy group, a halogen atom, a methyl group or an ethyl group;

$R^{561}$ represents a methoxy group;

$R^{511}$, $R^{521}$, $R^{541}$ and $R^{551}$ represent independently of each other a hydrogen atom or a fluorine atom; and $L^3$ represents a nitro group, an amino group, an isocyanato group, a carboxyl group, an C2-C6 alkoxycarbonyl group, a halogen atom, a halogenated acyl group, NSO, $CON_3$, $CONH_2$, CONHCl, CONHBr or CONHOH.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents a nitro group.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents an amino group.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents an isocyanato group.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents a carboxyl group.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents an C2-C6 alkoxycarbonyl group.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents a halogen atom.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents a halogenated acyl group.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents NSO.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents $CON_3$.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents $CONH_2$.

a pyrazole compound wherein $R^{531}$ represents a methoxy group, a halogen atom, a methyl group or an ethyl group;

$R^{561}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents CONHCl.

a pyrazole compound wherein $R^{531}$ represents a methoxy group, a halogen atom, a methyl group or an ethyl group;

$R^{551}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents CONHBr.

a pyrazole compound wherein $R^{531}$ represents a methoxy group, a halogen atom, a methyl group or an ethyl group;

$R^{551}$ represents a methyl group, a cyclopropyl group, a chlorine atom, a bromine atom, an ethyl group or a methoxy group;

$R^{511}$, $R^{521}$, $R^{541}$ and $R^{551}$ represent independently of each other a hydrogen atom or a fluorine atom; and $L^3$ represents CONHOH.

Herein, although a structural formula of a compound represents a definite isomeric form for convenience, the compound of the present invention is not limited to the expediential description of the structure formula, and encompasses all isomeric forms including active geometric isomers, optical isomers, stereoisomers, and tautomers which each may be arisen due to the structure of the compound and isomeric mixtures thereof, and may be either one of the isomeric forms or mixtures thereof. For example, although the compound of the present invention has an asymmetric carbon atom and may thus include optically active substances and racemates, the compound of the present invention is not specifically limited thereto, and may encompass any ones.

Next, a process for preparing the present compound is explained.

The present compound can be prepared, for example, according to the below-mentioned process.

(Process A)

The present compound of the formula (1) can be prepared by reacting a compound of a formula (A1) (hereinafter, described as Compound (A1)) with a compound of a formula (A2) (hereinafter, described as Compound (A2)) in the presence of a base.

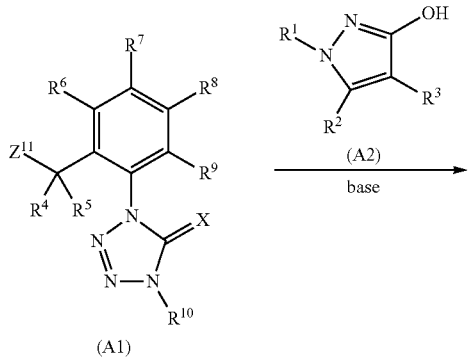

(A1)

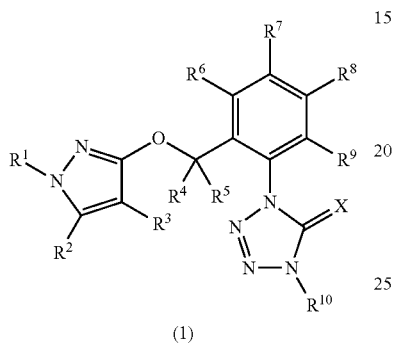

(1)

[wherein

R$^1$, R$^2$, R$^4$, R$^5$, R$^6$, R$^7$, R$^8$, R$^9$, R$^{10}$ and X are the same as defined above, Z$^{11}$ represents a leaving group such as a chlorine atom, a bromine atom, an iodine atom, a methanesulfonyloxy group, a trifluoromethanesulfonyloxy group, or a p-toluenesulfonyloxy group]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (A2) is used usually within a range of 1 to 10 molar ratio(s), and the base is used usually within a range of 0.5 to 5 molar ratio(s), as opposed to 1 mole of Compound (A1).

The reaction temperature is usually within a range of −20 to 150° C. The reaction period of the reaction is usually within a range of 0.1 to 24 hours. If necessary, sodium iodide, tetrabutylammonium iodide and the others may be added to the reaction and these compounds are used usually within a range of 0.001 to 1.2 molar ratios as opposed to 1 mole of Compound (A1).

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process B)

The present compound of the formula (1) wherein R$^1$ is a hydrogen atom, i.e., the compound of a formula (1-10) (hereinafter, described as Compound (1-10)), can be prepared by treating a compound of a formula (B1) (hereinafter, described as Compound (B1)) with a deprotection agent.

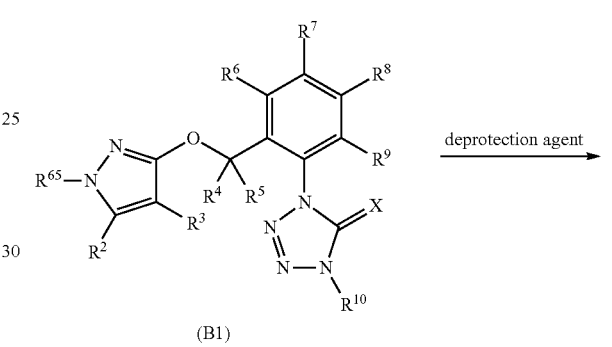

(B1)

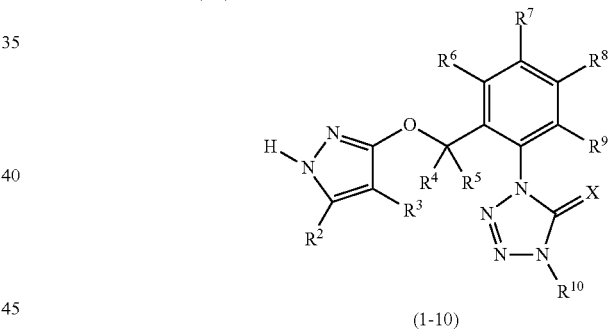

(1-10)

[wherein

R$^2$, R$^3$, R$^4$, R$^5$, R$^6$, R$^7$, R$^8$, R$^9$, R$^{10}$ and X are the same as defined above, R$^{65}$ represents a protection agent such as an acyl group, a haloacyl group, an alkoxycarbonyl group, an aryloxycarbonyl group, an arylalkyloxycarbonyl group]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the protection agent to be used in the reaction include a base or an acid. Examples of the base include organic bases such as triethylamine, pyridine, N-methylmorpholine, N-methylpiperidine, 4-dimethylaminopyridine, diisopropylethylamine, lutidine, collidine, diazabicycloundecene, diazabicyclononene, piperidine; alkali metal hydroxides such as lithium hydroxide, sodium hydroxide, potassium hydroxide, cesium hydroxide; alkali metal alkoxides such as sodium methoxide, sodium ethoxide, sodium tert-butoxide, potassium tert-butoxide. Examples of the base include trifluoroacetic acid, hydrochloric acid, sulfuric acid.

In the reaction, the protection agent is used usually within a range of 1 to 100 molar ratio(s) as opposed to 1 mole of Compound (B1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (1-10). The isolated Compound (1-10) may be further purified, for example, by distillation, chromatography and recrystallization.

(Process C)

The present compound of the formula (1) wherein X represents a sulfur atom, i.e., the compound of a formula (1-S) (hereinafter, described as Compound (1-S)) can be prepared by reacting a compound of the formula (1) wherein X represents an oxygen atom (hereinafter, described as Compound (1-O)) by well-known sulfurization.

anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; and mixed solvents thereof.

Examples of the sulfurating agent to be used in the reaction include phosphorus pentasulfide, Lawesson's reagent (2,4-bis(4-methoxyphenyl)-1,3,2,4-dithiadiphosphetane 2,4-disulfide). In the reaction, the sulfurating agent is used within a range of 0.5 to 1.5 molar ratios as opposed to 1 mole of Compound (1-0).

The reaction temperature is usually within a range of −20 to 150° C. The reaction period of the reaction is usually within a range of 0.1 to 24 hours. If necessary, organic bases such as pyridine and triethylamine and inorganic bases such as alkali metal hydroxides and alkali metal carbonates and the others may be added to the reaction and these compounds are used usually within a range of 0.5 to 1.5 molar ratios as opposed to 1 mole of Compound (1-O).

When the reaction is completed, the reaction mixtures are extracted with organic solvent(s), and the resulting organic layers are worked up (for example, drying and concentration) to isolate the present compound of the formula (1-S). The isolated present compound may be further purified, for example, by chromatography and recrystallization.

(Process D)

The present compound of the formula (1) can be prepared by reacting a compound of a formula (D1) (hereinafter, described as Compound (D1)) with a compound of a formula (D2) (hereinafter, described as Compound (D2)) in the presence of a base.

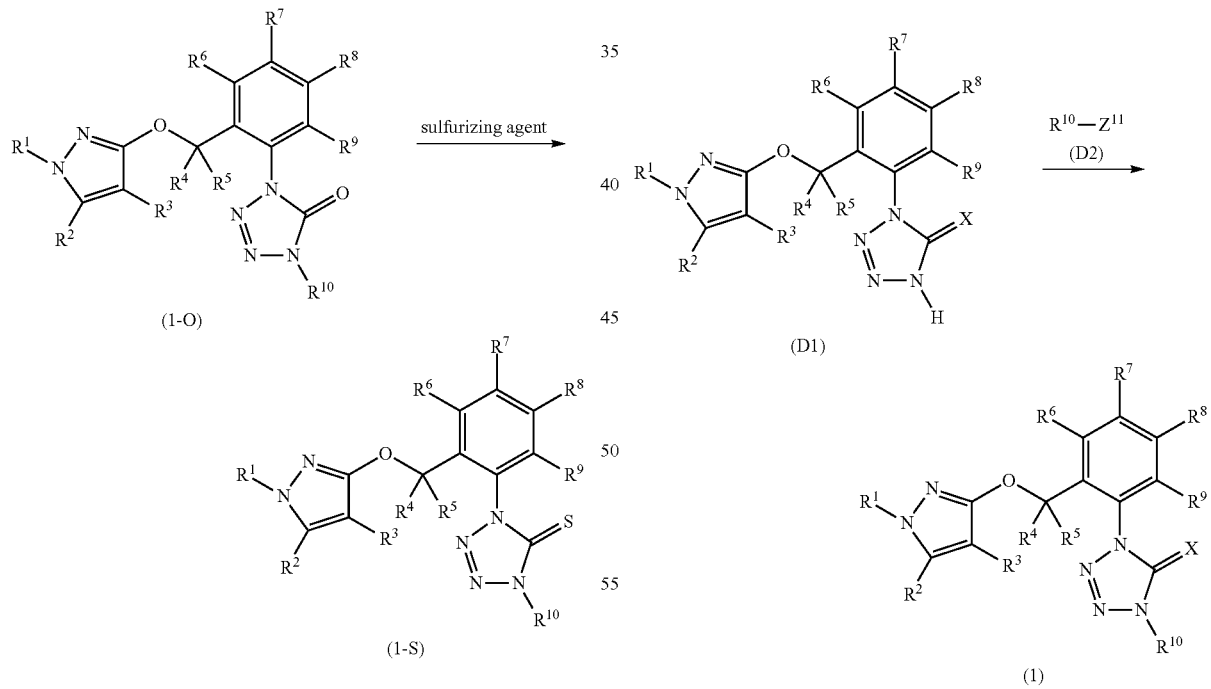

[wherein
$R^1$, $R^2$, $R^3$, $R^4$, $R^5$, $R^6$, $R^7$, $R^8$, $R^9$ and $R^{10}$ are the same as defined above.]

This reaction is usually carried out in a solvent.
Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether,

[wherein
$R^1$, $R^2$, $R^3$, $R^4$, $R^5$, $R^6$, $R^7$, $R^8$, $R^9$, $R^{10}$, $Z^{11}$ and X are the same as defined above.]

This reaction is usually carried out in a solvent.
Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (D2) to be used in the reaction can be usually used as a commercially available product. Specific examples include alkyl halides such as chlorodifluoromethane, methyl bromide, ethyl bromide, n-propyl bromide, methyl iodide, ethyl iodide, n-propyl bromide, aryl bromide, cyclopropyl bromide, benzyl bromide, 1,1-difluoro-2-iodoethane; dialkyl sulfates such as dimethyl sulfate; alkyl or aryl sulfates such as methyl p-toluenesulfonate, ethyl p-toluenesulfonate, n-propyl p-toluenesulfonate, methyl methanesulfonate, ethyl methanesulfonate and n-propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide. In the reaction, Compound (D2) is used usually within a range of 1 to 10 molar ratio(s), and the base is used usually within a range of 0.5 to 10 molar ratios, as opposed to 1 mole of Compound (D1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process E)

The present compound of the formula (1) wherein $R^1$ represents $R^{61}$, i.e., the compound of a formula (1-15) (hereinafter, described as Compound (1-15)), can be prepared by reacting Compound (1-10) with a compound of a formula (E1) (hereinafter, described as Compound (E1)) in the presence of a catalyst and a base.

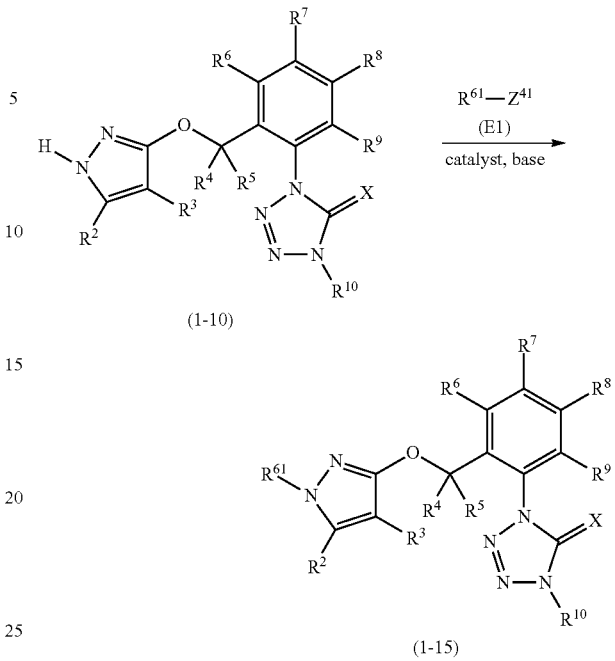

[wherein
$R^1$, $R^2$, $R^3$, $R^4$, $R^5$, $R^6$, $R^7$, $R^8$, $R^9$, $R^{10}$ and X are the same as defined above, $R^{61}$ represents an C6-C16 aryl group optionally having one or more substituents selected from the above-mentioned Group P which may be same or different from each other when the number of the selected substituent is two or more, $Z^{41}$ represents a leaving group such as a chlorine atom, a bromine atom, an iodine atom, a methanesulfonyloxy group, a trifluoromethanesulfonyloxy group or p-toluenesulfonyloxy group, a $B(OH)_2$, an alkoxyboryl group or a trifluoroborate ($BF_3^-K^+$).]

The reaction is performed according to the methods described in J. Am. Chem. Soc. 1989, 111, 314 or Chem. Rev. 1995, 95, 2457.

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Compound (E1) to be used in the reaction can be usually used as a commercially available product. Specific examples include chlorobenzene, bromobenzene, iodobenzene, paradichlorobenzene, 4-chlorobromobenzene, 4-chloroiodobenzene, paradibromobenzene, 4-chloroiodobenzene, 4-bromoiodobenzene, phenylboronic acid, 4-fluorophenylboronic acid, 4-chlorophenylboronic acid, 4-methylphenylboronic acid, 4-methoxyphenylboronic acid.

Examples of the catalyst to be used in the reaction include copper(I) iodide, copper(II) acetate, dichlorobis(triphenylphosphine)palladium, tetrakistriphenylphosphinepalladium (0), palladium(II) acetate/triscyclohexylphosphine, bis(diphenylphoshine ferrocenyl)palladium(II) dichloride, 1,3-bis (2,6-diisopropylphenyl)imidazole-2-ylidene (1,4-naphthoquinone)palladium dimer, aryl(chloro)(1,3-dimethyl-1,3-dihydro-2H-imidazole-2-ylidene)palladium or palladium(II) acetate/dicyclohexyl(2',4',6'-triisopropylbiphenyl-2-yl)phosphine, and tris(dibenzylideneacetone)dipalladium.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (E1) is used usually within a range of 1 to 10 molar ratio(s), and the catalyst is used usually within a range of 0.001 to 5 molar ratio(s), and the base is used usually within a range of 0.5 to 10 molar ratio(s), as opposed to 1 mole of Compound (1-10).

If necessary, a ligand such as phenanthroline and tetramethylenediamine and the others may be added to the reaction and these compounds are used usually within a range of 0.001 to 5 molar ratio(s) as opposed to 1 mole of Compound (1-10).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-15). The isolated present compound may be further purified, for example, by chromatography and recrystallization.

(Process F)

The present compound of the formula (1) wherein $R^6$ represents $R^{71}$, i.e., the compound of a formula (1-1) (hereinafter, described as Compound (1-1)), can be prepared by coupling a compound of a formula (F11) (hereinafter, described as Compound (F11)) with a compound of a formula (F21) (hereinafter, described as Compound (F21)) in the presence of a base and a catalyst.

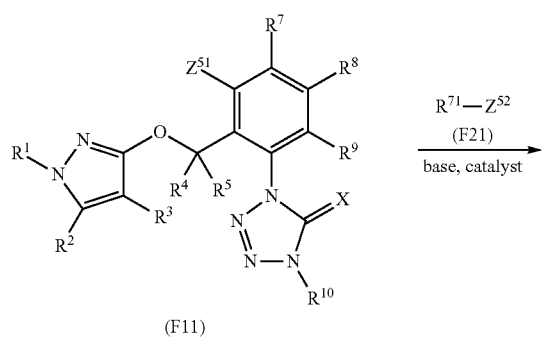

[wherein
$R^1$, $R^2$, $R^3$, $R^4$, $R^5$, $R^7$, $R^8$, $R^9$, $R^{10}$ and X are the same as defined above, $Z^{51}$ represents a chlorine atom, a bromine atom, an iodine atom or a trifluoromethanesulfonyloxy group, $R^{71}$ represents an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group or a C3-C6 halocycloalkyl group and $Z^{52}$ represents a B(OH)$_2$, an alkoxyboryl group or a trifluoroborate (BF$_3^-$K$^+$).]

The reaction is performed according to the methods described in J. Am. Chem. Soc. 1989, 111, 314 or Chem. Rev. 1995, 95, 2457.

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Examples of organoboron compound (F21) to be used in the reaction include boronic acid derivatives, boronate ester derivatives and trifluoroborate salts, and these compounds are used as a commercially available product, or may be prepared according to a method described in a review article of N. Miyaura and A. Suzuki, Chem. Rev. 1995, 95, 2457 and the others. The organoboron compound (F21) to be used in the reaction can be prepared, for example, by reacting an iodo compound ($R^{71}$—I) or a bromo compound ($R^{71}$—Br) with an alkyl lithium (such as butyl lithium), followed by reacting the resulting mixtures with boronate esters to obtain boronate ester derivatives. Also, the boronate ester derivatives obtained in the above-mentioned reaction can be hydrolyzed to the corresponding boronic acid derivatives as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts (BF$_3^-$K$^+$).

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-diisopropylphenyl)imidazole-2-ylidene (1,4-naphthoquinone)palladium dimer, aryl(chloro)(1,3-dimethyl-1,3-dihydro-2H-imidazole-2-ylidene)palladium or palladium(II) acetate/dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (F21) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (F11).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-1). The isolated present compound may be further purified, for example, by chromatography and recrystallization.

According to the process for preparing the above-mentioned Compound (1-1), the present compound of the formula (1) wherein $R^7$ represents $R^{72}$, i.e., compound of a below-mentioned formula (1-2) (hereinafter, described as Compound (1-2)), can be prepared by coupling compound of a formula (F12) (hereinafter, describes as Compound (F12)) with compound of a formula (F22) (hereinafter, describes as Compound (F22)) in the presence of a base and the catalyst.

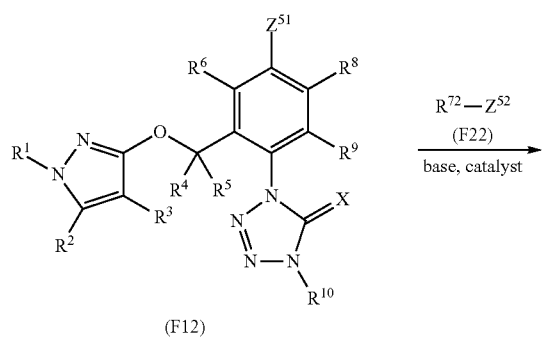

(F12)

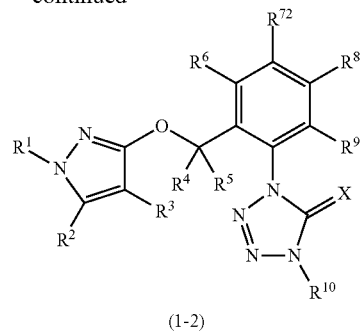

(1-2)

[wherein
$R^1$, $R^3$, $R^4$, $R^5$, $R^6$, $R^8$, $R^9$, $R^{10}$, $Z^{51}$, $Z^{52}$ and X are the same as defined above, $R^{72}$ represents an C1-C4 alkyl group, a C1-C4 haloalkyl group, a C3-C5 cycloalkyl group or a C3-C5 halocycloalkyl group]

According to the process for preparing the above-mentioned Compound (1-1), the present compound of the formula (1) wherein $R^8$ represents $R^{72}$, i.e., a compound of a below-mentioned formula (1-3) (hereinafter, described as Compound (1-3)), can be prepared by coupling a compound of a below-mentioned formula (F13) (hereinafter, described as Compound (F13)) with Compound (F22) in the presence of a base and a catalyst.

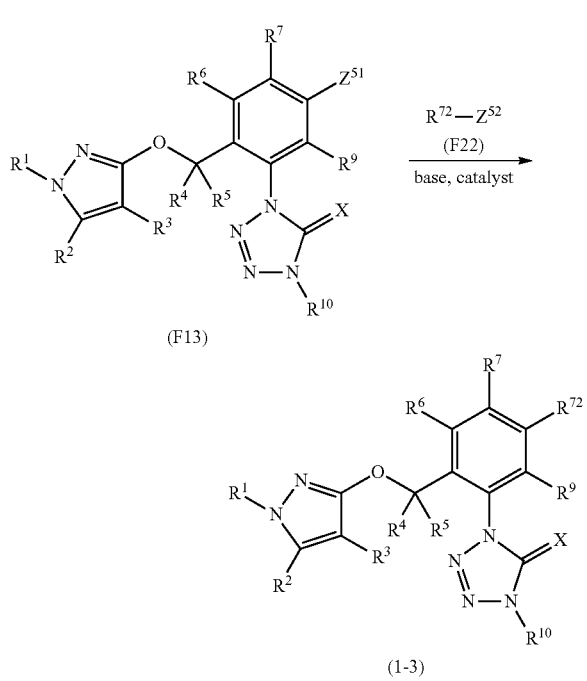

[wherein
$R^1$, $R^2$, $R^3$, $R^4$, $R^5$, $R^6$, $R^7$, $R^9$, $R^{10}$, $R^{72}$, $Z^{51}$, $Z^{52}$ and X are the same as defined above.]

According to the process for preparing the above-mentioned Compound (1-1), the present compound of the formula (1) wherein $R^9$ represents $R^{72}$, i.e., a compound of a below-mentioned formula (1-4) (hereinafter, described as Compound (1-4)), can be prepared by coupling compound of a below-mentioned formula (F14) (hereinafter, described as Compound (F14)) with Compound (F22) in the presence of a base and a catalyst.

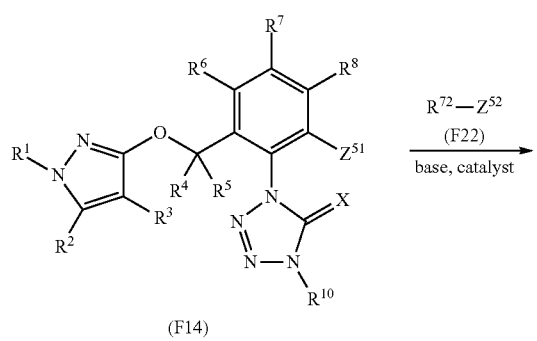

(F14)

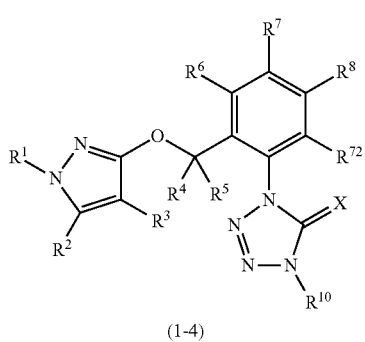

(1-4)

[wherein $R^1$, $R^2$, $R^3$, $R^4$, $R^5$, $R^6$, $R^7$, $R^8$, $R^{10}$, $R^{72}$, $R^{51}$, $Z^{52}$ and X are the same as defined above.]

According to the process for preparing the above-mentioned Compound (1-1), the present compound of the formula (1) wherein $R^2$ represents $R^{73}$, i.e., a compound of a below-mentioned formula (1-5) (hereinafter, described as Compound (1-5)), can be prepared by coupling compound of a below-mentioned formula (F15) (hereinafter, described as Compound (F15)) with compound of a below-mentioned formula (F23) (hereinafter, described as Compound (F23)) in the presence of a base and a catalyst.

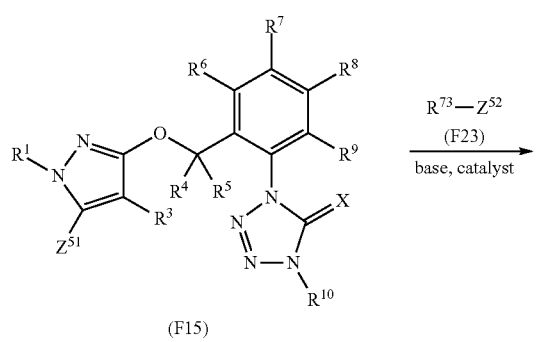

(F15)

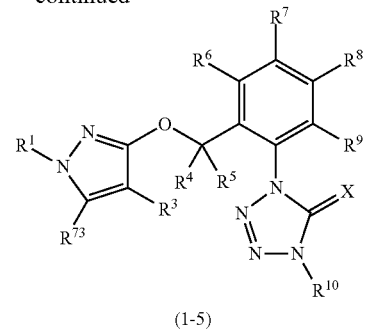

(1-5)

[wherein $R^1$, $R^3$, $R^4$, $R^5$, $R^6$, $R^7$, $R^8$, $R^9$, $R^{10}$, $Z^{51}$, $Z^{52}$ and X are the same as defined above, $R^{73}$ represents an C1-C3 alkyl group or a C1-C3 haloalkyl group]

According to the process for preparing the above-mentioned Compound (1-1), the present compound of the formula (1) wherein $R^3$ represents $R^{74}$, i.e., a compound of a below-mentioned formula (1-6) (hereinafter, described as Compound (1-6)), can be prepared by coupling a compound of a below-mentioned formula (F16) (hereinafter, described as Compound (F16)) with Compound (F23) in the presence of a base and a catalyst.

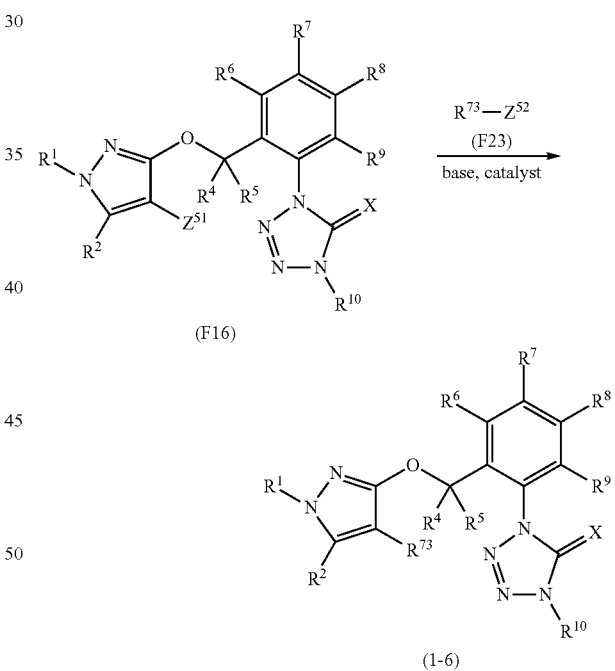

(1-6)

[wherein $R^1$, $R^2$, $R^4$, $R^5$, $R^6$, $R^7$, $R^8$, $R^9$, $R^{10}$, $R^{73}$, $Z^{51}$, $Z^{52}$ and X are the same as defined above.]

According to the above-mentioned Process F, the compound of the formula (1) wherein two or more substituents selected from $R^2$, $R^3$, $R^6$, $R^7$, $R^8$ or $R^9$ represents either $R^{71}$, $R^{72}$ or $R^{73}$ can be prepared.

The present compound of the formula (1) can be also prepared by using the other known coupling methods instead of the coupling reaction described in the above-mentioned Process F.

(Process G)

The present compound of the formula (1) wherein $R^1$ represents $R^{75}$, i.e., the compound of a formula (1-20) (hereinafter, described as Compound (1-20)), can be prepared by coupling Compound (1-10) with compound of a formula (G1) (hereinafter, described as Compound (G1)) in the presence of a base.

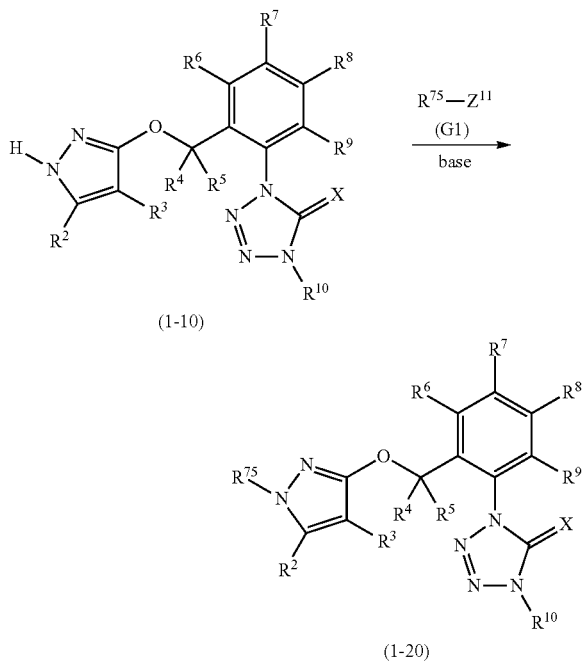

[wherein
$R^2$, $R^3$, $R^4$, $R^5$, $R^6$, $R^7$, $R^8$, $R^9$, $R^{10}$, $Z^{11}$ and X are the same as defined above, and $R^{75}$ represents an C1-C12 alkyl group optionally having one or more substituents selected from the below-mentioned Group P which may be same or different from each other when the number of the selected substituents is two or more, a C3-C12 cycloalkyl group optionally having one or more substituents selected from the below-mentioned Group P which may be same or different from each other when the number of the selected substituents is two or more, or an C2-C12 acyl group optionally having one or more substituents selected from the below-mentioned Group P which may be same or different from each other when the number of the selected substituents is two or more]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (G1) to be used in the reaction can be usually used as a commercially available product. Specific examples include halogenated alkyls such as chlorodifluoromethane, methyl bromide, ethyl bromide, n-propyl bromide, methyl iodide, ethyl iodide, n-propyl bromide, aryl bromide, cyclopropyl bromide, benzyl bromide, 1,1-difluoro-2-iodomethane; dialkyl sulfates such as dimethyl sulfates, diethyl sulfates, di-n-propyl sulfates; alkyl or aryl sulfonates such as methyl p-toluenesulfonate, ethyl methanesulfonate, n-propyl methanesulfonate; and carboxylic halides such as acetyl chloride, benzolyl chloride.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononenene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (G1) is used usually within a range of 1 to 10 molar ratio(s), and the base is used usually within a range of 0.5 to 10 molar ratios, as opposed to 1 mole of Compound (1-10).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-20). The isolated present compound may be further purified, for example, by chromatography and recrystallization.

Hereinafter, processes for preparing the present tetrazolinone compound X, the present tetrazolinone compound X2, the present tetrazolinone compound X3, the present tetrazolinone compound Y, the present pyrazole compound Z, the present pyrazole compound Z2 and the present pyrazole compound Z3 are described in detail.

The present tetrazolinone compound X, the present tetrazolinone compound X2, the present tetrazolinone compound X3, the present tetrazolinone compound Y, the present pyrazole compound Z, the present pyrazole compound Z2 and the present pyrazole compound Z3 can be prepared, for example, by the below-mentioned process.

(Synthesis A)

A compound of a below-mentioned formula (TXA5) (hereinafter, described as Compound (TXA5)), can be prepared by reacting a compound of a below-mentioned formula (TXA4) (hereinafter, described as Compound (TXA4)) with an azidation agent.

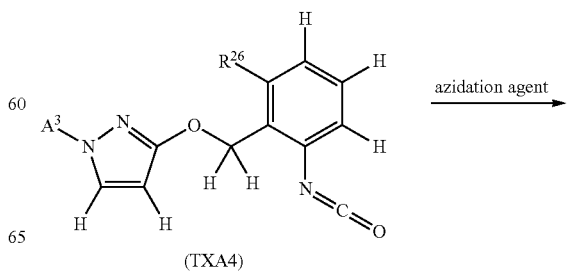

(TXA4)

-continued

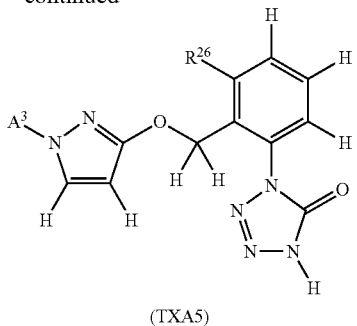

(TXA5)

[wherein $A^3$ represents any group as below-mentioned:

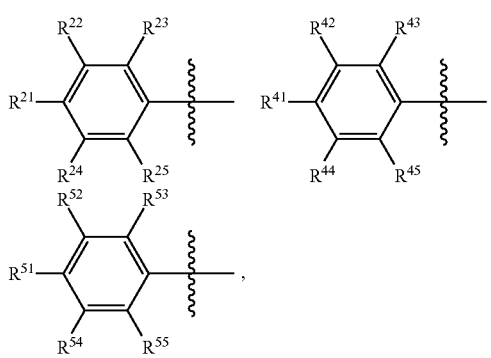

$R^{21}$, $R^{22}$, $R^{23}$, $R^{24}$, $R^{25}$, $R^{26}$, $R^{41}$, $R^{42}$, $R^{43}$, $R^{44}$, $R^{45}$, $R^{51}$, $R^{52}$, $R^{53}$, $R^{54}$ and $R^{55}$ are the same as described above.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (TXA4).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (TXA4).

When the reaction is completed, the reaction mixtures are extracted with organic solvent(s), and the resulting organic layers are worked up (for example, drying and concentration) to isolate the present tetrazolinone compound X, the present tetrazolinone compound X2 or the present tetrazolinone compound X3, which each is represented by a formula (TAX5). The isolated present tetrazolinone compound X, the isolated present tetrazolinone compound X2 or the isolated present tetrazolinone compound X3 may be further purified, for example, by chromatography and recrystallization.

(Synthesis B)

A compound of a below-mentioned formula (TXA3) (hereinafter, described as Compound (TXA3)), can be prepared by reacting a compound of a below-mentioned formula (TXA1) (hereinafter, described as Compound (TXA1)) or a compound of a below-mentioned formula (TXA2) (hereinafter, described as Compound (TXA2)) with an azidation agent.

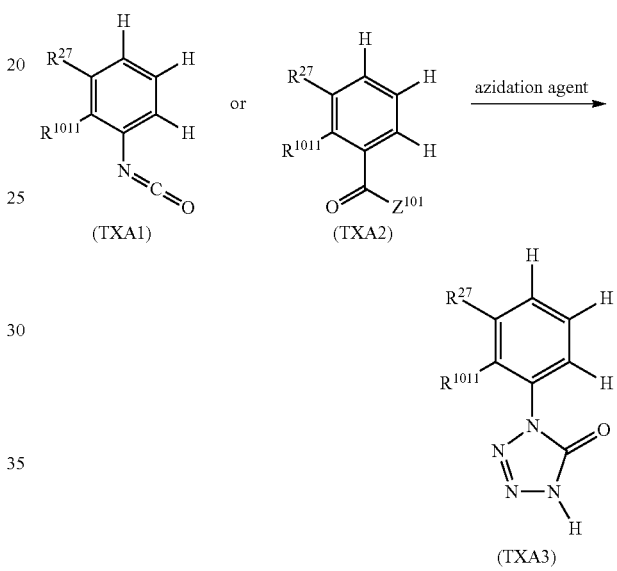

[wherein $R^{27}$ is the same as described above, $R^{1011}$ represents an (C1-C3 alkoxy)methyl group, a methyl group, or an C2-C6 alkoxycarbonyl group, and $Z^{101}$ represents a chlorine atom or a bromine atom.]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (TXA1) or Compound (TXA2).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (TXA1) or Compound (TXA2).

When the reaction is completed, the reaction mixtures are extracted with organic solvent(s), and the resulting organic layers are worked up (for example, drying and concentration) to isolate the present tetrazolinone compound Y represented by a formula (TAX3). The isolated present tetrazolinone compound Y may be further purified, for example, by chromatography and recrystallization.

(Synthesis C)

A compound of a below-mentioned formula (TXG2) (hereinafter, described as Compound (TXG2)), can be prepared by reacting Compound (TXA3) with a compound of a below-mentioned formula (TD2) (hereinafter, described as Compound (TD2)) in the presence of a base.

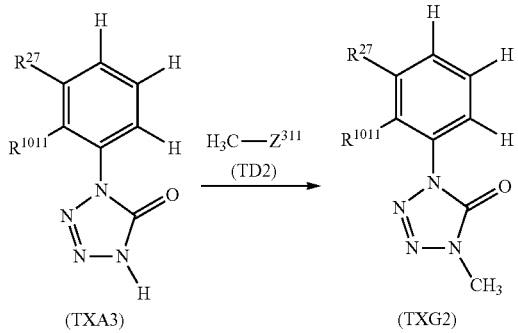

[wherein
$R^{27}$ and $R^{1011}$ are the same as described above, and $Z^{311}$ represents a leaving group such as a bromine atom, an iodine atom, a methanesulfonyloxy group, a trifluoromethanesulfonyloxy group or p-toluenesulfonyloxy group]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (TD2) to be used in the reaction can be usually used as a commercially available product. Specific examples include alkyl halides such as methyl bromide, methyl iodide; dialkyl sulfates such as dimethyl sulfate; alkyl or aryl sulfates such as methyl p-toluenesulfonate, methyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (TD2) is used usually within a range of 1 to 10 molar ratio(s), and the base is used usually within a range of 0.5 to 10 molar ratios, as opposed to 1 mole of Compound (TXA3).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXG2). The isolated present compound Y may be further purified, for example, by chromatography and recrystallization.

(Synthesis D)

A compound of a below-mentioned formula (TXH2) (hereinafter, described as Compound (TXH2)), can be prepared by reacting a compound of a below-mentioned formula (TXH1) (hereinafter, described as Compound (TXH1)) with a halogenating agent.

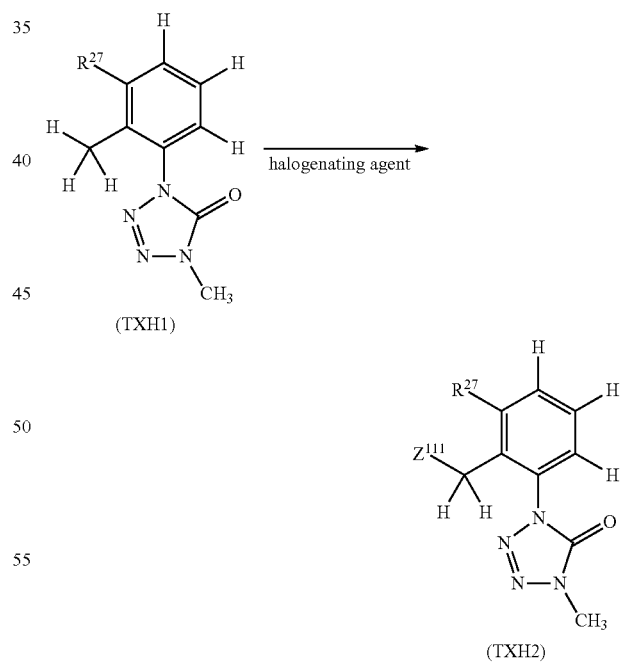

[wherein
$R^{27}$ is the same as described above, and $Z^{111}$ represents a chlorine atom, a bromine atom, or an iodine atom.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, α,α,α-trichlorotoluene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include a chlorinating agent, a brominating agent or iodinating agent such as chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonamide and N-bromophthalimide.

A radical initiator can be used in the reaction.

Examples of the radical initiator to be used in the reaction include benzoyl peroxide, azobisisobutyronitrile (AIBN), azobiscyclohexanecarbonitrile, diacylperoxide, dialkyl peroxydicarbonate, tert-alkyl peroxyester, monoperoxy carbonate, di(tert-alkylperoxy)ketal and ketone peroxide.

In the reaction, the halogenating agent is used usually within a range of 1 to 10 molar ratio(s), and the radical initiator is used usually within a range of 0.01 to 1 molar ratio(s), as opposed to 1 mole of Compound (TXH1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXH2). The isolated present compound Y may be further purified, for example, by chromatography and recrystallization.

(Synthesis E)

A compound of a below-mentioned formula (TXJ2) (hereinafter, described as Compound (TXJ2)), can be prepared by reacting Compound (TXH2) with a compound of a below-mentioned formula (TXJ1) (hereinafter, described as Compound (TXJ1)).

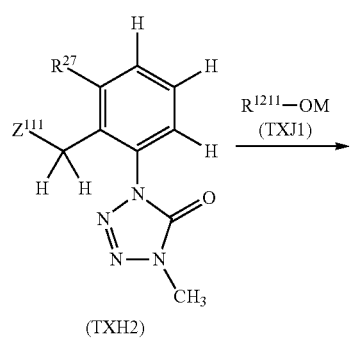

(TXH2)

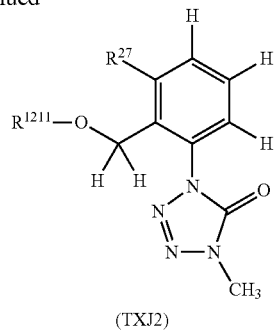

(TXJ2)

[wherein $R^{27}$ and $Z^{111}$ are the same as described above, $R^{1211}$ represents an C1-C3 alkyl group, and M represents a sodium, a potassium or a lithium.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of Compound (TXJ1) include sodium methoxide, sodium ethoxide, sodium n-propoxide, sodium isopropoxide, sodium sec-butoxide, potassium methoxide, potassium ethoxide, potassium n-propoxide, and potassium isopropoxide.

In the reaction, Compound (TXJ1) is used usually within a range of 1 to 10 molar ratio(s) as opposed to 1 mole of Compound (TXH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXJ2). The isolated present compound Y may be further purified, for example, by chromatography and recrystallization.

(Synthesis F)

A compound of a below-mentioned formula (TXK1) (hereinafter, described as Compound (TXK1)), can be prepared by reacting Compound (TXH2) with water in the presence of a base.

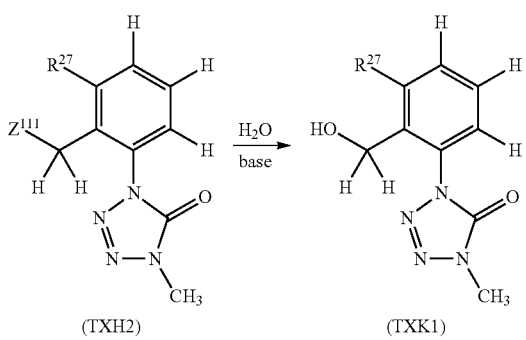

(TXH2)        (TXK1)

[wherein

R$^{27}$ and Z$^{111}$ are the same as described above.]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the base to be, used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; metallic organic acid salts such as lithium formate, lithium acetate, sodium formate, sodium acetate, potassium formate, potassium acetate; metallic nitrates such as silver nitrate, sodium nitrate; alkali metal carbonates such as lithium carbonate, sodium carbonate, potassium carbonate, calcium carbonate, cesium carbonate; alkali metal bicarbonates such as lithium bicarbonate, sodium bicarbonate, potassium bicarbonate, cesium bicarbonate; alkali-metal hydroxides such as lithium hydroxide, sodium hydroxide, potassium hydroxide, cesium hydroxide; alkali metal alkoxides such as sodium methoxide, sodium ethoxide, sodium tert-butoxide, potassium tert-butoxide.

In the reaction, the base is used usually within a range of 1 to 100 molar ratio(s) as opposed to 1 mole of Compound (TXH2).

In the reaction, water is used usually within a range of 1 to a large excess molar ratio(s) as opposed to 1 mole of Compound (TXH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXK1). The isolated present compound Y may be further purified, for example, by chromatography and recrystallization.

(Synthesis G)

Compound (TXH2) can be prepared by reacting Compound (TXJ2) with a halogenating agent.

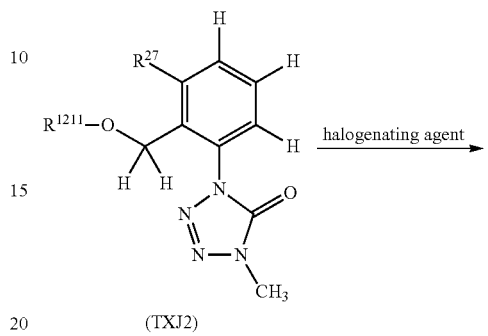

(TXJ2)

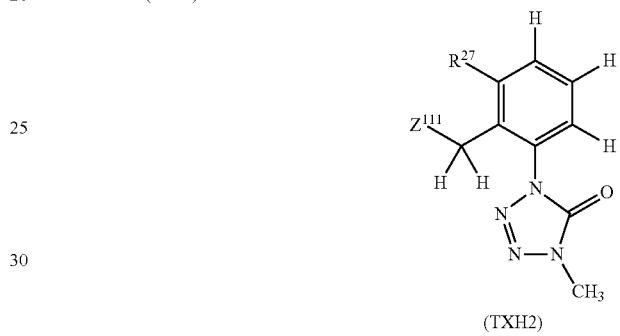

(TXH2)

[wherein

R$^{27}$, R$^{1211}$ and Z$^{111}$ are the same as described above.]

This reaction is usually carried out in a solvent.

Examples of the solvent to be used in the reaction include hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent include hydrochloric acid, hydrobromic acid and hydroiodic acid.

In the reaction, the halogenating agent is used usually within a range of 1 or more molar ratio(s) as opposed to 1 mole of Compound (TXJ2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXH2). The isolated present compound Y may be further purified, for example, by chromatography and recrystallization.

(Synthesis H)

Compound (TXH2) can be prepared by reacting Compound (TXK1) with a halogenating agent.

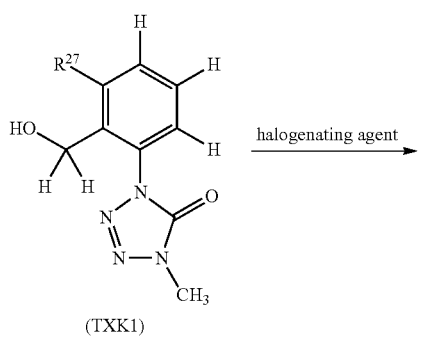

(TXK1)

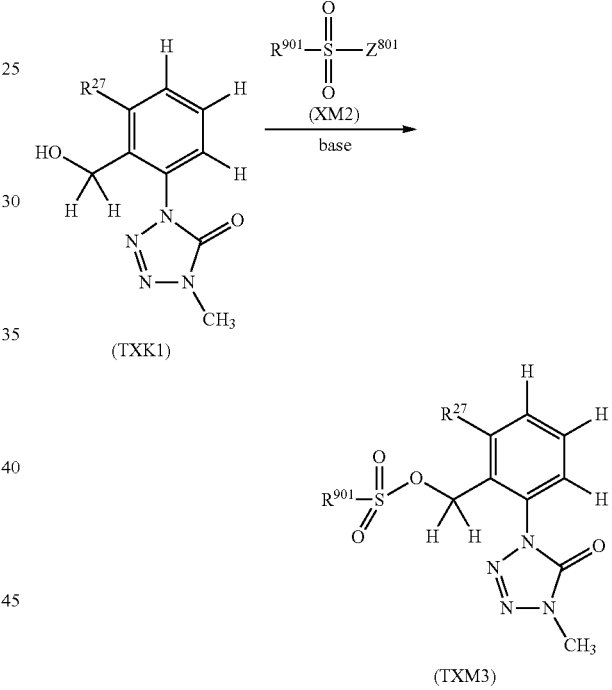

[wherein

R²⁷ and $Z^{111}$ are the same as described above.]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, lithium chloride, sodium iodide and acetyl bromide.

In the reaction, the halogenating agent is used usually within a range of 1 to 10 molar ratio(s) as opposed to 1 mole of Compound (TXK1).

To promote the reaction, an additive agent may be added depending on the halogenating agent used, and specifically includes zinc chloride for acetyl chloride; triphenylphosphine for carbon tetrabromide; dimethyl sulfide for N-bromosuccinimide; boron trifluoride diethyl etherate complex for sodium iodide; boron trifluoride diethyl etherate complex for acetyl bromide; triethylamine and methanesulfonyl chloride for lithium chloride; aluminium chloride for sodium iodide; and trimethylsilyl chloride for sodium iodide. The amount of each additive agent is used usually within a range of 0.01 to 5 molar ratio(s) as opposed to 1 mole of Compound (TXK1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXH2). The isolated present compound Y may be further purified, for example, by chromatography and recrystallization.

(Synthesis I)

A compound of a below-mentioned formula (TXM3) (hereinafter, described as Compound (TXM3)), can be prepared by reacting Compound (TXK1) with a compound of a below-mentioned formula (XM2) (hereinafter, described as Compound (XM2)) in the presence of a base.

[wherein

R²⁷ is the same as described above; $R^{901}$ represents an C1-C6 alkyl group, a C1-C6 haloalkyl group, an C6-C16 aryl group, or a C6-C16 haloaryl group; and $Z^{801}$ represents a fluorine atom, a chlorine atom, a bromine atom or an iodine atom]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal hydrides such as lithium hydride, sodium hydride, potassium hydride; and alkali metal alkoxides such as sodium methoxide, sodium ethoxide, sodium tert-butoxide, potassium tert-butoxide.

In the reaction, Compound (XM2) is used usually within a range of 1 to 10 molar ratio(s), and the base is used usually within a range of 0.5 to 5 molar ratio(s), as opposed to 1 mole of Compound (TXK1).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratio(s) as opposed to 1 mole of Compound (TXK1).

When the reaction is completed, the reaction mixtures are extracted with organic solvent(s), and the resulting organic layers are worked up (for example, drying and concentration) to isolate the present tetrazolinone compound Y represented by the formula (TXM3). The isolated present compound Y may be further purified, for example, by chromatography and recrystallization.

(Synthesis J)

A compound of a below-mentioned formula (TXN12) (hereinafter, described as Compound (TXN12)), can be prepared by coupling a compound of a below-mentioned formula (TXN11) (hereinafter, described as Compound (TXN11)) with a compound of a below-mentioned formula (TF21) (hereinafter, described as Compound (TF21)) in the presence of a base and a catalyst.

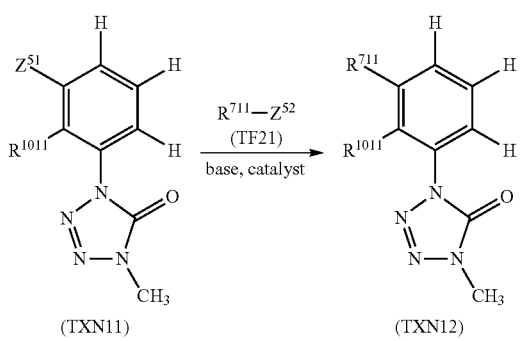

[wherein
$R^{1011}$, $Z^{51}$ and $Z^{52}$ are the same as defined above, $R^{711}$ represents an C1-C3 alkyl group, a C1-C3 haloalkyl group, an C2-C3 alkenyl group, an C2-C3 alkynyl group or a C3-C4 cycloalkyl group]

The reaction is performed according to the methods described in J. Am. Chem. Soc. 1989, 111, 314 or Chem. Rev. 1995, 95, 2457.

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Examples of organoboron compound (TF21) to be used in the reaction include boronic acid derivatives, boronate ester derivatives and trifluoroborate salts, and these compounds are used as a commercially available product, or may be prepared according to a method described in a review article of N. Miyaura and A. Suzuki, Chem. Rev. 1995, 95, 2457 and the others. The organoboron compound (TF21) to be used in the reaction can be prepared, for example, by reacting an iodo compound ($R^{711}$—I) or a bromo compound ($R^{711}$—Br) with an alkyl lithium (such as butyl lithium), followed by reacting the resulting mixtures with boronate esters such as trimethyl borate to obtain boronate ester derivatives. Also, the boronate ester derivatives obtained in the above-mentioned reaction can be hydrolyzed to the organoboron compound (TF21) to be used in the reaction as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts ($BF_3^-K^+$).

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-naphthoquinone)palladium dimer, aryl(chloro)(1,3-dimethyl-1,3-dihydro-2H-imidazole-2-ylidene)palladium or palladium(II) acetate/dicyclohexyl(2',4',6'-triisopropylbiphenyl-2-yl) phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (TF21) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (TXN11).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXN12). The isolated present compound Y may be further purified, for example, by chromatography and recrystallization.

Further, the present compound of the formula (TXN12) can be prepared by using the other known coupling methods instead of the coupling reaction described in the above-mentioned Synthesis J.

(Synthesis K)

Compound (TXK1) can be prepared by reacting a below-mentioned formula (TXX1) (hereinafter, described as Compound (TXX1)) with a reducing agent.

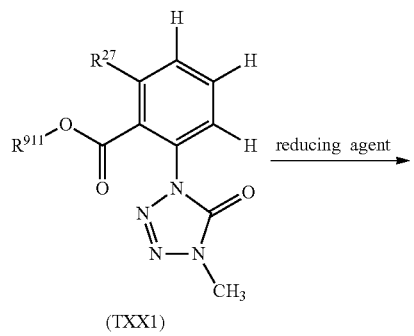

(TXX1)

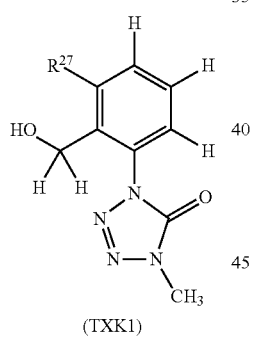

(TXK1)

[wherein
$R^{27}$ are the same as described above, and $R^{911}$ represents an C1-C5 alkyl group]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; alcohols such as methanol, ethanol, propanol, butanol; water; and mixed solvents thereof.

Examples of the reducing agent to be used in the reaction include lithium triethylborohydride, diisobutylaluminium hydride, lithium aminoborohydride, lithium borohydride, sodium borohydride, borane, borane-dimethyl sulfide complex and borane-tetrahydrofuran complex.

In the reaction, the reducing agent is used usually within a range of 1 to 10 molar ratio(s) as opposed to 1 mole of Compound (TXX1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXK1). The isolated present compound Y may be further purified, for example, by chromatography and recrystallization.

(Synthesis L)

A compound of a below-mentioned formula (TXL2) (hereinafter, described as Compound (TXL2)), can be prepared by reacting Compound (TXH2) with a compound of a below-mentioned formula (TXL1) (hereinafter, described as Compound (TXL1)) in the presence of a base.

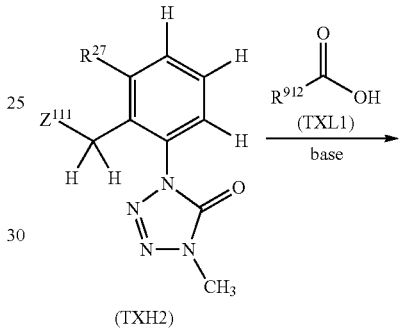

(TXH2)

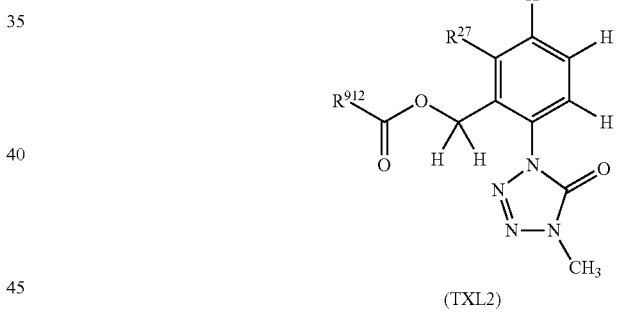

(TXL2)

[wherein
$R^{27}$ and $Z^{111}$ are the same as described above, and $R^{912}$ represents $R^{911}$ or a hydrogen atom]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; and mixed solvents thereof.

Examples of Compound (TXL1) include methanoic acid, ethanoic acid, propanoic acid, butanoic acid, pentanoic acid, and hexanoic acid.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (TXL1) is used usually within a range of 1 to 10 molar ratio(s), as opposed to 1 mole of Compound (TXH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXL2). The isolated present compound Y may be further purified, for example, by chromatography and recrystallization.

(Synthesis M)

A compound of a below-mentioned formula (TXM2) (hereinafter, described as Compound (TXM2)), can be prepared by reacting Compound (TXH2) with a compound of a below-mentioned formula (TXM1) (hereinafter, described as Compound (TXM1)).

ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; and mixed solvents thereof.

Examples of Compound (TXM1) include sodium thiomethoxide, sodium thioethoxide, sodium thio-n-propoxide, sodium thioisopropoxide, potassium thiomethoxide, potassium thioethoxide, potassium thio-n-propoxide, potassium thioisopropoxide, lithium thiomethoxide, and lithium thioethoxide.

In the reaction, Compound (TXM1) is used usually within a range of 1 to 10 molar ratio(s), as opposed to 1 mole of Compound (TXH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXM2). The isolated present compound Y may be further purified, for example, by chromatography and recrystallization.

(Synthesis N)

A compound of a below-mentioned formula (TXN2) (hereinafter, described as Compound (TXN2)), can be prepared by reacting Compound (TXH2) with a compound of a below-mentioned formula (TXN1) (hereinafter, described as Compound (TXN1)).

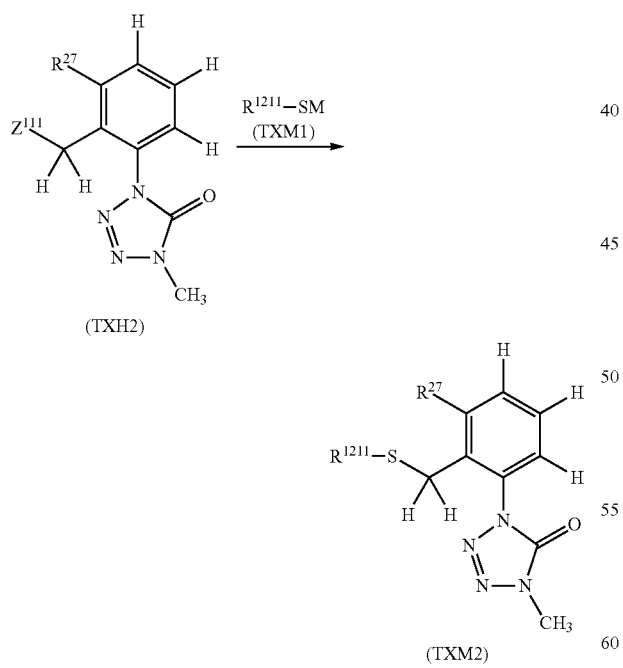

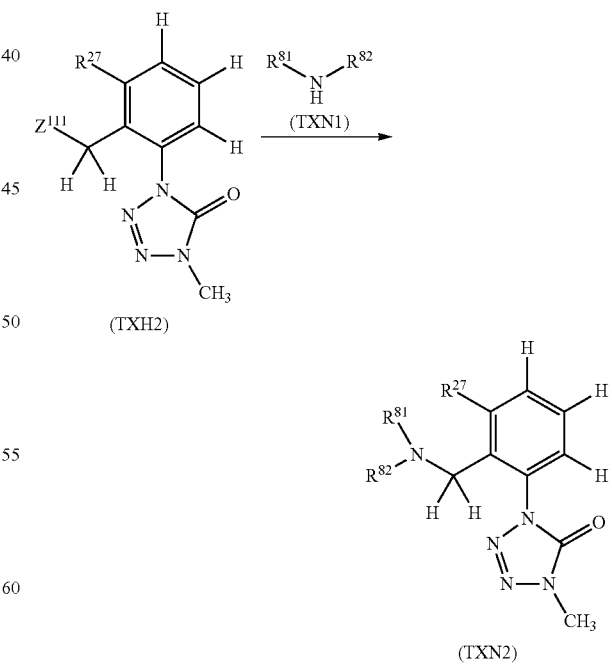

[wherein
R$^{27}$, R$^{1211}$, Z$^{111}$ and M are the same as described above]

This reaction is usually carried out in a solvent.

Examples of the solvent to be used in the reaction include ethers such as diethyl ether, tetrahydrofuran, 1,4-dioxane,

[wherein
R$^{27}$ and Z$^{111}$ are the same as described above; R$^{81}$ and R$^{82}$ represent an C1-C6 alkyl group, or combine each other together with a nitrogen atom to which they are attached to form a five-membered, six-membered or seven-membered heterocycle and the heterocycle may further contain one or more oxygen atom, nitrogen atom or sulfur atom]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; and mixed solvents thereof.

Examples of Compound (TXN1) include dimethylamine, diethylamine, dipropylamine, methylethylamine, methylpropylamine, ethylpropylamine, pyrrolidine, piperidine, piperazine, morpholine and thiomorpholine.

In the reaction, Compound (TXN1) is used usually within a range of 1 to 10 molar ratio(s), as opposed to 1 mole of Compound (TXH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXN2). The isolated present compound Y may be further purified, for example, by chromatography and recrystallization.

(Synthesis O)

A compound of a below-mentioned formula (TXO1) (hereinafter, described as Compound (TXO1)), can be prepared by reacting Compound (TXX1) with a reducing agent.

[wherein $R^{27}$ and $R^{911}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; and mixed solvents thereof.

Examples of the reducing agent to be used in the reaction include diisobutylaluminium hydride and sodium aluminium hydride.

In the reaction, the reducing agent is used usually within a range of 1 to 10 molar ratio(s), as opposed to 1 mole of Compound (TXX1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound Y represented by the formula (TXO1). The isolated present compound Y may be further purified, for example, by chromatography and recrystallization.

(Synthesis P)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a nitro group, i.e., a compound of a formula (H3) (hereinafter, described as Compound (H3)), can be prepared by reacting a compound of a formula (H1) (hereinafter, described as Compound (H1)) with a compound of a formula (H2) (hereinafter, described as Compound (H2)) in the presence of a base.

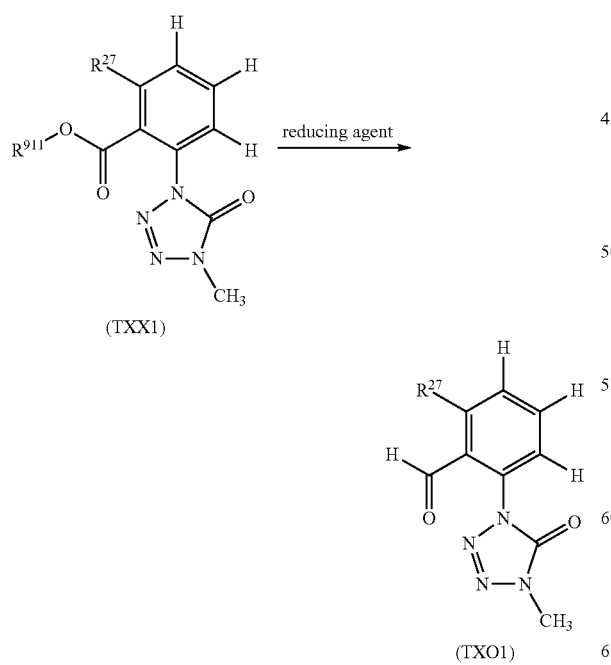

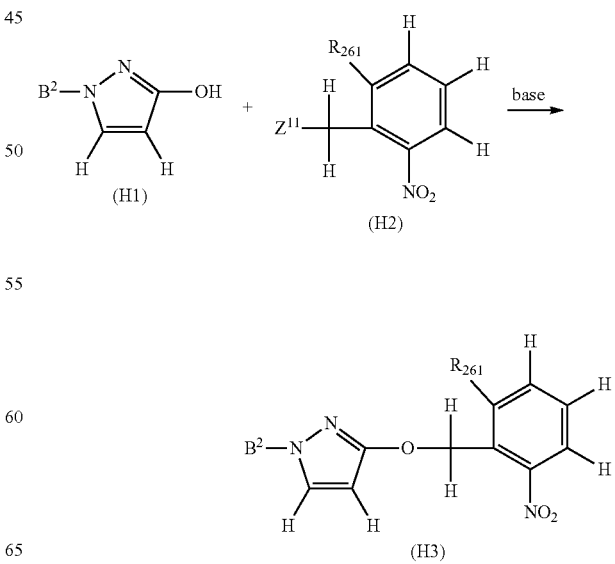

[wherein
B² represents any group as below-mentioned:

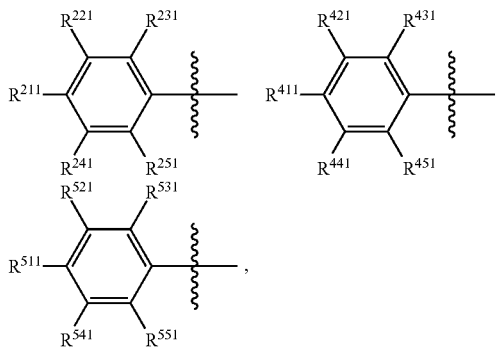

R²⁶¹, R²¹¹, R²²¹, R²³¹, R²⁴¹, R²⁵¹, R⁴¹¹, R⁴²¹, R⁴³¹, R⁴⁴¹, R⁴⁵¹, R⁵¹¹, R⁵²¹, R⁵³¹, R⁵⁴¹, R⁵⁵¹ and Z¹¹ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (H1) is used usually within a range of 1 to 10 molar ratio(s), and the base is used usually within a range of 0.5 to 5 molar ratio(s), as opposed to 1 mole of Compound (H2).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratio(s) as opposed to 1 mole of Compound (H2).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H3). The isolated present pyrazole compound Z, the isolated present pyrazole compound Z2 or the isolated present pyrazole compound Z3 may be further purified, for example, by chromatography and recrystallization.

(Synthesis Q)

The present pyrazole compound Z, the present pyrazole compound Z2 and the present pyrazole compound Z3 which is represented by the above-mentioned formula (9), formula (10) or formula (11) respectively, wherein L¹, L² or L³ is an amino group, i.e., a compound of a formula (H4) (hereinafter, described as Compound (H4)), can be prepared by reacting Compound (H3) with hydrogen gas in the presence of a catalyst.

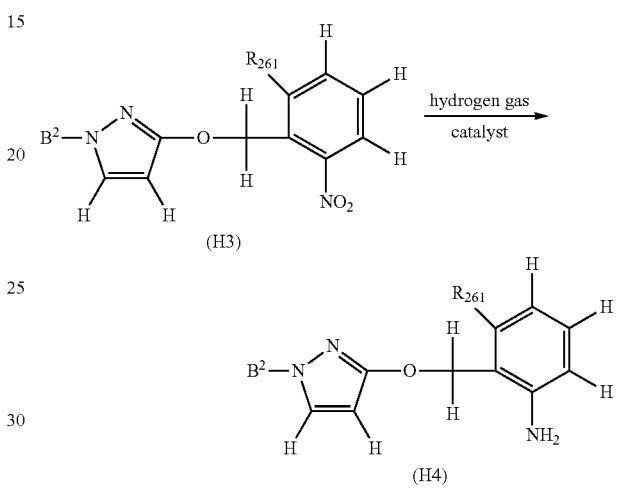

[wherein
B² and R²⁶¹ are the same as described above]

This reaction is usually carried out in a solvent.

Examples of the solvent to be used in the reaction include alcohols such as methanol, ethanol, propanol, butanol; esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; acidic acid; water; and mixed solvents thereof.

Examples of the catalyst to be used in the reaction include palladium on carbon (Pd/C), platinum on carbon (Pt/C), osmium on carbon (Os/C), ruthenium on carbon (Ru/C), rhodium on carbon (Rh/C) and Raney nickel.

The reaction temperature is usually within a range of −20 to 150° C. The reaction period of the reaction is usually within a range of 0.1 to 24 hours.

When the reaction is completed, the catalyst is filtered off, and the resulting organic layers are worked up (for example, concentration) to isolate the present pyrazole compound Z, the present pyrazole compound Z2 or the present pyrazole compound Z3, which each is represented by formula (H4). The isolated present pyrazole compound Z, the isolated present pyrazole compound Z2 or the isolated present pyrazole compound Z3 may be further purified, for example, by distillation, chromatography and recrystallization.

(Synthesis R)

Compound (H4) can be also prepared by reacting the above-mentioned Compound (H3) with a reducing agent.

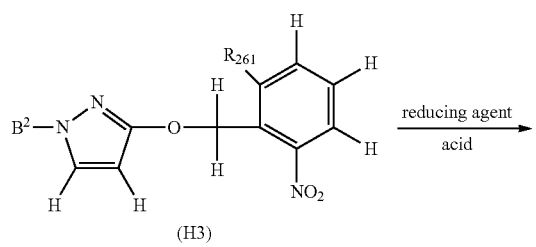

(H3)

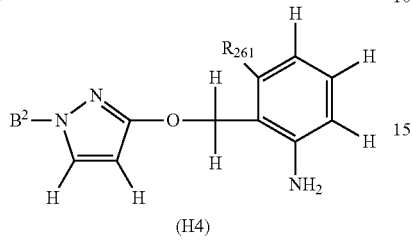

(H4)

[wherein
B² and $R^{261}$ are the same as described above]

This reaction is usually carried out in a solvent.

Examples of the solvent to be used in the reaction include aliphatic carboxylic acids such as acetic acid; alcohols such as methanol, ethanol; water and mixed solvents thereof.

Examples of the reducing agent to be used in the reaction include iron, tin and zinc.

Examples of the acid to be used in the reaction include hydrochloric acid, sulfuric acid, acetic acid, aqueous ammonium chloride solution.

In the reaction, the reducing agent is used usually within a range of 1 to 30 molar ratio(s), as opposed to 1 mole of Compound (H3).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H4). The isolated present pyrazole compound Z, the isolated present pyrazole compound Z2 or the isolated present pyrazole compound Z3 may be further purified, for example, by distillation, chromatography and recrystallization.

(Synthesis S)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is an isocyanato group, i.e., a compound of a formula (H5) (hereinafter, described as Compound (H5)), can be prepared by reacting Compound (H4) with phosgenes.

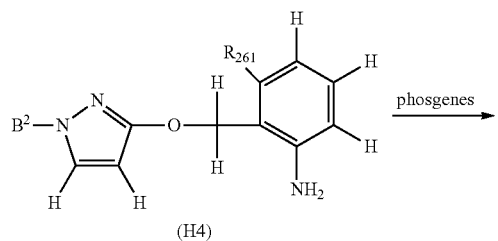

(H4)

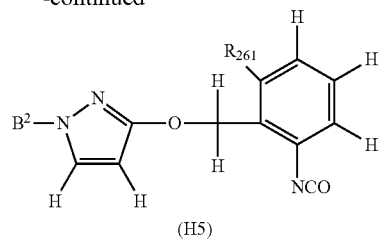

(H5)

[wherein
B² and $R^{261}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene and triphosgene.

In the reaction, phosgenes are used usually within a range of 1 to 10 molar ratio(s), as opposed to 1 mole of Compound (H4).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratio(s) as opposed to 1 mole of Compound (H4).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H5). The isolated present pyrazole compound Z, the isolated present pyrazole compound Z2 or the isolated present pyrazole compound Z3 may be further purified, for example, by distillation, chromatography and recrystallization.

(Synthesis T)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a NSO group, i.e., a compound of a formula (H6) (hereinafter, described as Compound (H6)), can be prepared by reacting Compound (H4) with a thionyl chloride.

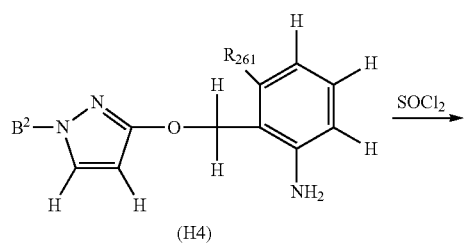

(H4)

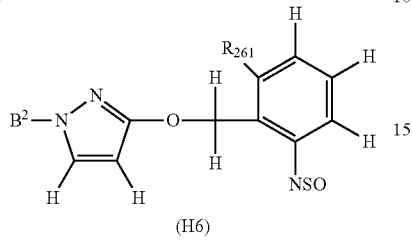

(H6)

[wherein

B² and R²⁶¹ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

In the reaction, thionyl chloride is used usually within a range of 1 to 10 molar ratio(s) as opposed to 1 mole of Compound (H4).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H6). The isolated present pyrazole compound Z, the isolated present pyrazole compound Z2 or the isolated present pyrazole compound Z3 may be further purified, for example, by distillation, chromatography and recrystallization.

(Synthesis U)

Compound (H5) represented by the below-mentioned formula (H5) can be prepared by reacting Compound (H6) with phosgenes.

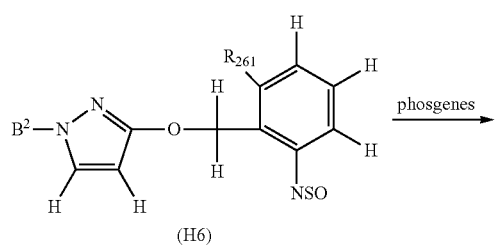

(H6)

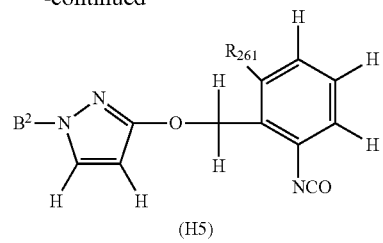

(H5)

[wherein

B² and R²⁶¹ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene and triphosgene.

In the reaction, phosgenes are used usually within a range of 1 to 10 molar ratio(s), as opposed to 1 mole of Compound (H6).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratio(s) as opposed to 1 mole of Compound (H6).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H5). The isolated present pyrazole compound Z, the isolated present pyrazole compound Z2 or the isolated present pyrazole compound Z3 may be further purified, for example, by distillation, chromatography and recrystallization.

(Synthesis V)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is an C2-C6 alkoxycarbonyl group, i.e., a compound of a formula (H8) (hereinafter, described as Compound (H8)), can be prepared by reacting Compound (H1) with a compound of a formula (H7) (hereinafter, described as Compound (H7)) in the presence of a base.

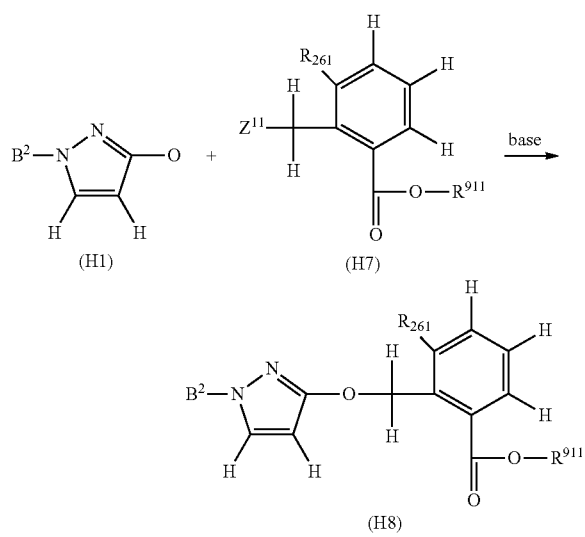

(H1)  (H7)

→ base (H8)

[wherein
B$^2$, R$^{261}$, Z$^{11}$ and R$^{911}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (H1) is used usually within a range of 1 to 10 molar ratio(s), and the base is used usually within a range of 0.5 to 5 molar ratio(s), as opposed to 1 mole of Compound (H7).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction, and these compounds are used usually within a range of 0.001 to 1.2 molar ratio(s) as opposed to 1 mole of Compound (H7).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H8). The isolated present pyrazole compound Z, the isolated present pyrazole compound Z2 or the isolated present pyrazole compound Z3 may be further purified, for example, by chromatography and recrystallization.

(Synthesis W)

The present pyrazole compound Z, the present pyrazole compound Z2 and the present pyrazole compound Z3 which is represented by the above-mentioned formula (9), formula (10) or formula (11) respectively, wherein L$^1$, L$^2$ or L$^3$ is a carbonyl group, i.e., a compound of a formula (H9) (hereinafter, described as Compound (H9)), can be prepared by reacting Compound (H8) with a hydrolytic agent.

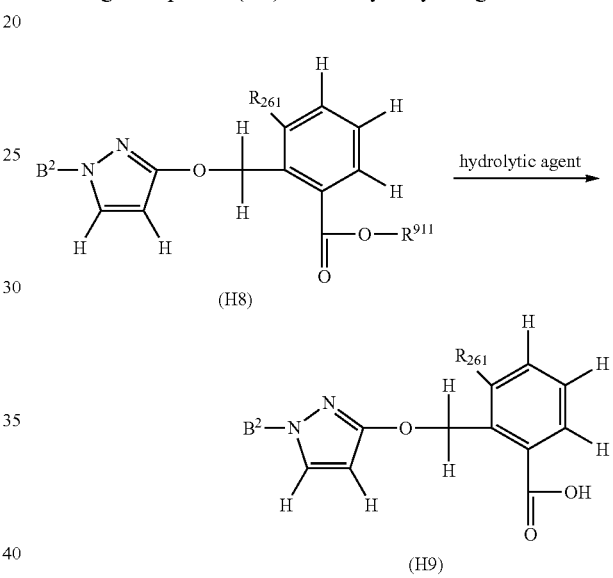

[wherein
B$^2$, R$^{261}$ and R$^{911}$ are the same as described above]

This reaction is usually carried out in a solvent.

Examples of the solvent to be used in the reaction include water; alcohols such as methanol, ethanol, propanol, butanol; hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; ketones such as acetone, methyl ethyl ketone, methyl isobutyl ketone; and mixed solvents thereof.

Examples of the hydrolytic agent to be used in the reaction include bases such as aqueous potassium hydroxide solution and aqueous sodium hydroxide solution; and acids such as hydrochloric acid and sulfuric acid.

In the reaction, the hydrolytic agent is used usually within a range of 0.5 to 20 molar ratio(s) as opposed to 1 mole of Compound (H8).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H9). The isolated present pyrazole compound Z, the isolated present pyrazole compound Z2 or the isolated present pyrazole compound Z3 may be further purified, for example, by distillation, chromatography and recrystallization.

(Synthesis X)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a halogenated acyl group, i.e., a compound of a formula (H10) (hereinafter, described as Compound (H10)), can be prepared by reacting Compound (H9) with a halogenating agent.

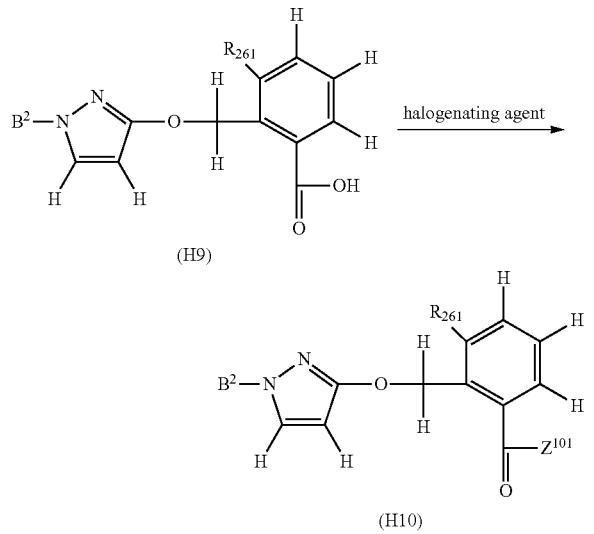

[wherein $B^2$, $R^{261}$ and $Z^{101}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorus tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (H9).

The reaction temperature is usually within a range of −20 to 150° C. The reaction period of the reaction is usually within a range of 0.1 to 24 hours.

A catalyst may be added to the reaction, and includes, for example, dimethylformamide. The catalyst is used usually within a range of 0.001 to 1 molar ratio(s) as opposed to 1 mole of Compound (H9).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonate such as lithium carbonate, sodium carbonate, potassium carbonate and cesium carbonate, alkali metal bicarbonate such as lithium bicarbonate, sodium bicarbonate, potassium bicarbonate and cesium bicarbonate and the other may be added to the reaction, and these compounds are used usually within a range of 0.05 to 5 molar ratios as opposed to 1 mole of Compound (H9).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H10). The isolated present pyrazole compound Z, the isolated present pyrazole compound Z2 or the isolated present pyrazole compound Z3 may be further purified, for example, by distillation, chromatography and recrystallization.

(Synthesis Y)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a $CON_3$ group, i.e., a compound of a formula (H11) (hereinafter, described as Compound (H11)), can be prepared by reacting Compound (H10) with sodium azide.

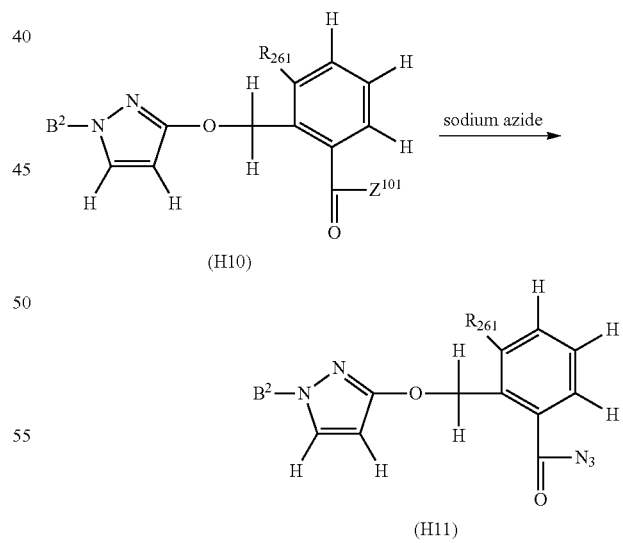

[wherein $B^2$, $R^{261}$ and $Z^{101}$ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

In the reaction, sodium azide is used usually within a range of 1 to 10 molar ratio(s) as opposed to 1 mole of Compound (H10).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H11). The isolated present pyrazole compound Z, the isolated present pyrazole compound Z2 or the isolated present pyrazole compound Z3 may be further purified, for example, by distillation, chromatography and recrystallization.

(Synthesis Z)

Compound (H5) can be prepared also by heating Compound (H11).

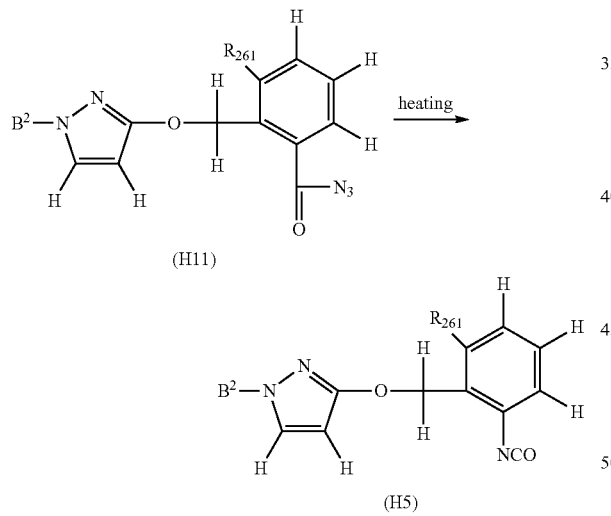

(H11)

(H5)

[wherein

B² and R²⁶¹ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H5). The isolated present pyrazole compound Z, the isolated present pyrazole compound Z2 or the isolated present pyrazole compound Z3 may be further purified, for example, by distillation, chromatography and recrystallization.

(Synthesis AA)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a $CONH_2$ group, i.e., a compound of a formula (H13) (hereinafter, described as Compound (H13)), can be prepared by reacting Compound (H10) with an ammonia.

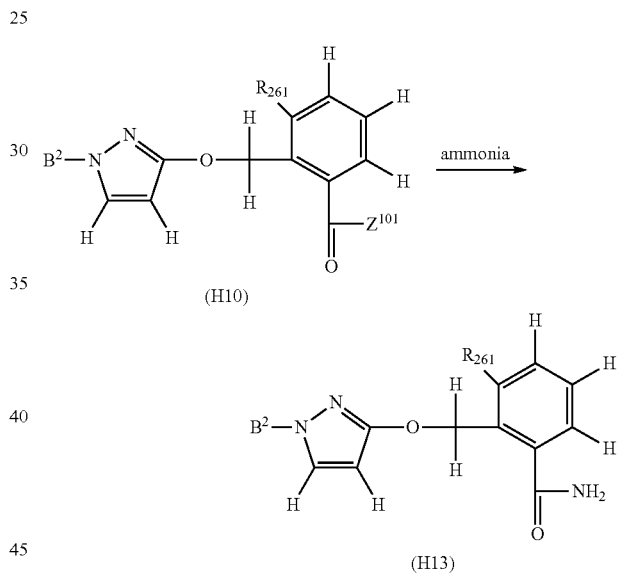

(H10)

(H13)

[wherein $B^2$, $R^{261}$ and $Z^{101}$ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the ammonia to be used in the reaction include aqueous ammonia, ammonia gas, ammonia methanol solution and ammonia ethanol solution.

In the reaction, ammonia is used usually within a range of 1 to a large excess molar ratio(s) as opposed to 1 mole of Compound (H10).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H13). The isolated present pyrazole compound Z, the isolated present pyrazole compound Z2 or the isolated present pyrazole compound Z3 may be further purified, for example, by chromatography and recrystallization.

(Synthesis AB)

Compound (H5) can be also prepared by reacting Compound (H13) with hypohalous acid salts.

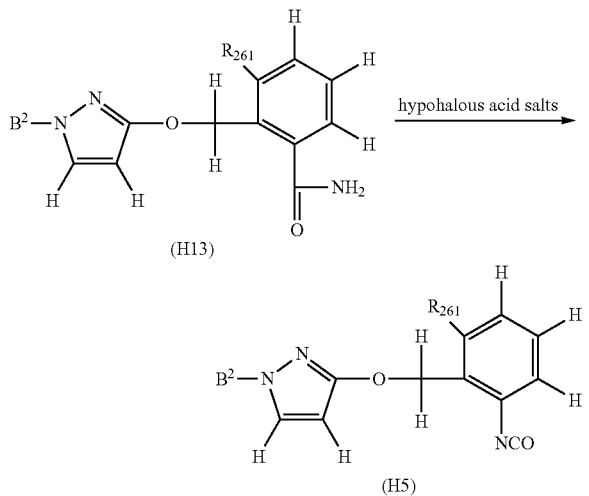

(H13)

(H5)

[wherein $B^2$ and $R^{261}$ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the hypohalous acid salts to be used in the reaction include sodium hypobromite, sodium hypochlorite, potassium hypobromite, potassium hypochlorite, barium hypobromite, barium hypochlorite, calcium hypobromite and calcium hypochlorite.

Also chlorine or bromine is mixed with sodium hydroxide, potassium hydroxide, barium hydroxide, calcium hydroxide and the others to form a hypochlorite or a hypobromite, which also can be used.

The reaction temperature is usually within a range of 0 to 150° C. The reaction period of the reaction is usually within a range of 0.1 to 24 hours.

In the reaction, the hypochlorite is used usually within a range of 1 to 10 molar ratio(s) as opposed to 1 mole of Compound (H13).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H5). The isolated present pyrazole compound Z, the isolated present pyrazole compound Z2 or the isolated present pyrazole compound Z3 may be further purified, for example, by distillation, chromatography and recrystallization.

(Synthesis AC)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a CONHOH group, i.e., a compound of a formula (H14) (hereinafter, described as Compound (H14)), can be prepared by reacting Compound (H10) with hydroxylamine.

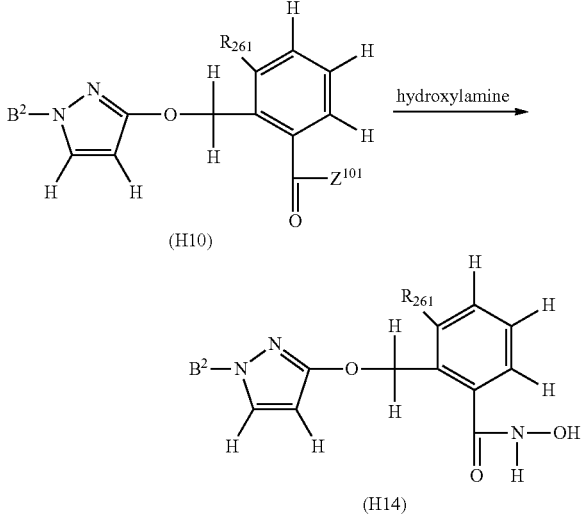

(H10)

(H14)

[wherein $B^2$, $R^{261}$ and $Z^{101}$ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

In the reaction, hydroxylamine is used usually within a range of 1 to 10 molar ratio(s) as opposed to 1 mole of Compound (H10).

The reaction temperature is usually within a range of −20 to 50° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H14). The isolated present pyrazole compound Z, the isolated present pyrazole compound Z2 or the isolated present pyrazole compound Z3 may be further purified, for example, by chromatography and recrystallization.

(Synthesis AD)

Compound (H5) can be prepared also by reacting Compound (H14) with an acylating agent.

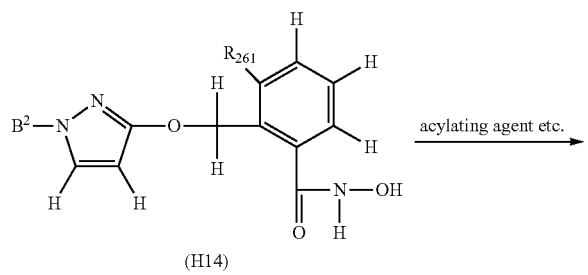

(H14)

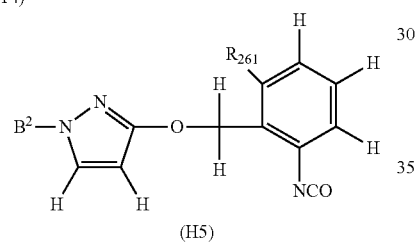

(H5)

[wherein
$B^2$ and $R^{261}$ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Example of the acylating agent to be used in the reaction include acid anhydride such as acetic anhydride, propionic anhydride; acyl halides such as acetyl chloride, acetyl bromide, benzolyl chloride; sulfonyl chlorides such as p-toluenesulfonyl chloride, methanesulfonyl chloride; sulfur trioxide-pyridine complex and thionyl chloride.

If necessary, a base such as pyridine, triethylamine, tributylamine, diazabicycloundecene, sodium hydroxide, potassium hydroxide may be added to the reaction, and these compounds are used usually within a range of 1 to 10 molar ratio(s) as opposed to 1 mole of Compound (H14).

The reaction temperature is usually within a range of −20 to 150° C. The reaction period of the reaction is usually within a range of 0.1 to 24 hours.

In the reaction, the acylating agent is used usually within a range of 1 to 10 molar ratio(s) as opposed to 1 mole of Compound (H14).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H5). The isolated present pyrazole compound Z, the isolated present pyrazole compound Z2 or the isolated present pyrazole compound Z3 may be further purified, for example, by distillation, chromatography and recrystallization.

(Synthesis AE)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a CONHCl group or a CONHBr group, i.e., a compound of a formula (H15) (hereinafter, described as Compound (H15)), can be prepared by reacting Compound (H13) with a halogenating agent.

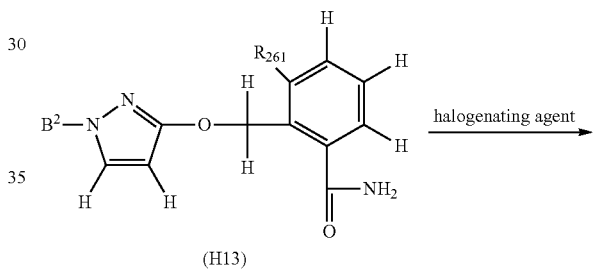

(H13)

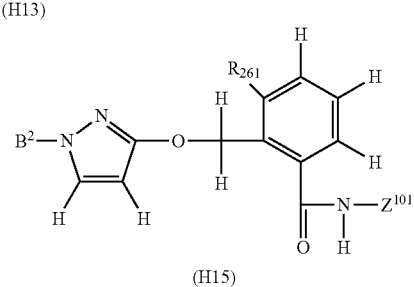

(H15)

[wherein
$B^2$, $R^{261}$ and $Z^{101}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include sodium hypochlorite, tert-butyl hypochlorite, isocyanuric acid, chlorine and sulfuryl chloride.

In the reaction, a halogenating agent is used usually within a range of 1 to 10 molar ratio(s) as opposed to 1 mole of Compound (H13).

The reaction temperature is usually within a range of −20 to 150° C. The reaction period of the reaction is usually within a range of 0.1 to 24 hours.

A catalyst may be added to the reaction, and includes, for example, dimethylformamide. The catalyst is used usually within a range of 0.001 to 1 molar ratio(s) as opposed to 1 mole of Compound (H13).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H15). The isolated present pyrazole compound Z, the isolated present pyrazole compound Z2 or the isolated present pyrazole compound Z3 may be further purified, for example, by distillation, chromatography and recrystallization.

(Synthesis AF)

Compound (H5) can be prepared also by reacting Compound (H15) with a base.

In the reaction, the base is used usually within a range of 1 to 10 molar ratio(s) as opposed to 1 mole of Compound (H15).

The reaction temperature is usually within a range of −20 to 150° C. The reaction period of the reaction is usually within a range of 0.1 to 24 hours.

When the reaction is completed, the reaction mixtures are extracted with organic solvent(s) and the resulting organic layers are worked up (for example, drying and concentration) to isolate the present pyrazole compound Z, the present pyrazole compound Z2 or the present pyrazole compound Z3, which each is represented by formula (H5). The isolated present pyrazole compound Z, the isolated present pyrazole compound Z2 or the isolated present pyrazole compound Z3 may be further purified, for example, by distillation, chromatography and recrystallization.

(Synthesis AG)

The present pyrazole compound Z, the present pyrazole compound Z2 and the present pyrazole compound Z3 which is represented by the above-mentioned formula (9), formula (10) or formula (11) respectively, wherein $L^1$, $L^2$ or $L^3$ is a halogen atom, i.e., a compound of a formula (H17) (hereinafter, described as Compound (H17)), can be prepared by reacting Compound (H1) with a compound of the below-mentioned formula (H16) (hereinafter, described as Compound (H16)) in the presence of a base.

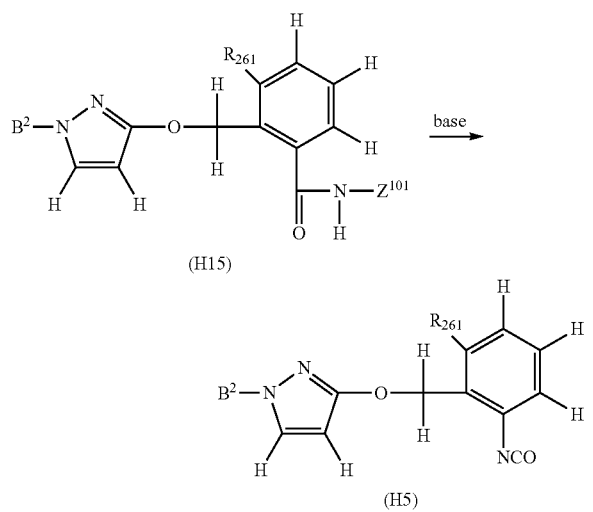

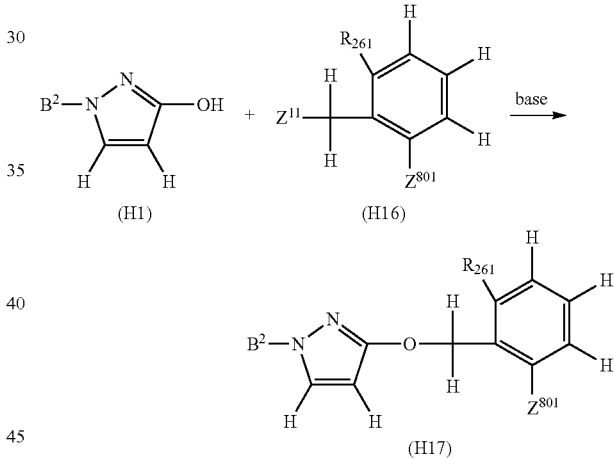

[wherein $B^2$, $Z^{101}$ and $R^{261}$ are the same as described above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; water; and mixed solvents thereof.

Examples of the base to be used in the reaction include pyridine, triethylamine, tributylamine, diazabicycloundecene, sodium hydroxide, potassium hydroxide.

[wherein $B^2$, $R^{261}$, $Z^{11}$ and $Z^{801}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate; alkali-metal hydroxides such as lithium hydroxide, sodium hydroxide, potassium hydroxide, cesium hydroxide; alkali-metal halides such as sodium fluoride, potassium fluoride, cesium fluoride; alkali-metal hydrides such as lithium hydride, sodium hydride, potassium hydride; alkali metal alkoxides such as sodium tert-butoxide, potassium tert-butoxide; and the others.

In the reaction, Compound (H1) is used usually within a range of 1 to 10 molar ratio(s), and the base is used usually within a range of 0.5 to 5 molar ratio(s), as opposed to 1 mole of Compound (H16).

The reaction temperature is usually within a range of −20 to 150° C. The reaction period of the reaction is usually within a range of 0.1 to 24 hours.

If necessary, sodium iodide, tetrabutylammonium iodide or the others may be added to the reaction, and these compounds is used usually within a range of 0.001 to 1.2 molar ratio(s) as opposed to 1 mole of Compound (H16).

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H17). The isolated present pyrazole compound Z, the isolated present pyrazole compound Z2 or the isolated present pyrazole compound Z3 may be further purified, for example, by chromatography and recrystallization.

(Synthesis AH)

Compound (H9) can be also prepared by reacting Compound (H17) with a carbonylating agent.

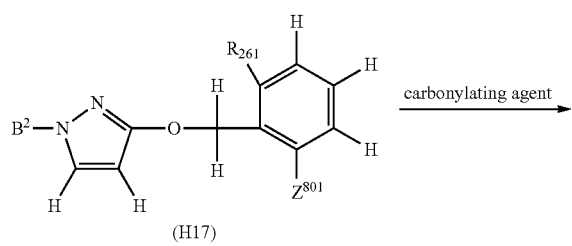

(H17)

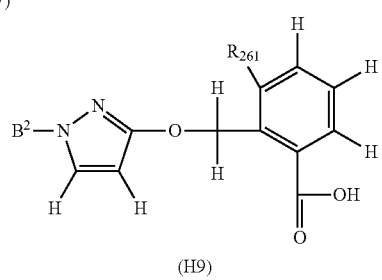

(H9)

[wherein $B^2$, $R^{261}$ and $Z^{801}$ are the same as described above]

This reaction is usually carried out in a solvent.

Examples of the solvent to be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; and mixed solvents thereof.

Examples of the carbonylating agent to be used in the reaction include a combination of metal or metallic compound and carbon homologation agent, such as that of magnesium and carbon dioxide, that of isopropylmagnesium bromide and carbon dioxide, and that of n-butyllitium and carbon dioxide.

In the reaction, the metal or metallic compound is used usually within a range of 1 to 20 molar ratio(s), and the carbon homologation agent is used usually within a range of 1 to a large excess molar ratio(s), as opposed to 1 mole of Compound (H17).

When carbon dioxide is used as carbon homologation agent, examples of the carbon dioxide include carbonic acid gas and dry ice.

The reaction temperature is usually within a range of −80 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate the present pyrazole compound Z, the present pyrazole compound Z2 or the present pyrazole compound Z3, which each is represented by formula (H9). The isolated present pyrazole compound Z, the isolated present pyrazole compound Z2 or the isolated present pyrazole compound Z3 may be further purified, for example, by distillation, chromatography and recrystallization Hereinafter, a process for preparing an intermediate compound is described in detail.

(Reference Process A)

A compound of a formula (XA3) (hereinafter, described as Compound (XA3)) can be prepared by reacting a compound of a formula (XA1) (hereinafter, described as Compound (XA1)) or a compound of a formula (XA2) (hereinafter, described as Compound (XA2)) with an azidation agent.

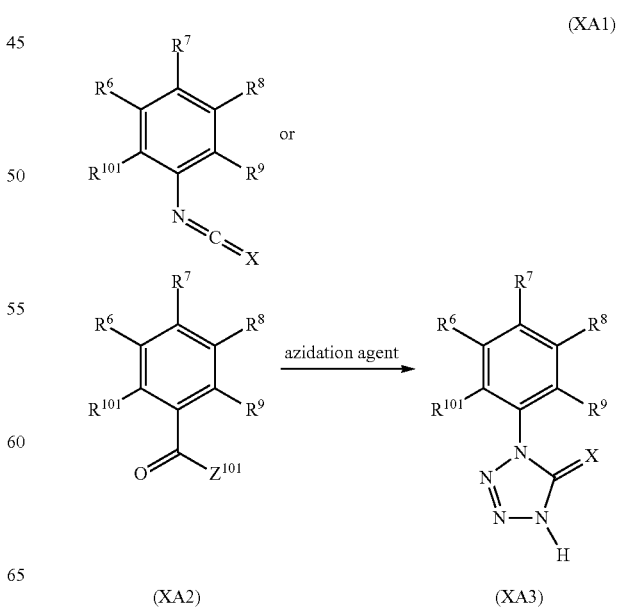

(XA1)

(XA2)            (XA3)

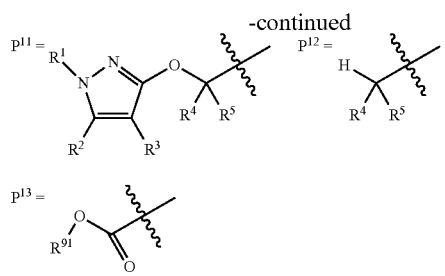

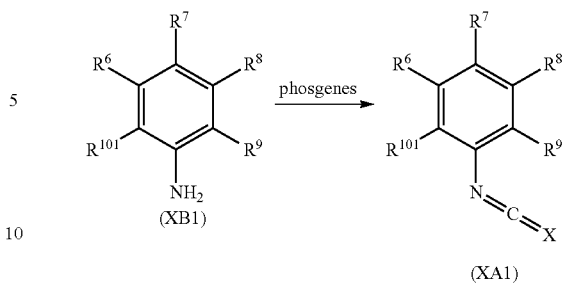

[wherein $R^1$, $R^2$, $R^3$, $R^4$, $R^5$, $R^6$, $R^7$, $R^8$, $R^9$, $Z^{101}$ and X are the same as described above; $R^{101}$ represents $P^{11}$, $P^{12}$ or $P^{13}$; $R^{91}$ represents an C1-C12 alkyl group; and a wavy line represents a binding site]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (XA1) or Compound (XA2).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.001 to 5 molar ratio(s) as opposed to 1 mole of Compound (XA1) or Compound (XA2).

When the reaction is completed, the reaction mixtures are extracted with organic solvent(s), and the resulting organic layers are worked up (for example, drying and concentration) to isolate Compound (XA3). The isolated Compound (XA3) may be further purified, for example, by chromatography and recrystallization.

(Reference Process B)

Compound (XA1) can be prepared by reacting a compound of a formula (XB1) (hereinafter, described as Compound (XB1)) with phosgenes.

[wherein $R^6$, $R^7$, $R^8$, $R^9$, $R^{101}$ and X are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the phosgenes to be used in the reaction include phosgene, diphosgene, triphosgene, and thiophosgene.

In the reaction, the phosgenes are used usually within a range of 1 to 10 molar ratios as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these compounds are used usually within a range of 0.05 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process C)

Compound (XA2) can be prepared by reacting a compound of a formula (XC1) (hereinafter, described as Compound (XC1)) with a halogenating agent.

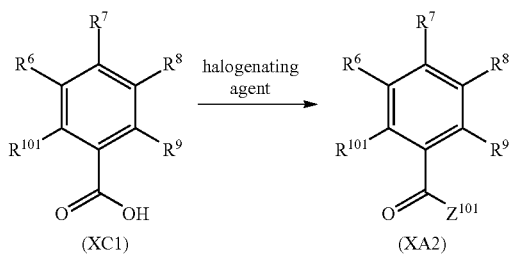

[wherein
$R^6$, $R^7$, $R^8$, $R^9$, $R^{101}$ and $Z^{101}$ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorus tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (XC1).

The reaction temperature is usually within a range of −20 to 150° C. The reaction period of the reaction is usually within a range of 0.1 to 24 hours.

A catalyst may be added to the reaction, and includes, for example, dimethylformamide. The catalyst is used usually within a range of 0.001 to 1 molar ratio(s) as opposed to 1 mole of Compound (XC1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these compounds are used usually within a range of 0.05 to 5 molar ratio(s) as opposed to 1 mole of Compound (XC1).

When the reaction is completed, the reaction mixtures are extracted with organic solvent(s), and the resulting organic layers are worked up (for example, drying and concentration) to isolate Compound (XA2). The isolated Compound (XA2) may be further purified, for example, by distillation, chromatography and recrystallization.

(Reference Process D)

Compound (XA1) can be prepared by reacting Compound (XB1) with a carbamating agent to form a compound of the below-mentioned formula (XD1) (hereinafter, described as Compound (XD1)), followed by reacting the resulting Compound (XD1) with Compound (XD2).

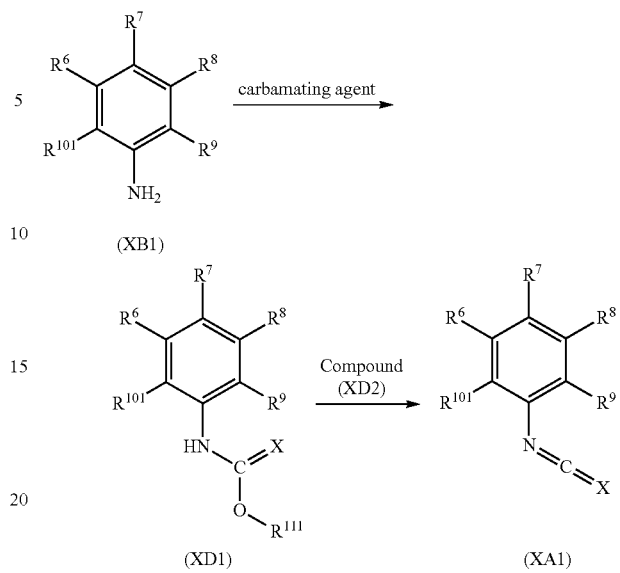

[wherein
$R^6$, $R^7$, $R^8$, $R^9$, $R^{101}$ and X are the same as described above; $R^{111}$ represents an C1-C12 alkyl group or a phenyl group]

Hereinafter, the process for preparing Compound (XD1) from Compound (XB1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the carbamating agent to be used in the reaction include phenyl chloroformate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate and O-ethyl chlorothioformate.

In the reaction, the carbamating agent is used usually within a range of 1 to 10 molar ratio(s) as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these compounds are used usually within a range of 0.05 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XD1). The isolated Compound (XD1) may be further purified, for example, by distillation, chromatography and recrystallization.

Hereinafter, the process for preparing Compound (XA1) from Compound (XD1) is explained.

This reaction is usually carried out in a solvent.

Examples of the solvent that can be used in the reaction include ethers such as tetrahydrofuran, dioxane, ethyleneglycol dimethyl ether, methyl tert-butyl ether; hydrocarbons such as toluene, xylene; halogenated hydrocarbons such as carbon tetrachloride, chloroform, 1,2-dichloroethane, chlorobenzene; nitriles such as acetonitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; and mixed solvents thereof.

Examples of Compound (XD2) include phosphorous pentachloride, phosphorous oxychloride, diphosphorus pentoxide, trichlorosilane, dichlorosilane, monochlorosilane, boron trichloride, 2-chloro-1,3,2-benzodioxaborole, diiodosilane, methyl trichlorosilane, montmorillonite K-10, dimethyl dichlorosilane, chlorotrimethylsilane.

In the reaction, Compound (XD2) is used usually within a range of 1 to 10 molar ratio(s) as opposed to 1 mole of Compound (XD1).

The reaction temperature is usually within a range of −20 to 250° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these compounds are used usually within a range of 0.05 to 5 molar ratios as opposed to 1 mole of Compound (XD1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process E)

A compound of a formula (XE2) (hereinafter, described as Compound (XE2)) can be prepared by reacting a compound of a formula (XE1) (hereinafter, described as Compound (XE1)) with a hydrogen gas in the presence of a catalyst.

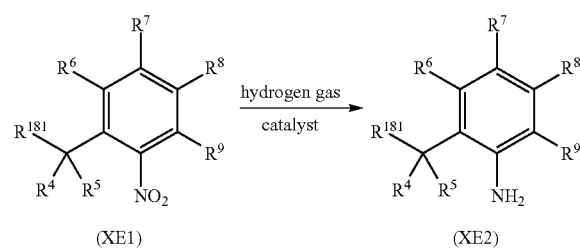

(XE1) (XE2)

-continued

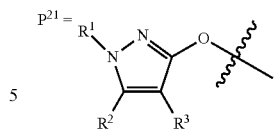

[wherein
$R^1$, $R^2$, $R^3$, $R^4$, $R^5$, $R^6$, $R^7$, $R^8$ and $R^9$ are the same as described above; $R^{181}$ represents a hydrogen atom or $P^{21}$; and a wavy bond represents a binding site]

This reaction is usually carried out in a solvent.

Examples of the solvent that can be used in the reaction include alcohols such as methanol, ethanol, propanol, butanol: esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; water; and mixed solvents thereof.

Examples of the catalyst to be used in the reaction includes palladium on carbon (Pd/C), platinum on carbon (Pt/C), osmium on carbon (Os/C), ruthenium on carbon (Ru/C), rhodium on carbon (Rh/C) and Raney nickel.

The reaction temperature is usually within a range of −20 to 150° C. The reaction period of the reaction is usually within a range of 0.1 to 24 hours.

When the reaction is completed, the catalyst is filtered off, and the resulting organic layers are worked up (for example, concentration) to isolate Compound (XE2). The isolated Compound (XE2) may be further purified, for example, by distillation, chromatography and recrystallization.

(Reference Process F)

Compound (XE2) can be prepared by reducing the above-mentioned Compound (XE1) with a reducing agent in the presence of an acid.

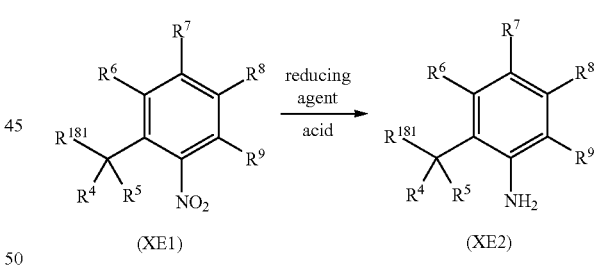

(XE1) (XE2)

[wherein
$R^4$, $R^5$, $R^6$, $R^7$, $R^8$, $R^9$ and $R^{181}$ are the same as described above]

This reaction is usually carried out in a solvent.

Examples of the solvent that can be used in the reaction include aliphatic carboxylic acid such as acetic acid; alcohols such as methanol, ethanol; water; and mixed solvents thereof.

Examples of the reducing agent to be used in the reaction include iron, tin and zinc.

Examples of the acid to be used in the reaction include hydrochloric acid, sulfuric acid, acetic acid, aqueous ammonium chloride solution.

In the reaction, the reducing agent is used usually within a range of 1 to 30 molar ratio(s) as opposed to 1 mole of Compound (XE1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XE2). Compound (XE2) may be further purified, for example, by distillation, chromatography and recrystallization.

(Reference Process G)

A compound of a formula (XG2) (hereinafter, described as Compound (XG2)) can be prepared by reacting a compound of a formula (XG1) (hereinafter, described as Compound (XG1)) and Compound (D2) in the presence of a base.

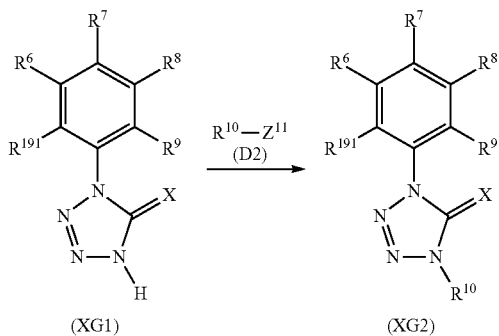

[wherein
$R^6$, $R^7$, $R^8$, $R^9$, $R^{10}$, X and $Z^{11}$ are the same as described above; and $R^{191}$ represents $P^{12}$ or $P^{13}$]

The reaction can be carried out according to the above-mentioned process D.

(Reference Process H)

A compound of a formula (XH2) (hereinafter, described as Compound (XH2)) can be prepared by reacting a compound of a formula (XH1) (hereinafter, described as Compound (XH1)) with a halogenating agent.

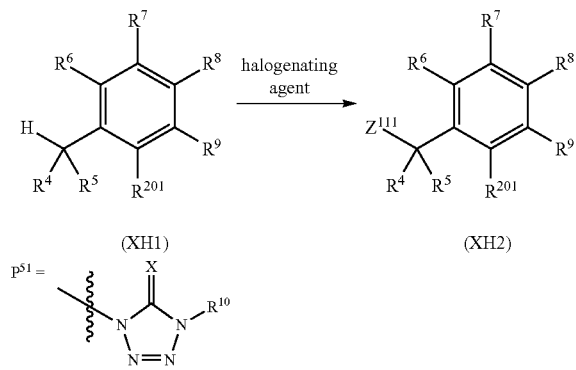

[wherein
$R^4$, $R^5$, $R^6$, $R^7$, $R^8$, $R^9$, $R^{10}$, $Z^{111}$ and X are the same as described above; $R^{201}$ represents a $P^{51}$ group or a nitro group, and a wavy bond represents a binding site]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, α,α,α-trichlorotoluene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include a chlorinating agent, a brominating agent or iodinating agent such as chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonamide and N-bromophthalimide.

In the reaction, a radical initiator can be used.

Examples of the radical initiator to be used in the reaction include benzoyl peroxide, azobisisobutyronitrile (AIBN), diacylperoxide, dialkyl peroxydicarbonate, tert-alkyl peroxyester, monoperoxy carbonate, di(tert-alkylperoxy)ketal and ketone peroxide.

In the reaction, the halogenating agent is used usually within a range of 1 to 10 molar ratio(s), and the radical initiator is used usually within a range of 0.01 to 1 molar ratio(s), as opposed to 1 mole of Compound (XH1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). Compound (XH2) may be further purified, for example, by distillation, chromatography and recrystallization.

(Reference Process I)

A compound of a formula (XJ2) (hereinafter, described as Compound (XJ2)) can be prepared by reacting Compound (XH2) with a compound of a formula (XJ1) (hereinafter, described as Compound (XJ1)).

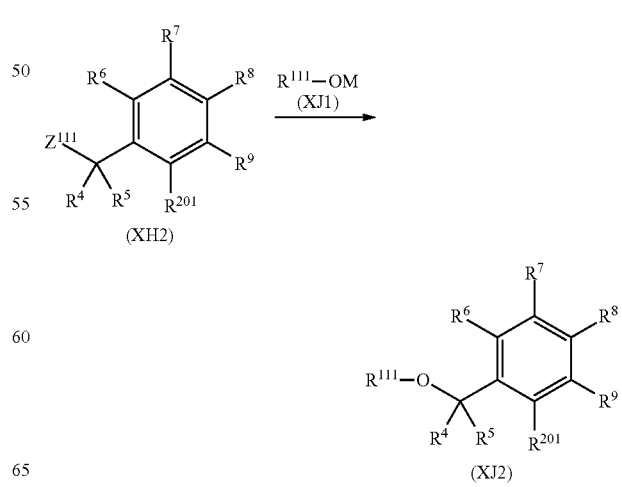

[wherein
R$^4$, R$^5$, R$^6$, R$^7$, R$^8$, R$^9$, R$^{201}$, R$^{111}$ and Z$^{111}$ are the same as described above; and M represents sodium, potassium or lithium]

This reaction is usually carried out in a solvent.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of Compound (XJ1) include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide and sodium phenoxide.

In the reaction, Compound (XJ1) is used usually within a range of 1 to 10 molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XJ2). Compound (XJ2) may be further purified, for example, by distillation, chromatography and recrystallization.

(Reference Process J)

A compound of a formula (XK1) (hereinafter, described as Compound (XK1)) can be prepared by reacting Compound (XH2) and water in the presence of a base.

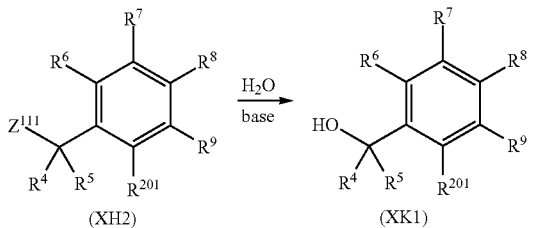

[wherein
R$^4$, R$^5$, R$^6$, R$^7$, R$^8$, R$^9$, R$^{201}$ and Z$^{111}$ are the same as described above]

This reaction is usually carried out in water or a solvent containing water.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; metallic organic acid salts such as lithium formate, lithium acetate, sodium formate, sodium acetate, potassium formate, potassium acetate; metallic nitrates such as silver nitrate, sodium nitrate; alkali-metal bicarbonates such as lithium bicarbonate, sodium bicarbonate, potassium bicarbonate, cesium bibicarbonate; alkali-metal hydroxides such as lithium hydroxide, sodium hydroxide, potassium hydroxide, cesium hydroxide; alkali metal alkoxides such as sodium methoxide, sodium ethoxide, sodium tert-butoxide, potassium tert-butoxide.

In the reaction, the base is used usually within a range of 1 to 100 molar ratio(s) as opposed to 1 mole of Compound (XH2).

In the reaction, water is used usually within a range of 1 to a large excess molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XK1). Compound (XK1) may be further purified, for example, by distillation, chromatography and recrystallization.

(Reference Process K)

Compound (XH2) can be prepared by reacting Compound (XJ2) and a halogenating agent.

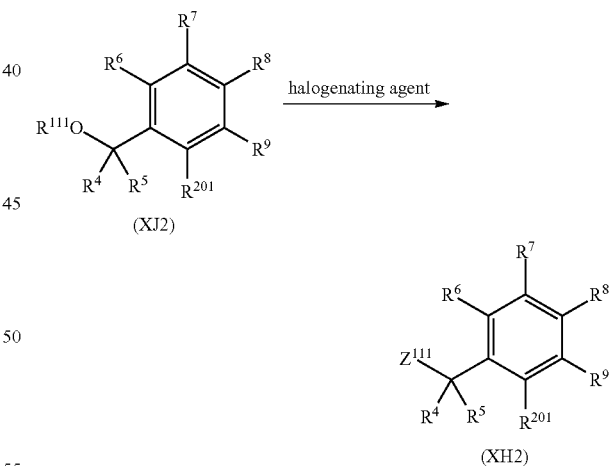

[wherein
R$^4$, R$^5$, R$^6$, R$^7$, R$^8$, R$^9$, R$^{111}$, R$^{201}$ and Z$^{111}$ are the same as described above]

This reaction is usually carried out in a solvent.

Examples of the solvent that can be used in the reaction include hydrocarbons such as n-heptane, n-hexane, cyclohexane, n-pentane, toluene, xylene; halogenated hydrocarbons such as carbon tetrachloride, chloroform, dichloromethane, 1,2-dichloroethane, tetrachloroethane, chlorobenzene; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent include hydrochloric acid, hydrobromic acid and hydroiodic acid.

In the reaction, the halogenating agent is used usually in 1 or more molar ratio(s) as opposed to 1 mole of Compound (XJ2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). Compound (XH2) may be further purified, for example, by distillation, chromatography and recrystallization.

(Reference Process L)

Compound (XH2) can be prepared by reacting a compound of a formula (XK1) (hereinafter, described as Compound (XK1)) and a halogenating agent.

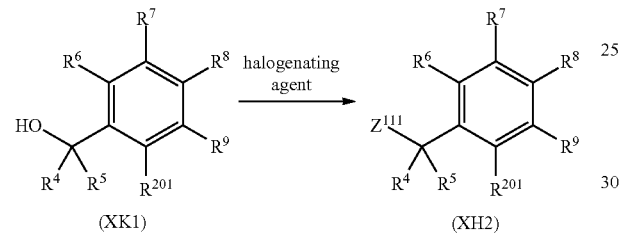

[wherein
$R^4$, $R^5$, $R^6$, $R^7$, $R^8$, $R^9$, $R^{201}$ and $R^{111}$ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, lithium chloride, sodium iodide and acetyl bromide.

In the reaction, the halogenating agent is used usually within a range of 1 to 10 molar ratio(s) as opposed to 1 mole of Compound (XK1).

To promote the reaction, an additive agent may be added depending on the halogenating agent used, and specifically includes zinc chloride for acetyl chloride; triphenylphosphine for carbon tetrabromide; dimethyl sulfide for N-bromosuccinimide; boron trifluoride diethyl etherate complex for sodium iodide; boron trifluoride diethyl etherate complex for acetyl bromide; triethylamine and methanesulfonyl chloride for lithium chloride; aluminium chloride for sodium iodide; and trimethylsilyl chloride for sodium iodide. The amount of the additive agent is used usually within a range of 0.01 to 5 molar ratio(s) as opposed to 1 mole of Compound (XK1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). Compound (XH2) may be further purified, for example, by distillation, chromatography and recrystallization.

(Reference Process M)

A compound of a formula (XM3) (hereinafter, described as Compound (XM3)) can be prepared by reacting Compound (XK1) with a compound of a formula (XM2) (hereinafter, described as Compound (XM2)) in the presence of a base.

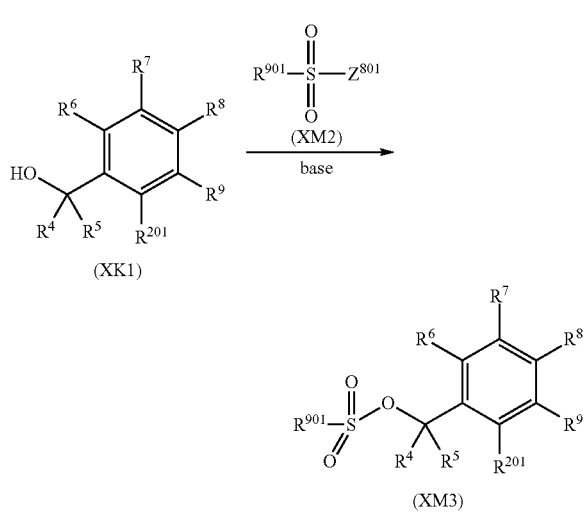

[wherein
$R^4$, $R^5$, $R^6$, $R^7$, $R^8$, $R^9$, $R^{201}$, $R^{901}$ and $Z^{801}$ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; water; and mixed solvents thereof.

Examples of the based to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal hydrides such as lithium hydride, sodium hydride, potassium hydride; alkali metal alkoxides such as sodium methoxide, sodium ethoxide, sodium tert-butoxide, potassium tert-butoxide.

In the reaction, Compound (XM2) is used usually within a range of 1 to 10 molar ratio(s), and the base is used usually within a range of 1 to 5 molar ratio(s), as opposed to 1 mole of Compound (XK1).

The reaction temperature is usually within a range of −20 to 150° C. The reaction period of the reaction is usually within a range of 0.1 to 24 hours.

If necessary, sodium iodide and tetrabutylammonium iodide and the like may be added to the reaction, and these compounds are used usually within a range of 0.001 to 1.2 molar ratio(s) as opposed to 1 mole of Compound (XK1).

When the reaction is completed, the reaction mixtures are extracted with organic solvent(s), and the resulting organic layers are worked up (for example, drying and concentration) to isolate Compound (XM3). Compound (XM3) may be further purified, for example, by distillation, chromatography and recrystallization.

(Reference Process N)

A compound of a formula (XN12) (hereinafter, described as Compound (XN12)) can be prepared by coupling a compound of a formula (XN11) (hereinafter, described as Compound (XN11)) with Compound (F21) in the presence of a base and a catalyst.

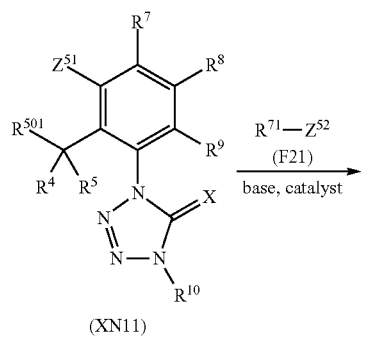

(XN11)

[wherein $R^{501}$ represents a hydrogen atom or an $OR^{111}$ group; $R^{111}$, $R^4$, $R^5$, $R^7$, $R^8$, $R^9$, $R^{10}$, $R^{71}$, X, $Z^{51}$ and $Z^{52}$ are the same as described above]

The reaction can be carried out according to the above-mentioned Process F.

A compound of a formula (XN22) (hereinafter, described as Compound (XN22)) can be prepared by coupling a compound of a formula (XN21) (hereinafter, described as Compound (XN21)) with Compound (F22) in the presence of a base and a catalyst.

(XN21)

(XN22)

[wherein $R^{501}$, $R^4$, $R^5$, $R^6$, $R^8$, $R^9$, $R^{10}$, $R^{72}$, X, $Z^{51}$ and $Z^{52}$ are the same as described above]

The reaction can be carried out according to the above-mentioned Process F.

A compound of a formula (XN32) (hereinafter, described as Compound (XN32)) can be prepared by coupling a compound of a formula (XN31) (hereinafter, described as Compound (XN31)) with Compound (F22) in the presence of a base and a catalyst.

(XN31)

Also, among a compound of a formula (XN50):

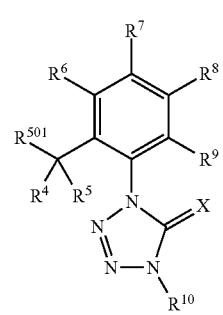

(XN50)

[wherein
R$^4$, R$^5$, R$^6$, R$^7$, R$^8$, R$^9$, R$^{10}$, R$^{501}$ and X are the same as described above],
a compound wherein two or more substituents selected from R$^6$, R$^7$, R$^8$ or R$^9$ represent R$^{71}$ or R$^{72}$ can be prepared according to the above-mentioned Process F.

Further, Compound (XN50) can be prepared according to a known coupling method instead of the above-mentioned coupling reaction described in Process F.

(Reference Process O)

A compound of a formula (XW2) (hereinafter, described as Compound (XW2)) can be prepared by reacting a compound of a formula (XW1) (hereinafter, described as Compound (XW1)) with an alcohol in the presence of a reaction accelerator.

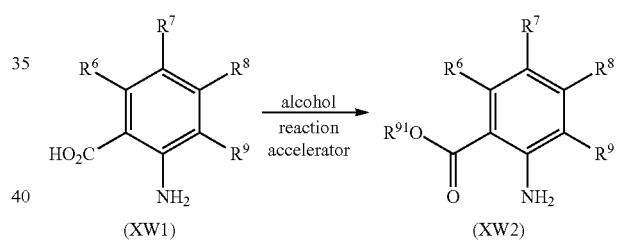

[wherein
R$^6$, R$^7$, R$^8$, R$^9$ and R$^{91}$ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and the alcohol to be reacted with Compound (XW1) may be used as solvent.

Examples of the alcohols include methanol, ethanol, n-propanol, isopropanol, n-butanol, sec-butanol, t-butanol, and n-pentanol.

Examples of the reaction accelerator include mineral acids such as hydrochloric acid, sulfuric acid; carbodiimides such as dicyclohexylcarbodiimide, diisopropylcarbodiimide, N'-(3-dimethylaminopropyl)-N-ethylcarbodiimide;

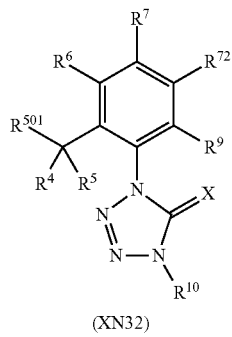

(XN32)

[wherein
R$^{501}$, R$^4$, R$^5$, R$^6$, R$^7$, R$^9$, R$^{10}$, R$^{72}$, X, Z$^{51}$ and Z$^{52}$ are the same as described above]

The reaction can be carried out according to the above-mentioned Process F.

A compound of a formula (XN42) (hereinafter, described as Compound (XN42)) can be prepared by coupling a compound of a formula (XN41) (hereinafter, described as Compound (XN41)) with Compound (F22) in the presence of a base and a catalyst.

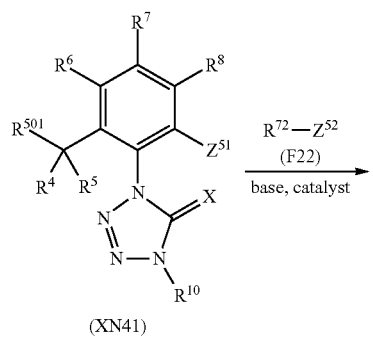

(XN41)

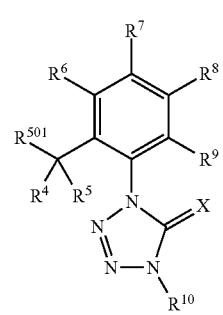

(XN42)

[wherein
R$^{501}$, R$^4$, R$^5$, R$^6$, R$^7$, R$^8$, R$^{10}$, R$^{72}$, X, Z$^{51}$ and Z$^{52}$ are the same as described above]

The reaction can be carried out according to the above-mentioned Process F.

organic acids such as methanesulfonic acid, toluenesulfonic acid; Mitsunobu reagents such as triphenylphosphine/diethyl azodicarboxylate; thionyl chloride; boron trifluoride-ethyl ether complex.

In the reaction, the reaction accelerator is used usually within a range of 0.01 to 10 molar ratios, as opposed to 1 mole of Compound (XW1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate may be added to the reaction, and these compounds are used usually within a range of 0.001 to 5 molar ratio(s) as opposed to 1 mole of Compound (XW1).

In the reaction, the alcohol is used usually in a large excess amounts as opposed to 1 mole of Compound (XW1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XW2). Compound (XW2) may be further purified, for example, by distillation, chromatography and recrystallization.

(Reference Process P)

Compound (XW2) can be prepared by reacting Compound (XW1) with a halogenating agent to form a compound of a formula (XV1) (hereinafter, described as Compound (XV1)), followed by reacting the resulting Compound (XV1) with an alcohol.

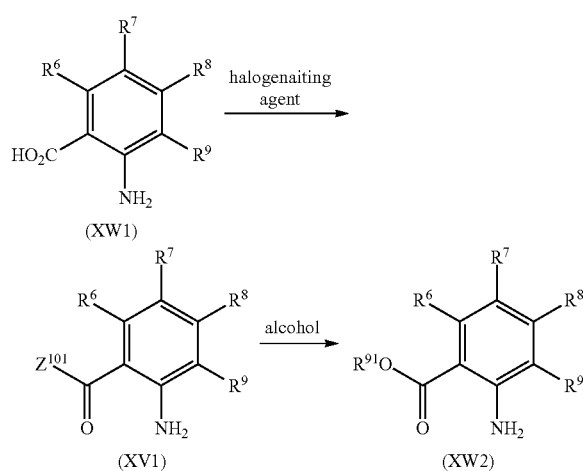

[wherein
$R^6$, $R^7$, $R^8$, $R^9$, $R^{91}$ and $Z^{101}$ are the same as described above]

The process for preparing Compound (XV1) by reacting Compound (XW1) and a halogenating agent can be carried out according to Reference Process C.

Hereinafter, a process for preparing Compound (XW2) from Compound (XV1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and the alcohol to be reacted with Compound (XV1) may be used as solvent.

Examples of the alcohols include methanol, ethanol, n-propanol, isopropanol, n-butanol, sec-butanol, t-butanol, and n-pentanol.

In the reaction, the alcohol is used usually within a range of 1 to 50 molar ratio(s) as opposed to 1 mole of Compound (XV1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XW2). Compound (XW2) may be further purified, for example, by distillation, chromatography and recrystallization.

(Reference Process Q)

Compound (XW2) can be prepared by reacting Compound (XW1) with an alkylating agent.

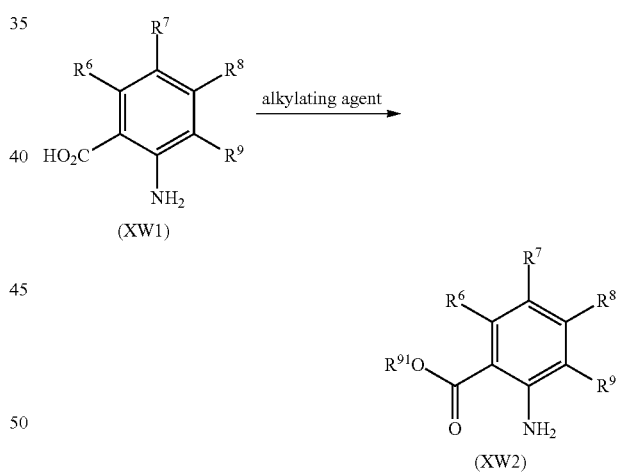

[wherein
$R^6$, $R^7$, $R^8$, $R^9$ and $R^{91}$ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the alkylating agent to be used in the reaction include diazoalkyls such as diazomethane, trimethylsilyldiazomethane; halogenated alkyls such as chlorodifluoromethane, methyl bromide, ethyl bromide, n-propyl bromide, methyl iodide, ethyl iodide, n-propyl bromide, aryl bromide, cyclopropyl bromide, benzyl bromide, 1,1-difluoro-2-iodomethane; dialkyl sulfates such as dimethyl sulfates, diethyl sulfates, di-n-propyl sulfates; alkyl or aryl sulfonates such as methyl p-toluenesulfonate, ethyl p-toluenesulfonate, n-propyl p-toluenesulfonate, methyl methanesulfonate, ethyl methanesulfonate, n-propyl methanesulfonate.

In the reaction, the alkylating agent is used usually within a range of 1 to 10 molar ratios as opposed to 1 mole of Compound (XW1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate, or quaternary ammonium salts such as tetra(n-butyl)ammonium hydroxide may be added to the reaction, and these compounds are used usually within a range of 0.001 to 5 molar ratios as opposed to 1 mole of Compound (XW1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XW2). Compound (XW2) may be further purified, for example, by distillation, chromatography and recrystallization.

(Reference Process R)

A compound of a formula (XX2) (hereinafter, described as Compound (XX2)) can be prepared by reacting a compound of a formula (XX1) (hereinafter, described as Compound (XX1)) with a reducing agent.

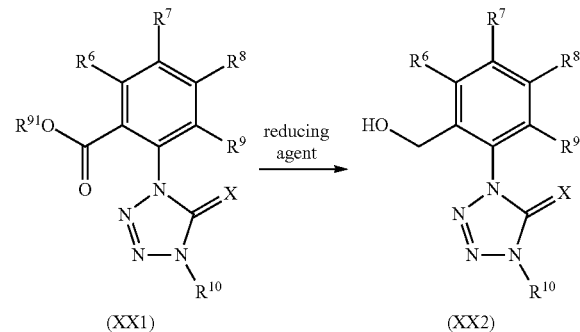

[wherein
$R^6$, $R^7$, $R^8$, $R^9$, $R^{10}$, $R^{91}$ and X are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; alcohols such as methanol, ethanol, propanol, butanol; water; and mixed solvents thereof.

Examples of the reducing agent to be used in the reaction include lithium triethylborohydride, diisobutylaluminium hydride, lithium aminoborohydride, lithium borohydride, sodium borohydride, borane, borane-dimethyl sulfide complex and borane-tetrahydrofuran complex.

In the reaction, the reducing agent is used usually within a range of 1 to 10 molar ratio(s) as opposed to 1 mole of Compound (XX1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XX2). Compound (XX2) may be further purified, for example, by distillation, chromatography and recrystallization.

(Reference Process S)

A compound of a formula (XZ2) (hereinafter, described as Compound (XZ2)) can be prepared by reacting a compound of a formula (XZ1) (hereinafter, described as Compound (XZ1)) with a reducing agent.

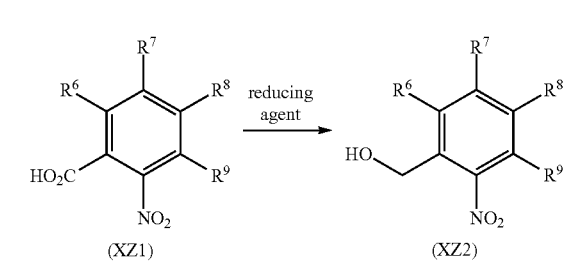

[wherein
$R^6$, $R^7$, $R^8$ and $R^9$ are the same as described above]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

Examples of the reducing agent to be used in the reaction include, borane, borane-tetrahydrofuran complex, borane-dimethyl sulfide complex. Also, borohydrides such as sodium borohydride and potassium borohydride are mixed with acids such as sulfuric acid, hydrochloric acid, methanesulfonic acid and boron trifluoride diethyl etherate complex to develop a borane, which also can be used.

In the reaction, the reducing agent is used usually within a range of 1 to 10 molar ratio(s) as opposed as 1 mole of Compound (XZ1).

The reaction temperature is usually within a range of −20 to 100° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (XZ2). Compound (XZ2) may be further purified, for example, by distillation, chromatography and recrystallization.

(Reference Process T)

Compound (B1) can be prepared by reacting Compound (A1) with a compound of a formula (P1) (hereinafter, described as Compound (P1)) in the presence of a base.

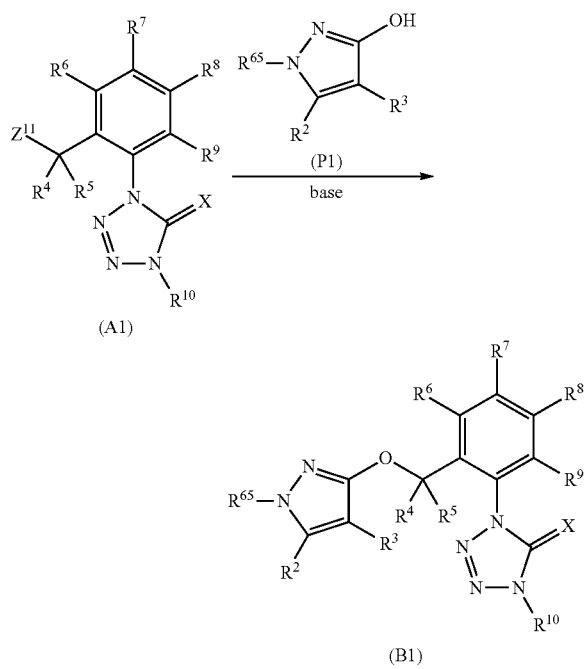

[wherein
$R^2, R^3, R^4, R^5, R^6, R^7, R^8, R^9, R^{10}, R^{65}$, X and $Z^{11}$ are the same as described above]

The reaction can be carried out according to the above-mentioned Process A.

(Reference Process U)

Compound (A2) can be prepared by reacting a compound of a formula (XQ1) (hereinafter, described as Compound (XQ1)) with a compound of a formula (XQ2) (hereinafter, described as Compound (XQ2)) to form a compound of a formula (XQ3) (hereinafter, described as Compound (XQ3)), followed by reacting Compound (XQ3) with an acid.

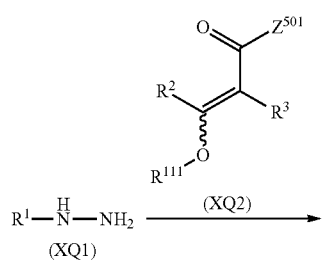

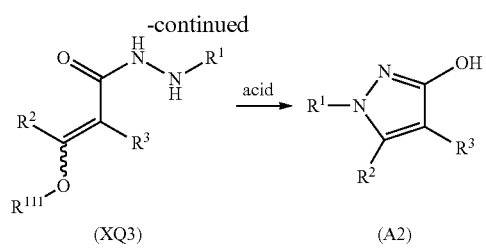

[wherein
$R^1, R^2, R^3$ and $R^{111}$ are the same as defined above; $Z^{501}$ represents a leaving group such as a chlorine atom, a bromine atom, an iodine atom, a N-succinimidyloxy group, an 1H-imidazole-1-yl group, and a 1-benzotriazoleoxy group; and a wavy line represents a cis form, a trans form or a mixture of the cis and the trans forms]

Hereinafter, a process for preparing Compound (XQ3) from Compound (XQ1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; and mixed solvents thereof.

Compound (XQ1) to be used in the reaction can be usually used as a commercially available product, or may be prepared according to a well-known method. Compound (XQ1) may be salt forms thereof with hydrochloric acid, sulfuric acid, formic acid, toluenesulfonic acid such as p-toluenesulfonic acid, methanesulfonic acid and the others. Further, Compound (XQ1) can be used in either cis form or a trans form as a geometric isomer on a double bond, or in a mixture of the trans and the cis forms.

Examples of Compound (XQ2) includes an alkoxyacrylyl halide such as 3-methoxyacrylyl chloride and 3-ethoxyacrylyl chloride; an alkoxyacrylyl N-succinimidyl such as 3-methoxyacrylyl N-succinimidyl and 3-ethoxyacrylyl N-succinimidyl. The alkoxyacrylyl halide is usually used as a commercially available product, or may be prepared according to a well-known method. The alkoxyacrylyl N-succinimidyl is prepared according to the below-mentioned Reference Process R or Reference Process S.

In the reaction, Compound (XQ2) is used usually within a range of 1 to 10 molar ratio(s) as opposed to 1 mole of Compound (XQ1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate may be added to the reaction, and these compound are used usually within a range of 1 to 5 molar ratio(s) as opposed to 1 mole of Compound (XQ1).

When the reaction is completed, the reaction mixtures are extracted with organic solvent(s), and the resulting organic layers are worked up (for example, drying and concentration) to isolate Compound (XQ3). Compound (XQ3) may be further purified, for example, by distillation, chromatography and recrystallization.

Hereinafter, a process for preparing Compound (A2) from Compound (XQ3) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; organic acids such as formic acid, acetic acid, trifluoroacetic acid; water; and mixed solvents thereof.

Compound (XQ3) to be used in the reaction can be used in either cis form or a trans form as a geometric isomer on a double bond, or in a mixture of the trans and the cis forms.

Examples of the acid to be used in the reaction include concentrated hydrochloric acid, concentrated sulfuric acid, trifluoroacetic acid, methanesulfonic acid, trifluoromethanesulfonic acid, toluenesulfonic acid and nitric acid.

In the reaction, the acid is used usually within a range of 0.1 to 100 molar ratio(s) as opposed to 1 mole of Compound (XQ3).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (A2). Compound (A2) may be further purified, for example, by distillation, chromatography and recrystallization.

(Reference Process V)

The above-mentioned Compound (XQ2) wherein $Z^{501}$ represents a N-succinimidyloxy group, i.e., a compound of a formula (XR2) (hereinafter, described as Compound (XR2)) can be prepared by reacting the above-mentioned Compound (XQ2) wherein $Z^{501}$ represents $Z^{111}$, i.e., a compound of a formula (XR1) (hereinafter, described as Compound (XR1)) with N-hydroxysuccinimide in the presence of a base.

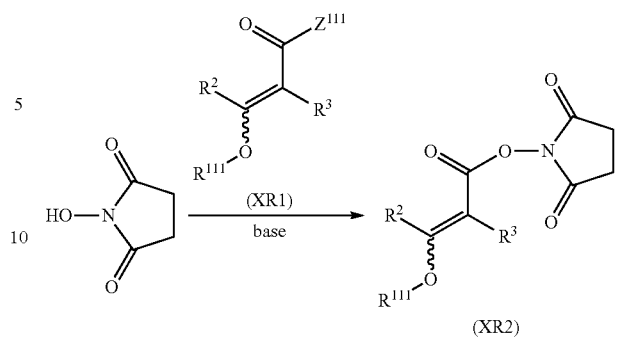

[wherein $R^2$, $R^3$, $Z^{111}$ and $R^{111}$ are the same as defined above; and a wavy line represents a cis form, a trans form or a mixture of the cis and the trans forms]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; and mixed solvents thereof.

Examples of Compound (XR1) to be used in the reaction include an alkoxyacrylyl halide such as 3-methoxyacrylyl chloride and 3-ethoxyacrylyl chloride, and Compound (XR1) can be usually used as a commercially available product, or may be prepared according to a well-known method. Also, Compound (XR1) can be used in either cis form or a trans form as a geometric isomer on a double bond, or in a mixture of the trans and the cis forms.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; and alkali metal bicarbonates such as lithium bicarbonate, sodium bicarbonate, potassium bicarbonate, cesium bicarbonate.

In the reaction, Compound (XR1) is used usually within a range of 1 to 10 molar ratio(s), and the base is used usually within a range of 1 to 10 molar ratio(s), as opposed to 1 mole of N-hydroxysuccinimide.

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XR2). Compound (XR2) may be further purified, for example, by distillation, chromatography and recrystallization.

(Reference Process W)

The above-mentioned Compound (XR2) can be prepared by reacting a compound of a formula (XS1) (hereinafter, described as Compound (XS1)) with N-hydroxysuccinimide in the presence of a condensation agent.

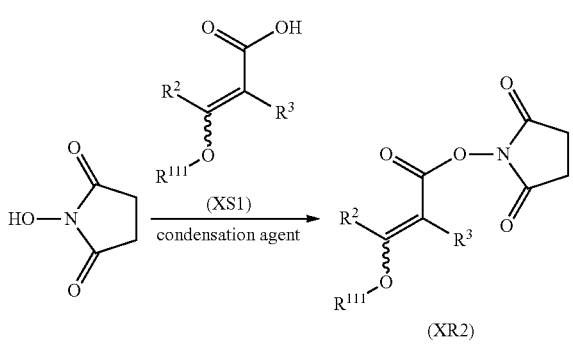

[wherein

R², R³ and R¹¹¹ are the same as defined above; and a wavy line represents a cis form, a trans form or a mixture of the cis and the trans forms]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; and mixed solvents thereof.

Examples of Compound (XS1) to be used in the reaction include an alkoxyacrylic acid such as 3-methoxyacrylic acid and 3-ethoxyacrylic acid, and Compound (XS1) can be usually used as a commercially available product, or may be prepared according to a well-known method. Also, Compound (XQ1) may be salt forms thereof with an alkali metal such as sodium, potassium and lithium or an organic base such as triethylamine and pyridine. Further, Compound (XS1) can be used in either cis form or a trans form as a geometric isomer on a double bond, or in a mixture of the trans and the cis forms.

Examples of the condensation agent to be used in the reaction include N,N'-dicyclohexylcarbodiimide (DCC), N,N'-diisopropylcarbodiimide (DIC), 1-ethyl-3-(3-dimethylpropyl)carbodiimide (EDC), 1-ethyl-3-(3-dimethylaminopropyl)carbodiimide hydrochloride salt (EDC.HCl), 1H-benzotriazole-1-yloxytris(dimethylamino)phosphonium hexafluorophosphate (BOP), 1H-benzotriazole-1-yloxytripyrrolizinophosphonium hexafluorophosphate (PyBOP), O-(benzotriazole-1-yl)-N,N,N',N'-tetramethyluronium hexafluorophosphate (HBTU), O-(benzotriazole-1-yl)-N,N,N',N'-tetramethyluronium tetrafluoroborate (TBTU), O-(7-azabenzotriazole-1-yl)-N,N,N',N'-tetramethyluronium hexafluorophosphate (HATU), O-(7-azabenzotriazole-1-yl)-N,N,N',N'-tetramethyluronium hexafluorophosphate (TATU), and 1,1'-carbonylbis-1H-imidazole (CDI).

In the reaction, Compound (XS1) is used usually within a range of 0.1 to 10 molar ratio(s), and the condensation agent is used usually within a range of 1 to 10 molar ratio(s), as opposed to 1 mole of N-hydroxysuccinimide.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate may be added to the reaction, and these compound are used usually within a range of 1 to 5 molar ratio(s) as opposed to 1 mole of N-hydroxysuccinimide.

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XR2). Compound (XR2) may be further purified, for example, by distillation, chromatography and recrystallization.

(Reference Process X)

The above-mentioned Compound (A2) wherein R³ represents a hydrogen atom, i.e., a compound of a formula (XT2) (hereinafter, described as Compound (XT2)) can be prepared by reacting the above-mentioned Compound (XQ1) with a compound of a formula (XT1) (hereinafter, described as Compound (XT1)).

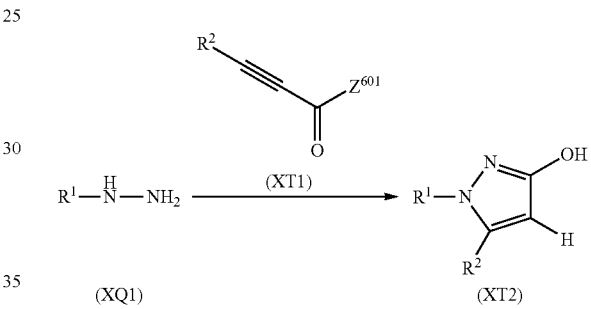

[wherein

R¹ and R² are the same as defined above; and $Z^{601}$ represents a leaving group such as a chlorine atom, a bromine atom, an iodine atom, a N-succinimidyloxy group, an 1H-imidazole-1-yl group, and a 1-benzotriazoleoxy group or an C1-C12 alkoxy group or an optionally substituted phenyloxy group]

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; organic acids such as formic acid, acetic acid, trifluoroacetic acid; water; and mixed solvents thereof.

Examples of Compound (XT1) include methyl propiolate and ethyl propiolate.

In the reaction, Compound (XT1) is used usually within a range of 1 to 10 molar ratio(s) as opposed to 1 mole of Compound (XQ1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate may be added to the reaction, and these compound are used usually within a range of 1 to 5 molar ratio(s) as opposed to 1 mole of Compound (XQ1).

When the reaction is completed, the reaction mixtures are extracted with organic solvent(s), and the resulting organic layers are worked up (for example, drying and concentration) to isolate Compound (XT2). Compound (XT2) may be further purified, for example, by distillation, chromatography and recrystallization.

(Reference Process Y)

The above-mentioned Compound (A2) can be prepared by reacting the above-mentioned Compound (XQ1) with the below-mentioned compound of a formula (XU1) (hereinafter, described as Compound (XU1)) to form a compound of the below-mentioned formula (XU2) (hereinafter, described as Compound (XU2)), followed by treating the resulting Compound (XU2) with an oxidizing agent.

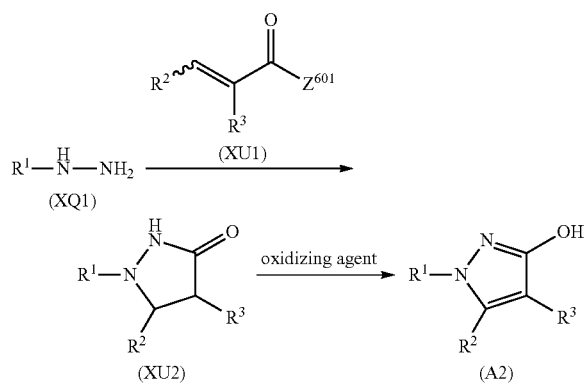

[wherein $R^1$, $R^2$, $R^3$ and $Z^{601}$ are the same as defined above; and a wavy line represents a cis form, a trans form or a mixture of the cis and the trans forms]

Hereinafter, a process for preparing Compound (XU2) from Compound (XQ1) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

Examples of Compound (XU1) to be used in the reaction include methyl acrylate, ethyl methyl, propyl acrylate, isopropyl acrylate, methyl 2-methylacrylate, ethyl 2-methylacrylate, isopropyl 2-methylacrylate, methyl 3-methylacrylate, ethyl 3-methylacrylate, propyl 3-methylacrylate, isopropyl 3-methylacrylate, methyl 2,3-dimethylacrylate. Also, Compound (XU1) can be used in either cis form or a trans form as a geometric isomer on a double bond, or in a mixture of the trans and the cis forms.

In the reaction, Compound (XU1) is used usually within a range of 1 to 10 molar ratio(s), as opposed to 1 mole of Compound (XQ1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate, alkali metal hydroxides such as sodium hydroxide, potassium hydroxide, cesium hydroxide; alkali metal hydrides such as lithium hydride, sodium hydride, potassium hydride, and alkali metal alkoxides such as sodium methoxide, potassium methoxide, sodium tert-butoxide, potassium tert-butoxide may be added to the reaction, and these compound are used usually within a range of 1 to 5 molar ratio(s) as opposed to 1 mole of Compound (XQ1).

When the reaction is completed, the reaction mixtures are extracted with organic solvent(s), and the resulting organic layers are worked up (for example, drying and concentration) to isolate Compound (XU2). Compound (XU2) may be further purified, for example, by distillation, chromatography and recrystallization.

Hereinafter, a process for preparing Compound (A2) from Compound (XU2) is explained.

This reaction is usually carried out in a solvent.

Examples of the solvent that can be used in the reaction include hydrocarbons such as n-heptane, n-hexane, cyclohexane, n-pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

Examples of the oxidizing agent include oxygen gas, ferrous chloride, copper(I) chloride, potassium hexacyanoferrate(II), m-chloroperoxybenzoic acid, iodine and mixtures thereof.

In the reaction, the oxidizing agent is used usually within a range of 0.01 to 10 molar ratio(s), as opposed to 1 mole of Compound (XU2).

To promote the reaction, an acid or a base may be added as needed. Examples of the base include alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate, alkali metal hydroxides such as sodium hydroxide, potassium hydroxide, cesium hydroxide, alkali metal alkoxides such as sodium methoxide, sodium ethoxide, sodium tert-butoxide, potassium tert-butoxide. Examples of the acid include hydrochloric acid and sulfuric acid. These compound are used usually within a range of 1 to 5 molar ratio(s) as opposed to 1 mole of Compound (XU2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (A2). Compound (A2) may be further purified, for example, by distillation, chromatography and recrystallization.

Although a form used for the present compound may be the present compound as itself, the present compound is usually prepared by mixing the present compound with solid carriers, liquid carriers, gas carriers, surfactants and the others, and if necessary, adding stickers, dispersers and stabilizers, to formulate into wettable powders, water dispersible granules, flowables, granules, dry flowables, emulsifiable concentrates, aqueous solutions, oil solutions, smoking agents, aerosols, microcapsules and the others, In these formulations, the present compound is contained in a range of usually 0.1 to 990, preferably 0.2 to 90% by weight.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, n-hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide (DMF) and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers, dispersers and stabilizers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for applying the present compound is not particularly limited, as far as the applying form is a form by which the present compound may be applied substantially, and includes, for example, an application to plants such as a foliage application; an application to area for cultivating plants such as a submerged treatment; and an application to soil such as seed disinfection.

The application dose varies depending on weather conditions, dosage forms, timing of application, methods of application, areas to be applied, target diseases and target crops etc., but is in the range of usually from 1 to 500 g, and preferably from 2 to 200 g per 1,000 m$^2$ of the area to be applied. The emulsifiable concentrate, the wettable powder or the suspension concentrate, etc., is usually applied by diluting it with water. In this case, the concentration of the present compound after dilution is in the range of usually 0.0005 to 2% by weight, and preferably 0.005 to 1% by weight. The dust formulation or the granular formulation etc., is usually applied as itself without diluting it. In the application to seeds, the amount of the present compound is in the range of usually from 0.001 to 100 g, and preferably from 0.01 to 50 g per 1 kg of the seeds.

Herein, examples of the place where the pests live include paddy fields, fields, tea gardens, orchards, non-agricultural lands, houses, nursery trays, nursery boxes, nursery soils and nursery bed.

Also, in another embodiment, for example, the present compound can be administered to the inside (inside of the body) or the outside (body surface) of the below-mentioned vertebrate to exterminate systemically or unsystemically the living things or parasites which are parasitic on the vertebrate. Examples of a method of the internal medication include an oral administration, an anal administration, a transplanation, an administration via injection subcutaneously, intramuscularly or intravenously. Examples of a method of outside medication include a transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., but it is desirable in general to administer the present compound so that a dose of the active ingredient (the present compound or salts thereof) is in the range of generally from 0.1 mg to 2,000 mg and preferably 0.5 mg to 1,000 mg per 1 kg of body weight of the animal.

The present compound can be used as agent for controlling plant disease in agricultural lands such as fields, paddy fields, lawns, orchards. The compound of the present invention can control diseases occurred in the agricultural lands or the others for cultivating the following "plant".

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip),
chenopodiaceous vegetables (for example, spinach and Swiss chard),
lamiaceous vegetables (for example, *Perilla frutescens*, mint and basil),
strawberry, sweet potato, *Dioscorea japonica, colocasia* and the others;

Flowers:

Ornamental foliage plants:

Fruits:

pomaceous fruits (for example, apple, pear, Japanese pear, Chinese quince and quince), stone fruits (for example, peach, plum, nectarine, *Prunus mume*, cherry fruit, apricot and prune), citrus fruits (for example, *Citrus unshiu*, orange, lemon, lime and grapefruit), nuts (for example, chestnut, walnuts, hazelnuts, almond, pistachio, cashew nuts and *macadamia* nuts), berry fruits (for example, blueberry, cranberry, blackberry and raspberry), grape, kaki persimmon, olive, Japanese plum, banana, coffee, date palm, coconuts, and the others;

Trees other than fruit trees:

tea, mulberry, flowering plant, roadside trees (for example, ash, birch, dogwood, Eucalyptus, *Ginkgo biloba*, lilac, maple, *Quercus*, poplar, Judas tree, *Liquidambar formosana*, plane tree, zelkova, Japanese arborvitae, fir wood, hemlock, juniper, *Pinus*, *Picea*, and *Taxus cuspidate*);

and the others.

The above-mentioned "plant" includes genetically modified crops.

The pests on which the present compound has a control efficacy include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take all disease (*Gaeumannomyces graminis*);

Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and *phaeosphaeria* leaf spot (*Phaeosphaeria maydis*);

Cotton diseases: anthracnose (*Colletotrichum gossypii*), grey mildew (*Ramuraria areola*), alternaria leaf spot (*Alternaria macrospora, A. gossypii*);

Coffee diseases: rust (*Hemileia vastatrix*);

Rape seed diseases: sclerotinia rot (*Sclerotinia sclerotiorum*), black spot (*Alternaria brassicae*), and black leg (*Phoma lingam*);

Citrus diseases: melanose (*Diaporthe citri*), scab (*Elsinoe fawcetti*), and fruit rot (*Penicillium digitatum, P. italicum*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Colletotrichum acutatum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), septoria brown spot (*Septoria glycines*), and frog eye leaf spot (*Cercospora sojina*);

Kindney bean diseases: anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), and verticillium wilt (*verticillium albo-atrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*) and aphanomyces root rot (*Aphanomyces sochlioides*);

Rose diseases: black spot (*Diplocarpon rosae*) and powdery mildew (*Sphaerotheca pannosa*);

Diseases of Chrysanthemum: leaf blight (*Septoria chrysanthemi-indici*) and white rust (*Puccinia horiana*);

Onion diseases: botrytis leaf blight (*Botrytis cinerea, B. byssoidea, B. squamosa*), gray-mold neck rot (*Botrytis slli*), and small sclerotial rot (*Botrytis squamosa*);

Various crops diseases: gray mold (*Botrytis cinerea*), and sclerotinia rot (*Sclerotinia sclerotiorum*);

Diseases of Japanese radish: alternaria leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*).

Hemiptera:
Delphacidae (for example, *Laodelphax striatellus, Nilaparvata lugens,* or *Sogatella furcifera*);
Deltocephalidae (for example, *Nephotettix cincticeps,* or *Nephotettix virescens*);
Aphididae (for example, *Aphis gossypii, Myzus persicae, Brevicoryne brassicae, Macrosiphum euphorbiae, Aulacorthum solani, Rhopalosiphum padi, Toxoptera citricidus*);
Pentatomidae (for example, *Nezara antennata, Riptortus clavetus, Leptocorisa chinensis, Eysarcoris parvus, Halyomorpha mista,* or *Lygus lineolaris*);
Aleyrodidae (for example, *Trialeurodes vaporariorum,* or *Bemisia argentifolii*);
Coccoidea (for example, *Aonidiella aurantii, Comstockaspis perniciosa, Unaspis citri, Ceroplastes rubens,* or *Icerya purchasi*);
Tingidae;
Psyllidae;
Bed bugs (*Cimex lectularius*) and the others;
Lepidoptera:
Pyralidae (for example, *Chilo suppressalis, Tryporyza incertulas, Cnaphalocrocis medinalis, Notarcha derogata, Plodia interpunctella, Ostrinia furnacalis, Hellula undalis, Pediasia teterrellus*);
Noctuidae (for example, *Spodoptera litura, Spodoptera exigua, Pseudaletia separata, Mamestra brassicae, Agrotis ipsilon, Plusia nigrisigna, Trichoplusia* spp., *Heliothis* spp., or *Helicoverpa* spp.;
Pieridae (for example, *Pieris rapae*);
Tortricidae (for example, *Adoxophyes* spp., *Grapholita molesta, Cydia pomonella, Leguminivora glycinivorella, Matsumuraeses azukivora, Adophyes orana fasciata, Adoxophyes* sp., *Homona magnanima, Archips fuscocupreanus, Cydia pomonella*);
Gracillariidae (for example, *Caloptilia theivora, Phyllonorycter ringoneella*);
Carposimidae (for example, *Carposina niponensis*);
Lyonetiidae (for example, *Lyonetia* spp.);
Lymantriidae (for example, *Lymantria* spp., or *Euproctis* spp.);
Yponomeutidae (for example, *Plutella xylostella*);
Gelechiidae (for example, *Pectinophora gossypiella* or *Phthorimaea operculella*);
Arctiidae (for example, *Hyphantria cunea*);
Tineidae (for example, *Tinea translucens,* or *Tineola bisselliella*); and the others;
Thysanoptera;
Thysanoptera (for example, *Frankliniella occidentalis, Thrips palmi, Scirtothrips dorsalis, Thrips tabaci, Frankliniella intonsa, Frankliniella fusca*);

Diptera:
*Musca domestica, Culex popiens pallens, Tabanus trigonus, Hylemya antiqua, Hylemya platura, Anopheles sinensis, Agromyza oryzae, Hydrellia griseola, Chlorops oryzae, Dacus cucurbitae, Ceratitis capitata, Liriomyza trifolii,* and the others;
Coleoptera:
*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*), and the others;
Orthoptera:
*Locusta migratoria, Gryllotalpa africana, Oxya yezoensis, Oxya japanica,* and the others;
Hymenoptera:
*Athalia rosae, Acromyrmex* spp., *Solenopsis* spp., and the others;
Nematodes:
*Aphelenchoides besseyi, Nothotylenchus acris, Heterodera glycines, Meloidogyne incognita, Pratylenchus, Nacobbus aberrans,* and the others;
Blattariae:
*Blattella germanica, Periplaneta fuliginosa, Periplaneta americana, Periplaneta brunnea, Blatta orientalis,* and the others;
Acarina:
Tetranychidae (for example, *Tetranychus urticae, Panonychus citri,* or *Oligonychus* spp.);
Eriophyidae (for example, *Aculops pelekassi*);
Tarsonemidae (for example, *Polyphagotarsonemus latus*);
Tenuipalpidae;
Tuckerellidae;
Acaridae (for example, *Tyrophagus putrescentiae*);
Pyroglyphidae (for example, *Dermatophagoides farinae,* or *Dermatophagoides ptrenyssnus*);
Cheyletidae (for example, *Cheyletus eruditus, Cheyletus malaccensis,* or *Cheyletus moorei*);
Dermanyssidae;
and the others.

Also the formulation comprising the present compound or salts thereof can be used in the field relating to a treatment of livestock diseases or livestock industry, and for example, can exterminate the living things or parasites which are parasitic on the inside and/or the outside of a vertebrate such as human being, cow, sheep, pig, poultry, dog, cat and fish, so as to maintain public health. Examples of the pests include *Isodes* spp. (for example, *Isodes scapularis*), *Boophilus* spp. (for example, *Boophilus microplus*), *Amblyomma* spp., *Hyalomma* spp., *Rhipicephalus* spp. (for example, *Rhipicephalus sanguineus*), *Haemaphysalis* spp. (for example, *Haemaphysalis longicornis*), *dermacentor* spp., *Ornithodoros* spp. (for example, *Ornithodoros moubata*), *Dermahyssus gallinae, Ornithonyssus sylviarum, Sarcoptes* spp. (for example, *Sarcoptes scabiei*), *Psoroptes* spp., *Chorioptes* spp., *Demodex* spp., *Eutrombicula* spp., *Ades* spp. (for example, *Aedes albopictus*), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., Phthiraptera (for example, *Damalinia* spp.), *Linognathus* spp., *Haematopinus* spp., *Ctenocephalides* spp. (for example, *Ctenocephalides felis*) *Xenosylla* spp., *monomorium pharaonis* and nematodes [for example, hairworm (for example, *Nippostrongylus brasiliensis, Trichostrongylus axei, Trichostrongylus colubriformis*),

*Trichinella* spp. (for example, *Trichinella spiriralis*), *Haemonchus contortus*, *Nematodirus* spp. (for example, *Nematodirus battus*), *Ostertagia circumcincta*, *Cooperia* spp., *Hymenolepis nana*, and the others.

EXAMPLES

The following Examples including Preparation examples, Formulation examples and Test examples, serve to illustrate the present invention in more detail, which should not intend to limit the present invention.

The Preparation examples are shown below. ¹H NMR means a proton nuclear magnetic resonance, spectrum and Tetramethyl silane is used as an internal standard and chemical shift (δ) is expressed in ppm.

Preparation Example 1

A mixture of 1-(2-bromomethyl-3-fluorophenyl)-4-methyl-1,4-dihydrotetrazole-5-one (described in Synthesis example 3) 1.15 g, 1-(4-chlorophenyl)-1H-pyrazole-3-ol (described in Reference Preparation example 24) 0.78 g, potassium carbonate 0.66 g and acetonitrile 30 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-fluorophenyl)-4-methyl-1,4-dihydrotetrazole-5-one (hereinafter, referred to as "Present compound 1") 0.54 g.

Present compound 1

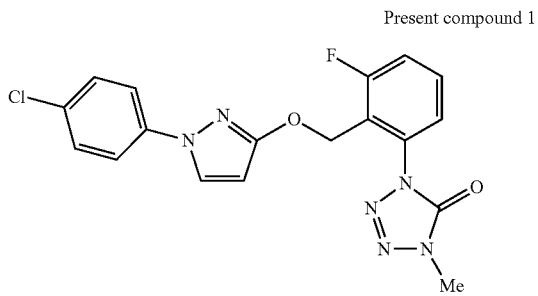

¹H-NMR (CDCl₃) δ (ppm): 7.63 (1H, d, J=2.7 Hz), 7.52-7.46 (3H, m), 7.38-7.35 (2H, m), 7.31-7.28 (2H, m), 5.79 (1H, d, J=2.7 Hz), 5.48 (2H, s), 3.62 (3H, s).

Preparation Example 2

A mixture of 1-(2-bromomethyl-3-chlorophenyl)-4-methyl-1,4-dihydrotetrazole-5-one (described in Synthesis example 6) 0.30 g, 1-(4-fluorophenyl)-1H-pyrazole-3-ol (described in Reference Preparation example 29) 0.19 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-chlorophenyl)-4-methyl-1,4-dihydrotetrazole-5-one (hereinafter, referred to as "Present compound 2") 0.18 g.

Present compound 2

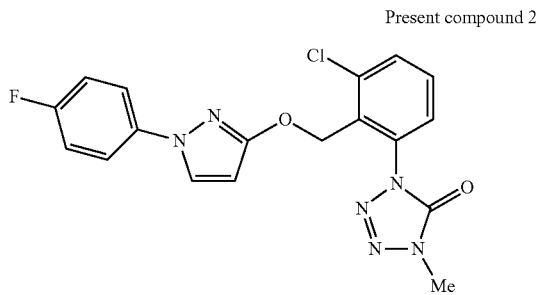 [SMILES: Cn1nnn(-c2cccc(Cl)c2COc2ccn(-c3ccc(F)cc3)n2)c1=O]

¹H-NMR (CDCl₃) δ (ppm): 7.62-7.59 (2H, m), 7.55-7.50 (2H, m), 7.45 (1H, t, J=8.1 Hz), 7.37 (1H, dd, J=8.1, 1.2 Hz), 7.13-7.07 (2H, m), 5.78 (1H, d, J=2.7 Hz), 5.53 (2H, s), 3.60 (3H, s).

Preparation Example 3

A mixture of 1-(2-bromomethyl-3-chlorophenyl)-4-methyl-1,4-dihydrotetrazole-5-one (described in Synthesis example 6) 1.21 g, 1-(4-chlorophenyl)-1H-pyrazole-3-ol (described in Reference Preparation example 24) 0.78 g, potassium carbonate 0.66 g and acetonitrile 30 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-chlorophenyl)-4-methyl-1,4-dihydrotetrazole-5-one (hereinafter, referred to as "Present compound 3") 0.61 g.

Present compound 3

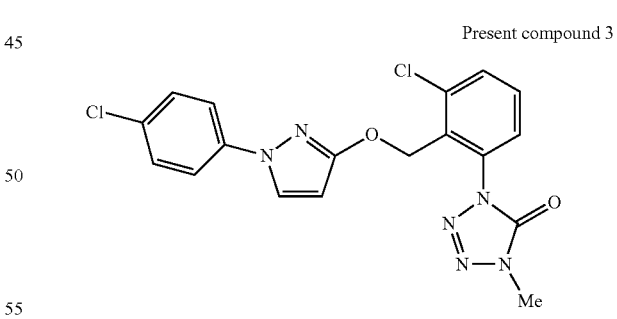

¹H-NMR (CDCl₃) δ (ppm): 7.64 (1H, d, J=2.7 Hz), 7.62-7.60 (1H, m), 7.53-7.49 (2H, m), 7.45 (1H, t, J=8.0 Hz), 7.39-7.35 (3H, m), 5.80 (1H, d, J=2.7 Hz), 5.54 (2H, s), 3.61 (3H, s).

Preparation Example 4

A mixture of 1-(2-bromomethyl-3-chlorophenyl)-4-methyl-1,4-dihydrotetrazole-5-one (described in Synthesis example 6) 0.30 g, 1-(4-methylphenyl)-1H-pyrazole-3-ol (described in Reference Preparation example 27) 0.18 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylphenyl)-1H-pyrazole-3-yl]oxymethyl}-3-chlorophenyl)-4-methyl-1,4-dihydrotetrazole-5-one (hereinafter, referred to as "Present compound 4") 0.06 g.

Present compound 4

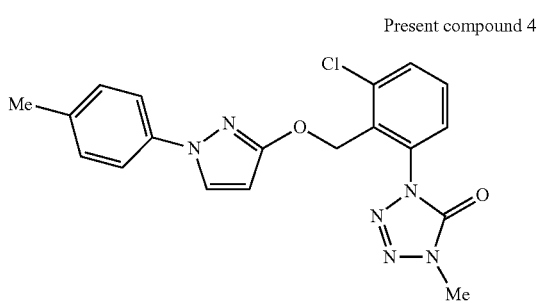

$^1$H-NMR (CDCl$_3$) δ (ppm): 7.63 (1H, d, J=2.7 Hz), 7.60 (1H, dd, J=8.0, 1.2 Hz), 7.46-7.42 (3H, m), 7.36 (1H, dd, J=8.0, 1.2 Hz), 7.20 (2H, d, J=8.5 Hz), 5.76 (1H, d, J=2.7 Hz), 5.54 (2H, s), 3.57 (3H, s), 2.36 (3H, s).

Preparation Example 5

A mixture of 1-(2-bromomethyl-3-chlorophenyl)-4-methyl-1,4-dihydrotetrazole-5-one (described in Synthesis example 6) 0.30 g, 1-(4-methoxyphenyl)-1H-pyrazole-3-ol (described in Reference Preparation example 26) 0.20 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-chlorophenyl)-4-methyl-1,4-dihydrotetrazole-5-one (hereinafter, referred to as "Present compound 5") 0.18 g.

Present compound 5

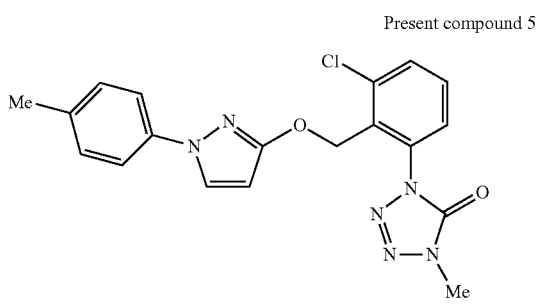 [SMILES: Cc1ccc(-n2ccc(OCc3c(Cl)cccc3-n3nnn(C)c3=O)n2)cc1]

$^1$H-NMR (CDCl$_3$) δ (ppm): 7.60 (1H, d, J=8.0 Hz), 7.56 (1H, d, J=2.4 Hz), 7.49-7.42 (3H, m), 7.36 (1H, d, J=8.0 Hz), 6.94 (2H, d, J=8.9 Hz), 5.75 (1H, d, J=2.4 Hz), 5.54 (2H, s), 3.83 (3H, s), 3.57 (3H, s).

Preparation Example 6

A mixture of 1-(2-bromomethyl-3-bromophenyl)-4-methyl-1,4-dihydrotetrazole-5-one (described in Synthesis example 11) 0.30 g, 1-(4-fluorophenyl)-1H-pyrazole-3-ol (described in Reference Preparation example 29) 0.16 g, potassium carbonate 0.14 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-bromophenyl)-4-methyl-1,4-dihydrotetrazole-5-one (hereinafter, referred to as "Present compound 6") 0.28 g.

Present compound 6

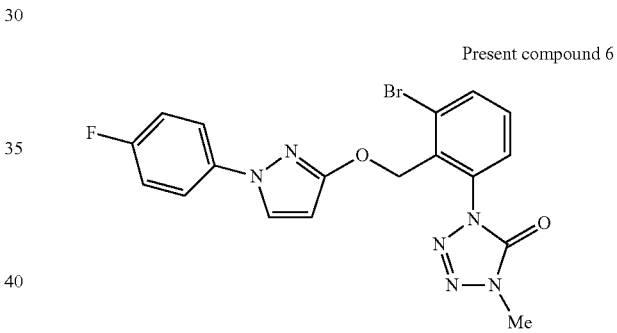

$^1$H-NMR (CDCl$_3$) δ (ppm): 7.80 (1H, dd, J=7.6, 1.6 Hz), 7.61 (1H, d, J=2.4 Hz), 7.56-7.51 (2H, m), 7.42-7.35 (2H, m), 7.14-7.07 (2H, m), 5.79 (1H, d, J=2.4 Hz), 5.53 (2H, s), 3.59 (3H, s).

Preparation Example 7

A mixture of 1-(2-bromomethyl-3-bromophenyl)-4-methyl-1,4-dihydrotetrazole-5-one (described in Synthesis example 11) 18.5 g, 1-(4-chlorophenyl)-1H-pyrazole-3-ol (described in Reference Preparation example 24) 10.4 g, potassium carbonate 8.8 g and acetonitrile 400 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-bromophenyl)-4-methyl-1,4-dihydrotetrazole-5-one (hereinafter, referred to as "Present compound 7") 24.6 g.

Present compound 7

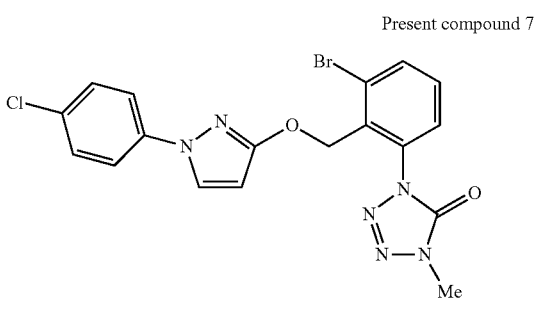 [SMILES: Cn1nnn(-c2cccc(Br)c2COc2ccn(-c3ccc(Cl)cc3)n2)c1=O]

¹H-NMR (CDCl₃) δ (ppm): 7.81-7.79 (1H, m), 7.65 (1H, d, J=2.4 Hz), 7.54-7.50 (2H, m), 7.42-7.35 (4H, m), 5.81 (1H, d, J=2.4 Hz), 5.53 (2H, s), 3.60 (3H, s).

Preparation Example 8

A mixture of 1-(2-bromomethyl-3-bromophenyl)-4-methyl-1,4-dihydrotetrazole-5-one (described in Synthesis example 11) 0.30 g, 1-(4-methoxyphenyl)-1H-pyrazole-3-ol (described in Reference Preparation example 26) 0.17 g, potassium carbonate 0.14 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-bromophenyl)-4-methyl-1,4-dihydrotetrazole-5-one (hereinafter, referred to as "Present compound 8") 0.22 g.

Present compound 8

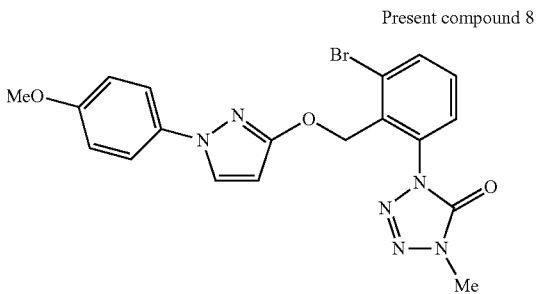 [SMILES: COc1ccc(-n2ccc(OCc3c(C)cccc3-n3nnn(C)c3=O)n2)cc1]

¹H-NMR (CDCl₃) δ (ppm): 7.80-7.78 (1H, m), 7.57 (1H, d, J=2.4 Hz), 7.50-7.46 (2H, m), 7.41-7.34 (2H, m), 6.96-6.92 (2H, m), 5.76 (1H, d, J=2.4 Hz), 5.53 (2H, s), 3.83 (3H, s), 3.57 (3H, s).

Preparation Example 9

A mixture of 1-(2-bromomethyl-3-iodophenyl)-4-methyl-1,4-dihydrotetrazole-5-one (described in Synthesis example 14) 3.11 g, 1-(4-chlorophenyl)-1H-pyrazole-3-ol (described in Reference Preparation example 24) 1.53 g, potassium carbonate 1.30 g and acetonitrile 60 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-iodophenyl)-4-methyl-1,4-dihydrotetrazole-5-one (hereinafter, referred to as "Present compound 9") 2.13 g.

Present compound 9

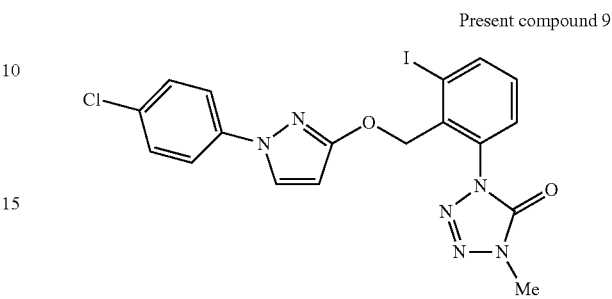

¹H-NMR (DMSO-d₆) δ (ppm): 8.35 (1H, d, J=2.7 Hz), 8.18 (1H, d, J=8.0 Hz), 7.76-7.72 (2H, m), 7.58 (1H, d, J=8.0 Hz), 7.53-7.51 (2H, m), 7.39-7.35 (1H, m), 5.97 (1H, d, J=2.7 Hz), 5.32 (2H, s), 3.54 (3H, s).

Preparation Example 10

A mixture of 1-(2-bromomethyl-3-methylphenyl)-4-methyl-1,4-dihydrotetrazole-5-one (described in Synthesis example 33) 0.40 g, 1-phenyl-1H-pyrazole-3-ol (described in Reference Preparation example 25) 0.24 g, potassium carbonate 0.25 g and acetonitrile 10 mL was stirred with heating under reflux for two and a half hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-phenyl-1H-pyrazole-3-yl]oxymethyl}-3-methylphenyl)-4-methyl-1,4-dihydrotetrazole-5-one (hereinafter, referred to as "Present compound 10") 0.31 g.

Present compound 10

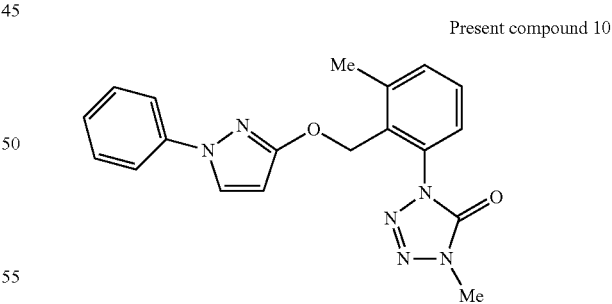

¹H-NMR (CDCl₃) δ (ppm): 7.68 (1H, d, J=2.7 Hz), 7.58-7.56 (2H, m), 7.44-7.38 (4H, m), 7.29-7.23 (1H, m), 7.18-7.23 (1H, m), 5.81 (1H, d, J=2.7 Hz), 5.35 (2H, s), 3.61 (3H, s), 2.57 (3H, s).

Preparation Example 11

A mixture of 1-(2-bromomethyl-3-methylphenyl)-4-methyl-1,4-dihydrotetrazole-5-one (described in Synthesis example 33) 0.30 g, 1-(4-fluorophenyl)-1H-pyrazole-3-ol (described in Reference Preparation example 29) 0.20 g, potassium carbonate 0.19 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-methylphenyl)-4-methyl-1,4-dihydrotetrazole-5-one (hereinafter, referred to as "Present compound 11") 0.34 g.

Present compound 11

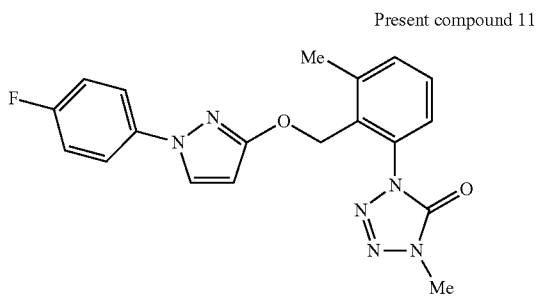

$^1$H-NMR (CDCl$_3$) δ (ppm): 7.61 (1H, d, J=2.7 Hz), 7.55-7.49 (2H, m), 7.40-7.38 (2H, m), 7.27-7.24 (1H, m), 7.14-7.07 (2H, m), 5.80 (1H, d, J=2.7 Hz), 5.32 (2H, s), 3.62 (3H, s), 2.56 (3H, s).

Preparation Example 12

A mixture of Present compound 70.92 g, methylboronic acid 0.18 g, tripotassium phosphate 1.27 g, water 0.11 mL, [1,1'-bis(diphenylphosphino)ferrocene]palladium(II) dichloride dichloromethane adduct 0.16 g and dioxane 7 mL was stirred with heating under reflux for one and a half hours. To the reaction solutions after cooling was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-methylphenyl)-4-methyl-1,4-dihydrotetrazole-5-one (hereinafter, referred to as "Present compound 12") 0.27 g.

Present compound 12

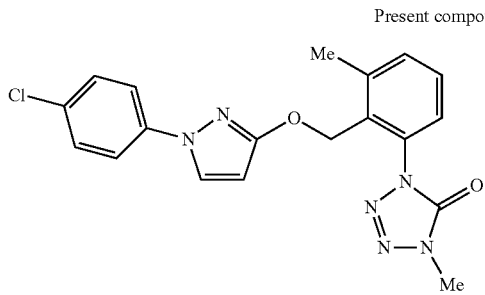

$^1$H-NMR (CDCl$_3$) δ (ppm): 7.64 (1H, d, J=2.7 Hz), 7.52-7.49 (2H, m), 7.42-7.35 (4H, m), 7.27-7.24 (1H, m), 5.82 (1H, d, J=2.7 Hz), 5.33 (2H, s), 3.63 (3H, s), 2.56 (3H, s).

Preparation Example 13

A mixture of 1-(2-bromomethyl-3-methylphenyl)-4-methyl-1,4-dihydrotetrazole-5-one (described in Synthesis example 33) 0.30 g, 1-(4-methylphenyl)-1H-pyrazole-3-ol (described in Reference Preparation example 27) 0.19 g, potassium carbonate 0.19 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylphenyl)-1H-pyrazole-3-yl]oxymethyl}-3-methylphenyl)-4-methyl-1,4-dihydrotetrazole-5-one (hereinafter, referred to as "Present compound 13") 0.33 g.

Present compound 13

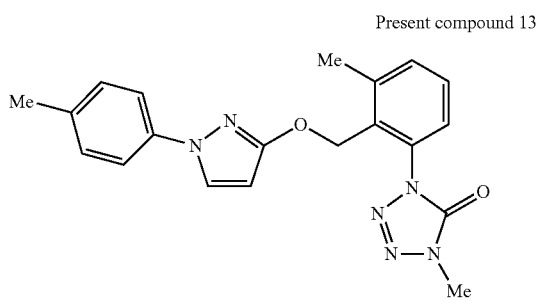

$^1$H-NMR (CDCl$_3$) δ (ppm): 7.63 (1H, d, J=2.6 Hz), 7.44 (2H, d, J=8.3 Hz), 7.39-7.38 (2H, m), 7.27-7.23 (1H, m), 7.20 (2H, d, J=8.3 Hz), 5.78 (1H, d, J=2.6 Hz), 5.33 (2H, s), 3.61 (3H, s), 2.56 (3H, s), 2.36 (3H, s).

Preparation Example 14

A mixture of 1-(2-bromomethyl-3-methylphenyl)-4-methyl-1,4-dihydrotetrazole-5-one (described in Synthesis example 33) 0.30 g, 1-(4-methoxyphenyl)-1H-pyrazole-3-ol (described in Reference Preparation example 26) 0.21 g, potassium carbonate 0.19 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-methylphenyl)-4-methyl-1,4-dihydrotetrazole-5-one (hereinafter, referred to as "Present compound 14") 0.28 g.

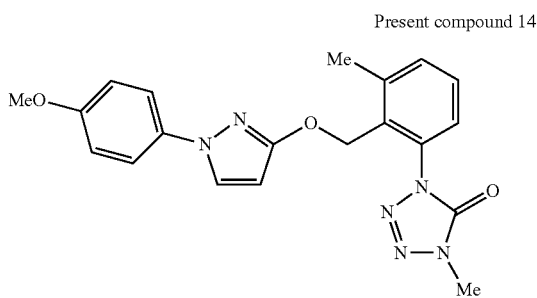

Present compound 14

¹H-NMR (CDCl₃) δ (ppm): 7.57 (1H, d, J=2.7 Hz), 7.49-7.44 (2H, m), 7.39-7.36 (2H, m), 7.27-7.23 (1H, m), 6.96-6.91 (2H, m), 5.77 (1H, d, J=2.7 Hz), 5.32 (2H, s), 3.83 (3H, s), 3.61 (3H, s), 2.56 (3H, s).

Preparation Example 15

A mixture of 1-(2-bromomethyl-3-methylphenyl)-4-methyl-1,4-dihydrotetrazole-5-one (described in Synthesis example 33) 0.40 g, 1-(1,1-dimethylethyl)-1H-pyrazole-3-ol (described in Reference Preparation example 32) 0.25 g, potassium carbonate 0.30 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(1,1-dimethylethyl)-1H-pyrazole-3-yl]oxymethyl}-3-methylphenyl)-4-methyl-1,4-dihydrotetrazole-5-one (hereinafter, referred to as "Present compound 15") 0.50 g.

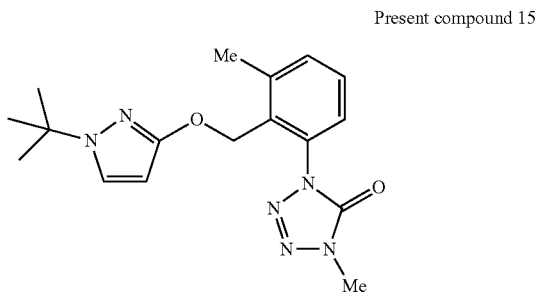 [SMILES: Cc1cccc(-n2nnn(C)c2=O)c1COc1ccn(C(C)(C)C)n1]

Present compound 15

¹H-NMR (CDCl₃) δ (ppm): 7.38-7.33 (2H, m), 7.24-7.21 (2H, m), 5.49 (1H, d, J=2.4 Hz), 5.22 (2H, s), 3.67 (3H, s), 2.54 (3H, s), 1.47 (9H, s).

Preparation Example 16

A mixture of 1-(2-bromomethyl-3-methylphenyl)-4-methyl-1,4-dihydrotetrazole-5-one (described in Synthesis example 33) 0.30 g, 1-(4-cyanophenyl)-1H-pyrazole-3-ol (described in Reference Preparation example 28) 0.21 g, potassium carbonate 0.19 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-cyanophenyl)-1H-pyrazole-3-yl]oxymethyl}-3-methylphenyl)-4-methyl-1,4-dihydrotetrazole-5-one (hereinafter, referred to as "Present compound 16") 0.25 g.

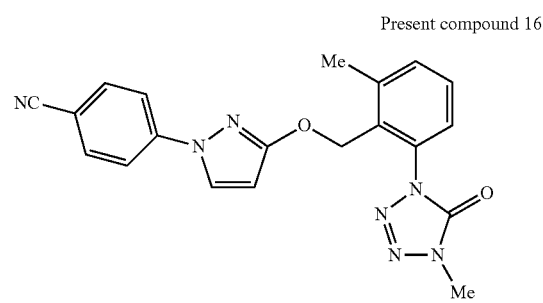 [SMILES: Cc1cccc(-n2nnn(C)c2=O)c1COc1ccn(-c2ccc(C#N)cc2)n1]

Present compound 16

¹H-NMR (CDCl₃) δ (ppm): 7.75 (1H, d, J=2.7 Hz), 7.71-7.65 (4H, m), 7.43-7.38 (2H, m), 7.27-7.25 (1H, m), 5.90 (1H, d, J=2.7 Hz), 5.34 (2H, s), 3.64 (3H, s), 2.55 (3H, s).

Preparation Example 17

A mixture of 1-(2-bromomethyl-3-methylphenyl)-4-methyl-1,4-dihydrotetrazole-5-one (described in Synthesis example 33) 1.0 g, 1-acetyl-1H-pyrazole-3-ol (described in Reference Preparation example 34) 0.47 g, potassium carbonate 0.63 g and acetonitrile 20 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-acetyl-1H-pyrazole-3-yl]oxymethyl}-3-methylphenyl)-4-methyl-1,4-dihydrotetrazole-5-one (hereinafter, referred to as "Present compound 17") 0.58 g.

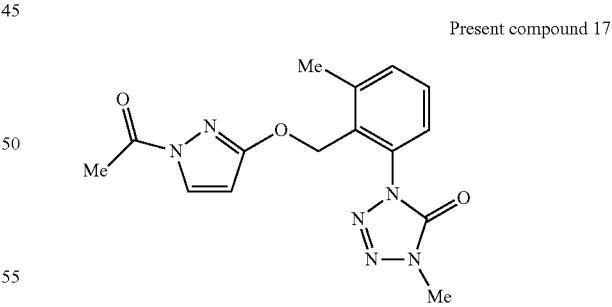

Present compound 17

¹H-NMR (CDCl₃) δ (ppm): 8.01 (1H, d, J=2.9 Hz), 7.43-7.38 (2H, m), 7.26 (1H, dd, J=6.9, 2.1 Hz), 5.88 (1H, d, J=2.9 Hz), 5.31 (2H, s), 3.69 (3H, s), 2.55 (3H, s), 2.54 (3H, s).

Preparation Example 18

A mixture of Present compound 17 3.4 g, sodium methoxide 0.59 g and methanol 30 mL was stirred at room temperature for two hours. To aqueous saturated sodium bicarbonate solution was added the reaction mixtures and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{([1H-pyrazole-3-yl]oxymethyl}-3-methylphenyl)-4-methyl-1,4-dihydrotetrazole-5-one (hereinafter, referred to as "Present compound 18") 2.5 g.

Present compound 18

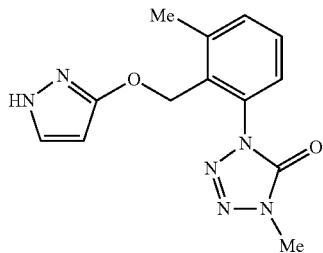

$^1$H-NMR (CDCl$_3$) δ (ppm): 9.61 (1H, s), 7.40-7.35 (2H, m), 7.27 (1H, d, J=2.4 Hz), 7.24 (1H, dd, J=6.5, 2.8 Hz), 5.63 (1H, d, J=2.4 Hz), 5.23 (2H, d, J=11.2 Hz), 3.66 (3H, s), 2.52 (3H, s).

Preparation Example 19

A mixture of Present compound 180.30 g, 4-methylthiophenylboronic acid 0.19 g, copper(II) acetate 0.27 g, pyridine 0.18 mL, molecular sieve 4A 1.00 g and acetonitrile 8 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylthiophenyl)-1H-pyrazole-3-yl]oxymethyl}-3-methylphenyl)-4-methyl-1,4-dihydrotetrazole-5-one (hereinafter, referred to as "Present compound 19") 0.08 g.

Present compound 19

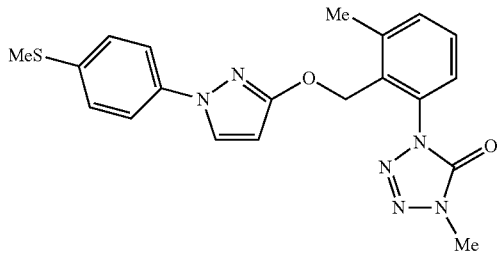

$^1$H-NMR (CDCl$_3$) δ (ppm): 7.64 (1H, d, J=2.7 Hz), 7.51-7.47 (2H, m), 7.40-7.38 (2H, m), 7.33-7.29 (2H, m), 7.27-7.23 (1H, m), 5.80 (1H, d, J=2.7 Hz), 5.33 (2H, s), 3.62 (3H, s), 2.56 (3H, s), 2.50 (3H, s).

Preparation Example 20

A mixture of Present compound 180.30 g, 4-methoxy-3-fluorophenylboronic acid 0.20 g, copper(II) acetate 0.27 g, pyridine 0.18 mL, molecular sieve 4A 1.00 g and acetonitrile 8 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxy-3-fluorophenyl)-1H-pyrazole-3-yl]oxymethyl}-3-methylphenyl)-4-methyl-1,4-dihydrotetrazole-5-one (hereinafter, referred to as "Present compound 20") 0.12 g.

Present compound 20

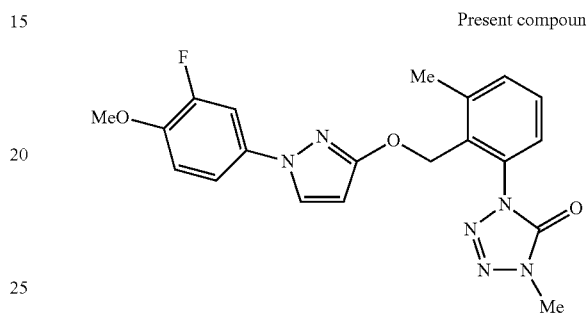

$^1$H-NMR (CDCl$_3$) δ (ppm): 7.57 (1H, d, J=2.7 Hz), 7.40-7.34 (3H, m), 7.27-7.22 (2H, m), 6.98 (1H, t, J=8.8 Hz), 5.79 (1H, d, J=2.7 Hz), 5.32 (2H, s), 3.91 (3H, s), 3.64 (3H, s), 2.56 (3H, s).

Preparation Example 21

A mixture of Present compound 180.30 g, 4-ethoxyphenylboronic acid 0.19 g, copper(II) acetate 0.27 g, pyridine 0.18 mL, molecular sieve 4A 1.00 g and acetonitrile 8 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-ethoxyphenyl)-1H-pyrazole-3-yl]oxymethyl}-3-methylphenyl)-4-methyl-1,4-dihydrotetrazole-5-one (hereinafter, referred to as "Present compound 21") 0.07 g.

Present compound 21

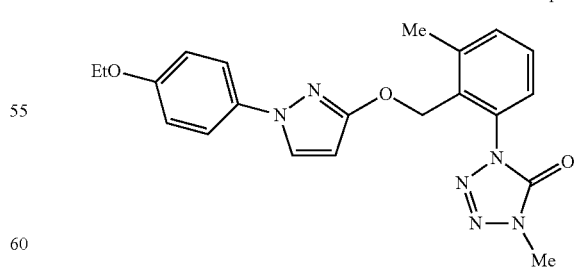

$^1$H-NMR (CDCl$_3$) δ (ppm): 7.57 (1H, d, J=2.7 Hz), 7.48-7.44 (2H, m), 7.41-7.37 (2H, m), 7.27-7.23 (1H, m), 6.95-6.91 (2H, m), 5.76 (1H, d, J=2.7 Hz), 5.32 (2H, s), 4.05 (2H, q, J=7.0 Hz), 3.61 (3H, s), 2.56 (3H, s), 1.43 (3H, t, J=7.0 Hz).

Preparation Example 22

A mixture of Present compound 180.30 g, 4-methyl-3-fluorophenylboronic acid 0.18 g, copper(II) acetate 0.27 g, pyridine 0.18 mL, molecular sieve 4A 1.00 g and acetonitrile 8 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methyl-3-fluorophenyl)-1H-pyrazole-3-yl]oxymethyl}-3-methylphenyl)-4-methyl-1,4-dihydrotetrazole-5-one (hereinafter, referred to as "Present compound 22") 0.21 g.

Present compound 22

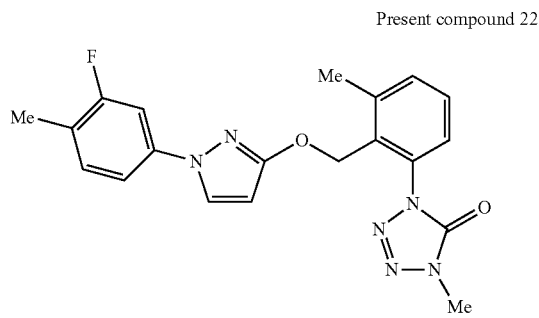 [SMILES: Cc1ccc(-n2ccc(OCc3c(C)cccc3-n3nnn(C)c3=O)n2)cc1F]

$^1$H-NMR (CDCl$_3$) δ (ppm): 7.62 (1H, d, J=2.7 Hz), 7.42-7.37 (2H, m), 7.28-7.16 (4H, m), 5.80 (1H, d, J=2.7 Hz), 5.33 (2H, s), 3.64 (3H, s), 2.56 (3H, s), 2.27 (3H, d, J=1.9 Hz).

Preparation Example 23

A mixture of Present compound 180.30 g, 4-methyl-2-fluorophenylboronic acid 0.18 g, copper(II) acetate 0.17 g, pyridine 0.18 mL, molecular sieve 4A 1.00 g and acetonitrile 8 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methyl-2-fluorophenyl)-1H-pyrazole-3-yl]oxymethyl}-3-methylphenyl)-4-methyl-1,4-dihydrotetrazole-5-one (hereinafter, referred to as "Present compound 23") 0.03 g.

Present compound 23

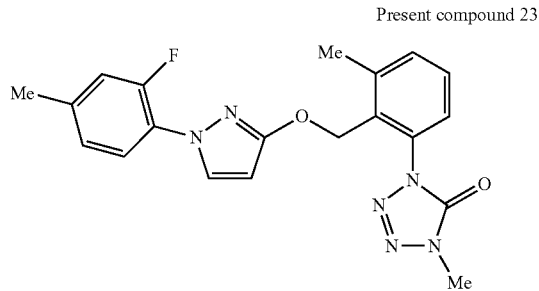

$^1$H-NMR (CDCl$_3$) δ (ppm): 7.74-7.73 (1H, m), 7.66 (1H, t, J=8.3 Hz), 7.42-7.37 (2H, m), 7.27-7.24 (1H, m), 7.03-6.96 (2H, m), 5.80 (1H, d, J=2.7 Hz), 5.32 (2H, s), 3.63 (3H, s), 2.56 (3H, s), 2.36 (3H, s).

Preparation Example 24

A mixture of Present compound 120.61 g, Lawesson's reagent (2,4-Bis(4-methoxyphenyl)-1,3,2,4-dithiadiphosphetane-2,4-disulfide) 0.38 g and toluene 5 mL was stirred with heating under reflux for six hours and the resulting mixtures were then concentrated under reduced pressure. The resulting residues were subjected to a silica gel column chromatography to give 1-(2-{[1-(4-chlorophenyl)-1H-pyrazole-3-yl]oxymethyl}-3-methylphenyl)-4-methyl-1,4-dihydrotetrazole-5-thione (hereinafter, referred to as "Present compound 24") 0.36 g.

Present compound 24

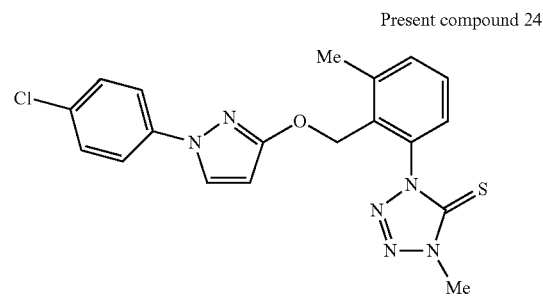

$^1$H-NMR (CDCl$_3$) δ (ppm): 7.64 (1H, d, J=2.7 Hz), 7.51-7.42 (4H, m), 7.39-7.35 (2H, m), 7.27-7.25 (1H, m), 5.80 (1H, d, J=2.7 Hz), 5.26 (2H, s), 3.88 (3H, s), 2.58 (3H, s).

Preparation Example 25

A mixture of 1-(2-bromomethyl-3-methoxyphenyl)-4-methyl-1,4-dihydrotetrazole-5-one (described in Synthesis example 17) 0.30 g, 1-(4-fluorophenyl)-1H-pyrazole-3-ol (described in Reference Preparation example 29) 0.18 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-methoxyphenyl)-4-methyl-1,4-dihydrotetrazole-5-one (hereinafter, referred to as "Present compound 25") 0.22 g.

Present compound 25

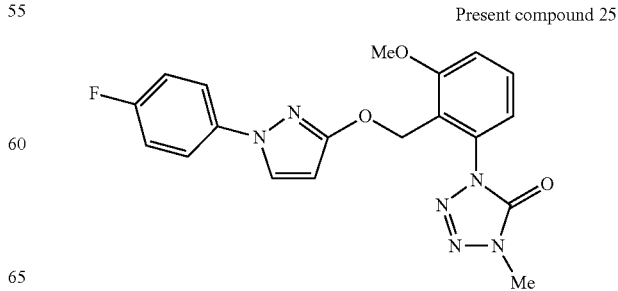

¹H-NMR (CDCl₃) δ (ppm): 7.59 (1H, d, J=2.4 Hz), 7.55-7.50 (2H, m), 7.46 (1H, t, J=8.2 Hz), 7.12-7.03 (4H, m), 5.78 (1H, d, J=2.4 Hz), 5.43 (2H, s), 3.92 (3H, s), 3.56 (3H, s).

Preparation Example 26

A mixture of 1-(2-bromomethyl-3-methoxyphenyl)-4-methyl-1,4-dihydrotetrazole-5-one (described in Synthesis example 17) 1.20 g, 1-(4-chlorophenyl)-1H-pyrazole-3-ol (described in Reference Preparation example 24) 0.78 g, potassium carbonate 0.66 g and acetonitrile 30 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-methoxyphenyl)-4-methyl-1,4-dihydrotetrazole-5-one (hereinafter, referred to as "Present compound 26") 0.97 g.

Present compound 26

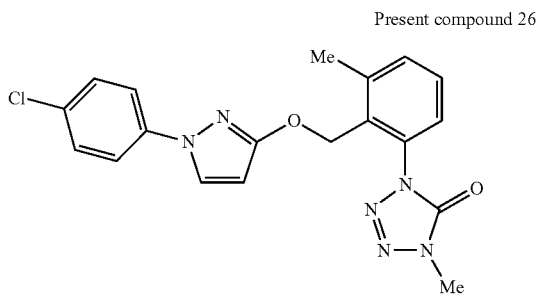 [SMILES: Cc1cccc(-n2nnn(C)c2=S)c1COc1ccn(-c2ccc(Cl)cc2)n1]

¹H-NMR (CDCl₃) δ (ppm): 7.63 (1H, d, J=2.7 Hz), 7.53-7.49 (2H, m), 7.46 (1H, dd, J=8.5, 8.0 Hz), 7.38-7.34 (2H, m), 7.08 (1H, d, J=8.5 Hz), 7.04 (1H, d, J=8.0 Hz), 5.80 (1H, d, J=2.7 Hz), 5.43 (2H, s), 3.92 (3H, s), 3.57 (3H, s).

Preparation Example 27

A mixture of 1-(2-bromomethyl-3-methoxyphenyl)-4-methyl-1,4-dihydrotetrazole-5-one (described in Synthesis example 17) 0.30 g, 1-(4-methylphenyl)-1H-pyrazole-3-ol (described in Reference Preparation example 27) 0.18 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylphenyl)-1H-pyrazole-3-yl]oxymethyl}-3-methoxyphenyl)-4-methyl-1,4-dihydrotetrazole-5-one (hereinafter, referred to as "Present compound 27") 0.20 g.

Present compound 27

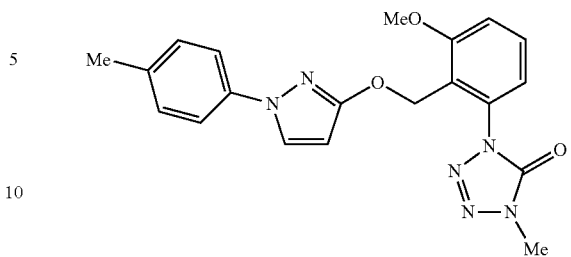

¹H-NMR (CDCl₃) δ (ppm): 7.61 (1H, d, J=2.7 Hz), 7.47-7.43 (3H, m), 7.19 (2H, d, J=8.2 Hz), 7.08 (1H, d, J=7.7 Hz), 7.03 (1H, d, J=8.0 Hz), 5.76 (1H, d, J=2.7 Hz), 5.44 (2H, s), 3.92 (3H, s), 3.54 (3H, s), 2.35 (3H, s).

Preparation Example 28

A mixture of 1-(2-bromomethyl-3-methoxyphenyl)-4-methyl-1,4-dihydrotetrazole-5-one (described in Synthesis example 17) 0.30 g, 1-(4-methylphenyl)-1H-pyrazole-3-ol (described in Reference Preparation example 26) 0.20 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-methoxyphenyl)-4-methyl-1,4-dihydrotetrazole-5-one (hereinafter, referred to as "Present compound 28") 0.22 g.

Present compound 28

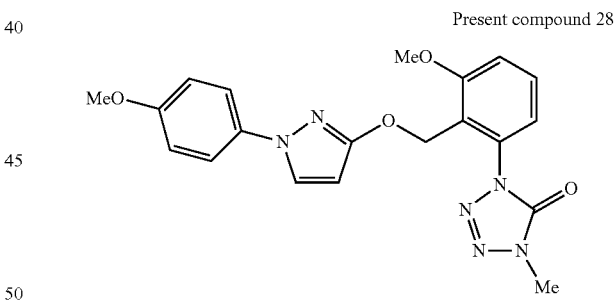

¹H-NMR (CDCl₃) δ (ppm): 7.55 (1H, d, J=2.4 Hz), 7.50-7.43 (3H, m), 7.08 (1H, d, J=8.2 Hz), 7.04 (1H, d, J=8.0 Hz), 6.95-6.91 (2H, m), 5.75 (1H, d, J=2.4 Hz), 5.43 (2H, s), 3.92 (3H, s), 3.83 (3H, s), 3.54 (3H, s).

Preparation Example 29

A mixture of Present compound 70.92 g, zinc dicyanide 0.47 g, tetrakis(triphenylphosphine)palladium 0.46 g and N,N-dimethylformamide 10 mL was stirred at 80° C. for nine hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-cyanophenyl)-4-methyl-1,4-dihydrotetrazole-5-one (hereinafter, referred to as "Present compound 29") 0.04 g.

Present compound 29

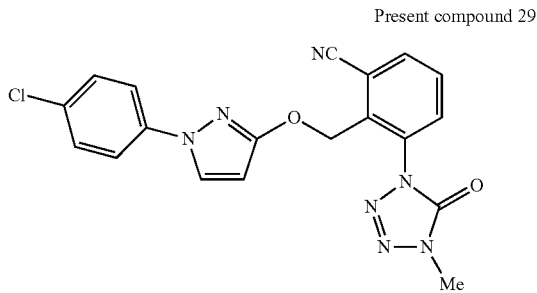

$^1$H-NMR (CDCl$_3$) δ (ppm): 7.85 (1H, dd, J=7.8, 1.2 Hz), 7.70 (1H, dd, J=7.8, 1.2 Hz), 7.63 (1H, d, J=2.4 Hz), 7.61 (1H, t, J=7.8 Hz), 7.53-7.48 (2H, m), 7.38-7.35 (2H, m), 5.80 (1H, d, J=2.4 Hz), 5.64 (2H, s), 3.66 (3H, s).

Preparation Example 30

A mixture of 1-(2-bromomethyl-3-nitrophenyl)-4-methyl-1,4-dihydrotetrazole-5-one (described in Synthesis example 21) 0.30 g, 1-(4-chlorophenyl)-1H-pyrazole-3-ol (described in Reference Preparation example 24) 0.18 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-nitrophenyl)-4-methyl-1,4-dihydrotetrazole-5-one (hereinafter, referred to as "Present compound 30") 0.22 g.

Present compound 30

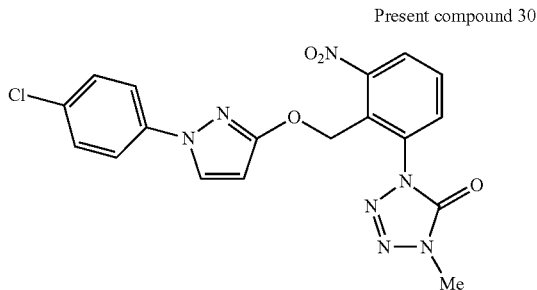

$^1$H-NMR (CDCl$_3$) δ (ppm): 7.97 (1H, dd, J=8.0, 1.5 Hz), 7.70 (1H, dd, J=8.0, 1.5 Hz), 7.62 (1H, t, J=8.0 Hz), 7.58 (1H, d, J=2.7 Hz), 7.40 (2H, dt, J=9.1, 2.4 Hz), 7.35 (2H, dt, J=9.0, 2.4 Hz), 5.74 (1H, d, J=2.4 Hz), 5.64 (2H, s), 3.72 (3H, s).

Preparation Example 31

A mixture of 1-(2-bromomethyl-3-difluoromethylphenyl)-4-methyl-1,4-dihydrotetrazole-5-one (described in Synthesis example 23) 1.21 g, 1-(4-chlorophenyl)-1H-pyrazole-3-ol (described in Reference Preparation example 24) 0.49 g, potassium carbonate 0.42 g and acetonitrile 20 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-difluoromethylphenyl)-4-methyl-1,4-dihydrotetrazole-5-one (hereinafter, referred to as "Present compound 31") 0.57 g.

Present compound 31

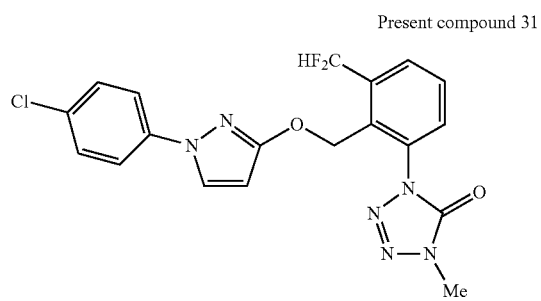

$^1$H-NMR (CDCl$_3$) δ (ppm): 7.85 (1H, d, J=8.0 Hz), 7.62 (1H, d, J=2.7 Hz), 7.61 (1H, dd, J=8.0, 7.9 Hz), 7.55 (1H, d, J=7.9 Hz), 7.46-7.42 (2H, m), 7.39-7.35 (2H, m), 7.26 (1H, t, J=55.2 Hz), 5.81 (1H, d, J=2.7 Hz), 5.46 (2H, s), 3.67 (3H, s).

Preparation Example 32

A mixture of 1-(2-bromomethyl-3-trifluoromethylphenyl)-4-methyl-1,4-dihydrotetrazole-5-one (described in Synthesis example 19) 1.21 g, 1-(4-chlorophenyl)-1H-pyrazole-3-ol (described in Reference Preparation example 24) 0.42 g, potassium carbonate 0.36 g and N,N-dimethylformamide 10 mL was stirred at 80° C. for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-trifluoromethylphenyl)-4-methyl-1,4-dihydrotetrazole-5-one (hereinafter, referred to as "Present compound 32") 0.58 g.

Present compound 32

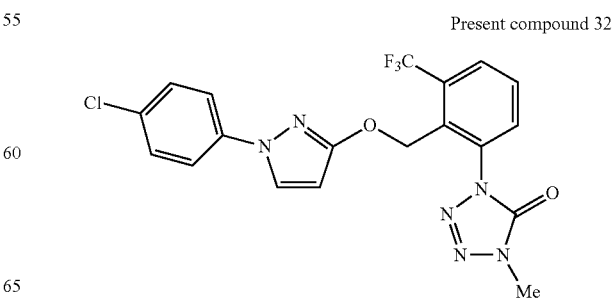

¹H-NMR (CDCl₃) δ (ppm): 7.93-7.88 (1H, m), 7.65-7.64 (3H, m), 7.51 (2H, dt, J=9.3, 2.4 Hz), 7.37 (2H, dt, J=9.2, 2.3 Hz), 5.77 (1H, d, J=2.7 Hz), 5.56 (2H, s), 3.55 (3H, s).

Preparation Example 33

A mixture of Present compound 70.92 g, ethylboronic acid 0.22 g, tripotassium phosphate 1.27 g, water 0.11 mL, [1,1'-bis(diphenylphosphino)ferrocene]palladium(II) dichloride dichloromethane adduct 0.16 g and dioxane 15 mL was stirred with heating under reflux for two hours. To the reaction solutions after cooling was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-ethylphenyl)-4-methyl-1,4-dihydrotetrazole-5-one (hereinafter, referred to as "Present compound 33") 0.24 g.

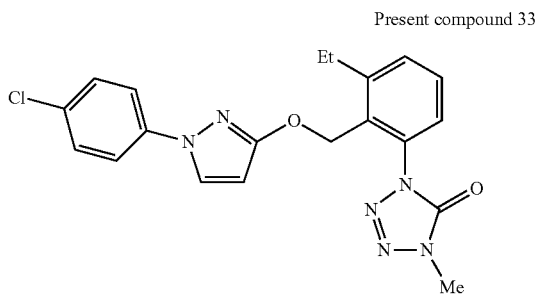

Present compound 33

¹H-NMR (CDCl₃) δ (ppm): 7.65 (1H, d, J=2.7 Hz), 7.53-7.49 (2H, m), 7.47-7.42 (2H, m), 7.39-7.35 (2H, m), 7.27-7.24 (1H, m), 5.81 (1H, d, J=2.7 Hz), 5.34 (2H, s), 3.61 (3H, s), 2.90 (2H, q, J=7.6 Hz), 1.30 (3H, t, J=7.6 Hz).

Preparation Example 34

A mixture of Present compound 70.92 g, cyclopropylboronic acid 0.26 g, tripotassium phosphate 1.27 g, water 0.11 mL, [1,1'-bis(diphenylphosphino)ferrocene]palladium(II) dichloride dichloromethane adduct 0.16 g and dioxane 7 mL was stirred with heating under reflux for one and a half hours. To the reaction solutions after cooling was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-cyclopropylphenyl)-4-methyl-1,4-dihydrotetrazole-5-one (hereinafter, referred to as "Present compound 34") 0.35 g.

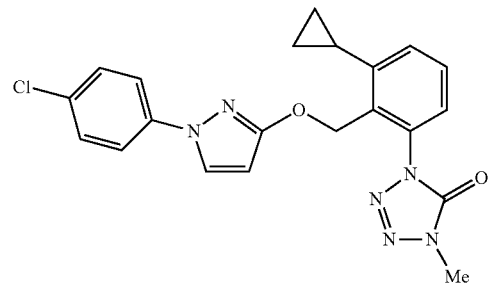

Present compound 34

¹H-NMR (CDCl₃) δ (ppm): 7.63 (1H, d, J=2.7 Hz), 7.51-7.46 (2H, m), 7.41-7.37 (1H, m), 7.36-7.32 (2H, m), 7.24-7.21 (2H, m), 5.80 (1H, d, J=2.7 Hz), 5.53 (2H, s), 3.58 (3H, s), 2.26-2.19 (1H, m), 1.03-0.99 (2H, m), 0.78-0.74 (2H, m).

Preparation Example 35

A mixture of Present compound 70.92 g, 1-propenylboronic acid 0.26 g, tripotassium phosphate 1.27 g, water 0.11 mL, [1,1'-bis(diphenylphosphino)ferrocene]palladium(II) dichloride dichloromethane adduct 0.16 g and dioxane 7 mL was stirred with heating under reflux for two hours. To the reaction solutions after cooling was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-(1-propenyl)phenyl)-4-methyl-1,4-dihydrotetrazole-5-one (hereinafter, referred to as "Present compound 35") 0.70 g.

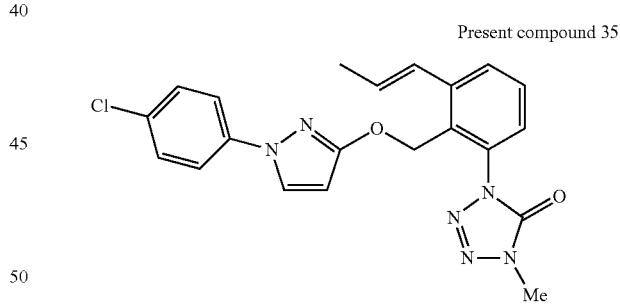

Present compound 35

¹H-NMR (CDCl₃) δ (ppm): 7.65 (1H, d, J=2.7 Hz), 7.62 (1H, d, J=7.8 Hz), 7.53-7.50 (2H, m), 7.44 (1H, t, J=7.8 Hz), 7.39-7.35 (2H, m), 7.27 (1H, d, J=7.8 Hz), 6.85 (1H, dd, J=15.5, 1.6 Hz), 6.22 (1H, dq, J=15.5, 6.7 Hz), 5.82 (1H, d, J=2.7 Hz), 5.35 (2H, s), 3.61 (3H, s), 1.92 (3H, dd, J=6.7, 1.6 Hz).

Preparation Example 36

A mixture of Present compound 350.60 g, palladium fibroin complex 0.06 g and methanol 12 mL was stirred at room temperature under hydrogen atmosphere for eight hours. The reaction mixtures were filtered and the filtrates were concentrated under reduced pressure. The resulting residues were subjected to a silica gel column chromatography to give 1-(2-{([1-(4-chlorophenyl)-1H-pyrazole-3-yl]oxymethyl}-3-propylphenyl)-4-methyl-1,4-dihydrotetrazole-5-one (hereinafter, referred to as "Present compound 36") 0.60 g.

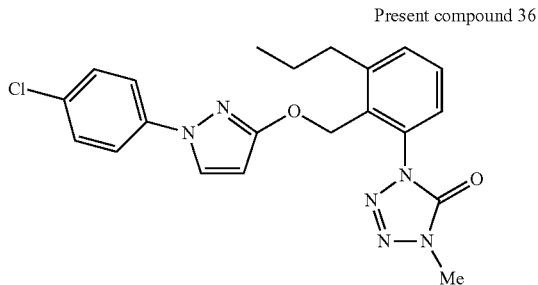 [SMILES: CCCc1cccc(-n2nnn(C)c2=O)c1COc1ccn(-c2ccc(Cl)cc2)n1]

Present compound 36

$^1$H-NMR (CDCl$_3$) δ (ppm): 7.64 (1H, d, J=2.7 Hz), 7.53-7.49 (2H, m), 7.45-7.35 (4H, m), 7.26-7.24 (1H, m), 5.80 (1H, d, J=2.7 Hz), 5.35 (2H, s), 3.59 (3H, s), 2.86-2.82 (2H, m), 1.75-1.65 (2H, m), 1.00 (3H, t, J=7.4 Hz).

Preparation Example 37

A mixture of Present compound 70.92 g, a solution of diisopropyl zinc in toluene (1.0 M) 5 mL, [1,1'-bis(diphenylphosphino)ferrocene]palladium(II) dichloride dichloromethane adduct 0.16 g and dioxane 5 mL was stirred with heating under reflux for three hours. To the reaction solutions after cooling was added 10% hydrochloric acid and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-(1-methylethyl)phenyl)-4-methyl-1,4-dihydrotetrazole-5-one (hereinafter, referred to as "Present compound 37") 0.44 g.

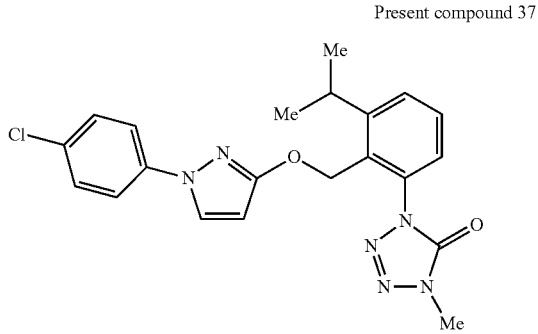 [SMILES: CC(C)c1cccc(-n2nnn(C)c2=O)c1COc1ccn(-c2ccc(Cl)cc2)n1]

Present compound 37

$^1$H-NMR (CDCl$_3$) δ (ppm): 7.65 (1H, d, J=2.7 Hz), 7.55-7.47 (4H, m), 7.43-7.36 (2H, m), 7.24 (1H, dd, J=7.7, 1.3 Hz), 5.82 (1H, d, J=2.7 Hz), 5.34 (2H, s), 3.61 (3H, s), 3.49-3.38 (1H, m), 1.31 (6H, d, J=6.8 Hz).

Preparation Example 38

A mixture of Present compound 70.92 g, butylboronic acid 0.31 g, tripotassium phosphate 1.27 g, water 0.11 mL, [1,1'-bis(diphenylphosphino)ferrocene]palladium(II) dichloride dichloromethane adduct 0.16 g and dioxane 7 mL was stirred with heating under reflux for three hours. To the reaction solutions after cooling was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-butylphenyl)-4-methyl-1,4-dihydrotetrazole-5-one (hereinafter, referred to as "Present compound 38") 0.34 g.

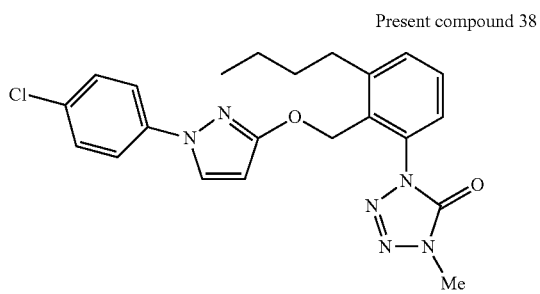 [SMILES: CCCCc1cccc(-n2nnn(C)c2=O)c1COc1ccn(-c2ccc(Cl)cc2)n1]

Present compound 38

$^1$H-NMR (CDCl$_3$) δ (ppm): 7.64 (1H, d, J=2.7 Hz), 7.52-7.49 (2H, m), 7.44-7.35 (4H, m), 7.26-7.23 (1H, m), 5.80 (1H, d, J=2.7 Hz), 5.35 (2H, s), 3.59 (3H, s), 2.85 (2H, t, J=8.0 Hz), 1.68-1.61 (2H, m), 1.36-1.46 (2H, m), 0.93 (3H, t, J=7.4 Hz).

Preparation Example 39

A mixture of Present compound 70.92 g, tributyl vinyl tin 0.70 g, tetrakistriphenylphosphine palladium 0.23 g and toluene 10 mL was stirred with heating under reflux for three hours. After cooling the reaction solutions, thereto was added saturated aqueous ammonium chloride solution and the resulting mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-ethenylphenyl)-4-methyl-1,4-dihydrotetrazole-5-one (hereinafter, referred to as "Present compound 39") 0.39 g.

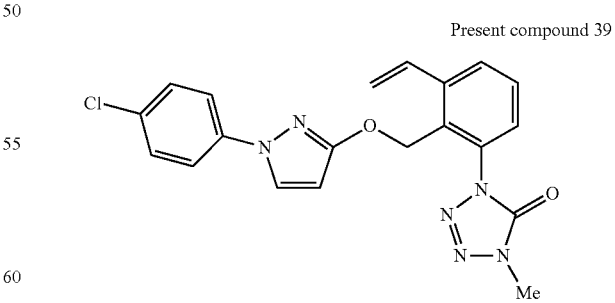

Present compound 39

$^1$H-NMR (CDCl$_3$) δ (ppm): 7.69 (1H, d, J=7.7 Hz), 7.63 (1H, d, J=2.7 Hz), 7.51-7.45 (3H, m), 7.37-7.32 (3H, m), 7.19 (1H, dd, J=17.3, 11.0 Hz), 5.81 (1H, d, J=2.7 Hz), 5.75 (1H, dd, J=17.3, 1.2 Hz), 5.46 (1H, dd, J=11.0, 1.2 Hz), 5.36 (2H, s), 3.61 (3H, s).

Preparation Example 40

A mixture of Present compound 70.92 g, allylboronic acid pinacol ester 0.50 g, tripotassium phosphate 1.27 g, water 0.11 mL, [1,1'-bis(diphenylphosphino)ferrocene]palladium (II) dichloride dichloromethane adduct 0.16 g and dioxane 10 mL was stirred with heating under reflux for one and a half hours. To the reaction solutions after cooling was added water and the resulting mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{([1-(4-chlorophenyl)-1H-pyrazole-3-yl]oxymethyl}-3-(2-propenyl)phenyl)-4-methyl-1,4-dihydrotetrazole-5-one (hereinafter, referred to as "Present compound 40") 0.50 g.

Present compound 40

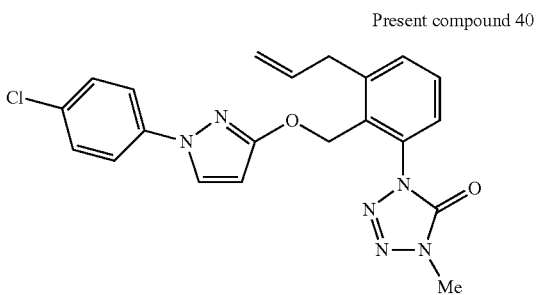 [SMILES: C=CCc1cccc(-n2nnn(C)c2=O)c1COc1ccn(-c2ccc(Cl)cc2)n1]

$^1$H-NMR (CDCl$_3$) δ (ppm): 7.64 (1H, d, J=2.7 Hz), 7.52-7.48 (2H, m), 7.47-7.40 (2H, m), 7.39-7.35 (2H, m), 7.30-7.28 (1H, m), 6.06-5.96 (1H, m), 5.81 (1H, d, J=2.7 Hz), 5.34 (2H, s), 5.14-5.04 (2H, m), 3.68-3.65 (2H, m), 3.61 (3H, s).

Preparation Example 41

A mixture of Present compound 70.92 g, isopropenylboronic acid pinacol ester 0.50 g, tripotassium phosphate 1.27 g, water 0.11 mL, [1,1'-bis(diphenylphosphino)ferrocene]palladium(II) dichloride dichloromethane adduct 0.16 g and dioxane 7 mL was stirred with heating under reflux for one and a half hours. To the reaction solutions after cooling was added water and the resulting mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-(1-methylethenyl)phenyl)-4-methyl-1,4-dihydrotetrazole-5-one (hereinafter, referred to as "Present compound 41") 0.34 g.

Present compound 41

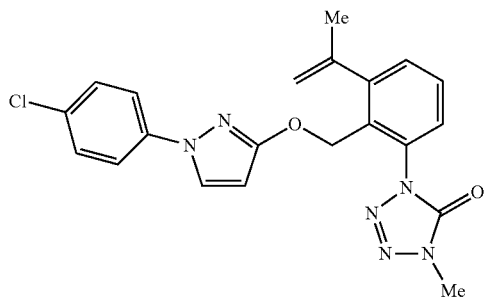

$^1$H-NMR (CDCl$_3$) δ (ppm): 7.63 (1H, d, J=2.6 Hz), 7.52-7.49 (2H, m), 7.47 (1H, t, J=7.8 Hz), 7.40-7.33 (4H, m), 5.77 (1H, d, J=2.6 Hz), 5.37 (2H, s), 5.30-5.29 (1H, m), 5.01-5.01 (1H, m), 3.55 (3H, s), 2.12 (3H, s).

Preparation Example 42

A mixture of Present compound 71.39 g, trimethylsilylacetylene 0.88 g, bis(triphenylphosphine) palladium(II) dichloride 0.17 g, copper iodide 0.06 g, triethylamine 20 mL and N,N-dimethylformamide 10 mL was stirred at 50° C. for six hours. To the reaction solutions after cooling was added water and the resulting mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{([1-(4-chlorophenyl)-1H-pyrazole-3-yl]oxymethyl}-3-trimethylsilanylethynylphenyl)-4-methyl-1,4-dihydrotetrazole-5-one (hereinafter, referred to as "Present compound 42") 0.40 g.

Present compound 42

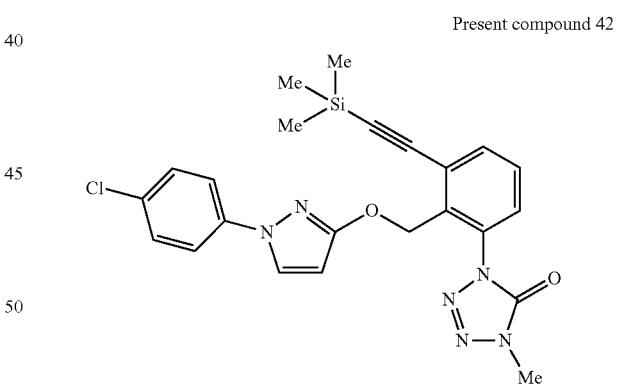

$^1$H-NMR (CDCl$_3$) δ (ppm): 7.66-7.63 (2H, m), 7.54-7.50 (2H, m), 7.45-7.33 (4H, m), 5.80 (1H, d, J=2.6 Hz), 5.59 (2H, s), 3.60 (3H, s), 0.18 (9H, s).

Preparation Example 43

A mixture of Present compound 420.35 g, potassium carbonate 0.03 g, methanol 1.5 mL and chloroform 1.5 mL was stirred at room temperature for one hour. To the reaction mixtures was added water and the resulting mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-ethynylphenyl)-4-methyl-1,4-dihydrotetrazole-5-one (hereinafter, referred to as "Present compound 43") 0.10 g.

Present compound 43

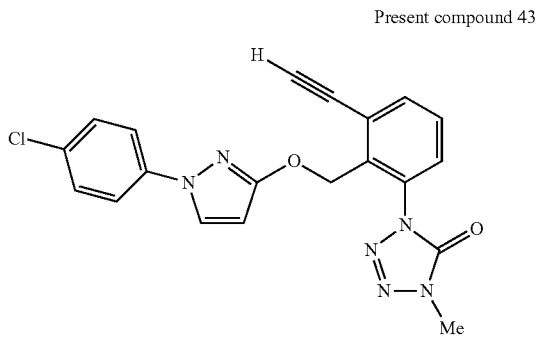 [SMILES: C#Cc1cccc(-n2nnn(C)c2=O)c1COc1ccn(-c2ccc(Cl)cc2)n1]

¹H-NMR (CDCl₃) δ (ppm): 7.71-7.69 (1H, m), 7.63 (1H, d, J=2.7 Hz), 7.53-7.42 (4H, m), 7.37-7.34 (2H, m), 5.78 (1H, d, J=2.7 Hz), 5.63 (2H, s), 3.59 (3H, 3.40 (1H, s).

Preparation Example 44

To a mixture of 1-(2-{[1-(4-chlorophenyl)-1H-pyrazole-3-yl]oxymethyl}-3-methylphenyl)-1,4-dihydro-4-tetrazole-5-one (described in Synthesis example 43) 0.50 g, potassium carbonate 0.36 g and N,N-dimethylformamide 7 mL was added ethyl iodide 0.21 mL under ice-cooling. The mixtures were raised to room temperature and were stirred for sixteen hours. To the reaction mixtures was added water and the mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-methylphenyl)-4-ethyl-1,4-dihydrotetrazole-5-one (hereinafter, referred to as "Present compound 44") 0.45 g.

Present compound 44

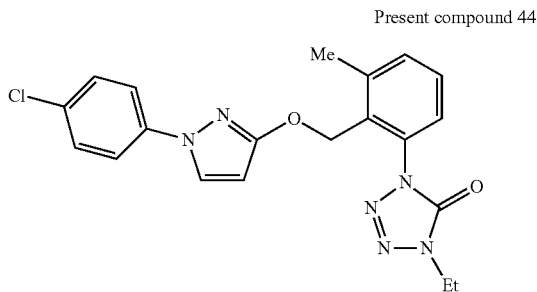 [SMILES: CCn1nnn(-c2cccc(C)c2COc2ccn(-c3ccc(Cl)cc3)n2)c1=O]

¹H-NMR (CDCl₃) δ (ppm): 7.63 (1H, d, J=2.7 Hz), 7.51-7.46 (2H, m), 7.39-7.33 (4H, m), 7.28-7.26 (1H, m), 5.80 (1H, d, J=2.7 Hz), 5.33 (2H, s), 4.01 (2H, q, J=7.3 Hz), 2.55 (3H, s), 1.43 (3H, t, J=7.3 Hz).

Preparation Example 45

To a mixture of 1-(2-{[1-(4-chlorophenyl)-1H-pyrazole-3-yl]oxymethyl}-3-methylphenyl)-1,4-dihydro-4-tetrazole-5-one (described in Synthesis example 43) 0.50 g, potassium carbonate 0.36 g, potassium iodide 0.02 g and N,N-dimethylformamide 7 mL was added chloromethyl methyl ether 0.2 mL under ice-cooling. The mixtures were raised to room temperature and were stirred for sixteen hours. To the reaction mixtures was added water and the mixtures were extracted with ethyl acetate. The organic layers were washed with water and saturated saline, and dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-methylphenyl)-4-methoxymethyl-1,4-dihydrotetrazole-5-one (hereinafter, referred to as "Present compound 45") 0.28 g.

Present compound 45

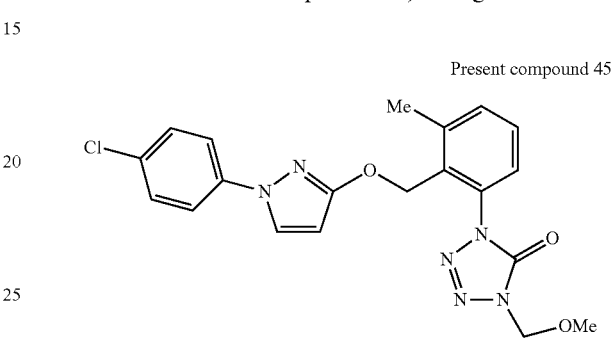

¹H-NMR (CDCl₃) δ (ppm): 7.63 (1H, d, J=2.7 Hz), 7.50-7.46 (2H, m), 7.41-7.34 (4H, m), 7.30-7.27 (1H, m), 5.81 (1H, d, J=2.7 Hz), 5.34 (2H, s), 5.28 (2H, s), 3.42 (3H, s), 2.57 (3H, s).

Preparation Example 46

A mixture of 1-(2-bromomethyl-3-methylphenyl)-4-methyl-1,4-dihydrotetrazole-5-one (described in Synthesis example 33) 0.30 g, 1-(4-bromophenyl)-1H-pyrazole-3-ol (described in Reference Preparation example 37) 0.27 g, potassium carbonate 0.19 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-bromophenyl)-1H-pyrazole-3-yl]oxymethyl}-3-methylphenyl)-4-methyl-1,4-dihydrotetrazole-5-one (hereinafter, referred to as "Present compound 46") 0.37 g.

Present compound 46

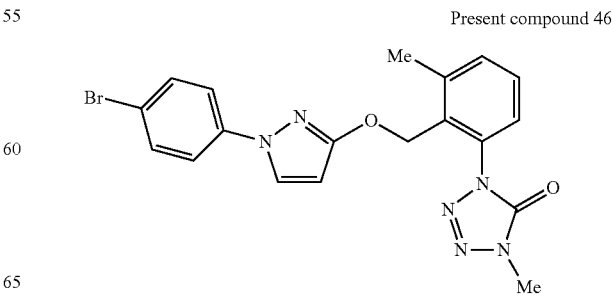

$^1$H-NMR (CDCl$_3$) δ (ppm): 7.64 (1H, d, J=2.4 Hz), 7.53-7.49 (2H, m), 7.45-7.37 (4H, m), 7.27-7.24 (1H, m), 5.82 (1H, d, J=2.4 Hz), 5.33 (2H, s), 3.62 (3H, s), 2.55 (3H, s).

Preparation Example 47

A mixture of 1-(2-bromomethyl-3-chlorophenyl)-4-methyl-1,4-dihydrotetrazole-5-one (described in Synthesis example 6) 0.30 g, 1-(4-bromophenyl)-1H-pyrazole-3-ol (described in Reference Preparation example 37) 0.25 g, potassium carbonate 0.18 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-bromophenyl)-1H-pyrazole-3-yl]oxymethyl}-3-chlorophenyl)-4-methyl-1,4-dihydrotetrazole-5-one (hereinafter, referred to as "Present compound 47") 0.37 g.

Present compound 47

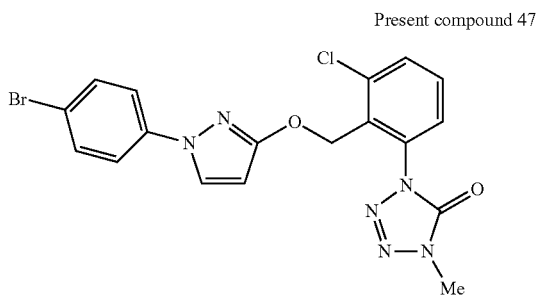

$^1$H-NMR (CDCl$_3$) δ (ppm): 7.64 (1H, d, J=2.7 Hz), 7.60 (1H, dd, J=8.0, 1.2 Hz), 7.53-7.50 (2H, m), 7.47-7.42 (3H, m), 7.36 (1H, dd, J=7.8, 1.1 Hz), 5.80 (1H, d, J=2.7 Hz), 5.53 (2H, s), 3.60 (3H, s).

Preparation Example 48

A mixture of 1-(2-bromomethyl-3-bromophenyl)-4-methyl-1,4-dihydrotetrazole-5-one (described in Synthesis example 11) 0.30 g, 1-(4-bromophenyl)-1H-pyrazole-3-ol (described in Reference Preparation example 37) 0.22 g, potassium carbonate 0.16 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-bromophenyl)-1H-pyrazole-3-yl]oxymethyl}-3-bromophenyl)-4-methyl-1,4-dihydrotetrazole-5-one (hereinafter, referred to as "Present compound 48") 0.36 g.

Present compound 48

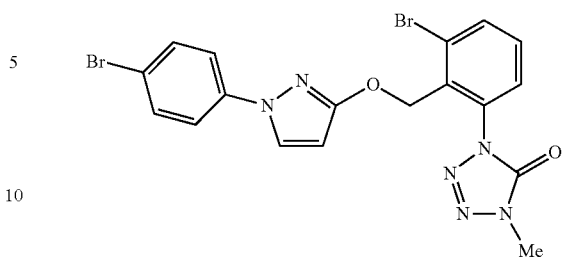

$^1$H-NMR (CDCl$_3$) δ (ppm): 7.79 (1H, dd, J=7.7, 1.7 Hz), 7.64 (1H, d, J=2.7 Hz), 7.53-7.50 (2H, m), 7.47-7.44 (2H, m), 7.41-7.34 (2H, m), 5.81 (1H, d, J=2.7 Hz), 5.53 (2H, s), 3.60 (3H, s).

Preparation Example 49

A mixture of 1-(2-bromomethyl-3-methoxyphenyl)-4-methyl-1,4-dihydrotetrazole-5-one (described in Synthesis example 17) 0.30 g, 1-(4-bromophenyl)-1H-pyrazole-3-ol (described in Reference Preparation example 37) 0.25 g, potassium carbonate 0.18 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-bromophenyl)-1H-pyrazole-3-yl]oxymethyl}-3-methoxyphenyl)-4-methyl-1,4-dihydrotetrazole-5-one (hereinafter, referred to as "Present compound 49") 0.33 g.

Present compound 49

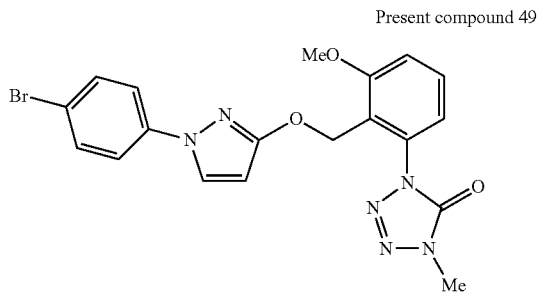 [SMILES: COc1cccc(-n2nnn(C)c2=O)c1COc1ccn(-c2ccc(Br)cc2)n1]

$^1$H-NMR (CDCl$_3$) δ (ppm): 7.64 (1H, d, J=2.4 Hz), 7.53-7.44 (5H, m), 7.09 (1H, d, J=8.5 Hz), 7.04 (1H, dd, J=8.0, 1.0 Hz), 5.81 (1H, d, J=2.4 Hz), 5.43 (2H, s), 3.93 (3H, s), 3.57 (3H, s).

Preparation Example 50

A mixture of 1-(2-bromomethyl-3-methylphenyl)-4-methyl-1,4-dihydrotetrazole-5-one (described in Synthesis example 33) 0.40 g, 1-cyclohexyl-1H-pyrazole-3-ol (described in Reference Preparation example 41) 0.25 g, cesium carbonate 0.25 g and N,N-dimethylformamide 10 mL was stirred at 80° C. for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-{2-[(1-cyclohexyl-1H-pyrazole-3-yl)oxymethyl]-3-methylphenyl}-4-methyl-1,4-dihydrotetrazole-5-one (hereinafter, referred to as "Present compound 50") 0.31 g.

Present compound 50

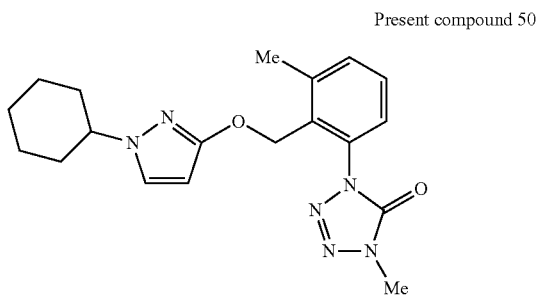 [SMILES: Cc1cccc(-n2nnn(C)c2=O)c1COc1ccn(C2CCCCC2)n1]

¹H-NMR (CDCl₃) δ (ppm): 7.39-7.34 (2H, m), 7.25-7.21 (1H, m), 7.13 (1H, d, J=2.2 Hz), 5.51 (1H, d, J=2.2 Hz), 5.19 (2H, s), 3.85 (1H, tt, J=11.6, 3.8 Hz), 3.67 (3H, s), 2.53 (3H, s), 2.11-2.07 (2H, m), 1.86 (2H, dt, J=13.5, 3.2 Hz), 1.73-1.68 (1H, m), 1.58 (2H, ddd, J=24.5, 12.5, 3.5 Hz), 1.38 (2H, tdd, J=17.0, 8.6, 4.2 Hz), 1.28-1.20 (1H, m).

Preparation Example 51

A mixture of 1-(2-bromomethyl-3-methylphenyl)-4-methyl-1,4-dihydrotetrazole-5-one (described in Synthesis example 33) 0.30 g, 1-(4-trifluoromethoxyphenyl)-1H-pyrazole-3-ol (described in Reference Preparation example 39) 0.27 g, potassium carbonate 0.19 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-trifluoromethoxyphenyl)-1H-pyrazole-3-yl]oxymethyl}-3-methylphenyl)-4-methyl-1,4-dihydrotetrazole-5-one (hereinafter, referred to as "Present compound 51") 0.34 g.

Present compound 51

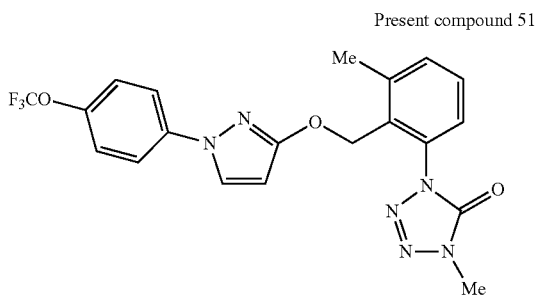 [SMILES: Cc1cccc(-n2nnn(C)c2=O)c1COc1ccn(-c2ccc(OC(F)(F)F)cc2)n1]

¹H-NMR (CDCl₃) δ (ppm): 7.65 (1H, d, J=2.7 Hz), 7.60-7.56 (2H, m), 7.42-7.38 (2H, m), 7.28-7.24 (3H, m), 5.83 (1H, d, J=2.7 Hz), 5.33 (2H, 3.62 (3H, s), 2.56 (3H, s).

Preparation Example 52

A mixture of 1-(2-bromomethyl-3-cyclopropylphenyl)-4-methyl-1,4-dihydrotetrazole-5-one (described in Synthesis example 35) 0.29 g, 1-(4-fluorophenyl)-1H-pyrazole-3-ol (described in Reference Preparation example 29) 0.19 g, potassium carbonate 0.17 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-cyclopropylphenyl)-4-methyl-1,4-dihydrotetrazole-5-one (hereinafter, referred to as "Present compound 52") 0.29 g.

Present compound 52

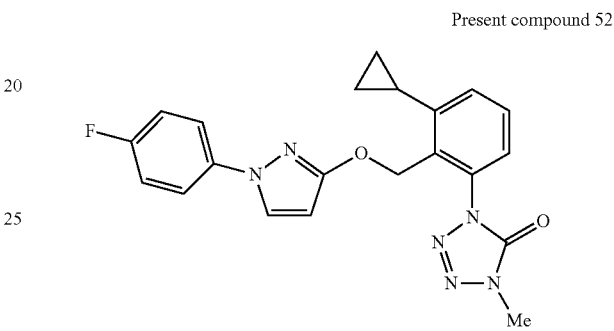

¹H-NMR (CDCl₃) δ (ppm): 7.61 (1H, d, J=2.7 Hz), 7.56-7.50 (2H, m), 7.41 (1H, t, J=7.9 Hz), 7.24 (2H, d, J=7.9 Hz), 7.14-7.08 (2H, m), 5.81 (1H, d, J=2.7 Hz), 5.53 (2H, s), 3.60 (3H, s), 2.28-2.21 (1H, m), 1.05-1.00 (2H, m), 0.80-0.76 (2H, m).

Preparation Example 53

A mixture of Present compound 180.49 g, 4-chloro-3-fluorophenylboronic acid 0.33 g, copper(II) acetate 0.51 g, pyridine 0.28 g, molecular sieve 4A 1.00 g and acetonitrile 10 mL was stirred with heating under reflux for 48 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{([1-(4-chloro-3-fluorophenyl)-1H-pyrazole-3-yl]oxymethyl}-3-methylphenyl)-4-methyl-1,4-dihydrotetrazole-5-one (hereinafter, referred to as "Present compound 53") 0.12 g.

Present compound 53

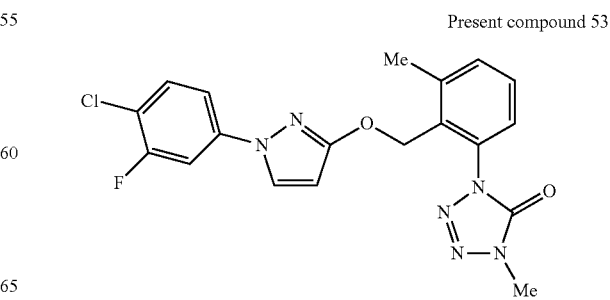

¹H-NMR (CDCl₃) δ (ppm): 7.64 (1H, d, J=2.7 Hz), 7.44-7.38 (4H, m), 7.28-7.23 (2H, m), 5.84 (1H, d, J=2.7 Hz), 5.33 (2H, s), 3.65 (3H, s), 2.56 (3H, s).

Preparation Example 54

A mixture of 1-(2-bromomethyl-3-ethylphenyl)-4-methyl-1,4-dihydrotetrazole-5-one (described in Synthesis example 38) 0.30 g, 1-(4-fluorophenyl)-1H-pyrazole-3-ol (described in Reference Preparation example 29) 0.21 g, potassium carbonate 0.18 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-ethylphenyl)-4-methyl-1,4-dihydrotetrazole-5-one (hereinafter, referred to as "Present compound 54") 0.32 g.

Present compound 54

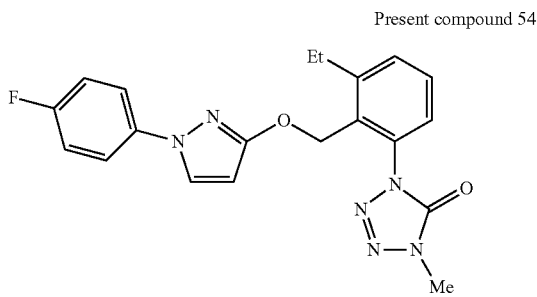 [SMILES: CCc1cccc(-n2nnn(C)c2=O)c1COc1ccn(-c2ccc(F)cc2)n1]

¹H-NMR (CDCl₃) δ (ppm): 7.61 (1H, d, J=2.4 Hz), 7.54-7.51 (2H, m), 7.47-7.42 (2H, m), 7.28-7.24 (1H, m), 7.13-7.09 (2H, m), 5.80 (1H, d, J=2.4 Hz), 5.34 (2H, s), 3.60 (3H, s), 2.91 (2H, q, J=7.6 Hz), 1.30 (3H, t, J=7.6 Hz).

Preparation Example 55

A mixture of 1-(2-bromomethyl-3-ethylphenyl)-4-methyl-1,4-dihydrotetrazole-5-one (described in Synthesis example 38) 0.30 g, 1-(4-bromophenyl)-1H-pyrazole-3-ol (described in Reference Preparation example 37) 0.27 g, potassium carbonate 0.18 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{([1-(4-bromophenyl)-1H-pyrazole-3-yl]oxymethyl}-3-ethylphenyl)-4-methyl-1,4-dihydrotetrazole-5-one (hereinafter, referred to as "Present compound 55") 0.40 g.

Present compound 55

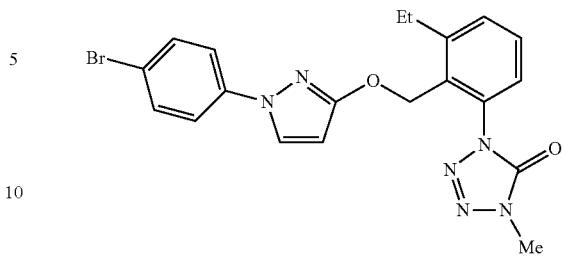

¹H-NMR (CDCl₃) δ (ppm): 7.65 (1H, d, J=2.7 Hz), 7.54-7.50 (2H, m), 7.47-7.42 (4H, m), 7.28-7.24 (1H, m), 5.81 (1H, d, J=2.7 Hz), 5.34 (2H, s), 3.60 (3H, s), 2.90 (2H, q, J=7.6 Hz), 1.30 (3H, t, J=7.6 Hz).

Preparation Example 56

A mixture of 1-(2-bromomethyl-3-cyclopropylphenyl)-4-methyl-1,4-dihydrotetrazole-5-one (described in Synthesis example 35) 0.30 g, 1-(4-bromophenyl)-1H-pyrazole-3-ol (described in Reference Preparation example 37) 0.26 g, potassium carbonate 0.17 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-bromophenyl)-1H-pyrazole-3-yl]oxymethyl}-3-cyclopropylphenyl)-4-methyl-1,4-dihydrotetrazole-5-one (hereinafter, referred to as "Present compound 56") 0.45 g.

Present compound 56

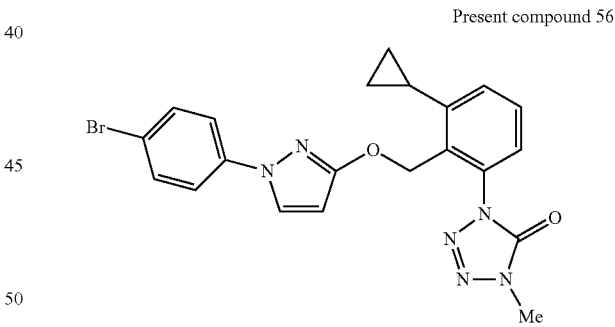

¹H-NMR (CDCl₃) δ (ppm): 7.65 (1H, d, J=2.4 Hz), 7.53-7.44 (4H, m), 7.41 (1H, t, J=7.8 Hz), 7.24 (2H, d, J=7.8 Hz), 5.83 (1H, d, J=2.4 Hz), 5.53 (2H, s), 3.61 (3H, s), 2.27-2.20 (1H, m), 1.05-1.00 (2H, m), 0.80-0.76 (2H, m).

Preparation Example 57

A mixture of Present compound 180.31 g, 3-methylthiophenylboronic acid 0.20 g, copper(II) acetate 0.33 g, pyridine 0.18 g, molecular sieve 4A 0.40 g and acetonitrile 5 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-methylthiophenyl)-1H-pyrazole-3-yl]oxymethyl}-3-methylphenyl)-4-methyl-1,4-dihydrotetrazole-5-one (hereinafter, referred to as "Present compound 57") 0.18 g.

Present compound 57

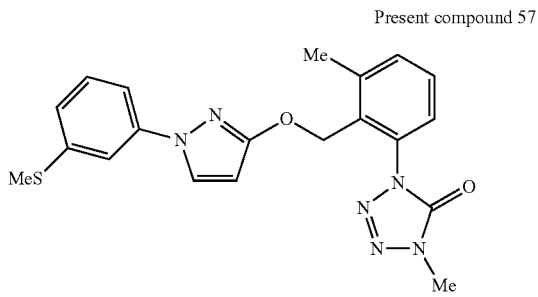 [SMILES: CSc1cccc(-n2ccc(OCc3c(C)cccc3-n3nnn(C)c3=O)n2)c1]

$^1$H-NMR (CDCl$_3$) δ (ppm): 7.66 (1H, d, J=2.7 Hz), 7.49-7.48 (1H, m), 7.40-7.38 (2H, m), 7.33-7.24 (3H, m), 7.09-7.06 (1H, m), 5.81 (1H, d, J=2.7 Hz), 5.34 (2H, s), 3.62 (3H, s), 2.57 (3H, s), 2.54 (3H, s).

Preparation Example 58

A mixture of 1-(2-bromomethyl-3-ethylphenyl)-4-methyl-1,4-dihydrotetrazole-5-one (described in Synthesis example 38) 0.30 g, 1-(4-methoxyphenyl)-1H-pyrazole-3-ol (described in Reference Preparation example 26) 0.22 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-ethylphenyl)-4-methyl-1,4-dihydrotetrazole-5-one (hereinafter, referred to as "Present compound 58") 0.27 g.

Present compound 58

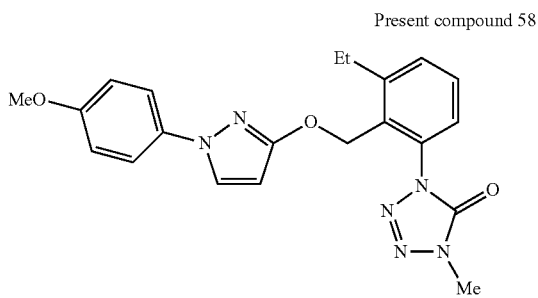

$^1$H-NMR (CDCl$_3$) δ (ppm): 7.57 (1H, d, J=2.4 Hz), 7.50-7.41 (4H, m), 7.27-7.24 (1H, m), 6.96-6.92 (2H, m), 5.76 (1H, d, J=2.4 Hz), 5.34 (2H, s), 3.83 (3H, s), 3.59 (3H, s), 2.91 (2H, q, J=7.6 Hz), 1.30 (3H, t, J=7.6 Hz).

Preparation Example 59

A mixture of 1-(2-bromomethyl-3-cyclopropylphenyl)-4-methyl-1,4-dihydrotetrazole-5-one (described in Synthesis example 35) 0.30 g, 1-(4-methoxyphenyl)-1H-pyrazole-3-ol (described in Reference Preparation example 26) 0.21 g, potassium carbonate 0.17 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-cyclopropylphenyl)-4-methyl-1,4-dihydrotetrazole-5-one (hereinafter, referred to as "Present compound 59") 0.25 g.

Present compound 59

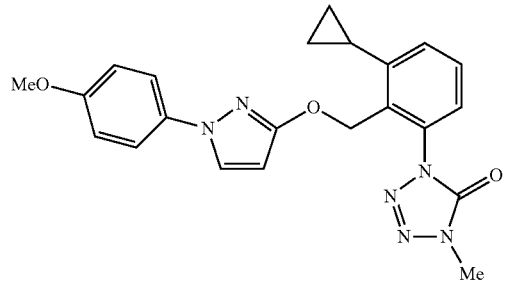

$^1$H-NMR (CDCl$_3$) δ (ppm): 7.57 (1H, d, J=2.7 Hz), 7.50-7.46 (2H, m), 7.40 (1H, t, J=8.0 Hz), 7.24 (2H, d, J=8.0 Hz), 6.96-6.92 (2H, m), 5.77 (1H, d, J=2.7 Hz), 5.53 (2H, s), 3.83 (3H, s), 3.59 (3H, s), 2.29-2.21 (1H, m), 1.05-1.00 (2H, m), 0.79-0.75 (2H, m).

Preparation Example 60

A mixture of 1-(2-bromomethyl-3-cyclopropylphenyl)-4-methyl-1,4-dihydrotetrazole-5-one (described in Synthesis example 35) 0.30 g, 1-(4-methylphenyl)-1H-pyrazole-3-ol (described in Reference Preparation example 27) 0.19 g, potassium carbonate 0.17 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylphenyl)-1H-pyrazole-3-yl]oxymethyl}-3-cyclopropylphenyl)-4-methyl-1,4-dihydrotetrazole-5-one (hereinafter, referred to as "Present compound 60") 0.23 g.

Present compound 60

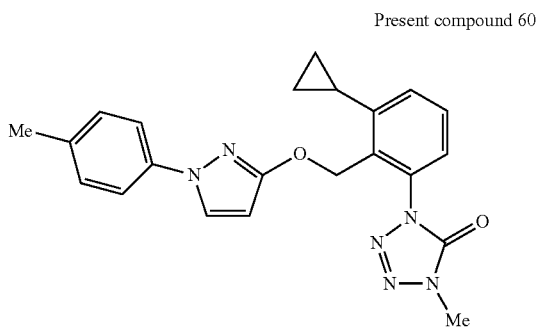 [SMILES: Cc1ccc(-n2ccc(OCc3c(C4CC4)cccc3-n3nnn(C)c3=O)n2)cc1]

¹H-NMR (CDCl₃) δ (ppm): 7.64 (1H, d, J=2.4 Hz), 7.45 (2H, d, J=8.3 Hz), 7.40 (1H, t, J=7.8 Hz), 7.25-7.19 (4H, m), 5.79 (1H, d, J=2.4 Hz), 5.54 (2H, s), 3.59 (3H, s), 2.36 (3H, s), 2.29-2.21 (1H, m), 1.05-1.00 (2H, m), 0.79-0.75 (2H, m).

Preparation Example 61

A mixture of 1-(2-bromomethyl-3-ethylphenyl)-4-methyl-1,4-dihydrotetrazole-5-one (described in Synthesis example 38) 0.30 g, 1-(4-methylphenyl)-1H-pyrazole-3-ol (described in Reference Preparation example 27) 0.26 g, potassium carbonate 0.18 g and acetonitrile 10 mL was stirred with heating under reflux for two hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylphenyl)-1H-pyrazole-3-yl]oxymethyl}-3-ethylphenyl)-4-methyl-1,4-dihydrotetrazole-5-one (hereinafter, referred to as "Present compound 61") 0.30 g.

Present compound 61

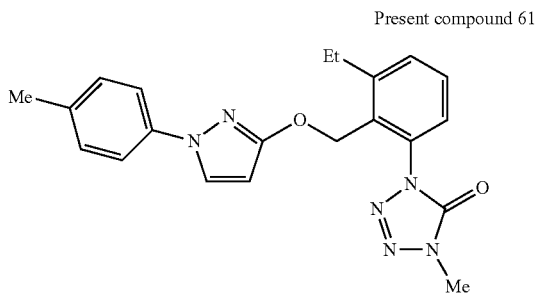 [SMILES: CCc1cccc(-n2nnn(C)c2=O)c1COc1ccn(-c2ccc(C)cc2)n1]

¹H-NMR (CDCl₃) δ (ppm): 7.64 (1H, d, J=2.4 Hz), 7.46-7.42 (4H, m), 7.27-7.20 (3H, m), 5.78 (1H, d, J=2.4 Hz), 5.35 (2H, s), 3.59 (3H, s), 2.91 (2H, q, J=7.6 Hz), 2.36 (3H, s), 1.30 (3H, t, J=7.6 Hz).

Preparation Example 62

A mixture of 1-(2-bromomethyl-3-bromophenyl)-4-methyl-1,4-dihydrotetrazole-5-one (described in Synthesis example 11) 0.30 g, 1-(4-methylphenyl)-1H-pyrazole-3-ol (described in Reference Preparation example 27) 0.17 g, potassium carbonate 0.16 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methylphenyl)-1H-pyrazole-3-yl]oxymethyl}-3-bromophenyl)-4-methyl-1,4-dihydrotetrazole-5-one (hereinafter, referred to as "Present compound 62") 0.28 g.

Present compound 62

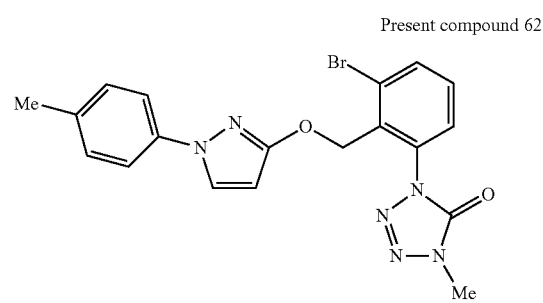

¹H-NMR (CDCl₃) δ (ppm): 7.79 (1H, dd, J=7.6, 1.7 Hz), 7.63 (1H, d, J=2.7 Hz), 7.46-7.44 (2H, m), 7.41-7.34 (2H, m), 7.23-7.19 (2H, m), 5.77 (1H, d, J=2.7 Hz), 5.54 (2H, s), 3.57 (3H, s), 2.36 (3H, s).

Preparation Example 63

A mixture of Present compound 18 0.23 g, 2-methylthiophenylboronic acid 0.15 g, copper(II) acetate 0.24 g, pyridine 0.13 g, molecular sieve 4A 0.30 g and acetonitrile 5 mL was stirred with heating under reflux for 48 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methylthiophenyl)-1H-pyrazole-3-yl]oxymethyl}-3-methylphenyl)-4-methyl-1,4-dihydrotetrazole-5-one (hereinafter, referred to as "Present compound 63") 0.10 g.

Present compound 63

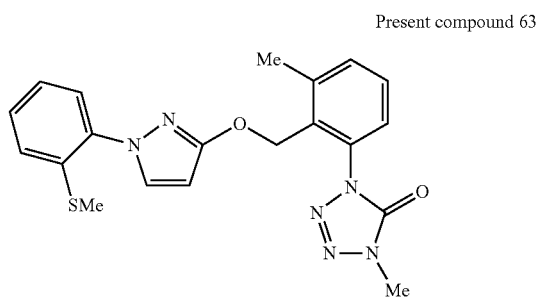

¹H-NMR (CDCl₃) δ (ppm): 7.54 (1H, d, J=2.4 Hz), 7.40-7.28 (5H, m), 7.26-7.20 (2H, m), 5.80 (1H, d, J=2.4 Hz), 5.31 (2H, s), 3.58 (3H, s), 2.54 (3H, s), 2.36 (3H, s).

Preparation Example 64

A mixture of 1-(2-bromomethyl-3-methylphenyl)-4-methyl-1,4-dihydrotetrazole-5-one (described in Synthesis example 33) 0.28 g, 1-(2,3,4,5,6-pentafluorophenyl)-1H- pyrazole-3-ol (described in Reference Preparation example 51) 0.18 g, potassium carbonate 0.20 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2,3,4,5,6-pentafluorophenyl)-1H-pyrazole-3-yl]oxymethyl}-3-methylphenyl)-4-methyl-1,4-dihydrotetrazole-5-one (hereinafter, referred to as "Present compound 64") 0.22 g.

Present compound 64

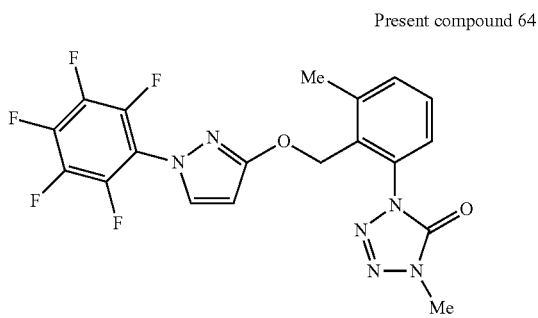 [SMILES: Cc1cccc(-n2nnn(C)c2=O)c1COc1ccn(-c2c(F)c(F)c(F)c(F)c2F)n1]

$^1$H-NMR (CDCl$_3$) δ (ppm): 7.39-7.35 (3H, m), 7.24-7.21 (1H, m 5.88 (1H, d, J=2.7 Hz), 5.28 (2H, s), 3.65 (3H, s), 2.54 (3H, s).

Preparation Example 65

A mixture of 1-(2-bromomethyl-3-methylphenyl)-4-methyl-1,4-dihydrotetrazole-5-one (described in Synthesis example 33) 0.46 g, 1-(2-chlorophenyl)-1H-pyrazole-3-ol (described in Reference Preparation example 46) 0.28 g, potassium carbonate 0.39 g and acetonitrile 10 mL was stirred with heating under reflux for six hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-chlorophenyl)-1H-pyrazole-3-yl]oxymethyl}-3-methylphenyl)-4-methyl-1,4-dihydrotetrazole-5-one (hereinafter, referred to as "Present compound 65") 0.46 g.

Present compound 65

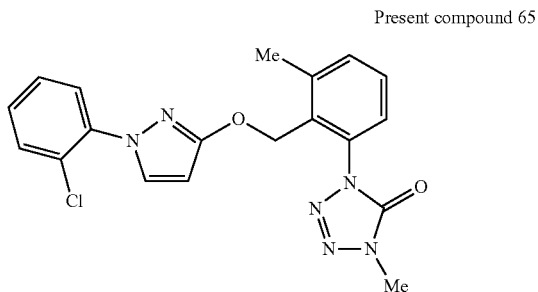

$^1$H-NMR (CDCl$_3$) δ (ppm): 7.70 (1H, d, J=2.7 Hz), 7.56 (1H, dd, J=8.0, 1.5 Hz), 7.48 (1H, d, J=8.0 Hz), 7.42-7.33 (3H, m), 7.28-7.23 (2H, m), 5.82 (1H, d, J=2.7 Hz), 5.31 (2H, s), 3.61 (3H, s), 2.55 (3H, s).

Preparation Example 66

A mixture of 1-(2-bromomethyl-3-ethoxyphenyl)-4-methyl-1,4-dihydrotetrazole-5-one (described in Synthesis example 26) 0.30 g, 1-(4-chlorophenyl)-1H-pyrazole-3-ol (described in Reference Preparation example 24) 0.23 g, potassium carbonate 0.17 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-ethoxyphenyl)-4-methyl-1,4-dihydrotetrazole-5-one (hereinafter, referred to as "Present compound 66") 0.27 g.

Present compound 66

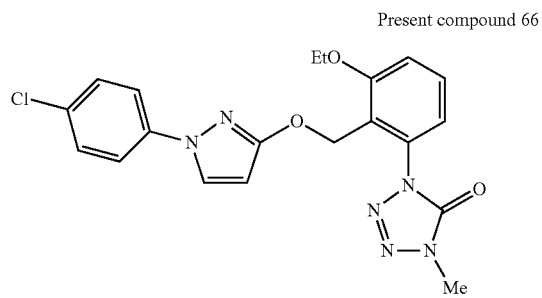

$^1$H-NMR (CDCl$_3$) δ (ppm): 7.63 (1H, d, J=2.7 Hz), 7.54-7.50 (2H, m), 7.43 (1H, dd, J=8.5, 8.0 Hz), 7.38-7.34 (2H, m), 7.06 (1H, d, J=8.5 Hz), 7.02 (1H, d, J=8.0 Hz), 5.80 (1H, d, J=2.7 Hz), 5.45 (2H, s), 4.14 (2H, q, J=7.0 Hz), 3.57 (3H, s), 1.43 (3H, t, J=7.0 Hz).

Preparation Example 67

A mixture of 1-(2-bromomethyl-3-ethoxyphenyl)-4-methyl-1,4-dihydrotetrazole-5-one (described in Synthesis example 26) 0.30 g, 1-(4-fluorophenyl)-1H-pyrazole-3-ol (described in Reference Preparation example 29) 0.21 g, potassium carbonate 0.17 g and acetonitrile 10 mL was stirred with heating under reflux for eight hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-fluorophenyl)-1H-pyrazole-3-yl]oxymethyl}-3-ethoxyphenyl)-4-methyl-1,4-dihydrotetrazole-5-one (hereinafter, referred to as "Present compound 67") 0.22 g.

Present compound 67

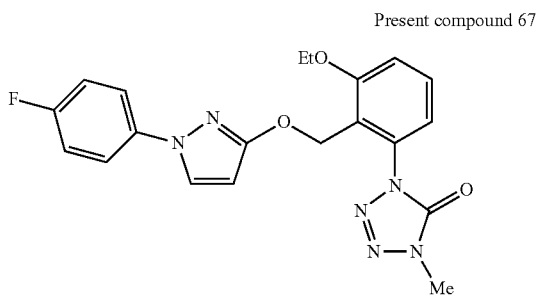

¹H-NMR (CDCl₃) δ (ppm): 7.59 (1H, d, J=2.4 Hz), 7.56-7.51 (2H, m), 7.43 (1H, t, J=8.2 Hz), 7.13-7.01 (4H, m), 5.78 (1H, d, J=2.4 Hz), 5.45 (2H, s), 4.14 (2H, q, J=6.9 Hz), 3.57 (3H, s), 1.43 (3H, t, J=7.0 Hz).

Preparation Example 68

A mixture of 1-(2-bromomethyl-3-ethoxyphenyl)-4-methyl-1,4-dihydrotetrazole-5-one (described in Synthesis example 26) 0.30 g, 1-(4-methoxyphenyl)-1H-pyrazole-3-ol (described in Reference Preparation example 26) 0.23 g, potassium carbonate 0.17 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-methoxyphenyl)-1H-pyrazole-3-yl]oxymethyl}-3-ethoxyphenyl)-4-methyl-1,4-dihydrotetrazole-5-one (hereinafter, referred to as "Present compound 68") 0.18 g.

Present compound 68

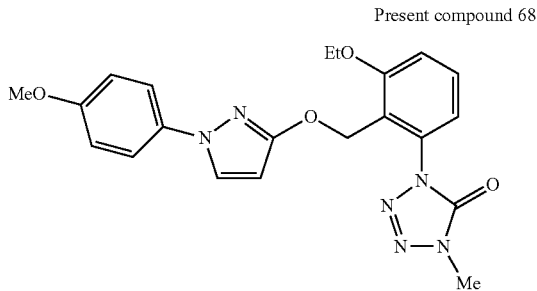

¹H-NMR (CDCl₃) δ (ppm): 7.56 (1H, d, J=2.4 Hz), 7.50-7.46 (2H, m), 7.43 (1H, dd, J=8.5, 8.0 Hz), 7.06 (1H, d, J=8.5 Hz), 7.02 (1H, d, J=8.0 Hz), 6.95-6.91 (2H, m), 5.75 (1H, d, J=2.4 Hz), 5.45 (2H, s), 4.14 (2H, q, J=7.0 Hz), 3.83 (3H, s), 3.55 (3H, s), 1.43 (3H, t, J=7.0 Hz).

Preparation Example 69

A mixture of 1-(2-bromomethyl-3-ethoxyphenyl)-4-methyl-1,4-dihydrotetrazole-5-one (described in Synthesis example 26) 0.30 g, 1-(4-bromophenyl)-1H-pyrazole-3-ol (described in Reference Preparation example 37) 0.28 g, potassium carbonate 0.17 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-bromophenyl)-1H-pyrazole-3-yl]oxymethyl}-3-ethoxyphenyl)-4-methyl-1,4-dihydrotetrazole-5-one (hereinafter, referred to as "Present compound 69") 0.20 g.

Present compound 69

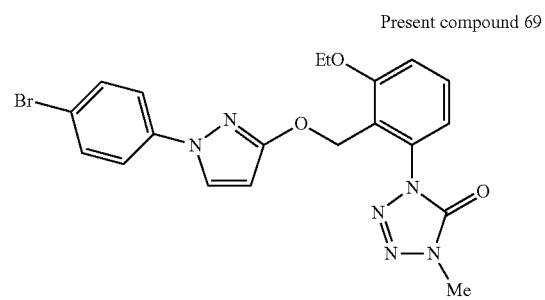

¹H-NMR (CDCl₃) δ (ppm): 7.64 (1H, d, J=2.7 Hz), 7.53-7.41 (5H, m), 7.06 (1H, d, J=8.2 Hz), 7.02 (1H, d, J=8.0 Hz), 5.81 (1H, d, J=2.7 Hz), 5.45 (2H, s), 4.14 (2H, q, J=7.0 Hz), 3.57 (3H, s), 1.43 (3H, t, J=7.0 Hz).

Preparation Example 70

A mixture of 1-(2-bromomethyl-3-ethoxyphenyl)-4-methyl-1,4-dihydrotetrazole-5-one (described in Synthesis example 26) 0.30 g, 1-phenyl-1H-pyrazole-3-ol (described in Reference Preparation example 25) 0.19 g, potassium carbonate 0.17 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-{2-[(1-phenyl-1H-pyrazole-3-yl)oxymethyl]-3-ethoxyphenyl}-4-methyl-1,4-dihydrotetrazole-5-one (hereinafter, referred to as "Present compound 70") 0.22 g.

Present compound 70

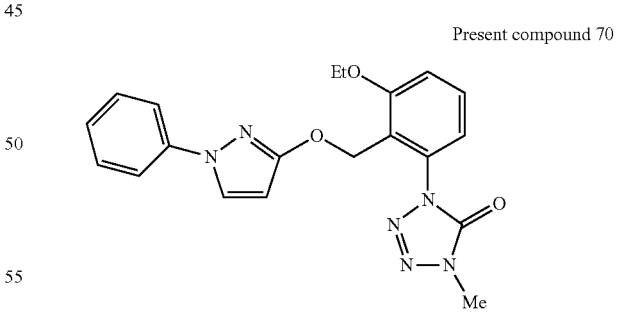

¹H-NMR (CDCl₃) δ (ppm): 7.67 (1H, d, J=2.2 Hz), 7.58 (2H, d, J=7.5 Hz), 7.45-7.39 (3H, m), 7.20 (1H, t, J=7.5 Hz), 7.07 (1H, d, J=8.5 Hz), 7.02 (1H, d, J=8.0 Hz), 5.79 (1H, d, J=2.2 Hz), 5.47 (2H, s), 4.15 (2H, q, J=7.0 Hz), 3.55 (3H, s), 1.44 (3H, t, J=7.0 Hz).

Preparation Example 71

A mixture of 1-(2-bromomethyl-3-methylthiophenyl)-4-methyl-1,4-dihydrotetrazole-5-one (described in Synthesis example 30) 0.20 g, 1-(4-chlorophenyl)-1H-pyrazole-3-ol (described in Reference Preparation example 24) 0.14 g, potassium carbonate 0.20 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-methylthiophenyl)-4-methyl-1,4-dihydrotetrazole-5-one (hereinafter, referred to as "Present compound 71") 0.24 g.

Present compound 71

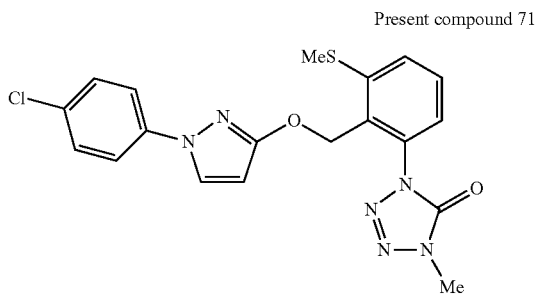

$^1$H-NMR (CDCl$_3$) δ (ppm): 7.64 (1H, d, J=2.7 Hz), 7.54-7.46 (4H, m), 7.38-7.34 (2H, m), 7.23 (1H, dd, J=6.2, 2.8 Hz), 5.84 (1H, d, J=2.7 Hz), 5.46 (2H, s), 3.60 (3H, s), 2.54 (3H, s).

Preparation Example 72

A mixture of 1-(2-bromomethyl-3-methylphenyl)-4-methyl-1,4-dihydrotetrazole-5-one (described in Synthesis example 33) 0.30 g, 1-(3-chlorophenyl)-1H-pyrazole-3-ol (described in Reference Preparation example 47) 0.21 g, potassium carbonate 0.29 g and acetonitrile 10 mL was stirred with heating under reflux for six hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-chlorophenyl)-1H-pyrazole-3-yl]oxymethyl}-3-methylphenyl)-4-methyl-1,4-dihydrotetrazole-5-one (hereinafter, referred to as "Present compound 72") 0.29 g.

Present compound 72

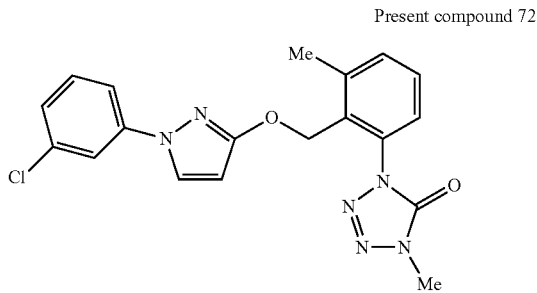 [SMILES: Cc1cccc(-n2nnn(C)c2=O)c1COc1ccn(-c2cccc(Cl)c2)n1]

$^1$H-NMR (CDCl$_3$) δ (ppm): 7.65 (1H, d, J=2.7 Hz), 7.60 (1H, t, J=2.1 Hz), 7.43-7.36 (3H, m), 7.30 (1H, t, J=8.1 Hz), 7.27-7.23 (1H, m), 7.16-7.14 (1H, m), 5.81 (1H, d, J=2.7 Hz), 5.34 (2H, s), 3.63 (3H, s), 2.55 (3H, s).

Preparation Example 73

A mixture of 1-(2-bromomethyl-3,6-dimethylphenyl)-4-methyl-1,4-dihydrotetrazole-5-one (described in Reference preparation example 79) 0.62 g, 1-(4-chlorophenyl)-1H-pyrazole-3-ol (described in Reference Preparation example 24) 0.41 g, potassium carbonate 0.35 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{([1-(4-chlorophenyl)-1H-pyrazole-3-yl]oxymethyl}-3,6-dimethylphenyl)-4-methyl-1,4-dihydrotetrazole-5-one (hereinafter, referred to as "Present compound 73") 0.85 g.

Present compound 73

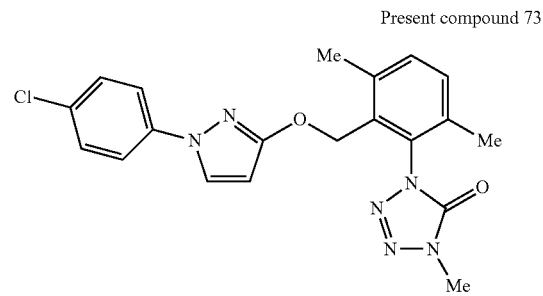 [SMILES: Cc1ccc(C)c(-n2nnn(C)c2=O)c1COc1ccn(-c2ccc(Cl)cc2)n1]

$^1$H-NMR (CDCl$_3$) δ (ppm): 7.64 (1H, d, J=2.7 Hz), 7.52-7.48 (2H, m), 7.37-7.33 (2H, m), 7.29 (1H, d, J=8.0 Hz), 7.24 (1H, d, J=8.0 Hz), 5.81 (1H, d, J=2.7 Hz), 5.26 (1H, d, J=11.9 Hz), 5.15 (1H, d, J=11.9 Hz), 3.59 (3H, s), 2.49 (3H, s), 2.13 (3H, s).

Preparation Example 74

A mixture of 1-(2-bromomethyl-3-methylphenyl)-4-methyl-1,4-dihydrotetrazole-5-one (described in Synthesis example 33) 0.30 g, 1-(4-trifluoroacetylphenyl)-1H-pyrazole-3-ol (described in Reference Preparation example 58) 0.29 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-trifluoroacetylphenyl)-1H-pyrazole-3-yl]oxymethyl}-3-methylphenyl)-4-methyl-1,4-dihydrotetrazole-5-one (hereinafter, referred to as "Present compound 74") 0.17 g.

Present compound 74

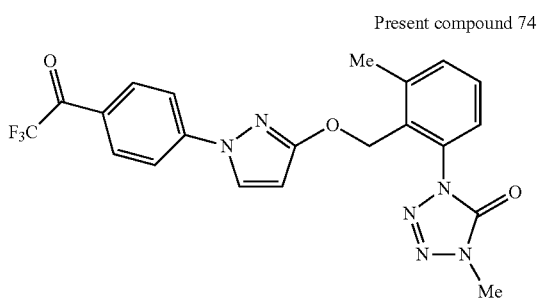 [SMILES: Cc1cccc(-n2nnn(C)c2=O)c1COc1ccn(-c2ccc(C(=O)C(F)(F)F)cc2)n1]

¹H-NMR (CDCl₃) δ (ppm): 8.14 (2H, d, J=8.7 Hz), 7.81 (1H, d, J=2.4 Hz), 7.72 (2H, d, J=8.7 Hz), 7.43-7.39 (2H, m), 7.29-7.24 (1H, m), 5.93 (1H, d, J=2.4 Hz), 5.37 (2H, s), 3.65 (3H, s), 2.57 (3H, s).

Preparation Example 75

A mixture of 1-(2-bromomethyl-3-methylphenyl)-4-methyl-1,4-dihydrotetrazole-5-one (described in Synthesis example 33) 0.30 g, 1-(4-nitrophenyl)-1H-pyrazole-3-ol (described in Reference Preparation example 56) 0.22 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-nitrophenyl)-1H-pyrazole-3-yl]oxymethyl}-3-methylphenyl)-4-methyl-1,4-dihydrotetrazole-5-one (hereinafter, referred to as "Present compound 75") 0.09 g.

Present compound 75

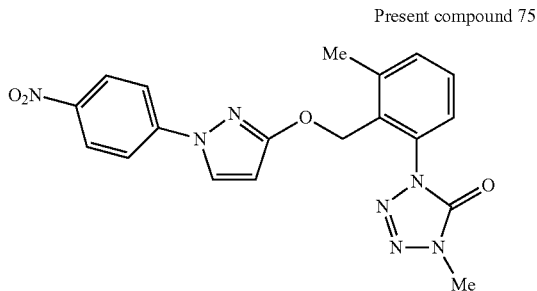 [SMILES: Cc1cccc(-n2nnn(C)c2=O)c1COc1ccn(-c2ccc([N+](=O)[O-])cc2)n1]

¹H-NMR (CDCl₃) δ (ppm): 8.30 (2H, d, J=9.2 Hz), 7.79 (1H, d, J=2.7 Hz), 7.70 (2H, d, J=9.2 Hz), 7.44-7.39 (2H, m), 7.29-7.26 (1H, m), 5.94 (1H, d, J=2.7 Hz), 5.36 (2H, s), 3.66 (3H, s), 2.57 (3H, s).

Preparation Example 76

A mixture of 1-(2-bromomethyl-3-methylphenyl)-4-methyl-1,4-dihydrotetrazole-5-one (described in Synthesis example 33) 0.30 g, 1-(2-fluorophenyl)-1H-pyrazole-3-ol (described in Reference Preparation example 48) 0.20 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-fluorophenyl)-1H-pyrazole-3-yl]oxymethyl}-3-methylphenyl)-4-methyl-1,4-dihydrotetrazole-5-one (hereinafter, referred to as "Present compound 76") 0.19 g.

Present compound 76

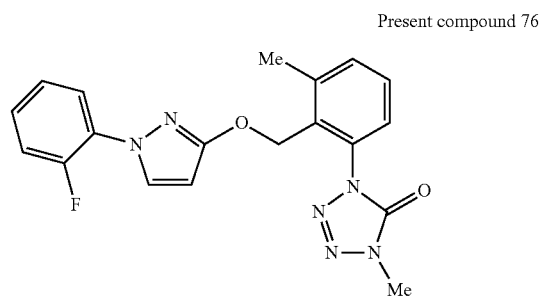 [SMILES: Cc1cccc(-n2nnn(C)c2=O)c1COc1ccn(-c2ccccc2F)n1]

¹H-NMR (CDCl₃) δ (ppm): 7.85-7.79 (2H, m), 7.42-7.38 (2H, m), 7.28-7.15 (4H, m), 5.83 (1H, d, J=2.5 Hz), 5.33 (2H, s), 3.62 (3H, s), 2.56 (3H, s).

Preparation Example 77

A mixture of 1-(2-bromomethyl-3-methylphenyl)-4-methyl-1,4-dihydrotetrazole-5-one (described in Synthesis example 33) 0.30 g, 1-(2-methylphenyl)-1H-pyrazole-3-ol (described in Reference Preparation example 49) 0.19 g, potassium carbonate 0.18 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methylphenyl)-1H-pyrazole-3-yl]oxymethyl}-3-methylphenyl)-4-methyl-1,4-dihydrotetrazole-5-one (hereinafter, referred to as "Present compound 77") 0.27 g.

Present compound 77

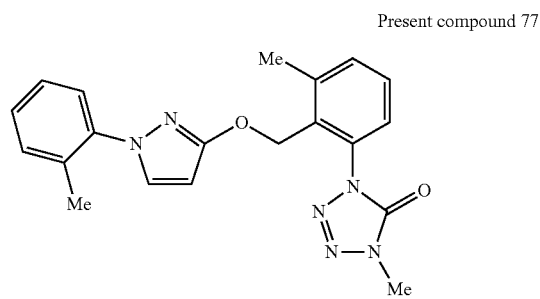

¹H-NMR (CDCl₃) δ (ppm): 7.41-7.36 (2H, m), 7.33 (1H, d, J=2.5 Hz), 7.30-7.23 (5H, m), 5.76 (1H, d, J=2.5 Hz), 5.30 (2H, s), 3.55 (3H, s), 2.55 (3H, s), 2.27 (3H, s).

Preparation Example 78

A mixture of 1-(2-bromomethyl-3-methylphenyl)-4-methyl-1,4-dihydrotetrazole-5-one (described in Synthesis example 33) 0.30 g, 1-(2-methoxyphenyl)-1H-pyrazole-3-ol (described in Reference Preparation example 50) 0.20 g, potassium carbonate 0.19 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methoxyphenyl)-1H-pyrazole-3-yl]oxymethyl}-3-methylphenyl)-4-methyl-1,4-dihydrotetrazole-5-one (hereinafter, referred to as "Present compound 78") 0.23 g.

Present compound 78

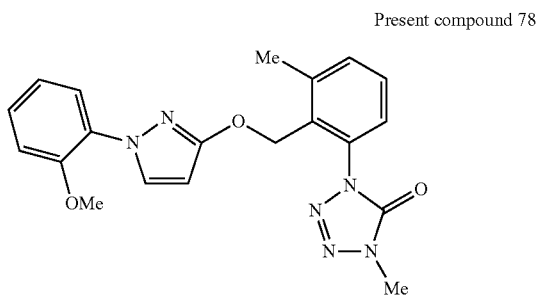 [SMILES: COc1ccccc1-n1ccc(OCc2c(C)cccc2-n2nnn(C)c2=O)n1]

$^1$H-NMR (CDCl$_3$) δ (ppm): 7.89 (1H, d, J=2.5 Hz), 7.70 (1H, dd, J=8.0, 1.6 Hz), 7.41-7.37 (2H, m), 7.26-7.18 (2H, m), 7.06-6.99 (2H, m), 5.76 (1H, d, J=2.5 Hz), 5.32 (2H, s), 3.88 (3H, s), 3.61 (3H, s), 2.55 (3H, s).

Preparation Example 79

A mixture of 1-(2-bromomethyl-3-methylphenyl)-4-methyl-1,4-dihydrotetrazole-5-one (described in Synthesis example 33) 0.30 g, 1-(2-bromophenyl)-1H-pyrazole-3-ol (described in Reference Preparation example 64) 0.25 g, potassium carbonate 0.18 g and acetonitrile 10 mL was stirred with heating under reflux for three hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-bromophenyl)-1H-pyrazole-3-yl]oxymethyl}-3-methylphenyl)-4-methyl-1,4-dihydrotetrazole-5-one (hereinafter, referred to as "Present compound 79") 0.34 g.

Present compound 79

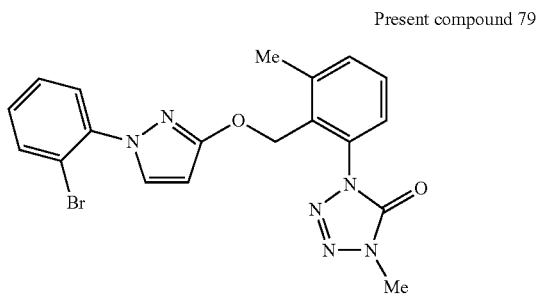 [SMILES: Cc1cccc(-n2nnn(C)c2=O)c1COc1ccn(-c2ccccc2Br)n1]

$^1$H-NMR (CDCl$_3$) δ (ppm): 7.67 (1H, dd, J=8.1, 1.0 Hz), 7.63 (1H, d, J=2.7 Hz), 7.50-7.48 (1H, m), 7.42-7.38 (3H, 7.28-7.19 (2H, m), 5.82 (1H, d, J=2.7 Hz), 5.31 (2H, s), 3.61 (3H, s), 2.55 (3H, s).

Preparation Example 80

A mixture of 1-(2-bromomethyl-3-methylphenyl)-4-methyl-1,4-dihydrotetrazole-5-one (described in Synthesis example 33) 0.30 g, 1-(3-fluorophenyl)-1H-pyrazole-3-ol (described in Reference Preparation example 72) 0.19 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-fluorophenyl)-1H-pyrazole-3-yl]oxymethyl}-3-methylphenyl)-4-methyl-1,4-dihydrotetrazole-5-one (hereinafter, referred to as "Present compound 80") 0.34 g.

Present compound 80

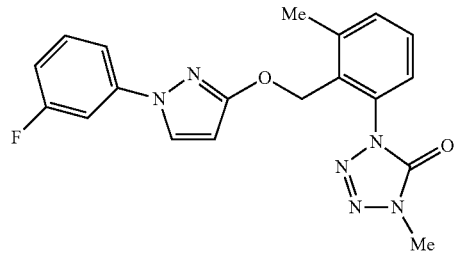

$^1$H-NMR (CDCl$_3$) δ (ppm): 7.67 (1H, d, J=2.7 Hz), 7.42-7.24 (6H, m), 6.92-6.87 (1H, m), 5.83 (1H, d, J=2.7 Hz), 5.34 (2H, s), 3.64 (3H, s), 2.56 (3H, s).

Preparation Example 81

A mixture of 1-(2-bromomethyl-3-methylphenyl)-4-methyl-1,4-dihydrotetrazole-5-one (described in Synthesis example 33) 0.30 g, 1-(3-methylphenyl)-1H-pyrazole-3-ol (described in Reference Preparation example 70) 0.19 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-methylphenyl)-1H-pyrazole-3-yl]oxymethyl}-3-methylphenyl)-4-methyl-1,4-dihydrotetrazole-5-one (hereinafter, referred to as "Present compound 81") 0.28 g.

Present compound 81

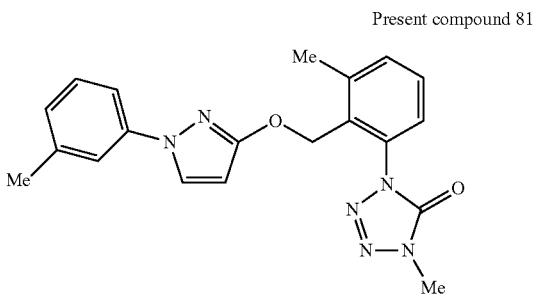 [SMILES: Cc1cccc(-n2ccc(OCc3c(C)cccc3-n3nnn(C)c3=O)n2)c1]

$^1$H-NMR (CDCl$_3$) δ (ppm): 7.67 (1H, d, J=2.7 Hz), 7.42-7.24 (6H, m), 7.02 (1H, d, J=7.3 Hz), 5.80 (1H, d, J=2.7 Hz), 5.34 (2H, s), 3.61 (3H, s), 2.56 (3H, s), 2.41 (3H, s).

Preparation Example 82

A mixture of 1-(2-bromomethyl-3-methylphenyl)-4-methyl-1,4-dihydrotetrazole-5-one (described in Synthesis example 33) 0.30 g, 1-(3-bromophenyl)-1H-pyrazole-3-ol (described in Reference Preparation example 66) 0.25 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-bromo-phenyl)-1H-pyrazole-3-yl]oxymethyl}-3-methylphenyl)-4-methyl-1,4-dihydrotetrazole-5-one (hereinafter, referred to as "Present compound 82") 0.37 g.

Present compound 82

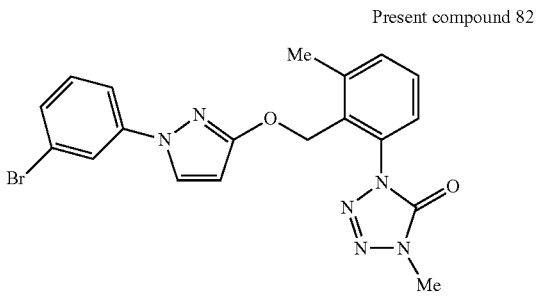

$^1$H-NMR (CDCl$_3$) δ (ppm): 7.76 (1H, t, J=1.9 Hz), 7.66 (1H, d, J=2.7 Hz), 7.49-7.46 (1H, m), 7.43-7.38 (2H, m), 7.33-7.24 (3H, m), 5.83 (1H, d, J=2.7 Hz), 5.33 (2H, s), 3.64 (3H, s), 2.56 (3H, s).

Preparation Example 83

A mixture of 1-(2-bromomethyl-3-methylphenyl)-4-methyl-1,4-dihydrotetrazole-5-one (described in Synthesis example 33) 0.30 g, 1-(3-methoxyphenyl)-1H-pyrazole-3-ol (described in Reference Preparation example 68) 0.20 g, potassium carbonate 0.18 g and acetonitrile 10 mL was stirred with heating under reflux for five hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-methoxyphenyl)-1H-pyrazole-3-yl]oxymethyl}-3-methylphenyl)-4-methyl-1,4-dihydrotetrazole-5-one (hereinafter, referred to as "Present compound 83") 0.19 g.

Present compound 83

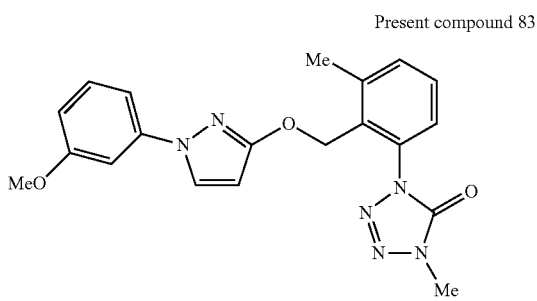 [SMILES: COc1cccc(-n2ccc(OCc3c(C)cccc3-n3nnn(C)c3=O)n2)c1]

$^1$H-NMR (CDCl$_3$) δ (ppm): 7.67 (1H, d, J=2.5 Hz), 7.42-7.37 (2H, m), 7.30 (1H, t, J=8.2 Hz), 7.27-7.22 (1H, m), 7.17 (1H, t, J=2.2 Hz), 7.11 (1H, dd, J=8.0, 1.8 Hz), 6.75 (1H, dd, J=8.2, 2.3 Hz), 5.80 (1H, d, J=2.5 Hz), 5.34 (2H, s), 3.87 (3H, s), 3.62 (3H, s), 2.57 (3H, s).

Preparation Example 84

A mixture of 1-(2-bromomethyl-3-methyl-4-fluorophenyl)-4-methyl-1,4-dihydrotetrazole-5-one (described in Reference Preparation example 92) 0.72 g, 1-(4-chlorophenyl)-1H-pyrazole-3-ol (described in Reference Preparation example 24) 0.47 g, potassium carbonate 0.40 g and acetonitrile 12 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chlorophenyl)-1H-pyrazole-3-yl]oxymethyl}-3-methyl-4-fluorophenyl)-4-methyl-1,4-dihydrotetrazole-5-one (hereinafter, referred to as "Present compound 84") 0.89 g.

Present compound 84

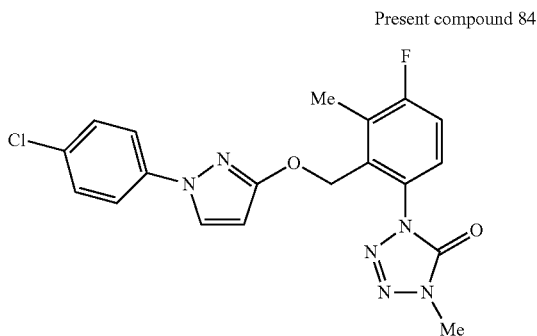 [SMILES: Cc1c(F)ccc(-n2nnn(C)c2=O)c1COc1ccn(-c2ccc(Cl)cc2)n1]

$^1$H-NMR (CDCl$_3$) δ (ppm): 7.65 (1H, d, J=2.7 Hz), 7.51-7.48 (2H, m), 7.39-7.35 (2H, m), 7.26-7.23 (1H, m), 7.18 (1H, t, J=8.7 Hz), 5.82 (1H, d, J=2.7 Hz), 5.31 (2H, s), 3.63 (3H, s), 2.45 (3H, d, J=2.4 Hz).

Preparation Example 85

A mixture of 1-(2-bromomethyl-3-methyl-6-fluorophenyl)-4-methyl-1,4-dihydrotetrazole-5-one (described in Reference Preparation example 86) 0.66 g, 1-(4-chlorophenyl)-1H-pyrazole-3-ol (described in Reference Preparation example 24) 0.43 g, potassium carbonate 0.37 g and acetonitrile 10 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{([1-(4-chlorophenyl)-1H-pyrazole-3-yl]oxymethyl}-3-methyl-6-fluorophenyl)-4-methyl-1,4-dihydrotetrazole-5-one (hereinafter, referred to as "Present compound 85") 0.82 g.

Present compound 85

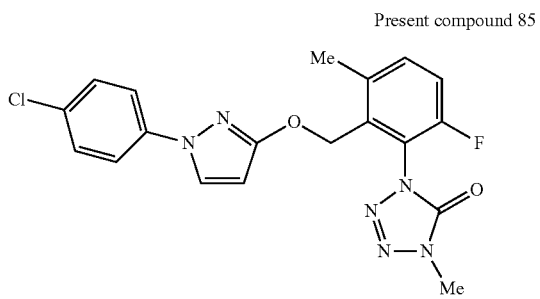 [SMILES: Cc1ccc(F)c(-n2nnn(C)c2=O)c1COc1ccn(-c2ccc(Cl)cc2)n1]

$^1$H-NMR (CDCl$_3$) δ (ppm): 7.65 (1H, d, J=2.7 Hz), 7.52-7.48 (2H, m), 7.39-7.36 (3H, m), 7.18 (1H, t, J=8.7 Hz), 5.82 (1H, d, J=2.7 Hz), 5.33 (1H, d, J=11.8 Hz), 5.22 (1H, d, J=11.8 Hz), 3.62 (3H, s), 2.51 (3H, s).

Preparation Example 86

A mixture of 1-(2-bromomethyl-3-chlorophenyl)-4-methyl-1,4-dihydrotetrazole-5-one (described in Synthesis example 6) 0.30 g, 1-(2-methoxyphenyl)-1H-pyrazole-3-ol (described in Reference Preparation example 50) 0.20 g, potassium carbonate 0.21 g and acetonitrile 10 mL was stirred with heating under reflux for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methoxyphenyl)-1H-pyrazole-3-yl]oxymethyl}-3-chlorophenyl)-4-methyl-1,4-dihydrotetrazole-5-one (hereinafter, referred to as "Present compound 86") 0.25 g.

Present compound 86

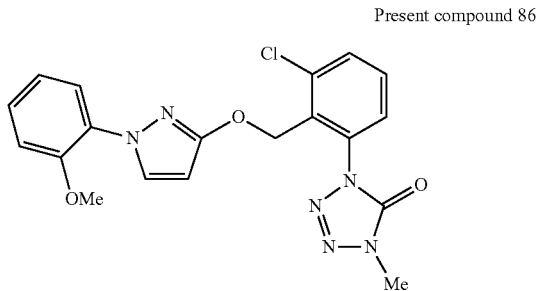 [SMILES: COc1ccccc1-n1ccc(OCc2c(Cl)cccc2-n2nnn(C)c2=O)n1]

$^1$H-NMR (CDCl$_3$) δ (ppm): 7.89 (1H, d, J=2.7 Hz), 7.71 (1H, dd, J=8.0, 1.6 Hz), 7.60 (1H, dd, J=8.0, 1.6 Hz), 7.45 (1H, t, J=8.0 Hz), 7.37 (1H, dd, J=7.9, 1.3 Hz), 7.21 (1H, ddd, J=8.6, 7.0, 1.2 Hz), 7.05 (1H, td, J=7.7, 1.3 Hz), 7.01 (1H, dd, J=8.2, 1.1 Hz), 5.75 (1H, d, J=2.7 Hz), 5.53 (2H, s), 3.88 (3H, s), 3.58 (3H, s).

Preparation Example 87

A mixture of 1-(2-bromomethyl-3-methoxyphenyl)-4-methyl-1,4-dihydrotetrazole-5-one (described in Synthesis example 17) 0.30 g, 1-(2-methoxyphenyl)-1H-pyrazole-3-ol (described in Reference Preparation example 50) 0.20 g, potassium carbonate 0.21 g and acetonitrile 10 mL was stirred with heating under reflux for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methoxyphenyl)-1H-pyrazole-3-yl]oxymethyl}-3-methoxyphenyl)-4-methyl-1,4-dihydrotetrazole-5-one (hereinafter, referred to as "Present compound 87") 0.21 g.

Present compound 87

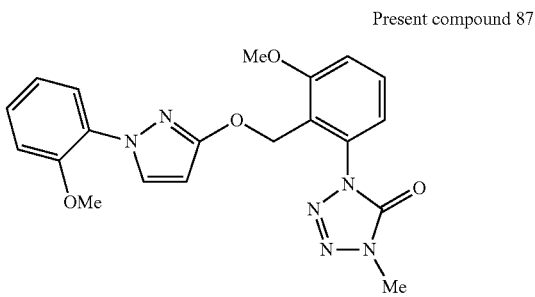

$^1$H-NMR (CDCl$_3$) δ (ppm): 7.88 (1H, d, J=2.5 Hz), 7.72 (1H, dd, J=8.1, 1.7 Hz), 7.46 (1H, t, J=8.1 Hz), 7.20 (1H, ddd, J=8.6, 7.0, 1.3 Hz), 7.09-6.99 (4H, m), 5.75 (1H, d, J=2.5 Hz), 5.43 (2H, s), 3.92 (3H, s), 3.88 (3H, s), 3.56 (3H, s).

Preparation Example 88

A mixture of 1-(2-bromomethyl-3-ethylphenyl)-4-methyl-1,4-dihydrotetrazole-5-one (described in Synthesis example 38) 0.30 g, 1-(2-methoxyphenyl)-1H-pyrazole-3-ol (described in Reference Preparation example 50) 0.20 g, potassium carbonate 0.21 g and acetonitrile 10 mL was stirred with heating under reflux for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methoxyphenyl)-1H-pyrazole-3-yl]oxymethyl}-3-ethylphenyl)-4-methyl-1,4-dihydrotetrazole-5-one (hereinafter, referred to as "Present compound 88") 0.27 g.

Present compound 88

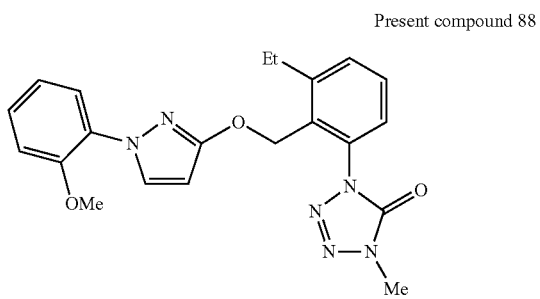

¹H-NMR (CDCl₃) δ (ppm): 7.89 (1H, d, J=2.5 Hz), 7.71 (1H, dd, J=8.0, 1.6 Hz), 7.47-7.42 (2H, m), 7.28-7.19 (2H, m), 7.07-7.00 (2H, m), 5.76 (1H, d, J=2.5 Hz), 5.33 (2H, s), 3.89 (3H, s), 3.60 (3H, s), 2.90 (2H, q, J=7.6 Hz), 1.30 (3H, t, J=7.6 Hz).

Preparation Example 89

A mixture of 1-(2-bromomethyl-3-cyclopropylphenyl)-4-methyl-1,4-dihydrotetrazole-5-one (described in Synthesis example 35) 0.30 g, 1-(2-methoxyphenyl)-1H-pyrazole-3-ol (described in Reference Preparation example 50) 0.19 g, potassium carbonate 0.20 g and acetonitrile 10 mL was stirred with heating under reflux for seven hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-methoxyphenyl)-1H-pyrazole-3-yl]oxymethyl}-3-cyclopropylphenyl)-4-methyl-1,4-dihydrotetrazole-5-one (hereinafter, referred to as "Present compound 89") 0.23 g.

Present compound 89

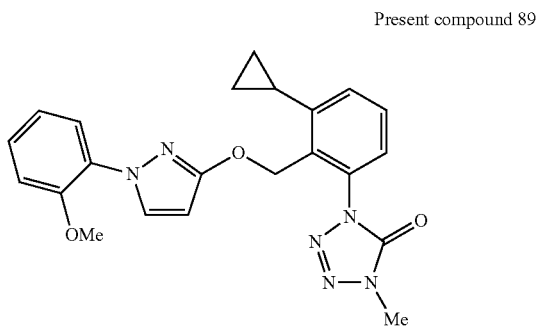 [SMILES: COc1ccccc1-n1ccc(OCc2c(C3CC3)cccc2-n2nnn(C)c2=O)n1]

¹H-NMR (CDCl₃) δ (ppm): 7.90 (1H, d, J=2.5 Hz), 7.72 (1H, dd, J=7.9, 1.7 Hz), 7.41 (1H, t, J=7.9 Hz), 7.25-7.19 (3H, m), 7.07-7.00 (2H, m), 5.77 (1H, d, J=2.5 Hz), 5.52 (2H, s), 3.89 (3H, s), 3.60 (3H, s), 2.25 (1H, tt, J=8.5, 3.9 Hz), 1.02 (2H, ddd, J=9.7, 5.1, 3.4 Hz), 0.79-0.75 (2H, m).

Preparation Example 90

A mixture of Present compound 180.90 g, 4-ethylphenylboronic acid 0.56 g, copper(II) acetate 0.85 g, pyridine 0.53 mL, molecular sieve 4A 1.00 g and acetonitrile 15 mL was stirred with heating under reflux for 10 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-ethylphenyl)-1H-pyrazole-3-yl]oxymethyl}-3-methylphenyl)-4-methyl-1,4-dihydrotetrazole-5-one (hereinafter, referred to as "Present compound 90") 0.39 g.

Present compound 90

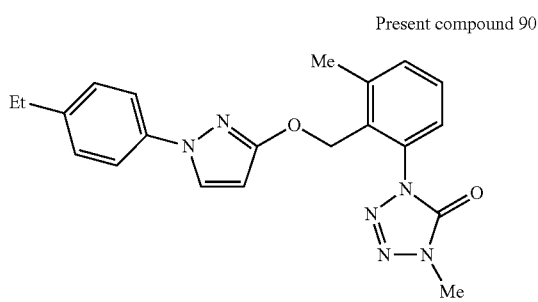 [SMILES: CCc1ccc(-n2ccc(OCc3c(C)cccc3-n3nnn(C)c3=O)n2)cc1]

¹H-NMR (CDCl₃) δ (ppm): 7.64 (1H, d, J=2.5 Hz), 7.47 (2H, d, J=7.6 Hz), 7.41-7.37 (2H, m), 7.26-7.22 (3H, m), 5.78 (1H, d, J=2.5 Hz), 5.33 (2H, s), 3.61 (3H, s), 2.66 (2H, q, J=7.6 Hz), 2.56 (3H, s), 1.25 (3H, t, J=7.6 Hz).

Preparation Example 91

A mixture of Present compound 180.90 g, 4-trifluoromethylphenylboronic acid 0.71 g, copper(II) acetate 0.85 g, pyridine 0.53 mL, molecular sieve 4A 1.00 g and acetonitrile 15 mL was stirred with heating under reflux for 10 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-trifluoromethylphenyl)-1H-pyrazole-3-yl]oxymethyl}-3-methylphenyl)-4-methyl-1,4-dihydrotetrazole-5-one (hereinafter, referred to as "Present compound 91") 0.33 g.

Present compound 91

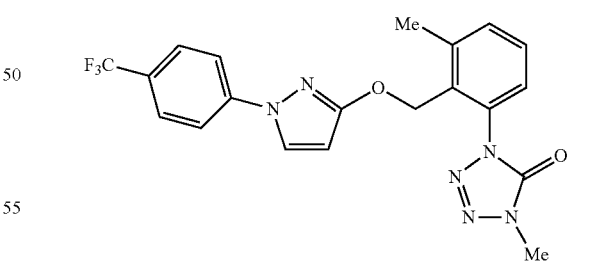

¹H-NMR (CDCl₃) δ (ppm): 7.75 (1H, d, J=2.3 Hz), 7.67 (4H, s), 7.43-7.38 (2H, m), 7.28-7.25 (1H, m), 5.88 (1H, d, J=2.3 Hz), 5.35 (2H, s), 3.64 (3H, s), 2.57 (3H, s).

Preparation Example 92

A mixture of Present compound 180.60 g, 1-naphthylboronic acid 0.45 g, copper(II) acetate 0.57 g, pyridine 0.36 mL, molecular sieve 4A 1.00 g and acetonitrile 15 mL was stirred with heating under reflux for 9 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(1-naphthyl)-1H-pyrazole-3-yl]oxymethyl}-3-methylphenyl)-4-methyl-1,4-dihydrotetrazole-5-one (hereinafter, referred to as "Present compound 92") 0.28 g.

Present compound 92

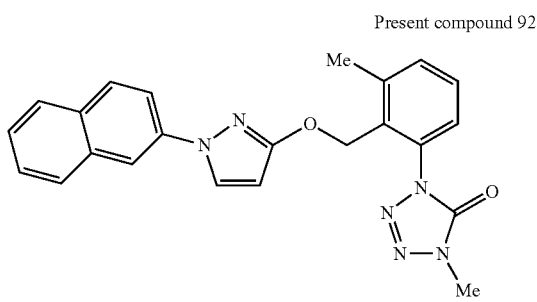 [SMILES: Cc1cccc(-n2nnn(C)c2=O)c1COc1ccn(-c2ccc3ccccc3c2)n1]

$^1$H-NMR (CDCl$_3$) δ: 7.98 (1H, d, J=1.6 Hz), 7.90-7.88 (2H, m), 7.84-7.82 (2H, m), 7.76 (1H, dd, J=8.8, 1.9 Hz), 7.51 (1H, dd, J=7.9, 7.0 Hz), 7.45 (1H, dd, J=8.0, 6.9 Hz), 7.41-7.40 (2H, m), 7.27-7.26 (1H, m), 5.87 (1H, d, J=2.5 Hz), 5.39 (2H, s), 3.60 (3H, s), 2.59 (3H, s).

Preparation Example 93

A mixture of Present compound 181.00 g, 5-chloro-2-methoxyphenylboronic acid 0.78 g, copper(II) acetate 0.98 g, pyridine 0.59 mL, molecular sieve 4A 1.50 g and acetonitrile 10 mL was stirred with heating under reflux for 20 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(5-chloro-2-methoxyphenyl)-1H-pyrazole-3-yl]oxymethyl}-3-methylphenyl)-4-methyl-1,4-dihydrotetrazole-5-one (hereinafter, referred to as "Present compound 93") 0.17 g.

Present compound 93

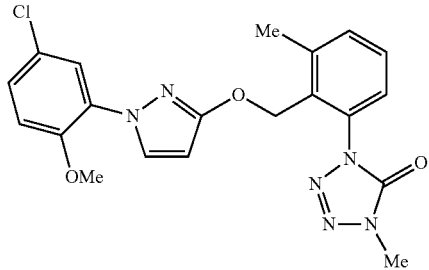

$^1$H-NMR (CDCl$_3$) δ: 7.94 (1H, d, J=2.7 Hz), 7.74 (1H, d, J=2.5 Hz), 7.41-7.39 (2H, m), 7.27-7.25 (1H, m), 7.14 (1H, dd, J=8.8, 2.6 Hz), 6.92 (1H, d, J=8.7 Hz), 5.77 (1H, d, J=2.5 Hz), 5.32 (2H, s), 3.88 (3H, s), 3.65 (3H, s), 2.56 (3H, s).

Preparation Example 94

A mixture of Present compound 181.00 g, 2-ethoxyphenylboronic acid 0.70 g, copper(II) acetate 0.98 g, pyridine 0.59 mL, molecular sieve 4A 1.50 g and acetonitrile 15 mL was stirred with heating under reflux for 10 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-ethoxyphenyl)-1H-pyrazole-3-yl]oxymethyl}-3-methylphenyl)-4-methyl-1,4-dihydrotetrazole-5-one (hereinafter, referred to as "Present compound 94") 0.39 g.

Present compound 94

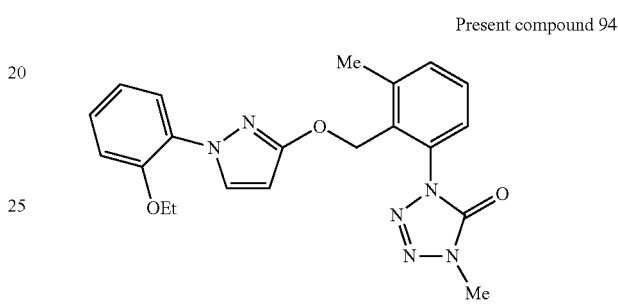

$^1$H-NMR (CDCl$_3$) δ: 7.98 (1H, d, J=2.7 Hz), 7.73 (1H, dd, J=8.0, 1.7 Hz), 7.41-7.39 (2H, m), 7.27-7.25 (1H, m), 7.17 (1H, ddd, J=8.7, 7.0, 1.2 Hz), 7.03 (1H, td, J=7.7, 1.2 Hz), 6.99 (1H, dd, J=8.2, 1.2 Hz), 5.76 (1H, d, J=2.7 Hz), 5.32 (2H, s), 4.10 (2H, q, J=7.0 Hz), 3.62 (3H, s), 2.56 (3H, s), 1.43 (3H, t, J=7.0 Hz).

Preparation Example 95

A mixture of Present compound 180.80 g, 2-isopropoxyphenylboronic acid 0.60 g, copper(II) acetate 0.76 g, pyridine 0.50 mL, molecular sieve 4A 1.00 g and acetonitrile 15 mL was stirred with heating under reflux for 10 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(2-isopropoxyphenyl)-1H-pyrazole-3-yl]oxymethyl}-3-methylphenyl)-4-methyl-1,4-dihydrotetrazole-5-one (hereinafter, referred to as "Present compound 95") 0.31 g.

Present compound 95

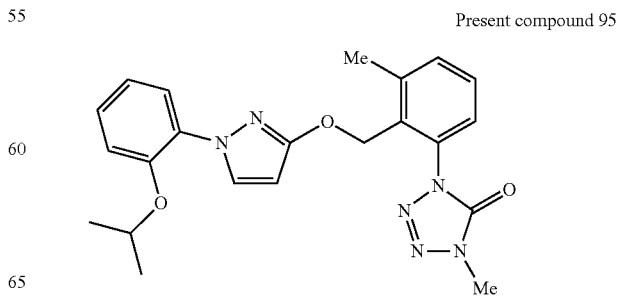

¹H-NMR (CDCl₃) δ: 7.98 (1H, d, J=2.4 Hz), 7.72 (1H, dd, J=8.0, 1.7 Hz), 7.41-7.39 (2H, m), 7.27-7.24 (1H, m), 7.16 (1H, td, J=7.6, 1.5 Hz), 7.04-6.99 (2H, m), 5.75 (1H, d, J=2.7 Hz), 5.32 (2H, s), 4.55 (1H, sept), 3.61 (3H, s), 2.56 (3H, s), 1.33 (6H, d, J=6.3 Hz).

Preparation Example 96

A mixture of Present compound 181.00 g, 4-chloro-2-methoxyphenylboronic acid 0.78 g, copper(II) acetate 0.98 g, pyridine 0.59 mL, molecular sieve 4A 1.50 g and acetonitrile 15 mL was stirred with heating under reflux for 15 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(4-chloro-2-methoxyphenyl)-1H-pyrazole-3-yl]oxymethyl}-3-methylphenyl)-4-methyl-1,4-dihydrotetrazole-5-one (hereinafter, referred to as "Present compound 96") 0.15 g.

Present compound 96

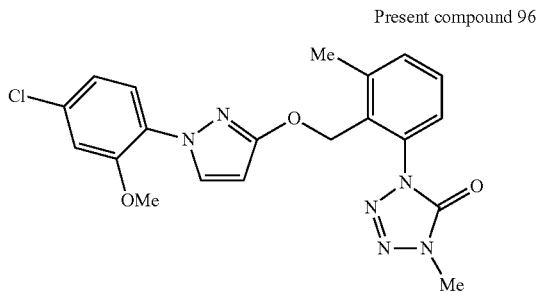 [SMILES: COc1cc(Cl)ccc1-n1ccc(OCc2c(C)cccc2-n2nnn(C)c2=O)n1]

¹H-NMR (CDCl₃) δ: 7.87 (1H, d, J=2.5 Hz), 7.65 (1H, d, J=8.5 Hz), 7.42-7.37 (2H, m), 7.26-7.24 (1H, m), 7.03 (1H, dd, J=8.5, 2.3 Hz), 6.99 (1H, d, J=2.3 Hz), 5.77 (1H, d, J=2.5 Hz), 5.30 (2H, s), 3.89 (3H, s), 3.63 (3H, s), 2.55 (3H, s).

Preparation Example 97

A mixture of Present compound 181.00 g, 3-chloro-2-methoxyphenylboronic acid 0.78 g, copper(II) acetate 0.98 g, pyridine 0.59 mL, molecular sieve 4A 1.50 g and acetonitrile 15 mL was stirred with heating under reflux for 48 hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-{[1-(3-chloro-2-methoxyphenyl)-1H-pyrazole-3-yl]oxymethyl}-3-methylphenyl)-4-methyl-1,4-dihydrotetrazole-5-one (hereinafter, referred to as "Present compound 97") 0.10 g.

Present compound 97

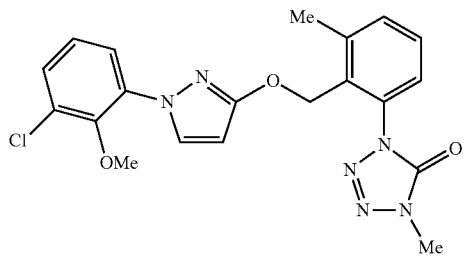

¹H-NMR (CDCl₃) δ: 7.95 (1H, d, J=2.5 Hz), 7.61 (1H, dd, J=8.1, 1.7 Hz), 7.43-7.38 (2H, m), 7.28-7.23 (2H, m), 7.13 (1H, t, J=8.1 Hz), 5.83 (1H, d, J=2.5 Hz), 5.33 (2H, s), 3.68 (3H, s), 3.61 (3H, s), 2.56 (3H, s).

Next, the Synthesis examples for preparing Present tetrazolinone compound X and Present tetrazolinone compound Y are shown below.

Synthesis Example 1

Anhydrous aluminium chloride 21.9 g was added to N,N-dimethylformamide 250 mL under ice-cooling, and the mixtures were stirred for fifteen minutes. Thereto was added sodium azide 10.7 g and the mixtures were stirred for fifteen minutes. Thereto was then added 1-fluoro-3-isocyanato-2-methylbenzene 22.5 g and the resulting mixtures were heated at 80° C. for three and a half hours. After cooling, the reaction solutions were added to a mixture of sodium nitrite 34 g, water 2 L and ice 500 g with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 1-(2-methyl-3-fluorophenyl)-1,4-dihydrotetrazole-5-one 27.5 g.

1-(2-methyl-3-fluorophenyl)-1,4-dihydrotetrazole-5-one

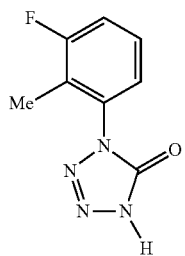 [SMILES: Cc1c(F)cccc1-n1nn[nH]c1=O]

¹H-NMR (CDCl₃) δ (ppm): 2.21 (3H, s), 7.07-7.36 (3H, m), 12.93 (1H, s).

Synthesis Example 2

To a mixture of 1-(2-methyl-3-fluorophenyl)-1,4-dihydrotetrazole-5-one (described in Synthesis example 1) 10.00 g and N,N-dimethylformamide 100 mL was added 600 sodium hydride 2.47 g under ice-cooling. The reaction mixtures were raised to room temperature and were stirred for one hour. To the reaction mixtures was added methyl iodide 3.5 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-fluorophenyl)-4-methyl-1,4-dihydrotetrazole-5-one 2.19 g.

1-(2-methyl-3-fluorophenyl)-4-methyl-1,4-dihydro-tetrazole-5-one

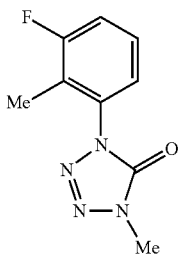 [SMILES: Cc1c(F)cccc1-n1nnn(C)c1=O]

$^1$H-NMR (CDCl$_3$) δ (ppm): 2.19 (3H, s), 3.70 (3H, s), 7.16-7.20 (2H, m), 7.29 (1H, dt, J=5.9, 8.3 Hz).

Synthesis Example 3

To a mixture of 1-(2-methyl-3-fluorophenyl)-4-methyl-1,4-dihydrotetrazole-5-one (described in Synthesis example 2) 2.19 g, 1,1'-azobis(cyclohexane-1-carbonitrile) 0.52 g, N-bromosuccinimide 2.16 g and chlorobenzene 40 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-fluorophenyl)-4-methyl-1,4-dihydrotetrazole-5-one 2.36 g.

1-(2-bromomethyl-3-fluorophenyl)-4-methyl-1,4-dihydrotetrazole-5-one

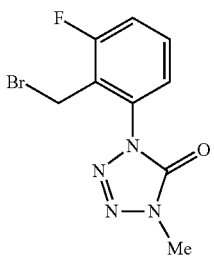 [SMILES: Cn1nnn(-c2cccc(F)c2CBr)c1=O]

$^1$H-NMR (CDCl$_3$) δ (ppm): 3.75 (3H, s), 4.64 (2H, s), 7.23-7.30 (2H, m), 7.47 (1H, dt, J=5.9, 8.0 Hz).

Synthesis Example 4

Anhydrous aluminium chloride 21.9 g was added to N,N-dimethylformamide 250 mL under ice-cooling, and the mixtures were stirred for fifteen minutes. Thereto was added sodium azide 10.7 g and the mixtures were stirred for fifteen minutes. Thereto was then added 1-chloro-3-isocyanato-2-methylbenzene 25.0 g and the resulting mixtures were heated at 80° C. for five hours. After cooling, the reaction solutions were added to a mixture of sodium nitrite 35 g, water 2 L and ice 500 g with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 1-(2-methyl-3-chlorophenyl)-1,4-dihydrotetrazole-5-one 17.0 g.

1-(2-methyl-3-chlorophenyl)-1,4-dihydrotetrazole-5-one

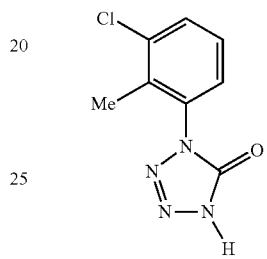

$^1$H-NMR (CDCl$_3$) δ (ppm): 2.32 (3H, s), 7.28-7.36 (2H, m), 7.57 (1H, dd, J=6.8, 2.2 Hz), 13.08 (1H, s).

Synthesis Example 5

To a mixture of 1-(2-methyl-3-chlorophenyl)-1,4-dihydrotetrazole-5-one (described in Synthesis example 4) 10.00 g and N,N-dimethylformamide 100 mL was added 600 sodium hydride 2.30 g under ice-cooling. The reaction mixtures were raised to room temperature and were stirred for one hour. To the reaction mixtures was added methyl iodide 3.2 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-chlorophenyl)-4-methyl-1,4-dihydrotetrazole-5-one 1.56 g.

1-(2-methyl-3-chlorophenyl)-4-methyl-1,4-dihydro-tetrazole-5-one

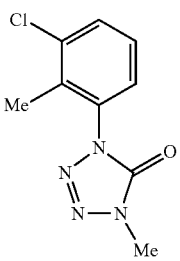 [SMILES: Cc1c(Cl)cccc1-n1nnn(C)c1=O]

$^1$H-NMR (CDCl$_3$) δ (ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Synthesis Example 6

To a mixture of 1-(2-methyl-3-chlorophenyl)-4-methyl-1,4-dihydrotetrazole-5-one (described in Synthesis example 5) 1.56 g, 1,1'-azobis(cyclohexane-1-carbonitrile) 0.34 g, N-bromosuccinimide 1.42 g and chlorobenzene 30 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-chlorophenyl)-4-methyl-1,4-dihydrotetrazole-5-one 1.94 g.

1-(2-bromomethyl-3-chlorophenyl)-4-methyl-1,4-dihydrotetrazole-5-one

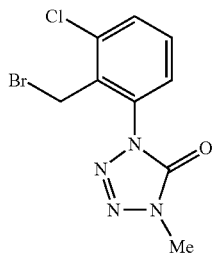 [SMILES: Cn1nnn(-c2cccc(Cl)c2CBr)c1=O]

$^1$H-NMR (CDCl$_3$) δ (ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Synthesis Example 7

A mixture of 3-chloro-2-methybenzoic acid 21.5 g, oxalyl dichloride 17.6 g, N,N-dimethylformamide about 50 mg and tetrahydrofuran 300 mL was stirred at 25° C. for one hour. The reaction mixtures were concentrated under reduced pressure to give 3-chloro-2-methylbenzoic acid chloride.

A mixture of aluminium chloride 33.6 g, sodium azide 49.2 g and tetrahydrofuran 100 mL was stirred with heating under reflux for two hours. After the reaction mixtures were ice-cooled, and thereto was added a mixture of 3-chloro-2-methylbenzoic acid chloride and tetrahydrofuran 100 mL and the resulting mixtures were stirred with heating under reflux for ten hours. After cooling the mixtures, to a mixture of sodium nitrite 75.6 g and water 500 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-chlorophenyl)-1,4-dihydrotetrazole-5-one.

A mixture of 1-(2-methyl-3-chlorophenyl)-1,4-dihydrotetrazole-5-one, potassium carbonate 57.5 g, dimethyl sulfate 19.1 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures, were concentrated under reduced pressure to give 1-(2-methyl-3-chlorophenyl)-4-methyl-1,4-dihydrotetrazole-5-one 21.6 g.

Synthesis Example 8

Under cooling, to a mixture of methyl chloroformate 30 mL and tetrahydrofuran 50 mL was added dropwise 3-amino-1-chloro-2-methylbenzene 5.00 g and the mixtures were stirred at 25° C. for a half hour. To the reaction mixtures was added water and the resulting mixtures were extracted with ethyl acetate. The organic layers were washed with aqueous saturated sodium bicarbonate solution and were dried over anhydrous sodium sulfate. The mixtures were concentrated under reduced pressure to give 1-chloro-2-methyl-3-methoxycarbonylaminobenzene 5.80 g.

A mixture of 1-chloro-2-methyl-3-methoxycarbonylaminobenzene 5.80 g, phosphorus pentachloride 7.53 g and chlorobenzene 50 mL was stirred with heating under reflux for one hour. The reaction mixtures were concentrated under reduced pressure to give 1-chloro-3-isocyanato-2-methylbenzene.

A mixture of aluminium chloride 4.71 g, sodium azide 6.89 g and tetrahydrofuran 100 mL was stirred with heating under reflux for one hour. After the reaction mixtures were ice-cooled, thereto were added a mixture of the above-mentioned 1-chloro-3-isocyanato-2-methylbenzene and tetrahydrofuran 10 mL and the resulting mixtures were stirred with heating under reflux for five hours. After cooling the mixtures, to a mixture of sodium nitrite 10.59 g and water 300 mL was added the reaction mixtures with stirring. The mixtures were acidified with concentrated hydrochloric acid and were extracted with ethyl acetate. The organic layers were dried over anhydrous sodium sulfate and were then concentrated under reduced pressure to give 1-(2-methyl-3-chlorophenyl)-1,4-dihydrotetrazole-5-one.

A mixture of the above-mentioned 1-(2-methyl-3-chlorophenyl)-1,4-dihydrotetrazole-5-one, potassium carbonate 16.11 g, dimethyl sulfate 5.34 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The mixtures were concentrated under reduced pressure to give 1-(2-methyl-3-chlorophenyl)-4-methyl-1,4-dihydrotetrazole-5-one 4.80 g.

Synthesis Example 9

Anhydrous aluminium chloride 19.7 g was added to N,N-dimethylformamide 220 mL under ice-cooling, and the mixtures were stirred for fifteen minutes. Thereto was added sodium azide 9.6 g and the mixtures were stirred for fifteen minutes. Thereto was then added 1-bromo-3-isocyanato-2-methylbenzene (described in Reference preparation example 1) 30.3 g and the resulting mixtures were heated at 80° C. for five hours. After cooling, the reaction solutions were added to a mixture of sodium nitrite 33 g, water 2 L and ice 500 g with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 1-(2-methyl-3-bromophenyl)-1,4-dihydrotetrazole-5-one 31.4 g.

1-(2-methyl-3-bromophenyl)-1,4-dihydrotetrazole-5-one

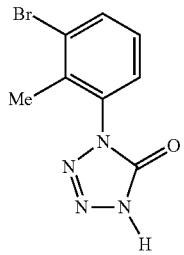 [SMILES: Cc1c(Br)cccc1-n1nn[nH]c1=O]

$^1$H-NMR (DMSO-d$_6$) δ (ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Synthesis Example 10

To a mixture of 1-(2-methyl-3-bromophenyl)-1,4-dihydrotetrazole-5-one (described in Synthesis example 9) 31.40 g and N,N-dimethylformamide 250 mL was added 60% sodium hydride 5.90 g under ice-cooling. The reaction mixtures were raised to room temperature and were stirred for one hour. To the reaction mixtures was added methyl iodide 8.4 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-bromophenyl)-4-methyl-1,4-dihydrotetrazole-5-one 8.47 g.

1-(2-methyl-3-bromophenyl)-4-methyl-1,4-dihydrotetrazole-5-one

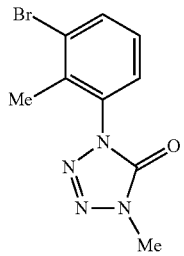

$^1$H-NMR (CDCl$_3$) δ (ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Synthesis Example 11

To a mixture of 1-(2-methyl-3-bromophenyl)-4-methyl-1,4-dihydrotetrazole-5-one (described in Synthesis example 10) 8.47 g, 1,1'-azobis(cyclohexane-1-carbonitrile) 1.54 g, N-bromosuccinimide 6.44 g and chlorobenzene 125 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-bromophenyl)-4-methyl-1,4-dihydrotetrazole-5-one 7.52 g.

1-(2-bromomethyl-3-bromophenyl)-4-methyl-1,4-dihydrotetrazole-5-one

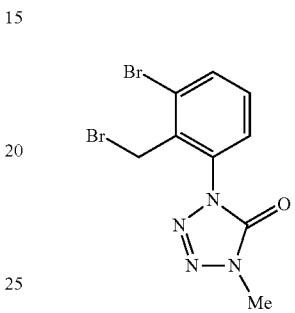

$^1$H-NMR (CDCl$_3$) δ (ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Synthesis Example 12

A mixture of 3-bromo-2-methybenzoic acid 146.0 g, oxalyl dichloride 94.8 g, N,N-dimethylformamide about 15 mg and tetrahydrofuran 500 mL was stirred at 25° C. for one hour. The reaction mixtures were concentrated under reduced pressure to give 3-bromo-2-methylbenzoic acid chloride.

A mixture of aluminium chloride 181.0 g, sodium azide 265.0 g and tetrahydrofuran 300 mL was stirred with heating under reflux for two hours. After the reaction mixtures were ice-cooled, and thereto was added a mixture of 3-bromo-2-methylbenzoic acid chloride and tetrahydrofuran 200 mL and the resulting mixtures were stirred with heating under reflux for ten hours. After cooling the mixtures, to a mixture of sodium nitrite 407 g and water 1,500 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-bromophenyl)-1,4-dihydrotetrazole-5-one.

A mixture of 1-(2-methyl-3-bromophenyl)-1,4-dihydrotetrazole-5-one, potassium carbonate 310.0 g, dimethyl sulfate 103.0 g and N,N-dimethylformamide 500 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methyl-3-bromophenyl)-4-methyl-1,4-dihydrotetrazole-5-one 142.0 g.

Synthesis Example 13

A mixture of 3-iodo-2-methybenzoic acid 10.00 g, oxalyl dichloride 5.33 g, N,N-dimethylformamide 5 drops and tetrahydrofuran 200 mL was stirred at 25° C. for one hour. The reaction mixtures were concentrated under reduced pressure to give 3-iodo-2-methylbenzoic acid chloride.

A mixture of aluminium chloride 10.20 g, sodium azide 14.90 g and tetrahydrofuran 100 mL was stirred with heating under reflux for two hours. After the reaction mixtures were ice-cooled, and thereto was added a mixture of 3-iodo-2-methylbenzoic acid chloride and tetrahydrofuran 100 mL and the resulting mixtures were stirred with heating under reflux for ten hours. After cooling the mixtures, to a mixture of sodium nitrite 22.90 g and water 200 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-iodophenyl)-1,4-dihydrotetrazole-5-one.

A mixture of 1-(2-methyl-3-iodophenyl)-1,4-dihydrotetrazole-5-one, potassium carbonate 17.40 g, dimethyl sulfate 5.78 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methyl-3-iodophenyl)-4-methyl-1,4-dihydrotetrazole-5-one 8.10 g.

1-(2-methyl-3-iodophenyl)-4-methyl-1,4-dihydrotetrazole-5-one

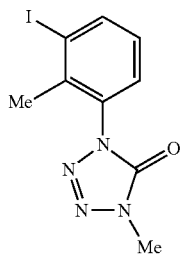

$^1$H-NMR (CDCl$_3$) δ (ppm): 2.37 (3H, s), 3.72 (3H, s), 7.04 (1H, t, J=8.0 Hz), 7.32 (1H, d, J=7.7 Hz), 7.99 (1H, d, 8.0 Hz).

Synthesis Example 14

To a mixture of 1-(2-methyl-3-iodophenyl)-4-methyl-1,4-dihydrotetrazole-5-one (described in Synthesis example 13) 8.10 g, 1,1'-azobis(cyclohexane-1-carbonitrile) 1.25 g, N-bromosuccinimide 5.24 g and chlorobenzene 100 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-iodophenyl)-4-methyl-1,4-dihydrotetrazole-5-one 3.11 g.

1-(2-bromomethyl-3-iodophenyl)-4-methyl-1,4-dihydrotetrazole-5-one

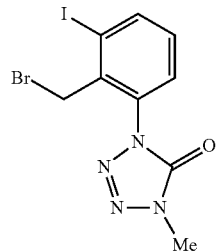 [SMILES: Cn1nnn(-c2cccc(I)c2CBr)c1=O]

$^1$H-NMR (CDCl$_3$) δ (ppm): 3.75 (3H, s), 4.71 (2H, s), 7.17 (1H, t, J=8.0 Hz), 7.39 (1H, d, J=8.0 Hz), 8.04 (1H, d, J=8.0 Hz).

Synthesis Example 15

Anhydrous aluminium chloride 16.0 g was added to N,N-dimethylformamide 180 mL under ice-cooling, and the mixtures were stirred for fifteen minutes. Thereto was added sodium azide 7.8 g and the mixtures were stirred for fifteen minutes. Thereto was then added 1-methoxy-3-isocyanato-2-methylbenzene (described in Reference preparation example 2) 17.0 g and the resulting mixtures were heated at 80° C. for four and a half hours. After cooling, the reaction solutions were added to a mixture of sodium nitrite 25 g, water 2 L and ice 500 g with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 1-(2-methyl-3-methoxyphenyl)-1,4-dihydrotetrazole-5-one 16.2 g.

1-(2-methyl-3-methoxyphenyl)-1,4-dihydrotetrazole-5-one

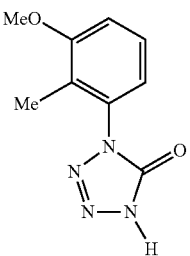 [SMILES: COc1cccc(-n2nn[nH]c2=O)c1C]

$^1$H-NMR (DMSO-d$_6$) δ (ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Synthesis Example 16

To a mixture of 1-(2-methyl-3-methoxyphenyl)-1,4-dihydrotetrazole-5-one (described in Synthesis example 15) 10.00 g and N,N-dimethylformamide 100 mL was added 60% sodium hydride 2.47 g under ice-cooling. The reaction mixtures were raised to room temperature and were stirred for one hour. To the reaction mixtures was added methyl iodide 3.5 mL under ice-cooling. The mixtures were raised to room temperature and were stirred for fourteen hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-methoxyphenyl)-4-methyl-1,4-dihydrotetrazole-5-one 2.19 g.

1-(2-methyl-3-methoxyphenyl)-4-methyl-1,4-dihydrotetrazole-5-one

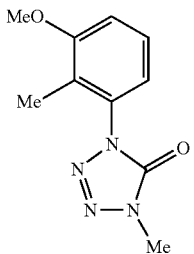 [SMILES: COc1cccc(-n2nnn(C)c2=O)c1C]

$^1$H-NMR (CDCl$_3$) δ (ppm): 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

Synthesis Example 17

To a mixture of 1-(2-methyl-3-methoxyphenyl)-4-methyl-1,4-dihydrotetrazole-5-one (described in Synthesis example 16) 2.19 g, 1,1'-azobis(cyclohexane-1-carbonitrile) 0.52 g, N-bromosuccinimide 2.16 g and chlorobenzene 40 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-methoxyphenyl)-4-methyl-1,4-dihydrotetrazole-5-one 2.36 g.

1-(2-bromomethyl-3-methoxyphenyl)-4-methyl-1,4-dihydrotetrazole-5-one

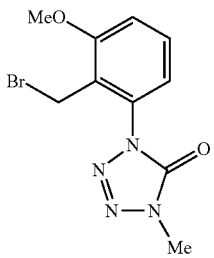 [SMILES: COc1cccc(-n2nnn(C)c2=O)c1CBr]

$^1$H-NMR (CDCl$_3$) δ (ppm): 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Synthesis Example 18

A mixture of 3-trifluoromethyl-2-methybenzoic acid 5.00 g, oxalyl dichloride 3.42 g, N,N-dimethylformamide about 50 mg and tetrahydrofuran 200 mL was stirred at 25° C. for one hour. The reaction mixtures were concentrated under reduced pressure to give 3-trifluoromethyl-2-methylbenzoic acid chloride.

A mixture of aluminium chloride 6.53 g, sodium azide 9.55 g and tetrahydrofuran 100 mL was stirred with heating under reflux for two hours. After the reaction mixtures were ice-cooled, and thereto was added a mixture of 3-trifluoromethyl-2-methylbenzoic acid chloride and tetrahydrofuran 100 mL and the resulting mixtures were stirred with heating under reflux for ten hours. After cooling the mixtures, to a mixture of sodium nitrite 14.7 g and water 200 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-trifluoromethylphenyl)-1,4-dihydrotetrazole-5-one.

A mixture of 1-(2-methyl-3-trifluoromethylphenyl)-1,4-dihydrotetrazole-5-one, potassium carbonate 11.20 g, dimethyl sulfate 3.71 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methyl-3-trifluoromethylphenyl)-4-methyl-1,4-dihydrotetrazole-5-one 5.13 g.

1-(2-methyl-3-trifluoromethylphenyl)-4-methyl-1,4-dihydrotetrazole-5-one

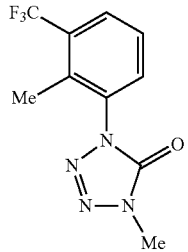

$^1$H-NMR (CDCl$_3$) δ (ppm): 2.42 (3H, s), 3.75 (3H, s), 7.52 (1H, t, J=8.2 Hz), 7.62 (1H, dd, J=1.2, 7.7 Hz), 8.02 (1H, dd, J=1.2, 8.2 Hz).

Synthesis Example 19

To a mixture of 1-(2-methyl-3-trifluoromethylphenyl)-4-methyl-1,4-dihydrotetrazole-5-one (described in Synthesis example 18) 1.00 g, 1,1'-azobis(cyclohexane-1-carbonitrile) 0.38 g, N-bromosuccinimide 0.79 g and chlorobenzene 30 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-trifluoromethylphenyl)-4-methyl-1,4-dihydrotetrazole-5-one 1.21 g.

1-(2-bromomethyl-3-trifluoromethylphenyl)-4-methyl-1,4-dihydrotetrazole-5-one

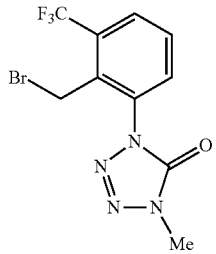 [SMILES: Cn1nnn(-c2cccc(C(F)(F)F)c2CBr)c1=O]

$^1$H-NMR (CDCl$_3$) δ (ppm): 3.77 (3H, s), 4.75 (2H, s), 7.62 (1H, d, J=5.5 Hz), 7.63 (1H, d, J=3.4 Hz), 7.85 (1H, dd, J=3.6, 5.8 Hz).

Synthesis Example 20

A mixture of 3-nitro-2-methybenzoic acid 5.00 g, oxalyl dichloride 3.85 g, N,N-dimethylformamide about 50 mg and tetrahydrofuran 200 mL was stirred at 25° C. for one hour. The reaction mixtures were concentrated under reduced pressure to give 3-nitro-2-methylbenzoic acid chloride.

A mixture of aluminium chloride 7.36 g, sodium azide 10.77 g and tetrahydrofuran 100 mL was stirred with heating under reflux for two hours. After the reaction mixtures were ice-cooled, and thereto was added a mixture of 3-nitro-2-methylbenzoic acid chloride and tetrahydrofuran 100 mL and the resulting mixtures were stirred with heating under reflux for ten hours. After cooling the mixtures, to a mixture of sodium nitrite 16.56 g and water 200 mL was added the reaction mixtures with stirring. The mixtures were acidified with concentrated hydrochloric acid and were then extracted with ethyl acetate. The organic layers were dried over anhydrous sodium sulfate and were then concentrated under reduced pressure to give 1-(2-methyl-3-nitrophenyl)-1,4-dihydrotetrazole-5-one.

A mixture of 1-(2-methyl-3-nitrophenyl)-1,4-dihydrotetrazole-5-one, potassium carbonate 12.59 g, dimethyl sulfate 13.79 g and N,N-dimethylformamide 150 mL was stirred at 25° C. for one hour. To the reaction mixtures was added aqueous saturated sodium bicarbonate solution and the mixtures were extracted with ethyl acetate. The organic layers were washed with aqueous saturated sodium bicarbonate solution and were dried over anhydrous sodium sulfate. The resulting mixtures were concentrated under reduced pressure to give 1-(2-methyl-3-nitrophenyl)-4-methyl-1,4-dihydrotetrazole-5-one 5.26 g.

1-(2-methyl-3-nitrophenyl)-4-methyl-1,4-dihydrotetrazole-5-one

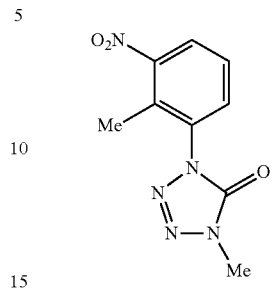

$^1$H-NMR (CDCl$_3$) δ (ppm): 2.42 (3H, s), 3.75 (3H, s), 7.52 (1H, t, J=8.2 Hz), 7.62 (1H, dd, J=1.2, 7.7 Hz), 8.02 (1H, d, J=1.2, 8.2 Hz).

Synthesis Example 21

To a mixture of 1-(2-methyl-3-nitrophenyl)-4-methyl-1,4-dihydrotetrazole-5-one (described in Synthesis example 20) 1.00 g, 1,1'-azobis(cyclohexane-1-carbonitrile) 0.42 g, N-bromosuccinimide 0.87 g and chlorobenzene 30 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-nitrophenyl)-4-methyl-1,4-dihydrotetrazole-5-one 1.00 g.

1-(2-bromomethyl-3-nitrophenyl)-4-methyl-1,4-dihydrotetrazole-5-one

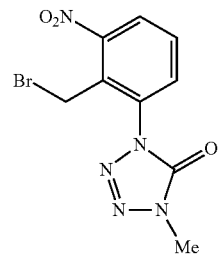 [SMILES: Cn1nnn(-c2cccc([N+](=O)[O-])c2CBr)c1=O]

$^1$H-NMR (CDCl$_3$) δ (ppm): 3.72 (3H, s), 5.63 (2H, s), 7.61 (1H, t, J=8.0 Hz), 7.70 (1H, d, J=8.1 Hz), 7.97 (1H, d, J=8.1 Hz).

Synthesis Example 22

Anhydrous aluminium chloride 3.62 g was added to N,N-dimethylformamide 40 mL under ice-cooling, and the mixtures were stirred for twenty minutes. Thereto was added sodium azide 1.76 g and the mixtures were stirred for fifteen minutes. Thereto was then added 3-difluoromethyl-2-methyl-1-isocyanatobenzene (described in Reference preparation example 7) 4.50 g and the resulting mixtures were heated at 80° C. for four hours. After cooling, the reaction solutions were added to a mixture of sodium nitrite 6 g, water 0.5 L and ice 100 g with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 1-(2-methyl-3-difluoromethylphenyl)-1,4-dihydrotetrazole-5-one 3.22 g.

A mixture of 1-(2-methyl-3-difluoromethylphenyl)-1,4-dihydrotetrazole-5-one 3.22 g, potassium carbonate 3.93 g, methyl iodide 4.04 g and N,N-dimethylformamide 70 mL was stirred at 25° C. for five hours. To the reaction mixtures was added water and the mixtures were extracted with ethyl acetate. The organic layers were washed with 10% hydrochloric acid, water and saturated saline, and were dried over anhydrous magnesium sulfate and were then concentrated under reduced pressure. The resulting residues were subjected to a silica gel column chromatography to give 1-(2-methyl-3-difluoromethylphenyl)-4-methyl-1,4-dihydrotetrazole-5-one 1.14 g.

1-(2-methyl-3-difluoromethylphenyl)-4-methyl-1,4-dihydrotetrazole-5-one

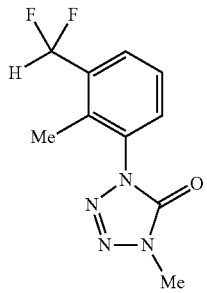 [SMILES: Cc1c(C(F)F)cccc1-n1nnn(C)c1=O]

$^1$H-NMR (CDCl$_3$) δ (ppm): 2.31 (3H, s), 3.73 (3H, s), 6.83 (1H, t, J=55.1 Hz), 7.44-7.46 (2H, m), 7.68-7.71 (1H, m).

Synthesis Example 23

To a mixture of 1-(2-methyl-3-difluoromethylphenyl)-4-methyl-1,4-dihydrotetrazole-5-one (described in Synthesis example 22) 1.14 g, 1,1'-azobis(cyclohexane-1-carbonitrile) 0.23 g, N-bromosuccinimide 0.97 g and chlorobenzene 20 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-difluoromethylphenyl)-4-methyl-1,4-dihydrotetrazole-5-one 1.21 g.

1-(2-bromomethyl-3-difluoromethylphenyl)-4-methyl-1,4-dihydrotetrazole-5-one

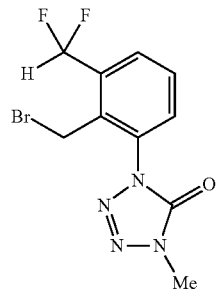 [SMILES: Cn1nnn(-c2cccc(C(F)F)c2CBr)c1=O]

$^1$H-NMR (CDCl$_3$) δ (ppm): 3.76 (3H, s), 4.66 (2H, s), 6.99 (1H, t, J=54.8 Hz), 7.55 (1H, d, J=8.0 Hz), 7.60 (1H, t, J=7.7 Hz), 7.56 (1H, d, J=7.5 Hz).

Synthesis Example 24

Under ice-cooling, to a mixture of N,N-dimethylformamide 350 mL and anhydrous aluminum chloride 33.6 g was added sodium azide 15 g and the resulting mixtures were stirred for one hour. Thereto was then added 1-ethoxy-3-isocyanato-2-methylbenzene (described in Reference preparation example 10) 37.2 g and the reaction mixtures were heated at 75° C. and were then stirred for five hours. After cooling the mixtures, to the reaction mixtures was added ice water 100 mL under ice-cooling, followed by addition of a mixture of sodium nitrite 23 g and water 150 mL, and then followed by addition of concentrated hydrochloric acid so as to make a pH of the mixtures about 4. The resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-methyl-3-ethoxyphenyl)-1,4-dihydrotetrazole-5-one 39.0 g.

1-(2-methyl-3-ethoxyphenyl)-1,4-dihydrotetrazole-5-one

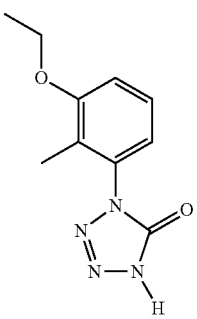 [SMILES: CCOc1cccc(-n2nn[nH]c2=O)c1C]

$^1$H-NMR (CDCl$_3$) δ (ppm): 7.30 (1H, t, J=8.1 Hz), 6.99 (1H, d, J=8.5 Hz), 6.96 (1H, d, J=8.0 Hz), 4.10 (2H, q, J=6.9 Hz), 2.13 (3H, s), 1.46 (3H, t, J=7.0 Hz).

Synthesis Example 25

Under ice-cooling, to a mixture of 1-(2-methyl-3-ethoxyphenyl)-1,4-dihydrotetrazole-5-one (described in Synthesis example 24) 39.0 g, potassium carbonate 36.7 g and N,N-dimethylformamide 400 mL was added dimethyl sulfate 44.7 g, and the mixtures were raised to room temperature and were stirred for seven hours. Thereto was water 100 mL and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-methyl-3-ethoxyphenyl)-4-methyl-1,4-dihydrotetrazole-5-one 38.2 g.

1-(2-methyl-3-ethoxyphenyl)-4-methyl-1,4-dihydro-tetrazole-5-one

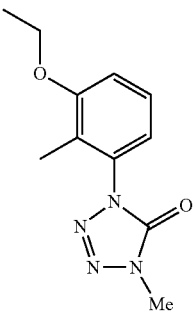 [SMILES: CCOc1cccc(-n2nnn(C)c2=O)c1C]

$^1$H-NMR (CDCl$_3$) δ (ppm): 7.29-7.23 (1H, m), 6.96 (1H, d, J=8.2 Hz), 6.93 (1H, d, J=8.2 Hz), 4.08 (2H, q, J=6.9 Hz), 3.72 (3H, s), 2.11 (3H, s), 1.45 (3H, t, J=7.1 Hz).

Synthesis Example 26

To a mixture of 1-(2-methyl-3-ethoxyphenyl)-4-methyl-1,4-dihydrotetrazole-5-one (described in Synthesis example 25) 38.2 g, 1,1'-azobis(cyclohexane-1-carbonitrile) 7.95 g, N-bromosuccinimide 33.4 g and chlorobenzene 380 mL was stirred with heating under reflux for five hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-ethoxyphenyl)-4-methyl-1,4-dihydrotetrazole-5-one 38.2 g.

1-(2-bromomethyl-3-ethoxyphenyl)-4-methyl-1,4-dihydrotetrazole-5-one

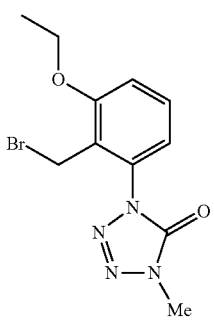 [SMILES: CCOc1cccc(-n2nnn(C)c2=O)c1CBr]

$^1$H-NMR (CDCl$_3$) δ (ppm): 7.40 (1H, t, J=8.2 Hz), 7.01 (2H, t, J=8.3 Hz), 4.64 (2H, s), 4.17 (2H, q, J=7.0 Hz), 3.74 (3H, s), 1.49 (3H, t, J=6.9 Hz).

Synthesis Example 27

Under ice-cooling, to a mixture of N,N-dimethylformamide 200 mL and anhydrous aluminium chloride 5.91 g was added sodium azide 2.64 g and the mixtures were stirred for one hour. Thereto was then added 1-difluoromethoxy-3-isocyanato-2-methylbenzene (described in Reference Preparation example 13) 7.36 g and the reaction mixtures were raised to 75° C. and were stirred for nine hours. After cooling the mixtures, to the reaction mixtures added ice water 50 mL under ice-cooling, followed by addition of a mixture of sodium nitrite 4.1 g and water 100 mL, and then followed by addition of concentrated hydrochloric acid so as to make a pH of the mixtures about 4. The resulting mixtures were extracted with ethyl acetate. The organic layers were washed with water and saturated saline, and were dried over anhydrous magnesium sulfate and were then concentrated under reduced pressure. To the resulting residues containing 1-(2-methyl-3-difluoromethoxyphenyl)-1,4-dihydrotetrazole-5-one were added N,N-dimethylformamide 100 mL, potassium carbonate 7.66 g and dimethyl sulfate 9.32 g, and the mixtures were stirred at room temperature for four hours. Thereto was added water 100 mL and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give to give 1-(2-methyl-3-difluoromethoxyphenyl)-4-methyl-1,4-dihydrotetrazole-5-one 1.0 g.

1-(2-methyl-3-difluoromethoxyphenyl)-4-methyl-1,4-dihydrotetrazole-5-one

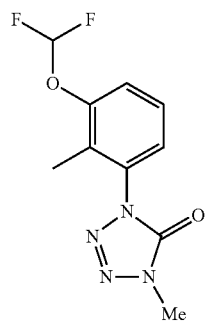

$^1$H-NMR (CDCl$_3$) δ (ppm): 7.34 (1H, t, J=8.1 Hz), 7.30-7.23 (2H, m), 6.55 (1H, t, J=72.8 Hz), 3.73 (3H, d, J=0.5 Hz), 2.21 (3H, s).

Synthesis Example 28

To a mixture of 1-(2-methyl-3-difluoromethoxyphenyl)-4-methyl-1,4-dihydrotetrazole-5-one (described in Synthesis example 27) 1.10 g, 1,1'-azobis(cyclohexane-1-carbonitrile) 0.19 g, N-bromosuccinimide 0.80 g and chlorobenzene 50 mL was stirred with heating under reflux for eight hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-difluoromethoxyphenyl)-4-methyl-1,4-dihydrotetrazole-5-one 1.1 g.

1-(2-bromomethyl-3-difluoromethoxyphenyl)-4-methyl-1,4-dihydrotetrazole-5-one

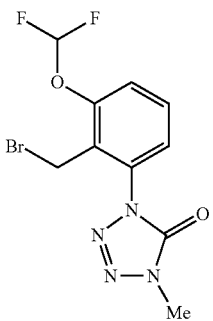 [SMILES: Cn1nnn(-c2cccc(OC(F)F)c2CBr)c1=O]

¹H-NMR (CDCl₃) δ (ppm): 7.50 (1H, t, J=8.2 Hz), 7.34 (2H, d, J=8.2 Hz), 6.62 (1H, t, J=72.8 Hz), 4.65 (2H, s), 3.76 (3H, d, J=0.5 Hz).

Synthesis Example 29

A mixture of 1-(2-methyl-3-triisopropylsilanylthiophenyl)-4-methyl-1,4-dihydrotetrazole-5-one (described in Reference Preparation example 14) 3.63 g, cesium fluoride 2.91 g and N,N-dimethylformamide 10 mL was stirred at room temperature for thirty minutes. To the mixtures was added methyl iodide 2.72 g and the mixtures were stirred at room temperature for three hours. To the reaction mixtures was added water and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-methyl-3-methylthiophenyl)-4-methyl-1,4-dihydrotetrazole-5-one 1.65 g.

1-(2-methyl-3-methylthiophenyl)-4-methyl-1,4-dihydrotetrazole-5-one

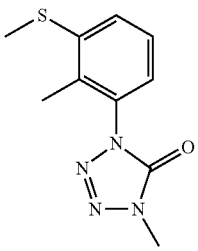 [SMILES: CSc1cccc(-n2nnn(C)c2=O)c1C]

¹H-NMR (CDCl₃) δ (ppm): 2.22 (3H, s), 2.51 (3H, s), 3.72 (3H, s), 7.10-7.16 (1H, m), 7.36-7.29 (2H, m).

Synthesis Example 30

To a mixture of 1-(2-methyl-3-methylthiophenyl)-4-methyl-1,4-dihydrotetrazole-5-one (described in Synthesis example 29) 1.50 g, 1,1'-azobis(cyclohexane-1-carbonitrile) 0.62 g, N-bromosuccinimide 1.30 g and chlorobenzene 15 mL was stirred with heating under reflux for four hours. After cooling the mixtures, to the reaction solutions was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-bromomethyl-3-methylthiophenyl)-4-methyl-1,4-dihydrotetrazole-5-one 0.400 g.

1-(2-bromomethyl-3-methylthiophenyl)-4-methyl-1,4-dihydrotetrazole-5-one

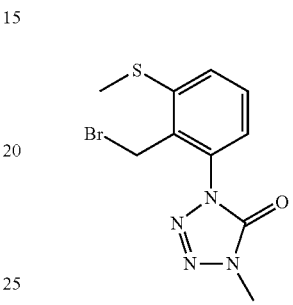

¹H-NMR (CDCl₃) δ (ppm): 2.57 (3H, s), 3.75 (3H, s), 4.69 (2H, s), 7.20 (1H, t, J=4.5 Hz), 7.44 (2H, d, J=4.5 Hz).

Synthesis Example 31

A mixture of 1-(2-bromomethyl-3-bromophenyl)-4-methyl-1,4-dihydrotetrazole-5-one (described in Synthesis example 11) 45.0 g, sodium methoxide 37.4 g and tetrahydrofuran 600 mL was stirred at room temperature for three hours. To the reaction mixtures was added aqueous saturated sodium bicarbonate solution and the resulting mixtures were extracted with ethyl acetate. The organic layers were washed with aqueous saturated sodium bicarbonate solution, and were dried over anhydrous sodium sulfate. The mixtures were concentrated under reduced pressure to give 1-(2-methoxymethyl-3-bromophenyl)-4-methyl-1,4-dihydrotetrazole-5-one 36.2 g.

1-(2-methoxymethyl-3-bromophenyl)-4-methyl-1,4-dihydrotetrazole-5-one

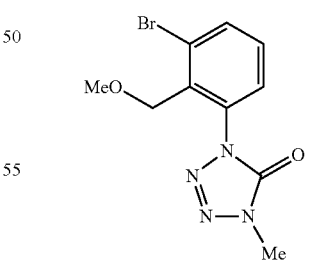

¹H-NMR (CDCl₃) δ (ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Synthesis Example 32

A mixture of 1-(2-methoxymethyl-3-bromophenyl)-4-methyl-1,4-dihydrotetrazole-5-one (described in Synthesis example 31) 36.2 g, methylboronic acid 23.2 g, cesium fluoride 66.7 g, [1,1'-bis(diphenylphosphino)ferrocene]palladium(II) dichloride dichloromethane adduct 10.6 g and dioxane 500 mL was stirred at 90° C. for five and a half hours. After cooling the reaction mixtures, the mixtures were filtered and the filtrates were concentrated under reduced pressure. The resulting residues were subjected to a silica gel column chromatography to give 1-(2-methoxymethyl-3-methylphenyl)-4-methyl-1,4-dihydrotetrazole-5-one 25.6 g.

1-(2-methoxymethyl-3-methylphenyl)-4-methyl-1,4-dihydrotetrazole-5-one

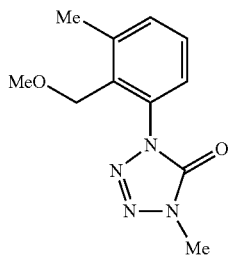

¹H-NMR (CDCl₃) δ (ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Synthesis Example 33

A mixture of 1-(2-methoxymethyl-3-methylphenyl)-4-methyl-1,4-dihydrotetrazole-5-one (described in Synthesis example 32) 25.6 g, acetic acid 50 mL and 25% hydrogen bromide-acetic acid solution 50 mL was stirred at 65° C. for one hour. To the reaction mixtures was added saturated saline, and the mixtures were extracted with ethyl acetate. The organic layers were washed with aqueous saturated sodium bicarbonate solution and were dried over anhydrous sodium sulfate. The mixtures were concentrated under reduced pressure to give 1-(2-bromomethyl-3-methylphenyl)-4-methyl-1,4-dihydrotetrazole-5-one 27.9 g.

1-(2-bromomethyl-3-methylphenyl)-4-methyl-1,4-dihydrotetrazole-5-one

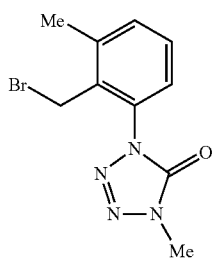

¹H-NMR (CDCl₃) δ (ppm): 2.51 (3H, s), 3.75 (3H, s), 4.51 (2H, s), 7.22-7.24 (1H, m), 7.36-7.39 (2H, m).

Synthesis Example 34

A mixture of 1-(2-methoxymethyl-3-bromophenyl)-4-methyl-1,4-dihydrotetrazole-5-one (described in Synthesis example 31) 30.1 g, cyclopropylboronic acid 12.9 g, cesium fluoride 46.2 g, [1,1'-bis(diphenylphosphino)ferrocene]palladium(II) dichloride dichloromethane adduct 8.2 g and dioxane 680 mL was stirred at 90° C. for four hours. After cooling the reaction mixtures, the mixtures were filtered and the filtrates were concentrated under reduced pressure. The resulting residues were subjected to a silica gel column chromatography to give 1-(2-methoxymethyl-3-cyclopropylphenyl)-4-methyl-1,4-dihydrotetrazole-5-one 26.0 g.

1-(2-methoxymethyl-3-cyclopropylphenyl)-4-methyl-1,4-dihydrotetrazole-5-one

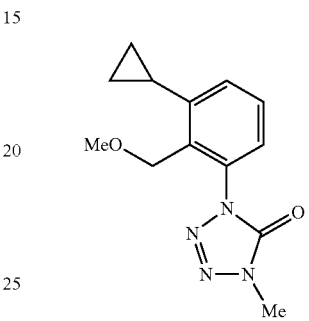

¹H-NMR (CDCl₃) δ (ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Synthesis Example 35

A mixture of 1-(2-methoxymethyl-3-cyclopropylphenyl)-4-methyl-1,4-dihydrotetrazole-5-one (described in Synthesis example 34) 26.0 g, acetic acid 40 mL and 25% hydrogen bromide-acetic acid solution 40 mL was stirred at 65° C. for two hours. To the reaction mixtures was added saturated saline, and the mixtures were extracted with ethyl acetate. The organic layers were washed with aqueous saturated sodium bicarbonate solution and were dried over anhydrous sodium sulfate. The mixtures were concentrated under reduced pressure to give 1-(2-bromomethyl-3-cyclopropylphenyl)-4-methyl-1,4-dihydrotetrazole-5-one 30.8 g.

1-(2-bromomethyl-3-cyclopropylphenyl)-4-methyl-1,4-dihydrotetrazole-5-one

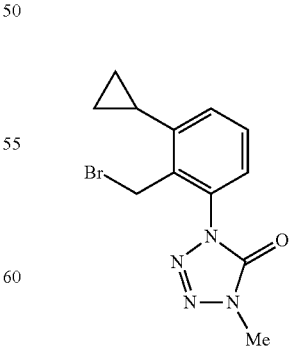

¹H-NMR (CDCl₃) δ (ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Synthesis Example 36

A mixture of 1-(2-methoxymethyl-3-bromophenyl)-4-methyl-1,4-dihydrotetrazole-5-one (described in Synthesis example 31) 29.8 g, tributylvinyltin 35.2 g, tetrakis(triphenylphosphine)palladium 11.6 g and toluene 500 mL was stirred with heating under reflux for fourteen hours. After cooling the reaction mixtures, to the reaction solutions were added aqueous saturated ammonium chloride solution and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-methoxymethyl-3-ethenylphenyl)-4-methyl-1,4-dihydrotetrazole-5-one 19.7 g.

1-(2-methoxymethyl-3-ethenylphenyl)-4-methyl-1,4-dihydrotetrazole-5-one

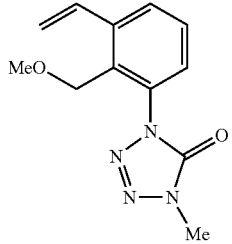 [SMILES: C=Cc1cccc(-n2nnn(C)c2=O)c1COC]

$^1$H-NMR (CDCl$_3$) δ (ppm): 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).

Synthesis Example 37

A mixture of 1-(2-methoxymethyl-3-ethenylphenyl)-4-methyl-1,4-dihydrotetrazole-5-one (described in Synthesis example 36) 19.7 g, palladium fibroin complex 3.02 g and methanol 1 L was stirred at room temperature under hydrogen atmosphere for eleven hours. The reaction mixtures were filtered and the filtrates were concentrated under reduced pressure. The resulting residues were subjected to a silica gel column chromatography to give 1-(2-methoxymethyl-3-ethylphenyl)-4-methyl-1,4-dihydrotetrazole-5-one 19.3 g.

1-(2-methoxymethyl-3-ethylphenyl)-4-methyl-1,4-dihydrotetrazole-5-one

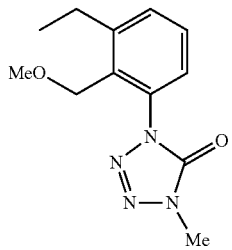 [SMILES: CCc1cccc(-n2nnn(C)c2=O)c1COC]

$^1$H-NMR (CDCl$_3$) δ (ppm): 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

Synthesis Example 38

A mixture of 1-(2-methoxymethyl-3-ethylphenyl)-4-methyl-1,4-dihydrotetrazole-5-one (described in Synthesis example 37) 19.3 g, acetic acid 40 mL and 25% hydrogen bromide-acetic acid solution 40 mL was stirred at 65° C. for one and a half hours. To the reaction mixtures was added saturated saline, and the mixtures were extracted with ethyl acetate. The organic layers were washed with aqueous saturated sodium bicarbonate solution and were dried over anhydrous sodium sulfate. The mixtures were concentrated under reduced pressure to give 1-(2-bromomethyl-3-ethylphenyl)-4-methyl-1,4-dihydrotetrazole-5-one 23.3 g.

1-(2-bromomethyl-3-ethylphenyl)-4-methyl-1,4-dihydrotetrazole-5-one

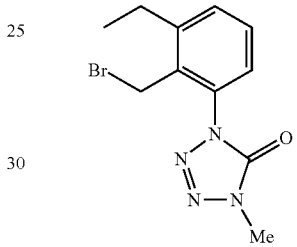

$^1$H-NMR (CDCl$_3$) δ (ppm): 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Synthesis Example 39

Under ice-cooling, to N,N-dimethylformamide 200 mL was added anhydrous aluminum chloride 16.0 g and the resulting mixtures were stirred for a half hour. Thereto was added sodium azide 7.2 g and the resulting mixtures were stirred for a half hour and thereto was then added 2-isocyanato-6-methylbenzoic acid methyl ester (described in Reference preparation example 16) 19.0 g and the resulting mixtures were heated at 80° C. for eight hours. After cooling the mixtures, to a mixture of sodium nitrite 11.5 g and ice water 300 mL was added the reaction solutions with stirring. The mixtures were acidified with 10'. %, hydrochloric acid and were extracted with ethyl acetate. The organic layers were washed with water and saturated saline, and were dried over anhydrous magnesium sulfate and were then concentrated under reduced pressure to give 2-methyl-6-(5-oxo-4,5-dihydrotetrazole-1-yl)benzoic acid methyl ester.

To a mixture of 2-methyl-6-(5-oxo-4,5-dihydrotetrazole-1-yl)benzoic acid methyl ester and N,N-dimethylformamide 300 mL were added potassium carbonate 42.0 g and dimethyl sulfate 18.9 g at room temperature, and the mixtures were stirred for 24 hours. To the reaction solutions was added water and the mixtures were extracted with ethyl acetate. The organic layers were washed with water and aqueous saturated sodium bicarbonate solution and were dried over anhydrous magnesium sulfate, and were then concentrated under reduced pressure. The resulting residues were subjected to a silica gel column chromatography to give 2-methyl-6-(4-methyl-5-oxo-4,5-dihydrotetrazole-1-yl)-benzoic acid methyl ester 13.9 g.

2-methyl-6-(4-methyl-5-oxo-4,5-dihydrotetrazole-1-yl)-benzoic acid methyl ester

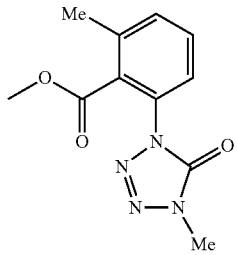 [SMILES: COC(=O)c1c(C)cccc1-n1nnn(C)c1=O]

$^1$H-NMR (CDCl$_3$) δ (ppm): 7.50-7.46 (2H, m), 7.35-7.33 (1H, m), 3.83 (3H, s), 3.69 (3H, s), 2.48 (3H, s).

Synthesis Example 40

Under ice-cooling, to a mixture of 2-methyl-6-(4-methyl-5-oxo-4,5-dihydrotetrazole-1-yl)-benzoic acid methyl ester (described in Synthesis example 39) 25.0 g and tetrahydrofuran 300 mL was added a 1.0 M solution of lithium triethylborohydride in toluene 201 mL and the mixtures were stirred at room temperature for a half hour. To the reactions solutions was added water, and the mixtures were acidified with 10% hydrochloric acid and were extracted with ethyl acetate. The organic layers were washed with water and then were dried over anhydrous magnesium sulfate and were then concentrated under reduced pressure to give 1-(2-hydroxymethyl-3-methylphenyl)-4-methyl-1,4-dihydrotetrazole-5-one 21.2 g.

1-(2-hydroxymethyl-3-methylphenyl)-4-methyl-1,4-dihydrotetrazole-5-one

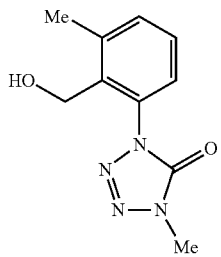

$^1$H-NMR (CDCl$_3$) δ (ppm): 7.39-7.34 (2H, m), 7.21 (1H, dd, J=6.5, 2.8 Hz), 4.48 (2H, s), 3.75 (3H, s), 2.57 (3H, s), 1.59 (1H, br s).

Synthesis Example 41

To a mixture of 1-(2-hydroxymethyl-3-methylphenyl)-4-methyl-1,4-dihydrotetrazole-5-one 21.2 g (described in Synthesis example 40) and chloroform 300 mL was added phosphorus tribromide 52.1 g and the mixtures were stirred at room temperature for one hour. To the reaction solutions was added ice water 200 mL and the mixtures were extracted with ethyl acetate. The organic layers were washed with water and saline and then were dried over anhydrous magnesium sulfate, and were then concentrated under reduced pressure to give 1-(2-bromomethyl-3-methylphenyl)-4-methyl-1,4-dihydrotetrazole-5-one 26.0 g.

Synthesis Example 42

Anhydrous aluminium chloride 6.16 g was added to N,N-dimethylformamide 100 mL under ice-cooling, and the mixtures were stirred for thirty minutes. Thereto was added sodium azide 3.00 g and the mixtures were stirred for thirty minutes. Thereto was then added 3-methyl-2-methoxymethyl-1-isocyanatobenzene (described in Reference Preparation example 18) 6.30 g and the resulting mixtures were heated at 80° C. for ten hours. After cooling, the reaction solutions were added to a mixture of sodium nitrite 4.62 g, water 100 mL and ice 100 g with stirring. The mixtures were acidified with 10% hydrochloric acid and were extracted with ethyl acetate. The organic layers were washed with water and 10% sodium hydrogen sulfide solution and then were dried over anhydrous sodium sulfate, and were then concentrated under reduced pressure to give 1-(2-methoxymethyl-3-methylphenyl)-1,4-dihydrotetrazole-5-one 7.00 g.

1-(2-methoxymethyl-3-methylphenyl)-1,4-dihydrotetrazole-5-one

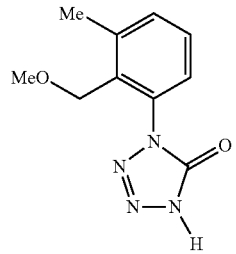 [SMILES: COCc1c(C)cccc1-n1nn[nH]c1=O]

$^1$H-NMR (CDCl$_3$) δ (ppm): 2.49 (3H, s), 3.25 (3H, s), 4.45 (2H, s), 7.24 (1H, t, J=4.9 Hz), 7.39 (2H, d, J=4.9 Hz), 13.00 (1H, s).

Synthesis Example 43

Anhydrous aluminium chloride 15.8 g was added to N,N-dimethylformamide 180 mL under ice-cooling, and the mixtures were stirred for fifteen minutes. Thereto was added sodium azide 7.7 g and the mixtures were stirred for fifteen minutes. Thereto was then added 3-[(2-isocyanato-6-methylphenyl)methyloxy]-1-(4-chlorophenyl)pyrazole (described in Reference Preparation example 23) 30.8 g and the resulting mixtures were heated at 80° C. for four hours. After cooling, the reaction solutions were added to a mixture of sodium nitrite 25.0 g, water 3 L and ice 500 g with stirring. The mixtures were acidified with 10% hydrochloric acid and the precipitated solids were filtered off. The resulting residues were washed with water and tert-butyl methyl ether to give 1-(2-{[1-(4-chlorophenyl)-1H-pyrazole-3-yl]oxymethyl}-3-methylphenyl)-4H-1,4-dihydrotetrazole-5-one 35.8 g.

1-(2-{[1-(4-chlorophenyl)-1H-pyrazole-3-yl]oxymethyl}-3-methylphenyl)-4H-1,4-dihydrotetrazole-5-one

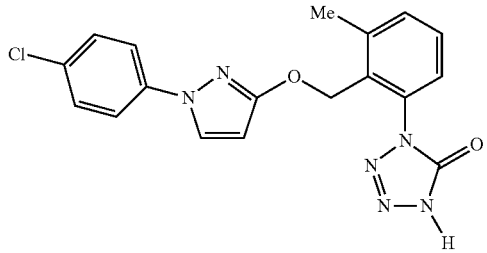 [SMILES: Cc1cccc(-n2nn[nH]c2=O)c1COc1ccn(-c2ccc(Cl)cc2)n1]

¹H-NMR (DMSO-d₆) δ (ppm): 8.33 (1H, d, J=2.7 Hz), 7.73-7.69 (2H, m), 7.52-7.47 (4H, m), 7.36-7.32 (1H, m), 5.94 (1H, d, J=2.7 Hz), 5.24 (2H, s), 2.51 (3H, s).

Next, regarding an intermediate for preparing the above-mentioned Present compounds, Reference Preparation examples are shown below.

Reference Preparation Example 1

A mixture of 1-bromo-2-methyl-3-aminobenzene 25.0 g, triphosgene 60.0 g and toluene 400 mL was stirred with heating under reflux for three hours. The reaction mixtures after standing to cool were concentrated under reduced pressure to give 1-bromo-3-isocyanato-2-methylbenzene 30.3 g.

1-bromo-3-isocyanato-2-methylbenzene

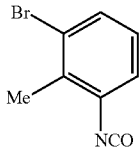

¹H-NMR (CDCl₃) δ (ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Preparation Example 2

A mixture of 3-amino-1-methoxy-2-methylbenzene 15.0 g, triphosgene 48.7 g and toluene 350 mL was stirred with heating under reflux for three hours. The reaction mixtures after standing to cool were concentrated under reduced pressure to give 1-methoxy-3-isocyanato-2-methylbenzene 17.0 g.

1-methoxy-3-isocyanato-2-methylbenzene

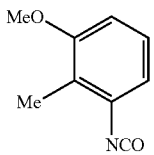

¹H-NMR (CDCl₃) δ (ppm): 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

Reference Preparation Example 3

A mixture of sodium borohydride 9.4 g and tetrahydrofuran 150 mL was stirred at room temperature for thirty minutes. Thereto was added 2-methyl-3-nitrobenzoic acid 30.8 g and the mixtures were stirred at room temperature for thirty minutes. The mixed solutions were ice-cooled and thereto was added slowly methanesulfonic acid 11.0 mL over 45 minutes. The reaction mixtures were stirred at room temperature for three days. To the reaction mixtures was added water and the mixtures were extracted with ethyl acetate. The organic layers were washed with 10% hydrochloric acid and saturated saline, and were dried over anhydrous magnesium sulfate and were then concentrated under reduced pressure to give 3-hydroxymethyl-2-methyl-1-nitrobenzene 27.0 g.

3-hydroxymethyl-2-methyl-1-nitrobenzene

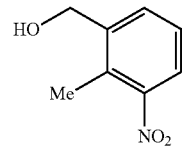 [SMILES: Cc1c(CO)cccc1[N+](=O)[O-]]

¹H-NMR (CDCl₃) δ (ppm): 1.81 (1H, s), 2.44 (3H,$), 4.79 (2H, s), 7.34 (1H, t, J=7.8 Hz), 7.65 (1H, d, 7.6 Hz), 7.72 (1H, d, J=8.1 Hz).

Reference Preparation Example 4

A mixture of 3-hydroxymethyl-2-methyl-1-nitrobenzene (described in Reference Preparation example 3) 17.0 g, manganese dioxide 65.0 g and chloroform 170 mL was stirred with heating under reflux for five hours. The reaction mixtures after standing to cool was filtered through Celite and the filtrates were concentrated under reduced pressure to give 3-formyl-2-methyl-1-nitrobenzene 14.0 g.

3-formyl-2-methyl-1-nitrobenzene

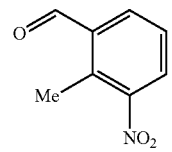 [SMILES: Cc1c(C=O)cccc1[N+](=O)[O-]]

¹H-NMR (CDCl₃) δ (ppm): 2.78 (3H, s), 7.53 (1H, t, J=8.1 Hz), 7.97 (1H, dd, J=1.5, 8.1 Hz), 8.06 (1H, dd, J=1.5, 7.8 Hz), 10.39 (1H, s).

Reference Preparation Example 5

To a mixture of 3-formyl-2-methyl-1-nitrobenzene (described in Reference Preparation example 4) 13.0 g and chloroform 200 mL under cooling at −78° C. was added dropwise N,N-diethylaminosulfur trifluoride 31.7 g, and the mixtures were stirred at room temperature for sixteen hours. To the reaction mixtures was added water and the mixtures were extracted with chloroform. The organic layers were washed with saturated saline, and were dried over anhydrous magnesium sulfate and were then concentrated under reduced pressure. The resulting residues were subjected to a silica gel column chromatography to give 3-difluoromethyl-2-methyl-1-nitrobenzene 6.80 g.

3-difluoromethyl-2-methyl-1-nitrobenzene

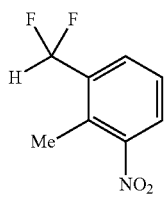

$^1$H-NMR (CDCl$_3$) δ (ppm): 2.54 (3H, s), 6.84 (1H, t, J=54.6 Hz), 7.45 (1H, t, J=7.7 Hz), 7.78 (1H, d, J=7.7 Hz), 7.89 (1H, d, J=8.0 Hz).

Reference Preparation Example 6

A mixture of 3-difluoromethyl-2-methyl-1-nitrobenzene (described in Reference Preparation example 5) 6.80 g, 5% platinum-activated carbon 0.30 g and methanol 50 mL was stirred at 35° C. under hydrogen atmosphere for eight hours. The reaction mixtures were filtered through Celite and the filtrates were concentrated under reduced pressure. The resulting residues were subjected to a silica gel column chromatography to give 3-difluoromethyl-2-methyl-1-aminobenzene 3.87 g.

3-difluoromethyl-2-methyl-1-aminobenzene

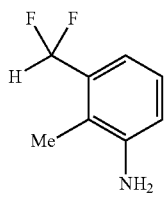 [SMILES: Cc1c(N)cccc1C(F)F]

$^1$H-NMR (CDCl$_3$) δ (ppm): 2.20 (3H, s), 3.71 (2H, s), 6.72 (1H, t, J=55.5 Hz), 6.79 (1H, d, J=8.0 Hz), 6.92 (1H, d, J=7.7 Hz), 7.09 (1H, t, J=7.7 Hz).

Reference Preparation Example 7

A mixture of 3-difluoromethyl-2-methyl-1-aminobenzene (described in Reference Preparation example 6) 3.87 g, triphosgene 10.96 g and toluene 80 mL was stirred with heating under reflux for three and a half hours. The reaction mixtures after standing to cool were concentrated under reduced pressure to give 3-difluoromethyl-2-methyl-1-isocyanatobenzene 4.50 g.

3-difluoromethyl-2-methyl-1-isocyanatobenzene

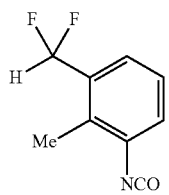

$^1$H-NMR (CDCl$_3$) δ (ppm): 2.39 (3H, s), 6.74 (1H, t, J=55.1 Hz), 7.21-7.27 (2H, m), 7.34 (1H, d, J=7.2 Hz).

Reference Preparation Example 8

A mixture of 2-methyl-3-nitrophenol 33.5 g, iodoethane 41 g and potassium carbonate 90 g in acetone 400 mL was stirred with heating under reflux for ten hours. The mixtures were cooled to room temperature and were filtered. The filtrates were then concentrated. The mixtures were extracted with ethyl acetate and the organic layers were washed with water and saturated saline, and were dried over anhydrous magnesium sulfate and were then concentrated under reduced pressure. The resulting residues were subjected to a silica gel column chromatography to give 1-ethoxy-2-methyl-3-nitrobenzene 39.9 g.

1-ethoxy-2-methyl-3-nitrobenzene

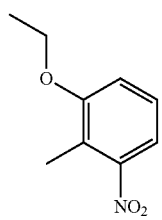

$^1$H-NMR (CDCl$_3$) δ (ppm): 7.39 (1H, dd, J=8.2, 1.0 Hz), 7.24 (1H, t, J=8.3 Hz), 7.02 (1H, d, J=8.2 Hz), 4.08 (2H, q, J=7.0 Hz), 2.37 (3H, s), 1.50-1.42 (3H, m).

Reference Preparation Example 9

A mixture of 1-ethoxy-2-methyl-3-nitrobenzene (described in Reference Preparation example 8) 39.9 g, palladium-carbon (palladium 50) 4 g and ethanol 200 mL was stirred at room temperature under hydrogen atmosphere for eighteen hours. The mixtures were filtered and the filtrates were concentrated to give 3-ethoxy-2-methylaniline 33.0 g.

3-ethoxy-2-methylaniline

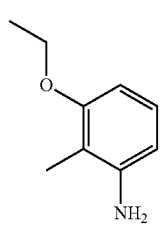

$^1$H-NMR (CDCl$_3$) δ (ppm): 6.95 (1H, t, J=8.1 Hz), 6.35 (1H, d, J=2.9 Hz), 6.33 (1H, d, J=3.1 Hz), 4.02-3.97 (2H, m), 3.61 (2H, br s), 2.05 (3H, s), 1.40 (3H, t, J=7.1 Hz).

Reference Preparation Example 10

At room temperature, to a mixture of 3-ethoxy-2-methylaniline (described in Reference Preparation example 9) 33.0 g and toluene 400 mL was added triphosgene 25 g, and the resulting mixtures were stirred with heating reflux for four hours. The mixtures were concentrated under reduced pressure to give 1-ethoxy-3-isocyanato-2-methylbenzene 37.2 g.

1-ethoxy-3-isocyanato-2-methylbenzene

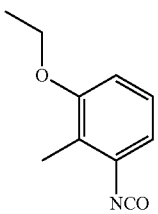

$^1$H-NMR (CDCl$_3$) δ (ppm): 7.07 (1H, t, J=8.2 Hz), 6.70 (1H, d, J=7.7 Hz), 6.68 (1H, d, J=8.2 Hz), 4.02 (2H, q, J=7.0 Hz), 2.20 (3H, s), 1.42 (3H, t, J=7.0 Hz).

Reference Preparation Example 11

A mixture of 2-methyl-3-nitrophenol 7.17 g, potassium carbonate 27 g, bromodifluoromethyl-diethylphosphonate 25 g, water 100 mL and acetonitrile 100 mL was stirred at room temperature for 24 hours. The mixtures were extracted with ethyl acetate and the organic layers were washed with water and saturated saline, and were dried over anhydrous magnesium sulfate and were then concentrated under reduced pressure. The resulting residues were subjected to a silica gel column chromatography to give 1-difluoromethoxy-2-methyl-3-nitrobenzene 7.50 g.

1-difluoromethoxy-2-methyl-3-nitrobenzene

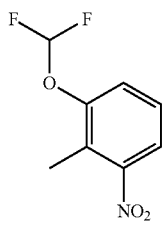

$^1$H-NMR (CDCl$_3$) δ (ppm): 7.74 (1H, dd, J=7.6, 1.8 Hz), 7.40-7.32 (2H, m), 6.56 (1H, t, J=72.4 Hz), 2.46 (3H, s).

Reference Preparation Example 12

A mixture of 1-difluoromethoxy-2-methyl-3-nitrobenzene (described in Reference Preparation example 11) 7.50 g, palladium-carbon (palladium 5%) 0.8 g and ethanol 80 mL was stirred at room temperature under hydrogen atmosphere for eight hours. The mixtures were filtered and the filtrates were concentrated to give 3-difluoromethoxy-2-methylaniline 6.4 g.

3-difluoromethoxy-2-methylaniline

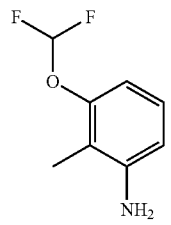

$^1$H-NMR (CDCl$_3$) δ (ppm): 6.99 (1H, t, J=8.1 Hz), 6.55 (1H, d, J=8.0 Hz), 6.51 (1H, d, J=8.2 Hz), 6.46 (1H, td, J=74.4, 0.4 Hz), 3.72 (2H, br s), 2.09 (3H, s).

Reference Preparation Example 13

To a mixture of 3-difluoromethoxy-2-methylaniline (described in Reference Preparation example 12) 6.4 g and toluene 100 mL was added triphosgene 5.48 g, and the mixtures were stirred with heating under reflux for one hour. The mixtures were concentrated under reduced pressure to give 1-difluoromethoxy-3-isocyanato-2-methylbenzene 7.36 g.

1-difluoromethoxy-3-isocyanato-2-methylbenzene

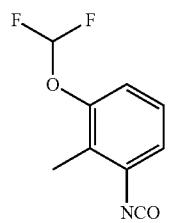

$^1$H-NMR (CDCl$_3$) δ (ppm): 7.14 (1H, t, J=8.1 Hz), 6.97 (2H, t, J=8.5 Hz), 6.50 (1H, td, J=73.6, 0.4 Hz), 2.27 (3H, s).

Reference Preparation Example 14

Under ice-cooling, to a mixture of triisopropyl silanethiol 4.99 g and toluene 30 mL was added 60% sodium hydride 0.63 g and the mixtures were stirred for thirty minutes. To the reaction mixtures were added 1-(2-methyl-3-bromophenyl)-4-methyl-1,4-dihydrotetrazole-5-one (described in Synthesis example 10) 2.82 g and [1,1'-bis(diphenylphosphino)ferrocene]palladium(II) dichloride dichloromethane adduct 0.856 g, and the reaction mixtures were raised to 90° C. and were stirred for four hours. After cooling the mixture, to the reaction mixtures was added water and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 1-(2-methyl-3-triisopropylsilanylthiophenyl)-4-methyl-1,4-dihydrotetrazole-5-one 3.64 g.

1-(2-methyl-3-triisopropylsilanylthiophenyl)-4-methyl-1,4-dihydrotetrazole-5-one

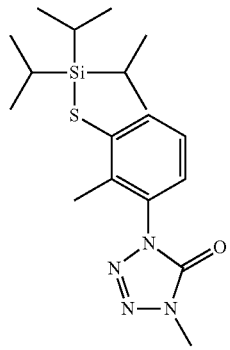 [SMILES: Cc1c(S[Si](C(C)C)(C(C)C)C(C)C)cccc1-n1nnn(C)c1=O]

$^1$H-NMR (CDCl$_3$) δ (ppm): 1.09 (18H, d, J=6.6 Hz), 1.31 (3H, q, J=6.6 Hz), 2.45 (3H, s), 3.71 (3H, s), 7.16-7.21 (2H, m), 7.64 (1H, dd, J=6.6, 2.7 Hz).

Reference Preparation Example 15

To a mixture of 1-amino-6-methylbenzoic acid 15.1 g, ethyl acetate 150 mL, ethanol 150 mL was added a 2.0 M solution of trimethylsilyl diazomethane in diethyl ether under ice-cooling. The mixtures were stirred at room temperature for four hours and were concentrated under reduced pressure to give 2-amino-6-methylbenzoic acid methyl ester 16.5 g.

2-amino-6-methylbenzoic acid methyl ester

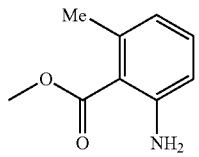

$^1$H-NMR (CDCl$_3$) δ (ppm): 6.94 (1H, t, J=8.0 Hz), 6.40-6.38 (2H, m), 4.96 (2H, s), 3.75 (3H, s), 2.29 (3H, s).

Reference Preparation Example 16

To a mixture of 2-amino-6-methylbenzoic acid methyl ester (described in Reference Preparation example 15) 16.5 g and toluene 300 mL was added triphosgene 44.5 g at room temperature and the mixtures were stirred with heating under reflux for two and a half hours. The mixtures were concentrated under reduced pressure to give 2-isocyanato-6-methylbenzoic acid methyl ester 19.0 g.

2-isocyanato-6-methylbenzoic acid methyl ester

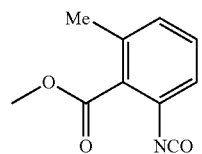

$^1$H-NMR (CDCl$_3$) δ (ppm): 7.28-7.24 (1H, m), 7.07-7.04 (1H, m), 6.98-6.95 (1H, m), 3.97 (3H, s), 2.36 (3H, s).

Reference Preparation Example 17

A mixture of 3-methyl-2-hydroxymethyl-1-aminobenzene (prepared according to the method described in WO 2010/58314) 8.10 g, concentrated sulfuric acid 6.94 g and methanol 450 mL was stirred at 50° C. for two hours. The reaction mixtures were cooled to 0° C. and thereto was added sodium hydroxide 5.66 g, and the mixtures were concentrated under reduced pressure. To the resulting residues was added aqueous saturated sodium bicarbonate solution and the mixtures were extracted with toluene. The organic layers were washed with water and aqueous saturated sodium bicarbonate solution and were dried over anhydrous sodium sulfate, and were then concentrated under reduced pressure to give 3-methyl-2-methoxymethyl-1-aminobenzene 8.62 g.

3-methyl-2-methoxymethyl-1-aminobenzene

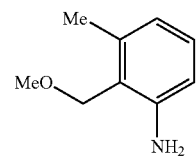 [SMILES: COCc1c(C)cccc1N]

$^1$H-NMR (CDCl$_3$) δ (ppm): 2.33 (3H, s), 3.36 (3H, s), 4.12 (2H, s), 4.54 (2H, s), 6.55 (1H, d, J=8.0 Hz), 6.58 (1H, d, J=7.3 Hz), 7.00 (1H, t, J=7.7 Hz).

Reference Preparation Example 18

A mixture of 3-methyl-2-methoxymethyl-1-aminobenzene (described in Reference Preparation example 17) 6.35 g, triphosgene 4.36 g, aqueous saturated sodium bicarbonate solution 150 mL and ethyl acetate 150 ml was stirred under ice-cooling for one hour. The organic layers of the reaction mixtures were washed with saturated saline and were concentrated under reduced pressure to give 3-methyl-2-methoxymethyl-1-isocyanatobenzene 6.30 g.

3-methyl-2-methoxymethyl-1-isocyanatobenzene

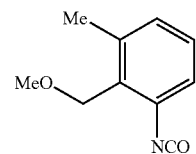

¹H-NMR (CDCl₃) δ (ppm): 2.40 (3H, s), 3.42 (3H, s), 4.51 (2H, s), 6.97 (1H, d, J=8.0 Hz), 7.03 (1H, d, J=7.6 Hz), 7.16 (1H, t, J=7.8 Hz).

Reference Preparation Example 19

A mixture of sodium borohydride 22.8 g and tetrahydrofuran 240 mL was stirred at room temperature for ten minutes. Thereto was added slowly an solution of 2-methyl-6-nitrobenzoic acid 75.0 g in toluene 120 mL, and after a completion of the dropping, the mixtures were stirred at room temperature for additional thirty minutes. The mixed solutions were ice-cooled and thereto was added slowly methanesulfonic acid 26.9 mL over two hours. The reaction mixtures were stirred at room temperature for two days. To the reaction mixtures was added water and the mixtures were extracted with ethyl acetate. The organic layers were washed with 10% hydrochloric acid and saturated saline, and were dried over anhydrous magnesium sulfate and were then concentrated under reduced pressure to give 2-(hydroxymethyl)-3-methyl-1-nitrobenzene 58.9 g.

2-(hydroxymethyl)-3-methyl-1-nitrobenzene

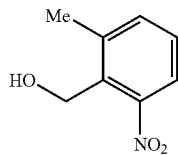

¹H-NMR (CDCl₃) δ (ppm): 7.70 (1H, d, J=8.3 Hz), 7.48 (1H, d, J=7.6 Hz), 7.35 (1H, t, J=7.6, Hz), 4.70 (2H, s), 2.65 (1H, t, J=7.3 Hz) 2.55 (3H, s).

Reference Preparation Example 20

A mixture of 2-(hydroxymethyl)-3-methyl-1-nitrobenzene (described in Reference Preparation example 19) 58.9 g and chloroform 620 mL was ice-cooled and thereto was added dropwise phosphorus tribromide 191.0 g. The mixtures were stirred at room temperature for fifteen hours. To the reaction mixtures was added water and the mixtures were extracted with ethyl acetate. The organic layers were washed with water and saturated saline and were dried over anhydrous magnesium sulfate, and were then concentrated under reduced pressure to give 2-(bromomethyl)-3-methyl-1-nitrobenzene 76.7 g.

2-(bromomethyl)-3-methyl-1-nitrobenzene

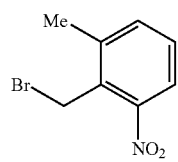

¹H-NMR (CDCl₃) δ (ppm): 7.75 (1H, d, J=8.2 Hz), 7.46 (1H, d, J=7.5 Hz), 7.36 (1H, dd, J=8.2, 7.5 Hz), 4.72 (2H, s), 2.54 (3H, s).

Reference Preparation Example 21

A mixture of 2-(bromomethyl)-3-methyl-1-nitrobenzene (described in Reference Preparation example 20) 13.8 g, 1-(4-chlorophenyl)-1H-pyrazole-3-ol (described in Reference Preparation example 24) 11.7 g, potassium carbonate 10.0 g and acetonitrile 300 mL was stirred with heating under reflux for four hours. To the reaction mixtures after standing to cool was added water and the resulting mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 3-[(2-nitro-6-methylphenyl)methyloxy]-1-(4-chlorophenyl)pyrazole 19.2 g.

3-[(2-nitro-6-methylphenyl)methyloxy]-1-(4-chlorophenyl)pyrazole

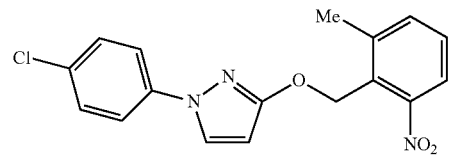

¹H-NMR (CDCl₃) δ (ppm): 7.67 (1H, d, J=2.7 Hz), 7.64 (1H, d, J=8.2 Hz), 7.53-7.49 (2H, m), 7.45 (1H, d, J=7.2 Hz), 7.39-7.34 (3H, m), 5.88 (1H, d, J=2.7 Hz), 5.55 (2H, s), 2.57 (3H, s).

Reference Preparation Example 22

A mixture of 3-[(2-nitro-6-methylphenyl)methyloxy]-1-(4-chlorophenyl)pyrazole (described in Reference Preparation example 21) 19.0 g, 5% platinum-activated carbon 1.1 g and ethyl acetate 280 mL was stirred at room temperature under hydrogen atmosphere for six hours. The reaction mixtures were filtered and the filtrates were concentrated under reduced pressure to give 3-[(2-amino-6-methylphenyl)methyloxy]-1-(4-chlorophenyl)pyrazole 16.9 g.

3-[(2-amino-6-methylphenyl)methyloxy]-1-(4-chlorophenyl)pyrazole

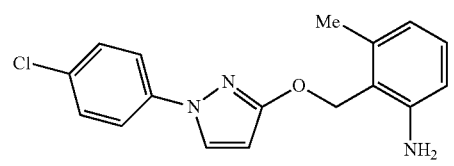 [SMILES: Cc1cccc([N+](=O)[O-])c1COc1ccn(-c2ccc(Cl)cc2)n1]

¹H-NMR (CDCl₃) δ (ppm): 7.68 (1H, d, J=2.7 Hz), 7.55-7.52 (2H, m), 7.40-7.36 (2H, m), 7.04 (1H, dd, J=7.5, 8.0 Hz), 6.64 (1H, d, J=7.5 Hz), 6.58 (1H, d, J=8.0 Hz), 5.91 (1H, d, J=2.7 Hz), 5.39 (2H, s), 4.24 (2H, brs), 2.45 (3H, s).

Reference Preparation Example 23

A mixture of 3-[(2-amino-6-methylphenyl)methyloxy]-1-(4-chlorophenyl)pyrazole (described in Reference Preparation example 22) 33.7 g, triphosgene 47.9 g and toluene 360 mL was stirred with heating under reflux for three hours. The reaction mixtures after standing to cool were concentrated under reduced pressure to give 3-[(2-isocyanato-6-methylphenyl)methyloxy]-1-(4-chlorophenyl)pyrazole 30.8 g.

3-[(2-isocyanato-6-methylphenyl)methyloxy]-1-(4-chlorophenyl)pyrazole

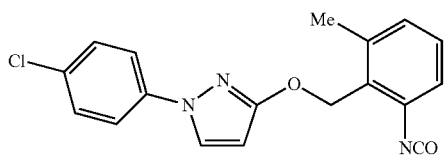

$^1$H-NMR (CDCl$_3$) δ (ppm): 7.71 (1H, d, J=2.7 Hz), 7.58 (2H, dt, J=8.9, 2.2 Hz), 7.39 (2H, dt, J=8.9, 2.2 Hz), 7.22 (1H, t, J=7.7 Hz), 7.07 (1H, d, J=7.7 Hz), 7.03 (1H, d, J=8.0 Hz), 5.93 (1H, d, J=2.7 Hz), 5.39 (2H, s), 2.47 (3H, s).

Reference Preparation Example 24

To a mixture of 4-chlorophenylhydrazine 28.5 g, 28% sodium methoxide-methanol solution 81.3 g and methanol 200 mL was added methyl propiolate 29.4 g under ice-cooling, and the mixtures were stirred at 100° C. for two hours. To the reaction mixtures after standing to cool was added ice water 100 mL, and the mixtures were acidified with 30% sulfuric acid and were stirred at 100° C. for two hours. To the reaction mixtures after standing to cool was added saturated saline and the mixtures were extracted with ethyl acetate. The organic layers were washed with water and saturated saline and then were dried over anhydrous magnesium sulfate and were then concentrated under reduced pressure to give 1-(4-chlorophenyl)-1H-pyrazole-3-ol 15.6 g.

1-(4-chlorophenyl)-1H-pyrazole-3-ol

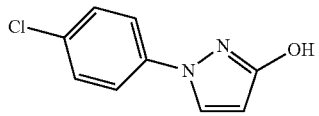

$^1$H-NMR (DMSO-d$_6$) δ (ppm): 5.84 (1H, d, J=2.4 Hz), 7.48 (2H, d, J=8.9 Hz), 7.70 (2H, d, J=8.9 Hz), 8.25 (1H, d, J=2.7 Hz), 10.32 (1H, s).

Reference Preparation Example 25

A similar reaction to Reference Preparation example 24 using phenylhydrazine instead of 4-chlorophenylhydrazine gave 1-phenyl-1H-pyrazole-3-ol.

1-phenyl-1H-pyrazole-3-ol

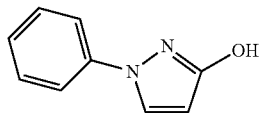 [SMILES: Oc1ccn(-c2ccccc2)n1]

$^1$H-NMR (CDCl$_3$) δ (ppm): 5.91 (1H, d, J=2.6 Hz), 7.25 (2H, tt, J=7.2, 1.2 Hz), 7.43-7.53 (4H, m), 7.67 (1H, d, J=2.7 Hz).

Reference Preparation Example 26

A similar reaction to Reference Preparation example 24 using 4-methoxyphenylhydrazine instead of 4-chlorophenylhydrazine gave 1-(4-methoxyphenyl)-1H-pyrazole-3-ol.

1-(4-methoxyphenyl)-1H-pyrazole-3-ol

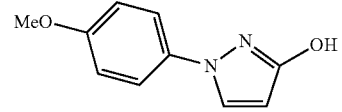

$^1$H-NMR (DMSO-d$_6$) δ (ppm): 3.77 (3H, s), 5.74 (1H, d, J=2.7 Hz), 6.99 (2H, d, J=8.9 Hz), 7.58 (2H, d, J=8.9 Hz), 8.09 (1H, d, J=2.4 Hz), 10.10 (1H, s).

Reference Preparation Example 27

A similar reaction to Reference Preparation example 24 using 4-methylphenylhydrazine instead of 4-chlorophenylhydrazine gave 1-(4-methylphenyl)-1H-pyrazole-3-ol.

1-(4-methylphenyl)-1H-pyrazole-3-ol

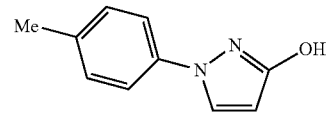

$^1$H-NMR (CDCl$_3$) δ (ppm): 2.36 (3H, s), 5.87 (1H, dd, J=2.7, 0.5 Hz), 7.25 (2H, d, J=8.5 Hz), 7.39 (2H, d, J=8.5 Hz), 7.60 (1H, dd, J=2.7, 0.5 Hz), 12.09 (1H, s).

Reference Preparation Example 28

A similar reaction to Reference Preparation example 24 using 4-cyanophenylhydrazine instead of 4-chlorophenylhydrazine gave 1-(4-cyanophenyl)-1H-pyrazole-3-ol.

1-(4-cyanophenyl)-1H-pyrazole-3-ol

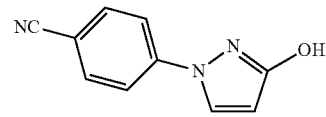 [SMILES: N#Cc1ccc(-n2ccc(O)n2)cc1]

$^1$H-NMR (DMSO-d$_6$) δ (ppm): 5.94 (1H, dd, J=2.7, 0.7 Hz), 7.86 (2H, d, J=8.7 Hz), 7.90 (2H, d, J=8.7 Hz), 8.41 (1H, d, J=2.2 Hz), 10.59 (1H, s).

Reference Preparation Example 29

A similar reaction to Reference Preparation example 24 using 4-fluorophenylhydrazine instead of 4-chlorophenylhydrazine gave 1-(4-fluorophenyl)-1H-pyrazole-3-ol.

1-(4-fluorophenyl)-1H-pyrazole-3-ol

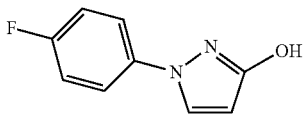

¹H-NMR (CDCl₃) δ (ppm): 5.89 (1H, d, J=2.7 Hz), 7.15 (2H, tt, J=8.5, 2.2 Hz), 7.47 (2H, ddt, J=9.2, 4.6, 2.2 Hz), 7.60 (1H, d, J=2.7 Hz).

Reference Preparation Example 30

A mixture of methyl 3-methoxyacrylate 100.0 g, sodium hydroxide 37.9 g and water 470 mL was stirred with heating under reflux for one hour. The reaction mixtures after standing to cool was concentrated under reduced pressure to give sodium 3-methoxyacrylate 92.8 g.

Sodium 3-Methoxyacrylate

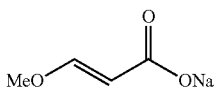

¹H-NMR (D₂O) δ (ppm): 3.52 (3H, s), 5.10 (1H, dd, J=12.7, 0.7 Hz), 7.23 (1H, d, J=12.7 Hz).

Reference Preparation Example 31

To a mixture of sodium 3-methoxyacrylate 5.00 g (described in Reference Preparation example 30) and tetrahydrofuran 50 mL was added thionyl chloride 5.0 mL under ice-cooling. The mixtures were stirred with heating under reflux for one hour and were then concentrated under reduced pressure to give crude 3-methoxyacrylic acid chloride.

To a mixture of tert-butylhydrazine hydrochloride salt 5.41 g and triethylamine 10.1 mL was added 3-methoxyacrylic acid chloride (the total amounts) under ice-cooling and the mixtures were stirred at room temperature for one hour. To the reaction mixtures was added water and the mixtures were extracted with ethyl acetate. The organic layers were washed with water, aqueous saturated sodium bicarbonate solution and saturated saline and were dried over anhydrous sodium sulfate, and were then concentrated under reduced pressure to give 3-methoxyacrylic acid N'-tert-butylhydrazide.

3-methoxyacrylic acid N'-tert-butylhydrazide

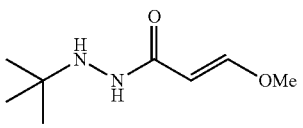

¹H-NMR (DMSO-d₆) δ (ppm): 0.98 (9H, s), 3.62 (3H, s), 4.68 (1H, s), 5.36 (1H, d, J=12.3 Hz), 7.36 (1H, d, J=12.3 Hz), 9.02 (1H, s).

Reference Preparation Example 32

A mixture of 3-methoxyacrylic acid N'-tert-butyl hydrazide (described in Reference Preparation example 31) and concentrated hydrochloric acid 10 mL was stirred at 25° C. for fifteen minutes. To the reaction mixtures was added aqueous sodium hydroxide and the precipitated solids were filtered to give 1-(1,1-dimethylethyl)-1H-pyrazole-3-ol 1.50 g.

1-(1,1-dimethylethyl)-1H-pyrazole-3-ol

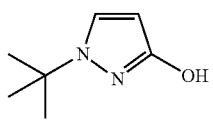

¹H-NMR (DMSO-d₆) δ (ppm): 1.42 (9H, s), 5.39 (1H, d, J=2.4 Hz), 7.42 (1H, d, J=2.4 Hz), 9.51 (1H, s).

Reference Preparation Example 33

A mixture of methyl 3-methoxyacrylate 21.1 g, hydrazine hydrate 10.0 g and methanol 20 mL was stirred with heating under reflux for two hours. The reaction mixtures were concentrated under reduced pressure to give 1H-pyrazole-3-ol 11.0 g.

1H-pyrazole-3-ol

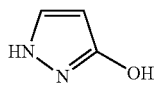

¹H-NMR (DMSO-d₆) δ (ppm): 5.43 (1H, d, J=2.2 Hz), 7.35 (1H, d, J=2.2 Hz), 10.22 (1H, s).

Reference Preparation Example 34

A mixture of 1H-pyrazole-3-ol (described in Reference Preparation example 33) 3.00 g, acetic anhydride 3.1 mL and acetic acid 90 mL was stirred at 25° C. for two hours. To the reaction mixtures was added water and the mixtures were extracted with ethyl acetate. The organic layers were washed with water, aqueous saturated sodium bicarbonate solution and saturated saline and were dried over anhydrous sodium sulfate, and were then concentrated under reduced pressure to give 1-acetyl-1H-pyrazole-3-ol 1.50 g.

1-acetyl-1H-pyrazole-3-ol

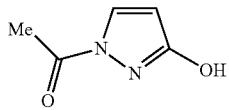

¹H-NMR (DMSO-d₆) δ (ppm): 2.49 (3H, s), 6.02 (1H, dd, J=2.9, 1.0 Hz), 8.14 (1H, dd, J=2.9, 1.0 Hz), 11.04 (1H, s).

Reference Preparation Example 35

A mixture of N-hydroxysuccinimide 200 g, sodium 3-methoxyacrylate (described in Reference Preparation example 30) 287 g, 1-ethyl-3-(3-dimethylaminopropyl)carbodiimide hydrochloride salt 528 g, pyridine 269 g and N,N-dimethylformamide 2 L was stirred at room temperature for 44 hours. To aqueous saturated sodium bicarbonate solution was added the reaction mixtures and the resulting mixtures were extracted with ethyl acetate. The organic layers were washed with aqueous saturated sodium bicarbonate solution, aqueous sodium hydrogen sulfide solution and saturated saline and were dried over anhydrous magnesium sulfate, and were then concentrated under reduced pressure. The resulting residues washed with a mixed solvent of tert-butyl methyl ether and hexane and were dried under reduced pressure to give 3-methoxyacrylic acid N-hydroxysuccinimide 174 g.

3-methoxyacrylic acid N-hydroxysuccinimide

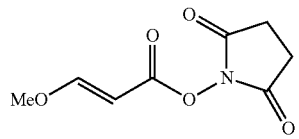 [SMILES: CO/C=C/C(=O)ON1C(=O)CCC1=O]

¹H-NMR (CDCl₃) δ (ppm): 7.84 (1H, d, J=12.7 Hz), 5.38 (1H, d, J=12.4 Hz), 3.80 (3H, s), 2.84 (4H, s).

Reference Preparation Example 36

A mixture of 3-methoxyacrylic acid N-hydroxysuccinimide (described in Reference Preparation example 35) 13.6 g, 4-bromophenylhydrazine hydrochloride salt 16.8 g, sodium hydroxide 3.0 g, dioxane 250 mL and water 250 mL was heated at 60° C. for sixteen hours. To water added the reaction solutions and the mixtures were extracted with ethyl acetate. The organic layers were washed with aqueous saturated sodium bicarbonate solution and saturated saline and were dried over anhydrous magnesium sulfate, and were then concentrated under reduced pressure. The resulting residues washed with a mixed solvent of tert-butyl methyl ether and hexane and were dried under reduced pressure to give 3-methoxyacrylic acid N'-(4-bromophenyl)hydrazide 16.4 g.

3-methoxyacrylic acid
N'-(4-bromophenyl)hydrazide

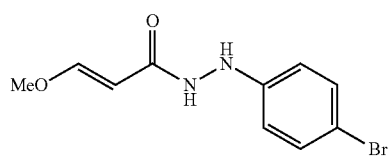 [SMILES: CO/C=C/C(=O)NNc1ccc(Br)cc1]

¹H-NMR (DMSO-D₆) δ (ppm): 9.48 (1H, d, J=1.7 Hz), 7.89 (1H, d, J=2.2 Hz), 7.43 (1H, d, J=12.3 Hz), 7.26 (2H, d, J=8.7 Hz), 6.62 (2H, d, J=8.2 Hz), 5.39 (1H, d, J=12.6 Hz), 3.64 (3H, s).

Reference Preparation Example 37

A mixture of 3-methoxyacrylic acid N'-(4-bromophenyl)hydrazide (described in Reference Preparation example 36) 16.4 g and concentrated hydrochloric acid 200 mL was stirred at room temperature for one hour and to the reaction mixtures was then added water. The precipitated solids were filtered off. The solids obtained were washed with aqueous saturated sodium bicarbonate solution, water and hexane, and were dried under reduced pressure to give 1-(4-bromophenyl)-1H-pyrazole-3-ol 123 g.

1-(4-bromophenyl)-1H-pyrazole-3-ol

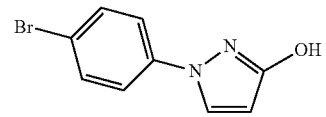

¹H-NMR (CDCl₃) δ (ppm): 7.64 (1H, d, J=2.7 Hz), 7.57 (2H, dt, J=9.5, 2.6 Hz), 7.39 (2H, dt, J=9.3, 2.5 Hz), 5.92 (1H, d, J=2.4 Hz).

Reference Preparation Example 38

A similar reaction to Reference Preparation example 36 using 4-trifluoromethoxyphenylhydrazine instead of 4-bromophenylhydrazine hydrochloride salt gave 3-methoxyacrylic acid N'-(4-trifluoromethoxyphenyl)hydrazide.

3-methoxyacrylic acid
N'-(4-trifluoromethoxyphenyl)hydrazide

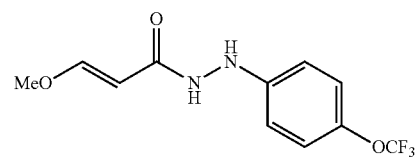 [SMILES: CO/C=C/C(=O)NNc1ccc(OC(F)(F)F)cc1]

¹H-NMR (DMSO-D₆) δ (ppm): 9.52 (1H, d, J=2.7 Hz), 7.97 (1H, d, J=2.4 Hz), 7.45 (1H, d, J=12.3 Hz), 7.12 (2H, d, J=8.9 Hz), 6.72 (2H, d, J=8.9 Hz), 5.41 (1H, d, J=12.3 Hz), 3.66 (3H, s).

Reference Preparation Example 39

A similar reaction to Reference Preparation example 37 using 3-methoxyacrylic acid N'-(4-trifluoromethoxyphenyl)hydrazide (described in Reference preparation example 38) instead of 3-methoxyacrylic acid N'-(4-bromophenyl)hydrazide gave 1-(4-trifluoromethoxyphenyl)-1H-pyrazole-3-ol.

1-(4-trifluoromethoxyphenyl)-1H-pyrazole-3-ol

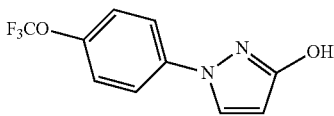

¹H-NMR (CDCl₃) δ (ppm): 11.65 (1H, s), 7.66 (1H, d, J=2.7 Hz), 7.53 (2H, dt, J=9.8, 2.7 Hz), 7.32 (2H, d, J=8.8 Hz), 5.94 (1H, d, J=2.7 Hz).

Reference Preparation Example 40

A similar reaction to Reference Preparation example 36 using cyclohexylhydrazine hydrochloride salt instead of 4-bromophenylhydrazine hydrochloride salt gave 3-methoxyacrylic acid N'-cyclohexylhydrazide.

3-methoxyacrylic acid N'-cyclohexylhydrazide

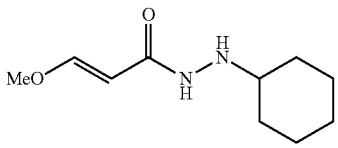 [SMILES: CO/C=C/C(=O)NNC1CCCCC1]

¹H-NMR (DMSO-D₆) δ (ppm): 9.11 (1H, s), 7.36 (1H, d, J=12.3 Hz), 5.27 (1H, d, J=12.6 Hz), 4.34 (1H, s), 3.60 (3H, s), 2.60-2.55 (1H, m), 1.74-0.99 (10H, m).

Reference Preparation Example 41

A similar reaction to Reference Preparation example 37 using 3-methoxyacrylic acid N'-cyclohexylhydrazide (described in Reference Preparation example 40) instead of 3-methoxyacrylic acid N'-(4-bromophenyl)hydrazide gave 1-cyclohexyl-1H-pyrazole-3-ol.

1-cyclohexyl-1H-pyrazole-3-ol 1

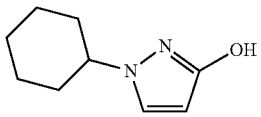 [SMILES: Oc1ccn(C2CCCCC2)n1]

¹H-NMR (CDCl₃) δ (ppm): 7.16 (1H, d, J=2.4 Hz), 5.58 (1H, d, J=2.4 Hz), 3.84 (1H, tt, J=11.7, 3.8 Hz), 2.12-2.09 (2H, m), 1.90-1.85 (2H, m), 1.73-1.55 (3H, m), 1.41-1.37 (2H, m), 1.30-1.22 (1H, m).

Reference Preparation Example 42

A similar reaction to Reference Preparation example 36 using 4-methoxyphenylhydrazine hydrochloride salt instead of 4-bromophenylhydrazine hydrochloride salt gave 3-methoxyacrylic acid N'-(4-methoxyphenyl)hydrazide.

3-methoxyacrylic acid N'-(4-methoxyphenyl)hydrazide

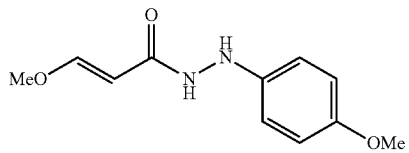 [SMILES: CO/C=C/C(=O)NNc1ccc(OC)cc1]

¹H-NMR (CDCl₃) δ (ppm): 7.53 (1H, d, J=2.7 Hz), 7.38 (2H, dt, J=9.7, 2.8 Hz), 6.94 (2H, dt, J=9.4, 2.5 Hz), 5.84 (1H, d, J=2.4 Hz), 3.83 (3H, s), 3.71 (3H, s).

Reference Preparation Example 43

A similar reaction to Reference Preparation example 37 using 3-methoxyacrylic acid N'-(4-methoxyphenyl)hydrazide (described in Reference Preparation example 42) instead of 3-methoxyacrylic acid N'-(4-bromophenyl)hydrazide gave 1-(4-methoxyphenyl)-1H-pyrazole-3-ol.

Reference Preparation Example 44

A similar reaction to Reference Preparation example 36 using 4-methylphenylhydrazine hydrochloride salt instead of 4-bromophenylhydrazine hydrochloride salt gave 3-methoxyacrylic acid N'-(4-methylphenyl)hydrazide.

3-methoxyacrylic acid N'-(4-methylphenyl)hydrazide

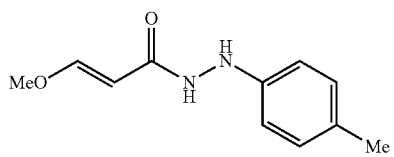 [SMILES: CO/C=C/C(=O)NNc1ccc(C)cc1]

¹H-NMR (CDCl₃) δ (ppm): 7.60 (1H, d, J=2.7 Hz), 7.36 (2H, dt, J=8.9, 2.2 Hz), 7.21 (2H, d, J=8.0 Hz), 5.86 (1H, d, J=2.7 Hz), 3.70 (3H, s), 2.36 (3H, s).

Reference Preparation Example 45

A similar reaction to Reference Preparation example 37 using 3-methoxyacrylic acid N'-(4-methylphenyl)hydrazide (described in Reference preparation example 44) instead of 3-methoxyacrylic acid N'-(4-bromophenyl)hydrazide gave 1-(4-methoxyphenyl)-1H-pyrazole-3-ol.

Reference Preparation Example 46

A mixture of 3-methoxyacrylic acid N-hydroxysuccinimide (described in Reference preparation example 35) 16.8 g, 2-chlorophenylhydrazine hydrochloride salt 15.5 g, sodium hydroxide 3.56 g, dioxane 250 mL and water 250 mL was heated at 60° C. for four days. To water was added the reaction solutions and the mixtures were extracted with ethyl acetate. The organic layers were washed with aqueous saturated saline and were dried over anhydrous magnesium sulfate, and were then concentrated under reduced pressure to give oil mixtures. The resulting mixtures and concentrated hydrochloric acid 60 mL was stirred at room temperature for two hours. To the reaction solutions was added 28% aqueous sodium hydroxide solution in ice-cooling. The precipitated solids were filtered off and the solids were washed with isopropyl alcohol to give 1-(2-chlorophenyl)-1H-pyrazole-3-ol 5.9 g.

1-(2-chlorophenyl)-1H-pyrazole-3-ol

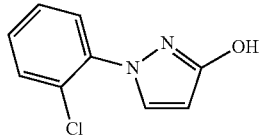 [SMILES: Oc1ccn(-c2ccccc2Cl)n1]

$^1$H-NMR (CDCl$_3$) δ (ppm): 7.63 (1H, d, J=2.7 Hz), 7.52 (2H, ddd, J=10.6, 8.0, 1.6 Hz), 7.40 (1H, td, J=7.7, 1.5 Hz), 7.30 (1H, td, J=7.7, 1.5 Hz), 5.86 (1H, d, J=2.7 Hz).

Reference Preparation Example 47

A similar reaction to Reference Preparation example 46 using 3-chlorophenylhydrazine hydrochloride salt instead of 2-chlorophenylhydrazine hydrochloride salt gave 1-(3-chlorophenyl)-1H-pyrazole-3-ol.

1-(3-chlorophenyl)-1H-pyrazole-3-ol

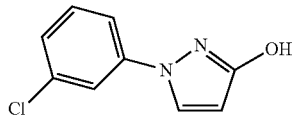 [SMILES: Oc1ccn(-c2cccc(Cl)c2)n1]

$^1$H-NMR (CDCl$_3$) δ (ppm): 7.68 (1H, d, J=2.7 Hz), 7.52 (1H, s), 7.43 (1H, d, J=8.9 Hz), 7.38 (1H, t, J=7.8 Hz), 7.22 (1H, d, J=7.2 Hz), 5.94 (1H, d, J=2.7 Hz).

Reference Preparation Example 48

A similar reaction to Reference Preparation example 46 using 2-fluorophenylhydrazine hydrochloride salt instead of 2-chlorophenylhydrazine hydrochloride salt gave 1-(2-fluorophenyl)-1H-pyrazole-3-ol.

1-(2-fluorophenyl)-1H-pyrazole-3-ol

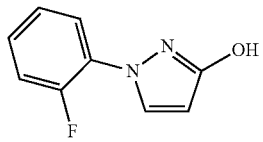 [SMILES: Oc1ccn(-c2ccccc2F)n1]

$^1$H-NMR (CDCl$_3$) δ (ppm): 7.73 (1H, t, J=2.7 Hz), 7.69-7.65 (1H, m), 7.30-7.19 (3H, m), 5.91 (1H, d, J=2.7 Hz).

Reference Preparation Example 49

A similar reaction to Reference Preparation example 46 using 2-methylphenylhydrazine hydrochloride salt instead of 2-chlorophenylhydrazine hydrochloride salt gave 1-(2-methylphenyl)-1H-pyrazole-3-ol.

1-(2-methylphenyl)-1H-pyrazole-3-ol

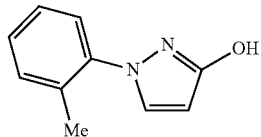 [SMILES: Cc1ccccc1-n1ccc(O)n1]

$^1$H-NMR (CDCl$_3$) δ (ppm): 7.32-7.28 (5H, m), 5.77 (1H, d, J=2.5 Hz), 2.29 (3H, s).

Reference Preparation Example 50

A similar reaction to Reference Preparation example 46 using 2-methoxyphenylhydrazine hydrochloride salt instead of 2-chlorophenylhydrazine hydrochloride salt gave 1-(2-methoxyphenyl)-1H-pyrazole-3-ol.

1-(2-methoxyphenyl)-1H-pyrazole-3-ol

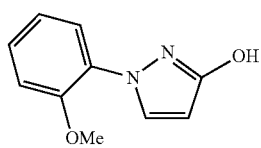 [SMILES: COc1ccccc1-n1ccc(O)n1]

$^1$H-NMR (CDCl$_3$) δ (ppm): 7.73 (1H, d, J=2.7 Hz), 7.50 (1H, dd, J=8.0, 1.6 Hz), 7.26 (1H, ddd, J=8.7, 7.0, 1.3 Hz), 7.07 (1H, td, J=7.7, 1.3 Hz), 7.02 (1H, dd, J=8.4, 1.3 Hz), 5.82 (1H, d, J=2.5 Hz), 3.88 (3H, s).

Reference Preparation Example 51

A similar reaction to Reference Preparation example 46 using 2,3,4,5,6-pentafluorophenylhydrazine hydrochloride salt instead of 2-chlorophenylhydrazine hydrochloride salt gave 1-(2,3,4,5,6-pentafluorophenyl)-1H-pyrazole-3-ol.

1-(2,3,4,5,6-pentafluorophenyl)-1H-pyrazole-3-ol

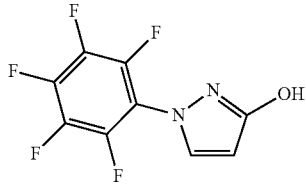 [SMILES: Oc1ccn(-c2c(F)c(F)c(F)c(F)c2F)n1]

$^1$H-NMR (CDCl$_3$) δ (ppm): 5.97 (1H, d, J=2.7 Hz), 7.41 (1H, t, J=1.3 Hz).

Reference Preparation Example 52

To oxalyl chloride 407 g was added dropwise ethyl vinyl ether 170 g in ice-cooling. After a completion of the dropping, the mixtures were raised to room temperature and were stirred for fifteen hours. The reaction mixtures were concentrated under reduced pressure. The resulting residues were raised to 120° C. and were stirred for thirty minutes. After cooling, the mixtures were distilled under reduced pressure to give 3-ethoxyacrylic acid chloride 137 g.

3-ethoxyacrylic acid chloride

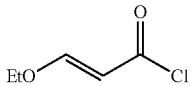

$^1$H-NMR (CDCl$_3$) δ (ppm): 7.79 (1H, d, J=12.0 Hz), 5.51 (1H, d, J=12.0 Hz), 4.06 (2H, q, J=7.1 Hz), 1.40 (3H, t, J=7.1 Hz).

Reference Preparation Example 53

To a mixture of 4-methylthiophenylhydrazine 4.47 g, pyridine 2.4 mL and N,N-dimethylformamide 30 mL was added dropwise 3-ethoxyacrylic acid chloride 3.9 g in ice-cooling. The reaction mixtures were raised to room temperature and were stirred for two hours. To the reaction solutions was added water and the mixtures were extracted with ethyl acetate. The organic layers were washed with saturated saline and were concentrated under reduced pressure. The resulting residues were washed with toluene and hexane and were dried in reduced pressure to give 3-ethoxyacrylic acid N'-(4-methylthiophenyl)hydrazide 1.4 g.

3-ethoxyacrylic acid
N'-(4-methylthiophenyl)hydrazide

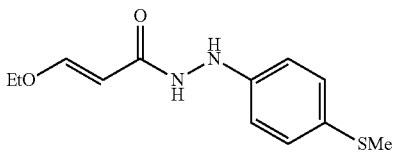 [SMILES: CCO/C=C/C(=O)NNc1ccc(SC)cc1]

$^1$H-NMR (DMSO-D$_6$) δ (ppm): 9.84 (1H, s), 9.11 (1H, s), 7.73 (1H, d, J=12.6 Hz), 7.40 (2H, dt, J=9.2, 2.3 Hz), 7.17 (2H, dt, J=9.3, 2.3 Hz), 5.38 (1H, d, J=12.6 Hz), 4.02 (2H, q, J=7.0 Hz), 2.40 (3H, s), 1.25 (3H, t, J=7.1 Hz).

Reference Preparation Example 54

A similar reaction to Reference Preparation example 37 using 3-ethoxyacrylic acid N'-(4-methylthiophenyl)hydrazide (described in Reference preparation example 53) instead of 3-methoxyacrylic acid N'-(4-bromophenyl)hydrazide gave 1-(4-methylthiophenyl)-1H-pyrazole-3-ol.

1-(4-methylthiophenyl)-1H-pyrazole-3-ol

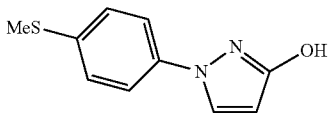

$^1$H-NMR (DMSO-D$_6$) δ (ppm): 10.21 (1H, s), 9.02 (1H, d, J=3.9 Hz), 7.54 (2H, dt, J=9.4, 2.4 Hz), 7.23 (2H, dt, J=9.2, 2.4 Hz), 5.70 (1H, d, J=3.9 Hz), 2.43 (3H, s).

Reference Preparation Example 55

A similar reaction to Reference Preparation example 53 using 4-nitrophenylhydrazine instead of 4-methylthiophenylhydrazine gave 3-ethoxyacrylic acid N'-(4-nitrophenyl)hydrazide.

3-ethoxyacrylic acid N'-(4-nitrophenyl)hydrazide

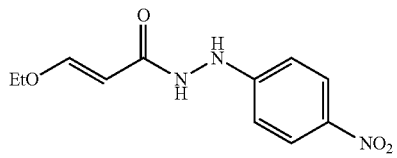 [SMILES: CCO/C=C/C(=O)NNc1ccc([N+](=O)[O-])cc1]

$^1$H-NMR (DMSO-D$_6$) δ (ppm): 9.76 (1H, s), 9.05 (1H, s), 8.06 (2H, d, J=9.2 Hz), 7.48 (1H, d, J=12.6 Hz), 6.72 (2H, d, J=9.2 Hz), 5.41 (1H, d, J=12.4 Hz), 3.95 (2H, q, J=7.0 Hz), 1.26 (3H, t, J=7.1 Hz).

Reference Preparation Example 56

A similar reaction to Reference Preparation example 37 using 3-ethoxyacrylic acid N'-(4-nitrophenyl)hydrazide (described in Reference preparation example 55) instead of 3-methoxyacrylic acid N'-(4-bromophenyl)hydrazide gave 1-(4-nitrophenyl)-1H-pyrazole-3-ol.

1-(4-nitrophenyl)-1H-pyrazole-3-ol

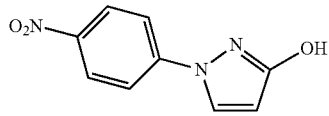 [SMILES: O=[N+]([O-])c1ccc(-n2ccc(O)n2)cc1]

$^1$H-NMR (DMSO-D$_6$) δ (ppm): 8.46 (1H, d, J=2.7 Hz), 8.31 (2H, dt, J=10.0, 2.6 Hz), 7.92 (2H, dt, J=9.9, 2.6 Hz), 6.00 (1H, d, J=2.7 Hz).

Reference Preparation Example 57

A similar reaction to Reference Preparation example 53 using 4-trifluoroacetylphenylhydrazine instead of 4-methylthiophenylhydrazine gave 3-ethoxyacrylic acid N'-(4-trifluoroacetylphenyl)hydrazide.

3-ethoxyacrylic acid
N'-(4-trifluoroacetylphenyl)hydrazide

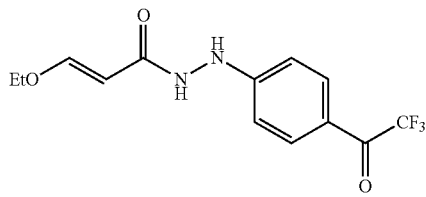 [SMILES: CCO/C=C/C(=O)NNc1ccc(C(=O)C(F)(F)F)cc1]

¹H-NMR (DMSO-D₆) δ (ppm): 9.78 (1H, s), 9.16 (1H, s), 7.87 (2H, d, J=8.5 Hz), 7.48 (1H, d, J=12.4 Hz), 6.78 (2H, d, J=8.9 Hz), 5.41 (1H, d, J=12.4 Hz), 3.95 (2H, q, J=6.3 Hz), 1.27 (3H, t, J=7.0 Hz).

Reference Preparation Example 58

A similar reaction to Reference Preparation example 37 using 3-ethoxyacrylic acid N'-(4-trifluoroacetylphenyl)hydrazide (described in Reference preparation example 57) instead of 3-methoxyacrylic acid N'-(4-bromophenyl)hydrazide gave 1-(4-trifluoroacetylphenyl)-1H-pyrazole-3-ol.

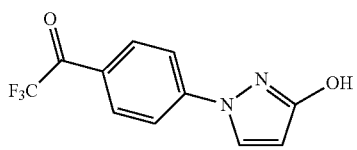 [SMILES: O=C(c1ccc(-n2ccc(O)n2)cc1)C(F)(F)F]

¹H-NMR (DMSO-D₆) δ (ppm): 10.76 (1H, s), 8.47 (1H, d, J=2.7 Hz), 8.12 (2H, d, J=8.2 Hz), 7.95 (2H, dt, J=9.3, 2.2 Hz), 6.01 (1H, d, J=2.7 Hz).

Reference Preparation Example 59

A similar reaction to Reference Preparation example 53 using 4-trifluoromethylthiophenylhydrazine instead of 4-methylthiophenylhydrazine gave 3-ethoxyacrylic acid N'-(4-trifluoromethylthiophenyl)hydrazide.

3-ethoxyacrylic acid N'-(4-trifluoromethylthiophenyl)hydrazide

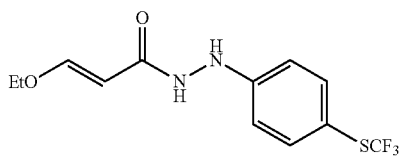

¹H-NMR (DMSO-D₆) δ (ppm): 10.10 (1H, s), 9.49 (1H, s), 7.77 (1H, d, J=12.4 Hz), 7.66-7.60 (4H, m), 5.43 (1H, d, J=12.6 Hz), 4.06 (2H, q, J=7.1 Hz), 1.28 (3H, t, J=7.1 Hz).

Reference Preparation Example 60

A similar reaction to Reference Preparation example 37 using 3-ethoxyacrylic acid N'-(4-trifluoromethylthiophenyl) hydrazide (described in Reference preparation example 59) instead of 3-methoxyacrylic acid N'-(4-bromophenyl)hydrazide gave 1-(4-trifluoromethylthiophenyl)-1H-pyrazole-3-ol.

1-(4-trifluoromethylthiophenyl)-1H-pyrazole-3-ol

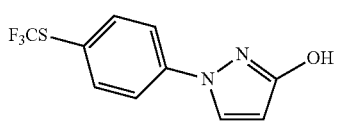

¹H-NMR (CDCl₃) δ (ppm): 8.53 (1H, d, J=4.0 Hz), 7.79 (1H, s), 7.68 (2H, d, J=8.3 Hz), 7.61 (2H, d, J=8.6 Hz), 5.57 (1H, d, J=3.8 Hz).

Reference Preparation Example 61

A similar reaction to Reference Preparation example 53 using 4-ethylphenylhydrazine instead of 4-methylthiophenylhydrazine gave 3-ethoxyacrylic acid N'-(4-ethylphenyl)hydrazide.

3-ethoxyacrylic acid N'-(4-ethylphenyl)hydrazide

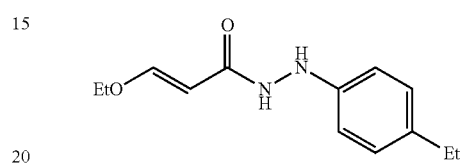

¹H-NMR (DMSO-D₆) δ (ppm): 9.79 (1H, s), 9.00 (1H, s), 7.76 (1H, d, J=12.6 Hz), 7.36 (2H, d, J=8.6 Hz), 7.11 (2H, d, J=8.6 Hz), 5.42 (1H, d, J=12.6 Hz), 4.05 (2H, q, J=7.1 Hz), 2.54 (2H, q, J=7.5 Hz), 1.28 (3H, t, J=7.1 Hz), 1.15 (3H, t, J=7.6 Hz).

Reference Preparation Example 62

A similar reaction to Reference Preparation example 37 using 3-ethoxyacrylic acid N'-(4-ethylphenyl)hydrazide (described in Reference preparation example 61) instead of 3-methoxyacrylic acid N'-(4-bromophenyl)hydrazide gave 1-(4-ethylphenyl)-1H-pyrazole-3-ol.

1-(4-ethylphenyl)-1H-pyrazole-3-ol

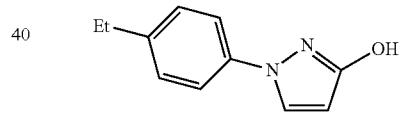

¹H-NMR (CDCl₃) δ (ppm): 8.52 (1H, d, J=4.0 Hz), 7.64 (1H, s), 7.40 (2H, d, J=8.3 Hz), 7.21 (2H, d, J=8.6 Hz), 5.51 (1H, d, J=3.8 Hz), 2.64 (2H, q, J=7.6 Hz), 1.23 (3H, t, J=7.6 Hz).

Reference Preparation Example 63

A similar reaction to Reference Preparation example 53 using 2-bromophenylhydrazine instead of 4-methylthiophenylhydrazine gave 3-ethoxyacrylic acid N'-(2-bromophenyl)hydrazide.

3-ethoxyacrylic acid N'-(2-bromo-phenyl)hydrazide

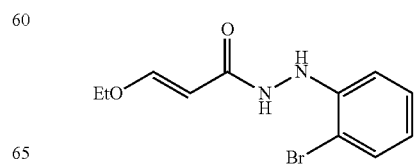

¹H-NMR (DMSO-D₆) δ (ppm): 9.65 (1H, d, J=2.5 Hz), 7.45-7.43 (2H, m), 7.22-7.17 (2H, m), 6.73-6.67 (2H, m), 5.43 (1H, d, J=12.4 Hz), 3.93 (2H, q, J=7.0 Hz), 1.26 (3H, t, J=6.9 Hz).

Reference Preparation Example 64

A similar reaction to Reference Preparation example 37 using 3-ethoxyacrylic acid N'-(2-bromophenyl)hydrazide (described in Reference preparation example 63) instead of 3-methoxyacrylic acid N'-(4-bromophenyl)hydrazide gave 1-(2-bromophenyl)-1H-pyrazole-3-ol.

1-(2-bromophenyl)-1H-pyrazole-3-ol

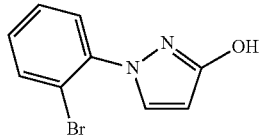

¹H-NMR (CDCl₃) δ (ppm): 7.69 (1H, d, J=8.1 Hz), 7.59 (1H, d, J=2.5 Hz), 7.50 (1H, dd, J=7.8, 1.5 Hz), 7.44 (1H, t, J=7.6 Hz), 7.25-7.22 (1H, m), 5.84 (1H, d, J=2.5 Hz).

Reference Preparation Example 65

A similar reaction to Reference Preparation example 53 using 3-bromophenylhydrazine instead of 4-methylthiophenylhydrazine gave 3-ethoxyacrylic acid N'-(3-bromophenyl)hydrazide.

3-ethoxyacrylic acid N'-(3-bromophenyl)hydrazide

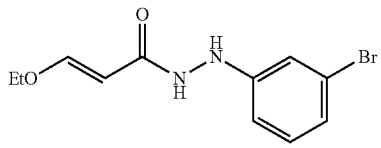 [SMILES: CCO/C=C/C(=O)NNc1cccc(Br)c1]

¹H-NMR (DMSO-D₆) δ (ppm): 9.48 (1H, s), 7.43 (1H, d, J=12.4 Hz), 7.08 (1H, t, J=8.0 Hz), 6.83 (1H, d, J=7.8 Hz), 6.80 (1H, s), 6.67 (1H, d, J=8.1 Hz), 5.40 (1H, d, J=12.4 Hz), 3.93 (2H, q, J=7.0 Hz), 1.26 (3H, t, J=6.9 Hz).

Reference Preparation Example 66

A similar reaction to Reference Preparation example 37 using 3-ethoxyacrylic acid N'-(3-bromophenyl)hydrazide (described in Reference preparation example 65) instead of 3-methoxyacrylic acid N'-(4-bromophenyl)hydrazide gave (3-bromophenyl)-1H-pyrazole-3-ol.

1-(3-bromophenyl)-1H-pyrazole-3-ol

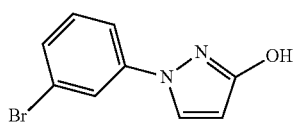

¹H-NMR (CDCl₃) δ (ppm): 7.67-7.65 (2H, m), 7.48 (1H, ddd, J=8.0, 1.1, 0.6 Hz), 7.38 (1H, ddd, J=7.9, 1.0, 0.5 Hz), 7.32 (1H, t, J=8.0 Hz), 5.94 (1H, d, J=2.8 Hz).

Reference Preparation Example 67

A similar reaction to Reference Preparation example 53 using 3-methoxyphenylhydrazine instead of 4-methylthiophenylhydrazine gave 3-ethoxyacrylic acid N'-(3-methoxyphenyl)hydrazide.

3-ethoxyacrylic acid N'-(3-methoxyphenyl)hydrazide

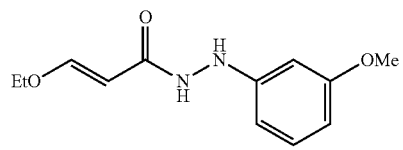 [SMILES: CCO/C=C/C(=O)NNc1cccc(OC)c1]

¹H-NMR (DMSO-D₆) δ (ppm): 9.38 (1H, d, J=2.8 Hz), 7.67 (1H, d, J=2.5 Hz), 7.40 (1H, d, J=12.4 Hz), 7.02 (1H, t, J=8.1 Hz), 6.27-6.24 (3H, m), 5.39 (1H, d, J=12.4 Hz), 3.91 (2H, q, J=7.0 Hz), 3.67 (3H, s), 1.25 (3H, t, J=6.9 Hz).

Reference Preparation Example 68

A similar reaction to Reference Preparation example 37 using 3-ethoxyacrylic acid N'-(3-methoxyphenyl)hydrazide (described in Reference preparation example 67) instead of 3-methoxyacrylic acid N'-(4-bromophenyl)hydrazide gave 1-(3-methoxyphenyl)-1H-pyrazole-3-ol.

1-(3-methoxyphenyl)-1H-pyrazole-3-ol

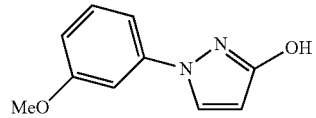 [SMILES: COc1cccc(-n2ccc(O)n2)c1]

¹H-NMR (CDCl₃) δ (ppm): 11.55 (1H, s), 7.66 (1H, d, J=2.5 Hz), 7.33 (1H, t, J=8.1 Hz), 7.11 (1H, t, J=2.3 Hz), 7.06 (1H, dd, J=7.8, 1.8 Hz), 6.80 (1H, dd, J=8.3, 2.3 Hz), 5.88 (1H, d, J=2.5 Hz), 3.88 (3H, s).

Reference Preparation Example 69

A similar reaction to Reference Preparation example 53 using 3-methylphenylhydrazine instead of 4-methylthiophenylhydrazine gave 3-ethoxyacrylic acid N'-(3-methylphenyl)hydrazide.

3-ethoxyacrylic acid N'-(3-methylphenyl)hydrazide

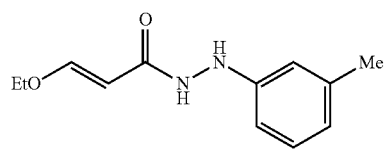 [SMILES: CCO/C=C/C(=O)NNc1cccc(C)c1]

$^1$H-NMR (DMSO-D$_6$) δ (ppm): 9.39 (1H, s), 7.40 (1H, d, J=12.4 Hz), 7.00 (1H, t, J=7.8 Hz), 6.51-6.49 (3H, m), 5.41 (1H, d, J=12.4 Hz), 3.92 (2H, q, J=7.0 Hz), 2.20 (3H, s), 1.26 (3H, t, J=6.9 Hz).

Reference Preparation Example 70

A similar reaction to Reference Preparation example 37 using 3-ethoxyacrylic acid N'-(3-methylphenyl)hydrazide (described in Reference preparation example 69) instead of 3-methoxyacrylic acid N'-(4-bromophenyl)hydrazide gave 1-(3-methylphenyl)-1H-pyrazole-3-ol.

1-(3-methylphenyl)-1H-pyrazole-3-ol

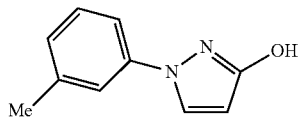 [SMILES: Cc1cccc(-n2ccc(O)n2)c1]

$^1$H-NMR (CDCl$_3$) δ (ppm): 7.65 (1H, d, J=2.3 Hz), 7.35-7.33 (3H, m), 7.08-7.07 (1H, m), 5.90 (1H, d, J=2.3 Hz), 2.39 (3H, d, J=20.0 Hz).

Reference Preparation Example 71

A similar reaction to Reference Preparation example 53 using 3-fluorophenylhydrazine instead of 4-methylthiophenylhydrazine gave 3-ethoxyacrylic acid N'-(3-fluorophenyl)hydrazide.

3-ethoxyacrylic acid N'-(3-fluorophenyl)hydrazide

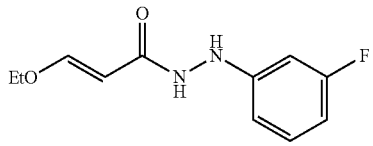 [SMILES: CCO/C=C/C(=O)NNc1cccc(F)c1]

$^1$H-NMR (DMSO-D$_6$) δ (ppm): 9.47 (1H, d, J=2.5 Hz), 7.99 (1H, d, J=2.0 Hz), 7.43 (1H, d, J=12.6 Hz), 7.14 (1H, dd, J=14.9, 8.1 Hz), 6.51 (1H, ddd, J=8.1, 0.9, 0.5 Hz), 6.46 (1H, td, J=8.5, 2.1 Hz), 6.39 (1H, dt, J=11.6, 2.3 Hz), 5.40 (1H, d, J=12.4 Hz), 3.93 (2H, q, J=7.0 Hz), 1.26 (3H, t, J=6.9 Hz).

Reference Preparation Example 72

A similar reaction to Reference Preparation example 37 using 3-ethoxyacrylic acid N'-(3-fluorophenyl)hydrazide (described in Reference preparation example 71) instead of 3-methoxyacrylic acid N'-(4-bromophenyl)hydrazide gave 1-(3-fluorophenyl)-1H-pyrazole-3-ol.

1-(3-fluorophenyl)-1H-pyrazole-3-ol

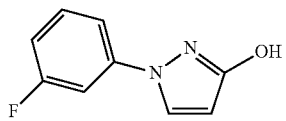

$^1$H-NMR (CDCl$_3$) δ (ppm): 7.67 (1H, d, J=2.8 Hz), 7.44-7.39 (1H, m), 7.31-7.22 (2H, m), 6.96-6.94 (1H, m), 5.94 (1H, d, J=2.5 Hz).

Reference Preparation Example 73

To a mixture of sodium sulfate 136.2 g, water 480 mL and Chloral hydrate 8.6 g was added a mixture of 2,5-dimethylaniline 6.1 mL, concentrated hydrochloric acid 4.2 mL and water 24 mL under stirring, followed by further addition of a mixture of hydroxylamine hydrochloride salt 10.6 g and water 30 mL. After the mixtures were stirred with heating under reflux for one and a half hours, the precipitated solids were filtered off to give N-(2,5-dimethylphenyl)-2-hydroxyiminoacetamide.

To a mixture of concentrated sulfuric acid 19.5 mL and water 4 mL was added N-(2,5-dimethylphenyl)-2-hydroxyiminoacetamide, and the mixtures were stirred at 80° C. for one hour. After cooling, the reaction solutions were added to ice water 140 mL. The precipitated solids were filtered off to give 4,7-dimethylisatin.

To a mixture of 4,7-dimethyl isatin, sodium hydroxide 9.0 g and water 40 mL was added 30% hydrogen peroxide solution 3 mL. To the reaction mixtures was added dropwise concentrated hydrochloric acid while the reaction temperature was being kept around 70° C., so that the pH of the reaction solutions was adjusted around 4. The precipitated solids were filtered off to give 2-amino-3,6-dimethyl benzoic acid 4.2 g.

2-amino-3,6-dimethyl benzoic acid

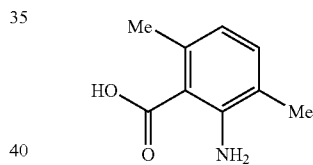

$^1$H-NMR (DMSO-D$_6$) δ (ppm): 6.90 (1H, d, J=7.5 Hz), 6.33 (1H, d, J=7.5 Hz), 2.29 (3H, s), 2.04 (3H, s).

Reference Preparation Example 74

To a mixture of 2-amino-3,6-dimethyl benzoic acid (described in Reference preparation example 73) 4.2 g, ethyl acetate 125 mL and ethanol 125 mL was added a 2.0 M solution of trimethylsilyl diazomethane in diethyl ether 25.4 mL under ice-cooling. The mixtures were stirred at room temperature for one and a half hours and were then concentrated under reduced pressure to give 2-amino-3,6-dimethyl benzoic acid methyl ester 4.6 g.

2-amino-3,6-dimethyl benzoic acid methyl ester

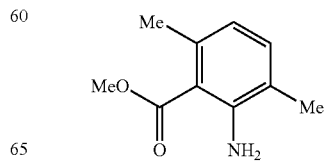

¹H-NMR (CDCl₃) δ (ppm): 7.00 (1H, d, J=7.6 Hz), 6.48 (1H, d, J=7.6 Hz), 5.13 (2H, brs), 3.89 (3H, s), 2.40 (3H, s), 2.13 (3H, s).

Reference Preparation Example 75

To a mixture of 2-amino-3,6-dimethyl benzoic acid methyl ester (described in Reference preparation example 74) 4.6 g and toluene 85 mL was added triphosgene 11.5 g at room temperature, and the mixtures were stirred with heating in reflux for two and a half hours. The mixtures were concentrated under reduced pressure to give 2-isocyanato-3,6-dimethyl benzoic acid methyl ester 5.3 g.

2-isocyanato-3,6-dimethyl benzoic acid methyl ester

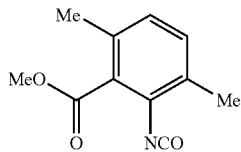

¹H-NMR (CDCl₃) δ (ppm): 7.14 (1H, d, J=7.7 Hz), 6.96 (1H, d, J=7.7 Hz), 3.96 (3H, s), 2.30 (6H, s).

Reference Preparation Example 76

Anhydrous aluminium chloride 3.8 g was added to N,N-dimethylformamide 40 mL under ice-cooling, and the mixtures were stirred for twenty minutes. Thereto was added sodium azide 1.9 g and the mixtures were stirred for fifteen minutes. Thereto was then added 2-isocyanato-3,6-dimethyl benzoic acid methyl ester (described in Reference preparation example 75) 5.3 g and the resulting mixtures were heated at 80° C. with stirring for four hours. After cooling, the reaction solutions were added to a mixture of sodium nitrite 6 g and ice water 500 mL with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 3,6-dimethyl-2-(5-oxo-4,5-dihydrotetrazole-1-yl)-benzoic acid methyl ester 8.3 g.

3,6-dimethyl-2-(5-oxo-4,5-dihydrotetrazole-1-yl)-benzoic acid methyl ester

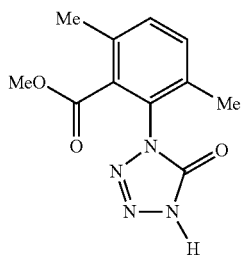 [SMILES: COC(=O)c1c(C)ccc(C)c1-n1nn[nH]c1=O]

¹H-NMR (DMSO-D₆) δ (ppm): 7.51 (1H, d, J=8.0 Hz), 7.45 (1H, d, J=8.0 Hz), 4.51 (1H, br s), 3.65 (3H, s), 2.34 (3H, s), 2.16 (3H, s).

Reference Preparation Example 77

To a mixture of 3,6-dimethyl-2-(5-oxo-4,5-dihydrotetrazole-1-yl)-benzoic acid methyl ester (described in Reference preparation example 76) 5.9 g and N,N-dimethylformamide 130 mL was added potassium carbonate 7.2 g and methyl iodide 7.4 g at room temperature, and the mixtures were stirred for seven hours. To the reaction solutions was added water and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 3,6-dimethyl-2-(4-methyl-5-oxo-4,5-dihydrotetrazole-1-yl)-benzoic acid methyl ester 5.9 g.

3,6-dimethyl-2-(4-methyl-5-oxo-4,5-dihydrotetrazole-1-yl)-benzoic acid methyl ester

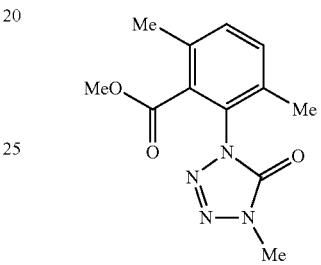

¹H-NMR (CDCl₃) δ (ppm): 7.34 (1H, d, J=8.0 Hz), 7.29 (1H, d, J=8.0 Hz), 3.76 (3H, s), 3.71 (3H, s), 2.42 (3H, s), 2.24 (3H, s).

Reference Preparation Example 78

Under ice-cooling, to a mixture of 3,6-dimethyl-2-(4-methyl-5-oxo-4,5-dihydrotetrazole-1-yl)-benzoic acid methyl ester (described in Reference preparation example 77) 5.9 g and tetrahydrofuran 125 mL was added a 1.0 M solution of lithium triethylborohydride in tetrahydrofuran 49 mL and the mixtures were stirred at room temperature for three hours. To the reactions solutions was added water, and the mixtures were acidified with 10% hydrochloric acid and were extracted with ethyl acetate. The organic layers were washed with water and saturated saline and were dried over anhydrous magnesium sulfate, and were then concentrated under reduced pressure. The resulting residues were subjected to a silica gel column chromatography to give 1-(2-hydroxymethyl-3,6-dimethylphenyl)-4-methyl-1,4-dihydrotetrazole-5-one 5.3 g.

1-(2-hydroxymethyl-3,6-dimethylphenyl)-4-methyl-1,4-dihydrotetrazole-5-one

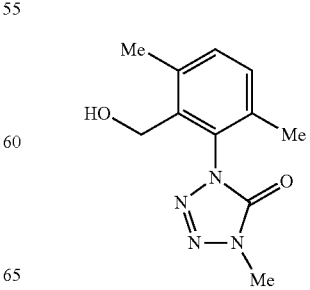

$^1$H-NMR (CDCl$_3$) δ (ppm): 7.30 (1H, d, J=8.0 Hz), 7.23 (1H, d, J=8.0 Hz), 4.48 (1H, dd, J=12.6, 9.4 Hz), 4.30 (1H, dd, J=12.6, 4.1 Hz), 3.77 (3H, s), 2.96 (1H, dd, J=9.4, 4.1 Hz), 2.49 (3H, s), 2.14 (3H, s).

Reference Preparation Example 79

To a mixture of 1-(2-hydroxymethyl-3,6-dimethylphenyl)-4-methyl-1,4-dihydrotetrazole-5-one (described in Reference preparation example 78) 5.3 g and chloroform 75 mL was added phosphorus tribromide 12.2 g and the mixtures were stirred at room temperature for eighteen hours. To the reaction solutions was added ice water and the mixtures were extracted with ethyl acetate. The organic layers were washed with water and saturated saline and were dried over anhydrous magnesium sulfate, and were then concentrated under reduced pressure. The resulting residues were subjected to a silica gel column chromatography to give 1-(2-bromomethyl-3,6-dimethylphenyl)-4-methyl-1,4-dihydrotetrazole-5-one 4.9 g.

1-(2-bromomethyl-3,6-dimethylphenyl)-4-methyl-1,4-dihydrotetrazole-5-one

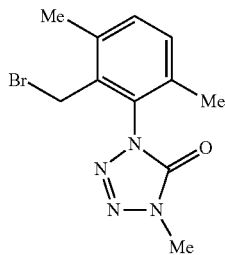 [SMILES: Cc1ccc(C)c(-n2nnn(C)c2=O)c1CBr]

$^1$H-NMR (CDCl$_3$) δ (ppm): 7.27 (1H, d, J=8.0 Hz), 7.22 (1H, d, J=8.0 Hz), 4.38 (1H, d, J=10.8 Hz), 4.27 (1H, d, J=10.8 Hz), 3.77 (3H, s), 2.45 (3H, s), 2.11 (3H, s).

Reference Preparation Example 80

To a mixture of sodium sulfate 136.2 g, water 480 mL and Chloral hydrate 8.6 g was added a mixture of 2-fluoro-5-methylaniline 6.1 g, concentrated hydrochloric acid 4.2 mL and water 24 mL under stirring, followed by further addition of a mixture of hydroxylamine hydrochloride salt 10.6 g and water 30 mL. After the mixtures were stirred with heating under reflux for one and a half hours, the precipitated solids were filtered off to give N-(2-fluoro-5-methylphenyl)-2-hydroxyiminoacetamide.
To a mixture of concentrated sulfuric acid 19.5 mL and water 4 mL was added N-(2-fluoro-5-methylphenyl)-2-hydroxyiminoacetamide, and the mixtures were stirred at 80° C. for one hour. After cooling, the reaction solutions were added to ice water. The precipitated solids were filtered off to give 4-methyl-7-fluoroisatin.
To a mixture of 4-methyl-7-fluoroisatin, sodium hydroxide 9.0 g and water 40 mL was added 30% hydrogen peroxide solution 3 mL. To the reaction mixtures was added dropwise concentrated hydrochloric acid while the reaction temperature was being kept around 70° C., so that the pH of the reaction solutions was adjusted around 4. The precipitated solids were filtered off to give 2-amino-3-fluoro-6-methyl benzoic acid 2.3 g.

2-amino-3-fluoro-6-methyl benzoic acid

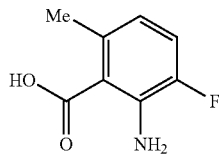

$^1$H-NMR (DMSO-D$_6$) δ (ppm): 7.03 (1H, dd, J=11.3, 8.2 Hz), 6.39 (1H, dd, J=8.2, 5.1 Hz), 2.32 (3H, s).

Reference Preparation Example 81

To a mixture of 2-amino-3-fluoro-6-methyl benzoic acid (described in Reference preparation example 80) 2.3 g, ethyl acetate 70 mL and ethanol 70 mL was added a 2.0 M solution of trimethylsilyl diazomethane in diethyl ether 13.7 mL under ice-cooling. The mixtures were stirred at room temperature for one and a half hours and were then concentrated under reduced pressure. To the resulting residues was added water and the mixtures were extracted with methyl tert-butyl ether. The organic layers were washed with water and saturated saline, and were dried over anhydrous magnesium sulfate and were then concentrated under reduced pressure. The resulting residues were subjected to a silica gel column chromatography to give 2-amino-3-fluoro-6-methyl-benzoic acid methyl ester 0.81 g.

2-amino-3-fluoro-6-methyl-benzoic acid methyl ester

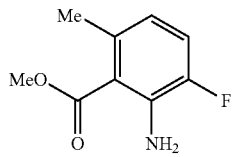

$^1$H-NMR (CDCl$_3$) δ (ppm): 6.94 (1H, dd, J=10.9, 8.2 Hz), 6.45-6.41 (1H, m), 5.26 (2H, br s), 3.91 (3H, s), 2.41 (3H, s).

Reference Preparation Example 82

To a mixture of 2-amino-3-fluoro-6-methyl-benzoic acid methyl ester (described in Reference preparation example 81) 0.81 g and toluene 15 mL was added triphosgene 2.0 g at room temperature, and the mixtures were stirred with heating in reflux for three hours. The mixtures were concentrated under reduced pressure to give 2-isocyanato-3-fluoro-6-methyl benzoic acid methyl ester 0.92 g.

2-isocyanato-3-fluoro-6-methyl benzoic acid methyl ester

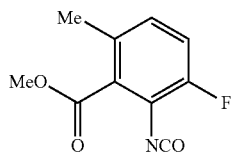

$^1$H-NMR (CDCl$_3$) δ (ppm): 7.09 (1H, t, J=8.7 Hz), 7.02-6.98 (1H, m), 3.96 (3H, s), 2.30 (3H, s).

Reference Preparation Example 83

Anhydrous aluminium chloride 0.65 g was added to N,N-dimethylformamide 10 mL under ice-cooling, and the mixtures were stirred for twenty minutes. Thereto was added sodium azide 0.32 g and the mixtures were stirred for fifteen minutes. Thereto was then added 2-isocyanato-3-fluoro-6-methyl benzoic acid methyl ester (described in Reference preparation example 82) 0.92 g and the resulting mixtures were heated at 80° C. with stirring for four hours. After cooling, the reaction solutions were added to a mixture of sodium nitrite 1.0 g and ice water 200 mL with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 3-fluoro-6-methyl-2-(5-oxo-4,5-dihydrotetrazole-1-yl)-benzoic acid methyl ester 1.4 g.

3-fluoro-6-methyl-2-(5-oxo-4,5-dihydrotetrazole-1-yl)-benzoic acid methyl ester

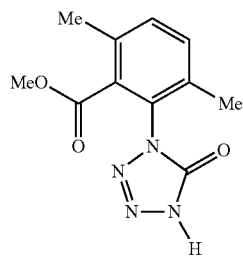 [SMILES: COC(=O)c1c(C)ccc(C)c1-n1nn[nH]c1=O]

$^1$H-NMR (DMSO-D$_6$) δ (ppm): 7.65-7.62 (1H, m), 7.59-7.56 (1H, m), 3.71 (3H, s), 2.38 (3H, s).

Reference Preparation Example 84

To a mixture of 3-fluoro-6-methyl-2-(5-oxo-4,5-dihydrotetrazole-1-yl)-benzoic acid methyl ester (described in Reference preparation example 83) 1.4 g and N,N-dimethylformamide 20 mL was added potassium carbonate 1.2 g and methyl iodide 1.3 g at room temperature, and the mixtures were stirred for four hours. To the reaction solutions was added water and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 3-fluoro-6-methyl-2-(4-methyl-5-oxo-4,5-dihydrotetrazole-1-yl)-benzoic acid methyl ester 0.65 g.

3-fluoro-6-methyl-2-(4-methyl-5-oxo-4,5-dihydrotetrazole-1-yl)-benzoic acid methyl ester

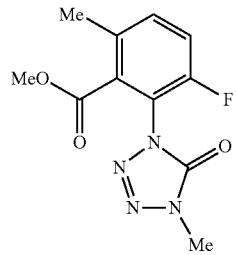 [SMILES: COC(=O)c1c(C)ccc(F)c1-n1nnn(C)c1=O]

$^1$H-NMR (CDCl$_3$) δ (ppm): 7.38 (1H, dd, J=8.6, 5.0 Hz), 7.28 (1H, t, J=8.6 Hz), 3.80 (3H, s), 3.71 (3H, s), 2.45 (3H, s).

Reference Preparation Example 85

Under ice-cooling, to a mixture of 3-fluoro-6-methyl-2-(4-methyl-5-oxo-4,5-dihydrotetrazole-1-yl)-benzoic acid methyl ester (described in Reference preparation example 84) 0.65 g and tetrahydrofuran 11 mL was added a 1.0 M solution of lithium triethylborohydride in tetrahydrofuran 5.4 mL and the mixtures were stirred at room temperature for one hour. To the reactions solutions was added water, and the mixtures were acidified with 10% hydrochloric acid and were extracted with ethyl acetate. The organic layers were washed with water and saturated saline and were dried over anhydrous magnesium sulfate, and were then concentrated under reduced pressure to give 1-(2-hydroxymethyl-3-methyl-6-fluorophenyl)-4-methyl-1,4-dihydrotetrazole-5-one 0.58 g.

1-(2-hydroxymethyl-3-methyl-6-fluorophenyl)-4-methyl-1,4-dihydrotetrazole-5-one

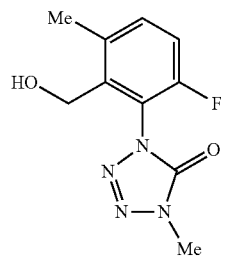

$^1$H-NMR (CDCl$_3$) δ (ppm): 7.37 (1H, dd, J=8.6, 5.4 Hz), 7.15 (1H, t, J=8.6 Hz), 4.54-4.36 (2H, m), 3.76 (3H, s), 3.28-3.24 (1H, m), 2.50 (3H, s).

Reference Preparation Example 86

To a mixture of 1-(2-hydroxymethyl-3-methyl-6-fluorophenyl)-4-methyl-1,4-dihydrotetrazole-5-one (described in Reference preparation example 85) 0.58 g and chloroform 8 mL was added phosphorus tribromide 1.32 g and the mixtures were stirred at room temperature for twenty hours. To the reaction solutions was added ice water and the mixtures were extracted with ethyl acetate. The organic layers were washed with water and saturated saline and were dried over anhydrous magnesium sulfate, and were then concentrated under reduced pressure. The resulting residues were subjected to a silica gel column chromatography to give 1-(2-bromomethyl-3-methyl-6-fluorophenyl)-4-methyl-1,4-dihydrotetrazole-5-one 0.66 g.

1-(2-bromomethyl-3-methyl-6-fluorophenyl)-4-methyl-1,4-dihydrotetrazole-5-one

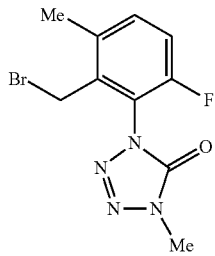 [SMILES: Cc1ccc(F)c(-n2nnn(C)c2=O)c1CBr]

$^1$H-NMR (CDCl$_3$) δ (ppm): 7.36 (1H, dd, J=8.7, 5.6 Hz), 7.16 (1H, t, J=8.7 Hz), 4.43 (1H, d, J=10.6 Hz), 4.32 (1H, d, J=10.6 Hz), 3.76 (3H, s), 2.46 (3H, s).

Reference Preparation Example 87

To a mixture of sodium sulfate 272.4 g, water 960 mL and Chloral hydrate 17.2 g was added a mixture of 4-fluoro-3-methylaniline 12.2 g, concentrated hydrochloric acid 8.4 mL and water 48 mL under stirring, followed by further addition of a mixture of hydroxylamine hydrochloride salt 21.1 g and water 60 mL. After the mixtures were stirred with heating under reflux for forty minutes, the precipitated solids were filtered off to give N-(4-fluoro-3-methylphenyl)-2-hydroxyiminoacetamide 25.4 g.

To a mixture of concentrated sulfuric acid 78 mL and water 16 mL was added N-(4-fluoro-3-methylphenyl)-2-hydroxyiminoacetamide 25.4 g. The mixtures were stirred at 80° C. for one hour and the reaction solutions were added to ice water 500 mL. The precipitated solids were filtered off to give a mixture of 4-methyl-5-fluoroisatin and 6-methyl-5-fluoroisatin.

To a mixture containing a mixture of 4-methyl-5-fluoroisatin and 6-methyl-5-fluoroisatin, sodium hydroxide 18.0 g and water 80 mL was added 30% hydrogen peroxide solution 6 mL. To the reaction mixtures was added dropwise acetic acid while the reaction temperature was being kept around 70° C., so that the pH of the reaction solutions was adjusted around 4. The precipitated solids were filtered off to give a mixture of 6-amino-3-fluoro-2-methyl benzoic acid and 2-amino-5-fluoro-4-methyl benzoic acid 11.5 g.

To a mixture containing a mixture of 6-amino-3-fluoro-2-methyl benzoic acid and 2-amino-5-fluoro-4-methyl benzoic acid 11.5 g, ethyl acetate 340 mL and ethanol 340 mL was added a 2.0 M solution of trimethylsilyl diazomethane in diethyl ether 68 mL under ice-cooling. The mixtures were stirred at room temperature for one and a half hours and were concentrated under reduced pressure. The resulting residues were subjected to a silica gel column chromatography to give 6-amino-3-fluoro-2-methyl-benzoic acid methyl ester 3.0 g.

6-amino-3-fluoro-2-methyl-benzoic acid methyl ester

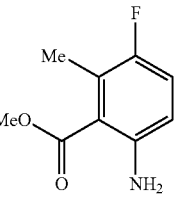

$^1$H-NMR (CDCl$_3$) δ (ppm): 6.93 (1H, t, J=9.0 Hz), 6.48 (1H, dd, J=9.0, 4.5 Hz), 4.82 (2H, br s), 3.91 (3H, s), 2.31 (3H, d, J=2.7 Hz).

Reference Preparation Example 88

To a mixture of 6-amino-3-fluoro-2-methyl-benzoic acid methyl ester (described in Reference preparation example 87) 3.0 g and toluene 60 mL was added triphosgene 7.6 g at room temperature, and the mixtures were stirred with heating in reflux for three hours. The mixtures were concentrated under reduced pressure to give 6-isocyanato-3-fluoro-2-methyl benzoic acid methyl ester 3.6 g.

6-isocyanato-3-fluoro-2-methyl benzoic acid methyl ester

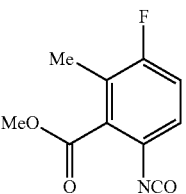

$^1$H-NMR (CDCl$_3$) δ (ppm): 7.04 (1H, t, J=8.8 Hz), 6.94 (1H, dd, J=8.8, 4.6 Hz), 3.98 (3H, s), 2.26 (3H, d, J=2.5 Hz).

Reference Preparation Example 89

Anhydrous aluminium chloride 2.5 g was added to N,N-dimethylformamide 30 mL under ice-cooling, and the mixtures were stirred for twenty minutes. Thereto was added sodium azide 1.2 g and the mixtures were stirred for fifteen minutes. Thereto was then added 6-isocyanato-3-fluoro-2-methyl benzoic acid methyl ester (described in Reference preparation example 88) 3.6 g and the resulting mixtures were heated at 80° C. with stirring for four hours. After cooling, the reaction solutions were added to a mixture of sodium nitrite 4.0 g and ice water 500 mL with stirring. The mixtures were acidified with 10% hydrochloric acid and were extracted with ethyl acetate. The organic layers were washed with water and saturated saline and then were dried over anhydrous magnesium sulfate and were then concentrated under reduced pressure to give 2-methyl-3-fluoro-6-(5-oxo-4,5-dihydrotetrazole-1-yl)-benzoic acid methyl ester 6.0 g.

2-methyl-3-fluoro-6-(5-oxo-4,5-dihydrotetrazole-1-yl)-benzoic acid methyl ester

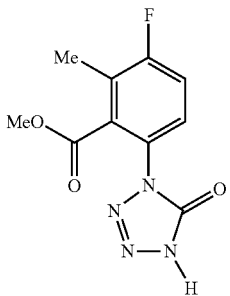 [SMILES: COC(=O)c1c(-n2nn[nH]c2=O)ccc(F)c1C]

¹H-NMR (DMSO-D₆) δ (ppm): 7.62-7.56 (2H, m), 5.29 (1H, br s), 3.73 (3H, s), 2.29 (3H, d, J=2.3 Hz).

Reference Preparation Example 90

To a mixture of 2-methyl-3-fluoro-6-(5-oxo-4,5-dihydrotetrazole-1-yl)-benzoic acid methyl ester (described in Reference preparation example 89) 6.0 g and N,N-dimethylformamide 85 mL was added potassium carbonate 4.7 g and methyl iodide 4.9 g at room temperature, and the mixtures were stirred for six hours. To the reaction solutions was added water and the mixtures were extracted with ethyl acetate. The organic layers were washed with water and saturated saline, and were dried over anhydrous magnesium sulfate and were then concentrated under reduced pressure. The resulting residues were subjected to a silica gel column chromatography to give 2-methyl-3-fluoro-6-(4-methyl-5-oxo-4,5-dihydrotetrazole-1-yl)-benzoic acid methyl ester 2.8 g.

2-methyl-3-fluoro-6-(4-methyl-5-oxo-4,5-dihydrotetrazole-1-yl)-benzoic acid methyl ester

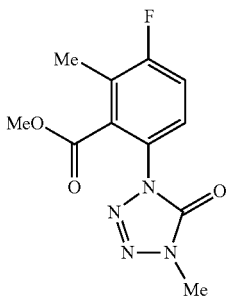

¹H-NMR (CDCl₃) δ (ppm): 7.47 (1H, dd, J=8.9, 4.6 Hz), 7.25 (1H, t, J=8.9 Hz), 3.84 (3H, s), 3.69 (3H, s), 2.36 (3H, d, J=2.4 Hz).

Reference Preparation Example 91

Under ice-cooling, to a mixture of 2-methyl-3-fluoro-6-(4-methyl-5-oxo-4,5-dihydrotetrazole-1-yl)-benzoic acid methyl ester (described in Reference preparation example 90) 2.8 g and tetrahydrofuran 46 mL was added a 1.0 M solution of lithium triethylborohydride in tetrahydrofuran 22.9 mL and the mixtures were stirred at room temperature for one hour. To the reactions solutions was added water, and the mixtures were acidified with 10% hydrochloric acid and were extracted with ethyl acetate. The organic layers were washed with water and saturated saline and were dried over anhydrous magnesium sulfate, and were then concentrated under reduced pressure to give 1-(2-hydroxymethyl-3-methyl-4-fluorophenyl)-4-methyl-1,4-dihydrotetrazole-5-one 2.4 g.

1-(2-hydroxymethyl-3-methyl-4-fluorophenyl)-4-methyl-1,4-dihydrotetrazole-5-one

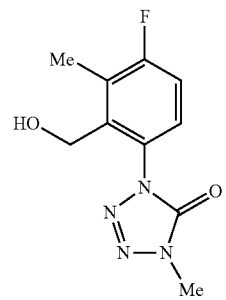 [SMILES: Cc1c(F)ccc(-n2nnn(C)c2=O)c1CO]

¹H-NMR (CDCl₃) δ (ppm): 7.21 (1H, dd, J=8.7, 5.1 Hz), 7.15 (1H, t, J=8.7 Hz), 4.47 (2H, dd, J=7.2, 1.0 Hz), 3.75 (3H, s), 2.45 (3H, d, J=2.4 Hz).

Reference Preparation Example 92

To a mixture of 1-(2-hydroxymethyl-3-methyl-4-fluorophenyl)-4-methyl-1,4-dihydrotetrazole-5-one (described in Reference preparation example 91) 2.4 g and chloroform 34 mL was added phosphorus tribromide 5.5 g and the mixtures were stirred at room temperature for twenty hours. To the reaction solutions was added ice water and the mixtures were extracted with ethyl acetate. The organic layers were washed with water and saturated saline and were dried over anhydrous magnesium sulfate, and were then concentrated under reduced pressure. The resulting residues were subjected to silica gel column chromatography to give 1-(2-bromomethyl-3-methyl-4-fluorophenyl)-4-methyl-1,4-dihydrotetrazole-5-one 2.5 g.

1-(2-bromomethyl-3-methyl-4-fluorophenyl)-4-methyl-1,4-dihydrotetrazole-5-one

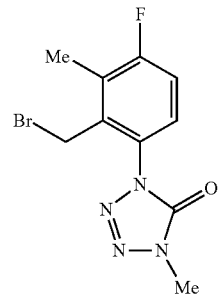 [SMILES: Cc1c(F)ccc(-n2nnn(C)c2=O)c1CBr]

¹H-NMR (CDCl₃) δ (ppm): 7.22 (1H, dd, J=8.7, 5.1 Hz), 7.16 (1H, t, J=8.7 Hz), 4.46 (2H, s), 3.75 (3H, s), 2.39 (3H, d, J=2.4 Hz).

According to the above-mentioned processes, the following compounds can be prepared:
Compounds A-001~A-716, B-001~B-716, C-001~C-716, D-001~D-716, E-001~E-716, F-001~F-716, G-001~G-716, H-001~H-716, I-001~I-716, J-001~J-716, K-001~K-716, L-001~L-716, M-001~M-716, N-001~N-716, O-001~O-716, P-001~P-716, Q-001~Q-716, R-001~R-716, S-001~S-716, T-001~T-716, U-001~U-716, V-001~V-716, W-001~W-716, X-001~X-716, Y-001~Y-716, Z-001~Z-716, AA-001~AA-716, AB-001~AB-716 and AC-001~AC-716.

Compounds A-001~A-716 represent tetrazolinone Compounds represented by a formula:

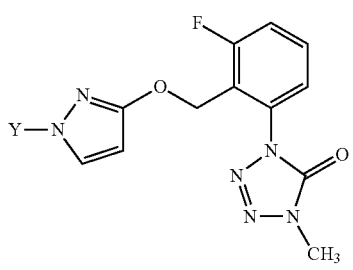

[wherein Y represents a substituent corresponding to each of substituents Nos. 1 to 716 indicated in Table 1 to Table 25 as below-mentioned];
Compounds B-001~B-716 represent tetrazolinone Compounds represented by a formula:

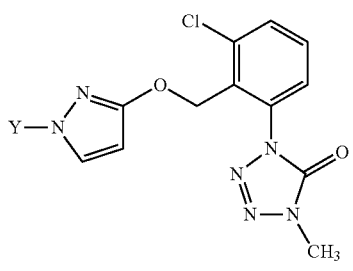

[wherein Y represents a substituent corresponding to each of substituents Nos. 1 to 716 indicated in Table 1 to Table 25 as below-mentioned];
Compounds C-001~C-716 represent tetrazolinone Compounds represented by a formula:

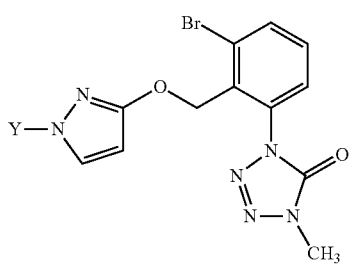

[wherein Y represents a substituent corresponding to each of substituents Nos. 1 to 716 indicated in Table 1 to Table 25 as below-mentioned];
Compounds D-001~D-716 represent tetrazolinone Compounds represented by a formula:

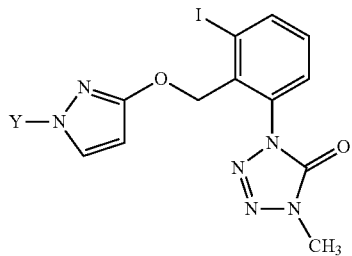

[wherein Y represents a substituent corresponding to each of substituents Nos. 1 to 716 indicated in Table 1 to Table 25 as below-mentioned];
Compounds E-001~E-716 represent tetrazolinone Compounds represented by a formula:

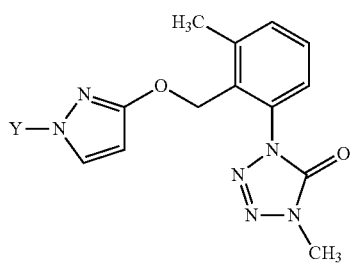

[wherein Y represents a substituent corresponding to each of substituents Nos. 1 to 716 indicated in Table 1 to Table 25 as below-mentioned];
Compounds F-001~F-716 represent tetrazolinone Compounds represented by a formula:

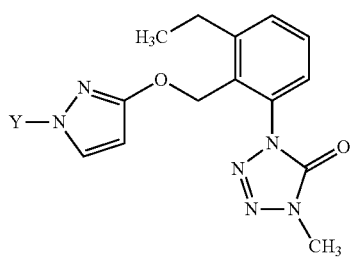

[wherein Y represents a substituent corresponding to each of substituents Nos. 1 to 716 indicated in Table 1 to Table 25 as below-mentioned];
Compounds G-001~G-716 represent tetrazolinone Compounds represented by a formula:

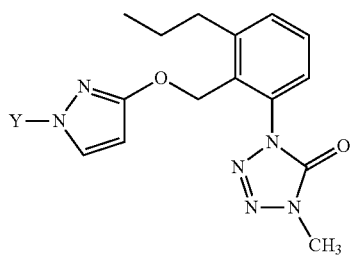

[wherein Y represents a substituent corresponding to each of substituents Nos. 1 to 716 indicated in Table 1 to Table 25 as below-mentioned];

Compounds H-001~H-716 represent tetrazolinone Compounds represented by a formula:

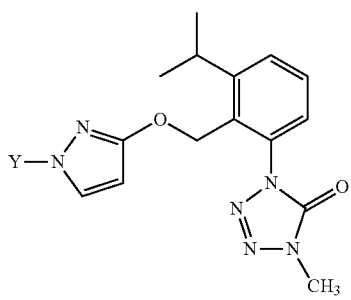

[wherein Y represents a substituent corresponding to each of substituents Nos. 1 to 716 indicated in Table 1 to Table 25 as below-mentioned];

Compounds I-001~I-716 represent tetrazolinone Compounds represented by a formula:

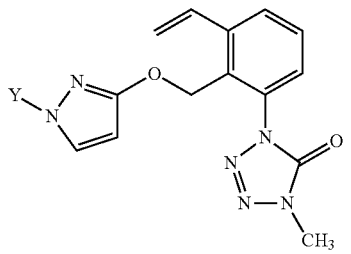

[wherein Y represents a substituent corresponding to each of substituents Nos. 1 to 716 indicated in Table 1 to Table 25 as below-mentioned];

Compounds J-001~J-716 represent tetrazolinone Compounds represented by a formula:

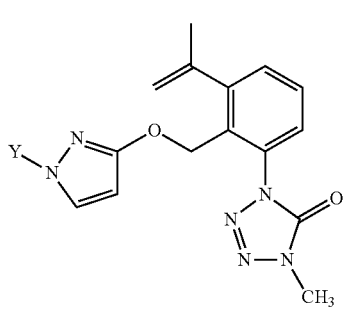

[wherein Y represents a substituent corresponding to each of substituents Nos. 1 to 716 indicated in Table 1 to Table 25 as below-mentioned];

Compounds K-001~K-716 represent tetrazolinone Compounds represented by a formula:

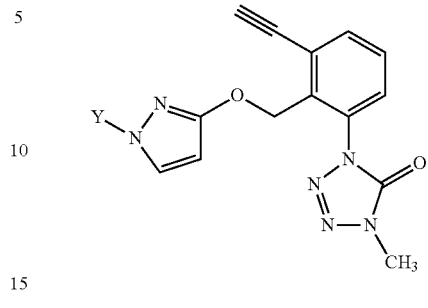

[wherein Y represents a substituent corresponding to each of substituents Nos. 1 to 716 indicated in Table 1 to Table 25 as below-mentioned];

Compounds L-001~L-716 represent tetrazolinone Compounds represented by a formula:

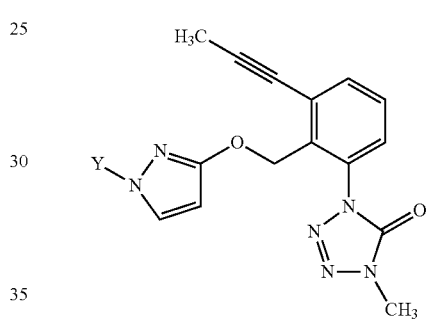

[wherein Y represents a substituent corresponding to each of substituents Nos. 1 to 716 indicated in Table 1 to Table 25 as below-mentioned];

Compounds M-001~M-716 represent tetrazolinone Compounds represented by a formula:

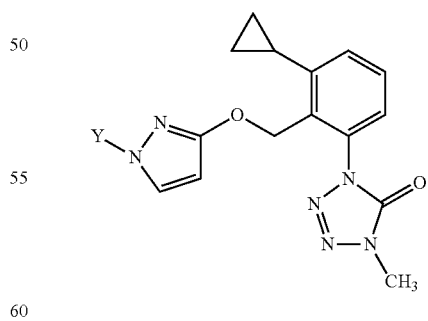

[wherein Y represents a substituent corresponding to each of substituents Nos. 1 to 716 indicated in Table 1 to Table 25 as below-mentioned];

Compounds N-001~N-716 represent tetrazolinone Compounds represented by a formula:

441

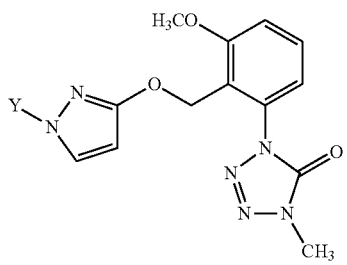

[wherein Y represents a substituent corresponding to each of substituents Nos. 1 to 716 indicated in Table 1 to Table 25 as below-mentioned];

Compounds O-001~O-716 represent tetrazolinone Compounds represented by a formula:

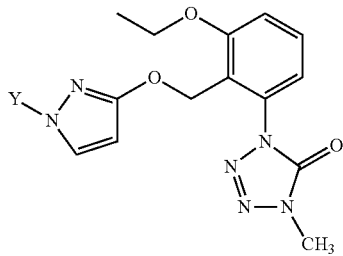

[wherein Y represents a substituent corresponding to each of substituents Nos. 1 to 716 indicated in Table 1 to Table 25 as below-mentioned];

Compounds P-001~P-716 represent tetrazolinone Compounds represented by a formula:

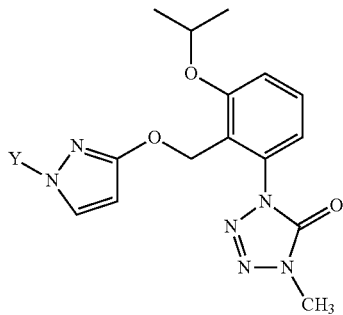

[wherein Y represents a substituent corresponding to each of substituents Nos. 1 to 716 indicated in Table 1 to Table 25 as below-mentioned];

Compounds Q-001~Q-716 represent tetrazolinone Compounds represented by a formula:

442

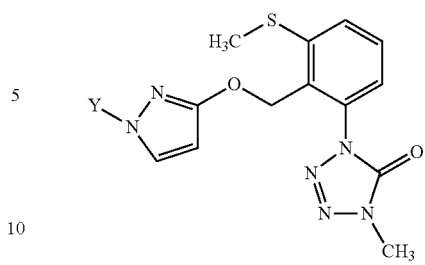

[wherein Y represents a substituent corresponding to each of substituents Nos. 1 to 716 indicated in Table 1 to Table 25 as below-mentioned];

Compounds R-001~R-716 represent tetrazolinone Compounds represented by a formula:

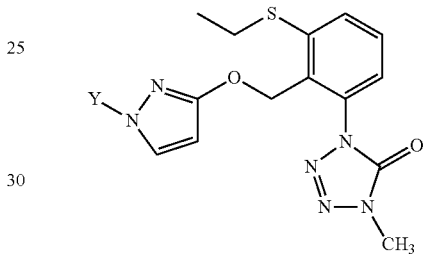

[wherein Y represents a substituent corresponding to each of substituents Nos. 1 to 716 indicated in Table 1 to Table 25 as below-mentioned];

Compounds S-001~S-716 represent tetrazolinone Compounds represented by a formula:

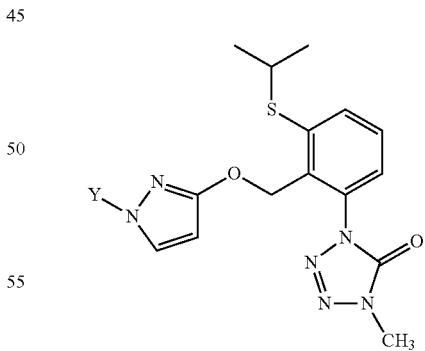

[wherein Y represents a substituent corresponding to each of substituents Nos. 1 to 716 indicated in Table 1 to Table 25 as below-mentioned];

Compounds T-001~T-716 represent tetrazolinone Compounds represented by a formula:

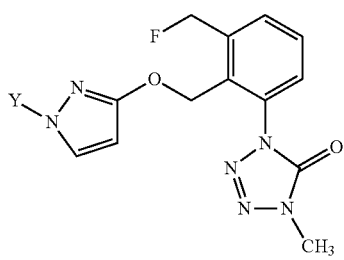

[wherein Y represents a substituent corresponding to each of substituents Nos. 1 to 716 indicated in Table 1 to Table 25 as below-mentioned];

Compounds U-001~U-716 represent tetrazolinone Compounds represented by a formula:

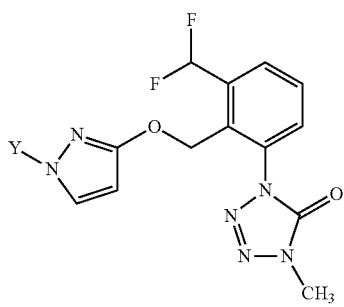

[wherein Y represents a substituent corresponding to each of substituents Nos. 1 to 716 indicated in Table 1 to Table 25 as below-mentioned];

Compounds V-001~V-716 represent tetrazolinone Compounds represented by a formula:

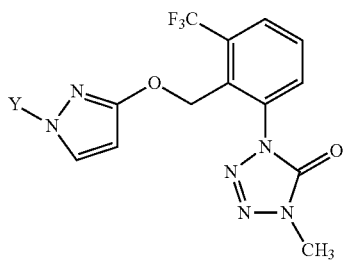

[wherein Y represents a substituent corresponding to each of substituents Nos. 1 to 716 indicated in Table 1 to Table 25 as below-mentioned];

Compounds W-001~W-716 represent tetrazolinone Compounds represented by a formula:

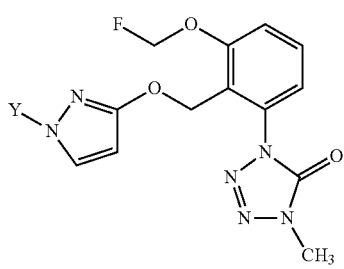

[wherein Y represents a substituent corresponding to each of substituents Nos. 1 to 716 indicated in Table 1 to Table 25 as below-mentioned];

Compounds X-001~X-716 represent tetrazolinone Compounds represented by a formula:

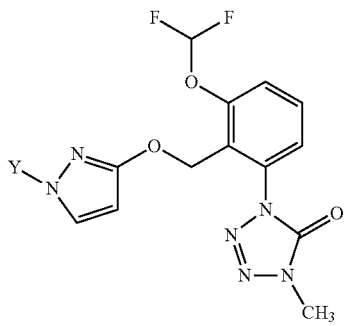

[wherein Y represents a substituent corresponding to each of substituents Nos. 1 to 716 indicated in Table 1 to Table 25 as below-mentioned];

Compounds Y-001~Y-716 represent tetrazolinone Compounds represented by a formula:

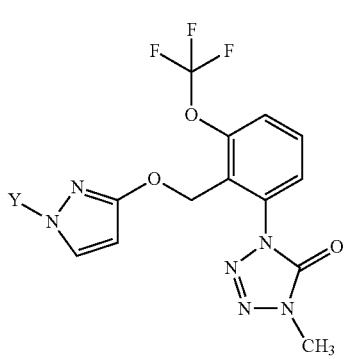

[wherein Y represents a substituent corresponding to each of substituents Nos. 1 to 716 indicated in Table 1 to Table 25 as below-mentioned];

Compounds Z-001~Z-716 represent tetrazolinone Compounds represented by a formula:

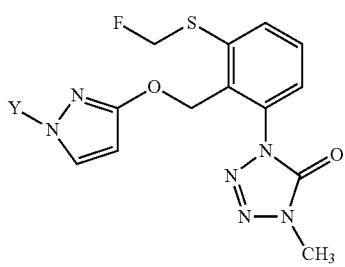

[wherein Y represents a substituent corresponding to each of substituents Nos. 1 to 716 indicated in Table 1 to Table 25 as below-mentioned];

Compounds AA-001~AA-716 represent tetrazolinone Compounds represented by a formula:

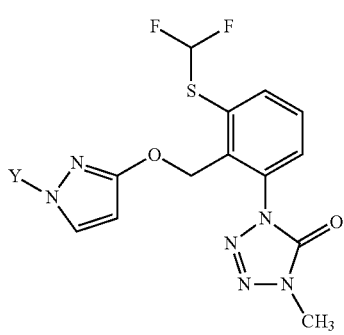

[wherein Y represents a substituent corresponding to each of substituents Nos. 1 to 716 indicated in Table 1 to Table 25 as below-mentioned];

Compounds AB-001~AB-716 represent tetrazolinone Compounds represented by a formula:

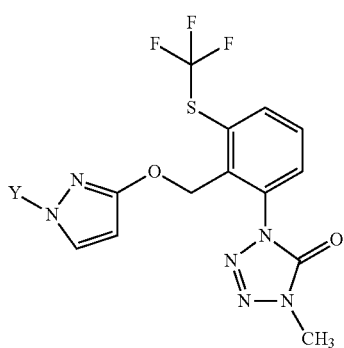

[wherein Y represents a substituent corresponding to each of substituents Nos. 1 to 716 indicated in Table 1 to Table 25 as below-mentioned]; and Compounds AC-001~AC-716 represent tetrazolinone Compounds represented by a formula:

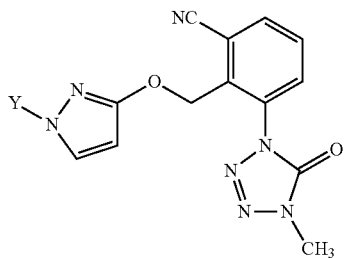

[wherein Y represents a substituent corresponding to each of substituents Nos. 1 to 716 indicated in Table 1 to Table 25 as below-mentioned].

TABLE 1

| substituents Nos. | Y |
|---|---|
| 1 | phenyl group |
| 2 | 2-fluorophenyl group |
| 3 | 3-fluorophenyl group |
| 4 | 4-fluorophenyl group |
| 5 | 2,4-difluorophenyl group |

TABLE 1-continued

| substituents Nos. | Y |
|---|---|
| 6 | 2,4,6-trifluorophenyl group |
| 7 | 2,3,4,5,6-pentafluorophenyl group |
| 8 | 2-3-difluorophenyl group |
| 9 | 2-chlorophenyl group |
| 10 | 3-chlorophenyl group |
| 11 | 4-chlorophenyl group |
| 12 | 2-3-dichlorophenyl group |
| 13 | 2,4-dichlorophenyl group |
| 14 | 2,5-dichlorophenyl group |
| 15 | 2,6-dichlorophenyl group |
| 16 | 3,4-dichlorophenyl group |
| 17 | 3,5-dichlorophenyl group |
| 18 | 2,3,4-trichlorophenyl group |
| 19 | 2,3,5-trichlorophenyl group |
| 20 | 2,3,6-trichlorophenyl group |
| 21 | 2,4,5-trichlorophenyl group |
| 22 | 2,4,6-trichlorophenyl group |
| 23 | 3,4,5-trichlorophenyl group |
| 24 | 2,3,4,6-tetrachlorophenyl group |
| 25 | 2,3,5,6-tetrachlorophenyl group |
| 26 | 2,3,4,5,6-pentachlorophenyl group |
| 27 | 2-bromophenyl group |
| 28 | 3-bromophenyl group |
| 29 | 4-bromophenyl group |

TABLE 2

| substituents Nos. | Y |
|---|---|
| 30 | 2,4-dibromophenyl group |
| 31 | 2,5-dibromophenyl group |
| 32 | 2,6-dibromophenyl group |
| 33 | 2,4,6-tribromophenyl group |
| 34 | 2,3,4,5,6-pentabromophenyl group |
| 35 | 2-iodophenyl group |
| 36 | 3-iodophenyl group |
| 37 | 4-iodophenyl group |
| 38 | 2,4-diiodophenyl group |
| 39 | 2-chloro-3-fluorophenyl group |
| 40 | 2-chloro-4-fluorophenyl group |
| 41 | 2-chloro-5-fluorophenyl group |
| 42 | 2-chloro-6-fluorophenyl group |
| 43 | 2-chloro-3-bromophenyl group |
| 44 | 2-chloro-4-bromophenyl group |
| 45 | 2-chloro-5-bromophenyl group |
| 46 | 2-chloro-6-bromophenyl group |
| 47 | 2-bromo-3-chlorophenyl group |
| 48 | 2-bromo-4-chlorophenyl group |
| 49 | 2-bromo-5-chlorophenyl group |
| 50 | 2-bromo-3-fluorophenyl group |
| 51 | 2-bromo-4-fluorophenyl group |
| 52 | 2-bromo-5-fluorophenyl group |
| 53 | 2-bromo-6-fluorophenyl group |
| 54 | 2-fluoro-3-chlorophenyl group |
| 55 | 2-fluoro-4-chlorophenyl group |
| 56 | 2-fluoro-5-chlorophenyl group |
| 57 | 2-fluoro-4-bromophenyl group |
| 58 | 3-chloro4-fluorophenyl group |

TABLE 3

| substituents Nos. | Y |
|---|---|
| 59 | 3-chloro-5-fluorophenyl group |
| 60 | 3-chloro-4-bromophenyl group |
| 61 | 3-chloro-5-bromophenyl group |
| 62 | 3-fluoro-4-chlorophenyl group |
| 63 | 3-fluoro-4-bromophenyl group |
| 64 | 3-bromo-4-chlorophenyl group |
| 65 | 3-bromo-4-fluorophenyl group |

TABLE 3-continued

| substituents Nos. | Y |
|---|---|
| 66 | 2,6-dichloro-4-bromophenyl group |
| 67 | 2-3-difluoro-4-chlorophenyl group |
| 68 | 2,6-difluoro-4-chlorophenyl group |
| 69 | 2,5-difluoro-4-chlorophenyl group |
| 70 | 3,5-difluoro-4-chlorophenyl group |
| 71 | 2,3,5-trifluoro-4-chlorophenyl group |
| 72 | 2,3,6-trifluoro-4-chlorophenyl group |
| 73 | 2,3,5,6-tetrafluoro-4-chlorophenyl group |
| 74 | 2-fluoro-4-bromophenyl group |
| 75 | 2-3-difluoro-4-bromophenyl group |
| 76 | 2,6-difluoro-4-bromophenyl group |
| 77 | 2,5-difluoro-4-bromophenyl group |
| 78 | 3,5-difluoro-4-bromophenyl group |
| 79 | 2,3,5-trifluoro-4-bromophenyl group |
| 80 | 2,3,6-trifluoro-4-bromophenyl group |
| 81 | 2,3,5,6-tetrafluoro-4-bromophenyl group |
| 82 | 2-fluoro-4-iodophenyl group |
| 83 | 3-fluoro-4-iodophenyl group |
| 84 | 2-3-difluoro-4-iodophenyl group |
| 85 | 2,6-difluoro-4-iodophenyl group |
| 86 | 2,5-difluoro-4-iodophenyl group |
| 87 | 3,5-difluoro-4-iodophenyl group |

TABLE 4

| substituents Nos. | Y |
|---|---|
| 88 | 2,3,5-trifluoro-4-iodophenyl group |
| 89 | 2,3,6-trifluoro-4-iodophenyl group |
| 90 | 2,3,5,6-tetrafluoro-4-iodophenyl group |
| 91 | 2-methylphenyl group |
| 92 | 3-methylphenyl group |
| 93 | 4-methylphenyl group |
| 94 | 2-3-dimethylphenyl group |
| 95 | 2,4-dimethylphenyl group |
| 96 | 2,5-dimethylphenyl group |
| 97 | 2,6-dimethylphenyl group |
| 98 | 3,4-dimethylphenyl group |
| 99 | 3,5-dimethylphenyl group |
| 100 | 2,3,5-trimethylphenyl group |
| 101 | 2,3,4-trimethylphenyl group |
| 102 | 2,3,6-trimethylphenyl group |
| 103 | 2,4,5-trimethylphenyl group |
| 104 | 2,4,6-trimethylphenyl group |
| 105 | 3,4,5-trimethylphenyl group |
| 106 | 2,3,4,6-tetramethylphenyl group |
| 107 | 2,3,5,6-tetramethylphenyl group |
| 108 | 2,3,4,5,6-pentamethylphenyl group |
| 109 | 2-ethylphenyl group |
| 110 | 3-ethylphenyl group |
| 111 | 4-ethylphenyl group |
| 112 | 2,4-diethylphenyl group |
| 113 | 2,6-diethylphenyl group |
| 114 | 3,5-diethylphenyl group |
| 115 | 2,4,6-triethylphenyl group |
| 116 | 2-n-propylphenyl group |

TABLE 5

| substituents Nos. | Y |
|---|---|
| 117 | 3-n-propylphenyl group |
| 118 | 4-n-propylphenyl group |
| 119 | 2-isopropylphenyl group |
| 120 | 3-isopropylphenyl group |
| 121 | 4-isopropylphenyl group |
| 122 | 2,4-diisopropylphenyl group |
| 123 | 2,6-diisopropylphenyl group |
| 124 | 3,5-diisopropylphenyl group |
| 125 | 2-s-butylphenyl group |

TABLE 5-continued

| substituents Nos. | Y |
|---|---|
| 126 | 3-s-butylphenyl group |
| 127 | 4-s-butylphenyl group |
| 128 | 2-t-butylphenyl group |
| 129 | 3-t-butylphenyl group |
| 130 | 4-t-butylphenyl group |
| 131 | 4-n-butylphenyl group |
| 132 | 4-n-nonylphenyl group |
| 133 | 2-methyl-4-t-butylphenyl group |
| 134 | 2-methyl-6-t-butylphenyl group |
| 135 | 2-methyl-4-isopropylphenyl group |
| 136 | 2-methyl-5-isopropylphenyl group |
| 137 | 3-methyl-4-isopropylphenyl group |
| 138 | 2-cyclohexylphenyl group |
| 139 | 3-cyclohexylphenyl group |
| 140 | 4-cyclohexylphenyl group |
| 141 | 4-cyclopropylphenyl group |
| 142 | 4-cyclobutylphenyl group |
| 143 | 4-cyclopentylphenyl group |
| 144 | 2-chloro-4-phenylphenyl group |
| 145 | 2-bromo-4-phenylphenyl group |

TABLE 6

| substituents Nos. | Y |
|---|---|
| 146 | 4-hydroxylphenyl group |
| 147 | 2-methoxyphenyl group |
| 148 | 3-methoxyphenyl group |
| 149 | 4-methoxyphenyl group |
| 150 | 2-ethoxyphenyl group |
| 151 | 3-ethoxyphenyl group |
| 152 | 4-ethoxyphenyl group |
| 153 | 2-n-propyloxyphenyl group |
| 154 | 3-n-propyloxyphenyl group |
| 155 | 4-n-propyloxyphenyl group |
| 156 | 2-isopropyloxyphenyl group |
| 157 | 3-isopropyloxyphenyl group |
| 158 | 4-isopropyloxyphenyl group |
| 159 | 2-n-hexyloxyphenyl group |
| 160 | 3-n-hexyloxyphenyl group |
| 161 | 4-n-hexyloxyphenyl group |
| 162 | 2-benzyloxyphenyl group |
| 163 | 3-benzyloxyphenyl group |
| 164 | 4-benzyloxyphenyl group |
| 165 | 2-3-dimethoxyphenyl group |
| 166 | 2,4-dimethoxyphenyl group |
| 167 | 2,5-dimethoxyphenyl group |
| 168 | 2,6-dimethoxyphenyl group |
| 169 | 3,4-dimethoxyphenyl group |
| 170 | 3,5-dimethoxyphenyl group |
| 171 | 2-t-butoxyphenyl group |
| 172 | 3-t-butoxyphenyl group |
| 173 | 4-t-butoxyphenyl group |
| 174 | 3-(3'-chlorophenyl)phenyl group |

TABLE 7

| substituents Nos. | Y |
|---|---|
| 175 | 4-(4'-chlorophenyl)phenyl group |
| 176 | 2-phenoxyphenyl group |
| 177 | 3-phenoxyphenyl group |
| 178 | 4-phenoxyphenyl group |
| 179 | 2-(2'-fluorophenoxy)phenyl group |
| 180 | 3-(3'-chlorophenoxy)phenyl group |
| 181 | 4-(4'-chlorophenoxy)phenyl group |
| 182 | 2,3,6-trimethyl-4-fluorophenyl group |
| 183 | 2,3,6-trimethyl-4-chlorophenyl group |
| 184 | 2,3,6-trimethyl-4-bromophenyl group |
| 185 | 2,4-dimethyl-6-fluorophenyl group |

TABLE 7-continued

| substituents Nos. | Y |
|---|---|
| 186 | 2,4-dimethyl-6-chlorophenyl group |
| 187 | 2,4-dimethyl-6-bromophenyl group |
| 188 | 2-isopropyl-4-chloro-5-methylphenyl group |
| 189 | 2-chloro-4-nitrophenyl group |
| 190 | 2-nitro-4-chlorophenyl group |
| 191 | 2-methoxy-5-nitrophenyl group |
| 192 | 2,4-dichloro-5-nitrophenyl group |
| 193 | 2,4-dichloro-6-nitrophenyl group |
| 194 | 2,6-dichloro-4-nitrophenyl group |
| 195 | 2,6-dibromo-4-nitrophenyl group |
| 196 | 2,6-diiodo-4-nitrophenyl group |
| 197 | 2-methyl-5-isopropyl-4-chlorophenyl group |
| 198 | 2-methoxycarbonylphenyl group |
| 199 | 3-methoxycarbonylphenyl group |
| 200 | 4-methoxycarbonylphenyl group |
| 201 | 4-acetoxyphenyl group |
| 202 | 2-methoxymethylphenyl group |
| 203 | 3-methoxymethylphenyl group |

TABLE 8

| substituents Nos. | Y |
|---|---|
| 204 | 4-methoxymethylphenyl group |
| 205 | 2-phenylphenyl group |
| 206 | 3-phenylphenyl group |
| 207 | 4-phenylphenyl group |
| 208 | 2-(2'-fluorophenyl)phenyl group |
| 209 | 2-methyl-5-bromophenyl group |
| 210 | 2-methyl-6-bromophenyl group |
| 211 | 2-chloro-3-methylphenyl group |
| 212 | 2-chloro-4-methylphenyl group |
| 213 | 2-chloro-5-methylphenyl group |
| 214 | 2-fluoro-3-methylphenyl group |
| 215 | 2-fluoro-4-methylphenyl group |
| 216 | 2-fluoro-5-methylphenyl group |
| 217 | 2-bromo-3-methylphenyl group |
| 218 | 2-bromo-4-methylphenyl group |
| 219 | 2-bromo-5-methylphenyl group |
| 220 | 3-methyl-4-chlorophenyl group |
| 221 | 3-methyl-5-chlorophenyl group |
| 222 | 3-methyl-4-fluorophenyl group |
| 223 | 3-methyl-5-fluorophenyl group |
| 224 | 3-methyl-4-bromophenyl group |
| 225 | 3-methyl-5-bromophenyl group |
| 226 | 3-fluoro-4-methylphenyl group |
| 227 | 3-chloro-4-methylphenyl group |
| 228 | 3-bromo-4-methylphenyl group |
| 229 | 2-chloro-4,5-dimethylphenyl group |
| 230 | 2-bromo-4,5-dimethylphenyl group |
| 231 | 2-chloro-3,5-dimethylphenyl group |
| 232 | 2-bromo-3,5-dimethylphenyl group |

TABLE 9

| substituents Nos. | Y |
|---|---|
| 233 | 2,6-dibromo-4-methylphenyl group |
| 234 | 2,4-dichloro-6-methylphenyl group |
| 235 | 2,4-difluoro-6-methylphenyl group |
| 236 | 2,4-dibromo-6-methylphenyl group |
| 237 | 2,6-dimethyl-4-fluorophenyl group |
| 238 | 2,6-dimethyl-4-chlorophenyl group |
| 239 | 2,6-dimethyl-4-bromophenyl group |
| 240 | 3,5-dimethyl-4-fluorophenyl group |
| 241 | 3,5-dimethyl-4-chlorophenyl group |
| 242 | 3,5-dimethyl-4-bromophenyl group |
| 243 | 2-3-difluoro-4-methylphenyl group |
| 244 | 2,5-difluoro-4-methylphenyl group |
| 245 | 3,5-difluoro-4-methylphenyl group |

TABLE 9-continued

| substituents Nos. | Y |
|---|---|
| 246 | 2,3,5-trifluoro-4-methylphenyl group |
| 247 | 2,3,6-trifluoro-4-methylphenyl group |
| 248 | 2,3,5,6-tetrafluoro-4-methylphenyl group |
| 249 | 2-fluoro-4-ethylphenyl group |
| 250 | 3-fluoro-4-ethylphenyl group |
| 251 | 2-3-difluoro-4-ethylphenyl group |
| 252 | 2,6-difluoro-4-ethylphenyl group |
| 253 | 2,5-difluoro-4-ethylphenyl group |
| 254 | 3,5-difluoro-4-ethylphenyl group |
| 255 | 2,3,5-trifluoro-4-ethylphenyl group |
| 256 | 2,3,6-trifluoro-4-ethylphenyl group |
| 257 | 2,3,5,6-tetrafluoro-4-ethylphenyl group |
| 258 | 2-trifluoromethylphenyl group |
| 259 | 3-trifluoromethylphenyl group |
| 260 | 4-trifluoromethylphenyl group |
| 261 | 4-(2,2,2-trifluoro-1-trifluoromethyl-ethyl)phenyl group |

TABLE 10

| substituents Nos. | Y |
|---|---|
| 262 | 2-trifluoromethoxyphenyl group |
| 263 | 3-trifluoromethoxyphenyl group |
| 264 | 4-trifluoromethoxyphenyl group |
| 265 | 4-(2,2-difluoroethoxy)phenyl group |
| 266 | 4-(2,2,2-trifluoroethoxy)phenyl group |
| 267 | 2-nitrophenyl group |
| 268 | 3-nitrophenyl group |
| 269 | 4-nitrophenyl group |
| 270 | 2-cyanophenyl group |
| 271 | 3-cyanophenyl group |
| 272 | 4-cyanophenyl group |
| 273 | 2-methyl-3-chlorophenyl group |
| 274 | 2-methyl-4-chlorophenyl group |
| 275 | 2-methyl-5-chlorophenyl group |
| 276 | 2-methyl-6-chlorophenyl group |
| 277 | 2-methyl-3-fluorophenyl group |
| 278 | 2-methyl-4-fluorophenyl group |
| 279 | 2-methyl-5-fluorophenyl group |
| 280 | 2-methyl-6-fluorophenyl group |
| 281 | 2-methyl-3-bromophenyl group |
| 282 | 2-methyl-4-bromophenyl group |
| 283 | 4-methylthiophenyl group |
| 284 | 4-methylsulfonylphenyl group |
| 285 | 4-methylsulfinylphenyl group |
| 286 | 4-trifluoromethylthiophenyl group |
| 287 | 4-ethynylphenyl group |
| 288 | 4-(1-propynyl)phenyl group |
| 289 | 4-vinylphenyl group |
| 290 | 4-(2,2-dichlorovinyl)phenyl group |

TABLE 11

| substituents Nos. | Y |
|---|---|
| 291 | 4-(2,2-difluorovinyl)phenyl group |
| 292 | cyclohexyl group |
| 293 | 2-chlorocyclohexyl group |
| 294 | 3-chlorocyclohexyl group |
| 295 | 4-chlorocyclohexyl group |
| 296 | 4,4-dichlorocyclohexyl group |
| 297 | 2-bromocyclohexyl group |
| 298 | 3-bromocyclohexyl group |
| 299 | 4-bromocyclohexyl group |
| 300 | 4,4-dibromocyclohexyl group |
| 301 | 2-iodocyclohexyl group |
| 302 | 3-iodocyclohexyl group |
| 303 | 4-iodocyclohexyl group |
| 304 | 2-fluorocyclohexyl group |

TABLE 11-continued

| substituents Nos. | Y |
|---|---|
| 305 | 3-fluorocyclohexyl group |
| 306 | 4-fluorocyclohexyl group |
| 307 | 4,4-difluorocyclohexyl group |
| 308 | 4-methylcyclohexyl group |
| 309 | 4-ethylcyclohexyl group |
| 310 | 1-cyclohexenyl group |
| 311 | 2-cyclohexenyl group |
| 312 | 3-cyclohexenyl group |
| 313 | 2-chloro-1-cyclohexenyl group |
| 314 | 3-chloro-1-cyclohexenyl group |
| 315 | 4-chloro-1-cyclohexenyl group |
| 316 | 5-chloro-1-cyclohexenyl group |
| 317 | 6-chloro-1-cyclohexenyl group |
| 318 | 1-chloro-2-cyclohexenyl group |
| 319 | 2-chloro-2-cyclohexenyl group |

TABLE 12

| substituents Nos. | Y |
|---|---|
| 320 | 3-chloro-2-cyclohexenyl group |
| 321 | 4-chloro-2-cyclohexenyl group |
| 322 | 5-chloro-2-cyclohexenyl group |
| 323 | 6-chloro-2-cyclohexenyl group |
| 324 | 1-chloro-3-cyclohexenyl group |
| 325 | 2-chloro-3-cyclohexenyl group |
| 326 | 3-chloro-3-cyclohexenyl group |
| 327 | 4-chloro-3-cyclohexenyl group |
| 328 | 5-chloro-3-cyclohexenyl group |
| 329 | 6-chloro-3-cyclohexenyl group |
| 330 | 4-bromo-1-cyclohexenyl group |
| 331 | 4-bromo-2-cyclohexenyl group |
| 332 | 4-bromo-3-cyclohexenyl group |
| 333 | 4-methyl-1-cyclohexenyl group |
| 334 | 4-methyl-2-cyclohexenyl group |
| 335 | 4-methyl-3-cyclohexenyl group |
| 336 | 4-ethyl-1-cyclohexenyl group |
| 337 | 4-ethyl-2-cyclohexenyl group |
| 338 | 4-ethyl-3-cyclohexenyl group |
| 339 | trifluoromethyl group |
| 340 | tert-butyl group |
| 341 | 3-fluoro-2-methoxyphenyl group |
| 342 | 4-fluoro-2-methoxyphenyl group |
| 343 | 5-fluoro-2-methoxyphenyl group |
| 344 | 6-fluoro-2-methoxyphenyl group |
| 345 | 3-chloro-2-methoxyphenyl group |
| 346 | 4-chloro-2-methoxyphenyl group |
| 347 | 5-chloro-2-methoxyphenyl group |
| 348 | 6-chloro-2-methoxyphenyl group |

TABLE 13

| Substituents Nos. | Y |
|---|---|
| 349 | 3-bromo-2-methoxyphenyl group |
| 350 | 4-bromo-2-methoxyphenyl group |
| 351 | 5-bromo-2-methoxyphenyl group |
| 352 | 6-bromo-2-methoxyphenyl group |
| 353 | 3-iodo-2-methoxyphenyl group |
| 354 | 4-iodo-2-methoxyphenyl group |
| 355 | 5-iodo-2-methoxyphenyl group |
| 356 | 6-iodo-2-methoxyphenyl group |
| 357 | 2,3-dimethoxyphenyl group |
| 358 | 2,4-dimethoxyphenyl group |
| 359 | 2,5-dimethoxyphenyl group |
| 360 | 2,6-dimethoxyphenyl group |
| 361 | 3-methyl-2-methoxyphenyl group |
| 362 | 4-methyl-2-methoxyphenyl group |
| 363 | 5-methyl-2-methoxyphenyl group |
| 364 | 6-methyl-2-methoxyphenyl group |

TABLE 13-continued

| Substituents Nos. | Y |
|---|---|
| 365 | 3-ethyl-2-methoxyphenyl group |
| 366 | 4-ethyl-2-methoxyphenyl group |
| 367 | 5-ethyl-2-methoxyphenyl group |
| 368 | 6-ethyl-2-methoxyphenyl group |
| 369 | 3-trifluoromethoxy-2-methoxyphenyl group |
| 370 | 4-trifluoromethoxy-2-methoxyphenyl group |
| 371 | 5-trifluoromethoxy-2-methoxyphenyl group |
| 372 | 6-trifluoromethoxy-2-methoxyphenyl group |
| 373 | 3-trifluoromethyl-2-methoxyphenyl group |
| 374 | 4-trifluoromethyl-2-methoxyphenyl group |
| 375 | 5-trifluoromethyl-2-methoxyphenyl group |
| 376 | 6-trifluoromethyl-2-methoxyphenyl group |
| 377 | 3-methylthio-2-methoxyphenyl group |

TABLE 14

| Substituents Nos. | Y |
|---|---|
| 378 | 4-methylthio-2-methoxyphenyl group |
| 379 | 5-methylthio-2-methoxyphenyl group |
| 380 | 6-methylthio-2-methoxyphenyl group |
| 381 | 3-trifluoromethylthio-2-methoxyphenyl group |
| 382 | 4-trifluoromethylthio-2-methoxyphenyl group |
| 383 | 5-trifluoromethylthio-2-methoxyphenyl group |
| 384 | 6-trifluoromethylthio-2-methoxyphenyl group |
| 385 | 3-ethynyl-2-methoxyphenyl group |
| 386 | 4-ethynyl-2-methoxyphenyl group |
| 387 | 5-ethynyl-2-methoxyphenyl group |
| 388 | 6-ethynyl-2-methoxyphenyl group |
| 389 | 3-cyclopropyl-2-methoxyphenyl group |
| 390 | 4-cyclopropyl-2-methoxyphenyl group |
| 391 | 5-cyclopropyl-2-methoxyphenyl group |
| 392 | 6-cyclopropyl-2-methoxyphenyl group |
| 393 | 3-cyclopropyloxy-2-methoxyphenyl group |
| 394 | 4-cyclopropyloxy-2-methoxyphenyl group |
| 395 | 5-cyclopropyloxy-2-methoxyphenyl group |
| 396 | 6-cyclopropyloxy-2-methoxyphenyl group |
| 397 | 2-ethoxy-3-fluorophenyl group |
| 398 | 2-ethoxy-4-fluorophenyl group |
| 399 | 2-ethoxy-5-fluorophenyl group |
| 400 | 2-ethoxy-6-fluorophenyl group |
| 401 | 3-chloro-2-ethoxyphenyl group |
| 402 | 4-chloro-2-ethoxyphenyl group |
| 403 | 5-chloro-2-ethoxyphenyl group |
| 404 | 6-chloro-2-ethoxyphenyl group |
| 405 | 3-bromo-2-ethoxyphenyl group |
| 406 | 4-bromo-2-ethoxyphenyl group |

TABLE 15

| Substituents Nos. | Y |
|---|---|
| 407 | 5-bromo-2-ethoxyphenyl group |
| 408 | 6-bromo-2-ethoxyphenyl group |
| 409 | 2-ethoxy-3-iodophenyl group |
| 410 | 2-ethoxy-4-iodophenyl group |
| 411 | 2-ethoxy-5-iodophenyl group |
| 412 | 2-ethoxy-6-iodophenyl group |
| 413 | 2,3-diethoxyphenyl group |
| 414 | 2,4-diethoxyphenyl group |
| 415 | 2,5-diethoxyphenyl group |
| 416 | 2,6-diethoxyphenyl group |
| 417 | 2-ethoxy-3-methylphenyl group |
| 418 | 2-ethoxy-4-methylphenyl group |
| 419 | 2-ethoxy-5-methylphenyl group |
| 420 | 2-ethoxy-6-methylphenyl group |
| 421 | 3-ethyl-2-ethoxyphenyl group |
| 422 | 4-ethyl-2-ethoxyphenyl group |
| 423 | 5-ethyl-2-ethoxyphenyl group |
| 424 | 6-ethyl-2-ethoxyphenyl group |

TABLE 15-continued

| Substituents Nos. | Y |
|---|---|
| 425 | 2-ethoxy-3-trifluoromethoxyphenyl group |
| 426 | 2-ethoxy-4-trifluoromethoxyphenyl group |
| 427 | 2-ethoxy-5-trifluoromethoxyphenyl group |
| 428 | 2-ethoxy-6-trifluoromethoxyphenyl group |
| 429 | 2-ethoxy-3-trifluoromethylphenyl group |
| 430 | 2-ethoxy-4-trifluoromethylphenyl group |
| 431 | 2-ethoxy-5-trifluoromethylphenyl group |
| 432 | 2-ethoxy-6-trifluoromethylphenyl group |
| 433 | 2-ethoxy-3-methylthiophenyl group |
| 434 | 2-ethoxy-4-methylthiophenyl group |
| 435 | 2-ethoxy-5-methylthiophenyl group |

TABLE 16

| Substituents Nos. | Y |
|---|---|
| 436 | 2-ethoxy-6-methylthiophenyl group |
| 437 | 2-ethoxy-3-trifluoromethylthiophenyl group |
| 438 | 2-ethoxy-4-trifluoromethylthiophenyl group |
| 439 | 2-ethoxy-5-trifluoromethylthiophenyl group |
| 440 | 2-ethoxy-6-trifluoromethylthiophenyl group |
| 441 | 3-ethynyl-2-ethoxyphenyl group |
| 442 | 4-ethynyl-2-ethoxyphenyl group |
| 443 | 5-ethynyl-2-ethoxyphenyl group |
| 444 | 6-ethynyl-2-ethoxyphenyl group |
| 445 | 3-cyclopropyl-2-ethoxyphenyl group |
| 446 | 4-cyclopropyl-2-ethoxyphenyl group |
| 447 | 5-cyclopropyl-2-ethoxyphenyl group |
| 448 | 6-cyclopropyl-2-ethoxyphenyl group |
| 449 | 3-cyclopropyloxy-2-ethoxyphenyl group |
| 450 | 4-cyclopropyloxy-2-ethoxyphenyl group |
| 451 | 5-cyclopropyloxy-2-ethoxyphenyl group |
| 452 | 6-cyclopropyloxy-2-ethoxyphenyl group |
| 453 | 3-methoxy-2-methylphenyl group |
| 454 | 4-methoxy-2-methylphenyl group |
| 455 | 5-methoxy-2-methylphenyl group |
| 456 | 6-methoxy-2-methylphenyl group |
| 457 | 3-ethoxy-2-methylphenyl group |
| 458 | 4-ethoxy-2-methylphenyl group |
| 459 | 5-ethoxy-2-methylphenyl group |
| 460 | 6-ethoxy-2-methylphenyl group |
| 461 | 3-ethyl-2-methylphenyl group |
| 462 | 4-ethyl-2-methylphenyl group |
| 463 | 5-ethyl-2-methylphenyl group |
| 464 | 6-ethyl-2-methylphenyl group |

TABLE 17

| Substituents Nos. | Y |
|---|---|
| 465 | 3-trifluoromethoxy-2-methylphenyl group |
| 466 | 4-trifluoromethoxy-2-methylphenyl group |
| 467 | 5-trifluoromethoxy-2-methylphenyl group |
| 468 | 6-trifluoromethoxy-2-methylphenyl group |
| 469 | 3-trifluoromethyl-2-methylphenyl group |
| 470 | 4-trifluoromethyl-2-methylphenyl group |
| 471 | 5-trifluoromethyl-2-methylphenyl group |
| 472 | 6-trifluoromethyl-2-methylphenyl group |
| 473 | 3-methylthio-2-methylphenyl group |
| 474 | 4-methylthio-2-methylphenyl group |
| 475 | 5-methylthio-2-methylphenyl group |
| 476 | 6-methylthio-2-methylphenyl group |
| 477 | 4-fluoro-2-isopropyloxyphenyl group |
| 478 | 4-chloro-2-isopropyloxyphenyl group |
| 479 | 4-bromo-2-isopropyloxyphenyl group |
| 480 | 4-iodo-2-isopropyloxyphenyl group |
| 481 | 4-methyl-2-isopropyloxyphenyl group |
| 482 | 4-ethyl-2-isopropyloxyphenyl |
| 483 | 4-methoxy-2-isopropyloxyphenyl group |
| 484 | 4-ethoxy-2-isopropyloxyphenyl group |

TABLE 17-continued

| Substituents Nos. | Y |
|---|---|
| 485 | 4-trifluoromethyl-2-isopropyloxyphenyl group |
| 486 | 4-trifluoromethoxy-2-isopropyloxyphenyl group |
| 487 | 4-methylthio-2-isopropyloxyphenyl group |
| 488 | 4-cyclopropyl-2-isopropyloxyphenyl group |
| 489 | 4-fluoro-2-cyclopropyloxyphenyl group |
| 490 | 4-chloro-2-cyclopropyloxyphenyl group |
| 491 | 4-bromo-2-cyclopropyloxyphenyl group |
| 492 | 4-iodo-2-cyclopropyloxyphenyl group |
| 493 | 4-methyl-2-cyclopropyloxyphenyl group |

TABLE 18

| Substituents Nos. | Y |
|---|---|
| 494 | 4-ethyl-2-cyclopropyloxyphenyl |
| 495 | 4-methoxy-2-cyclopropyloxyphenyl group |
| 496 | 4-ethoxy-2-cyclopropyloxyphenyl group |
| 497 | 4-trifluoromethyl-2-cyclopropyloxyphenyl group |
| 498 | 4-trifluoromethoxy-2-cyclopropyloxyphenyl group |
| 499 | 4-methylthio-2-cyclopropyloxyphenyl group |
| 500 | 4-cyclopropyl-2-cyclopropyloxyphenyl group |
| 501 | 3,4-difluoro-2-methoxyphenyl group |
| 502 | 4,5-difluoro-2-methoxyphenyl group |
| 503 | 4,6-difluoro-2-methoxyphenyl group |
| 504 | 3,4,5-trifluoro-2-methoxyphenyl group |
| 505 | 3,4,5,6-tetrafluoro-2-methoxyphenyl group |
| 506 | 4-chloro-3-fluoro-2-methoxyphenyl group |
| 507 | 4-chloro-5-fluoro-2-methoxyphenyl group |
| 508 | 4-chloro-6-fluoro-2-methoxyphenyl group |
| 509 | 4-bromo-3-fluoro-2-methoxyphenyl group |
| 510 | 4-bromo-5-fluoro-2-methoxyphenyl group |
| 511 | 4-bromo-6-fluoro-2-methoxyphenyl group |
| 512 | 3,4-difluoro-2-ethoxyphenyl group |
| 513 | 4,5-difluoro-2-ethoxyphenyl group |
| 514 | 4,6-difluoro-2-ethoxyphenyl group |
| 515 | 3,4,5-trifluoro-2-ethoxyphenyl group |
| 516 | 3,4,5,6-tetrafluoro-2-ethoxyphenyl group |
| 517 | 4-chloro-3-fluoro-2-ethoxyphenyl group |
| 518 | 4-chloro-5-fluoro-2-ethoxyphenyl group |
| 519 | 4-chloro-6-fluoro-2-ethoxyphenyl group |
| 520 | 4-bromo-3-fluoro-2-ethoxyphenyl group |
| 521 | 4-bromo-5-fluoro-2-ethoxyphenyl group |
| 522 | 4-bromo-6-fluoro-2-ethoxyphenyl group |

TABLE 19

| Substituents Nos. | Y |
|---|---|
| 523 | 3,4-difluoro-2-isopropyloxyphenyl group |
| 524 | 4,5-difluoro-2-isopropyloxyphenyl group |
| 525 | 4,6-difluoro-2-isopropyloxyphenyl group |
| 526 | 3,4,5-trifluoro-2-isopropyloxyphenyl group |
| 527 | 3,4,5,6-tetrafluoro-2-isopropyloxyphenyl group |
| 528 | 4-chloro-3-fluoro-2-isopropyloxyphenyl group |
| 529 | 4-chloro-5-fluoro-2-isopropyloxyphenyl group |
| 530 | 4-chloro-6-fluoro-2-isopropyloxyphenyl group |
| 531 | 4-bromo-3-fluoro-2-isopropyloxyphenyl group |
| 532 | 4-bromo-5-fluoro-2-isopropyloxyphenyl group |
| 533 | 4-bromo-6-fluoro-2-isopropyloxyphenyl group |
| 534 | 3,4-difluoro-2-cyclopropyloxyphenyl group |
| 535 | 4,5-difluoro-2-cyclopropyloxyphenyl group |
| 536 | 4,6-difluoro-2-cyclopropyloxyphenyl group |
| 537 | 3,4,5-trifluoro-2-cyclopropyloxyphenyl group |
| 538 | 3,4,5,6-tetrafluoro-2-cyclopropyloxyphenyl group |
| 539 | 4-chloro-3-fluoro-2-cyclopropyloxyphenyl group |
| 540 | 4-chloro-5-fluoro-2-cyclopropyloxyphenyl group |
| 541 | 4-chloro-6-fluoro-2-cyclopropyloxyphenyl group |
| 542 | 4-bromo-3-fluoro-2-cyclopropyloxyphenyl group |
| 543 | 4-bromo-5-fluoro-2-cyclopropyloxyphenyl group |
| 544 | 4-bromo-6-fluoro-2-cyclopropyloxyphenyl group |

TABLE 19-continued

| Substituents Nos. | Y |
|---|---|
| 545 | 3-ethynyl-2-methylphenyl group |
| 546 | 4-ethynyl-2-methylphenyl group |
| 547 | 5-ethynyl-2-methylphenyl group |
| 548 | 6-ethynyl-2-methylphenyl group |
| 549 | 3-cyclopropyl-2-methylphenyl group |
| 550 | 4-cyclopropyl-2-methylphenyl group |
| 551 | 5-cyclopropyl-2-methylphenyl group |

TABLE 20

| Substituents Nos. | Y |
|---|---|
| 552 | 6-cyclopropyl-2-methylphenyl group |
| 553 | 3-cyclopropyloxy-2-methylphenyl group |
| 554 | 4-cyclopropyloxy-2-methylphenyl group |
| 555 | 5-cyclopropyloxy-2-methylphenyl group |
| 556 | 6-cyclopropyloxy-2-methylphenyl group |
| 557 | 3-methoxy-2-fluorophenyl group |
| 558 | 4-methoxy-2-fluorophenyl group |
| 559 | 5-methoxy-2-fluorophenyl group |
| 560 | 6-methoxy-2-fluorophenyl group |
| 561 | 3-ethoxy-2-fluorophenyl group |
| 562 | 4-ethoxy-2-fluorophenyl group |
| 563 | 5-ethoxy-2-fluorophenyl group |
| 564 | 6-ethoxy-2-fluorophenyl group |
| 565 | 3-ethyl-2-fluorophenyl group |
| 566 | 5-ethyl-2-fluorophenyl group |
| 567 | 6-ethyl-2-fluorophenyl group |
| 568 | 2-fluoro-3-trifluoromethoxyphenyl group |
| 569 | 2-fluoro-4-trifluoromethoxyphenyl group |
| 570 | 2-fluoro-5-trifluoromethoxyphenyl group |
| 571 | 2-fluoro-6-trifluoromethoxyphenyl group |
| 572 | 2-fluoro-3-trifluoromethylphenyl group |
| 573 | 2-fluoro-4-trifluoromethylphenyl group |
| 574 | 2-fluoro-5-trifluoromethylphenyl group |
| 575 | 2-fluoro-6-trifluoromethylphenyl group |
| 576 | 2-fluoro-3-fluorothiophenyl group |
| 577 | 2-fluoro-4-fluorothiophenyl group |
| 578 | 2-fluoro-5-fluorothiophenyl group |
| 579 | 2-fluoro-6-fluorothiophenyl group |
| 580 | 3-ethynyl-2-fluorophenyl group |

TABLE 21

| Substituents Nos. | Y |
|---|---|
| 581 | 4-ethynyl-2-fluorophenyl group |
| 582 | 5-ethynyl-2-fluorophenyl group |
| 583 | 6-ethynyl-2-fluorophenyl group |
| 584 | 3-cyclopropyl-2-fluorophenyl group |
| 585 | 4-cyclopropyl-2-fluorophenyl group |
| 586 | 5-cyclopropyl-2-fluorophenyl group |
| 587 | 6-cyclopropyl-2-fluorophenyl group |
| 588 | 3-cyclopropyloxy-2-fluorophenyl group |
| 589 | 4-cyclopropyloxy-2-fluorophenyl group |
| 590 | 5-cyclopropyloxy-2-fluorophenyl group |
| 591 | 6-cyclopropyloxy-2-fluorophenyl group |
| 592 | 2-ethyl-3-fluorophenyl group |
| 593 | 2-ethyl-4-fluorophenyl group |
| 594 | 2-ethyl-5-fluorophenyl group |
| 595 | 2-ethyl-6-fluorophenyl group |
| 596 | 3-chloro-2-ethylphenyl group |
| 597 | 4-chloro-2-ethylphenyl group |
| 598 | 5-chloro-2-ethylphenyl group |
| 599 | 6-chloro-2-ethylphenyl group |
| 600 | 3-bromo-2-ethylphenyl group |
| 601 | 4-bromo-2-ethylphenyl group |
| 602 | 5-bromo-2-ethylphenyl group |
| 603 | 6-bromo-2-ethylphenyl group |
| 604 | 2-ethyl-3-iodophenyl group |

TABLE 21-continued

| Substituents Nos. | Y |
|---|---|
| 605 | 2-ethyl-4-iodophenyl group |
| 606 | 2-ethyl-5-iodophenyl group |
| 607 | 2-ethyl-6-iodophenyl group |
| 608 | 2-ethyl-3-ethoxyphenyl group |
| 609 | 2-ethyl-4-ethoxyphenyl group |

TABLE 22

| Substituents Nos. | Y |
|---|---|
| 610 | 2-ethyl-5-ethoxyphenyl group |
| 611 | 2-ethyl-6-ethoxyphenyl group |
| 612 | 2-ethyl-3-methylphenyl group |
| 613 | 2-ethyl-4-methylphenyl group |
| 614 | 2-ethyl-5-methylphenyl group |
| 615 | 2-ethyl-6-methylphenyl group |
| 616 | 2,3-diethylphenyl group |
| 617 | 2,4-diethylphenyl group |
| 618 | 2,5-diethylphenyl group |
| 619 | 2,6-diethylphenyl group |
| 620 | 2-ethyl-3-trifluoromethoxyphenyl group |
| 621 | 2-ethyl-4-trifluoromethoxyphenyl group |
| 622 | 2-ethyl-5-trifluoromethoxyphenyl group |
| 623 | 2-ethyl-6-trifluoromethoxyphenyl group |
| 624 | 2-ethyl-3-trifluoromethylphenyl group |
| 625 | 2-ethyl-4-trifluoromethylphenyl group |
| 626 | 2-ethyl-5-trifluoromethylphenyl group |
| 627 | 2-ethyl-6-trifluoromethylphenyl group |
| 628 | 2-ethyl-3-methylthiophenyl group |
| 629 | 2-ethyl-4-methylthiophenyl group |
| 630 | 2-ethyl-5-methylthiophenyl group |
| 631 | 2-ethyl-6-methylthiophenyl group |
| 632 | 2-ethyl-3-trifluoromethylthiophenyl group |
| 633 | 2-ethyl-4-trifluoromethylthiophenyl group |
| 634 | 2-ethyl-5-trifluoromethylthiophenyl group |
| 635 | 2-ethyl-6-trifluoromethylthiophenyl group |
| 636 | 3-ethynyl-2-ethylphenyl group |
| 637 | 4-ethynyl-2-ethylphenyl group |
| 638 | 5-ethynyl-2-ethylphenyl group |

TABLE 23

| Substituents Nos. | Y |
|---|---|
| 639 | 6-ethynyl-2-ethylphenyl group |
| 640 | 3-cyclopropyl-2-ethylphenyl group |
| 641 | 4-cyclopropyl-2-ethylphenyl group |
| 642 | 5-cyclopropyl-2-ethylphenyl group |
| 643 | 6-cyclopropyl-2-ethylphenyl group |
| 644 | 3-cyclopropyloxy-2-ethylphenyl group |
| 645 | 4-cyclopropyloxy-2-ethylphenyl group |
| 646 | 5-cyclopropyloxy-2-ethylphenyl group |
| 647 | 6-cyclopropyloxy-2-ethylphenyl group |
| 648 | 3-fluoro-2-trifluoromethylphenyl group |
| 649 | 4-fluoro-2-trifluoromethylphenyl group |
| 650 | 5-fluoro-2-trifluoromethylphenyl group |
| 651 | 6-fluoro-2-trifluoromethylphenyl group |
| 652 | 3-chloro-2-trifluoromethylphenyl group |
| 653 | 4-chloro-2-trifluoromethylphenyl group |
| 654 | 5-chloro-2-trifluoromethylphenyl group |
| 655 | 6-chloro-2-trifluoromethylphenyl group |
| 656 | 3-bromo-2-trifluoromethylphenyl group |
| 657 | 4-bromo-2-trifluoromethylphenyl group |
| 658 | 5-bromo-2-trifluoromethylphenyl group |
| 659 | 6-bromo-2-trifluoromethylphenyl group |
| 660 | 3-iodo-2-trifluoromethylphenyl group |
| 661 | 4-iodo-2-trifluoromethylphenyl group |
| 662 | 5-iodo-2-trifluoromethylphenyl group |
| 663 | 6-iodo-2-trifluoromethylphenyl group |
| 664 | 3-ethoxy-2-trifluoromethylphenyl group |

TABLE 23-continued

| Substituents Nos. | Y |
|---|---|
| 665 | 4-ethoxy-2-trifluoromethylphenyl group |
| 666 | 5-ethoxy-2-trifluoromethylphenyl group |
| 667 | 6-ethoxy-2-trifluoromethylphenyl group |

TABLE 24

| Substituents Nos. | Y |
|---|---|
| 668 | 3-methyl-2-trifluoromethylphenyl group |
| 669 | 4-methyl-2-trifluoromethylphenyl group |
| 670 | 5-methyl-2-trifluoromethylphenyl group |
| 671 | 6-methyl-2-trifluoromethylphenyl group |
| 672 | 2,3-ditrifluoromethylphenyl group |
| 673 | 2,4-ditrifluoromethylphenyl group |
| 674 | 2,5-ditrifluoromethylphenyl group |
| 675 | 2,6-ditrifluoromethylphenyl group |
| 676 | 2-trifluoromethyl-3-trifluoromethoxyphenyl group |
| 677 | 2-trifluoromethyl-4-trifluoromethoxyphenyl group |
| 678 | 2-trifluoromethyl-5-trifluoromethoxyphenyl group |
| 679 | 2-trifluoromethyl-6-trifluoromethoxyphenyl group |
| 680 | 2-ethyl-3-trifluoromethylphenyl group |
| 681 | 2-ethyl-4-trifluoromethylphenyl group |
| 682 | 2-ethyl-5-trifluoromethylphenyl group |
| 683 | 2-ethyl-6-trifluoromethylphenyl group |
| 684 | 3-methylthio-2-trifluoromethylphenyl group |
| 685 | 4-methylthio-2-trifluoromethylphenyl group |
| 686 | 5-methylthio-2-trifluoromethylphenyl group |
| 687 | 6-methylthio-2-trifluoromethylphenyl group |
| 688 | 2-trifluoromethyl-3-trifluoromethylthiophenyl group |
| 689 | 2-trifluoromethyl-4-trifluoromethylthiophenyl group |
| 690 | 2-trifluoromethyl-5-trifluoromethylthiophenyl group |
| 691 | 2-trifluoromethyl-6-trifluoromethylthiophenyl group |
| 692 | 3-ethynyl-2-trifluoromethylphenyl group |
| 693 | 4-ethynyl-2-trifluoromethylphenyl group |
| 694 | 5-ethynyl-2-trifluoromethylphenyl group |
| 695 | 6-ethynyl-2-trifluoromethylphenyl group |
| 696 | 3-cyclopropyl-2-trifluoromethylphenyl group |

TABLE 25

| Substituents Nos. | Y |
|---|---|
| 697 | 4-cyclopropyl-2-trifluoromethylphenyl group |
| 698 | 5-cyclopropyl-2-trifluoromethylphenyl group |
| 699 | 6-cyclopropyl-2-trifluoromethylphenyl group |
| 700 | 3-cyclopropyloxy-2-trifluoromethylphenyl group |
| 701 | 4-cyclopropyloxy-2-trifluoromethylphenyl group |
| 702 | 5-cyclopropyloxy-2-trifluoromethylphenyl group |
| 703 | 6-cyclopropyloxy-2-trifluoromethylphenyl group |
| 704 | 3-methoxynaphthalene-2-yl group |
| 705 | 6-chloro-3-methoxynaphthalene-2-yl group |
| 706 | 6-fluoro-3-methoxynaphthalene-2-yl group |
| 707 | 7-chloro-3-methoxynaphthalene-2-yl group |
| 708 | 7-fluoro-3-methoxynaphthalene-2-yl group |
| 709 | 8-chloro-3-methoxynaphthalene-2-yl group |
| 710 | 8-fluoro-3-methoxynaphthalene-2-yl group |
| 711 | 1-chloro-3-methoxynaphthalene-2-yl group |
| 712 | 1-fluoro-3-methoxynaphthalene-2-yl group |
| 713 | 4-chloro-3-methoxynaphthalene-2-yl group |
| 714 | 4-fluoro-3-methoxynaphthalene-2-yl group |
| 715 | 5-chloro-3-methoxynaphthalene-2-yl group |
| 716 | 5-fluoro-3-methoxynaphthalene-2-yl group |

According to the above-mentioned processes, the following compounds can be prepared:

Compounds HA-001~HA-144, HB-001~HB-144, HC-001~HC-144, HD-001~HD-144, HE-001~HE-144, HF-001~HF-144, HG-001~HG-144, HH-001~HH-144, HI-001~HI-144, HJ-001~HJ-144, HK-001~HK-144, HL-001~HL-144, HM-001~HM-144, HN-001~HN-144, HO-001~HO-144, HP-001~HP-144, HQ-001~HQ-144, HR-001~HR-144, HS-001~HS-144, HT-001~HT-144, HU-001~HU-144, HV-001~HV-144, HW-001~HW-144, HX-001~HX-144, HY-001~HY-144, HZ-001~HZ-144 and HAA-001~HAA-144.

Compounds HA-001~HA-144 represent tetrazolinone Compounds represented by a formula:

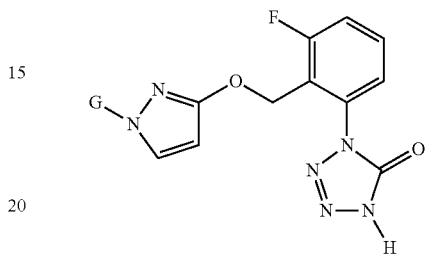

[wherein G represents a substituent corresponding to each of substituents Nos. 1 to 144 indicated in Table 26 to Table 30 as below-mentioned];

Compounds HB-001~HB-144 represent tetrazolinone Compounds represented by a formula:

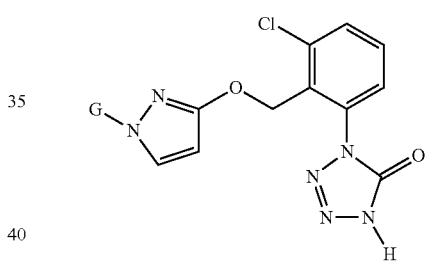

[wherein G represents a substituent corresponding to each of substituents Nos. 1 to 144 indicated in Table 26 to Table 30 as below-mentioned];

Compounds HC-001~HC-144 represent tetrazolinone Compounds represented by a formula:

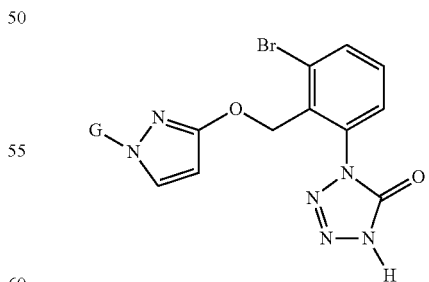

[wherein G represents a substituent corresponding to each of substituents Nos. 1 to 144 indicated in Table 26 to Table 30 as below-mentioned];

Compounds HD-001~HD-144 represent tetrazolinone Compounds represented by a formula:

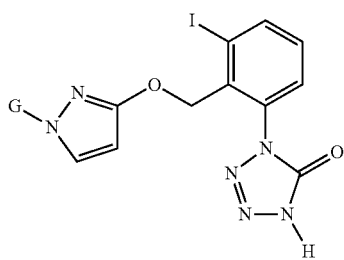

[wherein G represents a substituent corresponding to each of substituents Nos. 1 to 144 indicated in Table 26 to Table 30 as below-mentioned];
Compounds HE-001~HE-144 represent tetrazolinone Compounds represented by a formula:

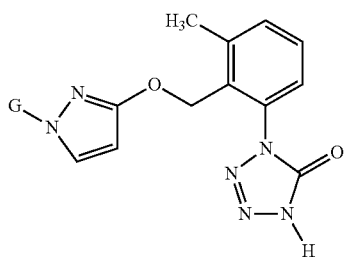

[wherein G represents a substituent corresponding to each of substituents Nos. 1 to 144 indicated in Table 26 to Table 30 as below-mentioned];
Compounds HF-001~HF-144 represent tetrazolinone Compounds represented by a formula:

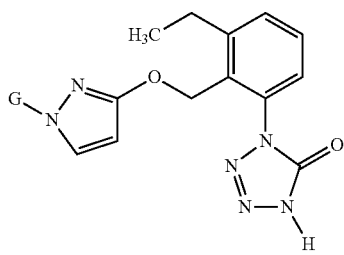

[wherein G represents a substituent corresponding to each of substituents Nos. 1 to 144 indicated in Table 26 to Table 30 as below-mentioned];
Compounds HG-001~HG-144 represent tetrazolinone Compounds represented by a formula:

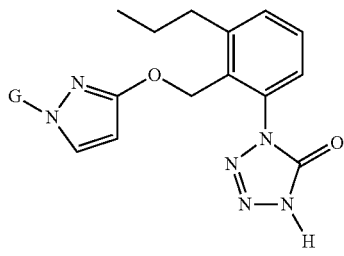

[wherein G represents a substituent corresponding to each of substituents Nos. 1 to 144 indicated in Table 26 to Table 30 as below-mentioned];

Compounds HH-001~HH-144 represent tetrazolinone Compounds represented by a formula:

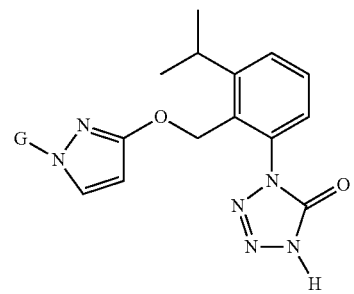

[wherein G represents a substituent corresponding to each of substituents Nos. 1 to 144 indicated in Table 26 to Table 30 as below-mentioned];
Compounds HI-001~HI-144 represent tetrazolinone Compounds represented by a formula:

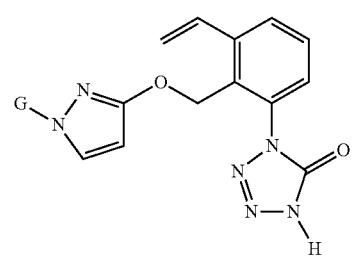

[wherein G represents a substituent corresponding to each of substituents Nos. 1 to 144 indicated in Table 26 to Table 30 as below-mentioned];
Compounds HJ-001~HJ-144 represent tetrazolinone Compounds represented by a formula:

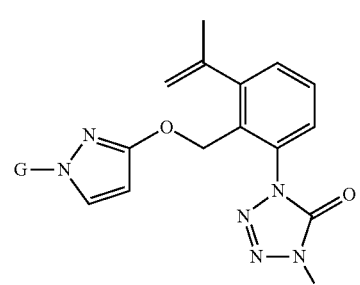

[wherein G represents a substituent corresponding to each of substituents Nos. 1 to 144 indicated in Table 26 to Table 30 as below-mentioned];
Compounds HK-001~HK-144 represent tetrazolinone Compounds represented by a formula:

461

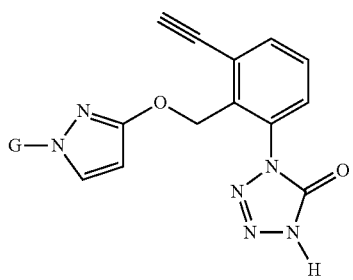

[wherein G represents a substituent corresponding to each of substituents Nos. 1 to 144 indicated in Table 26 to Table 30 as below-mentioned];

Compounds HL-001~HL-144 represent tetrazolinone Compounds represented by a formula:

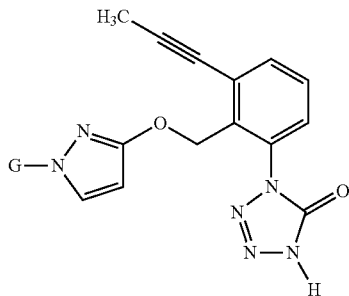

[wherein G represents a substituent corresponding to each of substituents Nos. 1 to 144 indicated in Table 26 to Table 30 as below-mentioned];

Compounds HM-001~HM-144 represent tetrazolinone Compounds represented by a formula:

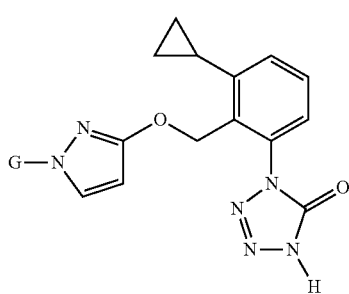

[wherein G represents a substituent corresponding to each of substituents Nos. 1 to 144 indicated in Table 26 to Table 30 as below-mentioned];

Compounds HN-001~HN-144 represent tetrazolinone Compounds represented by a formula:

462

[wherein G represents a substituent corresponding to each of substituents Nos. 1 to 144 indicated in Table 26 to Table 30 as below-mentioned];

Compounds HO-001~HO-144 represent tetrazolinone Compounds represented by a formula:

[wherein G represents a substituent corresponding to each of substituents Nos. 1 to 144 indicated in Table 26 to Table 30 as below-mentioned];

Compounds HP-001~HP-144 represent tetrazolinone Compounds represented by a formula:

[wherein G represents a substituent corresponding to each of substituents Nos. 1 to 144 indicated in Table 26 to Table 30 as below-mentioned];

Compounds HQ-001~HQ-144 represent tetrazolinone Compounds represented by a formula:

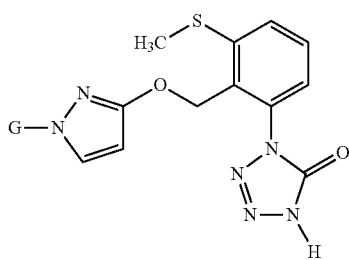

[wherein G represents a substituent corresponding to each of substituents Nos. 1 to 144 indicated in Table 26 to Table 30 as below-mentioned];
Compounds HR-001~HR-144 represent tetrazolinone Compounds represented by a formula:

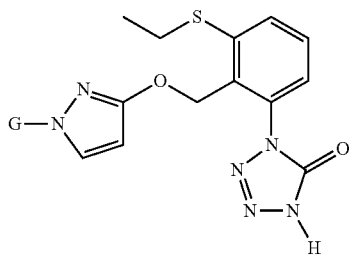

[wherein G represents a substituent corresponding to each of substituents Nos. 1 to 144 indicated in Table 26 to Table 30 as below-mentioned];
Compounds HS-001~HS-144 represent tetrazolinone Compounds represented by a formula:

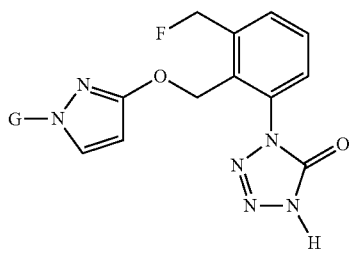

[wherein G represents a substituent corresponding to each of substituents Nos. 1 to 144 indicated in Table 26 to Table 30 as below-mentioned];
Compounds HT-001~HT-144 represent tetrazolinone Compounds represented by a formula:

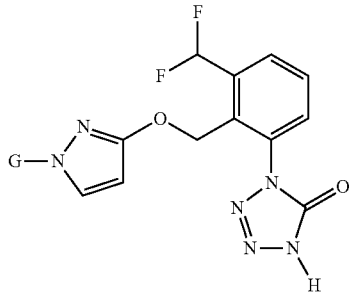

[wherein G represents a substituent corresponding to each of substituents Nos. 1 to 144 indicated in Table 26 to Table 30 as below-mentioned];
Compounds HU-001~HU-144 represent tetrazolinone Compounds represented by a formula:

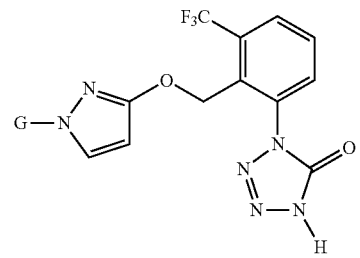

[wherein G represents a substituent corresponding to each of substituents Nos. 1 to 144 indicated in Table 26 to Table 30 as below-mentioned];
Compounds HV-001~HV-144 represent tetrazolinone Compounds represented by a formula:

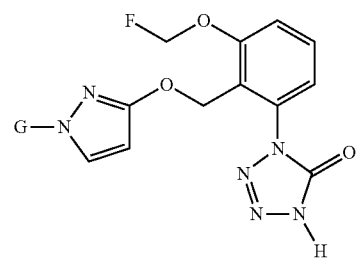

[wherein G represents a substituent corresponding to each of substituents Nos. 1 to 144 indicated in Table 26 to Table 30 as below-mentioned];
Compounds HW-001~HW-144 represent tetrazolinone Compounds represented by a formula:

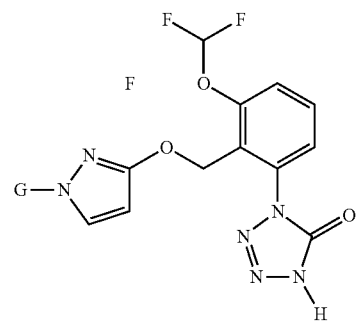

[wherein G represents a substituent corresponding to each of substituents Nos. 1 to 144 indicated in Table 26 to Table 30 as below-mentioned];
Compounds HX-001~HX-144 represent tetrazolinone Compounds represented by a formula:

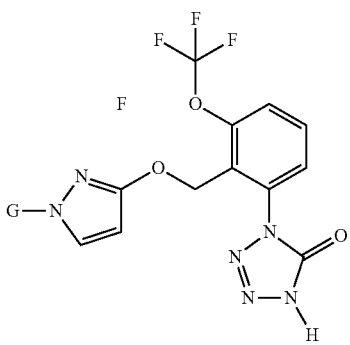

[wherein G represents a substituent corresponding to each of substituents Nos. 1 to 144 indicated in Table 26 to Table 30 as below-mentioned];

Compounds HY-001~HY-144 represent tetrazolinone Compounds represented by a formula:

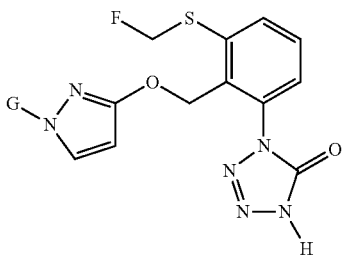

[wherein G represents a substituent corresponding to each of substituents Nos. 1 to 144 indicated in Table 26 to Table 30 as below-mentioned];

Compounds HZ-001~HZ-144 represent tetrazolinone Compounds represented by a formula:

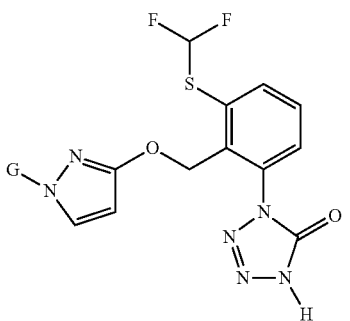

[wherein G represents a substituent corresponding to each of substituents Nos. 1 to 144 indicated in Table 26 to Table 30 as below-mentioned]; and Compounds HAA-001-HAA-144 represent tetrazolinone Compounds represented by a formula:

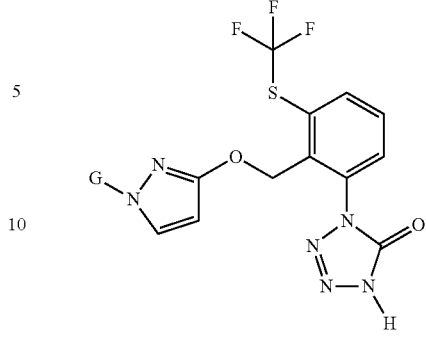

[wherein G represents a substituent corresponding to each of substituents Nos. 1 to 144 indicated in Table 26 to Table 30 as below-mentioned].

TABLE 26

| substituents Nos. | G |
|---|---|
| 1 | phenyl group |
| 2 | 2-fluorophenyl group |
| 3 | 3-fluorophenyl group |
| 4 | 4-fluorophenyl group |
| 5 | 2,4-difluorophenyl group |
| 6 | 2,4,6-trifluorophenyl group |
| 7 | 2,3,4,5,6-pentafluorophenyl group |
| 8 | 2-3-difluorophenyl group |
| 9 | 2-chlorophenyl group |
| 10 | 3-chlorophenyl group |
| 11 | 4-chlorophenyl group |
| 12 | 2-3-dichlorophenyl group |
| 13 | 2,4-dichlorophenyl group |
| 14 | 2,5-dichlorophenyl group |
| 15 | 2,6-dichlorophenyl group |
| 16 | 3,4-dichlorophenyl group |
| 17 | 3,5-dichlorophenyl group |
| 18 | 2,3,4-trichlorophenyl group |
| 19 | 2,3,5-trichlorophenyl group |
| 20 | 2,3,6-trichlorophenyl group |
| 21 | 2,4,5-trichlorophenyl group |
| 22 | 2,4,6-trichlorophenyl group |
| 23 | 3,4,5-trichlorophenyl group |
| 24 | 2,3,4,6-tetrachlorophenyl group |
| 25 | 2,3,5,6-tetrachlorophenyl group |
| 26 | 2,3,4,5,6-pentachlorophenyl group |
| 27 | 2-bromophenyl group |
| 28 | 3-bromophenyl group |
| 29 | 4-bromophenyl group |

TABLE 27

| substituents Nos. | G |
|---|---|
| 30 | 2,4-dibromophenyl group |
| 31 | 2,5-dibromophenyl group |
| 32 | 2,6-dibromophenyl group |
| 33 | 2,4,6-tribromophenyl group |
| 34 | 2,3,4,5,6-pentabromophenyl group |
| 35 | 2-iodophenyl group |
| 36 | 3-iodophenyl group |
| 37 | 4-iodophenyl group |
| 38 | 2,4-diiodophenyl group |
| 39 | 2-chloro-3-fluorophenyl group |
| 40 | 2-chloro-4-fluorophenyl group |
| 41 | 2-chloro-5-fluorophenyl group |
| 42 | 2-chloro-6-fluorophenyl group |
| 43 | 2-chloro-3-bromophenyl group |
| 44 | 2-chloro-4-bromophenyl group |
| 45 | 2-chloro-5-bromophenyl group |

TABLE 27-continued

| substituents Nos. | G |
|---|---|
| 46 | 2-chloro-6-bromophenyl group |
| 47 | 2-bromo-3-chlorophenyl group |
| 48 | 2-bromo-4-chlorophenyl group |
| 49 | 2-bromo-5-chlorophenyl group |
| 50 | 2-bromo-3-fluorophenyl group |
| 51 | 2-bromo-4-fluorophenyl group |
| 52 | 2-bromo-5-fluorophenyl group |
| 53 | 2-bromo-6-fluorophenyl group |
| 54 | 2-fluoro-3-chlorophenyl group |
| 55 | 2-fluoro-4-chlorophenyl group |
| 56 | 2-fluoro-5-chlorophenyl group |
| 57 | 2-fluoro-4-bromophenyl group |
| 58 | 3-chloro-4-fluorophenyl group |

TABLE 28

| substituents Nos. | G |
|---|---|
| 59 | 3-chloro-5-fluorophenyl group |
| 60 | 3-chloro-4-bromophenyl group |
| 61 | 3-chloro-5-bromophenyl group |
| 62 | 3-fluoro-4-chlorophenyl group |
| 63 | 3-fluoro-4-bromophenyl group |
| 64 | 3-bromo-4-chlorophenyl group |
| 65 | 3-bromo-4-fluorophenyl group |
| 66 | 2,6-dichloro-4-bromophenyl group |
| 67 | 2-3-difluoro-4-chlorophenyl group |
| 68 | 2,6-difluoro-4-chlorophenyl group |
| 69 | 2,5-difluoro-4-chlorophenyl group |
| 70 | 3,5-difluoro-4-chlorophenyl group |
| 71 | 2,3,5-trifluoro-4-chlorophenyl group |
| 72 | 2,3,6-trifluoro-4-chlorophenyl group |
| 73 | 2,3,5,6-tetrafluoro-4-chlorophenyl group |
| 74 | 2-fluoro-4-bromophenyl group |
| 75 | 2-3-difluoro-4-bromophenyl group |
| 76 | 2,6-difluoro-4-bromophenyl group |
| 77 | 2,5-difluoro-4-bromophenyl group |
| 78 | 3,5-difluoro-4-bromophenyl group |
| 79 | 2,3,5-trifluoro-4-bromophenyl group |
| 80 | 2,3,6-trifluoro-4-bromophenyl group |
| 81 | 2,3,5,6-tetrafluoro-4-bromophenyl group |
| 82 | 2-fluoro-4-iodophenyl group |
| 83 | 3-fluoro-4-iodophenyl group |
| 84 | 2-3-difluoro-4-iodophenyl group |
| 85 | 2,6-difluoro-4-iodophenyl group |
| 86 | 2,5-difluoro-4-iodophenyl group |
| 87 | 3,5-difluoro-4-iodophenyl group |

TABLE 29

| substituents Nos. | G |
|---|---|
| 88 | 2,3,5-trifluoro-4-iodophenyl group |
| 89 | 2,3,6-trifluoro-4-iodophenyl group |
| 90 | 2,3,5,6-tetrafluoro-4-iodophenyl group |
| 91 | 4-methylphenyl group |
| 92 | 4-ethylphenyl group |
| 93 | 4-n-propylphenyl group |
| 94 | 4-isopropylphenyl group |
| 95 | 4-s-butylphenyl group |
| 96 | 4-t-butylphenyl group |
| 97 | 4-n-butylphenyl group |
| 98 | 4-methoxyphenyl group |
| 99 | 4-ethoxyphenyl group |
| 100 | 4-n-propyloxyphenyl group |
| 101 | 4-isopropyloxyphenyl group |
| 102 | 4-n-hexyloxyphenyl group |
| 103 | 4-t-butoxyphenyl group |
| 104 | 2-chloro-4-nitrophenyl group |
| 105 | 2,6-dichloro-4-nitrophenyl group |

TABLE 29-continued

| substituents Nos. | G |
|---|---|
| 106 | 2,6-dibromo-4-nitrophenyl group |
| 107 | 2,6-diiodo-4-nitrophenyl group |
| 108 | 2-chloro-4-methylphenyl group |
| 109 | 2-fluoro-4-methylphenyl group |
| 110 | 2-bromo-4-methylphenyl group |
| 111 | 3-fluoro-4-methylphenyl group |
| 112 | 3-chloro-4-methylphenyl group |
| 113 | 3-bromo-4-methylphenyl group |
| 114 | 2,6-dibromo-4-methylphenyl group |
| 115 | 2-3-difluoro-4-methylphenyl group |
| 116 | 2,5-difluoro-4-methylphenyl group |

TABLE 30

| substituents Nos. | G |
|---|---|
| 117 | 3,5-difluoro-4-methylphenyl group |
| 118 | 2,3,5-trifluoro-4-methylphenyl group |
| 119 | 2,3,6-trifluoro-4-methylphenyl group |
| 120 | 2,3,5,6-tetrafluoro-4-methylphenyl group |
| 121 | 2-fluoro-4-ethylphenyl group |
| 122 | 3-fluoro-4-ethylphenyl group |
| 123 | 2-3-difluoro-4-ethylphenyl group |
| 124 | 2,6-difluoro-4-ethylphenyl group |
| 125 | 2,5-difluoro-4-ethylphenyl group |
| 126 | 3,5-difluoro-4-ethylphenyl group |
| 127 | 2,3,5-trifluoro-4-ethylphenyl group |
| 128 | 2,3,6-trifluoro-4-ethylphenyl group |
| 129 | 2,3,5,6-tetrafluoro-4-ethylphenyl group |
| 130 | 4-trifluoromethylphenyl group |
| 131 | 4-(2,2,2-trifluoro-1-trifluoromethylethyl)phenyl group |
| 132 | 4-trifluoromethoxyphenyl group |
| 133 | 4-(2,2-difluoroethoxy)phenyl group |
| 134 | 4-(2,2,2-trifluoroethoxy)phenyl group |
| 135 | 4-nitrophenyl group |
| 136 | 4-cyanophenyl group |
| 137 | 4-methylthiophenyl group |
| 138 | 4-trifluoromethylthiophenyl group |
| 139 | 3-methoxyphenyl group |
| 140 | 2-methoxyphenyl group |
| 141 | 3-ethoxyphenyl group |
| 142 | 2-ethoxyphenyl group |
| 143 | 4-fluoro-3-methoxyphenyl group |
| 144 | 4-fluoro-2-methoxyphenyl group |

According to the above-mentioned processes, the following compounds can be prepared:

Compounds TMA-001~TMA-044, TMB-001~TMB-044, TMC-001~TMC-044, TMD-001~TMD-044, TME-001~TME-044, TMF-001~TMF-044, TMG-001~TMG-044, TMH-001~TMH-044, TMI-001~TMI-044, TMJ-001~TMJ-044, TMK-001~TMK-044, TML-001~TML-044, TMM-001~TMM-044, TMN-001~TMN-044, TMO-001~TMO-044, TMP-001~TMP-044, TMQ-001~TMQ-044, TMR-001~TMR-044, TMS-001~TMS-044, TMT-001~TMT-044, TMU-001~TMU-044, TMV-001~TMV-044, TMW-001~TMW-044, TMX-001~TMX-044, TMY-001~TMY-044, TMZ-001~TMZ-044, TMAA-001~TMAA-044, THA-001~THA-044, THB-001~THB-044, THC-001~THC-044, THD-001~THD-044, THE-001~THE-044, THF-001~THF-044, THG-001~THG-044, THH-001~THH-044, THI-001~THI-044, THJ-001~THJ-044, THK-001~THK-044, THL-001~THL-044, THM-001~THM-044, THN-001~THN-044, THO-001~THO-044, THP-001~THP-044, THQ-001~THQ-044, THR-001~THR-044, THS-001~THS-044, THT-001~THT-044, THU-001~THU-044, THV-001~THV-044, THW-001~THW-044, THX-001~THX-044, THY-001~THY-044, THZ-001~THZ-044 and THAA-001~THAA-044.

Compounds TMA-001~TMA-044 represent tetrazolinone Compounds represented by a formula:

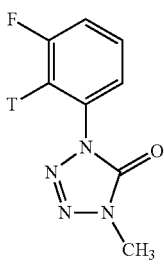

[wherein T represents a substituent corresponding to each of substituents Nos. 1 to 44 indicated in Table 31 to Table 32 as below-mentioned];

Compounds TMB-001~TMB-044 represent tetrazolinone Compounds represented by a formula:

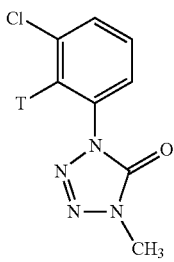

[wherein T represents a substituent corresponding to each of substituents Nos. 1 to 44 indicated in Table 31 to Table 32 as below-mentioned]; Compounds TMC-001~TMC-044 represent tetrazolinone Compounds represented by a formula:

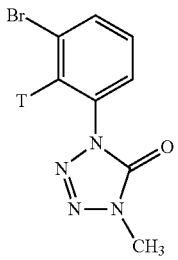

[wherein T represents a substituent corresponding to each of substituents Nos. 1 to 44 indicated in Table 31 to Table 32 as below-mentioned];

Compounds TMD-001~TMD-044 represent tetrazolinone Compounds represented by a formula:

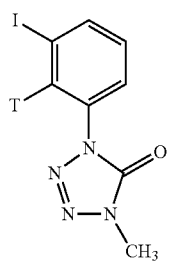

[wherein T represents a substituent corresponding to each of substituents Nos. 1 to 44 indicated in Table 31 to Table 32 as below-mentioned];

Compounds TME-001~TME-044 represent tetrazolinone Compounds represented by a formula:

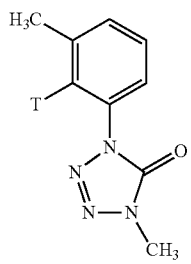

[wherein T represents a substituent corresponding to each of substituents Nos. 1 to 44 indicated in Table 31 to Table 32 as below-mentioned];

Compounds TMF-001~TMF-044 represent tetrazolinone Compounds represented by a formula:

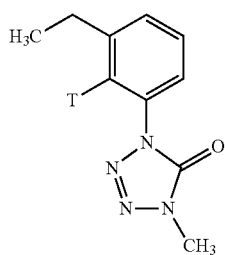

[wherein T represents a substituent corresponding to each of substituents Nos. 1 to 44 indicated in Table 31 to Table 32 as below-mentioned];

Compounds TMG-001~TMG-044 represent tetrazolinone Compounds represented by a formula:

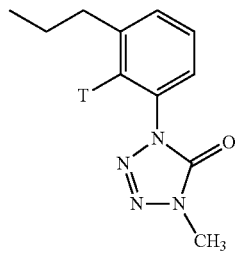

[wherein T represents a substituent corresponding to each of substituents Nos. 1 to 44 indicated in Table 31 to Table 32 as below-mentioned];

Compounds TMH-001~TMH-044 represent tetrazolinone Compounds represented by a formula:

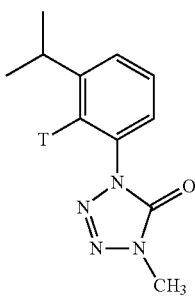

[wherein T represents a substituent corresponding to each of substituents Nos. 1 to 44 indicated in Table 31 to Table 32 as below-mentioned];

Compounds TMI-001~TMI-044 represent tetrazolinone Compounds represented by a formula:

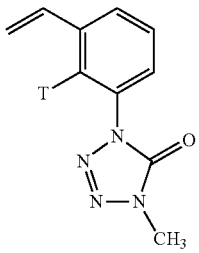

[wherein T represents a substituent corresponding to each of substituents Nos. 1 to 44 indicated in Table 31 to Table 32 as below-mentioned];

Compounds TMJ-001~TMJ-044 represent tetrazolinone Compounds represented by a formula:

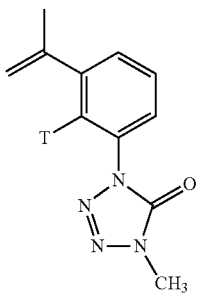

[wherein T represents a substituent corresponding to each of substituents Nos. 1 to 44 indicated in Table 31 to Table 32 as below-mentioned];

Compounds TMK-001~TMK-044 represent tetrazolinone Compounds represented by a formula:

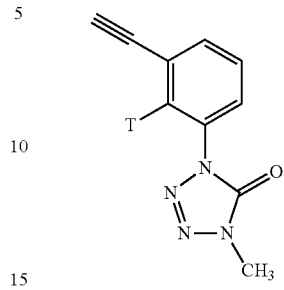

[wherein T represents a substituent corresponding to each of substituents Nos. 1 to 44 indicated in Table 31 to Table 32 as below-mentioned];

Compounds TML-001~TML-044 represent tetrazolinone Compounds represented by a formula:

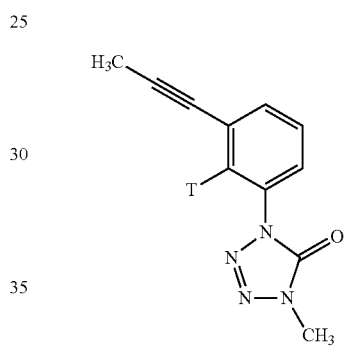

[wherein T represents a substituent corresponding to each of substituents Nos. 1 to 44 indicated in Table 31 to Table 32 as below-mentioned];

Compounds TMM-001~TMM-044 represent tetrazolinone Compounds represented by a formula:

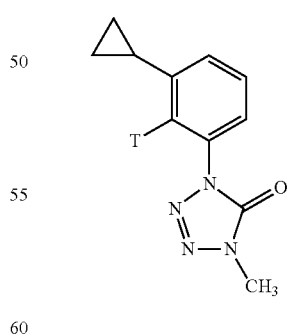

[wherein T represents a substituent corresponding to each of substituents Nos. 1 to 44 indicated in Table 31 to Table 32 as below-mentioned];

Compounds TMN-001~TMN-044 represent tetrazolinone Compounds represented by a formula:

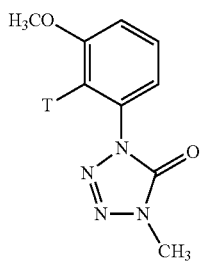

[wherein T represents a substituent corresponding to each of substituents Nos. 1 to 44 indicated in Table 31 to Table 32 as below-mentioned];

Compounds TMO-001~TMO-044 represent tetrazolinone Compounds represented by a formula:

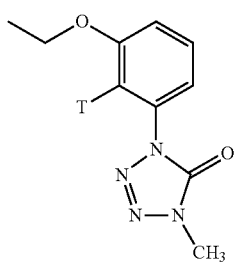

[wherein T represents a substituent corresponding to each of substituents Nos. 1 to 44 indicated in Table 31 to Table 32 as below-mentioned];

Compounds TMP-001~TMP-044 represent tetrazolinone Compounds represented by a formula:

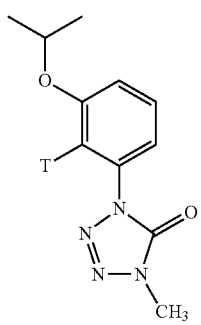

[wherein T represents a substituent corresponding to each of substituents Nos. 1 to 44 indicated in Table 31 to Table 32 as below-mentioned];

Compounds TMQ-001~TMQ-044 represent tetrazolinone Compounds represented by a formula:

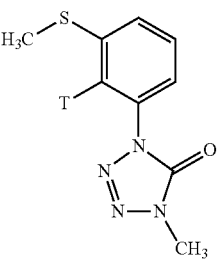

[wherein T represents a substituent corresponding to each of substituents Nos. 1 to 44 indicated in Table 31 to Table 32 as below-mentioned];

Compounds TMR-001~TMR-044 represent tetrazolinone Compounds represented by a formula:

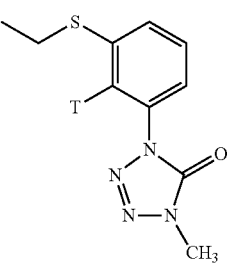

[wherein T represents a substituent corresponding to each of substituents Nos. 1 to 44 indicated in Table 31 to Table 32 as below-mentioned];

Compounds TMS-001~TMS-044 represent tetrazolinone Compounds represented by a formula:

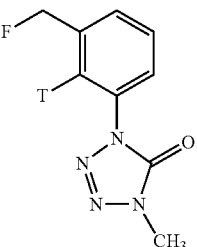

[wherein T represents a substituent corresponding to each of substituents Nos. 1 to 44 indicated in Table 31 to Table 32 as below-mentioned];

Compounds TMT-001~TMT-044 represent tetrazolinone Compounds represented by a formula:

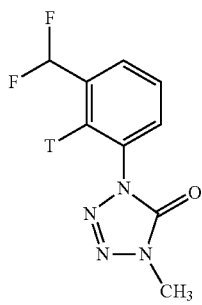

[wherein T represents a substituent corresponding to each of substituents Nos. 1 to 44 indicated in Table 31 to Table 32 as below-mentioned];

Compounds TMU-001~TMU-044 represent tetrazolinone Compounds represented by a formula:

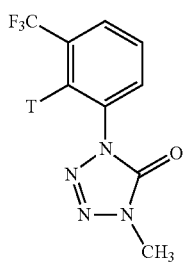

[wherein T represents a substituent corresponding to each of substituents Nos. 1 to 44 indicated in Table 31 to Table 32 as below-mentioned];

Compounds TMV-001~TMV-044 represent tetrazolinone Compounds represented by a formula:

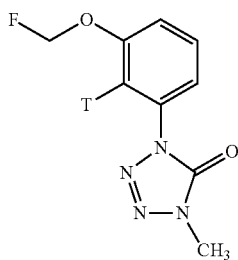

[wherein T represents a substituent corresponding to each of substituents Nos. 1 to 44 indicated in Table 31 to Table 32 as below-mentioned];

Compounds TMW-001~TMW-044 represent tetrazolinone Compounds represented by a formula:

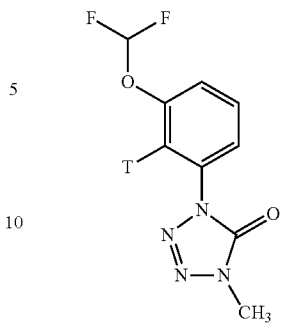

[wherein T represents a substituent corresponding to each of substituents Nos. 1 to 44 indicated in Table 31 to Table 32 as below-mentioned];

Compounds TMX-001~TMX-044 represent tetrazolinone Compounds represented by a formula:

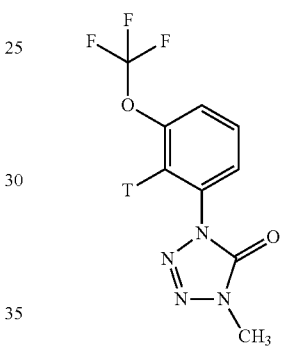

[wherein T represents a substituent corresponding to each of substituents Nos. 1 to 44 indicated in Table 31 to Table 32 as below-mentioned];

Compounds TMY-001~TMY-044 represent tetrazolinone Compounds represented by a formula:

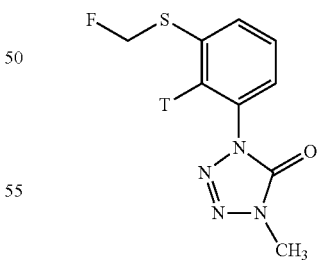

[wherein T represents a substituent corresponding to each of substituents Nos. 1 to 44 indicated in Table 31 to Table 32 as below-mentioned];

Compounds TMZ-001~TMZ-044 represent tetrazolinone Compounds represented by a formula:

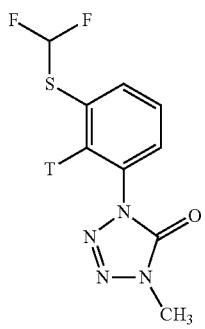

[wherein T represents a substituent corresponding to each of substituents Nos. 1 to 44 indicated in Table 31 to Table 32 as below-mentioned];

Compounds TMAA-001~TMAA-044 represent tetrazolinone Compounds represented by a formula:

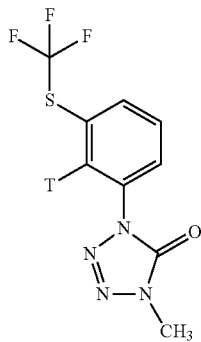

[wherein T represents a substituent corresponding to each of substituents Nos. 1 to 44 indicated in Table 31 to Table 32 as below-mentioned];

Compounds THA-001~THA-044 represent tetrazolinone Compounds represented by a formula:

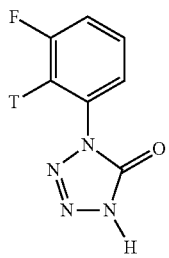

[wherein T represents a substituent corresponding to each of substituents Nos. 1 to 44 indicated in Table 31 to Table 32 as below-mentioned];

Compounds THB-001~THB-044 represent tetrazolinone Compounds represented by a formula:

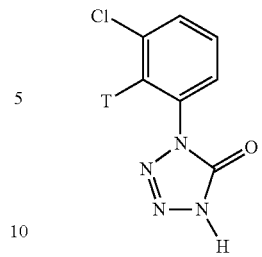

[wherein T represents a substituent corresponding to each of substituents Nos. 1 to 44 indicated in Table 31 to Table 32 as below-mentioned];

Compounds THC-001~THC-044 represent tetrazolinone Compounds represented by a formula:

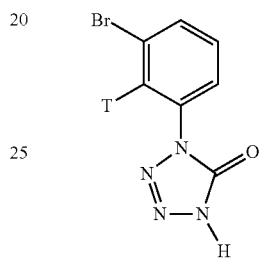

[wherein T represents a substituent corresponding to each of substituents Nos. 1 to 44 indicated in Table 31 to Table 32 as below-mentioned];

Compounds THD-001~THD-044 represent tetrazolinone Compounds represented by a formula:

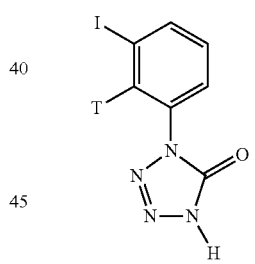

[wherein T represents a substituent corresponding to each of substituents Nos. 1 to 44 indicated in Table 31 to Table 32 as below-mentioned];

Compounds THE-001~THE-044 represent tetrazolinone Compounds represented by a formula:

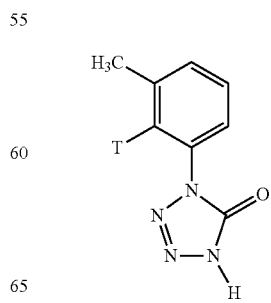

[wherein T represents a substituent corresponding to each of substituents Nos. 1 to 44 indicated in Table 31 to Table 32 as below-mentioned];

Compounds THF-001~THF-044 represent tetrazolinone Compounds represented by a formula:

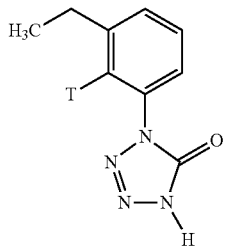

[wherein T represents a substituent corresponding to each of substituents Nos. 1 to 44 indicated in Table 31 to Table 32 as below-mentioned];

Compounds THG-001~THG-044 represent tetrazolinone Compounds represented by a formula:

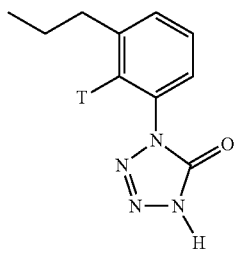

[wherein T represents a substituent corresponding to each of substituents Nos. 1 to 44 indicated in Table 31 to Table 32 as below-mentioned];

Compounds THH-001~THH-044 represent tetrazolinone Compounds represented by a formula:

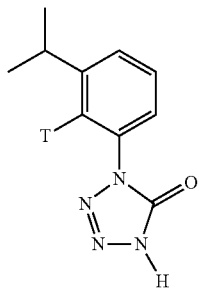

[wherein T represents a substituent corresponding to each of substituents Nos. 1 to 44 indicated in Table 31 to Table 32 as below-mentioned];

Compounds THI-001~THI-044 represent tetrazolinone Compounds represented by a formula:

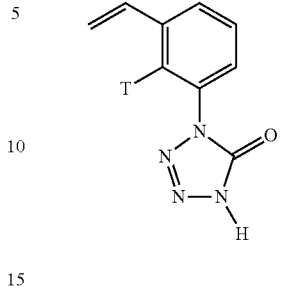

[wherein T represents a substituent corresponding to each of substituents Nos. 1 to 44 indicated in Table 31 to Table 32 as below-mentioned];

Compounds THJ-001~THJ-044 represent tetrazolinone Compounds represented by a formula:

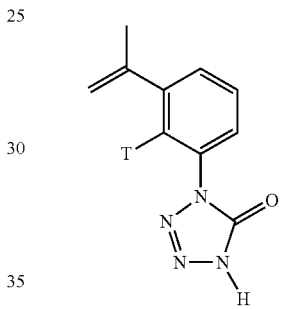

[wherein T represents a substituent corresponding to each of substituents Nos. 1 to 44 indicated in Table 31 to Table 32 as below-mentioned];

Compounds THK-001~THK-044 represent tetrazolinone Compounds represented by a formula:

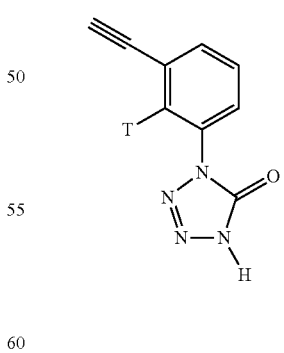

[wherein T represents a substituent corresponding to each of substituents Nos. 1 to 44 indicated in Table 31 to Table 32 as below-mentioned];

Compounds THL-001~THL-044 represent tetrazolinone Compounds represented by a formula:

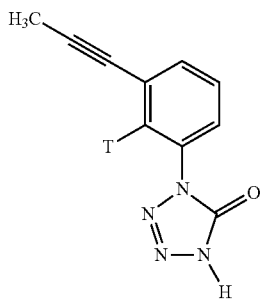

[wherein T represents a substituent corresponding to each of substituents Nos. 1 to 44 indicated in Table 31 to Table 32 as below-mentioned];

Compounds THM-001~THM-044 represent tetrazolinone Compounds represented by a formula:

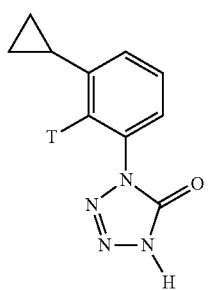

[wherein T represents a substituent corresponding to each of substituents Nos. 1 to 44 indicated in Table 31 to Table 32 as below-mentioned];

Compounds THN-001~THN-044 represent tetrazolinone Compounds represented by a formula:

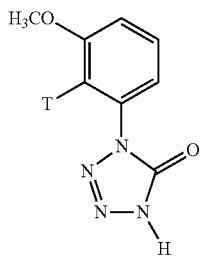

[wherein T represents a substituent corresponding to each of substituents Nos. 1 to 44 indicated in Table 31 to Table 32 as below-mentioned];

Compounds THO-001~THO-044 represent tetrazolinone Compounds represented by a formula:

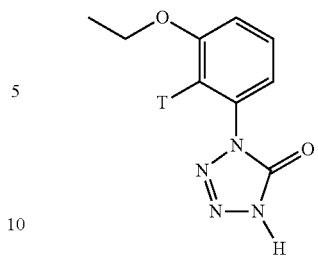

[wherein T represents a substituent corresponding to each of substituents Nos. 1 to 44 indicated in Table 31 to Table 32 as below-mentioned];

Compounds THP-001~THP-044 represent tetrazolinone Compounds represented by a formula:

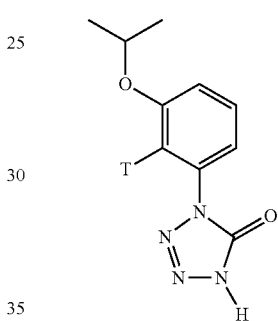

[wherein T represents a substituent corresponding to each of substituents Nos. 1 to 44 indicated in Table 31 to Table 32 as below-mentioned];

Compounds THQ-001~THQ-044 represent tetrazolinone Compounds represented by a formula:

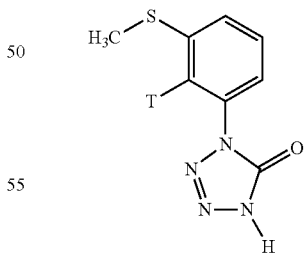

[wherein T represents a substituent corresponding to each of substituents Nos. 1 to 44 indicated in Table 31 to Table 32 as below-mentioned];

Compounds THR-001~THR-044 represent tetrazolinone Compounds represented by a formula:

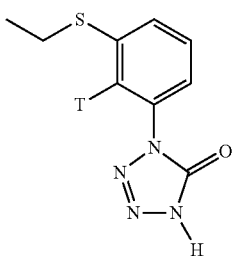

[wherein T represents a substituent corresponding to each of substituents No's. 1 to 44 indicated in Table 31 to Table 32 as below-mentioned];
Compounds THS-001~THS-044 represent tetrazolinone Compounds represented by a formula:

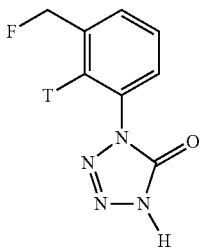

[wherein T represents a substituent corresponding to each of substituents Nos. 1 to 44 indicated in Table 31 to Table 32 as below-mentioned];
Compounds THT-001~THT-044 represent tetrazolinone Compounds represented by a formula:

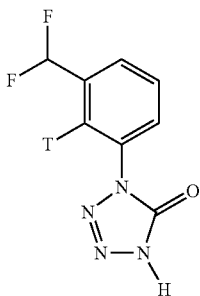

[wherein T represents a substituent corresponding to each of substituents Nos. 1 to 44 indicated in Table 31 to Table 32 as below-mentioned];
Compounds THU-001~THU-044 represent tetrazolinone Compounds represented by a formula:

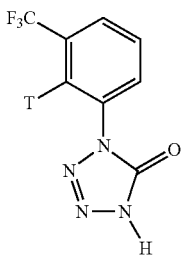

[wherein T represents a substituent corresponding to each of substituents Nos. 1 to 44 indicated in Table 31 to Table 32 as below-mentioned];
Compounds THV-001~THV-044 represent tetrazolinone Compounds represented by a formula:

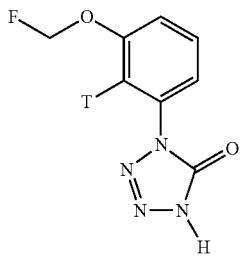

[wherein T represents a substituent corresponding to each of substituents Nos. 1 to 44 indicated in Table 31 to Table 32 as below-mentioned];
Compounds THW-001~THW-044 represent tetrazolinone Compounds represented by a formula:

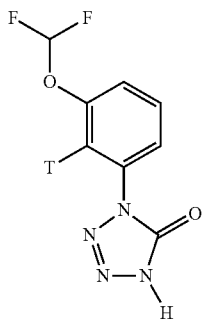

[wherein T represents a substituent corresponding to each of substituents Nos. 1 to 44 indicated in Table 31 to Table 32 as below-mentioned];
Compounds THX-001~THX-044 represent tetrazolinone Compounds represented by a formula:

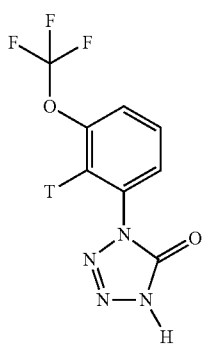

[wherein T represents a substituent corresponding to each of substituents Nos. 1 to 44 indicated in Table 31 to Table 32 as below-mentioned];
Compounds THY-001~THY-044 represent tetrazolinone Compounds represented by a formula:

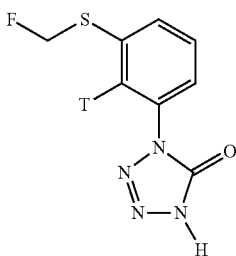

[wherein T represents a substituent corresponding to each of substituents Nos. 1 to 44 indicated in Table 31 to Table 32 as below-mentioned];

Compounds THZ-001~THZ-044 represent tetrazolinone Compounds represented by a formula:

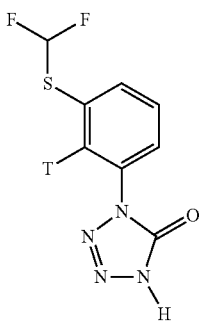

[wherein T represents a substituent corresponding to each of substituents Nos. 1 to 44 indicated in Table 31 to Table 32 as below-mentioned]; and Compounds THAA-001~THAA-044 represent tetrazolinone Compounds represented by a formula:

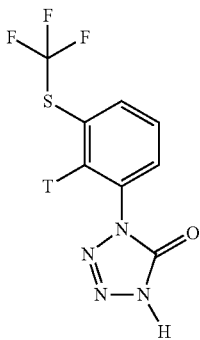

[wherein T represents a substituent corresponding to each of substituents Nos. 1 to 44 indicated in Table 31 to Table 32 as below-mentioned].

TABLE 31

| substituents Nos. | T |
|---|---|
| 1 | methyl group |
| 2 | chloromethyl group |
| 3 | bromomethyl group |
| 4 | iodomethyl group |
| 5 | hydroxymethyl group |
| 6 | methoxymethyl group |

TABLE 31-continued

| substituents Nos. | T |
|---|---|
| 7 | ethoxymethyl group |
| 8 | n-propyloxymethyl group |
| 9 | isopropyloxymethyl group |
| 10 | methylthiomethyl group |
| 11 | ethylthiomethyl group |
| 12 | n-propylthiomethyl group |
| 13 | isopropylthiomethyl group |
| 14 | acetoxymethyl group |
| 15 | propionyloxymethyl group |
| 16 | butanoyloxymethyl group |
| 17 | pentanoyloxymethyl group |
| 18 | hexanoyloxymethyl group |
| 19 | methylsulfonyloxymethyl group |
| 20 | ethylsulfonyloxymethyl group |
| 21 | propylsulfonyloxymethyl group |
| 22 | isopropylsulfonyloxymethyl group |
| 23 | trifluoromethylsulfonyloxymethyl group |
| 24 | phenylsulfonyloxymethyl group |
| 25 | 4-methylbenzenesulfonyloxymethyl group |
| 26 | N,N-dimethylaminomethyl group |
| 27 | N,N-diethylaminomethyl group |
| 28 | N,N-dipropylaminomethyl group |
| 29 | N,N-diisopropylaminomethyl group |

TABLE 32

| substituents Nos. | T |
|---|---|
| 30 | pyrrolidinylmethyl group |
| 31 | piperidinylmethyl group |
| 32 | piperazinylmethyl group |
| 33 | morpholinylmethyl group |
| 34 | thiomorpholinylmethyl group |
| 35 | azepanylmethyl group |
| 36 | methoxycarbonyl group |
| 37 | ethoxycarbonyl group |
| 38 | propyloxycarbonyl group |
| 39 | isopropyloxycarbonyl group |
| 40 | butyloxycarbonyl group |
| 41 | isobutyloxycarbonyl group |
| 42 | sec-butyloxycarbonyl group |
| 43 | tert-butyl oxycarbonyl group |
| 44 | formyloxymethyl group |

According to the above-mentioned processes, the following compounds can be prepared:

Compounds L1A-001~L1A-144, L1B-001~L1B-144, L1C-001~L1C-144, L1D-001~L1D-144, L1E-001~L1E-144, L1F-001-L1F-144, L1G-001~L1G-144, L1H-001~L1H-144, L1I-001-L1I-144, L1J-001~L1J-144, L1K-001~L1K-144, L1L-001~L1L-144, L1M-001~L1M-144, L1N-001~L1N-144, L1O-001~L1O-144, L1P-001-L1P-144, L1Q-001~L1Q-144, L1R-001~L1R-144, L1S-001-L1S-144, L1T-001~L1T-144, L1U-001~L1U-144, L1V-001~L1V-144, L1W-001~L1W-144, L1X-001~L1X-144, L1Y-001~L1Y-144, L1Z-001~L1Z-144, L1AA-001-L1AA-144, L2A-001~L2A-144, L2B-001~L2B-144, L2C-001~L2C-144, L2D-001~L2D-144, L2E-001~L2E-144, L2F-001~L2F-144, L2G-001~L2G-144, L2H-001~L2H-144, L2I-001~L2I-144, L2J-001~L2J-144, L2K-001~L2K-144, L2L-001~L2L-144, L2M-001~L2M-144, L2N-001~L2N-144, L2O-001~L2O-144, L2P-001~L2P-144, L2Q-001~L2Q-144, L2R-001~L2R-144, L2S-001~L2S-144, L2T-001~L2T-144, L2U-001~L2U-144, L2V-001~L2V-144, L2W-001~L2W-144, L2X-001~L2X-144, L2Y-001~L2Y-144, L2Z-001~L2Z-144, L2AA-001-L2AA-144, L3A-001~L3A-144, L3B-001~L3B-144, L3C-001~L3C-144, L3D-001~L3D-144, L3E-001~L3E-144, L3F-

001~L3F-144, L3G-001~L3G-144, L3H-001~L3H-144, L3I-001~L3I-144, L3J-001~L3J-144, L3K-001~L3K-144, L3L-001~L3L-144, L3M-001~L3M-144, L3N-001~L3N-144, L3O-001~L3O-144, L3P-001~L3P-144, L3Q-001~L3Q-144, L3R-001~L3R-144, L3S-001~L3S-144, L3T-001-L3T-144, L3U-001~L3U-144, L3V-001~L3V-144, L3W-001~L3W-144, L3X-001~L3X-144, L3Y-001~L3Y-144, L3Z-001~L3Z-144, L3AA-001~L3AA-144,

L4A-001~L4A-144, L4B-001~L4B-144, L4C-001~L4C-144, L4D-001~L4D-144, L4E-001~L4E-144, L4F-001~L4F-144, L4G-001~L4G-144, L4H-001~L4H-144, L4I-001~L4I-144, L4J-001~L4J-144, L4K-001~L4K-144, L4L-001~L4L-144, L4M-001~L4M-144, L4N-001~L4N-144, L4O-001~L4O-144, L4P-001~L4P-144, L4Q-001~L4Q-144, L4R-001~L4R-144, L4S-001-L4S-144, L4T-001-L4T-144, L4U-001~L4U-144, L4V-001~L4V-144, L4W-001~L4W-144, L4X-001~L4X-144, L4Y-001~L4Y-144, L4Z-001~L4Z-144, L4AA-001-L4AA-144,

L5A-001~L5A-144, L5B-001~L5B-144, L5C-001~L5C-144, L5D-001~L5D-144, L5E-001~L5E-144, L5F-001~L5F-144, L5G-001~L5G-144, L5H-001~L5H-144, L5I-001~L5I-144, L5J-001~L5J-144, L5K-001~L5K-144, L5L-001~L5L-144, L5M-001~L5M-144, L5N-001~L5N-144, L5O-001~L5O-144, L5P-001~L5P-144, L5Q-001~L5Q-144, L5R-001~L5R-144, L5S-001-L5S-144, L5T-001-L5T-144, L5U-001~L5U-144, L5V-001~L5V-144, L5W-001~L5W-144, L5X-001~L5X-144, L5Y-001~L5Y-144, L5Z-001~L5Z-144, L5AA-001~L5AA-144,

L6A-001~L6A-144, L6B-001~L6B-144, L6C-001~L6C-144, L6D-001~L6D-144, L6E-001~L6E-144, L6F-001~L6F-144, L6G-001~L6G-144, L6H-001~L6H-144, L6I-001~L6I-144, L6J-001~L6J-144, L6K-001~L6K-144, L6L-001~L6L-144, L6M-001~L6M-144, L6N-001~L6N-144, L6O-001~L6O-144, L6P-001~L6P-144, L6Q-001~L6Q-144, L6R-001~L6R-144, L6S-001-L6S-144, L6T-001-L6T-144, L6U-001~L6U-144, L6V-001~L6V-144, L6W-001~L6W-144, L6X-001~L6X-144, L6Y-001~L6Y-144, L6Z-001~L6Z-144, L6AA-001~L6AA-144,

L7A-001~L7A-144, L7B-001~L7B-144, L7C-001~L7C-144, L7D-001~L7D-144, L7E-001~L7E-144, L7F-001~L7F-144, L7G-001~L7G-144, L7H-001~L7H-144, L7I-001~L7I-144, L7J-001~L7J-144, L7K-001~L7K-144, L7L-001~L7L-144, L7M-001~L7M-144, L7N-001~L7N-144, L7O-001~L7O-144, L7P-001~L7P-144, L7Q-001~L7Q-144, L7R-001~L7R-144, L7S-001-L7S-144, L7T-001-L7T-144, L7U-001~L7U-144, L7V-001~L7V-144, L7W-001~L7W-144, L7X-001~L7X-144, L7Y-001~L7Y-144, L7Z-001~L7Z-144, L7AA-001~L7AA-144,

L8A-001~L8A-144, L8B-001~L8B-144, L8C-001~L8C-144, L8D-001~L8D-144, L8E-001~L8E-144, L8F-001~L8F-144, L8G-001~L8G-144, L8H-001~L8H-144, L8I-001-L8I-144, L8J-001~L8J-144, L8K-001~L8K-144, L8L-001~L8L-144, L8M-001~L8M-144, L8N-001~L8N-144, L8O-001~L8O-144, L8P-001~L8P-144, L8Q-001~L8Q-144, L8R-001~L8R-144, L8S-001-L8S-144, L8T-001-L8T-144, L8U-001~L8U-144, L8V-001~L8V-144, L8W-001~L8W-144, L8X-001~L8X-144, L8Y-001~L8Y-144, L8Z-001~L8Z-144, L8AA-001~L8AA-144,

L9A-001~L9A-144, L9B-001~L9B-144, L9C-001~L9C-144, L9D-001~L9D-144, L9E-001~L9E-144, L9F-001~L9F-144, L9G-001~L9G-144, L9H-001~L9H-144, L9I-001~L9I-144, L9J-001~L9J-144, L9K-001~L9K-144, L9L-001~L9L-144, L9M-001~L9M-144, L9N-001~L9N-144, L9O-001~L9O-144, L9P-001~L9P-144, L9Q-001~L9Q-144, L9R-001~L9R-144, L9S-001-L9S-144, L9T-001-L9T-144, L9U-001~L9U-144, L9V-001~L9V-144, L9W-001~L9W-144, L9X-001~L9X-144, L9Y-001~L9Y-144, L9Z-001~L9Z-144, L9AA-001~L9AA-144,

L10A-001~L10A-144, L10B-001~L10B-144, L10C-001~L10C-144, L10D-001~L10D-144, L10E-001~L10E-144, L10E-001~L10E-144, L10G-001~L10G-144, L10H-001~L10H-144, L10I-001~L10I-144, L10J-001~L10J-144, L10K-001~L10K-144, L10L-001~L10L-144, L10M-001~L10M-144, L10N-001~L10N-144, L10O-001~L10O-144, L10P-001~L10P-144, L10Q-001~L10Q-144, L10R-001~L10R-144, L10S-001~L10S-144, L10T-001~L10T-144, L10U-001~L10U-144, L10V-001~L10V-144, L10W-001~L10W-144, L10X-001~L10X-144, L10Y-001~L10Y-144, L10Z-001~L10Z-144, L10AA-001~L10AA-144,

L11A-001~L11A-144, L11B-001~L11B-144, L11C-001~L11C-144, L11D-001~L11D-144, L11E-001~L11E-144, L11F-001~L11F-144, L11G-001~L11G-144, L11H-001~L11H-144, L11I-001~L11I-144, L11J-001~L11J-144, L11K-001~L11K-144, L11L-001~L11L-144, L11M-001~L11M-144, L11N-001~L11N-144, L11O-001~L11O-144, L11P-001~L11P-144, L11Q-001~L11Q-144, L11R-001~L11R-144, L11S-001~L11S-144, L11T-001~L11T-144, L11U-001~L11U-144, L11V-001~L11V-144, L11W-001~L11W-144, L11X-001~L11X-144, L11Y-001~L11Y-144, L11Z-001~L11Z-144, L11AA-001~L11AA-144,

L12A-001~L12A-144, L12B-001~L12B-144, L12C-001~L12C-144, L12D-001~L12D-144, L12E-001~L12E-144, L12F-001~L12F-144, L12G-001~L12G-144, L12H-001~L12H-144, L12I-001~L12I-144, L12J-001~L12J-144, L12K-001~L12K-144, L12L-001~L12L-144, L12M-001~L12M-144, L12N-001~L12N-144, L12O-001~L12O-144, L12P-001~L12P-144, L12Q-001~L12Q-144, L12R-001~L12R-144, L12S-001~L12S-144, L12T-001~L12T-144, L12U-001~L12U-144, L12V-001~L12V-144, L12W-001~L12W-144, L12X-001~L12X-144, L12Y-001~L12Y-144, L12Z-001~L12Z-144, L12AA-001~L12AA-144,

L13A-001~L13A-144, L13B-001~L13B-144, L13C-001~L13C-144, L13D-001~L13D-144, L13E-001~L13E-144, L13F-001~L13F-144, L13G-001~L13G-144, L13H-001~L13H-144, L13I-001~L13I-144, L13J-001~L13J-144, L13K-001~L13K-144, L13L-001~L13L-144, L13M-001~L13M-144, L13N-001~L13N-144, L13O-001~L13O-144, L13P-001~L13P-144, L13Q-001~L13Q-144, L13R-001~L13R-144, L13S-001~L13S-144, L13T-001~L13T-144, L13U-001~L13U-144, L13V-001~L13V-144, L13W-001~L13W-144, L13X-001~L13X-144, L13Y-001~L13Y-144, L13Z-001~L13Z-144, L13AA-001~L13AA-144,

L14A-001~L14A-144, L14B-001~L14B-144, L14C-001~L14C-144, L14D-001~L14D-144, L14E-001~L14E-144, L14F-001~L14F-144, L14G-001~L14G-144, L14H-001~L14H-144, L14I-001~L14I-144, L14J-001~L14J-144, L14K-001~L14K-144, L14L-001~L14L-144, L14M-001~L14M-144, L14N-001~L14N-144, L14O-001~L14O-144, L14P-001~L14P-144, L14Q-001~L14Q-144, L14R-001~L14R-144, L14S-001~L14S-144, L14T-001~L14T-144, L14U-001~L14U-144, L14V-001~L14V-144, L14W-001~L14W-144, L14X-001~L14X-144, L14Y-001~L14Y-144, L14Z-001~L14Z-144, L14AA-001~L14AA-144,

L15A-001~L15A-144, L15B-001~L15B-144, L15C-001~L15C-144, L15D-001~L15D-144, L15E-001~L15E-144, L15F-001~L15F-144, L15G-001~L15G-144, L15H-001~L15H-144, L15I-001~L15I-144, L15J-001~L15J-144, L15K-001~L15K-144, L15L-001~L15L-144, L15M-001~L15M-144, L15N-001~L15N-144, L15O-001~L15O-144, L15P-001~L15P-144, L15Q-001~L15Q-144, L15R-001~L15R-144, L15S-001~L15S-144, L15T-001~L15T-144, L15U-001~L15U-144, L15V-001~L15V-144, L15W-

001~L15W-144, L15X-001~L15X-144, L15Y-001~L15Y-144, L15Z-001~L15Z-144, L15AA-001~L15AA-144,

L16A-001~L16A-144, L16B-001~L16B-144, L16C-001~L16C-144, L16D-001~L16D-144, L16E-001~L16E-144, L16F-001~L16F-144, L16G-001~L16G-144, L16H-001~L16H-144, L16I-001~L16I-144, L16J-001~L16J-144, L16K-001~L16K-144, L16L-001~L16L-144, L16M-001~L16M-144, L16N-001~L16N-144, L16O-001~L16O-144, L16P-001~L16P-144, L16Q-001~L16Q-144, L16R-001~L16R-144, L16S-001~L16S-144, L16T-001~L16T-144, L16U-001~L16U-144, L16V-001~L16V-144, L16W-001~L16W-144, L16X-001~L16X-144, L16Y-001~L16Y-144, L16Z-001~L16Z-144, L16AA-001~L16AA-144,

L17A-001~L17A-144, L17B-001~L17B-144, L17C-001~L17C-144, L17D-001~L17D-144, L17E-001~L17E-144, L17F-001~L17F-144, L17G-001~L17G-144, L17H-001~L17H-144, L17I-001~L17I-144, L17J-001~L17J-144, L17K-001~L17K-144, L17L-001~L17L-144, L17M-001~L17M-144, L17N-001~L17N-144, L17O-001~L17O-144, L17P-001~L17P-144, L17Q-001~L17Q-144, L17R-001~L17R-144, L17S-001~L17S-144, L17T-001~L17T-144, L17U-001~L17U-144, L17V-001~L17V-144, L17W-001~L17W-144, L17X-001~L17X-144, L17Y-001~L17Y-144, L17Z-001~L17Z-144, L17AA-001~L17AA-144,

L18A-001~L18A-144, L18B-001~L18B-144, L18C-001~L18C-144, L18D-001~L18D-144, L18E-001~L18E-144, L18F-001~L18F-144, L18G-001~L18G-144, L18H-001~L18H-144, L18I-001~L18I-144, L18J-001~L18J-144, L18K-001~L18K-144, L18L-001~L18L-144, L18M-001~L18M-144, L18N-001~L18N-144, L18O-001~L18O-144, L18P-001~L18P-144, L18Q-001~L18Q-144, L18R-001~L18R-144, L18S-001~L18S-144, L18T-001~L18T-144, L18U-001~L18U-144, L18V-001~L18V-144, L18W-001~L18W-144, L18X-001~L18X-144, L18Y-001~L18Y-144, L18Z-001~L18Z-144, L18AA-001~L18AA-144,

L19A-001~L19A-144, L19B-001~L19B-144, L19C-001~L19C-144, L19D-001~L19D-144, L19E-001~L19E-144, L19F-001~L19F-144, L19G-001~L19G-144, L19H-001~L19H-144, L19I-001~L19I-144, L19J-001~L19J-144, L19K-001~L19K-144, L19L-001~L19L-144, L19M-001~L19M-144, L19N-001~L19N-144, L19O-001~L19O-144, L19P-001~L19P-144, L19Q-001~L19Q-144, L19R-001~L19R-144, L19S-001~L19S-144, L19T-001~L19T-144, L19U-001~L19U-144, L19V-001~L19V-144, L19W-001~L19W-144, L19X-001~L19X-144, L19Y-001~L19Y-144, L19Z-001~L19Z-144 and L19AA-001~L19AA-144.

Compounds L1A-001~L1A-144 represent tetrazolinone Compounds represented by a formula:

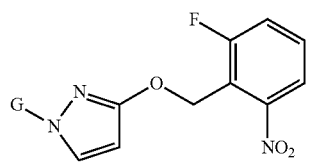

[wherein G represents a substituent corresponding to each of substituents Nos. 1 to 144 indicated in Table 26 to Table 30 as below-mentioned];

Compounds L1B-001~L1B-144 represent tetrazolinone Compounds represented by a formula:

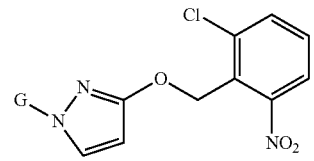

[wherein G represents a substituent corresponding to each of substituents Nos. 1 to 144 indicated in Table 26 to Table 30 as below-mentioned];

Compounds L1C-001~L1C-144 represent tetrazolinone Compounds represented by a formula:

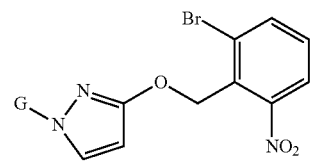

[wherein G represents a substituent corresponding to each of substituents Nos. 1 to 144 indicated in Table 26 to Table 30 as below-mentioned];

Compounds L1D-001~L1D-144 represent tetrazolinone Compounds represented by a formula:

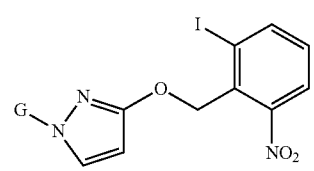

[wherein G represents a substituent corresponding to each of substituents Nos. 1 to 144 indicated in Table 26 to Table 30 as below-mentioned];

Compounds L1E-001~L1E-144 represent tetrazolinone Compounds represented by a formula:

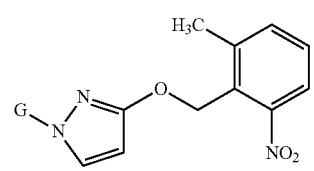

[wherein G represents a substituent corresponding to each of substituents Nos. 1 to 144 indicated in Table 26 to Table 30 as below-mentioned];

Compounds L1F-001~L1F-144 represent tetrazolinone Compounds represented by a formula:

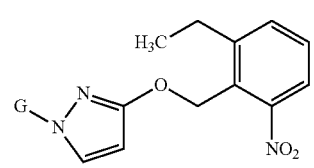

[wherein G represents a substituent corresponding to each of substituents Nos. 1 to 144 indicated in Table 26 to Table 30 as below-mentioned];

Compounds L1G-001~L1G-144 represent tetrazolinone Compounds represented by a formula:

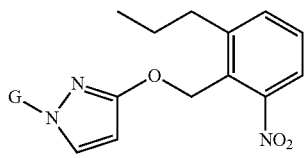

[wherein G represents a substituent corresponding to each of substituents Nos. 1 to 144 indicated in Table 26 to Table 30 as below-mentioned];

Compounds L1H-001~L1H-144 represent tetrazolinone Compounds represented by a formula:

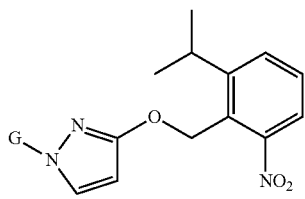

[wherein G represents a substituent corresponding to each of substituents Nos. 1 to 144 indicated in Table 26 to Table 30 as below-mentioned];

Compounds L1I-001~L1I-144 represent tetrazolinone Compounds represented by a formula:

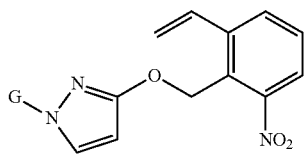

[wherein G represents a substituent corresponding to each of substituents Nos. 1 to 144 indicated in Table 26 to Table 30 as below-mentioned];

Compounds L1J-001~L1J-144 represent tetrazolinone Compounds represented by a formula:

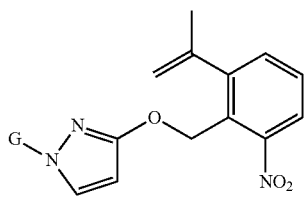

[wherein G represents a substituent corresponding to each of substituents Nos. 1 to 144 indicated in Table 26 to Table 30 as below-mentioned];

Compounds L1K-001~L1K-144 represent tetrazolinone Compounds represented by a formula:

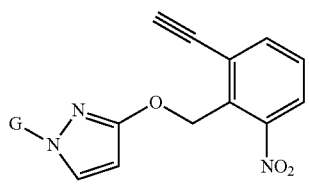

[wherein G represents a substituent corresponding to each of substituents Nos. 1 to 144 indicated in Table 26 to Table 30 as below-mentioned];

Compounds L1L-001~L1L-144 represent tetrazolinone Compounds represented by a formula:

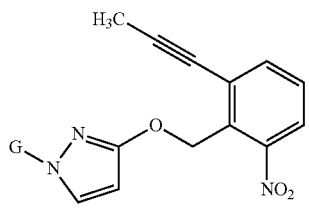

[wherein G represents a substituent corresponding to each of substituents Nos. 1 to 144 indicated in Table 26 to Table 30 as below-mentioned];

Compounds L1M-001~L1M-144 represent tetrazolinone Compounds represented by a formula:

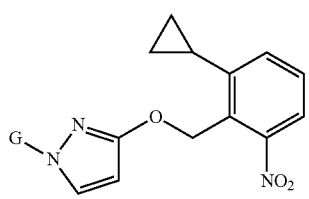

[wherein G represents a substituent corresponding to each of substituents Nos. 1 to 144 indicated in Table 26 to Table 30 as below-mentioned];

Compounds L1N-001~L1N-144 represent tetrazolinone Compounds represented by a formula:

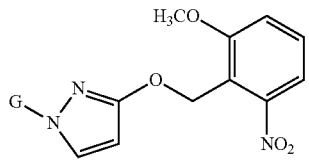

[wherein G represents a substituent corresponding to each of substituents Nos. 1 to 144 indicated in Table 26 to Table 30 as below-mentioned];

Compounds L1O-001~L1O-144 represent tetrazolinone Compounds represented by a formula:

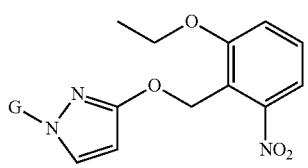

[wherein G represents a substituent corresponding to each of substituents Nos. 1 to 144 indicated in Table 26 to Table 30 as below-mentioned];
Compounds L1P-001~L1P-144 represent tetrazolinone Compounds represented by a formula:

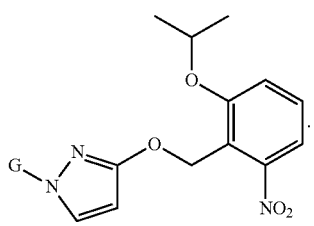

[wherein G represents a substituent corresponding to each of substituents Nos. 1 to 144 indicated in Table 26 to Table 30 as below-mentioned];
Compounds L1Q-001~L1Q-144 represent tetrazolinone Compounds represented by a formula:

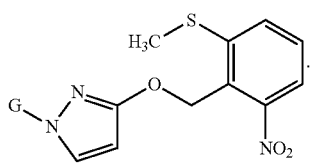

[wherein G represents a substituent corresponding to each of substituents Nos. 1 to 144 indicated in Table 26 to Table 30 as below-mentioned];
Compounds L1R-001~L1R-144 represent tetrazolinone Compounds represented by a formula:

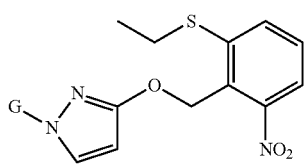

[wherein G represents a substituent corresponding to each of substituents Nos. 1 to 144 indicated in Table 26 to Table 30 as below-mentioned];
Compounds L1S-001~L1S-144 represent tetrazolinone Compounds represented by a formula:

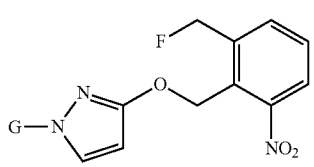

[wherein G represents a substituent corresponding to each of substituents Nos. 1 to 144 indicated in Table 26 to Table 30 as below-mentioned];
Compounds L1T-001~L1T-144 represent tetrazolinone Compounds represented by a formula:

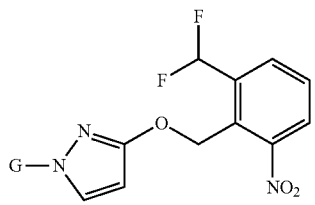

[wherein G represents a substituent corresponding to each of substituents Nos. 1 to 144 indicated in Table 26 to Table 30 as below-mentioned];
Compounds L1U-001~L1U-144 represent tetrazolinone Compounds represented by a formula:

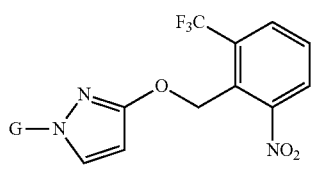

[wherein G represents a substituent corresponding to each of substituents Nos. 1 to 144 indicated in Table 26 to Table 30 as below-mentioned];
Compounds L1V-001~L1V-144 represent tetrazolinone Compounds represented by a formula:

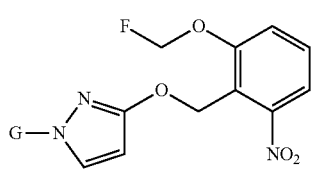

[wherein G represents a substituent corresponding to each of substituents Nos. 1 to 144 indicated in Table 26 to Table 30 as below-mentioned];
Compounds L1W-001~L1W-144 represent tetrazolinone Compounds represented by a formula:

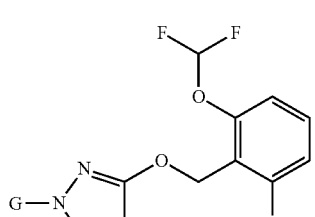

[wherein G represents a substituent corresponding to each of substituents Nos. 1 to 144 indicated in Table 26 to Table 30 as below-mentioned];
Compounds L1X-001~L1X-144 represent tetrazolinone Compounds represented by a formula:

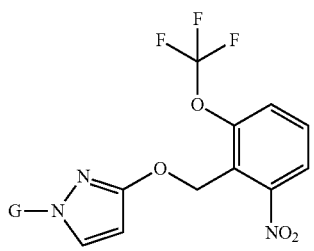

[wherein G represents a substituent corresponding to each of substituents Nos. 1 to 144 indicated in Table 26 to Table 30 as below-mentioned];

Compounds L1Y-001~L1Y-144 represent tetrazolinone Compounds represented by a formula:

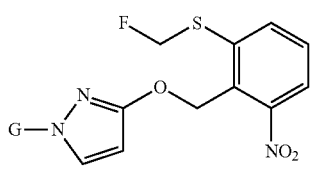

[wherein G represents a substituent corresponding to each of substituents Nos. 1 to 144 indicated in Table 26 to Table 30 as below-mentioned];

Compounds L1Z-001~L1Z-144 represent tetrazolinone Compounds represented by a formula:

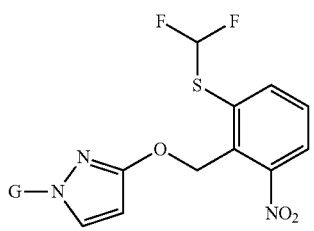

[wherein G represents a substituent corresponding to each of substituents Nos. 1 to 144 indicated in Table 26 to Table 30 as below-mentioned];

Compounds L1AA-001~L1AA-144 represent tetrazolinone Compounds represented by a formula:

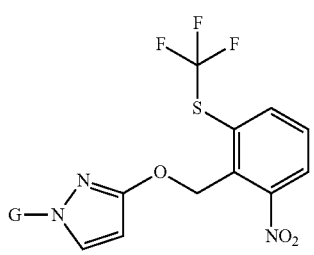

[wherein G represents a substituent corresponding to each of substituents Nos. 1 to 144 indicated in Table 26 to Table 30 as below-mentioned];

Compounds L2A-001~L2A-144 represent tetrazolinone Compounds represented by a formula:

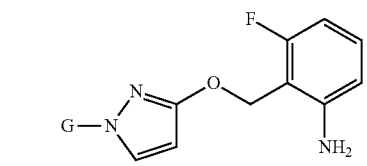

[wherein G represents a substituent corresponding to each of substituents Nos. 1 to 144 indicated in Table 26 to Table 30 as below-mentioned];

Compounds L2B-001~L2B-144 represent tetrazolinone Compounds represented by a formula:

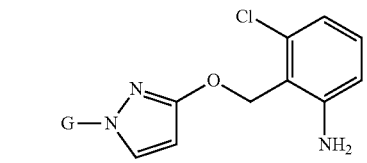

[wherein G represents a substituent corresponding to each of substituents Nos. 1 to 144 indicated in Table 26 to Table 30 as below-mentioned];

Compounds L2C-001~L2C-144 represent tetrazolinone Compounds represented by a formula:

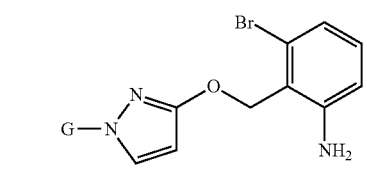

[wherein G represents a substituent corresponding to each of substituents Nos. 1 to 144 indicated in Table 26 to Table 30 as below-mentioned];

Compounds L2D-001~L2D-144 represent tetrazolinone Compounds represented by a formula:

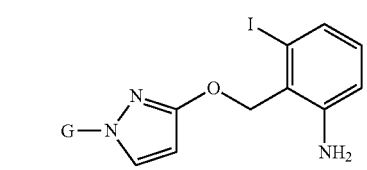

[wherein G represents a substituent corresponding to each of substituents Nos. 1 to 144 indicated in Table 26 to Table 30 as below-mentioned];

Compounds L2E-001~L2E-144 represent tetrazolinone Compounds represented by a formula:

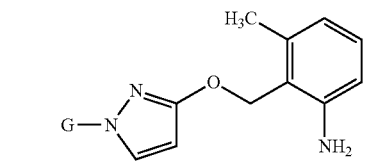

[wherein G represents a substituent corresponding to each of substituents Nos. 1 to 144 indicated in Table 26 to Table 30 as below-mentioned];

Compounds L2F-001~L2F-144 represent tetrazolinone Compounds represented by a formula:

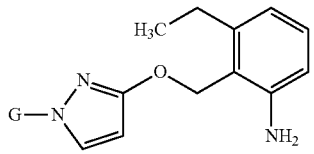

[wherein G represents a substituent corresponding to each of substituents Nos. 1 to 144 indicated in Table 26 to Table 30 as below-mentioned];

Compounds L2G-001~L2G-144 represent tetrazolinone Compounds represented by a formula:

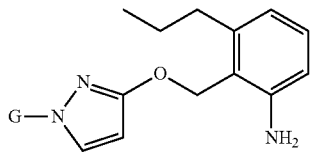

[wherein G represents a substituent corresponding to each of substituents Nos. 1 to 144 indicated in Table 26 to Table 30 as below-mentioned];

Compounds L2H-001~L2H-144 represent tetrazolinone Compounds represented by a formula:

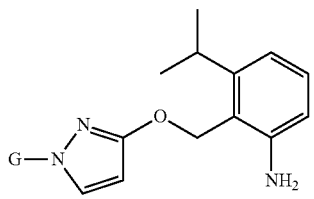

[wherein G represents a substituent corresponding to each of substituents Nos. 1 to 144 indicated in Table 26 to Table 30 as below-mentioned];

Compounds L2I-001~L2I-144 represent tetrazolinone Compounds represented by a formula:

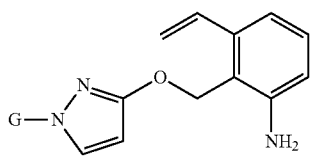

[wherein G represents a substituent corresponding to each of substituents Nos. 1 to 144 indicated in Table 26 to Table 30 as below-mentioned];

Compounds L2J-001~L2J-144 represent tetrazolinone Compounds represented by a formula:

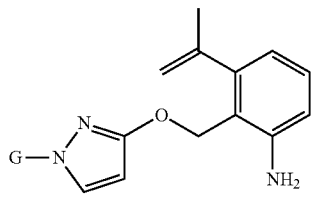

[wherein G represents a substituent corresponding to each of substituents Nos. 1 to 144 indicated in Table 26 to Table 30 as below-mentioned];

Compounds L2K-001~L2K-144 represent tetrazolinone Compounds represented by a formula:

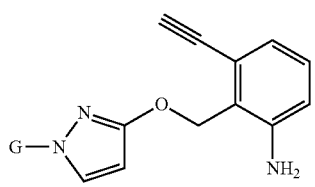

[wherein G represents a substituent corresponding to each of substituents Nos. 1 to 144 indicated in Table 26 to Table 30 as below-mentioned];

Compounds L2L-001~L2L-144 represent tetrazolinone Compounds represented by a formula:

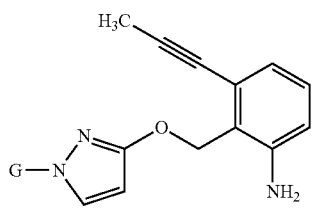

[wherein G represents a substituent corresponding to each of substituents Nos. 1 to 144 indicated in Table 26 to Table 30 as below-mentioned];

Compounds L2M-001~L2M-144 represent tetrazolinone Compounds represented by a formula:

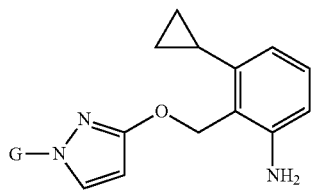

[wherein G represents a substituent corresponding to each of substituents Nos. 1 to 144 indicated in Table 26 to Table 30 as below-mentioned];

Compounds L2N-001~L2N-144 represent tetrazolinone Compounds represented by a formula:

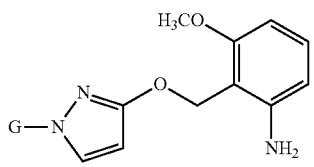

[wherein G represents a substituent corresponding to each of substituents Nos. 1 to 144 indicated in Table 26 to Table 30 as below-mentioned];

Compounds L2O-001~L2O-144 represent tetrazolinone Compounds represented by a formula:

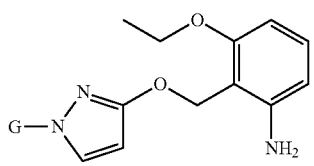

[wherein G represents a substituent corresponding to each of substituents Nos. 1 to 144 indicated in Table 26 to Table 30 as below-mentioned];

Compounds L2P-001~L2P-144 represent tetrazolinone Compounds represented by a formula:

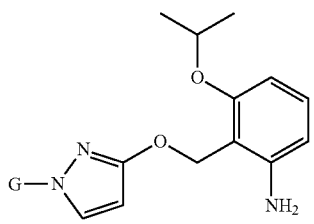

[wherein G represents a substituent corresponding to each of substituents Nos. 1 to 144 indicated in Table 26 to Table 30 as below-mentioned];

Compounds L2Q-001~L2Q-144 represent tetrazolinone Compounds represented by a formula:

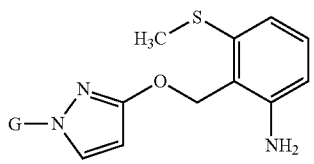

[wherein G represents a substituent corresponding to each of substituents Nos. 1 to 144 indicated in Table 26 to Table 30 as below-mentioned];

Compounds L2R-001~L2R-144 represent tetrazolinone Compounds represented by a formula:

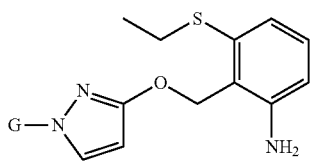

[wherein G represents a substituent corresponding to each of substituents Nos. 1 to 144 indicated in Table 26 to Table 30 as below-mentioned];

Compounds L2S-001~L2S-144 represent tetrazolinone Compounds represented by a formula:

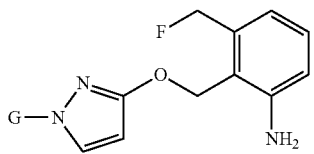

[wherein G represents a substituent corresponding to each of substituents Nos. 1 to 144 indicated in Table 26 to Table 30 as below-mentioned];

Compounds L2T-001~L2T-144 represent tetrazolinone Compounds represented by a formula:

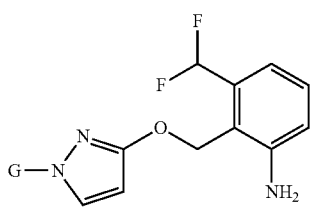

[wherein G represents a substituent corresponding to each of substituents Nos. 1 to 144 indicated in Table 26 to Table 30 as below-mentioned];

Compounds L2U-001~L2U-144 represent tetrazolinone Compounds represented by a formula:

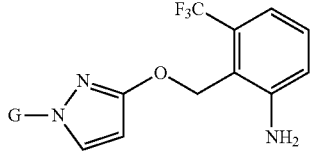

[wherein G represents a substituent corresponding to each of substituents Nos. 1 to 144 indicated in Table 26 to Table 30 as below-mentioned];

Compounds L2V-001~L2V-144 represent tetrazolinone Compounds represented by a formula:

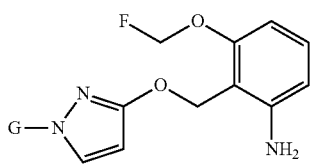

[wherein G represents a substituent corresponding to each of substituents Nos. 1 to 144 indicated in Table 26 to Table 30 as below-mentioned];

Compounds L2W-001~L2W-144 represent tetrazolinone Compounds represented by a formula:

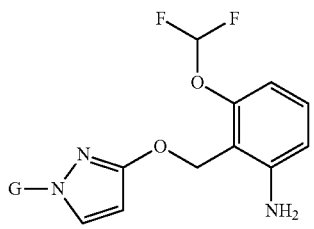

[wherein G represents a substituent corresponding to each of substituents Nos. 1 to 144 indicated in Table 26 to Table 30 as below-mentioned];

Compounds L2X-001~L2X-144 represent tetrazolinone Compounds represented by a formula:

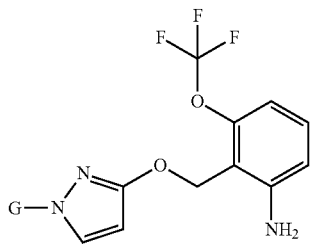

[wherein G represents a substituent corresponding to each of substituents Nos. 1 to 144 indicated in Table 26 to Table 30 as below-mentioned];

Compounds L2Y-001~L2Y-144 represent tetrazolinone Compounds represented by a formula:

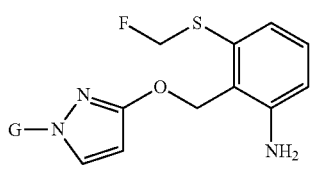

[wherein G represents a substituent corresponding to each of substituents Nos. 1 to 144 indicated in Table 26 to Table 30 as below-mentioned];

Compounds L2Z-001~L2Z-144 represent tetrazolinone Compounds represented by a formula:

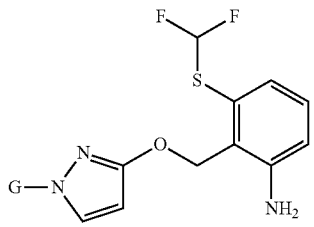

[wherein G represents a substituent corresponding to each of substituents Nos. 1 to 144 indicated in Table 26 to Table 30 as below-mentioned];

Compounds L2AA-001~L2AA-144 represent tetrazolinone Compounds represented by a formula:

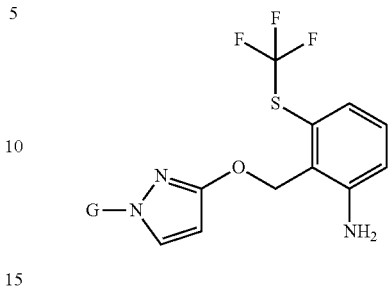

[wherein G represents a substituent corresponding to each of substituents Nos. 1 to 144 indicated in Table 26 to Table 30 as below-mentioned];

Compounds L3A-001~L3A-144 represent tetrazolinone Compounds represented by a formula:

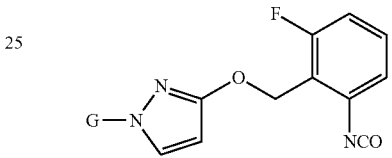

[wherein G represents a substituent corresponding to each of substituents Nos. 1 to 144 indicated in Table 26 to Table 30 as below-mentioned];

Compounds L3B-001~L3B-144 represent tetrazolinone Compounds represented by a formula:

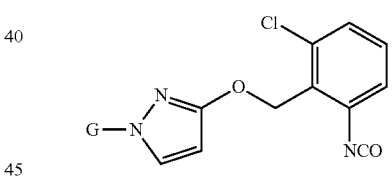

[wherein G represents a substituent corresponding to each of substituents Nos. 1 to 144 indicated in Table 26 to Table 30 as below-mentioned];

Compounds L3C-001~L3C-144 represent tetrazolinone Compounds represented by a formula:

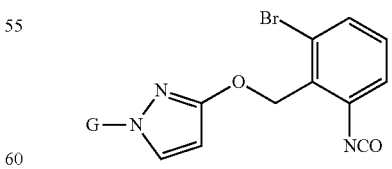

[wherein G represents a substituent corresponding to each of substituents Nos. 1 to 144 indicated in Table 26 to Table 30 as below-mentioned];

Compounds L3D-001~L3D-144 represent tetrazolinone Compounds represented by a formula:

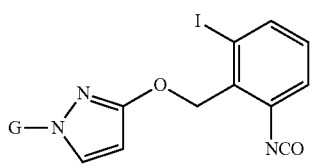

[wherein G represents a substituent corresponding to each of substituents Nos. 1 to 144 indicated in Table 26 to Table 30 as below-mentioned];
Compounds L3E-001~L3E-144 represent tetrazolinone Compounds represented by a formula:

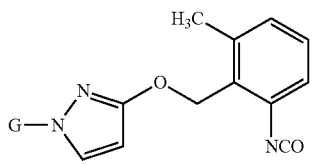

[wherein G represents a substituent corresponding to each of substituents Nos. 1 to 144 indicated in Table 26 to Table 30 as below-mentioned];
Compounds L3F-001~L3F-144 represent tetrazolinone Compounds represented by a formula:

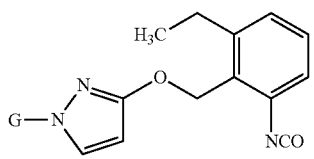

[wherein G represents a substituent corresponding to each of substituents Nos. 1 to 144 indicated in Table 26 to Table 30 as below-mentioned];
Compounds L3G-001~L3G-144 represent tetrazolinone Compounds represented by a formula:

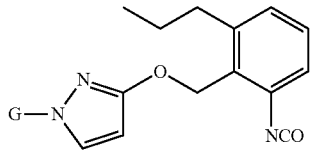

[wherein G represents a substituent corresponding to each of substituents Nos. 1 to 144 indicated in Table 26 to Table 30 as below-mentioned];
Compounds L3H-001~L3H-144 represent tetrazolinone Compounds represented by a formula:

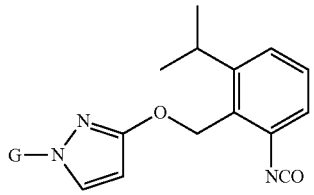

[wherein G represents a substituent corresponding to each of substituents Nos. 1 to 144 indicated in Table 26 to Table 30 as below-mentioned];
Compounds L3I-001~L3I-144 represent tetrazolinone Compounds represented by a formula:

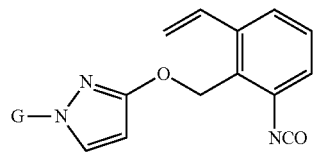

[wherein G represents a substituent corresponding to each of substituents Nos. 1 to 144 indicated in Table 26 to Table 30 as below-mentioned];
Compounds L3J-001~L3J-144 represent tetrazolinone Compounds represented by a formula:

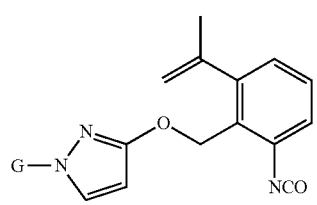

[wherein G represents a substituent corresponding to each of substituents Nos. 1 to 144 indicated in Table 26 to Table 30 as below-mentioned];
Compounds L3K-001~L3K-144 represent tetrazolinone Compounds represented by a formula:

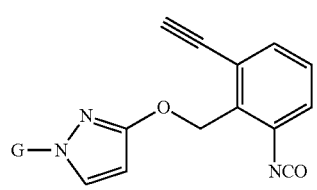

[wherein G represents a substituent corresponding to each of substituents Nos. 1 to 144 indicated in Table 26 to Table 30 as below-mentioned];
Compounds L3L-001~L3L-144 represent tetrazolinone Compounds represented by a formula:

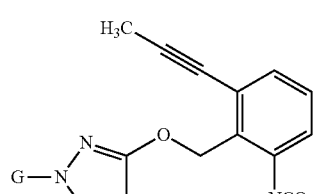

[wherein G represents a substituent corresponding to each of substituents Nos. 1 to 144 indicated in Table 26 to Table 30 as below-mentioned];
Compounds L3M-001~L3M-144 represent tetrazolinone Compounds represented by a formula:

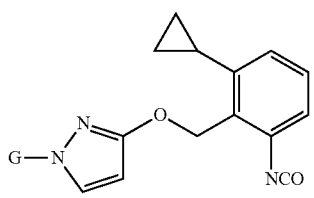

[wherein G represents a substituent corresponding to each of substituents Nos. 1 to 144 indicated in Table 26 to Table 30 as below-mentioned];

Compounds L3N-001~L3N-144 represent tetrazolinone Compounds represented by a formula:

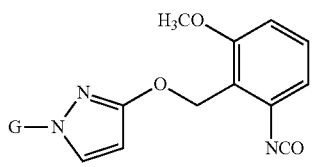

[wherein G represents a substituent corresponding to each of substituents Nos. 1 to 144 indicated in Table 26 to Table 30 as below-mentioned];

Compounds L3O-001~L3O-144 represent tetrazolinone Compounds represented by a formula:

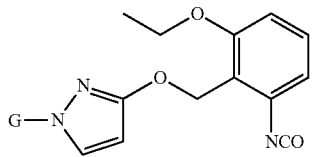

[wherein G represents a substituent corresponding to each of substituents Nos. 1 to 144 indicated in Table 26 to Table 30 as below-mentioned];

Compounds L3P-001~L3P-144 represent tetrazolinone Compounds represented by a formula:

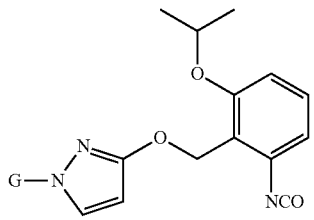

[wherein G represents a substituent corresponding to each of substituents Nos. 1 to 144 indicated in Table 26 to Table 30 as below-mentioned];

Compounds L3Q-001~L3Q-144 represent tetrazolinone Compounds represented by a formula:

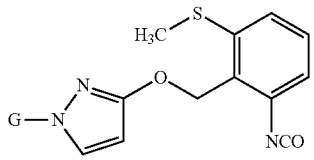

[wherein G represents a substituent corresponding to each of substituents Nos. 1 to 144 indicated in Table 26 to Table 30 as below-mentioned];

Compounds L3R-001~L3R-144 represent tetrazolinone Compounds represented by a formula:

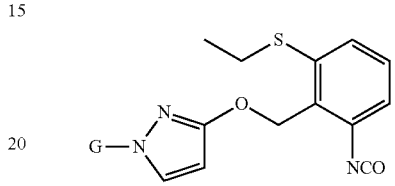

[wherein G represents a substituent corresponding to each of substituents Nos. 1 to 144 indicated in Table 26 to Table 30 as below-mentioned];

Compounds L3S-001~L3S-144 represent tetrazolinone Compounds represented by a formula:

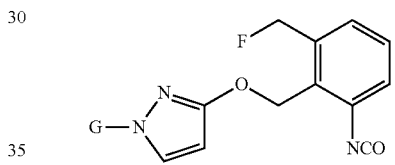

[wherein G represents a substituent corresponding to each of substituents Nos. 1 to 144 indicated in Table 26 to Table 30 as below-mentioned];

Compounds L3T-001~L3T-144 represent tetrazolinone Compounds represented by a formula:

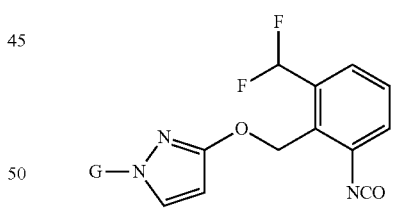

[wherein G represents a substituent corresponding to each of substituents Nos. 1 to 144 indicated in Table 26 to Table 30 as below-mentioned];

Compounds L3U-001~L3U-144 represent tetrazolinone Compounds represented by a formula:

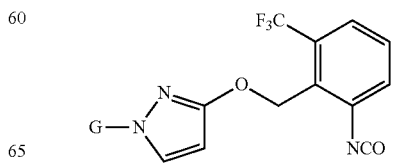

[wherein G represents a substituent corresponding to each of substituents Nos. 1 to 144 indicated in Table 26 to Table 30 as below-mentioned];
Compounds L3V-001~L3V-144 represent tetrazolinone Compounds represented by a formula:

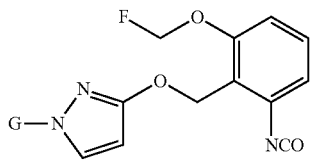

[wherein G represents a substituent corresponding to each of substituents Nos. 1 to 144 indicated in Table 26 to Table 30 as below-mentioned];
Compounds L3W-001~L3W-144 represent tetrazolinone Compounds represented by a formula:

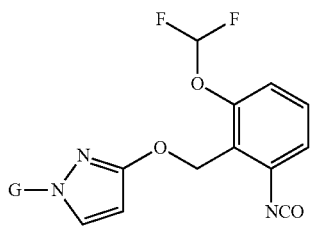

[wherein G represents a substituent corresponding to each of substituents Nos. 1 to 144 indicated in Table 26 to Table 30 as below-mentioned];
Compounds L3X-001~L3X-144 represent tetrazolinone Compounds represented by a formula:

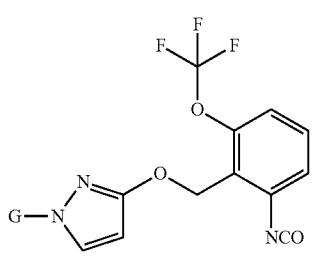

[wherein G represents a substituent corresponding to each of substituents Nos. 1 to 144 indicated in Table 26 to Table 30 as below-mentioned];
Compounds L3Y-001~L3Y-144 represent tetrazolinone Compounds represented by a formula:

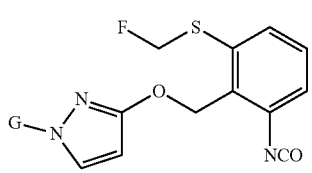

[wherein G represents a substituent corresponding to each of substituents Nos. 1 to 144 indicated in Table 26 to Table 30 as below-mentioned];
Compounds L3Z-001~L3Z-144 represent tetrazolinone Compounds represented by a formula:

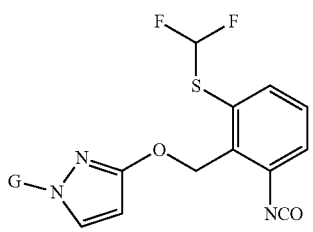

[wherein G represents a substituent corresponding to each of substituents Nos. 1 to 144 indicated in Table 26 to Table 30 as below-mentioned];
Compounds L3AA-001~L3AA-144 represent tetrazolinone Compounds represented by a formula:

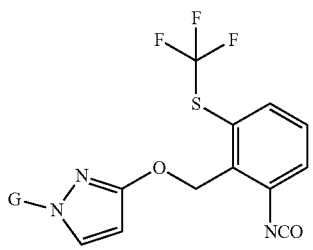

[wherein G represents a substituent corresponding to each of substituents Nos. 1 to 144 indicated in Table 26 to Table 30 as below-mentioned];
Compounds L4A-001~L4A-144 represent tetrazolinone Compounds represented by a formula:

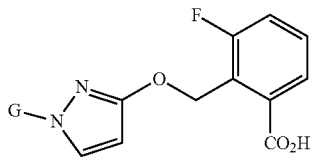

[wherein G represents a substituent corresponding to each of substituents Nos. 1 to 144 indicated in Table 26 to Table 30 as below-mentioned];
Compounds L4B-001~L4B-144 represent tetrazolinone Compounds represented by a formula:

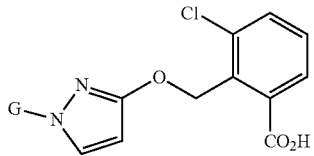

[wherein G represents a substituent corresponding to each of substituents Nos. 1 to 144 indicated in Table 26 to Table 30 as below-mentioned];
Compounds L4C-001~L4C-144 represent tetrazolinone Compounds represented by a formula:

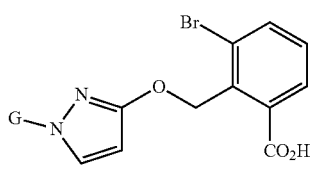

[wherein G represents a substituent corresponding to each of substituents Nos. 1 to 144 indicated in Table 26 to Table 30 as below-mentioned];
Compounds L4D-001~L4D-144 represent tetrazolinone Compounds represented by a formula:

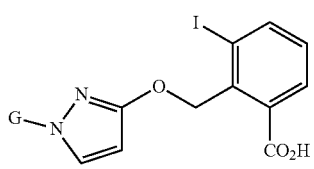

[wherein G represents a substituent corresponding to each of substituents Nos. 1 to 144 indicated in Table 26 to Table 30 as below-mentioned];
Compounds L4E-001~L4E-144 represent tetrazolinone Compounds represented by a formula:

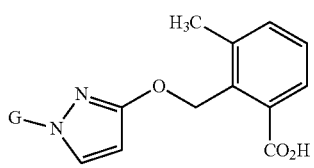

[wherein G represents a substituent corresponding to each of substituents Nos. 1 to 144 indicated in Table 26 to Table 30 as below-mentioned];
Compounds L4F-001~L4F-144 represent tetrazolinone Compounds represented by a formula:

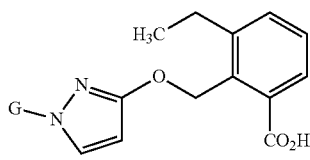

[wherein G represents a substituent corresponding to each of substituents Nos. 1 to 144 indicated in Table 26 to Table 30 as below-mentioned];
Compounds L4G-001~L4G-144 represent tetrazolinone Compounds represented by a formula:

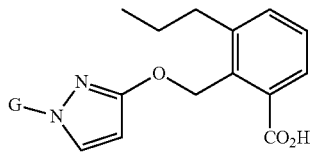

[wherein G represents a substituent corresponding to each of substituents Nos. 1 to 144 indicated in Table 26 to Table 30 as below-mentioned];

Compounds L4H-001~L4H-144 represent tetrazolinone Compounds represented by a formula:

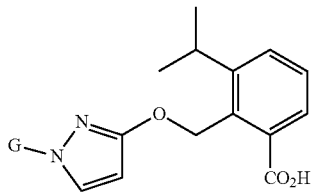

[wherein G represents a substituent corresponding to each of substituents Nos. 1 to 144 indicated in Table 26 to Table 30 as below-mentioned];
Compounds L4I-001~L4I-144 represent tetrazolinone Compounds represented by a formula:

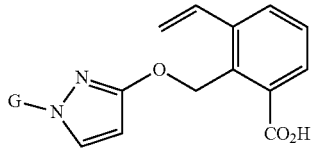

[wherein G represents a substituent corresponding to each of substituents Nos. 1 to 144 indicated in Table 26 to Table 30 as below-mentioned];
Compounds L4J-001~L4J-144 represent tetrazolinone Compounds represented by a formula:

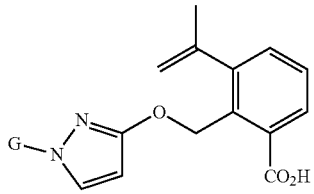

[wherein G represents a substituent corresponding to each of substituents Nos. 1 to 144 indicated in Table 26 to Table 30 as below-mentioned];
Compounds L4K-001~L4K-144 represent tetrazolinone Compounds represented by a formula:

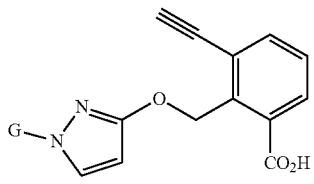

[wherein G represents a substituent corresponding to each of substituents Nos. 1 to 144 indicated in Table 26 to Table 30 as below-mentioned];
Compounds L4L-001~L4L-144 represent tetrazolinone Compounds represented by a formula:

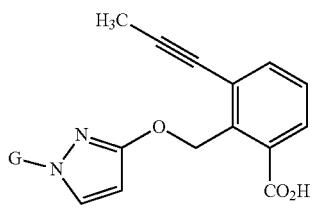

[wherein G represents a substituent corresponding to each of substituents Nos. 1 to 144 indicated in Table 26 to Table 30 as below-mentioned];

Compounds L4M-001~L4M-144 represent tetrazolinone Compounds represented by a formula:

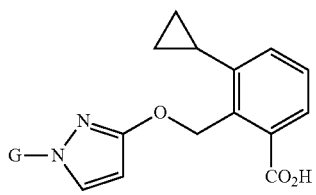

[wherein G represents a substituent corresponding to each of substituents Nos. 1 to 144 indicated in Table 26 to Table 30 as below-mentioned];

Compounds L4N-001~L4N-144 represent tetrazolinone Compounds represented by a formula:

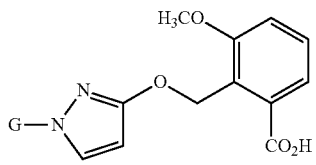

[wherein G represents a substituent corresponding to each of substituents Nos. 1 to 144 indicated in Table 26 to Table 30 as below-mentioned];

Compounds L4O-001~L4O-144 represent tetrazolinone Compounds represented by a formula:

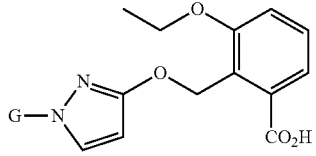

[wherein G represents a substituent corresponding to each of substituents Nos. 1 to 144 indicated in Table 26 to Table 30 as below-mentioned];

Compounds L4P-001~L4P-144 represent tetrazolinone Compounds represented by a formula:

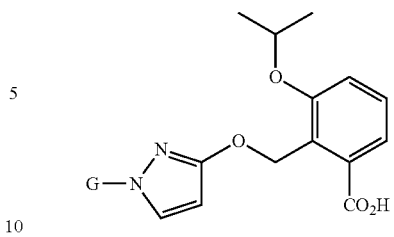

[wherein G represents a substituent corresponding to each of substituents Nos. 1 to 144 indicated in Table 26 to Table 30 as below-mentioned];

Compounds L4Q-001~L4Q-144 represent tetrazolinone Compounds represented by a formula:

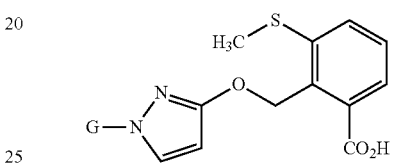

[wherein G represents a substituent corresponding to each of substituents Nos. 1 to 144 indicated in Table 26 to Table 30 as below-mentioned];

Compounds L4R-001~L4R-144 represent tetrazolinone Compounds represented by a formula:

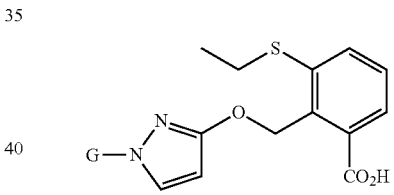

[wherein G represents a substituent corresponding to each of substituents Nos. 1 to 144 indicated in Table 26 to Table 30 as below-mentioned];

Compounds L4S-001~L4S-144 represent tetrazolinone Compounds represented by a formula:

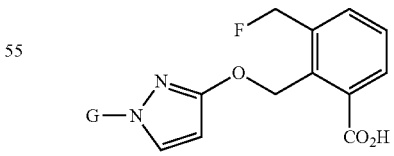

[wherein G represents a substituent corresponding to each of substituents Nos. 1 to 144 indicated in Table 26 to Table 30 as below-mentioned];

Compounds L4T-001~L4T-144 represent tetrazolinone Compounds represented by a formula:

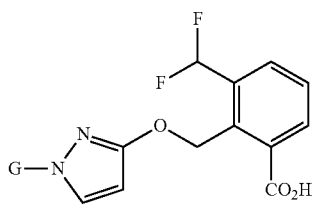

[wherein G represents a substituent corresponding to each of substituents Nos. 1 to 144 indicated in Table 26 to Table 30 as below-mentioned];

Compounds L4U-001~L4U-144 represent tetrazolinone Compounds represented by a formula:

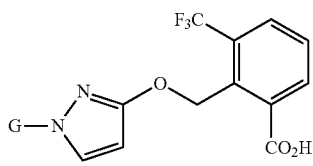

[wherein G represents a substituent corresponding to each of substituents Nos. 1 to 144 indicated in Table 26 to Table 30 as below-mentioned];

Compounds L4V-001~L4V-144 represent tetrazolinone Compounds represented by a formula:

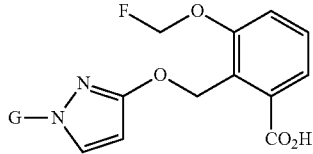

[wherein G represents a substituent corresponding to each of substituents Nos. 1 to 144 indicated in Table 26 to Table 30 as below-mentioned];

Compounds L4W-001~L4W-144 represent tetrazolinone Compounds represented by a formula:

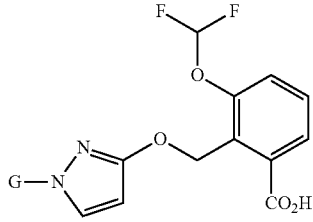

[wherein G represents a substituent corresponding to each of substituents Nos. 1 to 144 indicated in Table 26 to Table 30 as below-mentioned];

Compounds L4X-001~L4X-144 represent tetrazolinone Compounds represented by a formula:

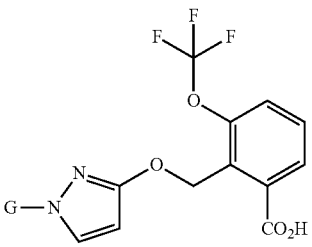

[wherein G represents a substituent corresponding to each of substituents Nos. 1 to 144 indicated in Table 26 to Table 30 as below-mentioned];

Compounds L4Y-001~L4Y-144 represent tetrazolinone Compounds represented by a formula:

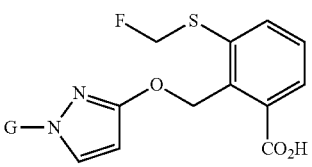

[wherein G represents a substituent corresponding to each of substituents Nos. 1 to 144 indicated in Table 26 to Table 30 as below-mentioned];

Compounds L4Z-001~L4Z-144 represent tetrazolinone Compounds represented by a formula:

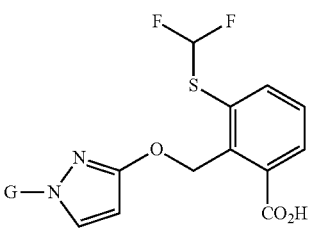

[wherein G represents a substituent corresponding to each of substituents Nos. 1 to 144 indicated in Table 26 to Table 30 as below-mentioned];

Compounds L4AA-001~L4AA-144 represent tetrazolinone Compounds represented by a formula:

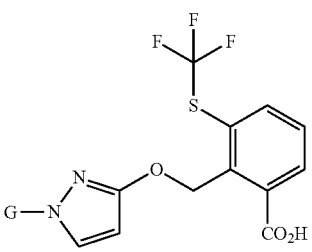

[wherein G represents a substituent corresponding to each of substituents Nos. 1 to 144 indicated in Table 26 to Table 30 as below-mentioned];

Compounds L5A-001~L5A-144 represent tetrazolinone Compounds represented by a formula:

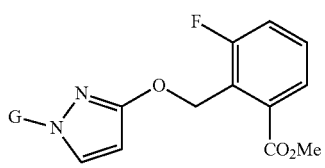

[wherein G represents a substituent corresponding to each of substituents Nos. 1 to 144 indicated in Table 26 to Table 30 as below-mentioned];
Compounds L5B-001~L5B-144 represent tetrazolinone Compounds represented by a formula:

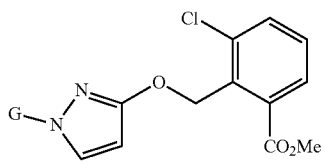

[wherein G represents a substituent corresponding to each of substituents Nos. 1 to 144 indicated in Table 26 to Table 30 as below-mentioned];
Compounds L5C-001~L5C-144 represent tetrazolinone Compounds represented by a formula:

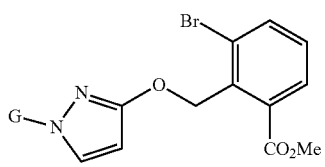

[wherein G represents a substituent corresponding to each of substituents Nos. 1 to 144 indicated in Table 26 to Table 30 as below-mentioned];
Compounds L5D-001~L5D-144 represent tetrazolinone Compounds represented by a formula:

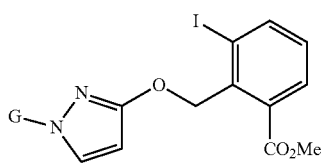

[wherein G represents a substituent corresponding to each of substituents Nos. 1 to 144 indicated in Table 26 to Table 30 as below-mentioned];
Compounds L5E-001~L5E-144 represent tetrazolinone Compounds represented by a formula:

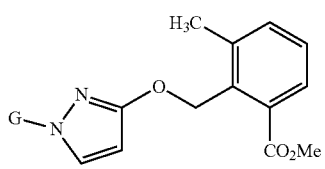

[wherein G represents a substituent corresponding to each of substituents Nos. 1 to 144 indicated in Table 26 to Table 30 as below-mentioned];
Compounds L5F-001~L5F-144 represent tetrazolinone Compounds represented by a formula:

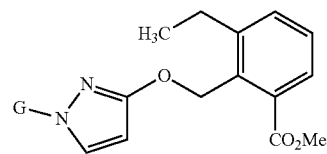

[wherein G represents a substituent corresponding to each of substituents Nos. 1 to 144 indicated in Table 26 to Table 30 as below-mentioned];
Compounds L5G-001~L5G-144 represent tetrazolinone Compounds represented by a formula:

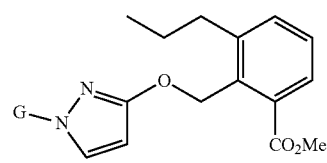

[wherein G represents a substituent corresponding to each of substituents Nos. 1 to 144 indicated in Table 26 to Table 30 as below-mentioned];
Compounds L5H-001~L5H-144 represent tetrazolinone Compounds represented by a formula:

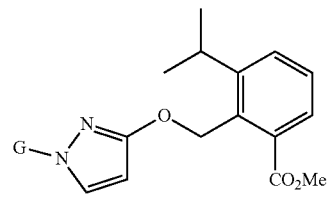

[wherein G represents a substituent corresponding to each of substituents Nos. 1 to 144 indicated in Table 26 to Table 30 as below-mentioned];
Compounds L5I-001~L5I-144 represent tetrazolinone Compounds represented by a formula:

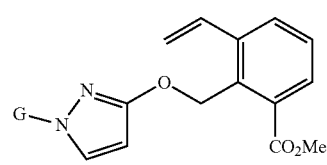

[wherein G represents a substituent corresponding to each of substituents Nos. 1 to 144 indicated in Table 26 to Table 30 as below-mentioned];
Compounds L5J-001~L5J-144 represent tetrazolinone Compounds represented by a formula:

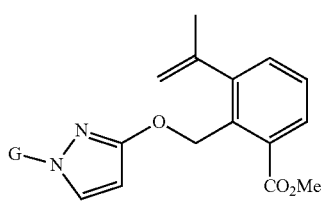

[wherein G represents a substituent corresponding to each of substituents Nos. 1 to 144 indicated in Table 26 to Table 30 as below-mentioned];

Compounds L5K-001~L5K-144 represent tetrazolinone Compounds represented by a formula:

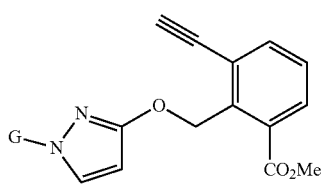

[wherein G represents a substituent corresponding to each of substituents Nos. 1 to 144 indicated in Table 26 to Table 30 as below-mentioned];

Compounds L5L-001~L5L-144 represent tetrazolinone Compounds represented by a formula:

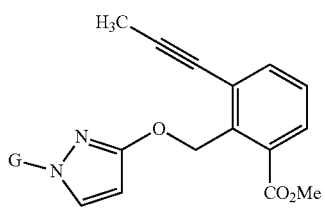

[wherein G represents a substituent corresponding to each of substituents Nos. 1 to 144 indicated in Table 26 to Table 30 as below-mentioned];

Compounds L5M-001~L5M-144 represent tetrazolinone Compounds represented by a formula:

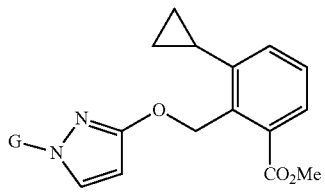

[wherein G represents a substituent corresponding to each of substituents Nos. 1 to 144 indicated in Table 26 to Table 30 as below-mentioned];

Compounds L5N-001~L5N-144 represent tetrazolinone Compounds represented by a formula:

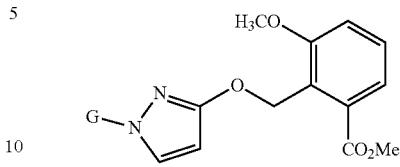

[wherein G represents a substituent corresponding to each of substituents Nos. 1 to 144 indicated in Table 26 to Table 30 as below-mentioned];

Compounds L5O-001~L5O-144 represent tetrazolinone Compounds represented by a formula:

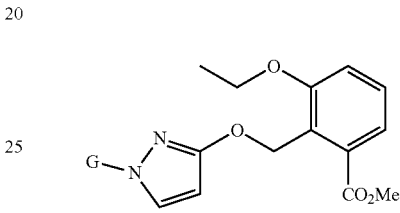

[wherein G represents a substituent corresponding to each of substituents Nos. 1 to 144 indicated in Table 26 to Table 30 as below-mentioned];

Compounds L5P-001~L5P-144 represent tetrazolinone Compounds represented by a formula:

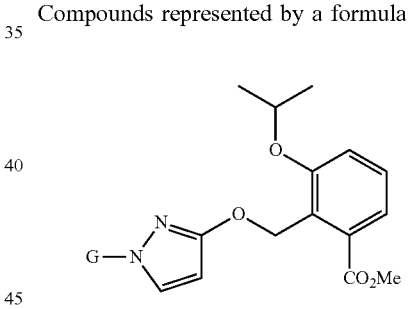

[wherein G represents a substituent corresponding to each of substituents Nos. 1 to 144 indicated in Table 26 to Table 30 as below-mentioned];

Compounds L5Q-001~L5Q-144 represent tetrazolinone Compounds represented by a formula:

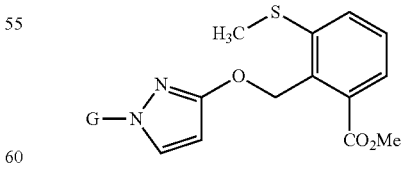

[wherein G represents a substituent corresponding to each of substituents Nos. 1 to 144 indicated in Table 26 to Table 30 as below-mentioned];

Compounds L5R-001~L5R-144 represent tetrazolinone Compounds represented by a formula:

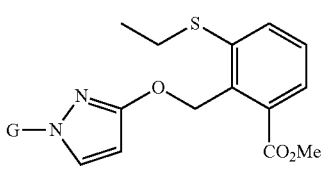

[wherein G represents a substituent corresponding to each of substituents Nos. 1 to 144 indicated in Table 26 to Table 30 as below-mentioned];

Compounds L5S-001~L5S-144 represent tetrazolinone Compounds represented by a formula:

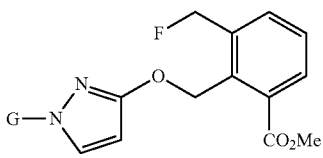

[wherein G represents a substituent corresponding to each of substituents Nos. 1 to 144 indicated in Table 26 to Table 30 as below-mentioned];

Compounds L5T-001~L5T-144 represent tetrazolinone Compounds represented by a formula:

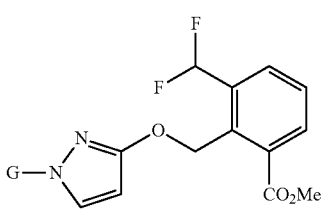

[wherein G represents a substituent corresponding to each of substituents Nos. 1 to 144 indicated in Table 26 to Table 30 as below-mentioned];

Compounds L5U-001~L5U-144 represent tetrazolinone Compounds represented by a formula:

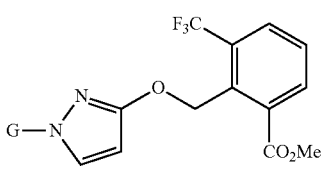

[wherein G represents a substituent corresponding to each of substituents Nos. 1 to 144 indicated in Table 26 to Table 30 as below-mentioned];

Compounds L5V-001~L5V-144 represent tetrazolinone Compounds represented by a formula:

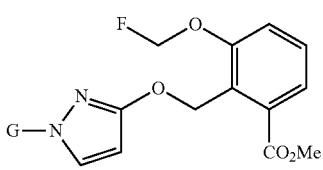

[wherein G represents a substituent corresponding to each of substituents Nos. 1 to 144 indicated in Table 26 to Table 30 as below-mentioned];

Compounds L5W-001~L5W-144 represent tetrazolinone Compounds represented by a formula:

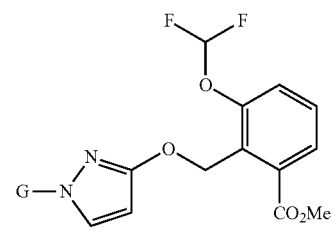

[wherein G represents a substituent corresponding to each of substituents Nos. 1 to 144 indicated in Table 26 to Table 30 as below-mentioned];

Compounds L5X-001~L5X-144 represent tetrazolinone Compounds represented by a formula:

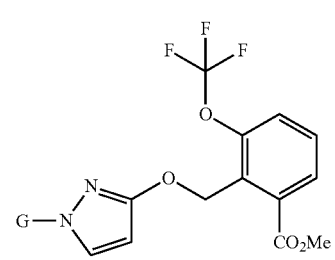

[wherein G represents a substituent corresponding to each of substituents Nos. 1 to 144 indicated in Table 26 to Table 30 as below-mentioned];

Compounds L5Y-001~L5Y-144 represent tetrazolinone Compounds represented by a formula:

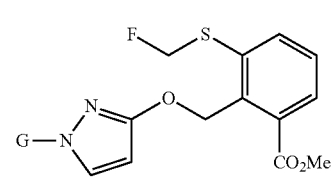

[wherein G represents a substituent corresponding to each of substituents Nos. 1 to 144 indicated in Table 26 to Table 30 as below-mentioned];

Compounds L5Z-001~L5Z-144 represent tetrazolinone Compounds represented by a formula:

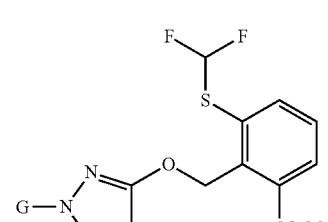

[wherein G represents a substituent corresponding to each of substituents Nos. 1 to 144 indicated in Table 26 to Table 30 as below-mentioned];

Compounds L5AA-001~L5AA-144 represent tetrazolinone Compounds represented by a formula:

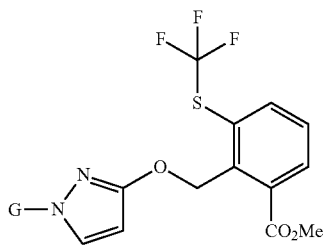

[wherein G represents a substituent corresponding to each of substituents Nos. 1 to 144 indicated in Table 26 to Table 30 as below-mentioned];

Compounds L6A-001~L6A-144 represent tetrazolinone Compounds represented by a formula:

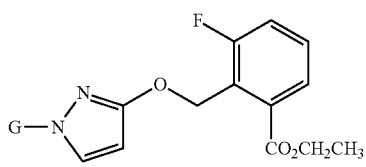

[wherein G represents a substituent corresponding to each of substituents Nos. 1 to 144 indicated in Table 26 to Table 30 as below-mentioned];

Compounds L6B-001~L6B-144 represent tetrazolinone Compounds represented by a formula:

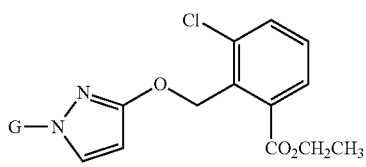

[wherein G represents a substituent corresponding to each of substituents Nos. 1 to 144 indicated in Table 26 to Table 30 as below-mentioned];

Compounds L6C-001~L6C-144 represent tetrazolinone Compounds represented by a formula:

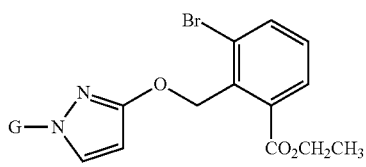

[wherein G represents a substituent corresponding to each of substituents Nos. 1 to 144 indicated in Table 26 to Table 30 as below-mentioned];

Compounds L6D-001~L6D-144 represent tetrazolinone Compounds represented by a formula:

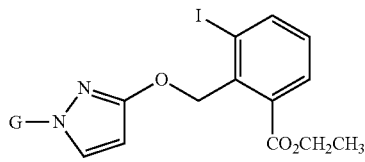

[wherein G represents a substituent corresponding to each of substituents Nos. 1 to 144 indicated in Table 26 to Table 30 as below-mentioned];

Compounds L6E-001~L6E-144 represent tetrazolinone Compounds represented by a formula:

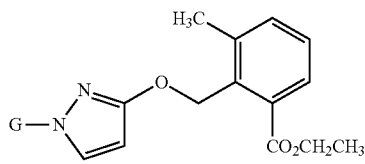

[wherein G represents a substituent corresponding to each of substituents Nos. 1 to 144 indicated in Table 26 to Table 30 as below-mentioned];

Compounds L6F-001~L6F-144 represent tetrazolinone Compounds represented by a formula:

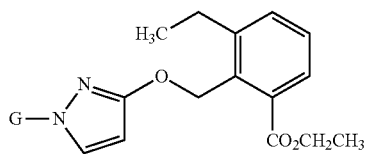

[wherein G represents a substituent corresponding to each of substituents Nos. 1 to 144 indicated in Table 26 to Table 30 as below-mentioned];

Compounds L6G-001~L6G-144 represent tetrazolinone Compounds represented by a formula:

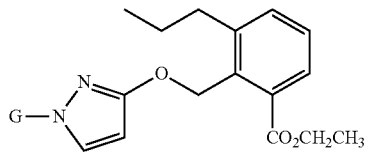

[wherein G represents a substituent corresponding to each of substituents Nos. 1 to 144 indicated in Table 26 to Table 30 as below-mentioned];

Compounds L6H-001~L6H-144 represent tetrazolinone Compounds represented by a formula:

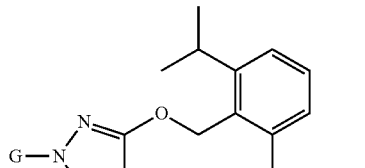

[wherein G represents a substituent corresponding to each of substituents Nos. 1 to 144 indicated in Table 26 to Table 30 as below-mentioned];

Compounds L6I-001~L6I-144 represent tetrazolinone Compounds represented by a formula:

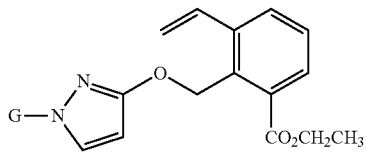

[wherein G represents a substituent corresponding to each of substituents Nos. 1 to 144 indicated in Table 26 to Table 30 as below-mentioned];

Compounds L6J-001~L6J-144 represent tetrazolinone Compounds represented by a formula:

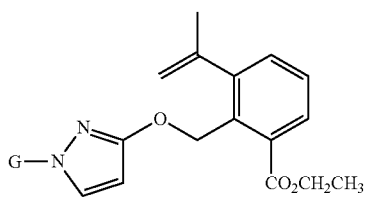

[wherein G represents a substituent corresponding to each of substituents Nos. 1 to 144 indicated in Table 26 to Table 30 as below-mentioned];

Compounds L6K-001~L6K-144 represent tetrazolinone Compounds represented by a formula:

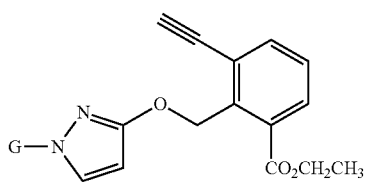

[wherein G represents a substituent corresponding to each of substituents Nos. 1 to 144 indicated in Table 26 to Table 30 as below-mentioned];

Compounds L6L-001~L6L-144 represent tetrazolinone Compounds represented by a formula:

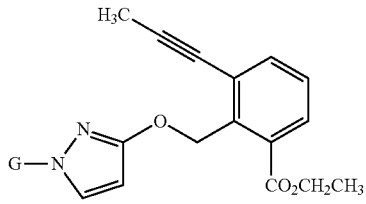

[wherein G represents a substituent corresponding to each of substituents Nos. 1 to 144 indicated in Table 26 to Table 30 as below-mentioned];

Compounds L6M-001~L6M-144 represent tetrazolinone Compounds represented by a formula:

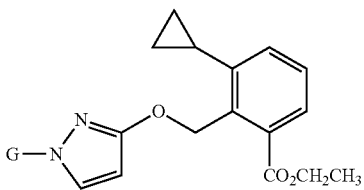

[wherein G represents a substituent corresponding to each of substituents Nos. 1 to 144 indicated in Table 26 to Table 30 as below-mentioned];

Compounds L6N-001~L6N-144 represent tetrazolinone Compounds represented by a formula:

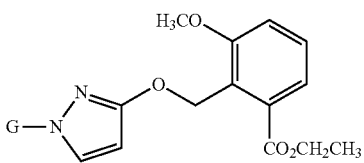

[wherein G represents a substituent corresponding to each of substituents Nos. 1 to 144 indicated in Table 26 to Table 30 as below-mentioned];

Compounds L6O-001~L6O-144 represent tetrazolinone Compounds represented by a formula:

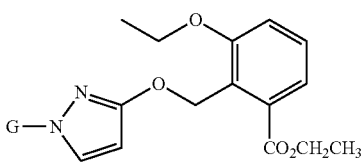

[wherein G represents a substituent corresponding to each of substituents Nos. 1 to 144 indicated in Table 26 to Table 30 as below-mentioned];

Compounds L6P-001~L6P-144 represent tetrazolinone Compounds represented by a formula:

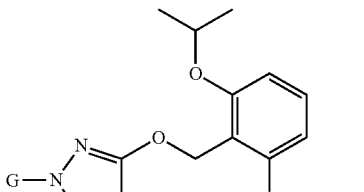

[wherein G represents a substituent corresponding to each of substituents Nos. 1 to 144 indicated in Table 26 to Table 30 as below-mentioned];

Compounds L6Q-001~L6Q-144 represent tetrazolinone Compounds represented by a formula:

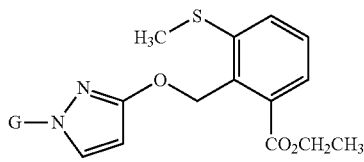

[wherein G represents a substituent corresponding to each of substituents Nos. 1 to 144 indicated in Table 26 to Table 30 as below-mentioned];
Compounds L6R-001~L6R-144 represent tetrazolinone Compounds represented by a formula:

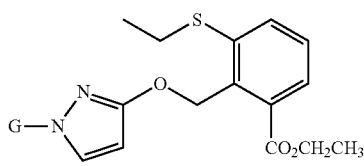

[wherein G represents a substituent corresponding to each of substituents Nos. 1 to 144 indicated in Table 26 to Table 30 as below-mentioned];
Compounds L6S-001~L6S-144 represent tetrazolinone Compounds represented by a formula:

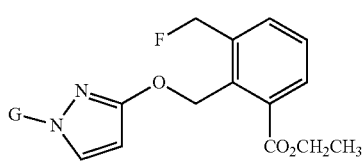

[wherein G represents a substituent corresponding to each of substituents Nos. 1 to 144 indicated in Table 26 to Table 30 as below-mentioned];
Compounds L6T-001~L6T-144 represent tetrazolinone Compounds represented by a formula:

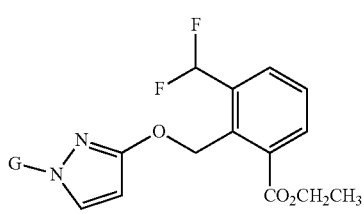

[wherein G represents a substituent corresponding to each of substituents Nos. 1 to 144 indicated in Table 26 to Table 30 as below-mentioned];
Compounds L6U-001~L6U-144 represent tetrazolinone Compounds represented by a formula:

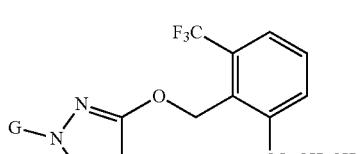

[wherein G represents a substituent corresponding to each of substituents Nos. 1 to 144 indicated in Table 26 to Table 30 as below-mentioned];
Compounds L6V-001~L6V-144 represent tetrazolinone Compounds represented by a formula:

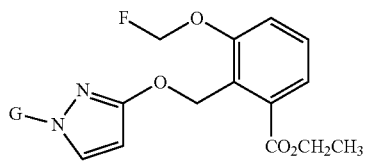

[wherein G represents a substituent corresponding to each of substituents Nos. 1 to 144 indicated in Table 26 to Table 30 as below-mentioned];
Compounds L6W-001~L6W-144 represent tetrazolinone Compounds represented by a formula:

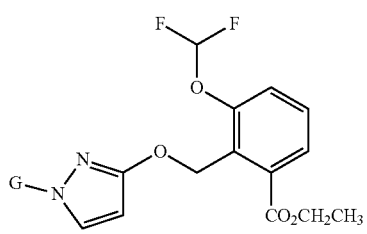

[wherein G represents a substituent corresponding to each of substituents Nos. 1 to 144 indicated in Table 26 to Table 30 as below-mentioned];
Compounds L6X-001~L6X-144 represent tetrazolinone Compounds represented by a formula:

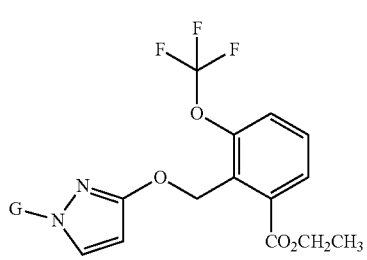

[wherein G represents a substituent corresponding to each of substituents Nos. 1 to 144 indicated in Table 26 to Table 30 as below-mentioned];
Compounds L6Y-001~L6Y-144 represent tetrazolinone Compounds represented by a formula:

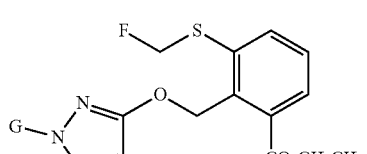

[wherein G represents a substituent corresponding to each of substituents Nos. 1 to 144 indicated in Table 26 to Table 30 as below-mentioned];
Compounds L6Z-001~L6Z-144 represent tetrazolinone Compounds represented by a formula:

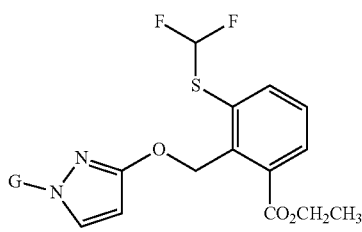

[wherein G represents a substituent corresponding to each of substituents Nos. 1 to 144 indicated in Table 26 to Table 30 as below-mentioned];

Compounds L6AA-001~L6AA-144 represent tetrazolinone Compounds represented by a formula:

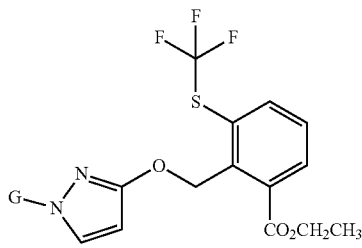

[wherein G represents a substituent corresponding to each of substituents Nos. 1 to 144 indicated in Table 26 to Table 30 as below-mentioned];

Compounds L7A-001~L7A-144 represent tetrazolinone Compounds represented by a formula:

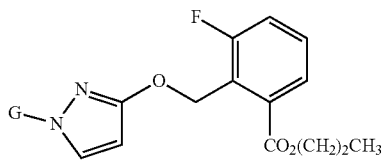

[wherein G represents a substituent corresponding to each of substituents Nos. 1 to 144 indicated in Table 26 to Table 30 as below-mentioned];

Compounds L7B-001~L7B-144 represent tetrazolinone Compounds represented by a formula:

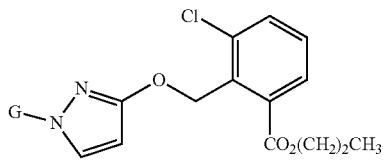

[wherein G represents a substituent corresponding to each of substituents Nos. 1 to 144 indicated in Table 26 to Table 30 as below-mentioned];

Compounds L7C-001~L7C-144 represent tetrazolinone

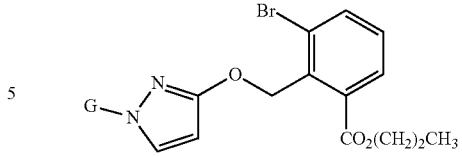

[wherein G represents a substituent corresponding to each of substituents Nos. 1 to 144 indicated in Table 26 to Table 30 as below-mentioned];

Compounds L7D-001~L7D-144 represent tetrazolinone Compounds represented by a formula:

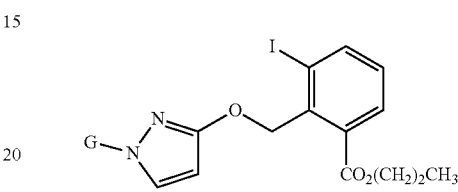

[wherein G represents a substituent corresponding to each of substituents Nos. 1 to 144 indicated in Table 26 to Table 30 as below-mentioned];

Compounds L7E-001~L7E-144 represent tetrazolinone Compounds represented by a formula:

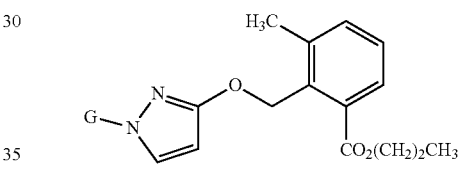

[wherein G represents a substituent corresponding to each of substituents Nos. 1 to 144 indicated in Table 26 to Table 30 as below-mentioned];

Compounds L7F-001~L7F-144 represent tetrazolinone Compounds represented by a formula:

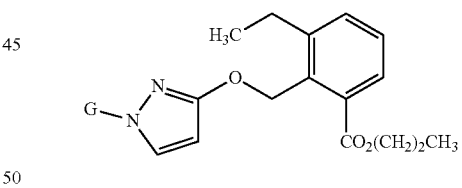

[wherein G represents a substituent corresponding to each of substituents Nos. 1 to 144 indicated in Table 26 to Table 30 as below-mentioned];

Compounds L7G-001~L7G-144 represent tetrazolinone Compounds represented by a formula:

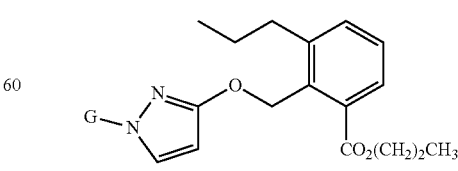

[wherein G represents a substituent corresponding to each of substituents Nos. 1 to 144 indicated in Table 26 to Table 30 as below-mentioned];

Compounds L7H-001~L7H-144 represent tetrazolinone Compounds represented by a formula:

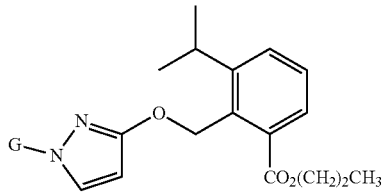

[wherein G represents a substituent corresponding to each of substituents Nos. 1 to 144 indicated in Table 26 to Table 30 as below-mentioned];

Compounds L7I-001~L7I-144 represent tetrazolinone Compounds represented by a formula:

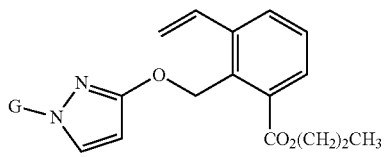

[wherein G represents a substituent corresponding to each of substituents Nos. 1 to 144 indicated in Table 26 to Table 30 as below-mentioned];

Compounds L7J-001~L7J-144 represent tetrazolinone Compounds represented by a formula:

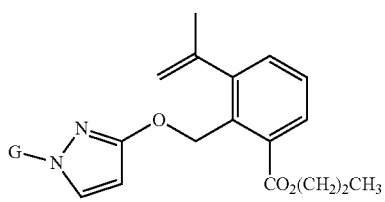

[wherein G represents a substituent corresponding to each of substituents Nos. 1 to 144 indicated in Table 26 to Table 30 as below-mentioned];

Compounds L7K-001~L7K-144 represent tetrazolinone Compounds represented by a formula:

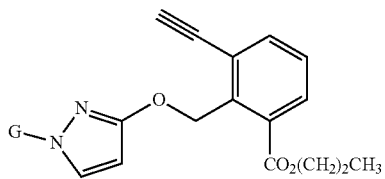

[wherein G represents a substituent corresponding to each of substituents Nos. 1 to 144 indicated in Table 26 to Table 30 as below-mentioned];

Compounds L7L-001~L7L-144 represent tetrazolinone Compounds represented by a formula:

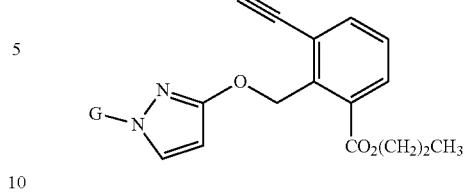

[wherein G represents a substituent corresponding to each of substituents Nos. 1 to 144 indicated in Table 26 to Table 30 as below-mentioned];

Compounds L7M-001~L7M-144 represent tetrazolinone Compounds represented by a formula:

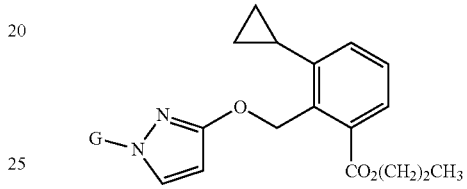

[wherein G represents a substituent corresponding to each of substituents Nos. 1 to 144 indicated in Table 26 to Table 30 as below-mentioned];

Compounds L7N-001~L7N-144 represent tetrazolinone Compounds represented by a formula:

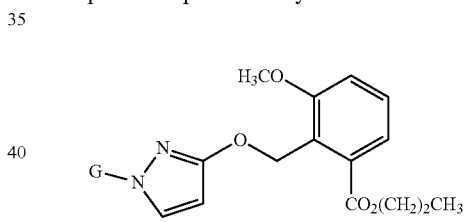

[wherein G represents a substituent corresponding to each of substituents Nos. 1 to 144 indicated in Table 26 to Table 30 as below-mentioned];

Compounds L7O-001~L7O-144 represent tetrazolinone Compounds represented by a formula:

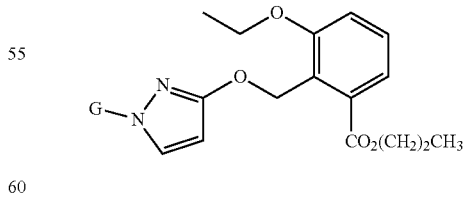

[wherein G represents a substituent corresponding to each of substituents Nos. 1 to 144 indicated in Table 26 to Table 30 as below-mentioned];

Compounds L7P-001~L7P-144 represent tetrazolinone Compounds represented by a formula:

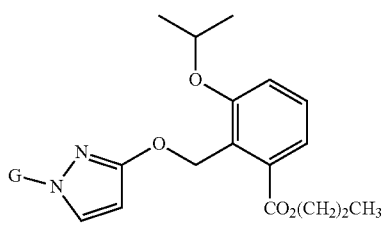

[wherein G represents a substituent corresponding to each of substituents Nos. 1 to 144 indicated in Table 26 to Table 30 as below-mentioned];

Compounds L7Q-001~L7Q-144 represent tetrazolinone Compounds represented by a formula:

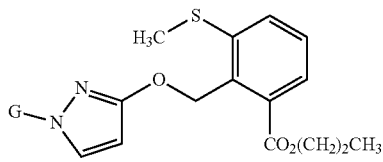

[wherein G represents a substituent corresponding to each of substituents Nos. 1 to 144 indicated in Table 26 to Table 30 as below-mentioned];

Compounds L7R-001~L7R-144 represent tetrazolinone Compounds represented by a formula:

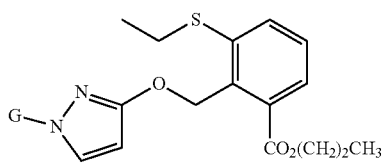

[wherein G represents a substituent corresponding to each of substituents Nos. 1 to 144 indicated in Table 26 to Table 30 as below-mentioned];

Compounds L7S-001~L7S-144 represent tetrazolinone Compounds represented by a formula:

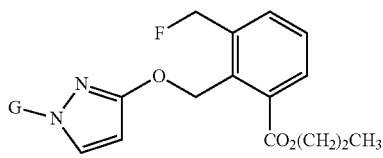

[wherein G represents a substituent corresponding to each of substituents Nos. 1 to 144 indicated in Table 26 to Table 30 as below-mentioned];

Compounds L7T-001~L7T-144 represent tetrazolinone Compounds represented by a formula:

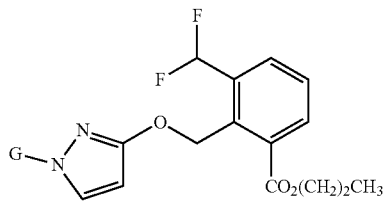

[wherein G represents a substituent corresponding to each of substituents Nos. 1 to 144 indicated in Table 26 to Table 30 as below-mentioned];

Compounds L7U-001~L7U-144 represent tetrazolinone Compounds represented by a formula:

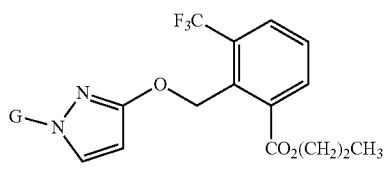

[wherein G represents a substituent corresponding to each of substituents Nos. 1 to 144 indicated in Table 26 to Table 30 as below-mentioned];

Compounds L7V-001~L7V-144 represent tetrazolinone Compounds represented by a formula:

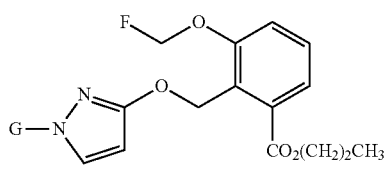

[wherein G represents a substituent corresponding to each of substituents Nos. 1 to 144 indicated in Table 26 to Table 30 as below-mentioned];

Compounds L7W-001~L7W-144 represent tetrazolinone Compounds represented by a formula:

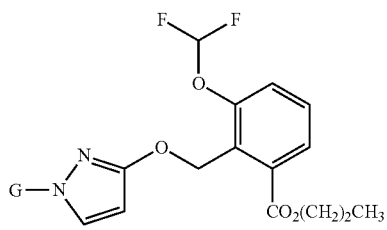

[wherein G represents a substituent corresponding to each of substituents Nos. 1 to 144 indicated in Table 26 to Table 30 as below-mentioned];

Compounds L7X-001~L7X-144 represent tetrazolinone Compounds represented by a formula:

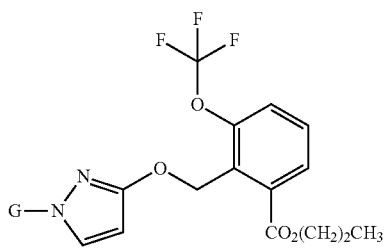

[wherein G represents a substituent corresponding to each of substituents Nos. 1 to 144 indicated in Table 26 to Table 30 as below-mentioned];

Compounds L7Y-001~L7Y-144 represent tetrazolinone Compounds represented by a formula:

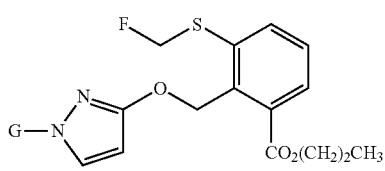

[wherein G represents a substituent corresponding to each of substituents Nos. 1 to 144 indicated in Table 26 to Table 30 as below-mentioned];

Compounds L7Z-001~L7Z-144 represent tetrazolinone Compounds represented by a formula:

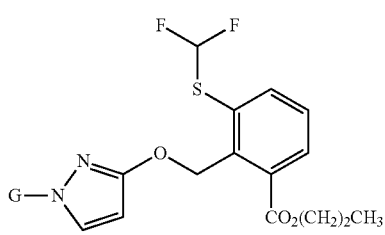

[wherein G represents a substituent corresponding to each of substituents Nos. 1 to 144 indicated in Table 26 to Table 30 as below-mentioned];

Compounds L7AA-001~L7AA-144 represent tetrazolinone. Compounds represented by a formula:

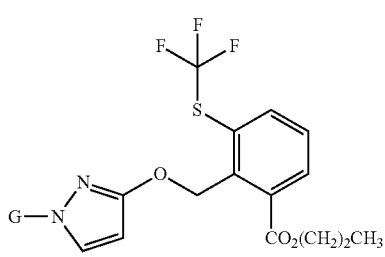

[wherein G represents a substituent corresponding to each of substituents Nos. 1 to 144 indicated in Table 26 to Table 30 as below-mentioned];

Compounds L8A-001~L8A-144 represent tetrazolinone Compounds represented by a formula:

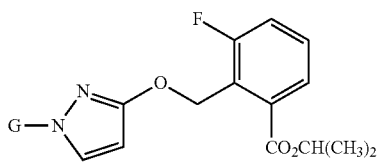

[wherein G represents a substituent corresponding to each of substituents Nos. 1 to 144 indicated in Table 26 to Table 30 as below-mentioned];

Compounds L8B-001~L8B-144 represent tetrazolinone Compounds represented by a formula:

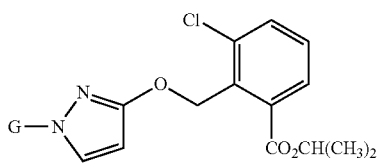

[wherein G represents a substituent corresponding to each of substituents Nos. 1 to 144 indicated in Table 26 to Table 30 as below-mentioned];

Compounds L8C-001~L8C-144 represent tetrazolinone Compounds represented by a formula:

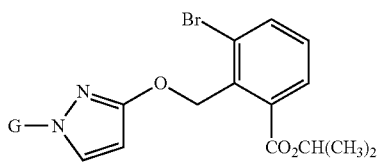

[wherein G represents a substituent corresponding to each of substituents Nos. 1 to 144 indicated in Table 26 to Table 30 as below-mentioned];

Compounds L8D-001~L8D-144 represent tetrazolinone Compounds represented by a formula:

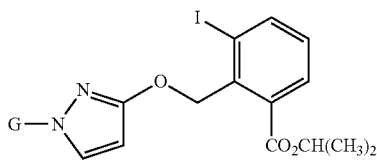

[wherein G represents a substituent corresponding to each of substituents Nos. 1 to 144 indicated in Table 26 to Table 30 as below-mentioned];

Compounds L8E-001~L8E-144 represent tetrazolinone Compounds represented by a formula:

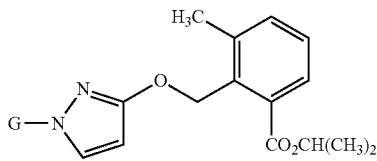

[wherein G represents a substituent corresponding to each of substituents Nos. 1 to 144 indicated in Table 26 to Table 30 as below-mentioned];

Compounds L8F-001~L8F-144 represent tetrazolinone Compounds represented by a formula:

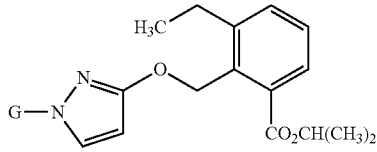

[wherein G represents a substituent corresponding to each of substituents Nos. 1 to 144 indicated in Table 26 to Table 30 as below-mentioned];

Compounds L8G-001~L8G-144 represent tetrazolinone Compounds represented by a formula:

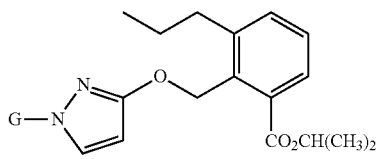

[wherein G represents a substituent corresponding to each of substituents Nos. 1 to 144 indicated in Table 26 to Table 30 as below-mentioned];

Compounds L8H-001~L8H-144 represent tetrazolinone Compounds represented by a formula:

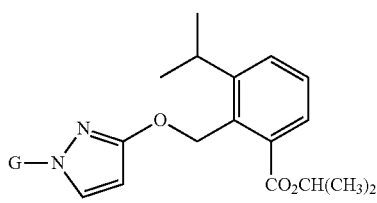

[wherein G represents a substituent corresponding to each of substituents Nos. 1 to 144 indicated in Table 26 to Table 30 as below-mentioned];

Compounds L8I-001~L8I-144 represent tetrazolinone Compounds represented by a formula:

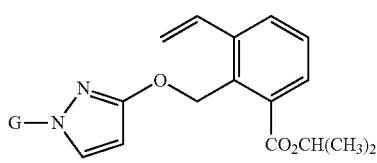

[wherein G represents a substituent corresponding to each of substituents Nos. 1 to 144 indicated in Table 26 to Table 30 as below-mentioned];

Compounds L8J-001~L8J-144 represent tetrazolinone Compounds represented by a formula:

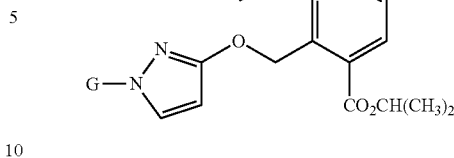

[wherein G represents a substituent corresponding to each of substituents Nos. 1 to 144 indicated in Table 26 to Table 30 as below-mentioned];

Compounds L8K-001~L8K-144 represent tetrazolinone Compounds represented by a formula:

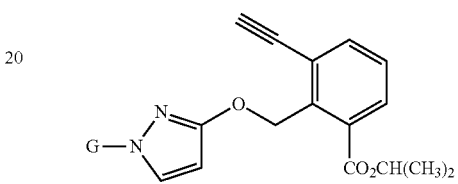

[wherein G represents a substituent corresponding to each of substituents Nos. 1 to 144 indicated in Table 26 to Table 30 as below-mentioned];

Compounds L8L-001~L8L-144 represent tetrazolinone Compounds represented by a formula:

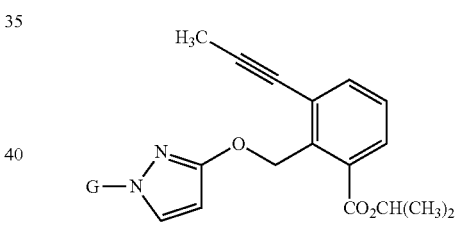

[wherein G represents a substituent corresponding to each of substituents Nos. 1 to 144 indicated in Table 26 to Table 30 as below-mentioned];

Compounds L8M-001~L8M-144 represent tetrazolinone Compounds represented by a formula:

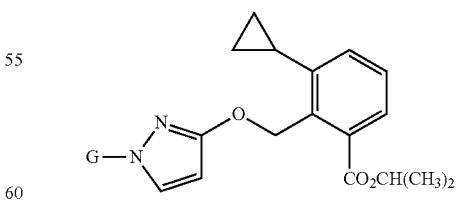

[wherein G represents a substituent corresponding to each of substituents Nos. 1 to 144 indicated in Table 26 to Table 30 as below-mentioned];

Compounds L8N-001~L8N-144 represent tetrazolinone Compounds represented by a formula:

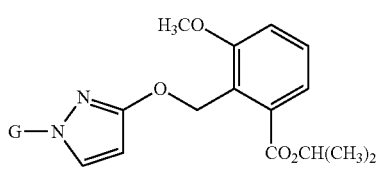

[wherein G represents a substituent corresponding to each of substituents Nos. 1 to 144 indicated in Table 26 to Table 30 as below-mentioned];
Compounds L8O-001~L8O-144 represent tetrazolinone Compounds represented by a formula:

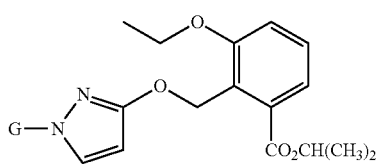

[wherein G represents a substituent corresponding to each of substituents Nos. 1 to 144 indicated in Table 26 to Table 30 as below-mentioned];
Compounds L8P-001~L8P-144 represent tetrazolinone Compounds represented by a formula:

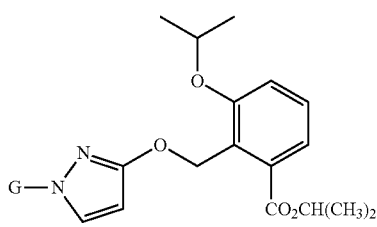

[wherein G represents a substituent corresponding to each of substituents Nos. 1 to 144 indicated in Table 26 to Table 30 as below-mentioned];
Compounds L8Q-001~L8Q-144 represent tetrazolinone Compounds represented by a formula:

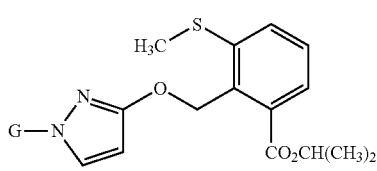

[wherein G represents a substituent corresponding to each of substituents Nos. 1 to 144 indicated in Table 26 to Table 30 as below-mentioned];
Compounds L8R-001~L8R-144 represent tetrazolinone Compounds represented by a formula:

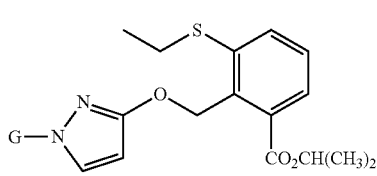

[wherein G represents a substituent corresponding to each of substituents Nos. 1 to 144 indicated in Table 26 to Table 30 as below-mentioned];
Compounds L8S-001~L8S-144 represent tetrazolinone Compounds represented by a formula:

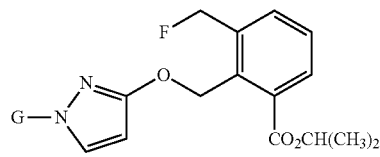

[wherein G represents a substituent corresponding to each of substituents Nos. 1 to 144 indicated in Table 26 to Table 30 as below-mentioned];
Compounds L8T-001~L8T-144 represent tetrazolinone Compounds represented by a formula:

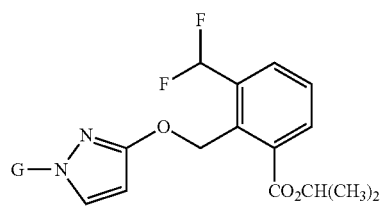

[wherein G represents a substituent corresponding to each of substituents Nos. 1 to 144 indicated in Table 26 to Table 30 as below-mentioned];
Compounds L8U-001~L8U-144 represent tetrazolinone Compounds represented by a formula:

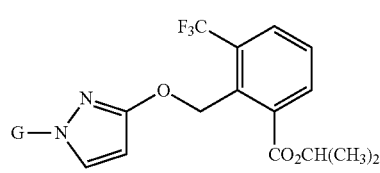

[wherein G represents a substituent corresponding to each of substituents Nos. 1 to 144 indicated in Table 26 to Table 30 as below-mentioned];
Compounds L8V-001~L8V-144 represent tetrazolinone Compounds represented by a formula:

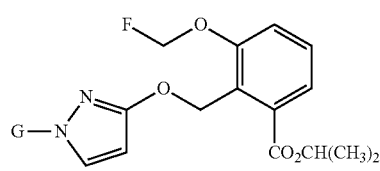

[wherein G represents a substituent corresponding to each of substituents Nos. 1 to 144 indicated in Table 26 to Table 30 as below-mentioned];
Compounds L8W-001~L8W-144 represent tetrazolinone Compounds represented by a formula:

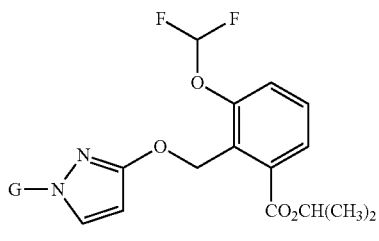

[wherein G represents a substituent corresponding to each of substituents Nos. 1 to 144 indicated in Table 26 to Table 30 as below-mentioned];

Compounds L8X-001~L8X-144 represent tetrazolinone Compounds represented by a formula:

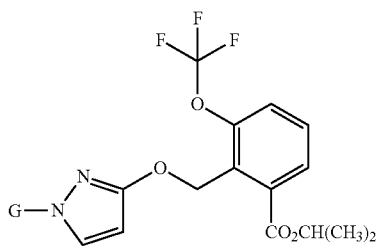

[wherein G represents a substituent corresponding to each of substituents Nos. 1 to 144 indicated in Table 26 to Table 30 as below-mentioned];

Compounds L8Y-001~L8Y-144 represent tetrazolinone Compounds represented by a formula:

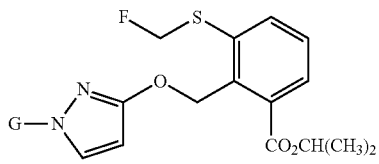

[wherein G represents a substituent corresponding to each of substituents Nos. 1 to 144 indicated in Table 26 to Table 30 as below-mentioned];

Compounds L8Z-001~L8Z-144 represent tetrazolinone Compounds represented by a formula:

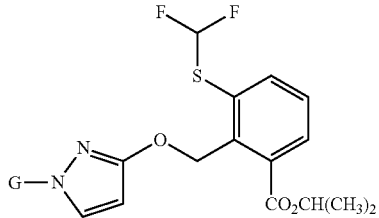

[wherein G represents a substituent corresponding to each of substituents Nos. 1 to 144 indicated in Table 26 to Table 30 as below-mentioned];

Compounds L8AA-001~L8AA-144 represent tetrazolinone Compounds represented by a formula:

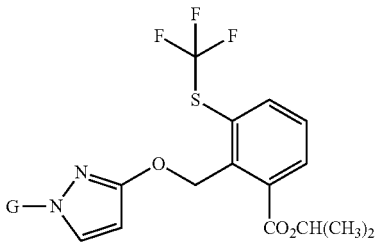

[wherein G represents a substituent corresponding to each of substituents Nos. 1 to 144 indicated in Table 26 to Table 30 as below-mentioned];

Compounds L9A-001~L9A-144 represent tetrazolinone Compounds represented by a formula:

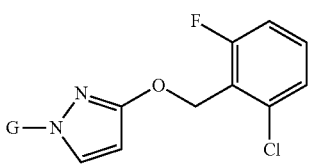

[wherein G represents a substituent corresponding to each of substituents Nos. 1 to 144 indicated in Table 26 to Table 30 as below-mentioned];

Compounds L9B-001~L9B-144 represent tetrazolinone Compounds represented by a formula:

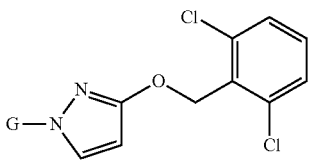

[wherein G represents a substituent corresponding to each of substituents Nos. 1 to 144 indicated in Table 26 to Table 30 as below-mentioned]

Compounds L9C-001~L9C-144 represent tetrazolinone Compounds represented by a formula:

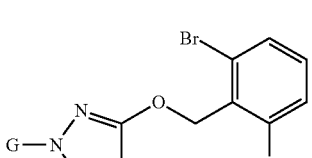

[wherein G represents a substituent corresponding to each of substituents Nos. 1 to 144 indicated in Table 26 to Table 30 as below-mentioned);

Compounds L9D-001~L9D-144 represent tetrazolinone Compounds represented by a formula:

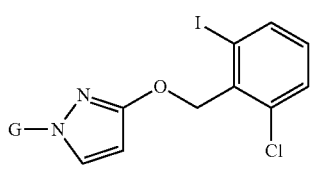

[wherein G represents a substituent corresponding to each of substituents Nos. 1 to 144 indicated in Table 26 to Table 30 as below-mentioned];
Compounds L9E-001~L9E-144 represent tetrazolinone Compounds represented by a formula:

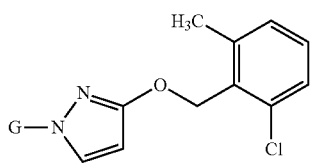

[wherein G represents a substituent corresponding to each of substituents Nos. 1 to 144 indicated in Table 26 to Table 30 as below-mentioned];
Compounds L9F-001~L9F-144 represent tetrazolinone Compounds represented by a formula:

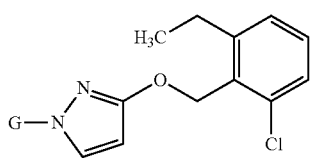

[wherein G represents a substituent corresponding to each of substituents Nos. 1 to 144 indicated in Table 26 to Table 30 as below-mentioned];
Compounds L9G-001~L9G-144 represent tetrazolinone Compounds represented by a formula:

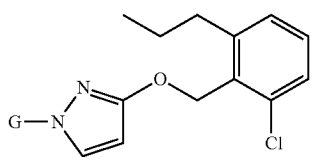

[wherein G represents a substituent corresponding to each of substituents Nos. 1 to 144 indicated in Table 26 to Table 30 as below-mentioned];
Compounds L9H-001~L9H-144 represent tetrazolinone Compounds represented by a formula:

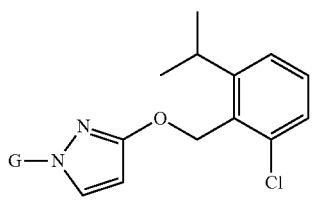

[wherein G represents a substituent corresponding to each of substituents Nos. 1 to 144 indicated in Table 26 to Table 30 as below-mentioned];
Compounds L9I-001~L9I-144 represent tetrazolinone Compounds represented by a formula:

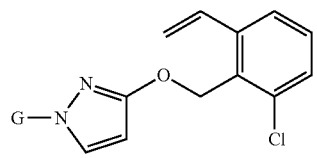

[wherein G represents a substituent corresponding to each of substituents Nos. 1 to 144 indicated in Table 26 to Table 30 as below-mentioned];
Compounds L9J-001~L9J-144 represent tetrazolinone Compounds represented by a formula:

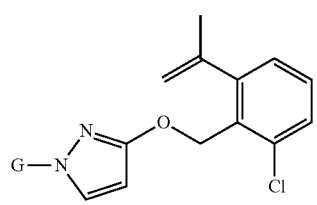

[wherein G represents a substituent corresponding to each of substituents Nos. 1 to 144 indicated in Table 26 to Table 30 as below-mentioned];
Compounds L9K-001~L9K-144 represent tetrazolinone Compounds represented by a formula:

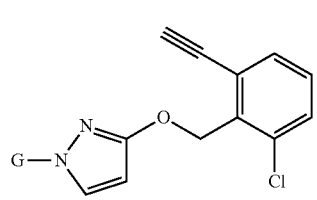

[wherein G represents a substituent corresponding to each of substituents Nos. 1 to 144 indicated in Table 26 to Table 30 as below-mentioned];
Compounds L9L-001~L9L-144 represent tetrazolinone Compounds represented by a formula:

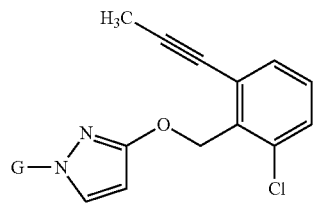

[wherein G represents a substituent corresponding to each of substituents Nos. 1 to 144 indicated in Table 26 to Table 30 as below-mentioned];
Compounds L9M-001~L9M-144 represent tetrazolinone Compounds represented by a formula:

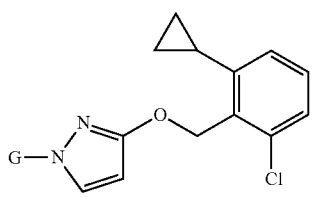

[wherein G represents a substituent corresponding to each of substituents Nos. 1 to 144 indicated in Table 26 to Table 30 as below-mentioned];

Compounds L9N-001~L9N-144 represent tetrazolinone Compounds represented by a formula:

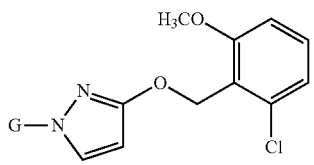

[wherein G represents a substituent corresponding to each of substituents Nos. 1 to 144 indicated in Table 26 to Table 30 as below-mentioned];

Compounds L9O-001~L9O-144 represent tetrazolinone Compounds represented by a formula:

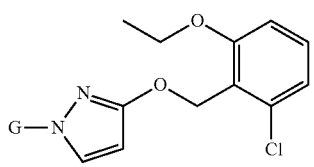

[wherein G represents a substituent corresponding to each of substituents Nos. 1 to 144 indicated in Table 26 to Table 30 as below-mentioned];

Compounds L9P-001~L9P-144 represent tetrazolinone Compounds represented by a formula:

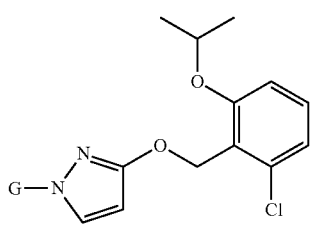

[wherein G represents a substituent corresponding to each of substituents Nos. 1 to 144 indicated in Table 26 to Table 30 as below-mentioned];

Compounds L9Q-001~L9Q-144 represent tetrazolinone Compounds represented by a formula:

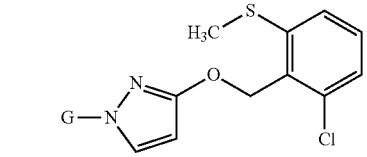

[wherein G represents a substituent corresponding to each of substituents Nos. 1 to 144 indicated in Table 26 to Table 30 as below-mentioned];

Compounds L9R-001~L9R-144 represent tetrazolinone Compounds represented by a formula:

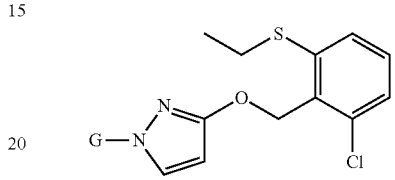

[wherein G represents a substituent corresponding to each of substituents Nos. 1 to 144 indicated in Table 26 to Table 30 as below-mentioned];

Compounds L9S-001~L9S-144 represent tetrazolinone Compounds represented by a formula:

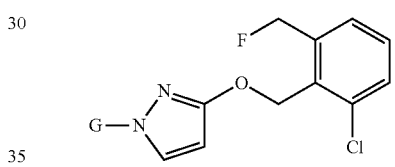

[wherein G represents a substituent corresponding to each of substituents Nos. 1 to 144 indicated in Table 26 to Table 30 as below-mentioned];

Compounds L9T-001~L9T-144 represent tetrazolinone Compounds represented by a formula:

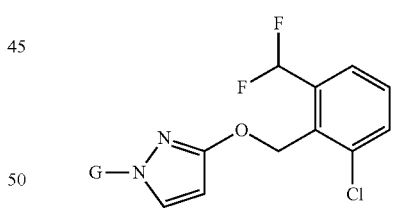

[wherein G represents a substituent corresponding to each of substituents Nos. 1 to 144 indicated in Table 26 to Table 30 as below-mentioned];

Compounds L9U-001~L9U-144 represent tetrazolinone Compounds represented by a formula:

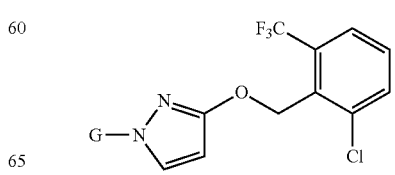

[wherein G represents a substituent corresponding to each of substituents Nos. 1 to 144 indicated in Table 26 to Table 30 as below-mentioned];

Compounds L9V-001~L9V-144 represent tetrazolinone Compounds represented by a formula:

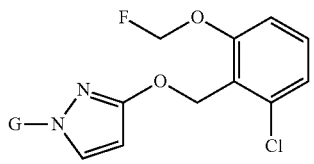

[wherein G represents a substituent corresponding to each of substituents Nos. 1 to 144 indicated in Table 26 to Table 30 as below-mentioned];

Compounds L9W-001~L9W-144 represent tetrazolinone Compounds represented by a formula:

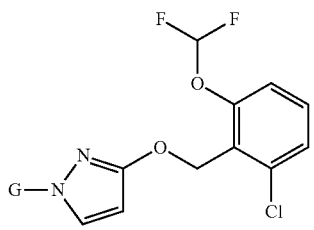

[wherein G represents a substituent corresponding to each of substituents Nos. 1 to 144 indicated in Table 26 to Table 30 as below-mentioned];

Compounds L9X-001~L9X-144 represent tetrazolinone Compounds represented by a formula:

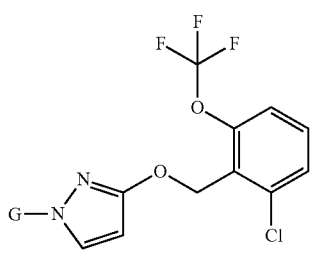

[wherein G represents a substituent corresponding to each of substituents Nos. 1 to 144 indicated in Table 26 to Table 30 as below-mentioned];

Compounds L9Y-001~L9Y-144 represent tetrazolinone Compounds represented by a formula:

[wherein G represents a substituent corresponding to each of substituents Nos. 1 to 144 indicated in Table 26 to Table 30 as below-mentioned];

Compounds L9Z-001~L9Z-144 represent tetrazolinone Compounds represented by a formula:

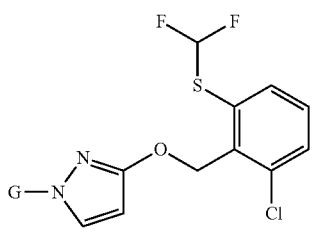

[wherein G represents a substituent corresponding to each of substituents Nos. 1 to 144 indicated in Table 26 to Table 30 as below-mentioned];

Compounds L9AA-001~L9AA-144 represent tetrazolinone Compounds represented by a formula:

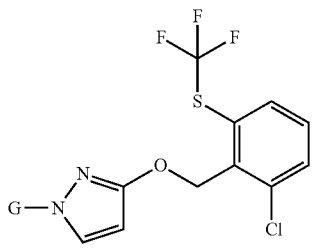

[wherein G represents a substituent corresponding to each of substituents Nos. 1 to 144 indicated in Table 26 to Table 30 as below-mentioned];

Compounds L10A-001~L10A-144 represent tetrazolinone Compounds represented by a formula:

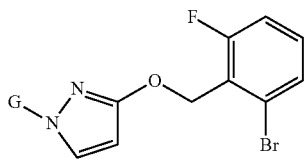

[wherein G represents a substituent corresponding to each of substituents Nos. 1 to 144 indicated in Table 26 to Table 30 as below-mentioned];

Compounds L10B-001~L10B-144 represent tetrazolinone Compounds represented by a formula:

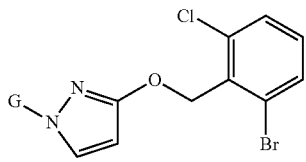

[wherein G represents a substituent corresponding to each of substituents Nos. 1 to 144 indicated in Table 26 to Table 30 as below-mentioned];

Compounds L10C-001~L10C-144 represent tetrazolinone Compounds represented by a formula:

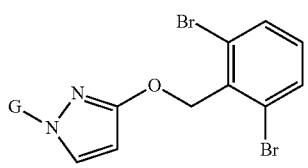

[wherein G represents a substituent corresponding to each of substituents Nos. 1 to 144 indicated in Table 26 to Table 30 as below-mentioned];

Compounds L10D-001~L10D-144 represent tetrazolinone Compounds represented by a formula:

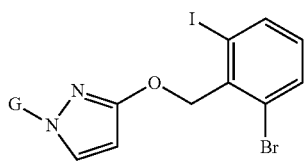

[wherein G represents a substituent corresponding to each of substituents Nos. 1 to 144 indicated in Table 26 to Table 30 as below-mentioned];

Compounds L10E-001~L10E-144 represent tetrazolinone Compounds represented by a formula:

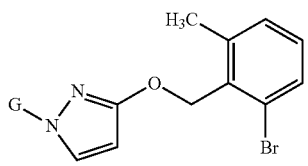

[wherein G represents a substituent corresponding to each of substituents Nos. 1 to 144 indicated in Table 26 to Table 30 as below-mentioned];

Compounds L10F-001~L10F-144 represent tetrazolinone Compounds represented by a formula:

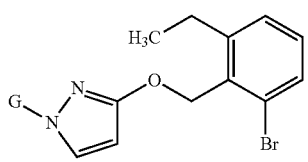

[wherein G represents a substituent corresponding to each of substituents Nos. 1 to 144 indicated in Table 26 to Table 30 as below-mentioned];

Compounds L10G-001~L10G-144 represent tetrazolinone Compounds represented by a formula:

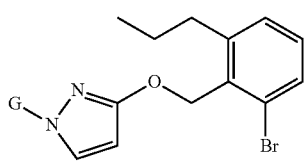

[wherein G represents a substituent corresponding to each of substituents Nos. 1 to 144 indicated in Table 26 to Table 30 as below-mentioned];

Compounds L10H-001~L10H-144 represent tetrazolinone Compounds represented by a formula:

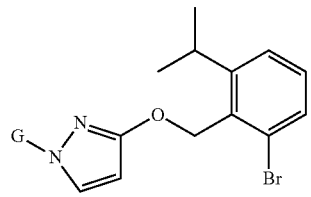

[wherein G represents a substituent corresponding to each of substituents Nos. 1 to 144 indicated in Table 26 to Table 30 as below-mentioned];

Compounds L10I-001~L10I-144 represent tetrazolinone Compounds represented by a formula:

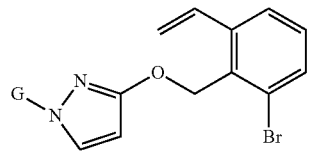

[wherein G represents a substituent corresponding to each of substituents Nos. 1 to 144 indicated in Table 26 to Table 30 as below-mentioned];

Compounds L10J-001~L10J-144 represent tetrazolinone Compounds represented by a formula:

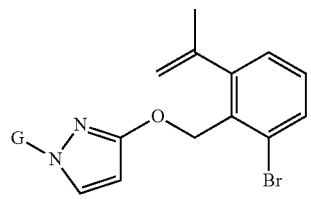

[wherein G represents a substituent corresponding to each of substituents Nos. 1 to 144 indicated in Table 26 to Table 30 as below-mentioned];

Compounds L10K-001~L10K-144 represent tetrazolinone Compounds represented by a formula:

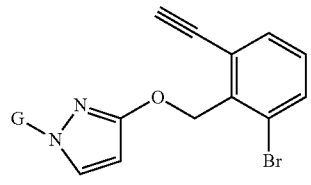

[wherein G represents a substituent corresponding to each of substituents Nos. 1 to 144 indicated in Table 26 to Table 30 as below-mentioned];

Compounds L10L-001~L10L-144 represent tetrazolinone Compounds represented by a formula:

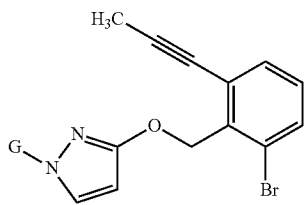

[wherein G represents a substituent corresponding to each of substituents Nos. 1 to 144 indicated in Table 26 to Table 30 as below-mentioned];

Compounds L10M-001~L10M-144 represent tetrazolinone Compounds represented by a formula:

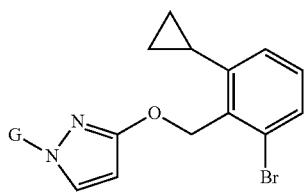

[wherein G represents a substituent corresponding to each of substituents Nos. 1 to 144 indicated in Table 26 to Table 30 as below-mentioned];

Compounds L10N-001~L10N-144 represent tetrazolinone Compounds represented by a formula:

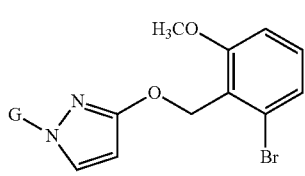

[wherein G represents a substituent corresponding to each of substituents Nos. 1 to 144 indicated in Table 26 to Table 30 as below-mentioned];

Compounds L10O-001~L10O-144 represent tetrazolinone Compounds represented by a formula:

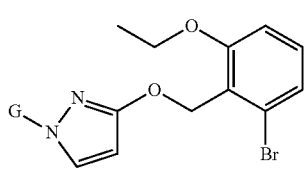

[wherein G represents a substituent corresponding to each of substituents Nos. 1 to 144 indicated in Table 26 to Table 30 as below-mentioned];

Compounds L10P-001~L10P-144 represent tetrazolinone Compounds represented by a formula:

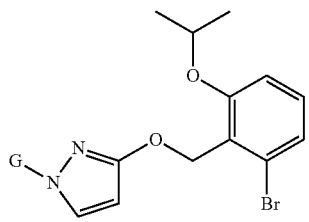

[wherein G represents a substituent corresponding to each of substituents Nos. 1 to 144 indicated in Table 26 to Table 30 as below-mentioned];

Compounds L10Q-001~L10Q-144 represent tetrazolinone Compounds represented by a formula:

[wherein G represents a substituent corresponding to each of substituents Nos. 1 to 144 indicated in Table 26 to Table 30 as below-mentioned];

Compounds L10R-001~L10R-144 represent tetrazolinone Compounds represented by a formula:

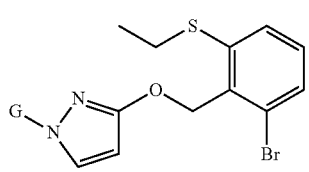

[wherein G represents a substituent corresponding to each of substituents Nos. 1 to 144 indicated in Table 26 to Table 30 as below-mentioned];

Compounds L10S-001~L10S-144 represent tetrazolinone Compounds represented by a formula:

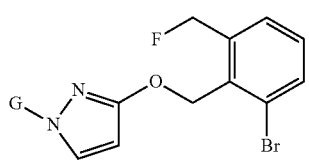

[wherein G represents a substituent corresponding to each of substituents Nos. 1 to 144 indicated in Table 26 to Table 30 as below-mentioned];

Compounds L10T-001~L10T-144 represent tetrazolinone Compounds represented by a formula:

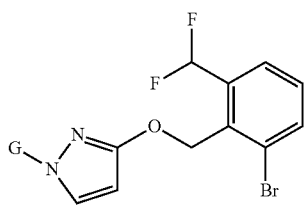

[wherein G represents a substituent corresponding to each of substituents Nos. 1 to 144 indicated in Table 26 to Table 30 as below-mentioned];

Compounds L10U-001~L10U-144 represent tetrazolinone Compounds represented by a formula:

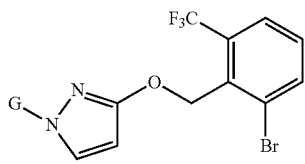

[wherein G represents a substituent corresponding to each of substituents Nos. 1 to 144 indicated in Table 26 to Table 30 as below-mentioned];

Compounds L10V-001~L10V-144 represent tetrazolinone Compounds represented by a formula:

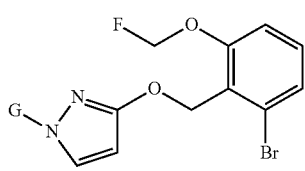

[wherein G represents a substituent corresponding to each of substituents Nos. 1 to 144 indicated in Table 26 to Table 30 as below-mentioned];

Compounds L10W-001~L10W-144 represent tetrazolinone Compounds represented by a formula:

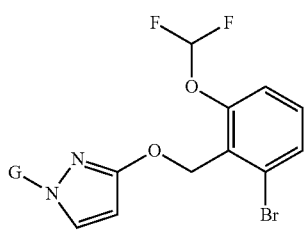

[wherein G represents a substituent corresponding to each of substituents Nos. 1 to 144 indicated in Table 26 to Table 30 as below-mentioned];

Compounds L10X-001~L10X-144 represent tetrazolinone Compounds represented by a formula:

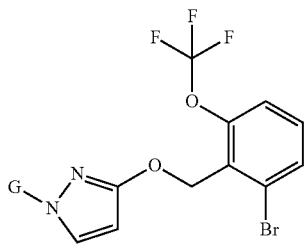

[wherein G represents a substituent corresponding to each of substituents Nos. 1 to 144 indicated in Table 26 to Table 30 as below-mentioned];

Compounds L10Y-001~L10Y-144 represent tetrazolinone Compounds represented by a formula:

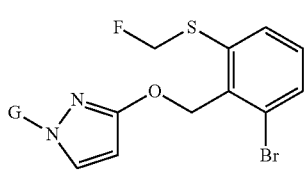

[wherein G represents a substituent corresponding to each of substituents Nos. 1 to 144 indicated in Table 26 to Table 30 as below-mentioned];

Compounds L10Z-001~L10Z-144 represent tetrazolinone Compounds represented by a formula:

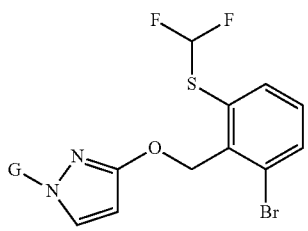

[wherein G represents a substituent corresponding to each of substituents Nos. 1 to 144 indicated in Table 26 to Table 30 as below-mentioned];

Compounds L10AA-001~L10AA-144 represent tetrazolinone Compounds represented by a formula:

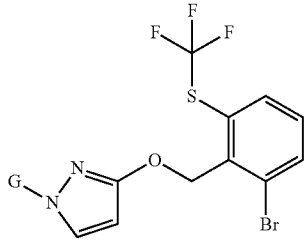

[wherein G represents a substituent corresponding to each of substituents Nos. 1 to 144 indicated in Table 26 to Table 30 as below-mentioned];

Compounds L11A-001~L11A-144 represent tetrazolinone Compounds represented by a formula:

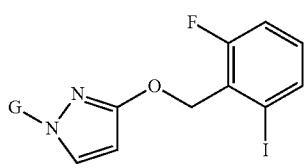

[wherein G represents a substituent corresponding to each of substituents Nos. 1 to 144 indicated in Table 26 to Table 30 as below-mentioned];

Compounds L11B-001~L11B-144 represent tetrazolinone Compounds represented by a formula:

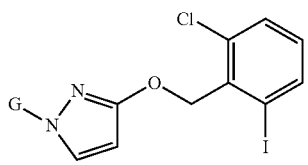

[wherein G represents a substituent corresponding to each of substituents Nos. 1 to 144 indicated in Table 26 to Table 30 as below-mentioned];

Compounds L11C-001~L11C-144 represent tetrazolinone Compounds represented by a formula:

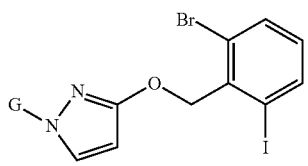

[wherein G represents a substituent corresponding to each of substituents Nos. 1 to 144 indicated in Table 26 to Table 30 as below-mentioned];

Compounds L11D-001~L11D-144 represent tetrazolinone Compounds represented by a formula:

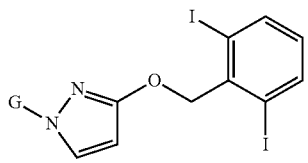

[wherein G represents a substituent corresponding to each of substituents Nos. 1 to 144 indicated in Table 26 to Table 30 as below-mentioned];

Compounds L11E-001~L11E-144 represent tetrazolinone Compounds represented by a formula:

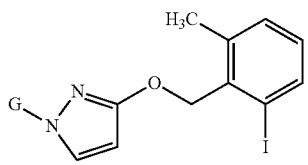

[wherein G represents a substituent corresponding to each of substituents Nos. 1 to 144 indicated in Table 26 to Table 30 as below-mentioned];

Compounds L11F-001~L11F-144 represent tetrazolinone Compounds represented by a formula:

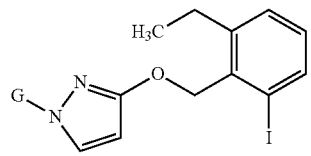

[wherein G represents a substituent corresponding to each of substituents Nos. 1 to 144 indicated in Table 26 to Table 30 as below-mentioned];

Compounds L11G-001~L11G-144 represent tetrazolinone Compounds represented by a formula:

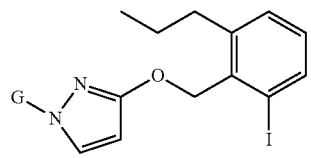

[wherein G represents a substituent corresponding to each of substituents Nos. 1 to 144 indicated in Table 26 to Table 30 as below-mentioned];

Compounds L11H-001~L11H-144 represent tetrazolinone Compounds represented by a formula:

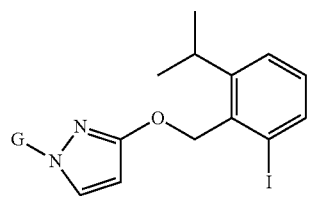

[wherein G represents a substituent corresponding to each of substituents Nos. 1 to 144 indicated in Table 26 to Table 30 as below-mentioned];

Compounds L11I-001~L11I-144 represent tetrazolinone Compounds represented by a formula:

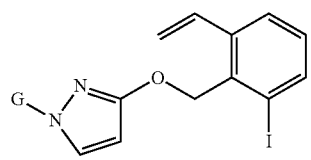

[wherein G represents a substituent corresponding to each of substituents. Nos. 1 to 144 indicated in Table 26 to Table 30 as below-mentioned];

Compounds L11J-001~L11J-144 represent tetrazolinone Compounds represented by a formula:

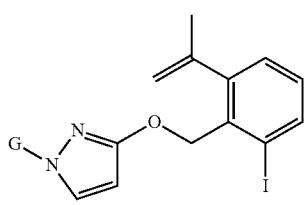

[wherein G represents a substituent corresponding to each of substituents Nos. 1 to 144 indicated in Table 26 to Table 30 as below-mentioned];

Compounds L11K-001~L11K-144 represent tetrazolinone Compounds represented by a formula:

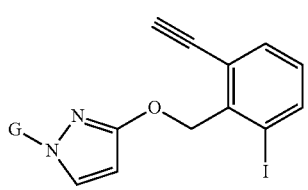

[wherein G represents a substituent corresponding to each of substituents Nos. 1 to 144 indicated in Table 26 to Table 30 as below-mentioned];

Compounds L11L-001~L11L-144 represent tetrazolinone Compounds represented by a formula:

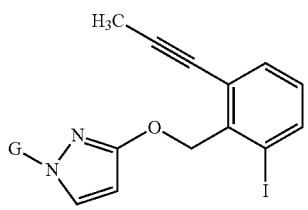

[wherein G represents a substituent corresponding to each of substituents Nos. 1 to 144 indicated in Table 26 to Table 30 as below-mentioned];

Compounds L11M-001~L11M-144 represent tetrazolinone Compounds represented by a formula:

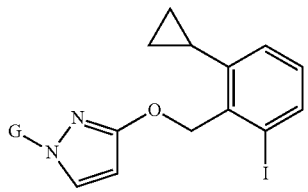

[wherein G represents a substituent corresponding to each of substituents Nos. 1 to 144 indicated in Table 26 to Table 30 as below-mentioned];

Compounds L11N-001~L11N-144 represent tetrazolinone Compounds represented by a formula:

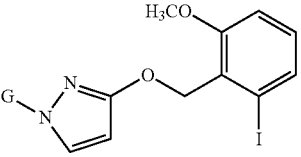

[wherein G represents a substituent corresponding to each of substituents Nos. 1 to 144 indicated in Table 26 to Table 30 as below-mentioned];

Compounds L11O-001~L11O-144 represent tetrazolinone Compounds represented by a formula:

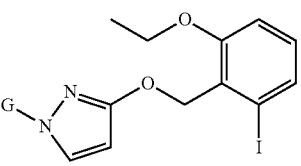

[wherein G represents a substituent corresponding to each of substituents Nos. 1 to 144 indicated in Table 26 to Table 30 as below-mentioned];

Compounds L11P-001~L11P-144 represent tetrazolinone Compounds represented by a formula:

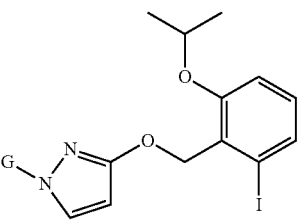

[wherein G represents a substituent corresponding to each of substituents Nos. 1 to 144 indicated in Table 26 to Table 30 as below-mentioned];

Compounds L11Q-001~L11Q-144 represent tetrazolinone Compounds represented by a formula:

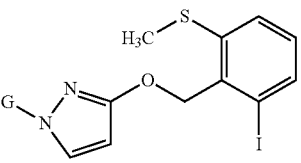

[wherein G represents a substituent corresponding to each of substituents Nos. 1 to 144 indicated in Table 26 to Table 30 as below-mentioned];

Compounds L11R-001~L11R-144 represent tetrazolinone Compounds represented by a formula:

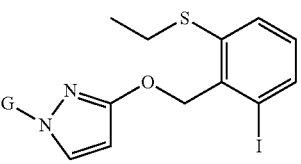

[wherein G represents a substituent corresponding to each of substituents Nos. 1 to 144 indicated in Table 26 to Table 30 as below-mentioned];

Compounds L11S-001~L11S-144 represent tetrazolinone Compounds represented by a formula:

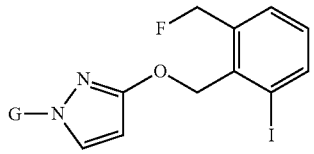

[wherein G represents a substituent corresponding to each of substituents Nos. 1 to 144 indicated in Table 26 to Table 30 as below-mentioned];

Compounds L11T-001~L11T-144 represent tetrazolinone Compounds represented by a formula:

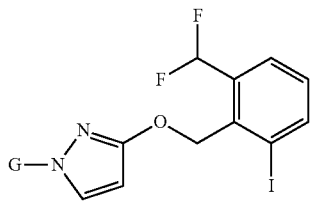

[wherein G represents a substituent corresponding to each of substituents Nos. 1 to 144 indicated in Table 26 to Table 30 as below-mentioned];

Compounds L11U-001~L11U-144 represent tetrazolinone Compounds represented by a formula:

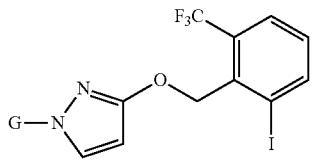

[wherein G represents a substituent corresponding to each of substituents Nos. 1 to 144 indicated in Table 26 to Table 30 as below-mentioned];

Compounds L11V-001~L11V-144 represent tetrazolinone Compounds represented by a formula:

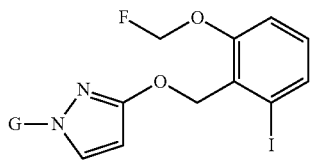

[wherein G represents a substituent corresponding to each of substituents Nos. 1 to 144 indicated in Table 26 to Table 30 as below-mentioned];

Compounds L11W-001~L11W-144 represent tetrazolinone Compounds represented by a formula:

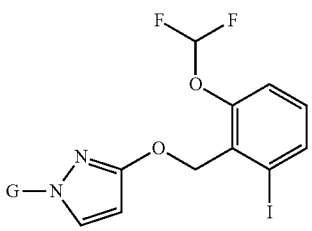

[wherein G represents a substituent corresponding to each of substituents Nos. 1 to 144 indicated in Table 26 to Table 30 as below-mentioned];

Compounds L11X-001~L11X-144 represent tetrazolinone Compounds represented by a formula:

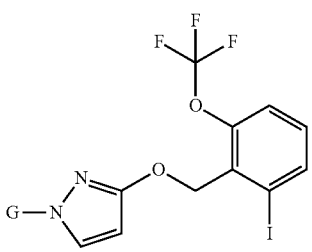

[wherein G represents a substituent corresponding to each of substituents Nos. 1 to 144 indicated in Table 26 to Table 30 as below-mentioned];

Compounds L11Y-001~L11Y-144 represent tetrazolinone Compounds represented by a formula:

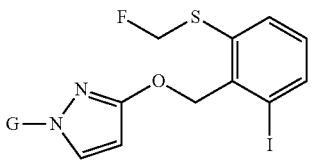

[wherein G represents a substituent corresponding to each of substituents Nos. 1 to 144 indicated in Table 26 to Table 30 as below-mentioned];

Compounds L11Z-001~L11Z-144 represent tetrazolinone Compounds represented by a formula:

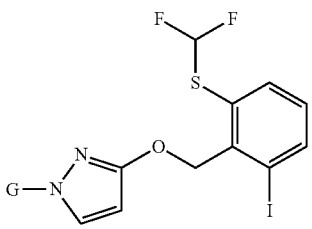

[wherein G represents a substituent corresponding to each of substituents Nos. 1 to 144 indicated in Table 26 to Table 30 as below-mentioned];

Compounds L11AA-001~L11AA-144 represent tetrazolinone Compounds represented by a formula:

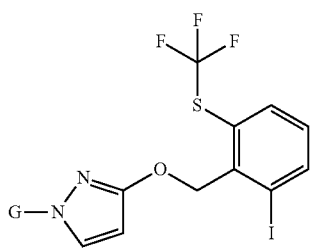

[wherein G represents a substituent corresponding to each of substituents Nos. 1 to 144 indicated in Table 26 to Table 30 as below-mentioned];

Compounds L12A-001~L12A-144 represent tetrazolinone Compounds represented by a formula:

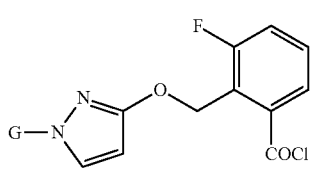

[wherein G represents a substituent corresponding to each of substituents Nos. 1 to 144 indicated in Table 26 to Table 30 as below-mentioned];

Compounds L12B-001~L12B-144 represent tetrazolinone Compounds represented by a formula:

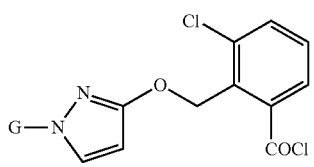

[wherein G represents a substituent corresponding to each of substituents Nos. 1 to 144 indicated in Table 26 to Table 30 as below-mentioned];

Compounds L12C-001~L12C-144 represent tetrazolinone Compounds represented by a formula:

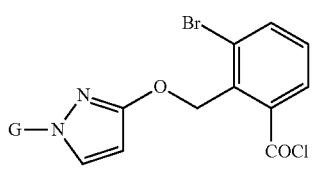

[wherein G represents a substituent corresponding to each of substituents Nos. 1 to 144 indicated in Table 26 to Table 30 as below-mentioned];

Compounds L12D-001~L12D-144 represent tetrazolinone Compounds represented by a formula:

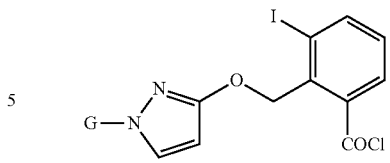

[wherein G represents a substituent corresponding to each of substituents Nos. 1 to 144 indicated in Table 26 to Table 30 as below-mentioned];

Compounds L12E-001~L12E-144 represent tetrazolinone Compounds represented by a formula:

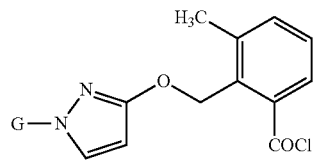

[wherein G represents a substituent corresponding to each of substituents Nos. 1 to 144 indicated in Table 26 to Table 30 as below-mentioned];

Compounds L12F-001~L12F-144 represent tetrazolinone Compounds represented by a formula:

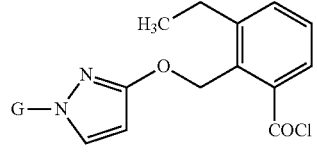

[wherein G represents a substituent corresponding to each of substituents Nos. 1 to 144 indicated in Table 26 to Table 30 as below-mentioned];

Compounds L12G-001~L12G-144 represent tetrazolinone Compounds represented by a formula:

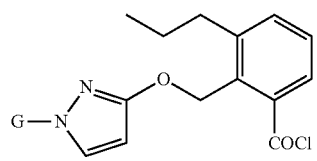

[wherein G represents a substituent corresponding to each of substituents Nos. 1 to 144 indicated in Table 26 to Table 30 as below-mentioned];

Compounds L12H-001~L12H-144 represent tetrazolinone Compounds represented by a formula:

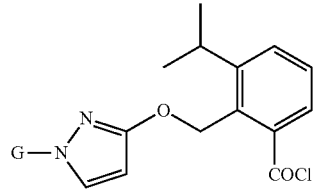

[wherein G represents a substituent corresponding to each of substituents Nos. 1 to 144 indicated in Table 26 to Table 30 as below-mentioned];

Compounds L12I-001~L12I-144 represent tetrazolinone Compounds represented by a formula:

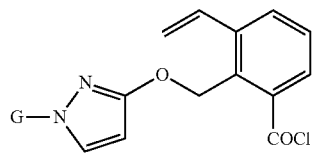

[wherein G represents a substituent corresponding to each of substituents Nos. 1 to 144 indicated in Table 26 to Table 30 as below-mentioned];

Compounds L12J-001~L12J-144 represent tetrazolinone Compounds represented by a formula:

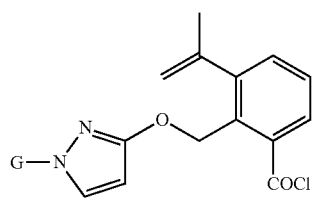

[wherein G represents a substituent corresponding to each of substituents Nos. 1 to 144 indicated in Table 26 to Table 30 as below-mentioned];

Compounds L12K-001~L12K-144 represent tetrazolinone Compounds represented by a formula:

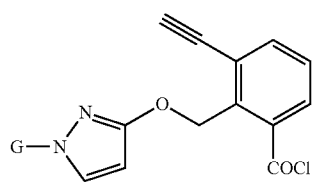

[wherein G represents a substituent corresponding to each of substituents Nos. 1 to 144 indicated in Table 26 to Table 30 as below-mentioned];

Compounds L12L-001~L12L-144 represent tetrazolinone Compounds represented by a formula:

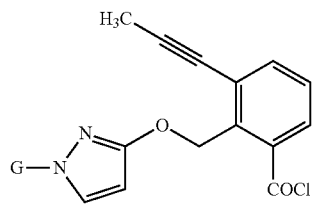

[wherein G represents a substituent corresponding to each of substituents Nos. 1 to 144 indicated in Table 26 to Table 30 as below-mentioned];

Compounds L12M-001~L12M-144 represent tetrazolinone Compounds represented by a formula:

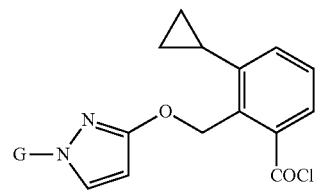

[wherein G represents a substituent corresponding to each of substituents Nos. 1 to 144 indicated in Table 26 to Table 30 as below-mentioned];

Compounds L12N-001~L12N-144 represent tetrazolinone Compounds represented by a formula:

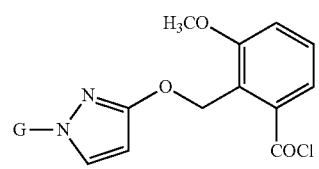

[wherein G represents a substituent corresponding to each of substituents Nos. 1 to 144 indicated in Table 26 to Table 30 as below-mentioned];

Compounds L12O-001~L12O-144 represent tetrazolinone Compounds represented by a formula:

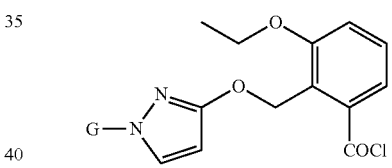

[wherein G represents a substituent corresponding to each of substituents Nos. 1 to 144 indicated in Table 26 to Table 30 as below-mentioned];

Compounds L12P-001~L12P-144 represent tetrazolinone Compounds represented by a formula:

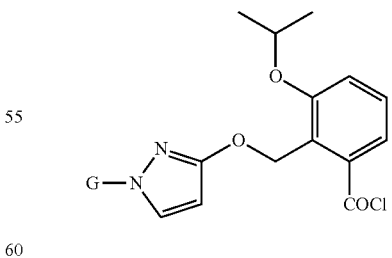

[wherein G represents a substituent corresponding to each of substituents Nos. 1 to 144 indicated in Table 26 to Table 30 as below-mentioned];

Compounds L12Q-001~L12Q-144 represent tetrazolinone Compounds represented by a formula:

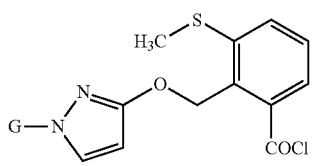

[wherein G represents a substituent corresponding to each of substituents Nos. 1 to 144 indicated in Table 26 to Table 30 as below-mentioned];
Compounds L12R-001~L12R-144 represent tetrazolinone Compounds represented by a formula:

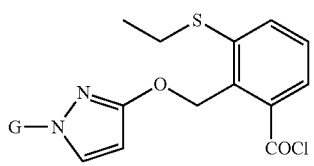

[wherein G represents a substituent corresponding to each of substituents Nos. 1 to 144 indicated in Table 26 to Table 30 as below-mentioned];
Compounds L12S-001~L12S-144 represent tetrazolinone Compounds represented by a formula:

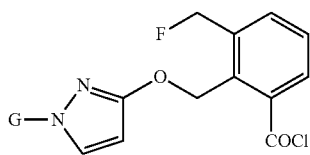

[wherein G represents a substituent corresponding to each of substituents Nos. 1 to 144 indicated in Table 26 to Table 30 as below-mentioned];
Compounds L12T-001~L12T-144 represent tetrazolinone Compounds represented by a formula:

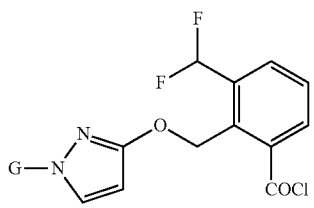

[wherein G represents a substituent corresponding to each of substituents Nos. 1 to 144 indicated in Table 26 to Table 30 as below-mentioned];
Compounds L12U-001~L12U-144 represent tetrazolinone Compounds represented by a formula:

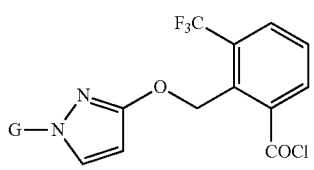

[wherein G represents a substituent corresponding to each of substituents Nos. 1 to 144 indicated in Table 26 to Table 30 as below-mentioned];
Compounds L12V-001~L12V-144 represent tetrazolinone Compounds represented by a formula:

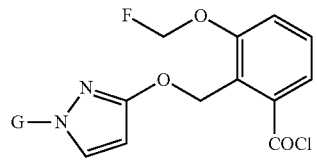

[wherein G represents a substituent corresponding to each of substituents Nos. 1 to 144 indicated in Table 26 to Table 30 as below-mentioned];
Compounds L12W-001~L12W-144 represent tetrazolinone Compounds represented by a formula:

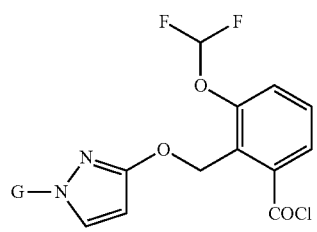

[wherein G represents a substituent corresponding to each of substituents Nos. 1 to 144 indicated in Table 26 to Table 30 as below-mentioned];
Compounds L12X-001~L12X-144 represent tetrazolinone Compounds represented by a formula:

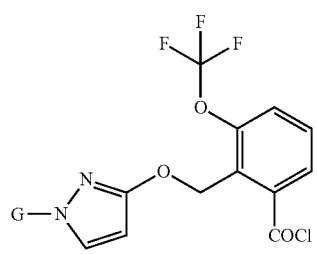

[wherein G represents a substituent corresponding to each of substituents Nos. 1 to 144 indicated in Table 26 to Table 30 as below-mentioned];
Compounds L12Y-001~L12Y-144 represent tetrazolinone Compounds represented by a formula:

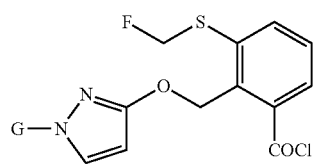

[wherein G represents a substituent corresponding to each of substituents Nos. 1 to 144 indicated in Table 26 to Table 30 as below-mentioned];
Compounds L12Z-001~L12Z-144 represent tetrazolinone Compounds represented by a formula:

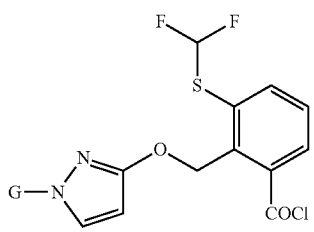

[wherein G represents a substituent corresponding to each of substituents Nos. 1 to 144 indicated in Table 26 to Table 30 as below-mentioned];

Compounds L12AA-001~L12AA-144 represent tetrazolinone Compounds represented by a formula:

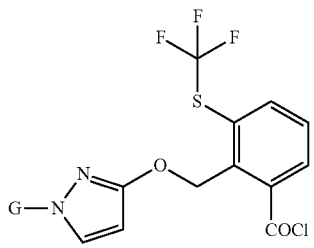

[wherein G represents a substituent corresponding to each of substituents Nos. 1 to 144 indicated in Table 26 to Table 30 as below-mentioned];

Compounds L13A-001~L13A-144 represent tetrazolinone Compounds represented by a formula:

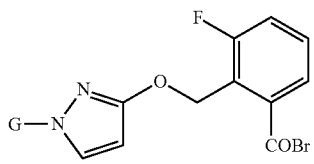

[wherein G represents a substituent corresponding to each of substituents Nos. 1 to 144 indicated in Table 26 to Table 30 as below-mentioned];

Compounds L13B-001~L13B-144 represent tetrazolinone Compounds represented by a formula:

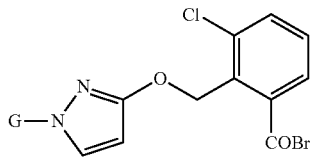

[wherein G represents a substituent corresponding to each of substituents Nos. 1 to 144 indicated in Table 26 to Table 30 as below-mentioned];

Compounds L13C-001~L13C-144 represent tetrazolinone Compounds represented by a formula:

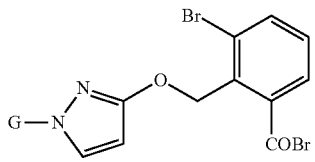

[wherein G represents a substituent corresponding to each of substituents Nos. 1 to 144 indicated in Table 26 to Table 30 as below-mentioned];

Compounds L13D-001~L13D-144 represent tetrazolinone Compounds represented by a formula:

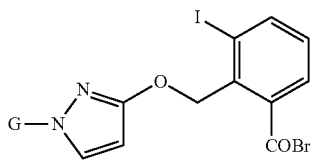

[wherein G represents a substituent corresponding to each of substituents Nos. 1 to 144 indicated in Table 26 to Table 30 as below-mentioned];

Compounds L13E-001~L13E-144 represent tetrazolinone Compounds represented by a formula:

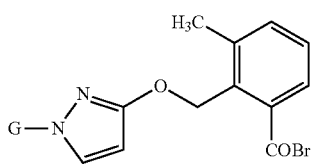

[wherein G represents a substituent corresponding to each of substituents Nos. 1 to 144 indicated in Table 26 to Table 30 as below-mentioned];

Compounds L13F-001~L13F-144 represent tetrazolinone Compounds represented by a formula:

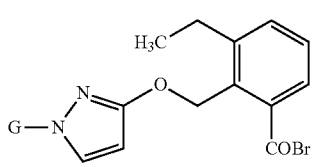

[wherein G represents a substituent corresponding to each of substituents Nos. 1 to 144 indicated in Table 26 to Table 30 as below-mentioned];

Compounds L13G-001~L13G-144 represent tetrazolinone Compounds represented by a formula:

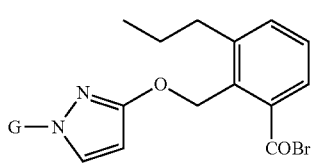

[wherein G represents a substituent corresponding to each of substituents Nos. 1 to 144 indicated in Table 26 to Table 30 as below-mentioned];

Compounds L13H-001~L13H-144 represent tetrazolinone Compounds represented by a formula:

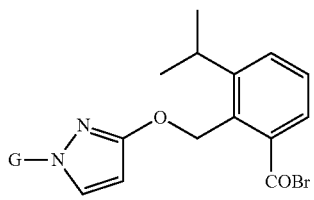

[wherein G represents a substituent corresponding to each of substituents Nos. 1 to 144 indicated in Table 26 to Table 30 as below-mentioned];

Compounds L13I-001~L13I-144 represent tetrazolinone Compounds represented by a formula:

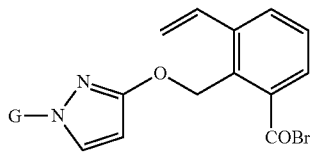

[wherein G represents a substituent corresponding to each of substituents Nos. 1 to 144 indicated in Table 26 to Table 30 as below-mentioned];

Compounds L13J-001~L13J-144 represent tetrazolinone Compounds represented by a formula:

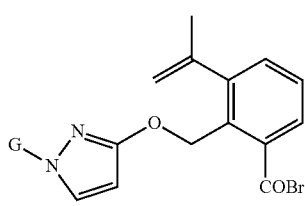

[wherein G represents a substituent corresponding to each of substituents Nos. 1 to 144 indicated in Table 26 to Table 30 as below-mentioned];

Compounds L13K-001~L13K-144 represent tetrazolinone Compounds represented by a formula:

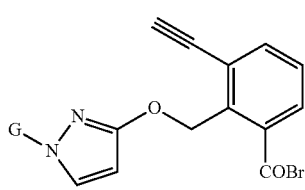

[wherein G represents a substituent corresponding to each of substituents Nos. 1 to 144 indicated in Table 26 to Table 30 as below-mentioned];

Compounds L13L-001~L13L-144 represent tetrazolinone Compounds represented by a formula:

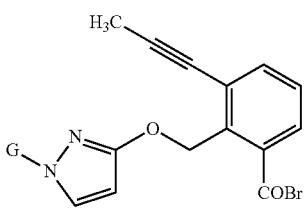

[wherein G represents a substituent corresponding to each of substituents Nos. 1 to 144 indicated in Table 26 to Table 30 as below-mentioned];

Compounds L13M-001~L13M-144 represent tetrazolinone Compounds represented by a formula:

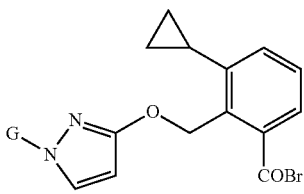

[wherein G represents a substituent corresponding to each of substituents Nos. 1 to 144 indicated in Table 26 to Table 30 as below-mentioned];

Compounds L13N-001~L13N-144 represent tetrazolinone Compounds represented by a formula:

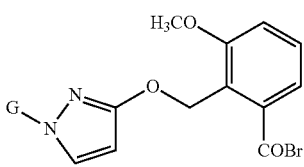

[wherein G represents a substituent corresponding to each of substituents Nos. 1 to 144 indicated in Table 26 to Table 30 as below-mentioned];

Compounds L13O-001~L13O-144 represent tetrazolinone Compounds represented by a formula:

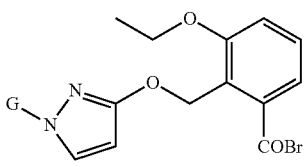

[wherein G represents a substituent corresponding to each of substituents Nos. 1 to 144 indicated in Table 26 to Table 30 as below-mentioned];

Compounds L13P-001~L13P-144 represent tetrazolinone Compounds represented by a formula:

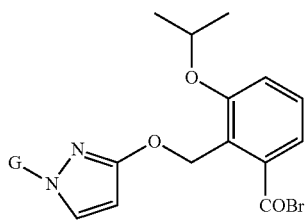

[wherein G represents a substituent corresponding to each of substituents Nos. 1 to 144 indicated in Table 26 to Table 30 as below-mentioned];

Compounds L13Q-001~L13Q-144 represent tetrazolinone Compounds represented by a formula:

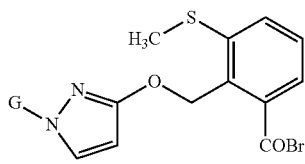

[wherein G represents a substituent corresponding to each of substituents Nos. 1 to 144 indicated in Table 26 to Table 30 as below-mentioned];

Compounds L13R-001~L13R-144 represent tetrazolinone Compounds represented by a formula:

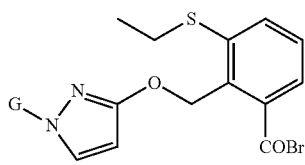

[wherein G represents a substituent corresponding to each of substituents Nos. 1 to 144 indicated in Table 26 to Table 30 as below-mentioned];

Compounds L13S-001~L13S-144 represent tetrazolinone Compounds represented by a formula:

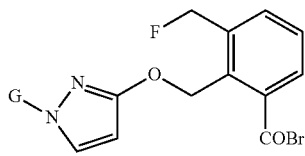

[wherein G represents a substituent corresponding to each of substituents Nos. 1 to 144 indicated in Table 26 to Table 30 as below-mentioned];

Compounds L13T-001~L13T-144 represent tetrazolinone Compounds represented by a formula:

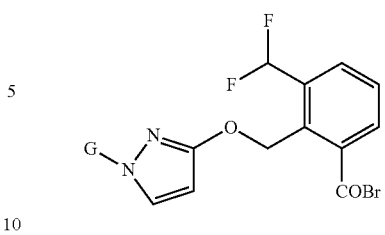

[wherein G represents a substituent corresponding to each of substituents Nos. 1 to 144 indicated in Table 26 to Table 30 as below-mentioned];

Compounds L13U-001~L13U-144 represent tetrazolinone Compounds represented by a formula:

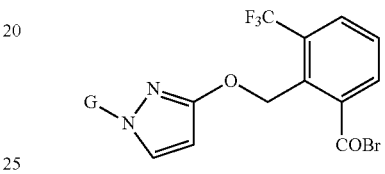

[wherein G represents a substituent corresponding to each of substituents Nos. 1 to 144 indicated in Table 26 to Table 30 as below-mentioned];

Compounds L13V-001~L13V-144 represent tetrazolinone Compounds represented by a formula:

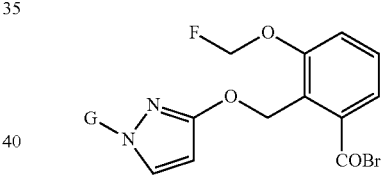

[wherein G represents a substituent corresponding to each of substituents Nos. 1 to 144 indicated in Table 26 to Table 30 as below-mentioned];

Compounds L13W-001~L13W-144 represent tetrazolinone Compounds represented by a formula:

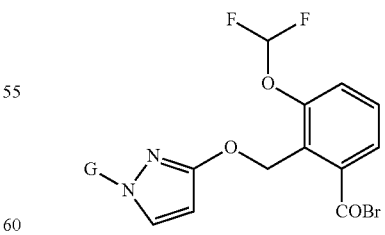

[wherein G represents a substituent corresponding to each of substituents Nos. 1 to 144 indicated in Table 26 to Table 30 as below-mentioned];

Compounds L13X-001~L13X-144 represent tetrazolinone Compounds represented by a formula:

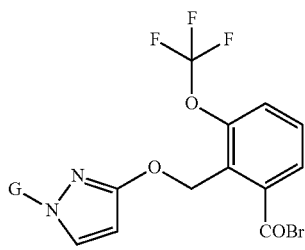

[wherein G represents a substituent corresponding to each of substituents Nos. 1 to 144 indicated in Table 26 to Table 30 as below-mentioned];

Compounds L13Y-001~L13Y-144 represent tetrazolinone Compounds represented by a formula:

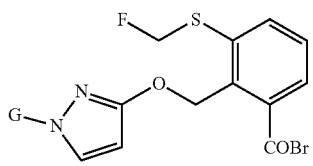

[wherein G represents a substituent corresponding to each of substituents Nos. 1 to 144 indicated in Table 26 to Table 30 as below-mentioned];

Compounds L13Z-001~L13Z-144 represent tetrazolinone Compounds represented by a formula:

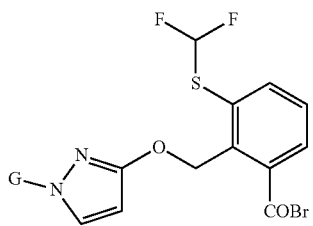

[wherein G represents a substituent corresponding to each of substituents Nos. 1 to 144 indicated in Table 26 to Table 30 as below-mentioned];

Compounds L13AA-001~L13AA-144 represent tetrazolinone Compounds represented by a formula:

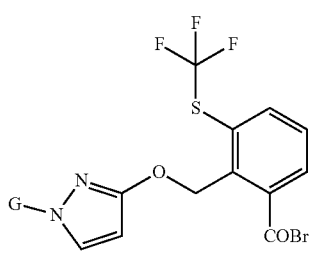

[wherein G represents a substituent corresponding to each of substituents Nos. 1 to 144 indicated in Table 26 to Table 30 as below-mentioned];

Compounds L14A-001~L14A-144 represent tetrazolinone Compounds represented by a formula:

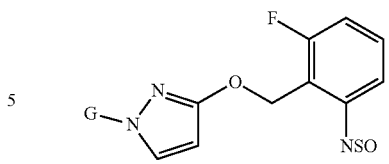

[wherein G represents a substituent corresponding to each of substituents Nos. 1 to 144 indicated in Table 26 to Table 30 as below-mentioned];

Compounds L14B-001~L14B-144 represent tetrazolinone Compounds represented by a formula:

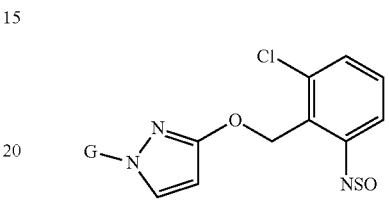

[wherein G represents a substituent corresponding to each of substituents Nos. 1 to 144 indicated in Table 26 to Table 30 as below-mentioned];

Compounds L14C-001~L14C-144 represent tetrazolinone Compounds represented by a formula:

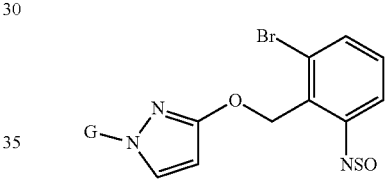

[wherein G represents a substituent corresponding to each of substituents Nos. 1 to 144 indicated in Table 26 to Table 30 as below-mentioned];

Compounds L14D-001~L14D-144 represent tetrazolinone Compounds represented by a formula:

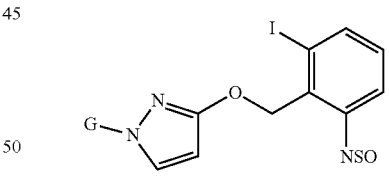

[wherein G represents a substituent corresponding to each of substituents Nos. 1 to 144 indicated in Table 26 to Table 30 as below-mentioned];

Compounds L14E-001~L14E-144 represent tetrazolinone Compounds represented by a formula:

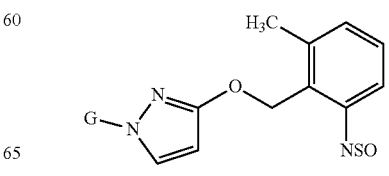

[wherein G represents a substituent corresponding to each of substituents Nos. 1 to 144 indicated in Table 26 to Table 30 as below-mentioned];

Compounds L14F-001~L14F-144 represent tetrazolinone Compounds represented by a formula:

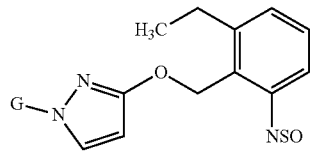

[wherein G represents a substituent corresponding to each of substituents Nos. 1 to 144 indicated in Table 26 to Table 30 as below-mentioned];

Compounds L14G-001~L14G-144 represent tetrazolinone Compounds represented by a formula:

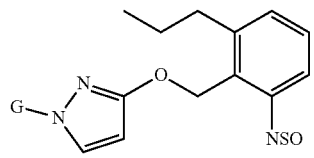

[wherein G represents a substituent corresponding to each of substituents Nos. 1 to 144 indicated in Table 26 to Table 30 as below-mentioned];

Compounds L14H-001~L14H-144 represent tetrazolinone Compounds represented by a formula:

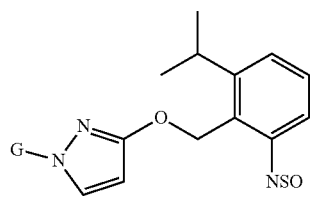

[wherein G represents a substituent corresponding to each of substituents Nos. 1 to 144 indicated in Table 26 to Table 30 as below-mentioned];

Compounds L14I-001~L14I-144 represent tetrazolinone Compounds represented by a formula:

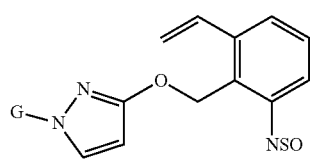

[wherein G represents a substituent corresponding to each of substituents Nos. 1 to 144 indicated in Table 26 to Table 30 as below-mentioned];

Compounds L14J-001~L14J-144 represent tetrazolinone Compounds represented by a formula:

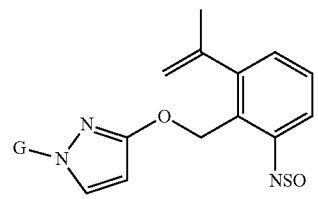

[wherein G represents a substituent corresponding to each of substituents Nos. 1 to 144 indicated in Table 26 to Table 30 as below-mentioned];

Compounds L14K-001~L14K-144 represent tetrazolinone Compounds represented by a formula:

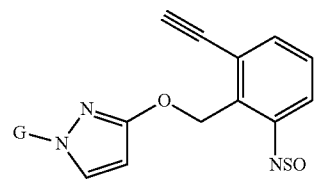

[wherein G represents a substituent corresponding to each of substituents Nos. 1 to 144 indicated in Table 26 to Table 30 as below-mentioned];

Compounds L14L-001~L14L-144 represent tetrazolinone Compounds represented by a formula:

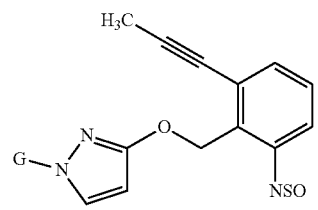

[wherein G represents a substituent corresponding to each of substituents Nos. 1 to 144 indicated in Table 26 to Table 30 as below-mentioned];

Compounds L14M-001~L14M-144 represent tetrazolinone Compounds represented by a formula:

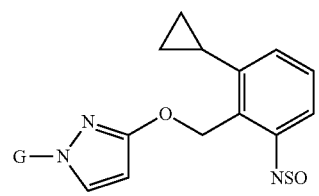

[wherein G represents a substituent corresponding to each of substituents Nos. 1 to 144 indicated in Table 26 to Table 30 as below-mentioned];

Compounds L14N-001~L14N-144 represent tetrazolinone Compounds represented by a formula:

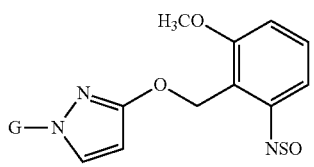

[wherein G represents a substituent corresponding to each of substituents Nos. 1 to 144 indicated in Table 26 to Table 30 as below-mentioned];

Compounds L14O-001~L14O-144 represent tetrazolinone Compounds represented by a formula:

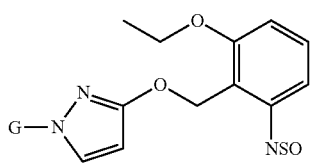

[wherein G represents a substituent corresponding to each of substituents Nos. 1 to 144 indicated in Table 26 to Table 30 as below-mentioned];

Compounds L14P-001~L14P-144 represent tetrazolinone Compounds represented by a formula:

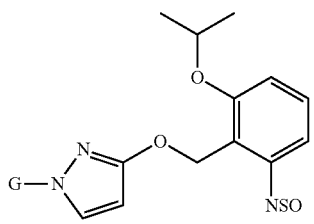

[wherein G represents a substituent corresponding to each of substituents Nos. 1 to 144 indicated in Table 26 to Table 30 as below-mentioned];

Compounds L14Q-001~L14Q-144 represent tetrazolinone Compounds represented by a formula:

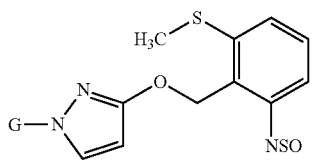

[wherein G represents a substituent corresponding to each of substituents Nos. 1 to 144 indicated in Table 26 to Table 30 as below-mentioned];

Compounds L14R-001~L14R-144 represent tetrazolinone Compounds represented by a formula:

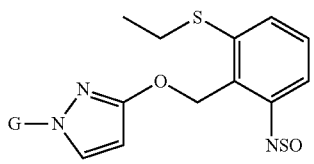

[wherein G represents a substituent corresponding to each of substituents Nos. 1 to 144 indicated in Table 26 to Table 30 as below-mentioned];

Compounds L14S-001~L14S-144 represent tetrazolinone Compounds represented by a formula:

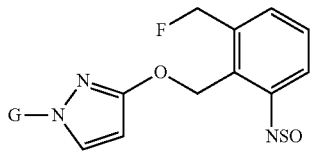

[wherein G represents a substituent corresponding to each of substituents Nos. 1 to 144 indicated in Table 26 to Table 30 as below-mentioned];

Compounds L14T-001~L14T-144 represent tetrazolinone Compounds represented by a formula:

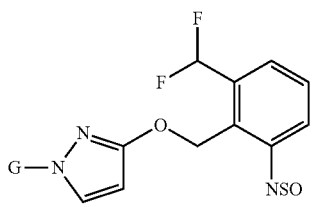

[wherein G represents a substituent corresponding to each of substituents Nos. 1 to 144 indicated in Table 26 to Table 30 as below-mentioned];

Compounds L14U-001~L14U-144 represent tetrazolinone Compounds represented by a formula:

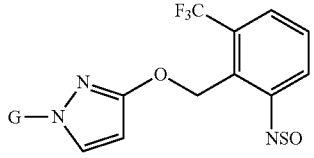

[wherein G represents a substituent corresponding to each of substituents Nos. 1 to 144 indicated in Table 26 to Table 30 as below-mentioned];

Compounds L14V-001~L14V-144 represent tetrazolinone Compounds represented by a formula:

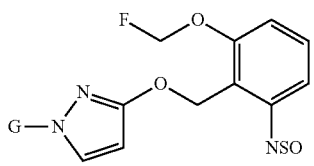

[wherein G represents a substituent corresponding to each of substituents Nos. 1 to 144 indicated in Table 26 to Table 30 as below-mentioned];

Compounds L14W-001~L14W-144 represent tetrazolinone Compounds represented by a formula:

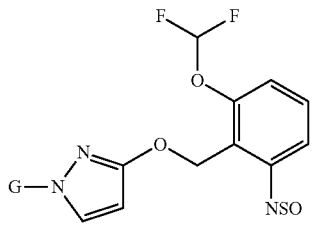

[wherein G represents a substituent corresponding to each of substituents Nos. 1 to 144 indicated in Table 26 to Table 30 as below-mentioned];

Compounds L14X-001~L14X-144 represent tetrazolinone Compounds represented by a formula:

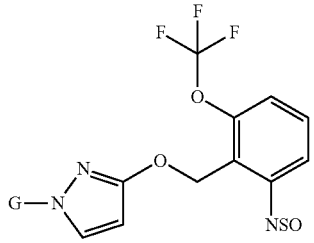

[wherein G represents a substituent corresponding to each of substituents Nos. 1 to 144 indicated in Table 26 to Table 30 as below-mentioned];

Compounds L14Y-001~L14Y-144 represent tetrazolinone Compounds represented by a formula:

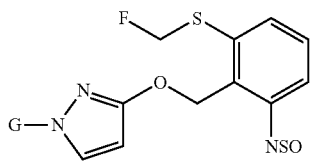

[wherein G represents a substituent corresponding to each of substituents Nos. 1 to 144 indicated in Table 26 to Table 30 as below-mentioned];

Compounds L14Z-001~L14Z-144 represent tetrazolinone Compounds represented by a formula:

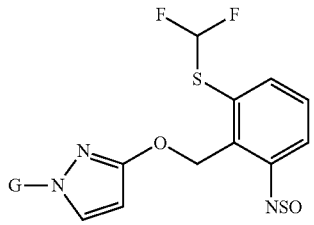

[wherein G represents a substituent corresponding to each of substituents Nos. 1 to 144 indicated in Table 26 to Table 30 as below-mentioned];

Compounds L14AA-001~L14AA-144 represent tetrazolinone Compounds represented by a formula:

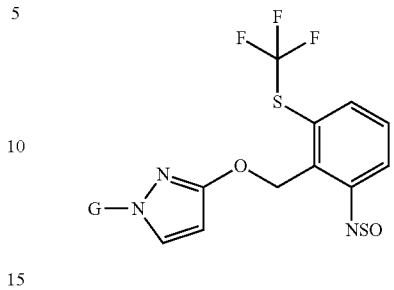

[wherein G represents a substituent corresponding to each of substituents Nos. 1 to 144 indicated in Table 26 to Table 30 as below-mentioned];

Compounds L15A-001~L15A-144 represent tetrazolinone Compounds represented by a formula:

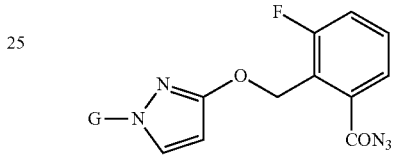

[wherein G represents a substituent corresponding to each of substituents Nos. 1 to 144 indicated in Table 26 to Table 30 as below-mentioned];

Compounds L15B-001~L15B-144 represent tetrazolinone Compounds represented by a formula:

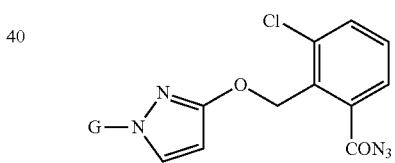

[wherein G represents a substituent corresponding to each of substituents Nos. 1 to 144 indicated in Table 26 to Table 30 as below-mentioned];

Compounds L15C-001~L15C-144 represent tetrazolinone Compounds represented by a formula:

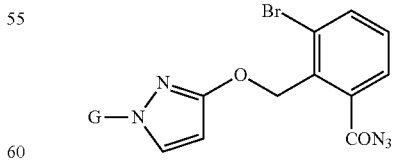

[wherein G represents a substituent corresponding to each of substituents Nos. 1 to 144 indicated in Table 26 to Table 30 as below-mentioned];

Compounds L15D-001~L15D-144 represent tetrazolinone Compounds represented by a formula:

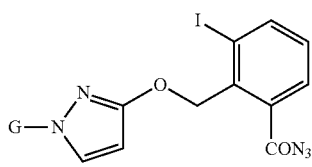

[wherein G represents a substituent corresponding to each of substituents Nos. 1 to 144 indicated in Table 26 to Table 30 as below-mentioned];
Compounds L15E-001~L15E-144 represent tetrazolinone Compounds represented by a formula:

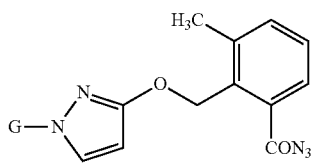

[wherein G represents a substituent corresponding to each of substituents Nos. 1 to 144 indicated in Table 26 to Table 30 as below-mentioned];
Compounds L15F-001~L15F-144 represent tetrazolinone Compounds represented by a formula:

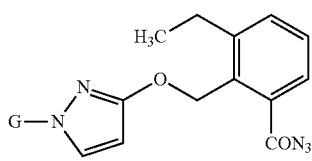

[wherein G represents a substituent corresponding to each of substituents Nos. 1 to 144 indicated in Table 26 to Table 30 as below-mentioned];
Compounds L15G-001~L15G-144 represent tetrazolinone Compounds represented by a formula:

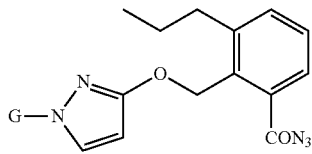

[wherein G represents a substituent corresponding to each of substituents Nos. 1 to 144 indicated in Table 26 to Table 30 as below-mentioned];
Compounds L15H-001~L15H-144 represent tetrazolinone Compounds represented by a formula:

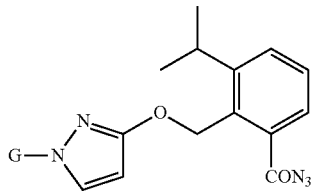

[wherein G represents a substituent corresponding to each of substituents Nos. 1 to 144 indicated in Table 26 to Table 30 as below-mentioned];
Compounds L15I-001~L15I-144 represent tetrazolinone Compounds represented by a formula:

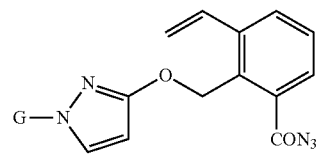

[wherein G represents a substituent corresponding to each of substituents Nos. 1 to 144 indicated in Table 26 to Table 30 as below-mentioned];
Compounds L15J-001~L15J-144 represent tetrazolinone Compounds represented by a formula:

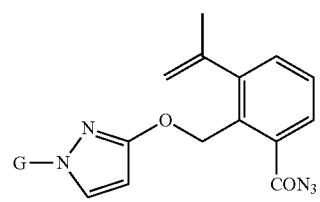

[wherein G represents a substituent corresponding to each of substituents Nos. 1 to 144 indicated in Table 26 to Table 30 as below-mentioned];
Compounds L15K-001~L15K-144 represent tetrazolinone Compounds represented by a formula:

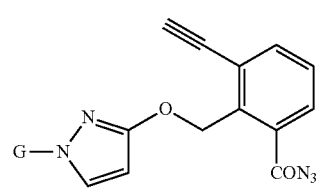

[wherein G represents a substituent corresponding to each of substituents Nos. 1 to 144 indicated in Table 26 to Table 30 as below-mentioned];
Compounds L15L-001~L15L-144 represent tetrazolinone Compounds represented by a formula:

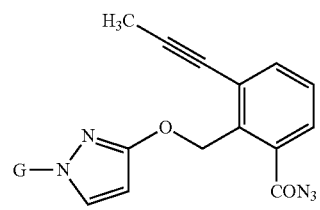

[wherein G represents a substituent corresponding to each of substituents Nos. 1 to 144 indicated in Table 26 to Table 30 as below-mentioned];
Compounds L15M-001~L15M-144 represent tetrazolinone Compounds represented by a formula:

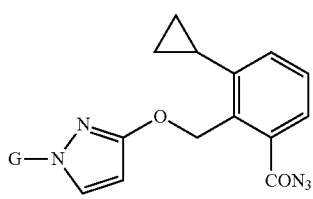

[wherein G represents a substituent corresponding to each of substituents Nos. 1 to 144 indicated in Table 26 to Table 30 as below-mentioned];

Compounds L15N-001~L15N-144 represent tetrazolinone Compounds represented by a formula:

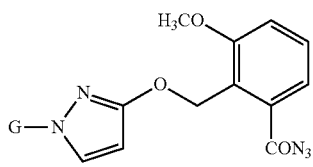

[wherein G represents a substituent corresponding to each of substituents Nos. 1 to 144 indicated in Table 26 to Table 30 as below-mentioned];

Compounds L15O-001~L15O-144 represent tetrazolinone Compounds represented by a formula:

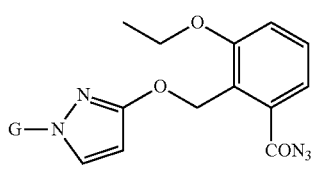

[wherein G represents a substituent corresponding to each of substituents Nos. 1 to 144 indicated in Table 26 to Table 30 as below-mentioned];

Compounds L15P-001~L15P-144 represent tetrazolinone Compounds represented by a formula:

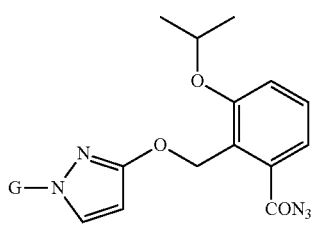

[wherein G represents a substituent corresponding to each of substituents Nos. 1 to 144 indicated in Table 26 to Table 30 as below-mentioned];

Compounds L15Q-001~L15Q-144 represent tetrazolinone Compounds represented by a formula:

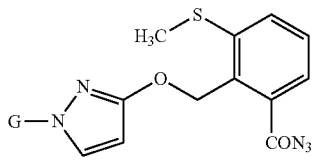

[wherein G represents a substituent corresponding to each of substituents Nos. 1 to 144 indicated in Table 26 to Table 30 as below-mentioned];

Compounds L15R-001~L15R-144 represent tetrazolinone Compounds represented by a formula:

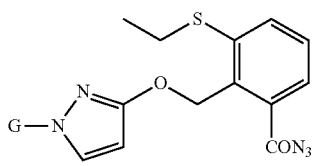

[wherein G represents a substituent corresponding to each of substituents Nos. 1 to 144 indicated in Table 26 to Table 30 as below-mentioned];

Compounds L15S-001~L15S-144 represent tetrazolinone Compounds represented by a formula:

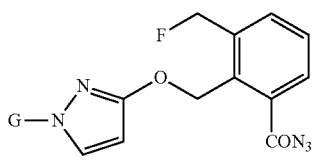

[wherein G represents a substituent corresponding to each of substituents Nos. 1 to 144 indicated in Table 26 to Table 30 as below-mentioned];

Compounds L15T-001~L15T-144 represent tetrazolinone Compounds represented by a formula:

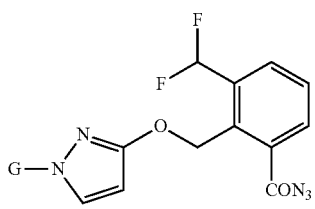

[wherein G represents a substituent corresponding to each of substituents Nos. 1 to 144 indicated in Table 26 to Table 30 as below-mentioned];

Compounds L15U-001~L15U-144 represent tetrazolinone Compounds represented by a formula:

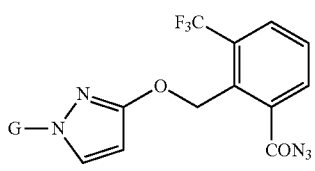

[wherein G represents a substituent corresponding to each of substituents Nos. 1 to 144 indicated in Table 26 to Table 30 as below-mentioned];

Compounds L15V-001~L15V-144 represent tetrazolinone Compounds represented by a formula:

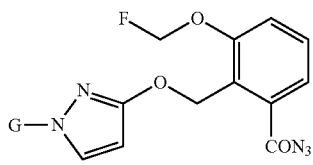

[wherein G represents a substituent corresponding to each of substituents Nos. 1 to 144 indicated in Table 26 to Table 30 as below-mentioned];

Compounds L15W-001~L15W-144 represent tetrazolinone Compounds represented by a formula:

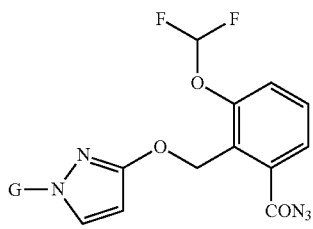

[wherein G represents a substituent corresponding to each of substituents Nos. 1 to 144 indicated in Table 26 to Table 30 as below-mentioned];

Compounds L15X-001~L15X-144 represent tetrazolinone Compounds represented by a formula:

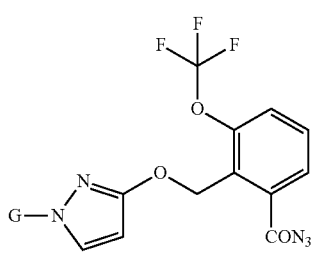

[wherein G represents a substituent corresponding to each of substituents Nos. 1 to 144 indicated in Table 26 to Table 30 as below-mentioned];

Compounds L15Y-001~L15Y-144 represent tetrazolinone Compounds represented by a formula:

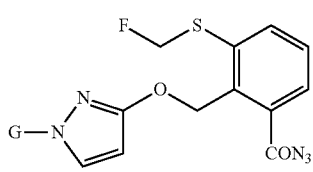

[wherein G represents a substituent corresponding to each of substituents Nos. 1 to 144 indicated in Table 26 to Table 30 as below-mentioned];

Compounds L15Z-001~L15Z-144 represent tetrazolinone Compounds represented by a formula:

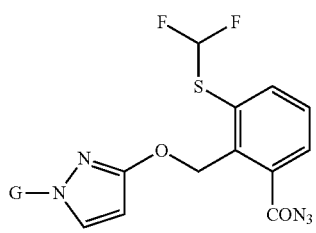

[wherein G represents a substituent corresponding to each of substituents Nos. 1 to 144 indicated in Table 26 to Table 30 as below-mentioned];

Compounds L15AA-001~L15AA-144 represent tetrazolinone Compounds represented by a formula:

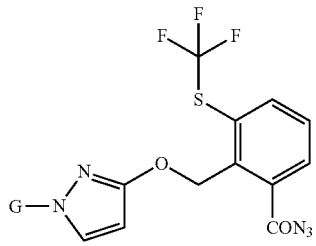

[wherein G represents a substituent corresponding to each of substituents Nos. 1 to 144 indicated in Table 26 to Table 30 as below-mentioned];

Compounds L16A-001~L16A-144 represent tetrazolinone Compounds represented by a formula:

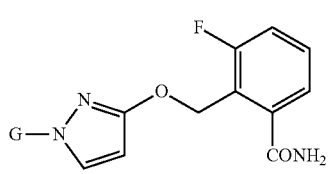

[wherein G represents a substituent corresponding to each of substituents Nos. 1 to 144 indicated in Table 26 to Table 30 as below-mentioned];

Compounds L16B-001~L16B-144 represent tetrazolinone Compounds represented by a formula:

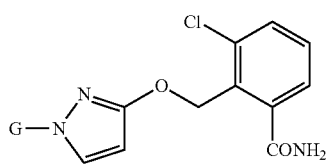

[wherein G represents a substituent corresponding to each of substituents Nos. 1 to 144 indicated in Table 26 to Table 30 as below-mentioned];

Compounds L16C-001~L16C-144 represent tetrazolinone Compounds represented by a formula:

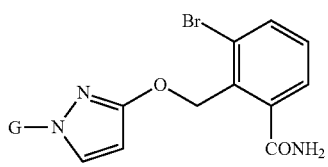

[wherein G represents a substituent corresponding to each of substituents Nos. 1 to 144 indicated in Table 26 to Table 30 as below-mentioned];
Compounds L16D-001~L16D-144 represent tetrazolinone Compounds represented by a formula:

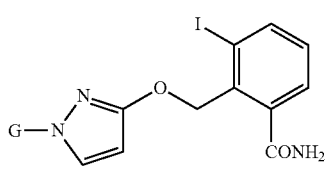

[wherein G represents a substituent corresponding to each of substituents Nos. 1 to 144 indicated in Table 26 to Table 30 as below-mentioned];
Compounds L16E-001~L16E-144 represent tetrazolinone Compounds represented by a formula:

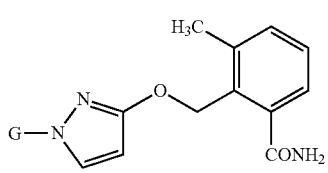

[wherein G represents a substituent corresponding to each of substituents Nos. 1 to 144 indicated in Table 26 to Table 30 as below-mentioned];
Compounds L16F-001~L16F-144 represent tetrazolinone Compounds represented by a formula:

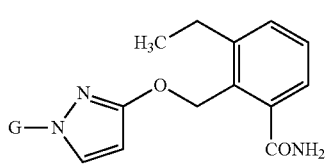

[wherein G represents a substituent corresponding to each of substituents Nos. 1 to 144 indicated in Table 26 to Table 30 as below-mentioned];
Compounds L16G-001~L16G-144 represent tetrazolinone Compounds represented by a formula:

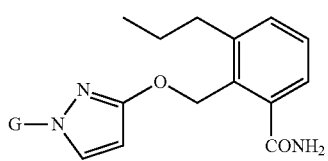

[wherein G represents a substituent corresponding to each of substituents Nos. 1 to 144 indicated in Table 26 to Table 30 as below-mentioned];

Compounds L16H-001~L16H-144 represent tetrazolinone Compounds represented by a formula:

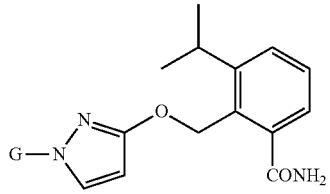

[wherein G represents a substituent corresponding to each of substituents Nos. 1 to 144 indicated in Table 26 to Table 30 as below-mentioned];
Compounds L16I-001~L16I-144 represent tetrazolinone Compounds represented by a formula:

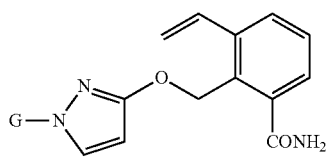

[wherein G represents a substituent corresponding to each of substituents Nos. 1 to 144 indicated in Table 26 to Table 30 as below-mentioned];
Compounds L16J-001~L16J-144 represent tetrazolinone Compounds represented by a formula:

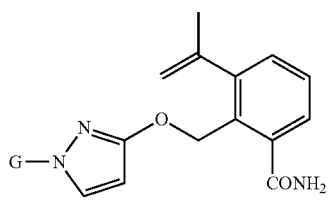

[wherein G represents a substituent corresponding to each of substituents Nos. 1 to 144 indicated in Table 26 to Table 30 as below-mentioned];
Compounds L16K-001~L16K-144 represent tetrazolinone Compounds represented by a formula:

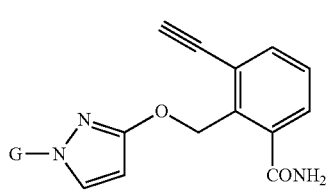

[wherein G represents a substituent corresponding to each of substituents Nos. 1 to 144 indicated in Table 26 to Table 30 as below-mentioned];
Compounds L16L-001~L16L-144 represent tetrazolinone Compounds represented by a formula:

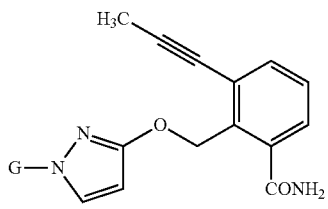

[wherein G represents a substituent corresponding to each of substituents Nos. 1 to 144 indicated in Table 26 to Table 30 as below-mentioned];

Compounds L16M-001~L16M-144 represent tetrazolinone Compounds represented by a formula:

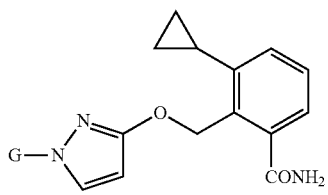

[wherein G represents a substituent corresponding to each of substituents Nos. 1 to 144 indicated in Table 26 to Table 30 as below-mentioned];

Compounds L16N-001~L16N-144 represent tetrazolinone Compounds represented by a formula:

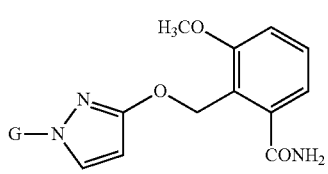

[wherein G represents a substituent corresponding to each of substituents Nos. 1 to 144 indicated in Table 26 to Table 30 as below-mentioned];

Compounds L16O-001~L16O-144 represent tetrazolinone Compounds represented by a formula:

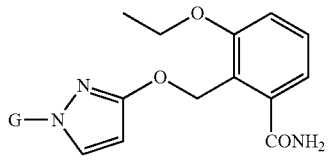

[wherein G represents a substituent corresponding to each of substituents Nos. 1 to 144 indicated in Table 26 to Table 30 as below-mentioned];

Compounds L16P-001~L16P-144 represent tetrazolinone Compounds represented by a formula:

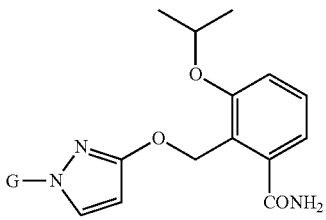

[wherein G represents a substituent corresponding to each of substituents Nos. 1 to 144 indicated in Table 26 to Table 30 as below-mentioned];

Compounds L16Q-001~L16Q-144 represent tetrazolinone Compounds represented by a formula:

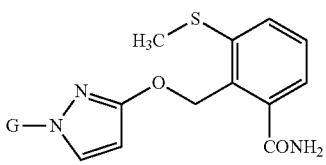

[wherein G represents a substituent corresponding to each of substituents Nos. 1 to 144 indicated in Table 26 to Table 30 as below-mentioned];

Compounds L16R-001~L16R-144 represent tetrazolinone Compounds represented by a formula:

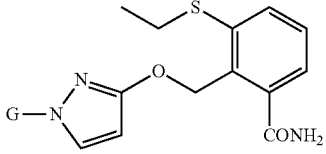

[wherein G represents a substituent corresponding to each of substituents Nos. 1 to 144 indicated in Table 26 to Table 30 as below-mentioned];

Compounds L16S-001~L16S-144 represent tetrazolinone Compounds represented by a formula:

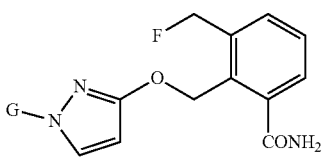

[wherein G represents a substituent corresponding to each of substituents Nos. 1 to 144 indicated in Table 26 to Table 30 as below-mentioned];

Compounds L16T-001~L16T-144 represent tetrazolinone Compounds represented by a formula:

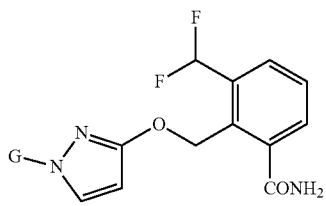

[wherein G represents a substituent corresponding to each of substituents Nos. 1 to 144 indicated in Table 26 to Table 30 as below-mentioned];

Compounds L16U-001~L16U-144 represent tetrazolinone Compounds represented by a formula:

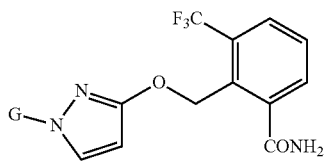

[wherein G represents a substituent corresponding to each of substituents Nos. 1 to 144 indicated in Table 26 to Table 30 as below-mentioned];

Compounds L16V-001~L16V-144 represent tetrazolinone Compounds represented by a formula:

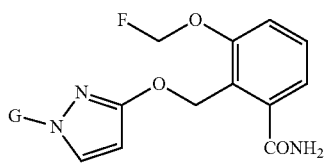

[wherein G represents a substituent corresponding to each of substituents Nos. 1 to 144 indicated in Table 26 to Table 30 as below-mentioned];

Compounds L16W-001~L16W-144 represent tetrazolinone Compounds represented by a formula:

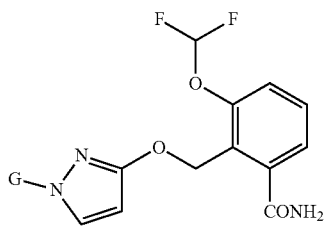

[wherein G represents a substituent corresponding to each of substituents Nos. 1 to 144 indicated in Table 26 to Table 30 as below-mentioned];

Compounds L16X-001~L16X-144 represent tetrazolinone Compounds represented by a formula:

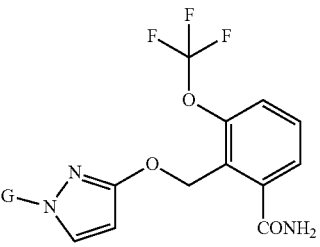

[wherein G represents a substituent corresponding to each of substituents Nos. 1 to 144 indicated in Table 26 to Table 30 as below-mentioned];

Compounds L16Y-001~L16Y-144 represent tetrazolinone Compounds represented by a formula:

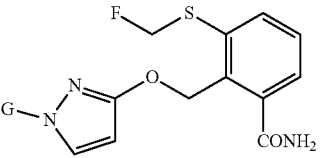

[wherein G represents a substituent corresponding to each of substituents Nos. 1 to 144 indicated in Table 26 to Table 30 as below-mentioned];

Compounds L16Z-001~L16Z-144 represent tetrazolinone Compounds represented by a formula:

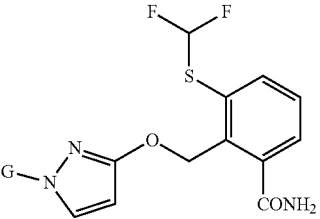

[wherein G represents a substituent corresponding to each of substituents Nos. 1 to 144 indicated in Table 26 to Table 30 as below-mentioned];

Compounds L16AA-001~L16AA-144 represent tetrazolinone Compounds represented by a formula:

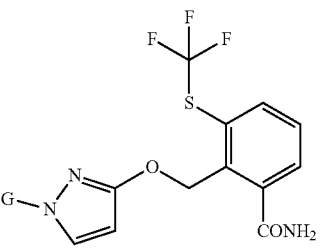

[wherein G represents a substituent corresponding to each of substituents Nos. 1 to 144 indicated in Table 26 to Table 30 as below-mentioned];

Compounds L17A-001~L17A-144 represent tetrazolinone Compounds represented by a formula:

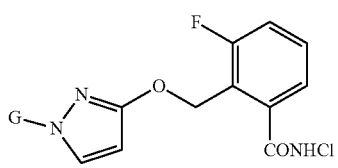

[wherein G represents a substituent corresponding to each of substituents Nos. 1 to 144 indicated in Table 26 to Table 30 as below-mentioned];
Compounds L17B-001~L17B-144 represent tetrazolinone Compounds represented by a formula:

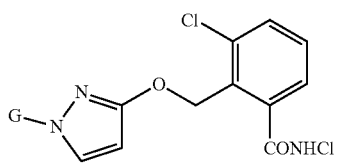

[wherein G represents a substituent corresponding to each of substituents Nos. 1 to 144 indicated in Table 26 to Table 30 as below-mentioned];
Compounds L17C-001~L17C-144 represent tetrazolinone Compounds represented by a formula:

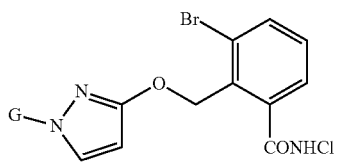

[wherein G represents a substituent corresponding to each of substituents Nos. 1 to 144 indicated in Table 26 to Table 30 as below-mentioned];
Compounds L17D-001~L17D-144 represent tetrazolinone Compounds represented by a formula:

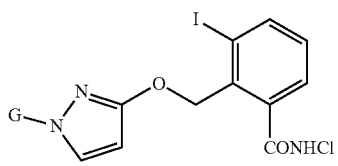

[wherein G represents a substituent corresponding to each of substituents Nos. 1 to 144 indicated in Table 26 to Table 30 as below-mentioned];
Compounds L17E-001~L17E-144 represent tetrazolinone Compounds represented by a formula:

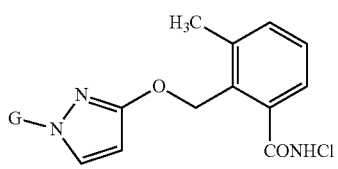

[wherein G represents a substituent corresponding to each of substituents Nos. 1 to 144 indicated in Table 26 to Table 30 as below-mentioned];
Compounds L17F-001~L17F-144 represent tetrazolinone Compounds represented by a formula:

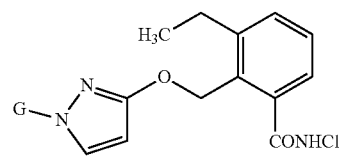

[wherein G represents a substituent corresponding to each of substituents Nos. 1 to 144 indicated in Table 26 to Table 30 as below-mentioned];
Compounds L17G-001~L17G-144 represent tetrazolinone Compounds represented by a formula:

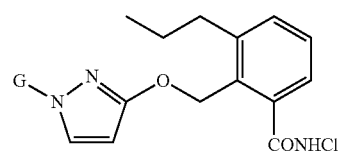

[wherein G represents a substituent corresponding to each of substituents Nos. 1 to 144 indicated in Table 26 to Table 30 as below-mentioned];
Compounds L17H-001~L17H-144 represent tetrazolinone Compounds represented by a formula:

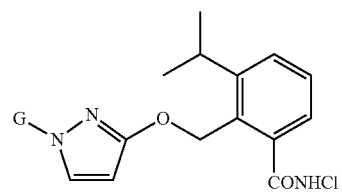

[wherein G represents a substituent corresponding to each of substituents Nos. 1 to 144 indicated in Table 26 to Table 30 as below-mentioned];
Compounds L17I-001~L17I-144 represent tetrazolinone Compounds represented by a formula:

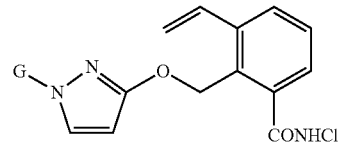

[wherein G represents a substituent corresponding to each of substituents Nos. 1 to 144 indicated in Table 26 to Table 30 as below-mentioned];
Compounds L17J-001~L17J-144 represent tetrazolinone Compounds represented by a formula:

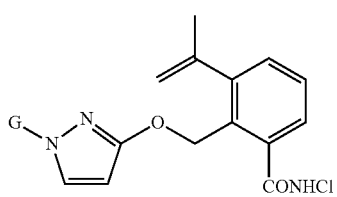

[wherein G represents a substituent corresponding to each of substituents Nos. 1 to 144 indicated in Table 26 to Table 30 as below-mentioned];

Compounds L17K-001~L17K-144 represent tetrazolinone Compounds represented by a formula:

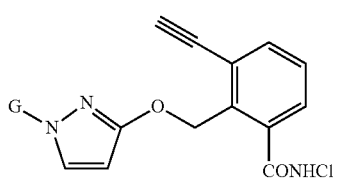

[wherein G represents a substituent corresponding to each of substituents Nos. 1 to 144 indicated in Table 26 to Table 30 as below-mentioned];

Compounds L17L-001~L17L-144 represent tetrazolinone Compounds represented by a formula:

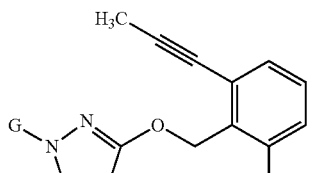

[wherein G represents a substituent corresponding to each of substituents Nos. 1 to 144 indicated in Table 26 to Table 30 as below-mentioned];

Compounds L17M-001~L17M-144 represent tetrazolinone Compounds represented by a formula:

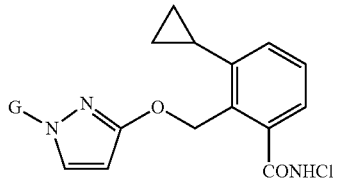

[wherein G represents a substituent corresponding to each of substituents Nos. 1 to 144 indicated in Table 26 to Table 30 as below-mentioned];

Compounds L17N-001~L17N-144 represent tetrazolinone Compounds represented by a formula:

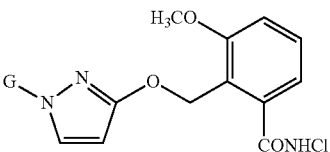

[wherein G represents a substituent corresponding to each of substituents Nos. 1 to 144 indicated in Table 26 to Table 30 as below-mentioned];

Compounds L17O-001~L17O-144 represent tetrazolinone Compounds represented by a formula:

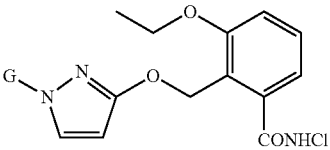

[wherein G represents a substituent corresponding to each of substituents Nos. 1 to 144 indicated in Table 26 to Table 30 as below-mentioned];

Compounds L17P-001~L17P-144 represent tetrazolinone Compounds represented by a formula:

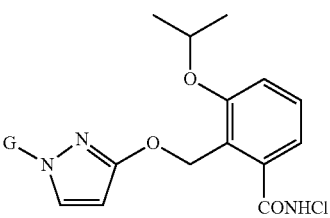

[wherein G represents a substituent corresponding to each of substituents Nos. 1 to 144 indicated in Table 26 to Table 30 as below-mentioned];

Compounds L17Q-001~L17Q-144 represent tetrazolinone Compounds represented by a formula:

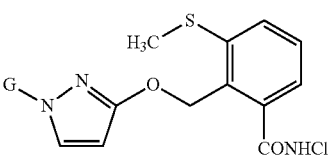

[wherein G represents a substituent corresponding to each of substituents Nos. 1 to 144 indicated in Table 26 to Table 30 as below-mentioned];

Compounds L17R-001~L17R-144 represent tetrazolinone Compounds represented by a formula:

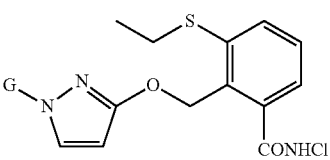

[wherein G represents a substituent corresponding to each of substituents Nos. 1 to 144 indicated in Table 26 to Table 30 as below-mentioned];

Compounds L17S-001~L17S-144 represent tetrazolinone Compounds represented by a formula:

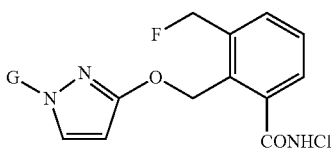

[wherein G represents a substituent corresponding to each of substituents Nos. 1 to 144 indicated in Table 26 to Table 30 as below-mentioned];

Compounds L17T-001~L17T-144 represent tetrazolinone Compounds represented by a formula:

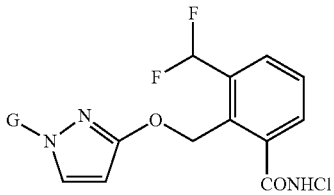

[wherein G represents a substituent corresponding to each of substituents Nos. 1 to 144 indicated in Table 26 to Table 30 as below-mentioned];

Compounds L17U-001~L17U-144 represent tetrazolinone Compounds represented by a formula:

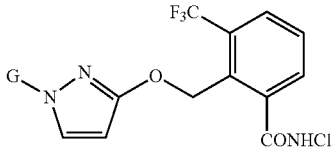

[wherein G represents a substituent corresponding to each of substituents Nos. 1 to 144 indicated in Table 26 to Table 30 as below-mentioned];

Compounds L17V-001~L17V-144 represent tetrazolinone Compounds represented by a formula:

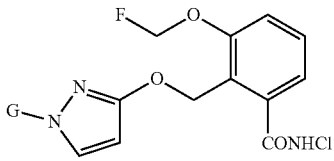

[wherein G represents a substituent corresponding to each of substituents Nos. 1 to 144 indicated in Table 26 to Table 30 as below-mentioned];

Compounds L17W-001~L17W-144 represent tetrazolinone Compounds represented by a formula:

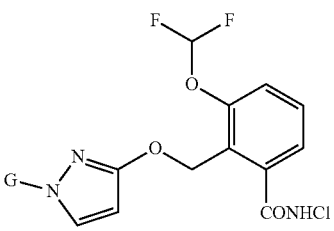

[wherein G represents a substituent corresponding to each of substituents Nos. 1 to 144 indicated in Table 26 to Table 30 as below-mentioned];

Compounds L17X-001~L17X-144 represent tetrazolinone Compounds represented by a formula:

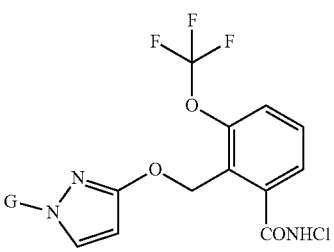

[wherein G represents a substituent corresponding to each of substituents Nos. 1 to 144 indicated in Table 26 to Table 30 as below-mentioned];

Compounds L17Y-001~L17Y-144 represent tetrazolinone Compounds represented by a formula:

[wherein G represents a substituent corresponding to each of substituents Nos. 1 to 144 indicated in Table 26 to Table 30 as below-mentioned];

Compounds L17Z-001~L17Z-144 represent tetrazolinone Compounds represented by a formula:

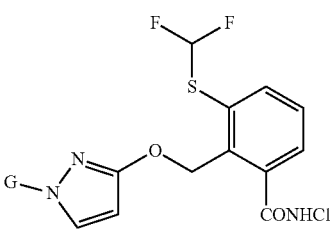

[wherein G represents a substituent corresponding to each of substituents Nos. 1 to 144 indicated in Table 26 to Table 30 as below-mentioned];

Compounds L17AA-001~L17AA-144 represent tetrazolinone Compounds represented by a formula:

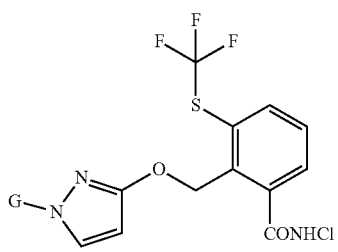

[wherein G represents a substituent corresponding to each of substituents Nos. 1 to 144 indicated in Table 26 to Table 30 as below-mentioned];

Compounds L18A-001~L18A-144 represent tetrazolinone Compounds represented by a formula:

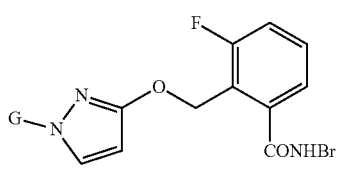

[wherein G represents a substituent corresponding to each of substituents Nos. 1 to 144 indicated in Table 26 to Table 30 as below-mentioned];

Compounds L18B-001~L18B-144 represent tetrazolinone Compounds represented by a formula:

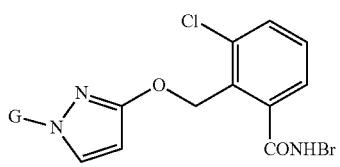

[wherein G represents a substituent corresponding to each of substituents Nos. 1 to 144 indicated in Table 26 to Table 30 as below-mentioned];

Compounds L18C-001~L18C-144 represent tetrazolinone Compounds represented by a formula:

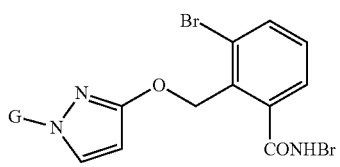

[wherein G represents a substituent corresponding to each of substituents Nos. 1 to 144 indicated in Table 26 to Table 30 as below-mentioned];

Compounds L18D-001~L18D-144 represent tetrazolinone Compounds represented by a formula:

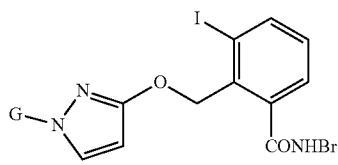

[wherein G represents a substituent corresponding to each of substituents Nos. 1 to 144 indicated in Table 26 to Table 30 as below-mentioned];

Compounds L18E-001~L18E-144 represent tetrazolinone Compounds represented by a formula:

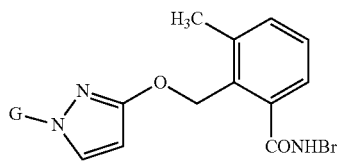

[wherein G represents a substituent corresponding to each of substituents Nos. 1 to 144 indicated in Table 26 to Table 30 as below-mentioned];

Compounds L18F-001~L18F-144 represent tetrazolinone Compounds represented by a formula:

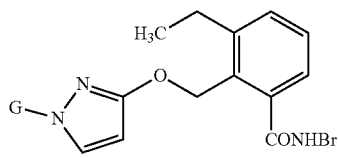

[wherein G represents a substituent corresponding to each of substituents Nos. 1 to 144 indicated in Table 26 to Table 30 as below-mentioned];

Compounds L18G-001~L18G-144 represent tetrazolinone Compounds represented by a formula:

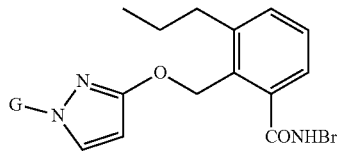

[wherein G represents a substituent corresponding to each of substituents Nos. 1 to 144 indicated in Table 26 to Table 30 as below-mentioned];

Compounds L18H-001~L18H-144 represent tetrazolinone Compounds represented by a formula:

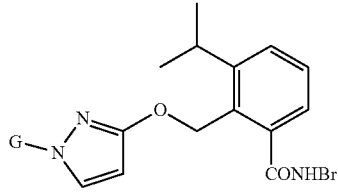

[wherein G represents a substituent corresponding to each of substituents Nos. 1 to 144 indicated in Table 26 to Table 30 as below-mentioned];

Compounds L18I-001~L18I-144 represent tetrazolinone Compounds represented by a formula:

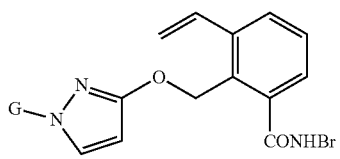

[wherein G represents a substituent corresponding to each of substituents Nos. 1 to 144 indicated in Table 26 to Table 30 as below-mentioned];

Compounds L18J-001~L18J-144 represent tetrazolinone Compounds represented by a formula:

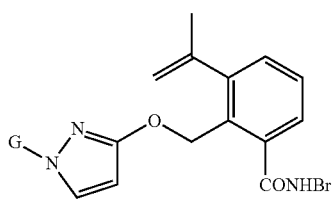

[wherein G represents a substituent corresponding to each of substituents Nos. 1 to 144 indicated in Table 26 to Table 30 as below-mentioned];

Compounds L18K-001~L18K-144 represent tetrazolinone Compounds represented by a formula:

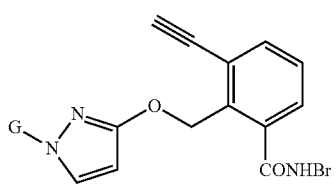

[wherein G represents a substituent corresponding to each of substituents Nos. 1 to 144 indicated in Table 26 to Table 30 as below-mentioned];

Compounds L18L-001~L18L-144 represent tetrazolinone Compounds represented by a formula:

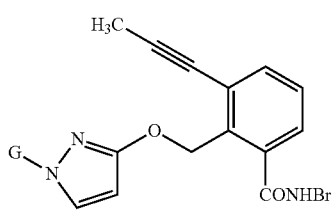

[wherein G represents a substituent corresponding to each of substituents Nos. 1 to 144 indicated in Table 26 to Table 30 as below-mentioned];

Compounds L18M-001~L18M-144 represent tetrazolinone Compounds represented by a formula:

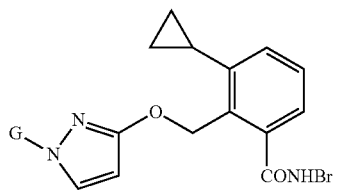

[wherein G represents a substituent corresponding to each of substituents Nos. 1 to 144 indicated in Table 26 to Table 30 as below-mentioned];

Compounds L18N-001~L18N-144 represent tetrazolinone Compounds represented by a formula:

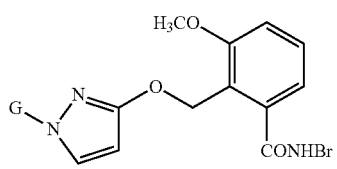

[wherein G represents a substituent corresponding to each of substituents Nos. 1 to 144 indicated in Table 26 to Table 30 as below-mentioned];

Compounds L18O-001~L18O-144 represent tetrazolinone Compounds represented by a formula:

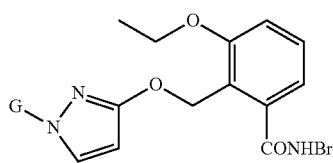

[wherein G represents a substituent corresponding to each of substituents Nos. 1 to 144 indicated in Table 26 to Table 30 as below-mentioned];

Compounds L18P-001~L18P-144 represent tetrazolinone Compounds represented by a formula:

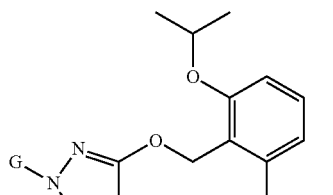

[wherein G represents a substituent corresponding to each of substituents Nos. 1 to 144 indicated in Table 26 to Table 30 as below-mentioned];

Compounds L18Q-001~L18Q-144 represent tetrazolinone Compounds represented by a formula:

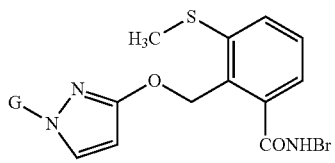

[wherein G represents a substituent corresponding to each of substituents Nos. 1 to 144 indicated in Table 26 to Table 30 as below-mentioned];
Compounds L18R-001~L18R-144 represent tetrazolinone Compounds represented by a formula:

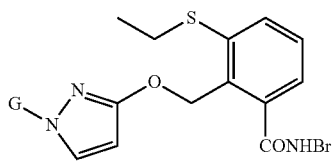

[wherein G represents a substituent corresponding to each of substituents Nos. 1 to 144 indicated in Table 26 to Table 30 as below-mentioned];
Compounds L18S-001~L18S-144 represent tetrazolinone Compounds represented by a formula:

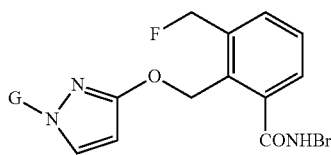

[wherein G represents a substituent corresponding to each of substituents Nos. 1 to 144 indicated in Table 26 to Table 30 as below-mentioned];
Compounds L18T-001~L18T-144 represent tetrazolinone Compounds represented by a formula:

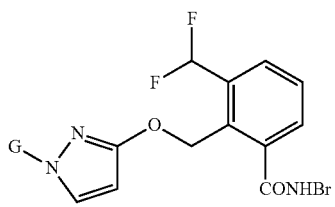

[wherein G represents a substituent corresponding to each of substituents Nos. 1 to 144 indicated in Table 26 to Table 30 as below-mentioned];
Compounds L18U-001~L18U-144 represent tetrazolinone Compounds represented by a formula:

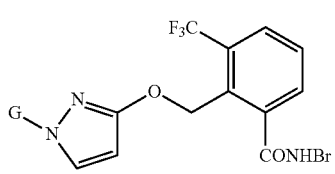

[wherein G represents a substituent corresponding to each of substituents Nos. 1 to 144 indicated in Table 26 to Table 30 as below-mentioned];
Compounds L18V-001~L18V-144 represent tetrazolinone Compounds represented by a formula:

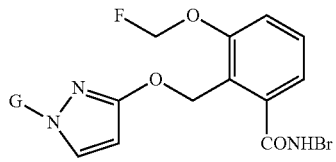

[wherein G represents a substituent corresponding to each of substituents Nos. 1 to 144 indicated in Table 26 to Table 30 as below-mentioned];
Compounds L18W-001~L18W-144 represent tetrazolinone Compounds represented by a formula:

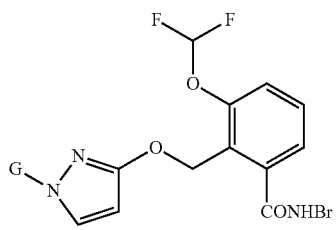

[wherein G represents a substituent corresponding to each of substituents Nos. 1 to 144 indicated in Table 26 to Table 30 as below-mentioned];
Compounds L18X-001~L18X-144 represent tetrazolinone Compounds represented by a formula:

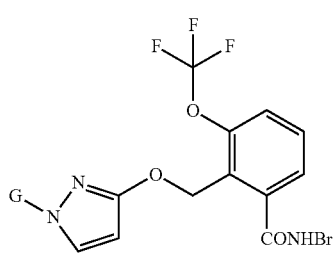

[wherein G represents a substituent corresponding to each of substituents Nos. 1 to 144 indicated in Table 26 to Table 30 as below-mentioned];
Compounds L18Y-001~L18Y-144 represent tetrazolinone Compounds represented by a formula:

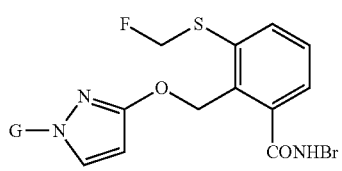

[wherein G represents a substituent corresponding to each of substituents Nos. 1 to 144 indicated in Table 26 to Table 30 as below-mentioned];
Compounds L18Z-001~L18Z-144 represent tetrazolinone Compounds represented by a formula:

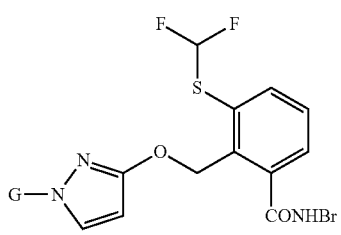

[wherein G represents a substituent corresponding to each of substituents Nos. 1 to 144 indicated in Table 26 to Table 30 as below-mentioned];

Compounds L18AA-001~L18AA-144 represent tetrazolinone Compounds represented by a formula:

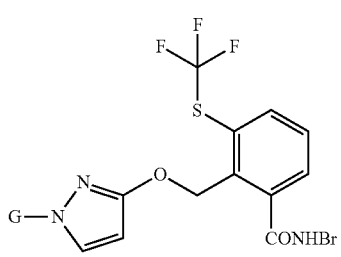

[wherein G represents a substituent corresponding to each of substituents Nos. 1 to 144 indicated in Table 26 to Table 30 as below-mentioned];

Compounds L19A-001~L19A-144 represent tetrazolinone Compounds represented by a formula:

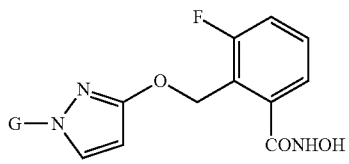

[wherein G represents a substituent corresponding to each of substituents Nos. 1 to 144 indicated in Table 26 to Table 30 as below-mentioned];

Compounds L19B-001~L19B-144 represent tetrazolinone Compounds represented by a formula:

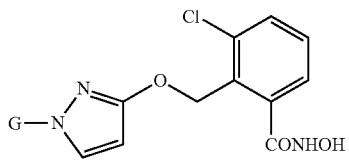

[wherein G represents a substituent corresponding to each of substituents Nos. 1 to 144 indicated in Table 26 to Table 30 as below-mentioned];

Compounds L19C-001~L19C-144 represent tetrazolinone Compounds represented by a formula:

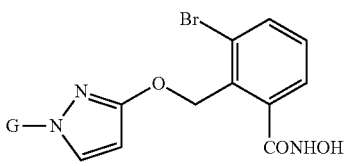

[wherein G represents a substituent corresponding to each of substituents Nos. 1 to 144 indicated in Table 26 to Table 30 as below-mentioned];

Compounds L19D-001~L19D-144 represent tetrazolinone Compounds represented by a formula:

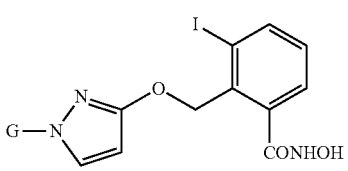

[wherein G represents a substituent corresponding to each of substituents Nos. 1 to 144 indicated in Table 26 to Table 30 as below-mentioned];

Compounds L19E-001~L19E-144 represent tetrazolinone Compounds represented by a formula:

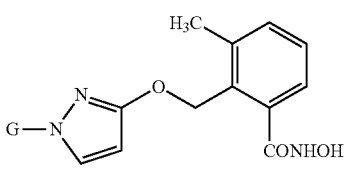

[wherein G represents a substituent corresponding to each of substituents Nos. 1 to 144 indicated in Table 26 to Table 30 as below-mentioned];

Compounds L19F-001~L19F-144 represent tetrazolinone Compounds represented by a formula:

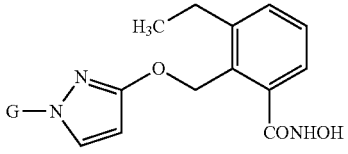

[wherein G represents a substituent corresponding to each of substituents Nos. 1 to 144 indicated in Table 26 to Table 30 as below-mentioned];

Compounds L19G-001~L19G-144 represent tetrazolinone Compounds represented by a formula:

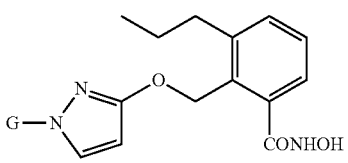

[wherein G represents a substituent corresponding to each of substituents Nos. 1 to 144 indicated in Table 26 to Table 30 as below-mentioned];

Compounds L19H-001~L19H-144 represent tetrazolinone Compounds represented by a formula:

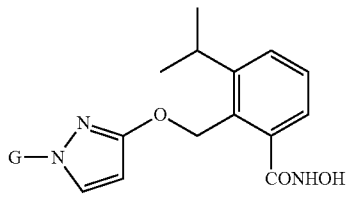

[wherein G represents a substituent corresponding to each of substituents Nos. 1 to 144 indicated in Table 26 to Table 30 as below-mentioned];

Compounds L19I-001~L19I-144 represent tetrazolinone Compounds represented by a formula:

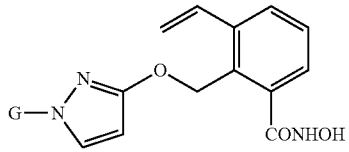

[wherein G represents a substituent corresponding to each of substituents Nos. 1 to 144 indicated in Table 26 to Table 30 as below-mentioned];

Compounds L19J-001~L19J-144 represent tetrazolinone Compounds represented by a formula:

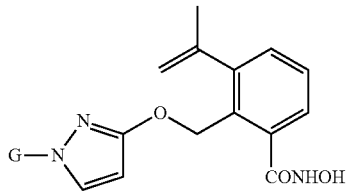

[wherein G represents a substituent corresponding to each of substituents Nos. 1 to 144 indicated in Table 26 to Table 30 as below-mentioned];

Compounds L19K-001~L19K-144 represent tetrazolinone Compounds represented by a formula:

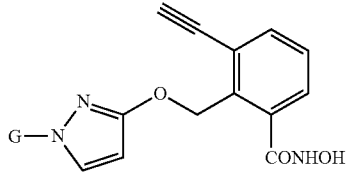

[wherein G represents a substituent corresponding to each of substituents Nos. 1 to 144 indicated in Table 26 to Table 30 as below-mentioned];

Compounds L19L-001~L19L-144 represent tetrazolinone Compounds represented by a formula:

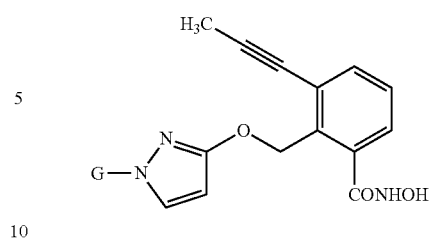

[wherein G represents a substituent corresponding to each of substituents Nos. 1 to 144 indicated in Table 26 to Table 30 as below-mentioned];

Compounds L19M-001~L19M-144 represent tetrazolinone Compounds represented by a formula:

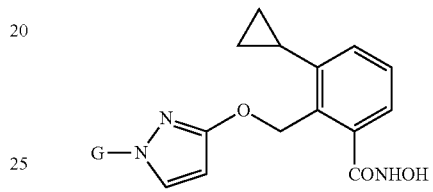

[wherein G represents a substituent corresponding to each of substituents Nos. 1 to 144 indicated in Table 26 to Table 30 as below-mentioned];

Compounds L19N-001~L19N-144 represent tetrazolinone Compounds represented by a formula:

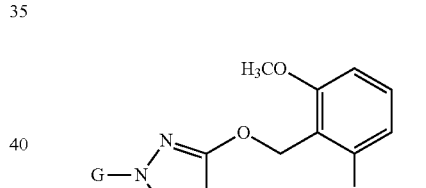

[wherein G represents a substituent corresponding to each of substituents Nos. 1 to 144 indicated in Table 26 to Table 30 as below-mentioned];

Compounds L19O-001~L19O-144 represent tetrazolinone Compounds represented by a formula:

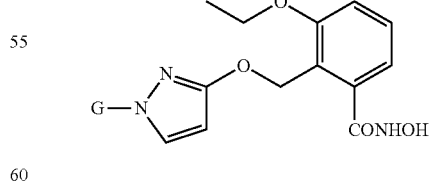

[wherein G represents a substituent corresponding to each of substituents Nos. 1 to 144 indicated in Table 26 to Table 30 as below-mentioned];

Compounds L19P-001~L19P-144 represent tetrazolinone Compounds represented by a formula:

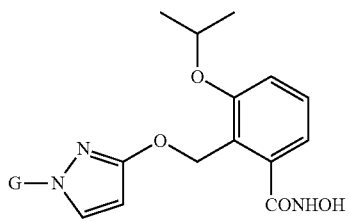

[wherein G represents a substituent corresponding to each of substituents Nos. 1 to 144 indicated in Table 26 to Table 30 as below-mentioned];

Compounds L19Q-001~L19Q-144 represent tetrazolinone Compounds represented by a formula:

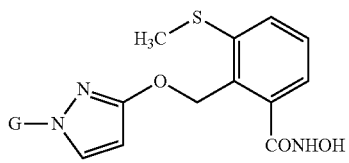

[wherein G represents a substituent corresponding to each of substituents Nos. 1 to 144 indicated in Table 26 to Table 30 as below-mentioned];

Compounds L19R-001~L19R-144 represent tetrazolinone Compounds represented by a formula:

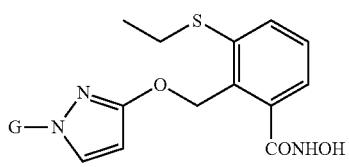

[wherein G represents a substituent corresponding to each of substituents Nos. 1 to 144 indicated in Table 26 to Table 30 as below-mentioned];

Compounds L19S-001~L19S-144 represent tetrazolinone Compounds represented by a formula:

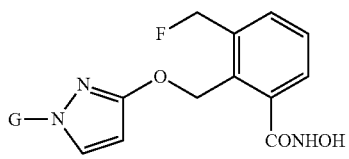

[wherein G represents a substituent corresponding to each of substituents Nos. 1 to 144 indicated in Table 26 to Table 30 as below-mentioned];

Compounds L19T-001~L19T-144 represent tetrazolinone Compounds represented by a formula:

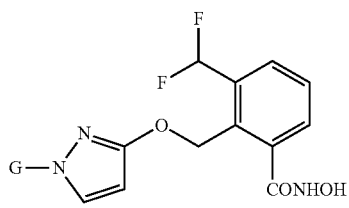

[wherein G represents a substituent corresponding to each of substituents Nos. 1 to 144 indicated in Table 26 to Table 30 as below-mentioned];

Compounds L19U-001~L19U-144 represent tetrazolinone Compounds represented by a formula:

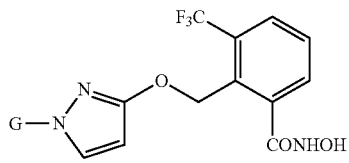

[wherein G represents a substituent corresponding to each of substituents Nos. 1 to 144 indicated in Table 26 to Table 30 as below-mentioned];

Compounds L19V-001~L19V-144 represent tetrazolinone Compounds represented by a formula:

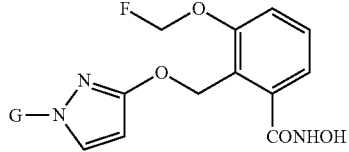

[wherein G represents a substituent corresponding to each of substituents Nos. 1 to 144 indicated in Table 26 to Table 30 as below-mentioned];

Compounds L19W-001~L19W-144 represent tetrazolinone Compounds represented by a formula:

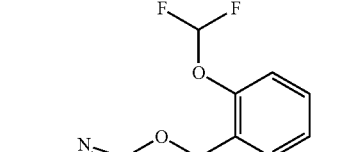

[wherein G represents a substituent corresponding to each of substituents Nos. 1 to 144 indicated in Table 26 to Table 30 as below-mentioned];

Compounds L19X-001~L19X-144 represent tetrazolinone Compounds represented by a formula:

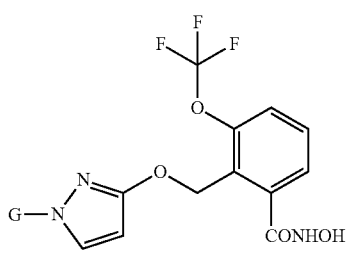

[wherein G represents a substituent corresponding to each of substituents Nos. 1 to 144 indicated in Table 26 to Table 30 as below-mentioned];

Compounds L19Y-001~L19Y-144 represent tetrazolinone Compounds represented by a formula:

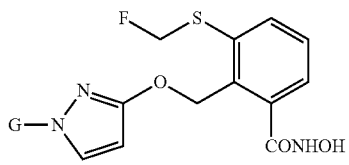

[wherein G represents a substituent corresponding to each of substituents Nos. 1 to 144 indicated in Table 26 to Table 30 as below-mentioned];

Compounds L19Z-001~L19Z-144 represent tetrazolinone Compounds represented by a formula:

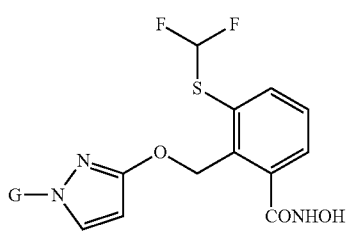

[wherein G represents a substituent corresponding to each of substituents Nos. 1 to 144 indicated in Table 26 to Table 30 as below-mentioned]; and Compounds L19AA-001~L19AA-144 represent tetrazolinone Compounds represented by a formula:

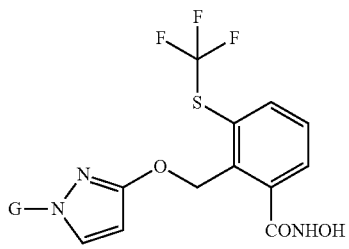

[wherein G represents a substituent corresponding to each of substituents Nos. 1 to 144 indicated in Table 26 to Table 30 as below-mentioned].

Next, the Formulation examples are shown below. In the Examples, the term "part(s)" means part(s) by weight unless otherwise specified.

Formulation Example 1

Fifty (50) parts of any one of the present Compounds 1 to 97, 3 parts of calcium lignosulfonate, 2 parts of magnesium lauryl sulfate and 45 parts of synthetic hydrated silicon dioxide are well mixed while grinding to obtain a formulation.

Formulation Example 2

Twenty (20) parts of any one of the present Compounds 1 to 97, 1.5 parts of sorbitan trioleate are mixed with 28.5 parts of an aqueous solution containing 2 parts of polyvinyl alcohol, and the mixture is then finely-ground by a wet grinding method. To this mixture is then added 40 parts of an aqueous solution containing 0.05 parts of xanthane gum and 0.1 parts of magnesium aluminium silicate, and 10 parts of propylene glycol is further added thereto. The mixture is stirred to obtain a formulation.

Formulation Example 3

Two (2) parts of any one of the present Compounds 1 to 97, 88 parts of kaolin clay and 10 parts of talc are mixed-grinding to obtain a formulation.

Formulation Example 4

Five (5) parts of any one of the present Compounds 1 to 97, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of any one of the present Compounds 1 to 97, one part of synthetic hydrated silicon dioxide, 2 parts of calcium lignosulfonate, 30 parts of bentonite and 65 parts of kaolin clay are mixed-grinding and thereto is added water and the mixture is well kneaded and is then granulated and dried to obtain a formulation.

Formulation Example 6

Ten (10) parts of any one of the present Compounds 1 to 97, 35 parts of white carbon containing 50 parts of ammonium polyoxyethylene alkyl ether sulfate, and 55 parts of water are mixed, and the mixture is then finely-ground by a wet grinding method to obtain a formulation.

Next, Test examples are used to show an efficacy of the present Compounds on controlling plant diseases.

Here the controlling effects were evaluated by visually observing a lesion area on the tested plants and followed by comparing the lesion area of the plants treated with the present Compounds with a lesion area of the untreated plants.

Test Example 1

A plastic pot was filled with soils and thereto was seeded rice (cv; Nipponbare) and the plants were grown in a greenhouse for twenty days. Thereafter, each of the present Compounds 5, 11, 14, 15, 28, 50, 54, 58, 76, 78, 88, 89, 92 to 95 and 96 was made to a formulation according to the above-mentioned Formulation examples and was then diluted with water so as to make a predetermined concentration (500 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*), and a lesion area was observed. As a result, every of the lesion areas in plants treated with the present Compounds 5, 11, 14, 15, 28, 50, 54, 58, 76, 78, 88, 89, 92 to 95 and 96 showed 300 or less compared to the lesion area in an untreated plants.

Test Example 2

A plastic pot was filled with soils and thereto was seeded rice (cv; Nipponbare) and the plants were grown in a greenhouse for 20 days. Thereafter, each of the present Compounds 1, 7, 12, 14, 20, 23, 24, 26, 30, 33, 34, 36 to 40, 53, 56, 66, 73, 83, 84, 87 and 97 was made to a formulation according to the above-mentioned Formulation examples and was then diluted with water so as to make a predetermined concentration (200 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*) and a lesion area was observed. As a result, every of the lesion areas in plants treated with the present Compounds 1, 7, 12, 14, 20, 23, 24, 26, 30, 33, 34, 36 to 40, 53, 56, 66, 73, 83, 84, 87 and 97 showed 30% or less compared to the lesion area in an untreated plants.

Test Example 3

A plastic pot was filled with soils and thereto was seeded rice (cv; Nipponbare) and the plants were grown in a greenhouse for 20 days. Thereafter, the present Compound 35 was made to a formulation according to the above-mentioned Formulation examples and was then diluted with water so as to make a predetermined concentration (50 ppm). The dilutions were sprayed to stems and leaves so as to adhere adequately on the leaves of the above-mentioned rice. After spraying the dilution, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*) and a lesion area was observed. As a result, every of the lesion areas in plants treated with the present Compound 35 showed 30% or less compared to the lesion area in an untreated plants.

Test Example 4

A plastic pot was filled with soils and thereto was seeded wheat (cv; Shirogane) and the plants were grown in a greenhouse for 9 days. Thereafter, each of the present Compounds 12, 15, 46, 56, 59, 78, 88, 93 to 95 and 96 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds 12, 15, 46, 56, 59, 78, 88, 93 to 95 and 96 showed 30% or less compared to the lesion area in an untreated plants.

Test Example 5

A plastic pot was filled with soils and thereto was seeded wheat (cv; Shirogane) and the plants were grown in a greenhouse for 9 days. Thereafter, each of the present Compounds 1, 34, 51, 53, 58, 60, 72, 82, 84, 86, 89, 91 and was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds 1, 34, 51, 53, 58, 60, 72, 82, 84, 86, 89, 91 and 92 showed 30% or less compared to the lesion area in an untreated plants.

Test Example 6

A plastic pot was filled with soils and thereto was seeded wheat (cv; Shirogane) and the plants were grown in a greenhouse for 9 days. Thereafter, the present Compound 35 was made to a formulation according to the above-mentioned Formulation examples and was then diluted with water so as to make a predetermined concentration (50 ppm). The dilutions were sprayed to foliar parts so as to adhere adequately on the leaves of the above-mentioned wheat. After spraying the dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compound 35 showed 300 or less compared to the lesion area in an untreated plants.

Test Example 7

A plastic pot was filled with soils and thereto was seeded wheat (cv; Shirogane) and the plants were grown in a greenhouse for 9 days. Thereafter, to the wheat were sprinkling-inoculated the spores of wheat rust fungi (*Puccinia recondita*). The wheat was placed under a dark and humid condition at 23° C. for 1 day and was air-dried. The present Compound 12 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were placed under lighting for 8 days and a lesion area was observed. As a result, every of the lesion areas in plants treated with the present Compound 12 showed 30% or less compared to the lesion area in an untreated plants.

Test Example 8

A plastic pot was filled with soils and thereto was seeded barley (cv; Mikamo Golden) and the plants were grown in a greenhouse for 7 days. Thereafter, each of the present Compounds 2, 5, 6, 8, 10 to 17, 25, 27, 28, 31, 38, 39, 44, 46 to 52, 54 to 63, 65 to 67, 71 to 96 and 97 was made to a formulation according to the above-mentioned Formulation examples and was then diluted with water so as to make a predetermined concentration (500 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds 2, 5, 6, 8, 10 to 17, 25, 27, 28, 31, 38, 39, 44, 46 to 52, 54 to 63, 65 to 67, 71 to 96 and 97 showed 30% or less compared to the lesion area in an untreated plants.

Test Example 9

A plastic pot was filled with soils and thereto was seeded barley (cv; Mikamo Golden) and the plants were grown in a greenhouse for 7 days. Thereafter, each of the present Compounds 1, 3, 4, 7, 9, 20 to 24, 26, 29, 32 to 34, 36, 37, 40, 42, 43, 53, 64, 68 and 69 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds 1, 3, 4, 7, 9, 20 to 24, 26, 29, 32 to 34, 36, 37, 40, 42, 43, 53, 64, 68 and 69 showed 300 or less compared to the lesion area in an untreated plants.

Test Example 10

A plastic pot was filled with soils and thereto was seeded barley (cv; Mikamo Golden) and the plants were grown in a greenhouse for 7 days. The present Compound 35 was made to a formulation according to the above-mentioned Formulation examples and was then diluted with water so as to make a predetermined concentration (50 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compound 35 showed 30% or less compared to the lesion area in an untreated plants.

Test Example 11

A plastic pot was filled with soils and thereto was seeded Kidney bean (cv; Nagauzurasaitou) and the plants were grown in a greenhouse for 8 days. Either of the present Compounds 5, 8, 10 to 14, 46, 50 to 52, 54, 56, 57, 59, 60, 63 to 67, 70, 72, 79 to 83, 86 to 96 and 97 was made to a formulation according to the above-mentioned Formulation examples and was then diluted with water so as to make a predetermined concentration (500 ppm). The dilutions were sprayed to foliar parts so as to adhere adequately on the leaves of the above-mentioned kidney bean. After spraying the dilutions, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds 5, 8, 10 to 14, 46, 50 to 52, 54, 56, 57, 59, 60, 63 to 67, 70, 72, 79 to 83, 86 to 96 and 97 showed 30% or less compared to the lesion area in an untreated plants.

Test Example 12

A plastic pot was filled with soils and thereto was seeded Kidney bean (cv; Nagauzurasaitou) and the plants were grown in a greenhouse for 8 days. Either of the present Compounds 22, 76, 77 and 78 was made to a formulation according to the above-mentioned Formulation examples and was then diluted with water so as to make a predetermined concentration (200 ppm). The dilutions were sprayed to foliar parts so as to adhere adequately on the leaves of the above-mentioned kidney bean. After spraying the dilutions, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds 22, 76, 77 and 78 showed 30% or less compared to the lesion area in an untreated plants.

Test Example 13

A plastic pot was filled with soils and thereto was seeded wheat (cv; Apogee) and the plants were grown in a greenhouse for 10 days. Each of the present Compounds 1 to 3, 5, 6, 8, 10 to 17, 25, 28, 31, 32, 38, 39, 44, 46 to 52, 54 to 61, 63 to 68, 70 to 73, 76 to 78, 81 to 86, 88 to 95 and 96 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds 1 to 3, 5, 6, 8, 10 to 17, 25, 28, 31, 32, 38, 39, 44, 46 to 52, 54 to 61, 63 to 68, 70 to 73, 76 to 78, 81 to 86, 88 to 95 and 96 showed 30% or less compared to the lesion area in an untreated plants.

Test Example 14

A plastic pot was filled with soils and thereto was seeded wheat (cv; Apogee) and the plants were grown in a greenhouse for 10 days. Each of the present Compounds 7, 9, 20 to 27, 29, 33, 34, 36, 37, 40 to 43, 53, 69, 74, 79, 80 and 87 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds 7, 9, 20 to 27, 29, 33, 34, 36, 37, 40 to 43, 53, 69, 74, 79, 80 and 87 showed 30% or less compared to the lesion area in an untreated plants.

Test Example 15

A plastic pot was filled with soils and thereto was seeded wheat (cv; Apogee) and the plants were grown in a greenhouse for 10 days. The present compound 19 was made to a formulation according to the above-mentioned Formulation examples and was then diluted with water so as to make a predetermined concentration (50 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present compound 19 showed 30% or less compared to the lesion area in untreated plants.

Test Example 16

A plastic pot was filled with soils and thereto was seeded wheat (cv; Apogee) and the plants were grown in a greenhouse for 10 days. Thereafter, to the wheat was spraying-inoculated an aqueous suspension of the spores of wheat leaf blotch fungi (*Septoria tritici*). The wheat was placed at 18° C. under a high humidity for 3 days and was air-dried. Each of the present Compounds 1, 3, 5, 7, 8, 10, 11, 12, 13, 14, 15, 22 to 24, 26, 29, 31 to 34, 36, 38 to 40, 42, 44, 46 to 48, 51 to 56, 58 to 60, 63, 65, 68, 71 to 73, 76, 78, 82 to 84, 86 to 89, 93 to 95 and 96 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were further placed under lighting for 14 to 18 days, and a lesion area was observed. As a result, every of the lesion areas in plants treated with the present Compounds 1, 3, 5, 7, 8, 10, 11, 12, 13, 14, 15, 22 to 24, 26, 29, 31 to 34, 36, 38 to 40, 42, 44, 46 to 48, 51 to 56, 58 to 60, 63, 65, 68, 71 to 73, 76, 78, 82 to 84, 86 to 89, 93 to 95 and 96 showed 300 or less compared to the lesion area in an untreated plants.

Test Example 17

A plastic pot was filled with soils and thereto was seeded cucumber (cv; Sagamihanjiro) and the plants were grown in a greenhouse for 12 days. Each of the present Compounds 2, 5, 6, 10 to 12, 14, 25, 31, 39, 46, 49 to 52, 54 to 56, 59 to 61, 63 to 65, 71, 72, 76, 78 to 84, 86 to 96 and 97 was made to a formulation according to the above-mentioned Formulation examples and was then diluted with water so as to make a predetermined concentration (500 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds 2, 5, 6, 10 to 12, 14, 25, 31, 39, 46, 49 to 52, 54 to 56, 59 to 61, 63 to 65, 71, 72, 76, 78 to 84, 86 to 96 and 97 showed 30% or less compared to the lesion area in an untreated plants.

Test Example 18

A plastic pot was filled with soils and thereto was seeded cucumber (cv; Sagamihanjiro) and the plants were grown in a greenhouse for 12 days. Each of the present Compounds 1, 3, 7, 11, 13, 22, 26, 33 and 53 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds 1, 3, 7, 11, 13, 22, 26, 33 and 53 showed 30% or less compared to the lesion area in an untreated plants.

Test Example 19

A plastic pot was filled with soils and thereto was seeded cucumber (cv; Sagamihanjiro) and the plants were grown in a greenhouse for 12 days. The present Compound 34 was made to a formulation according to the above-mentioned Formulation examples and was then diluted with water so as to make a predetermined concentration (50 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compound 34 showed 30% or less compared to the lesion area in an untreated plants.

Test Example 20

A plastic pot was filled with soils and thereto was seeded soybean (cv: Kurosengoku) and the plants were grown in a greenhouse for 13 days. Each of the present Compounds 8, 12, 15, 23, 46, 50, 51, 78, 86 to 89, 91, 92, 94, 95 and was made to a formulation according to the above-mentioned Formulation examples and was then diluted with water so as to make a predetermined concentration (200 ppm). The dilutions were sprayed to foliar parts so as to adhere adequately on the leaves of the above-mentioned soybean. After spraying the dilutions, the plants were air-dried and after 2 days, an aqueous suspension of the spores of soybean rust fungi (*phakopsora pachyrhizi*) was spraying-inoculated. After inoculation, the plants were placed in a greenhouse of 23° C. during daytime and 20° C. during nighttime under a high humidity for 3 days and were then cultivated in the greenhouse for 14 days, and a lesion area was observed. As a result, every of the lesion areas in plants treated with the present Compounds 8, 12, 15, 23, 46, 50, 51, 78, 86 to 89, 91, 92, 94, 95 and 96 showed 30% or less compared to the lesion area in an untreated plants.

Test Example 21

A plastic pot was filled with soils and thereto was seeded soybean (cv; Kurosengoku) and the plants were grown in a greenhouse for 13 days. Thereafter, to the soybean was spraying-inoculated an aqueous suspension of the spores of soybean rust fungi (*phakopsora pachyrhizi*). The soybean was placed at 23° C. under a high humidity for one day and was air-dried. Each of the present Compounds 13 and 15 was made to a formulation according to the above-mentioned Formulation examples and was then diluted with water so as to make a predetermined concentration (200 ppm). The dilutions were sprayed to foliar parts so as to adhere adequately on the leaves of the above-mentioned soybean. After spraying the dilutions, the plants were air-dried and were further placed under lighting for 14 days, and a lesion area was observed. As a result, every of the lesion areas in plants treated with the present compounds 13 and 15 showed 30% or less compared to the lesion area in an untreated plants.

Test Example 22

A plastic pot was filled with soils and thereto was seeded barley (cv; Mikamo Golden) and the plants were grown in a greenhouse for 7 days. Each of the present Compounds 1, 4, 5, 8, 10, 12 to 15, 20, 22, 23, 26, 31, 33, 34, 36, 40, 46, 50 to 55, 57 to 61, 63 to 65, 71 to 73, 76 to 91, 93 to 95 and 96 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley leaf blotch fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, every of the lesion areas in plants treated with the present Compounds 1, 4, 5, 8, 10, 12 to 15, 20, 22, 23, 26, 31, 33, 34, 36, 40, 46, 50 to 55, 57 to 61, 63 to 65, 71 to 73, 76 to 91, 93 to 95 and 96 showed 30% or less compared to the lesion area in an untreated plants.

Test Example 23

A plastic pot was filled with soils and thereto was seeded barley (cv; Mikamo Golden) and the plants were grown in a greenhouse for 7 days. Each of the present Compounds 11, 19 and 70 was made to a formulation according to the above-mentioned Formulation examples and was then diluted with water so as to make a predetermined concentration (50 ppm). The dilutions were sprayed to foliar parts so as to adhere adequately on the leaves of the above-mentioned barley. After spraying the dilutions, the plants were air-dried and after 2 days, an aqueous suspension of the spores of barley scald fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, every of the lesion areas in plants treated with the present Compounds 11, 19 and 70 showed 10% or less compared to the lesion area in an untreated plants.

Test Example 24

A plastic pot was filled with soils and thereto was seeded grapes (Seeding of Chardonnay) and the plants were grown in a greenhouse for 40 days. Each of the present Compounds 12 and 34 was made to a formulation according to the above-mentioned Formulation examples and was then diluted with water so as to make a predetermined concentration (200 ppm). The dilutions were sprayed to foliar parts so as to adhere adequately on the leaves of the above-mentioned grapes. After spraying the dilutions, the plants were air-dried to such an extent that the diluted solutions were dried, and a suspension of the zoosporangium of grapes downy mildew fungi was spraying-inoculated. After inoculation, the plants were placed at 23° C. under a high humidity for 1 day and were then transferred to a greenhouse of 23° C. during a daytime and 20° C. during a nighttime and were cultivated therein for 5 days. Thereafter, the plants were placed under a high humidity for 1 day, and a lesion area was observed. As a result, the lesion areas in plants treated with every of the present Compounds 12 and 34 showed 30% or less compared to the lesion area in an untreated plants.

Test Example 25

A plastic pot was filled with soils and thereto was seeded tomato (cv; Patio) and the plants were grown in a greenhouse for 20 days. The present compound 26 was made to a flowable according to the above-mentioned Formulation examples and was then diluted with water so as to make a predetermined concentration (200 ppm). The dilutions were sprayed to foliar parts so as to adhere adequately on the leaves of the above-mentioned tomato. After the plants were air-dried to such an extent that the dilutions were dried, an aqueous suspension of the spores of tomato late blight fungi (*Phytophthora infestans*) was spraying-inoculated. After inoculation, the plants were at first placed at 23° C. under a high humidity for 1 day and were then cultivated at 20° C.

in an air-conditioned room for 4 days, and a lesion area was observed. As a result, every of the lesion areas in plants treated with the present compound 26 showed 30% or less compared to the lesion area in untreated plants.

Test Example 26

A plastic pot was filled with soils and thereto was seeded tomato (cv; Patio) and the plants were grown in a greenhouse for 20 days. The present Compound 12 were made to flowables according to the above-mentioned Formulation examples and were then diluted with water so as to make a predetermined concentration (50 ppm). The dilutions were sprayed to foliar parts so as to adhere adequately on the leaves of the above-mentioned tomato. After the plants were air-dried to such an extent that the dilutions were dried, an aqueous suspension of the spores of tomato late blight fungi (*Phytophthora infestans*) was spraying-inoculated. After inoculation, the plants were at first placed at 23° C. under a high humidity for 1 day and were then cultivated at 20° C. in an air-conditioned room for 4 days, and a lesion area was observed. As a result, every of the lesion areas in plants treated with the present Compound 12 showed 30% or less compared to the lesion area in an untreated plants.

Test Example 27

A plastic pot was filled with soils and thereto was seeded cucumber (cv; Sagamihanjiro) and the plants were grown in a greenhouse for 19 days. Each of the present Compounds 72, 73, 74, 76, 78, 80 to 84, 87 to 89, 91 to 93, 95, 96 and 97 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber target spot fungi (*Corynespora cassiicola*) was spaying-inoculated. After an inoculation, the plants were placed at 24° C. during daytime and 20° C. during nighttime under a high humidity for 7 days, and a lesion area was observed. As a result, every of the lesion areas in plants treated with the present Compounds 72, 73, 74, 76, 78, 80 to 84, 87 to 89, 91 to 93, 95, 96 and 97 showed 30% or less compared to the lesion area in an untreated plants.

Test Example 28

A plastic pot was filled with soils and thereto was seeded cucumber (cv; Sagamihanjiro) and the plants were grown in a greenhouse for 19 days. Each of the present Compounds 12, 33 and 46 was made to a formulation according to the above-mentioned Formulation examples and was then diluted with water so as to make a predetermined concentration (50 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber target spot fungi (*Corynespora cassiicola*) was spaying-inoculated. After an inoculation, the plants were placed at 24° C. during daytime and 20° C. during nighttime under a high humidity for 7 days, and a lesion area was observed. As a result, every of the lesion areas in plants treated with the present Compounds 12, 33 and 46 showed 30% or less compared to the lesion area in an untreated plants.

Test Example 29

A plastic pot was filled with soils and thereto was seeded cucumber (cv; Sagamihanjiro) and the plants were grown in a greenhouse for 19 days. Each of the present Compounds 72, 73, 76, 78 to 81, 84, 86 to 96 and 97 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber anthracnose fungi (*Colletotrichum lagenarium*) was spraying-inoculated. After an inoculation, the plants were placed firstly at 23° C. under a high humidity for 1 day and were then cultivated in a greenhouse of 24° C. during daytime and 20° C. during nighttime for 6 days, and a lesion area was observed. As a result, every of the lesion areas in plants treated with the present Compounds 72, 73, 76, 78 to 81, 84, 86 to 96 and 97 showed 30% or less compared to the lesion area in an untreated plants.

Test Example 30

A plastic pot was filled with soils and thereto was seeded cucumber (cv; Sagamihanjiro) and the plants were grown in a greenhouse for 19 days. Each of the present Compounds 12, 34, 46 and 85 was made to a formulation according to the above-mentioned Formulation examples and was then diluted with water so as to make a predetermined concentration (50 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber anthracnose fungi (*Colletotrichum lagenarium*) was spraying-inoculated. After an inoculation, the plants were placed firstly at 23° C. under a high humidity for 1 day and were then cultivated in a greenhouse of 24° C. during daytime and 20° C. during nighttime for 6 days, and a lesion area was observed. As a result, every of the lesion areas in plants treated with the present Compounds 12, 34, 46 and 85 showed 30% or less compared to the lesion area in an untreated plants.

Test Example 31

The testing drug solutions to be used in this Test example were prepared by diluting the formulations prepared according to the above-mentioned Formulation examples with an ion-exchange water so that the active ingredient concentration was set to 500 ppm.

Cucumber (*Sagami-hanjiro-fushinari*) was grown in a polyethylene cup until the first true leaf was developed. Thirty (30) heads of cotton aphid (*Aphis gossypii*) (including the adults and the larvae) was released onto the leaves of the cabbage and next day, the above-mentioned testing drug solutions 20 mL were spread. After 6 days, the number of the surviving insects was counted and the control value was calculated by the following equation.

$$\text{Control value (\%)} = \{1-(Cb \times Tai)/(Cai \times Tb)\} \times 100$$

wherein the symbols in the formula represent the following descriptions.

Cb: Number of the insects before treatment in untreated area;

Cai: Number of the insects at the time of the observation in untreated area;

Tb: Number of the insects before treatment in treated area;

Tai: Number of the insects at the time of the observation in treated area;

As a result, the present Compounds 18, 39 47 and 96 showed 90% or more as the control value.

Test Example 32

The testing drug solutions to be used in this Test example were prepared by diluting the formulations prepared according to the above-mentioned Formulation examples with an ion-exchange water so that the active ingredient concentration was set to 500 ppm. The above-mentioned drug solutions 0.7 mL were added to an ion-exchange water 100 mL so that the active ingredient concentration was set to 3.5 ppm. Twenty (20) last instar larvae of common house mosquito (*Culex pipiens pallens*) were released into the solutions and after 8 day, the number of the dead insects was counted.

The mortality of insects was calculated by the following equation.

Mortality of insects (%)=(Number of dead insects/Number of tested insects)×100

As a result, the present Compounds 38, 64 and 86 showed 100% as the mortality of insects.

Test Example 33

The testing drug solutions to be used in this Test example were prepared by diluting the formulations prepared according to the above-mentioned Formulation examples with an ion-exchange water so that the active ingredient concentration was set to 500 ppm. Cabbage (green ball) was planted in a polyethylene cup and was grown until the third true leaf or the fourth true leaf was developed. To the cabbage (*Brassicae oleracea*) was spread the above-mentioned testing solutions in a ratio of 20 mL/cup. After the drug solutions were dried, to a polyethylene cup (diameter 5.5 cm) covered with a filter paper on the bottom, the cabbage cut out from the root was installed and five heads of cabbage moth (*Plutella xylostella*) at the three instar larval stages were released into the cup and the cup was covered with the lid. The cup was held at 25° C. and after 5 days, the number of the surviving insects was counted and the mortality of insects was calculated by the following equation.

Mortality of insects (%)=(Number of dead insects/Number of tested insects)×100

As a result, the experiments treated with the present compounds 45 to 47, 49, 86 and 89 showed 80% as the mortality of insects.

Test Example 34

The testing drug solutions to be used in this Test example were prepared by diluting the formulations prepared according to the above-mentioned Formulation examples with an ion-exchange water so that the active ingredient concentration was set to 500 ppm.

A bottom of a polyethylene cup having 5.5 cm of diameter was lain with filter paper with the same size as the bottom and thereto was added dropwise the above-mentioned testing solutions 0.7 mL onto the filter paper and sucrose 30 mg as feed was placed uniformly thereon. Two (2) heads of male German cockroach (*Blattella germanica*) were released into the polyethylene cup and the cup was covered with the lid. After 6 days, the life and death of the insects of the German cockroach was observed. As a result, the experiment treated with the present compound 77 showed 1000 as the mortality of insects.

Comparative Test Example

A plastic pot was filled with soils and thereto was seeded barley (cv; Mikamo Golden) and the plants were grown in a greenhouse for 7 days. A control compound, 1-(2-{[1-(4-fluorophenyl)-1H-pyrazole-3-yl]oxymethyl}phenyl)-4-methyl-1,4-dihydrotetrazole-5-one was made to a formulation according to the above-mentioned Formulation examples and was then diluted with water so as to make a predetermined concentration (50 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, the lesion area in plants treated with the control compound, 1-(2-{[1-(4-fluorophenyl)-1H-pyrazole-3-yl]oxymethyl}phenyl)-4-methyl-1,4-dihydrotetrazole-5-one showed 70% or more compared to the lesion area in an untreated plants.

The invention claimed is:
1. A tetrazolinone compound of formula (1):

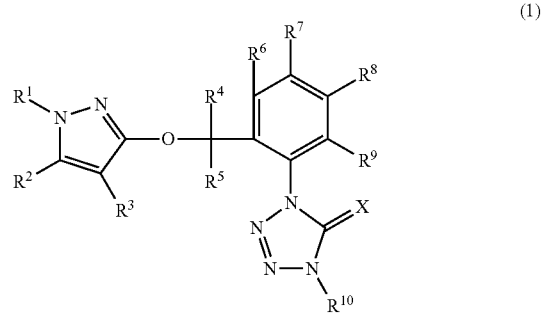

(1)

wherein
$R^1$ represents a group represented by formula (4):

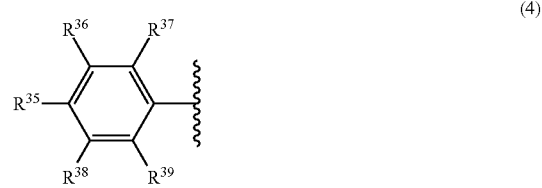

(4)

wherein
$R^{35}$, $R^{36}$, $R^{37}$, $R^{38}$ and $R^{39}$ represent independently of each other a hydrogen atom, an C1-C6 alkoxy group, a halogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a C3-C4 cycloalkyl group, a C3-C4 cycloalkyloxy group, a nitro group or a cyano group;
$R^2$, $R^3$, $R^4$ and $R^5$ represent independently of each other a hydrogen atom;
$R^6$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;
$R^7$, $R^8$ and $R^9$ represent independently of each other a hydrogen atom;
$R^{10}$ represents a methyl group; and
X represents an oxygen atom.

2. The tetrazolinone compound according to claim 1 wherein
$R^6$ represents an C1-C3 alkyl group, a C3-C4 cycloalkyl group, a halogen atom, a C1-C3 haloalkyl group, an C2-C3 alkenyl group, an C1-C3 alkoxy group, an C2-C3 alkynyl group or a C1-C3 haloalkoxy group; and
$R^{35}$, $R^{36}$, $R^{37}$, $R^{38}$ and $R^{39}$ represent independently of each other a hydrogen atom, an C1-C3 alkoxy group, a halogen atom, an C1-C3 alkyl group, a C1-C3 haloalkyl group, a C1-C3 haloalkoxy group, an C1-C3 alkylthio group, a C1-C3 haloalkylthio group, a nitro group or a cyano group.

3. The tetrazolinone compound according to claim 1 wherein
$R^6$ represents a methyl group, a cyclopropyl group, a chlorine atom, a bromine atom, an ethyl group or a methoxy group;
$R^{35}$, $R^{36}$, $R^{37}$, $R^{38}$ and $R^{39}$ represent independently of each other a hydrogen atom, a methoxy group, a ethoxy group, a halogen atom, a methyl group or an ethyl group.

4. An agent for controlling pests comprising the tetrazolinone compound according to claim 1.

5. A method for controlling pests comprising applying an effective amount of the tetrazolinone compound according to claim 1 to plant or soil.

6. A tetrazolinone compound represented by formula (5):

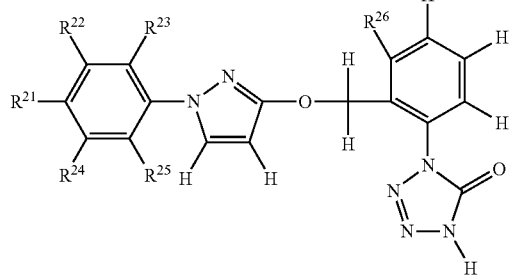

(5)

wherein
$R^{21}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{22}$, $R^{23}$, $R^{24}$ and $R^{25}$ represent independently of each other a hydrogen atom or a halogen atom; and
$R^{26}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group.

7. The tetrazolinone compound according to claim 6 wherein
$R^{21}$ represents a halogen atom, a methyl group, an ethyl group or a methoxy group;
$R^{26}$ represents a methyl group, a cyclopropyl group, a chlorine atom, a bromine atom, an ethyl group or a methoxy group; and
$R^{22}$, $R^{23}$, $R^{24}$ and $R^{25}$ represent independently of each other a hydrogen atom or fluorine atom.

8. A tetrazolinone compound represented by formula (6):

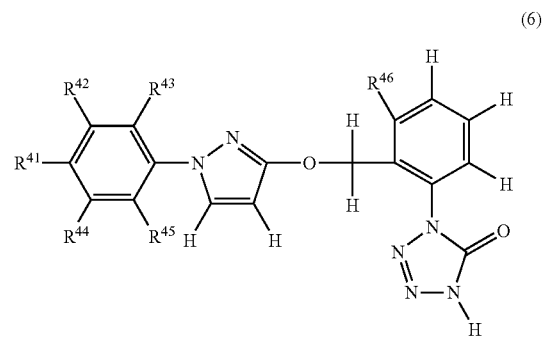

(6)

wherein
$R^{42}$ represents an C1-C6 alkoxy group, a halogen atom, a hydrogen atom, an C1-C6 alkyl group, C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{41}$, $R^{43}$, $R^{44}$ and $R^{45}$ represent independently of each other a hydrogen atom or a halogen atom;
$R^{46}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, C1-C2 haloalkylthio group or an C1-C4 alkylamino group.

9. The tetrazolinone compound according to claim 8 wherein
$R^{42}$ represents a methoxy group, a halogen atom, a methyl group or an ethyl group;
$R^{46}$ represents a methyl group, a cyclopropyl group, a chlorine atom, a bromine atom, an ethyl group or a methoxy group; and
$R^{41}$, $R^{43}$, $R^{44}$ and $R^{45}$ represent independently of each other a hydrogen atom or a fluorine atom.

10. A tetrazolinone compound represented by formula (7):

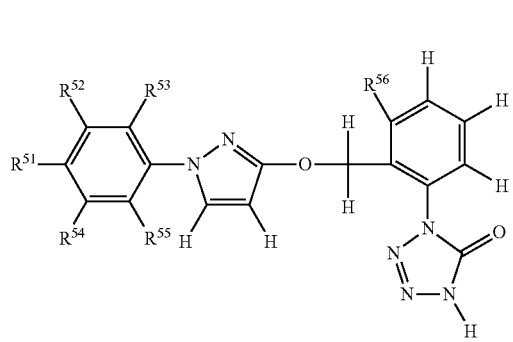

wherein
$R^{53}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{51}$, $R^{52}$, $R^{54}$ and $R^{55}$ represent independently of each other a hydrogen atom or a halogen atom;
$R^{56}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group.

11. The tetrazolinone compound according to claim 10 wherein
$R^{53}$ represents a methoxy group, an ethoxy group, a halogen atom, a methyl group or an ethyl group;
$R^{56}$ represents a methyl group, a cyclopropyl group, a chlorine atom, a bromine atom, an ethyl group or a methoxy group.

12. A tetrazolinone compound represented by formula (8):

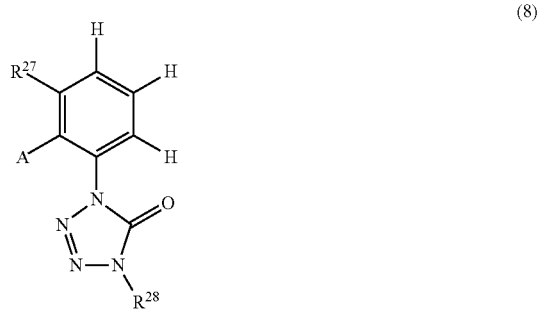

wherein
$R^{27}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group;
$R^{28}$ represents a methyl group or a hydrogen atom;
A represents a methyl group, a halomethyl group, a hydroxymethyl group, an (C1-C3 alkoxy)methyl group, an (C1-C3 alkylthio)methyl group, an (C1-C6 acyloxy)methyl group, an (C1-C6 alkylsulfonyloxy) methyl group, a (C1-C6 haloalkylsulfonyloxy)methyl group, an (C6-C16 arylsulfonyloxy)methyl group, a (C6-C16 haloarylsulfonyloxy)methyl group, an (C1-C6 alkylamino)methyl group, a methyl group having a heterocyclyl group with the proviso that the heterocyclyl group includes one or more nitrogen atoms as ring-constituent atom and may further include one or more oxygen atoms or sulfur atoms, and the nitrogen atom being the ring-constituent atom for the heterocyclyl group and a methyl group connects to each other, a formyl group or an C2-C6 alkoxycarbonyl group.

13. The tetrazolinone compound according to claim 12 wherein
$R^{27}$ represents a methyl group, a cyclopropyl group, a chlorine atom, a bromine atom, an ethyl group or a methoxy group; and
A represents a methyl group, a halomethyl group, a hydroxymethyl group, an (C1-C3 alkoxy)methyl group, an (C1-C6 alkylsulfonyloxy)methyl group, an (C6-C16 arylsulfonyloxy)methyl group, a formyl group or an C2-C6 alkoxycarbonyl group.

14. The tetrazolinone compound according to claim 12 wherein
$R^{27}$ represents a methyl group, an ethyl group, a halogen atom, a trifluoromethyl group or a methoxy group; and
A represents a methyl group, a chloromethyl group or bromomethyl group.

15. The tetrazolinone compound according to claim 12 wherein
$R^{27}$ represents an C2-C3 alkyl group, a C3-C4 cycloalkyl group, an C2-C3 alkenyl group, an C2-C3 alkoxy group, an C1-C2 alkylthio group, an C2-C3 alkynyl group, a C1-C3 haloalkoxy group, a C1-C2 haloalkylthio group or an C1-C4 alkylamino group.

16. A pyrazole compound represented by formula (9):

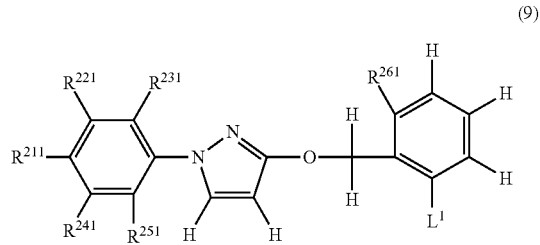

wherein
$R^{211}$ represents a halogen atom, a hydrogen atom, an C1-C6 alkyl group, a C1-C6 haloalkyl group, an C1-C6 alkoxy group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{221}$, $R^{231}$, $R^{241}$ and $R^{251}$ represent independently of each other a hydrogen atom or a halogen atom;
$R^{261}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^1$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH.

17. The pyrazole compound according to claim 16 wherein
$R^{211}$ represents a halogen atom, a methyl group, an ethyl group or methoxy group;
$R^{261}$ represents a methyl group, a cyclopropyl group, a chlorine atom, a bromine atom, an ethyl group or a methoxy group; and
$R^{221}$, $R^{231}$, $R^{241}$ and $R^{251}$ represent independently of each other a hydrogen atom or fluorine atom.

18. A pyrazole compound represented by formula (10):

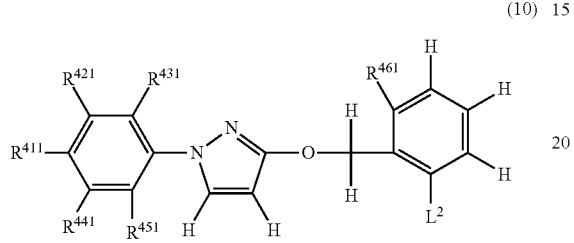

(10)

wherein
$R^{421}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{411}$, $R^{431}$, $R^{441}$ and $R^{451}$ represent independently of each other a hydrogen atom or a halogen atom;
$R^{461}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^2$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH.

19. The pyrazole compound according to claim 18 wherein
$R^{421}$ represents a methoxy group, a halogen atom, a methyl group or an ethyl group;

$R^{461}$ represents a methyl group, a cyclopropyl group, a chlorine atom, a bromine atom, an ethyl group or a methoxy group; and
$R^{411}$, $R^{431}$, $R^{441}$ and $R^{451}$ represent independently of each other a hydrogen atom or a fluorine atom.

20. A pyrazole compound represented by formula (11):

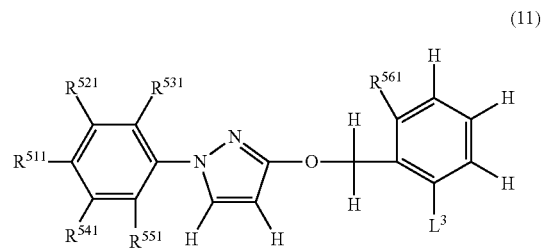

(11)

wherein
$R^{531}$ represents an C1-C6 alkoxy group, a halogen atom, a hydrogen atom, an C1-C6 alkyl group, a C1-C6 haloalkyl group, a C1-C6 haloalkoxy group, an C1-C6 alkylthio group, a C1-C6 haloalkylthio group, an C2-C6 acyl group, a C2-C6 haloacyl group, a nitro group or a cyano group;
$R^{511}$, $R^{521}$, $R^{541}$ and $R^{551}$ represent independently of each other a hydrogen atom or a halogen atom;
$R^{561}$ represents an C1-C3 alkyl group, a C3-C4 cycloalkyl group, a halogen atom, a C1-C3 haloalkyl group, an C2-C3 alkenyl group, an C1-C3 alkoxy group, an C1-C2 alkylthio group, an C2-C3 alkynyl group, a C1-C3 haloalkoxy group, a C1-C2 haloalkylthio group or an C1-C4 alkylamino group; and
$L^3$ represents a nitro group, an amino group, an isocyanato group, a carboxyl group, an C2-C6 alkoxycarbonyl group, a halogen atom, a halogenated acyl group, NSO, CON₃, CONH₂, CONHCl, CONHBr or CONHOH.

21. The pyrazole compound according to claim 20 wherein
$R^{531}$ represents a methoxy group, an ethoxy group, a halogen atom, a methyl group or an ethyl group; and
$R^{561}$ represents a methyl group, a cyclopropyl group, a chlorine atom, a bromine atom, an ethyl group a methoxy group.

* * * * *